US012629194B2

(12) United States Patent
Henderson et al.

(10) Patent No.: US 12,629,194 B2
(45) Date of Patent: May 19, 2026

(54) MODULAR SURGICAL ENERGY SYSTEM

(71) Applicant: Cilag GmbH International, Zug (CH)

(72) Inventors: Joshua M. Henderson, Cincinnati, OH (US); Joshua P. Morgan, Loveland, OH (US); Andrew W. Carroll, Cincinnati, OH (US); Jeffrey L. Aldridge, Lebanon, OH (US); Eitan T. Wiener, Loveland, OH (US); James M. Vachon, West Chester, OH (US); Ryan M. Asher, Cincinnati, OH (US); John B. Schulte, West Chester, OH (US); John E. Hein, Neenah, WI (US); James R. Hoch, Appleton, WI (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/131,107

(22) Filed: Apr. 5, 2023

(65) Prior Publication Data

US 2023/0346446 A1      Nov. 2, 2023

Related U.S. Application Data

(63) Continuation of application No. 16/562,123, filed on Sep. 5, 2019, now Pat. No. 11,666,368.

(Continued)

(51) Int. Cl.
*A61B 18/00*          (2006.01)
*A61B 17/072*          (2006.01)
(Continued)

(52) U.S. Cl.
CPC ............ *A61B 18/00* (2013.01); *A61B 17/072* (2013.01); *A61B 17/320068* (2013.01);
(Continued)

(58) Field of Classification Search
CPC ............ A61B 17/072; A61B 17/07207; A61B 17/320068; A61B 17/320092;
(Continued)

(56) References Cited

U.S. PATENT DOCUMENTS 4,122,854 A      10/1978  Blackett
4,171,700 A      10/1979  Farin
(Continued)

FOREIGN PATENT DOCUMENTS

CN          101069651 A      11/2007
CN          102008350 A      4/2011
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.

(Continued)

*Primary Examiner* — Minh N Trinh
(74) *Attorney, Agent, or Firm* — Vorys, Sater, Seymour and Pease LLP

(57)          ABSTRACT

A modular surgical system is disclosed. The modular surgical system can include a control module, a first surgical module, and a second surgical module that are arrangeable in a stack. The control module can include a pulse generator to generate a clock pulse signals. Each of the first and second surgical modules can include a timing circuit and a delay circuit. Each timing circuit can receive the clock pulse signal and start a timer. A first delay circuit of the first surgical module can also receive the clock pulse signal and transmit a first delayed sequence signal to the timing circuit of the first module. A second delay circuit of the second surgical can also receive the first delayed sequence signal from the (Continued)

first delay circuit and transmit a second delayed sequence signal to the clock timer of the second surgical module.

15 Claims, 182 Drawing Sheets

Related U.S. Application Data

(60) Provisional application No. 62/826,584, filed on Mar. 29, 2019, provisional application No. 62/826,588, filed on Mar. 29, 2019, provisional application No. 62/826,587, filed on Mar. 29, 2019, provisional application No. 62/826,592, filed on Mar. 29, 2019, provisional application No. 62/728,480, filed on Sep. 7, 2018.

(51) Int. Cl.

| | |
|---|---|
| *A61B 17/32* | (2006.01) |
| *A61B 18/12* | (2006.01) |
| *A61B 18/14* | (2006.01) |
| *A61B 18/16* | (2006.01) |
| *A61B 34/00* | (2016.01) |
| *A61B 34/20* | (2016.01) |
| *A61B 34/30* | (2016.01) |
| *A61B 34/35* | (2016.01) |
| *A61B 34/37* | (2016.01) |
| *A61B 90/00* | (2016.01) |
| *A61B 90/90* | (2016.01) |
| *G06F 8/65* | (2018.01) |
| *G16H 20/40* | (2018.01) |
| *H01R 43/26* | (2006.01) |
| *H04L 9/40* | (2022.01) |
| *H04L 27/04* | (2006.01) |
| *H04L 49/25* | (2022.01) |
| *H04L 67/10* | (2022.01) |
| *H04L 67/12* | (2022.01) |
| *H04M 1/72406* | (2021.01) |
| *H05K 5/30* | (2025.01) |
| *A61B 17/00* | (2006.01) |
| *A61B 90/30* | (2016.01) |
| *H05K 5/00* | (2006.01) |
| *H05K 7/02* | (2006.01) |

(52) U.S. Cl.
CPC .. *A61B 17/320092* (2013.01); *A61B 18/1206* (2013.01); *A61B 18/1233* (2013.01); *A61B 18/1445* (2013.01); *A61B 18/16* (2013.01); *A61B 34/20* (2016.02); *A61B 34/25* (2016.02); *A61B 34/35* (2016.02); *A61B 34/74* (2016.02); *A61B 90/361* (2016.02); *A61B 90/90* (2016.02); *G06F 8/65* (2013.01); *G16H 20/40* (2018.01); *H01R 43/26* (2013.01); *H04L 49/25* (2013.01); *H04L 63/0245* (2013.01); *H04L 67/10* (2013.01); *H04L 67/12* (2013.01); *H04M 1/72406* (2021.01); *H05K 5/30* (2025.01); *A61B 2017/00026* (2013.01); *A61B 2017/00199* (2013.01); *A61B 2017/00221* (2013.01); *A61B 2017/00225* (2013.01); *A61B 2017/00398* (2013.01); *A61B 2017/00477* (2013.01); *A61B 2017/00526* (2013.01); *A61B 2017/00973* (2013.01); *A61B 2017/07257* (2013.01); *A61B 2017/07271* (2013.01); *A61B 2017/07285* (2013.01); *A61B 2017/320074* (2017.08); *A61B 2018/00178* (2013.01); *A61B 2018/00208* (2013.01); *A61B 2018/00601* (2013.01); *A61B 2018/0063* (2013.01); *A61B 2018/00642* (2013.01); *A61B 2018/00702* (2013.01); *A61B 2018/00708* (2013.01); *A61B 2018/0072* (2013.01); *A61B 2018/00732* (2013.01); *A61B 2018/00767* (2013.01); *A61B 2018/00845* (2013.01); *A61B 2018/00875* (2013.01); *A61B 2018/00916* (2013.01); *A61B 2018/0094* (2013.01); *A61B 2018/00958* (2013.01); *A61B 2018/00994* (2013.01); *A61B 2018/1253* (2013.01); *A61B 2018/126* (2013.01); *A61B 2018/1273* (2013.01); *A61B 2018/128* (2013.01); *A61B 2018/1286* (2013.01); *A61B 2018/165* (2013.01); *A61B 2034/2048* (2016.02); *A61B 2034/2055* (2016.02); *A61B 2034/305* (2016.02); *A61B 34/37* (2016.02); *A61B 90/30* (2016.02); *A61B 90/37* (2016.02); *A61B 2090/371* (2016.02); *A61B 2090/378* (2016.02); *A61B 2218/002* (2013.01); *A61B 2218/007* (2013.01); *A61B 2218/008* (2013.01); *A61B 2560/0443* (2013.01); *A61B 2560/0456* (2013.01); *H01R 2201/12* (2013.01); *H04L 27/04* (2013.01); *H05K 5/0026* (2013.01); *H05K 5/0065* (2013.01); *H05K 7/023* (2013.01)

(58) Field of Classification Search
CPC ..... A61B 18/00; A61B 18/12; A61B 18/1206; A61B 18/1233; A61B 18/14; A61B 18/1442; A61B 18/1445; A61B 18/16; A61B 2017/00017; A61B 2017/00026; G06F 8/65; G16H 20/40; G16H 40/63; H01R 2201/12; H01R 43/26; Y04S 40/18; H05K 5/0021; H05K 5/0026; H05K 5/0065; H05K 7/023
See application file for complete search history.

(56) References Cited

U.S. PATENT DOCUMENTS

| | | | |
|---|---|---|---|
| 4,378,801 | A | 4/1983 | Oosten |
| 4,640,279 | A | 2/1987 | Beard |
| 4,849,752 | A | 7/1989 | Bryant |
| 4,856,514 | A | 8/1989 | Rabinowitz et al. |
| D303,787 | S | 10/1989 | Messenger et al. |
| 5,041,110 | A | 8/1991 | Fleenor |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,383,880 | A | 1/1995 | Hooven |
| 5,395,033 | A | 3/1995 | Byrne et al. |
| 5,425,375 | A | 6/1995 | Chin et al. |
| 5,514,129 | A | 5/1996 | Smith |
| 5,601,445 | A | 2/1997 | Schipper et al. |
| 5,613,158 | A | 3/1997 | Savage |
| D379,346 | S | 5/1997 | Mieki |
| 5,667,517 | A | 9/1997 | Hooven |
| 5,690,504 | A | 11/1997 | Scanlan et al. |
| 5,693,042 | A | 12/1997 | Boiarski et al. |
| 5,724,468 | A | 3/1998 | Leone et al. |
| 5,740,379 | A | 4/1998 | Hartwig |
| 5,788,688 | A | 8/1998 | Bauer et al. |
| 5,817,119 | A | 10/1998 | Klieman et al. |
| 5,849,020 | A | 12/1998 | Long et al. |
| 5,865,361 | A | 2/1999 | Milliman et al. |
| 5,872,481 | A | 2/1999 | Sevic et al. |
| 5,901,150 | A | 5/1999 | Jhuboo et al. |
| 5,910,139 | A | 6/1999 | Cochran et al. |
| 5,954,527 | A | 9/1999 | Jhuboo et al. |
| 6,019,745 | A | 2/2000 | Gray |
| 6,049,467 | A | 4/2000 | Tamarkin et al. |
| 6,055,062 | A | 4/2000 | Dina et al. |

(56) References Cited

U.S. PATENT DOCUMENTS

| | | | |
|---|---|---|---|
| 6,055,458 A | 4/2000 | Cochran et al. |
| D431,811 S | 10/2000 | Nishio et al. |
| 6,172,875 B1 | 1/2001 | Suzuki et al. |
| 6,179,136 B1 | 1/2001 | Kluge et al. |
| 6,203,541 B1 | 3/2001 | Keppel |
| 6,246,905 B1 | 6/2001 | Mogul |
| 6,269,411 B1 | 7/2001 | Reasoner |
| 6,273,750 B1 | 8/2001 | Malkowski, Jr. |
| 6,288,606 B1 | 9/2001 | Ekman et al. |
| H2037 H | 7/2002 | Yates et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,666,875 B1 | 12/2003 | Sakurai et al. |
| 6,731,514 B2 | 5/2004 | Evans |
| 6,760,218 B2 | 7/2004 | Fan |
| 6,761,698 B2 | 7/2004 | Shibata et al. |
| 6,839,238 B2 | 1/2005 | Derr et al. |
| 6,843,657 B2 | 1/2005 | Driscoll et al. |
| 6,888,848 B2 | 5/2005 | Beshai et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,118,563 B2 | 10/2006 | Weckwerth et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,268,684 B2 | 9/2007 | Tethrake et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| D575,792 S | 8/2008 | Benson |
| 7,408,439 B2 | 8/2008 | Wang et al. |
| 7,443,296 B2 | 10/2008 | Mezhinsky et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,695,485 B2 | 4/2010 | Whitman et al. |
| 7,722,603 B2 | 5/2010 | Mcpherson |
| 7,757,028 B2 | 7/2010 | Druke et al. |
| 7,794,457 B2 | 9/2010 | Mcpherson et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,967,022 B2 | 6/2011 | Grant et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| 8,057,492 B2 | 11/2011 | Ortiz et al. |
| D655,678 S | 3/2012 | Kobayashi et al. |
| D657,368 S | 4/2012 | Magee et al. |
| 8,187,263 B2 | 5/2012 | Behnke et al. |
| 8,218,279 B2 | 7/2012 | Liao et al. |
| 8,231,614 B2 | 7/2012 | Dunning et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| 8,568,400 B2 | 10/2013 | Gilbert |
| D704,839 S | 5/2014 | Juzkiw et al. |
| 8,749,485 B2 | 6/2014 | Tan et al. |
| 8,795,001 B1 | 8/2014 | Lam et al. |
| 8,819,581 B2 | 8/2014 | Nakamura et al. |
| 8,840,609 B2 | 9/2014 | Stuebe |
| D716,333 S | 10/2014 | Chotin et al. |
| 8,911,437 B2 | 12/2014 | Horlle et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,936,631 B2 | 1/2015 | Nguyen et al. |
| 8,961,441 B2 | 2/2015 | Cioanta et al. |
| 8,968,294 B2 | 3/2015 | Maass et al. |
| 8,968,296 B2 | 3/2015 | McPherson |
| 8,986,288 B2 | 3/2015 | Konishi |
| 9,017,326 B2 | 4/2015 | DiNardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,339,324 B2 | 5/2016 | Eisele et al. |
| 9,345,481 B2 | 5/2016 | Hall et al. |
| 9,345,900 B2 | 5/2016 | Wu et al. |
| 9,351,653 B1 | 5/2016 | Harrison |
| 9,370,361 B2 | 6/2016 | Viola et al. |
| 9,391,670 B2 | 7/2016 | Brukalo et al. |
| 9,427,255 B2 | 8/2016 | Griffith et al. |
| 9,430,438 B2 | 8/2016 | Biskup |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,647,918 B2 | 5/2017 | Raleigh et al. |
| 9,649,148 B2 | 5/2017 | Woloszko et al. |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,483 B2 | 2/2018 | Lee et al. |
| 9,892,564 B1 | 2/2018 | Cvetko et al. |
| 9,907,196 B2 | 2/2018 | Susini et al. |
| 9,949,785 B2 | 4/2018 | Price et al. |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,107 B2 | 10/2018 | Izmirli et al. |

(56) References Cited

U.S. PATENT DOCUMENTS

| | | |
|---|---|---|
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,219,858 B2 | 3/2019 | Danek et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,660,651 B2 | 5/2020 | Baril et al. |
| 10,675,027 B2 | 6/2020 | Aldridge et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,898,279 B2 | 1/2021 | Yang |
| 10,914,789 B2 | 2/2021 | Lemkin et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,077,312 B2 | 8/2021 | Sturman et al. |
| 11,083,489 B2 | 8/2021 | Fujii et al. |
| 11,096,737 B2 | 8/2021 | Friedrichs et al. |
| 11,116,587 B2 | 9/2021 | Wolf et al. |
| 11,185,379 B2 | 11/2021 | Shuma et al. |
| D939,545 S | 12/2021 | Oberkircher et al. |
| 11,218,822 B2 | 1/2022 | Morgan et al. |
| 11,246,618 B2 | 2/2022 | Hall et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,272,975 B2 | 3/2022 | Tonn et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,607,239 B2 | 3/2023 | Swensgard et al. |
| 11,628,006 B2 | 4/2023 | Henderson et al. |
| 11,638,602 B2 | 5/2023 | Henderson et al. |
| 11,659,023 B2 | 5/2023 | Shelton, IV et al. |
| 11,666,368 B2 | 6/2023 | Henderson et al. |
| 11,678,925 B2 | 6/2023 | Henderson et al. |
| 11,684,400 B2 | 6/2023 | Jayme et al. |
| 11,684,401 B2 | 6/2023 | Oberkircher et al. |
| 11,712,309 B2 | 8/2023 | Barak et al. |
| 11,931,039 B2 | 3/2024 | Williams et al. |
| 11,998,258 B2 * | 6/2024 | Henderson ........... A61B 17/072 |
| 2001/0029315 A1 | 10/2001 | Sakurai et al. |
| 2001/0031975 A1 | 10/2001 | Whitman et al. |
| 2002/0022836 A1 | 2/2002 | Goble et al. |
| 2002/0052563 A1 | 5/2002 | Penn et al. |
| 2002/0148942 A1 | 10/2002 | Payne et al. |
| 2002/0151770 A1 | 10/2002 | Noll et al. |
| 2002/0183734 A1 | 12/2002 | Bommannan et al. |
| 2003/0007321 A1 | 1/2003 | Dayley |
| 2003/0040670 A1 | 2/2003 | Govari |
| 2003/0050654 A1 | 3/2003 | Whitman et al. |
| 2003/0078631 A1 | 4/2003 | Nelson et al. |
| 2003/0093103 A1 | 5/2003 | Malackowski et al. |
| 2003/0114851 A1 | 6/2003 | Truckai et al. |
| 2003/0130677 A1 | 7/2003 | Whitman et al. |
| 2003/0199794 A1 | 10/2003 | Sakurai et al. |
| 2003/0199864 A1 | 10/2003 | Eick |
| 2004/0015163 A1 | 1/2004 | Buysse et al. |
| 2004/0030328 A1 | 2/2004 | Eggers et al. |
| 2004/0059323 A1 | 3/2004 | Sturm et al. |
| 2004/0094597 A1 | 5/2004 | Whitman et al. |
| 2004/0111045 A1 | 6/2004 | Sullivan et al. |
| 2004/0111081 A1 | 6/2004 | Whitman et al. |
| 2004/0122493 A1 | 6/2004 | Ishibashi et al. |
| 2004/0153724 A1 | 8/2004 | Clark et al. |
| 2004/0164983 A1 | 8/2004 | Khozai |
| 2004/0213291 A1 | 10/2004 | Beshai et al. |
| 2005/0010209 A1 | 1/2005 | Lee et al. |
| 2005/0013459 A1 | 1/2005 | Maekawa |
| 2005/0021026 A1 | 1/2005 | Baily |
| 2005/0070800 A1 | 3/2005 | Takahashi |
| 2005/0113815 A1 | 5/2005 | Ritchie et al. |
| 2005/0113823 A1 | 5/2005 | Reschke et al. |
| 2005/0127868 A1 | 6/2005 | Calhoon et al. |
| 2005/0127869 A1 | 6/2005 | Calhoon et al. |
| 2005/0131390 A1 | 6/2005 | Heinrich et al. |
| 2005/0159778 A1 | 7/2005 | Heinrich et al. |
| 2005/0165390 A1 | 7/2005 | Mauti et al. |
| 2005/0173490 A1 | 8/2005 | Shelton |
| 2005/0229110 A1 | 10/2005 | Gegner et al. |
| 2005/0251233 A1 | 11/2005 | Kanzius |
| 2006/0020213 A1 | 1/2006 | Whitman et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0212069 A1 | 9/2006 | Shelton |
| 2006/0256516 A1 | 11/2006 | Cho |
| 2006/0278680 A1 | 12/2006 | Viola et al. |
| 2006/0278681 A1 | 12/2006 | Viola et al. |
| 2006/0289600 A1 | 12/2006 | Wales et al. |
| 2007/0061393 A1 | 3/2007 | Moore |
| 2007/0076363 A1 | 4/2007 | Liang et al. |
| 2007/0085602 A1 | 4/2007 | Park et al. |
| 2007/0136218 A1 | 6/2007 | Bauer et al. |

(56) References Cited

U.S. PATENT DOCUMENTS

| | | |
|---|---|---|
| 2007/0282321 A1 | 12/2007 | Shah et al. |
| 2008/0072896 A1 | 3/2008 | Setzer et al. |
| 2008/0090652 A1 | 4/2008 | Kuehling et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0054908 A1 | 2/2009 | Zand et al. |
| 2009/0101692 A1 | 4/2009 | Whitman et al. |
| 2009/0131929 A1 | 5/2009 | Shimizu |
| 2009/0209990 A1 | 8/2009 | Yates et al. |
| 2009/0216091 A1 | 8/2009 | Arndt |
| 2009/0228024 A1 | 9/2009 | Whitfield et al. |
| 2009/0234352 A1 | 9/2009 | Behnke et al. |
| 2009/0273353 A1 | 11/2009 | Kroh et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0093226 A1 | 4/2010 | Hoerlle et al. |
| 2010/0120266 A1 | 5/2010 | Rimborg |
| 2010/0198200 A1 | 8/2010 | Horvath |
| 2010/0217099 A1 | 8/2010 | Leboeuf et al. |
| 2010/0312239 A1 | 12/2010 | Sclig |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0265195 A1 | 10/2012 | Gilbert |
| 2012/0319890 A1 | 12/2012 | McCormack et al. |
| 2013/0031201 A1 | 1/2013 | Kagan et al. |
| 2013/0154919 A1 | 6/2013 | Tan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0097903 A1 | 4/2014 | Aoki et al. |
| 2014/0108048 A1 | 4/2014 | Cohn |
| 2014/0155721 A1 | 6/2014 | Hauck et al. |
| 2014/0180274 A1 | 6/2014 | Kabaya et al. |
| 2014/0194683 A1 | 7/2014 | Nakaguchi |
| 2014/0194702 A1 | 7/2014 | Tran |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0097701 A1 | 4/2015 | Al-Ali et al. |
| 2015/0190189 A1 | 7/2015 | Yates et al. |
| 2015/0201899 A1 | 7/2015 | Uchinomiya et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2015/0373115 A1 | 12/2015 | Breakstone et al. |
| 2016/0000495 A1 | 1/2016 | Elliott et al. |
| 2016/0045247 A1 | 2/2016 | Heim et al. |
| 2016/0045365 A1 | 2/2016 | Foster et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0164466 A1 | 6/2016 | Briffa et al. |
| 2016/0199240 A1 | 7/2016 | Newkirk et al. |
| 2016/0203608 A1 | 7/2016 | Lzmirli et al. |
| 2016/0225192 A1 | 8/2016 | Jones et al. |
| 2016/0249945 A1 | 9/2016 | Shelton, IV et al. |
| 2016/0283427 A1 | 9/2016 | Chaudhari et al. |
| 2016/0287312 A1 | 10/2016 | Tegg et al. |
| 2016/0287337 A1 | 10/2016 | Aram et al. |
| 2016/0344604 A1 | 11/2016 | Raleigh et al. |
| 2017/0000553 A1 | 1/2017 | Wiener et al. |
| 2017/0007146 A1 | 1/2017 | Schulhauser et al. |
| 2017/0024978 A1 | 1/2017 | Gulrez et al. |
| 2017/0058617 A1 | 3/2017 | Bartel |
| 2017/0078455 A1 | 3/2017 | Fisher et al. |
| 2017/0080346 A1 | 3/2017 | Abbas |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis |
| 2017/0238839 A1 | 8/2017 | Hyde et al. |
| 2017/0251305 A1 | 8/2017 | Fathollahi |
| 2017/0252091 A1 | 9/2017 | Honda |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0116673 A1 | 5/2018 | Baril et al. |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0228528 A1 | 8/2018 | Fraasch et al. |
| 2018/0239856 A1 | 8/2018 | Takeuchi et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De la Barrera |
| 2018/0367870 A1 | 12/2018 | Shih |
| 2019/0069957 A1 | 3/2019 | Barral et al. |
| 2019/0125455 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0247664 A1 | 8/2019 | Lrazoqui et al. |
| 2019/0269457 A1 | 9/2019 | Schofield et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2019/0388137 A1 | 12/2019 | Henrywood |
| 2020/0004487 A1 | 1/2020 | Hanajima et al. |
| 2020/0008867 A1 | 1/2020 | Mcgregor et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078071 A1 | 3/2020 | Asher |
| 2020/0078080 A1* | 3/2020 | Henderson .............. H04L 67/12 |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |

(56) References Cited

U.S. PATENT DOCUMENTS

| | | |
|---|---|---|
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1* | 4/2020 | Henderson ..... A61B 17/320068 |
| 2020/0106220 A1 | 4/2020 | Henderson et al. |
| 2020/0129223 A1 | 4/2020 | Angeles et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0342228 A1 | 10/2020 | Prevrhal et al. |
| 2020/0405375 A1 | 12/2020 | Shelton, IV et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko et al. |
| 2021/0313938 A1 | 10/2021 | Tanaka et al. |
| 2021/0338343 A1 | 11/2021 | Swaffield et al. |
| 2021/0385889 A1 | 12/2021 | Patel |
| 2022/0031047 A1 | 2/2022 | Samain et al. |
| 2022/0032442 A1 | 2/2022 | Sheffield et al. |
| 2022/0104867 A1 | 4/2022 | Shelton et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |
| 2023/0346446 A1* | 11/2023 | Henderson ........... A61B 90/361 |

FOREIGN PATENT DOCUMENTS

| | | |
|---|---|---|
| CN | 202257661 U | 5/2012 |
| CN | 104626148 A | 5/2015 |
| EP | 0408160 A1 | 1/1991 |
| EP | 0473987 A1 | 3/1992 |
| EP | 0929263 B1 | 7/1999 |
| EP | 0947167 A1 | 10/1999 |
| EP | 1006892 B1 | 6/2009 |
| EP | 2772206 A2 | 9/2014 |
| EP | 2942023 A2 | 11/2015 |
| JP | S57117032 A | 7/1982 |
| JP | S635457 A | 1/1988 |
| JP | H02193658 A | 7/1990 |
| JP | H0341943 A | 2/1991 |
| JP | H03126447 A | 5/1991 |
| JP | H06506637 A | 7/1994 |
| JP | H0757819 A | 3/1995 |
| JP | H08117243 A | 5/1996 |
| JP | H08280706 A | 10/1996 |
| JP | H1069453 A | 3/1998 |
| JP | H11226026 A | 8/1999 |
| JP | H11318921 A | 11/1999 |
| JP | 2000089850 A | 3/2000 |
| JP | 2000217836 A | 8/2000 |
| JP | 2001029353 A | 2/2001 |
| JP | 2001104334 A | 4/2001 |
| JP | 2001128993 A | 5/2001 |
| JP | 2002336194 A | 11/2002 |
| JP | 2002343399 A | 11/2002 |
| JP | 2004008581 A | 1/2004 |
| JP | 2004290516 A | 10/2004 |
| JP | 2006223386 A | 8/2006 |
| JP | 2006300872 A | 11/2006 |
| JP | 2006303167 A | 11/2006 |
| JP | 2007319697 A | 12/2007 |
| JP | 2009291308 A | 12/2009 |
| JP | 2010088707 A | 4/2010 |
| JP | 2014210052 A | 11/2014 |
| JP | 2015093116 A | 5/2015 |
| JP | 2018177150 A | 11/2018 |
| KR | 20110081018 A | 7/2011 |
| WO | WO-0112089 A1 | 2/2001 |
| WO | WO-2008053485 A1 | 5/2008 |
| WO | WO-2012130326 A1 | 10/2012 |
| WO | WO-2013161624 A1 | 10/2013 |
| WO | WO-2014031800 A1 | 2/2014 |
| WO | WO-2014071184 A1 | 5/2014 |
| WO | WO-2015047693 A1 | 4/2015 |
| WO | WO-2015176074 A2 | 11/2015 |
| WO | WO-2017058617 A2 | 4/2017 |
| WO | WO-2017180428 A1 | 10/2017 |
| WO | WO-2018005631 A1 | 1/2018 |
| WO | WO-2018047352 A1 | 3/2018 |
| WO | WO-2018094159 A1 | 5/2018 |
| WO | WO-2018116247 A1 | 6/2018 |
| WO | WO-2018156804 A1 | 8/2018 |
| WO | WO-2019215354 A1 | 11/2019 |
| WO | WO-2021044136 A1 | 3/2021 |

OTHER PUBLICATIONS

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Zhu et al. "Haptic-feedback smart glove as a creative human-machine interface (HMI) for virtual/augmented reality applications," SCI. ADV, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

(56)　　References Cited

OTHER PUBLICATIONS

Yu et al., "Skin-Integrated Wireless Haptic Interfaces for Virtual and Augmented Reality," Nature, vol. 575, pp. 473-479, Nov. 21, 2019.
Li et al., "Wearable Energy Harvesters Generating Electricity From Low-Frequency Human Limb Movement," Microsystems & Nanoengineering (2018), vol. 4(24), 13 pages.
"BOWA ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).
"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).
"MD PnP OpenICE", Retrieved from:-https://web.archive.org, XP093271099, Jan. 1, 2015.
"MD PnP OpenICE", Retrieved from:-https://web.archive.org, XP093271099, Jan. 1, 2015, 5 pages.
Extended European Search Report, received for European Application No. 24164473.1, mailed on Jul. 5, 2024, 9 pages.
Extended European Search Report, received for European Application No. 25170069.6, mailed on Jun. 25, 2025, 15 pages.
International Search Report and Written Opinion, received for PCT Application No. PCT/US2019/049933, mailed on Dec. 5, 2019, 12 pages.
International Search Report and Written Opinion, received for PCT Application No. PCT/US2019/049937, mailed on Nov. 20, 2019, 15 pages.
International Search Report and Written Opinion, received for PCT Application No. PCT/US2019/049938, mailed on Jan. 13, 2020, 16 pages.
International Search Report and Written Opinion, received for PCT Application No. PCT/US2019/049948, mailed on Dec. 6, 2019, 14 pages.
International Search Report and Written Opinion, received for PCT Application No. PCT/US2019/049951, mailed on Dec. 4, 2019, 15 pages.
International Search Report and Written Opinion, received for PCT Application No. PCT/US2019/049960, mailed on Dec. 11, 2019, 15 pages.
International Search Report and Written Opinion, received for PCT Application No. PCT/US2019/049967, mailed on Nov. 22, 2019, 21 pages.
International Search Report and Written Opinion, received for PCT Application No. PCT/US2019/049970, mailed on Nov. 13, 2019, 16 pages.
International Search Report and Written Opinion, received for PCT Application No. PCT/US2019/049972, mailed on Feb. 28, 2020, 11 pages.
International Search Report and Written Opinion, received for PCT Application No. PCT/US2019/049979, mailed on Dec. 6, 2019, 18 pages.
International Search Report and Written Opinion, received for PCT Application No. PCT/US2019/049981, mailed on Nov. 19, 2019, 17 pages.
International Search Report and Written Opinion, received for PCT Application No. PCT/US2019/049982, mailed on Dec. 16,2019, 15 pages.
International Search Report and Written Opinion, received for PCT Application No. PCT/US2019/049983, mailed on Dec. 3, 2019, 17 pages.
International Search Report and Written Opinion, received for PCT Application No. PCT/US2019/049984, mailed on Dec. 19, 2019, 16 pages.
International Search Report and Written Opinion, received for PCT Application No. PCT/US2019/049987, mailed on Dec. 6, 2019, 15 pages.
International Search Report, received for PCT Application No. PCT/US2019/049947, mailed on Dec. 3, 2019, 05 pages.
Invitation to Pay Additional Fees, received for PCT Application No. PCT/US2019/049957, mailed on Dec. 19, 2019, 14 pages.
Invitation to Pay Additional Fees, received for PCT Application No. PCT/US2019/049931, mailed on Dec. 16, 2019, 11 pages.
Invitation to Pay Additional Fees, received for PCT Application No. PCT/US2019/049935, mailed on Nov. 29, 2019, 15 pages.
Invitation to Pay Additional Fees, received for PCT Application No. PCT/US2019/049941, mailed on Nov. 28, 2019, 13 pages.
Invitation to Pay Additional Fees, received for PCT Application No. PCT/US2019/049945, mailed on Nov. 29, 2019, 13 pages.
Invitation to Pay Additional Fees, received for PCT Application No. PCT/US2019/049985, mailed on Nov. 22, 2019, 18 pages.
Invitation to Pay Additional Fees, received for PCT Application No. PCT/US2019/049990, mailed on Dec. 6, 2019, 14 pages.
Partial European Search Report, received for European Application No. 25165615.3, mailed on Apr. 29, 2025, 16 pages.
Partial European Search Report, received for European Application No. 25166398.5, mailed on Apr. 29, 2025, 16 pages.
Written Opinion, received for PCT Application No. PCT/US2019/049947, mailed on Dec. 3, 2019, 09 pages.

* cited by examiner

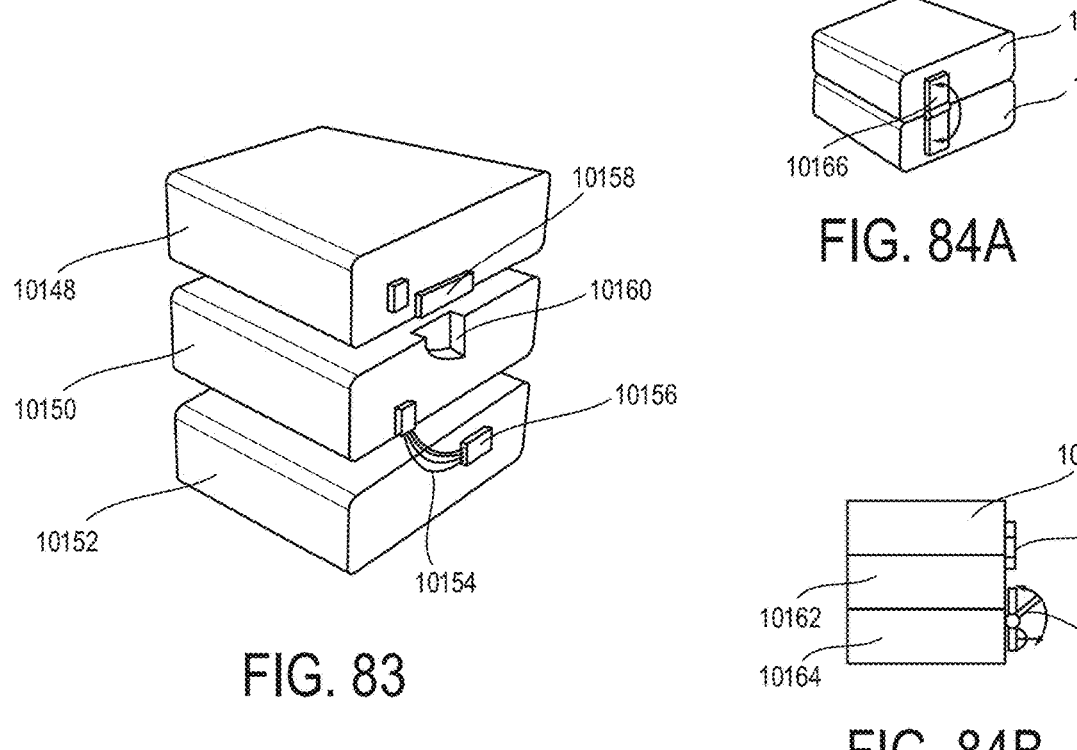
FIG. 83
FIG. 84A
FIG. 84B
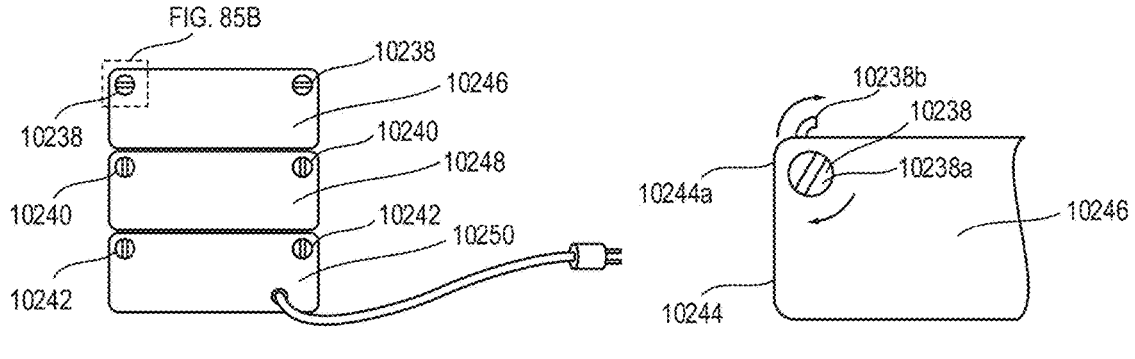
FIG. 85A
FIG. 85B

Port Receptacle and Switch Open

Port Receptacle and Switch Closed

Port Receptacle and Switch Open

Port Receptacle and Switch Closed

Port Receptacle and Inductive
Sensor Open

Port Receptacle and Inductive
Sensor Closed

17310

Carrier wave

17320

Message
wave

17330

Amplitude
modulated
wave

| Impedance (Ω) | Type of Return Pad | Description |
|---|---|---|
| 0<X<5 | Single-plated pad | Shortened return |
| 5-60 | Dual Plate Pad | Butterfly Pad, enables CQM |
| 65-75 | Ablation pad | Generator assumes impedance, uses impedance in algorithms |
| 85-95 | Patient Heating Pad | Generator loads pre-set parameters in conjunction with a patient heating pad |
| 105-115 | RD Detection Pad | Generator loads options to enable RF detection in GUI |
| 125-135 | Pediatric pad w/ Padding | Type of pad is acknowledged by system |
| 145-155 | Pediatric pad w/o Padding | Type of pad is acknowledged by system |
| 165-175 | Adult Pad w/ Padding | Type of pad is acknowledged by system |
| 185-195 | Adult Pad w/o Padding | Type of pad is acknowledged by system |

18640
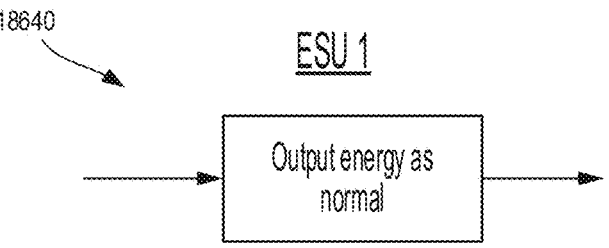
ESU 1
Output energy as normal
18642
ESU 2
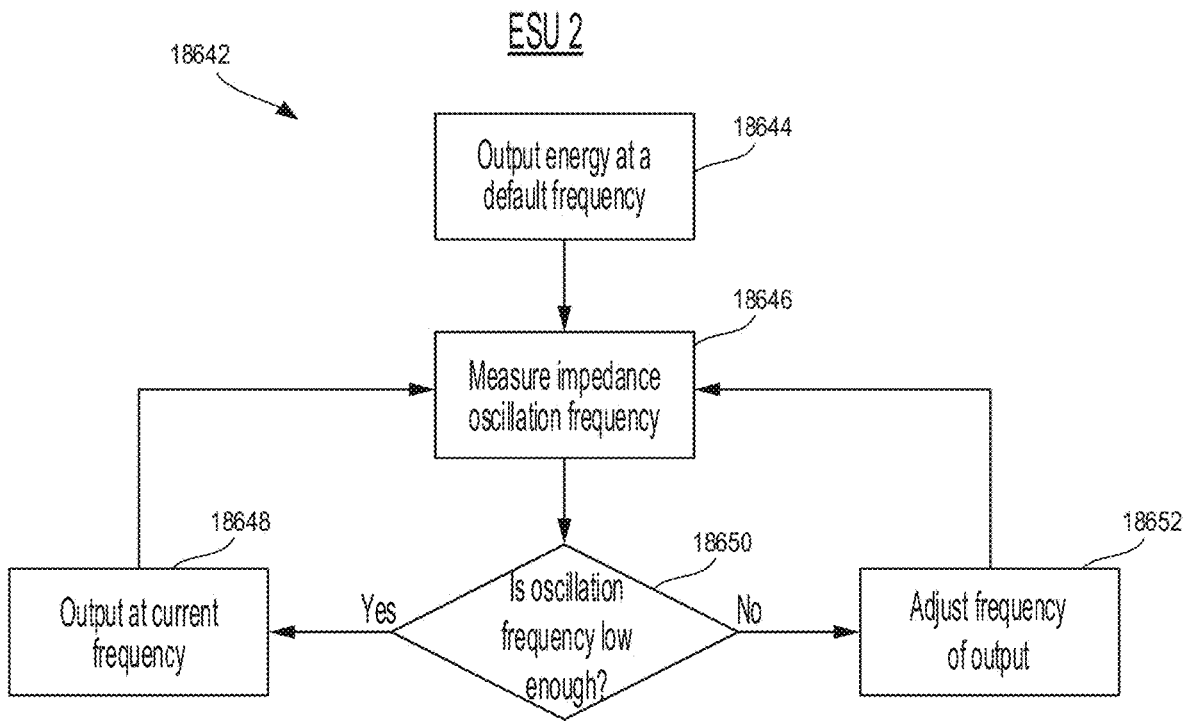
Output energy at a default frequency          18644
Measure impedance oscillation frequency          18646
18648          Output at current frequency
Yes          Is oscillation frequency low enough?          18650          No
Adjust frequency of output          18652
FIG. 158

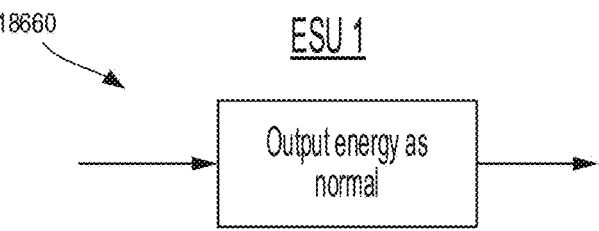
18660
ESU 1
Output energy as
normal
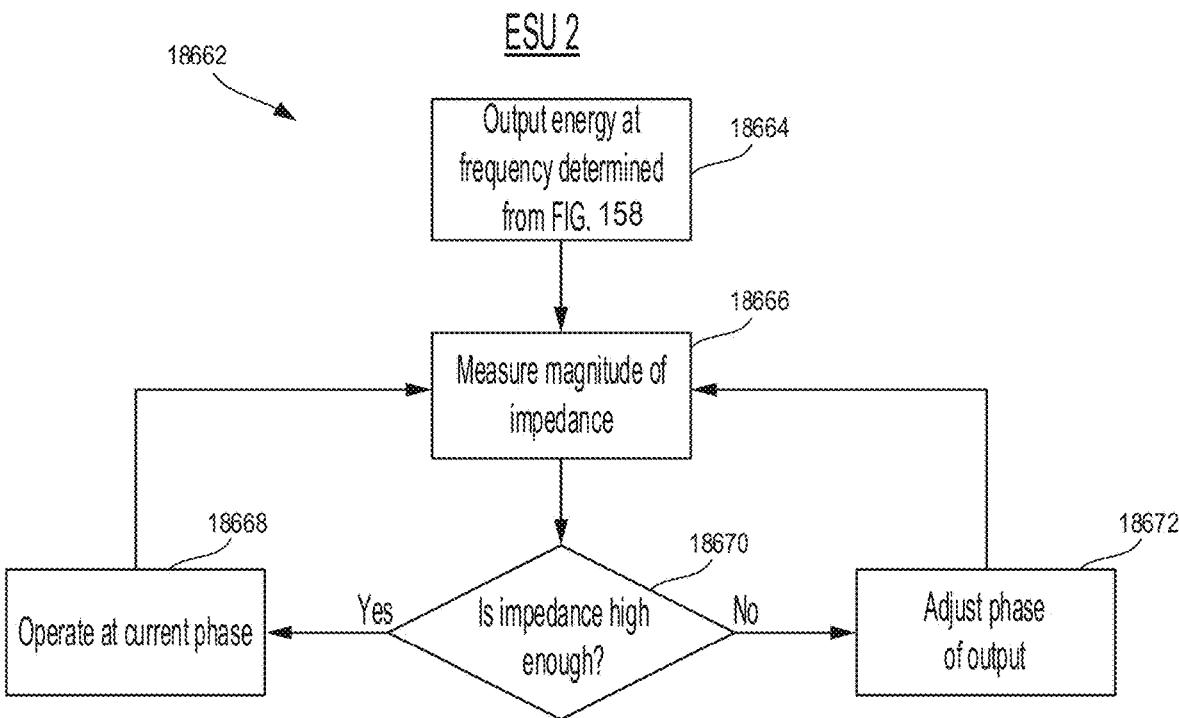
18662
ESU 2
Output energy at
frequency determined
from FIG. 158          18664
18666
Measure magnitude of
impedance
18668
Operate at current phase          Yes          Is impedance high
enough?          18670          No          Adjust phase
of output          18672
FIG. 159

Example
pulsed outputs
("Spray Coag")

18724

18722

18724

18722

ESU output

18720

• Only one ESU active at a time

• Each ESU output is equivalent to the single-ESU case

Port Receptacle and Switch Open

Port Receptacle and Switch Closed

Port Receptacle and Switch Open

Port Receptacle and Switch Closed

Port Receptacle and Inductive
Sensor Open

Port Receptacle and Inductive
Sensor Closed

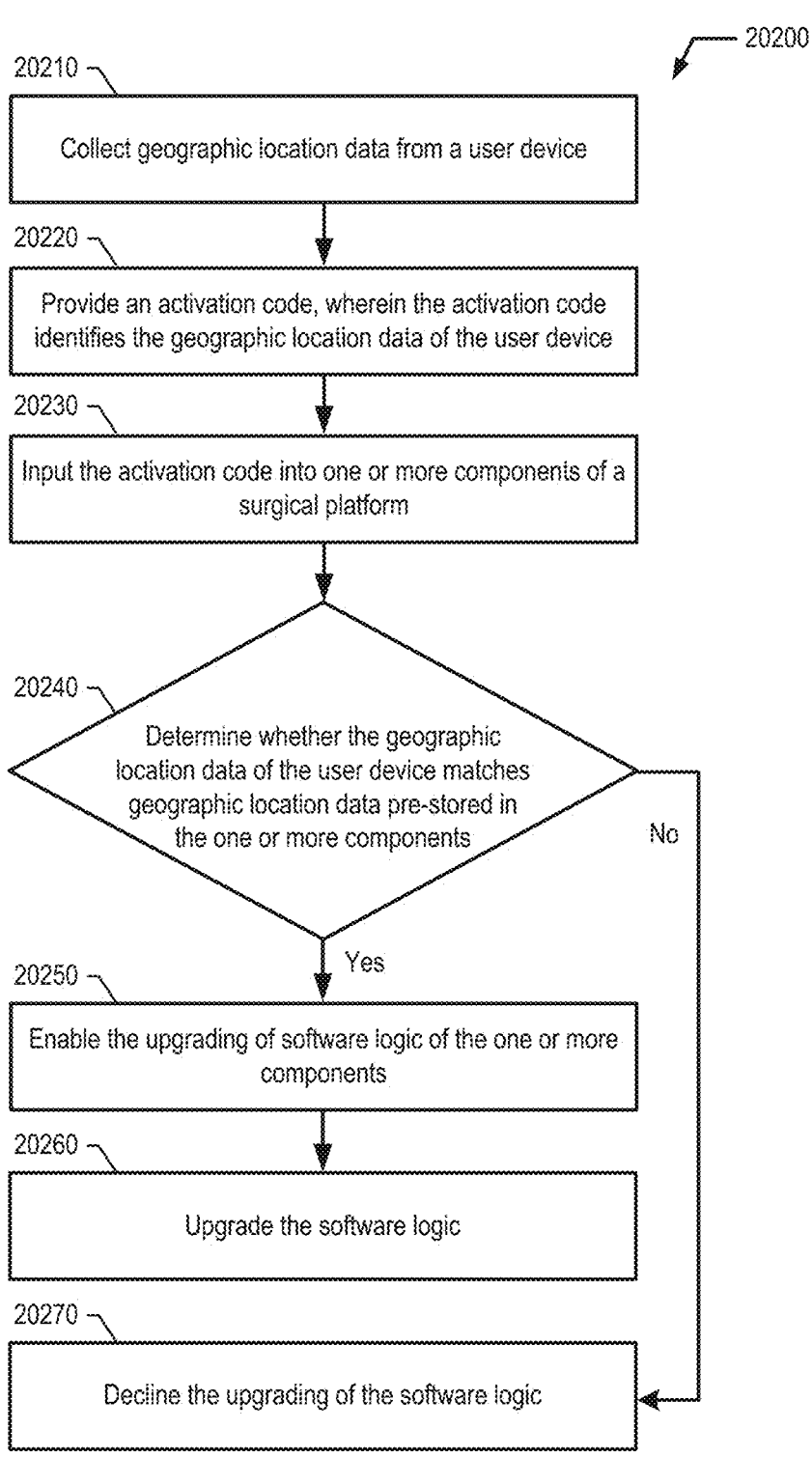

20200

20210

Collect geographic location data from a user device

20220

Provide an activation code, wherein the activation code identifies the geographic location data of the user device

20230

Input the activation code into one or more components of a surgical platform

20240

Determine whether the geographic location data of the user device matches geographic location data pre-stored in the one or more components No Yes

20250

Enable the upgrading of software logic of the one or more components

20260

Upgrade the software logic

20270

Decline the upgrading of the software logic

MODULAR SURGICAL ENERGY SYSTEM

CROSS-REFERENCE TO RELATED APPLICATIONS

The present application is a continuation application claiming priority under 35 U.S.C. § 120 to U.S. patent application Ser. No. 16/562,123, titled METHOD FOR CONSTRUCTING AND USING A MODULAR SURGICAL ENERGY SYSTEM WITH MULTIPLE DEVICES, filed Sep. 5, 2019, which issued on Jun. 6, 2023 as U.S. Pat. No. 11,666,368, the disclosure of which is herein incorporated by reference in its entirety.

U.S. patent application Ser. No. 16/562,123, which issued on Jun. 6, 2023 as U.S. Pat. No. 11,666,368, claims priority under 35 U.S.C. § 119 (e) to U.S. Provisional Patent Application Ser. No. 62/826,584, titled MODULAR SURGICAL PLATFORM ELECTRICAL ARCHITECTURE, filed Mar. 29, 2019, the disclosure of which is herein incorporated by reference in its entirety.

U.S. patent application Ser. No. 16/562,123, which issued on Jun. 6, 2023 as U.S. Pat. No. 11,666,368, claims priority under 35 U.S.C. § 119 (e) to U.S. Provisional Patent Application Ser. No. 62/826,587, titled MODULAR ENERGY SYSTEM CONNECTIVITY, filed Mar. 29, 2019, the disclosure of which is herein incorporated by reference in its entirety.

U.S. patent application Ser. No. 16/562,123, which issued on Jun. 6, 2023 as U.S. Pat. No. 11,666,368, claims priority under 35 U.S.C. § 119 (e) to U.S. Provisional Patent Application Ser. No. 62/826,588, titled MODULAR ENERGY SYSTEM INSTRUMENT COMMUNICATION TECHNIQUES, filed Mar. 29, 2019, the disclosure of which is herein incorporated by reference in its entirety.

U.S. patent application Ser. No. 16/562,123, which issued on Jun. 6, 2023 as U.S. Pat. No. 11,666,368, claims priority under 35 U.S.C. § 119 (e) to U.S. Provisional Patent Application Ser. No. 62/826,592, titled MODULAR ENERGY DELIVERY SYSTEM, filed Mar. 29, 2019, the disclosure of which is herein incorporated by reference in its entirety.

U.S. patent application Ser. No. 16/562,123, which issued on Jun. 6, 2023 as U.S. Pat. No. 11,666,368, claims priority under 35 U.S.C. § 119 (e) to U.S. Provisional Patent Application Ser. No. 62/728,480, titled MODULAR ENERGY SYSTEM AND USER INTERFACE, filed Sep. 7, 2018, the disclosure of which is herein incorporated by reference in its entirety.

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In various instances, a method for constructing a modular surgical system is disclosed. The method comprises providing a header module comprising a first power backplane segment, providing a surgical module comprising a second power backplane segment, assembling the header module and the surgical module to electrically couple the first power backplane segment and the second power backplane segment to each other to form a power backplane, and applying power to the surgical module through the power backplane.

FIGURES

The various aspects described herein, both as to organization and methods of operation, together with further objects and advantages thereof, may best be understood by reference to the following description, taken in conjunction with the accompanying drawings as follows.

FIG. 83 illustrates a modular energy system comprising a latch, in accordance with at least one aspect of the present disclosure.

FIG. 84A illustrates a modular energy system comprising a latch assembly, in accordance with at least one aspect of the present disclosure.

FIG. 84B illustrates a side view of the modular energy system of FIG. 84A.

FIG. 85A illustrates a modular energy system comprising a latch assembly, in accordance with at least one aspect of the present disclosure.

FIG. 85B illustrates a detail view of the modular energy system of FIG. 85A.

FIG. 127A depicts the magnetic device presence identification system in an unplugged state and FIG. 127B depicts the magnetic device presence identification system in a plugged state.

FIG. 128A depicts the depressible switch in an open configuration and FIG. 128B depicts the depressible switch in a closed configuration.

FIG. 129A depicts the push button switch in an open configuration and FIG. 129B depicts the push button switch in a closed configuration.

FIG. 130A depicts the non-contact proximity switch in an open configuration and FIG. 130B depicts the non-contact proximity switch in a closed configuration.

FIGS. 131A-134 illustrate a communication arrangement comprising a primary protocol and a secondary protocol synchronized to the primary protocol for communicating with and driving a primary device and secondary devices through a single port of an energy module, in accordance with at least one aspect of the present disclosure, where:

FIG. 131A illustrates a timing diagram of a primary communication frame and a secondary communications frame during a prefetch command, in accordance with at least one aspect of the present disclosure;

FIG. 132 illustrates a timing diagram of the primary communication frame and a secondary communications frame during a reset command, in accordance with at least one aspect of the present disclosure;

Figure 133:
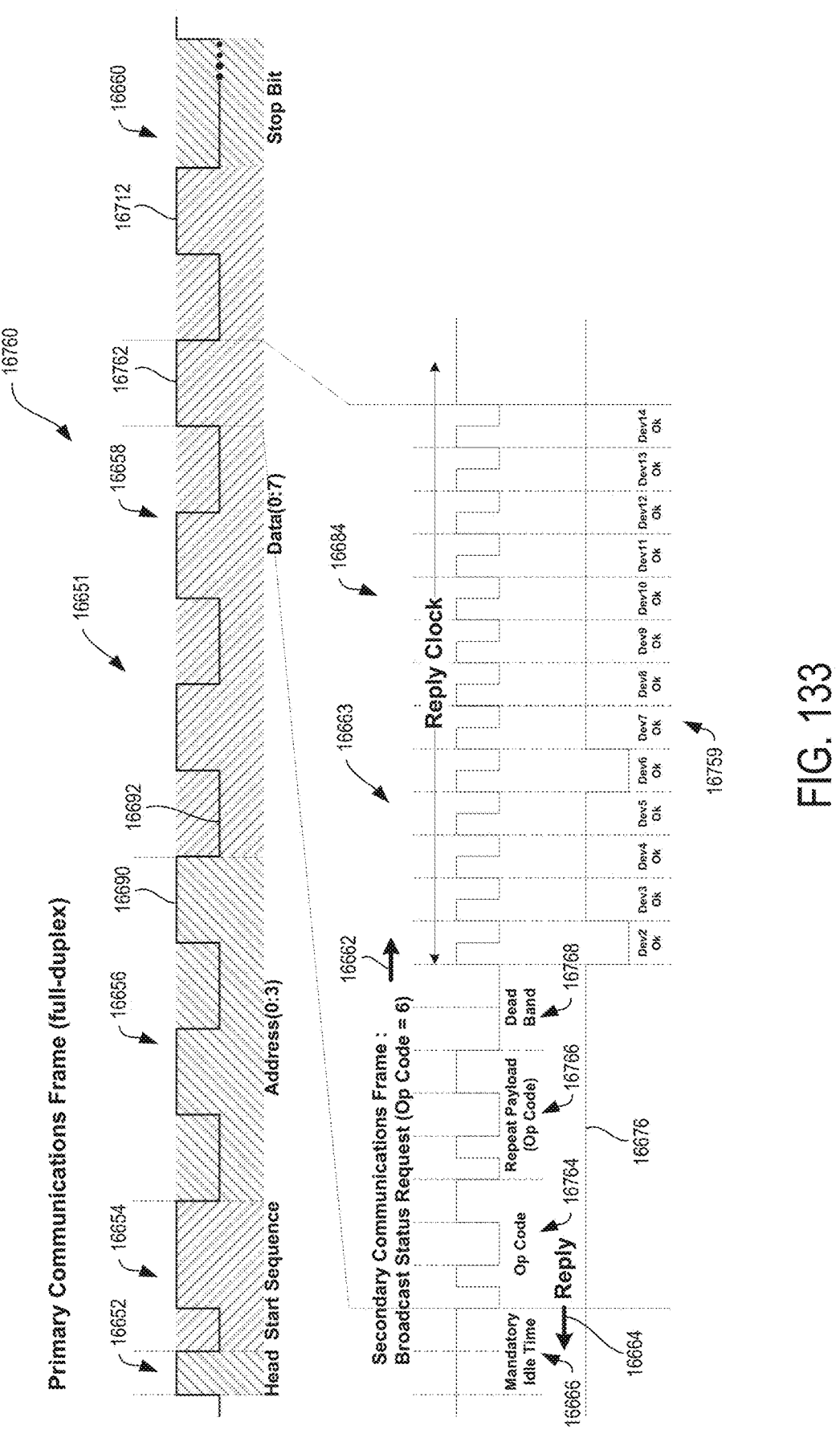
Figure 134:
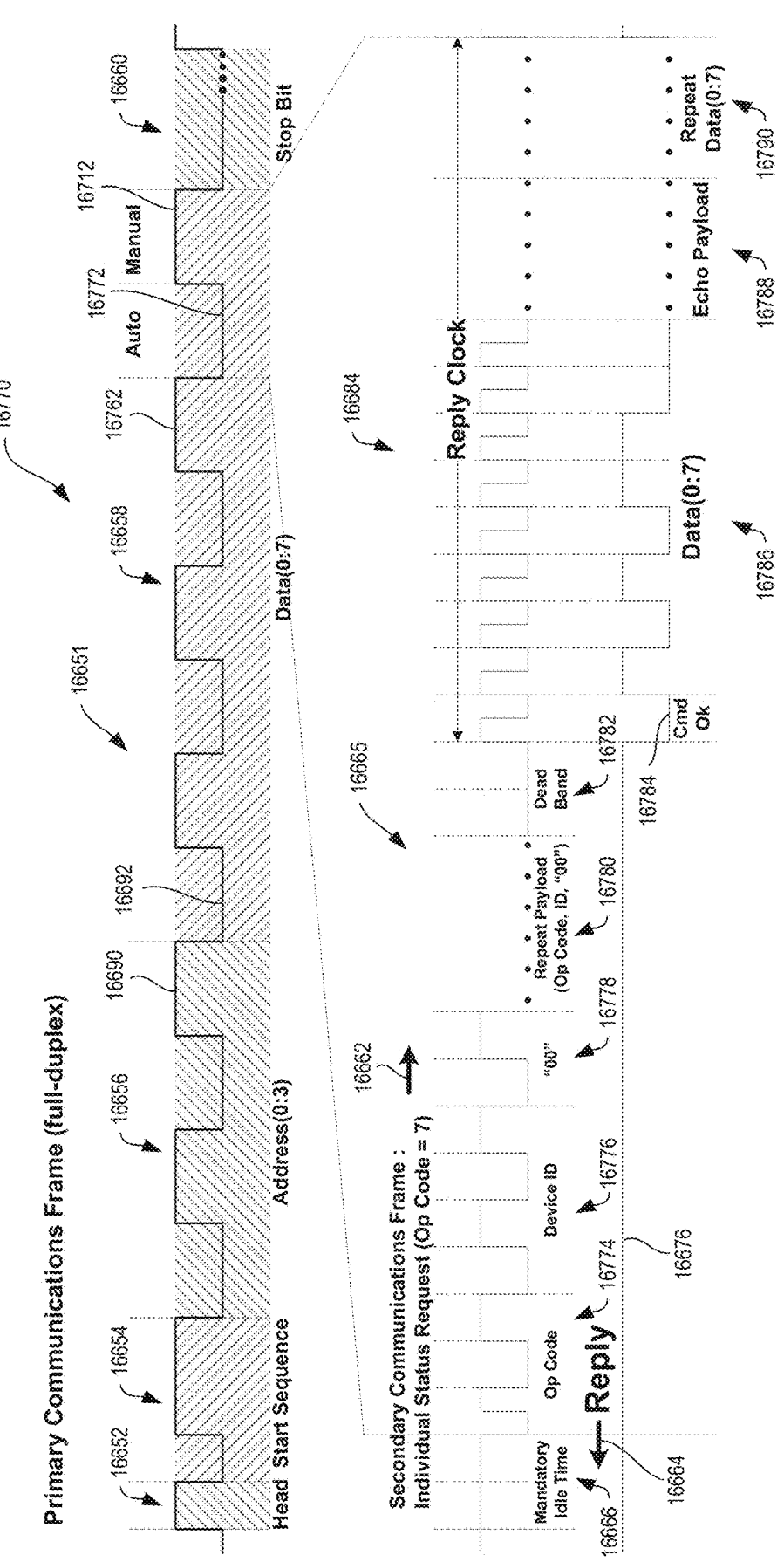

FIG. 133 illustrates a timing diagram of the primary communication frame and a secondary communications frame during a broadcast status request command, in accordance with at least one aspect of the present disclosure; and FIG. 134 illustrates a timing diagram of the primary communication frame and a secondary communications frame during an individual status request command, in accordance with at least one aspect of the present disclosure.

Figure 135:
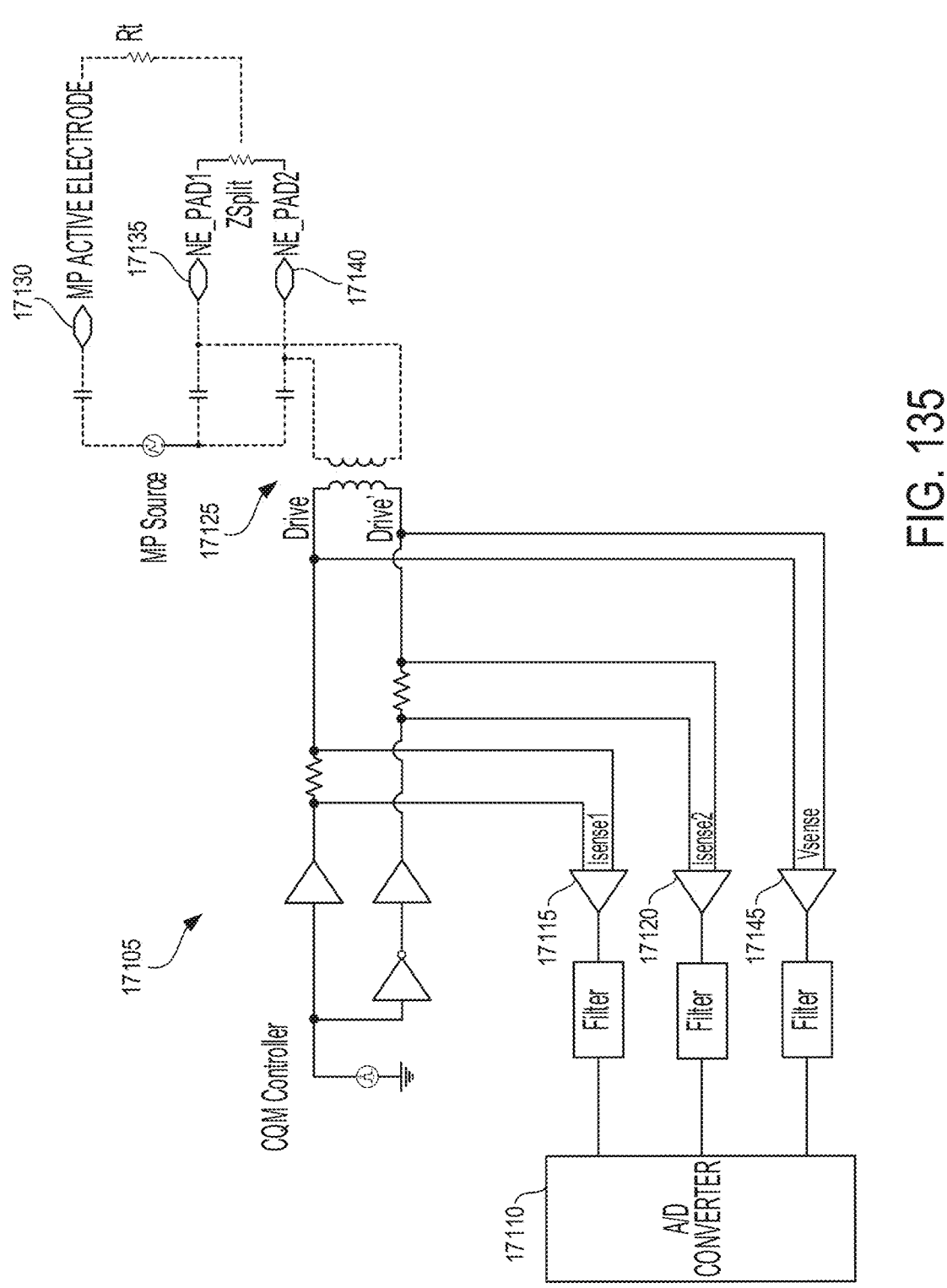

FIG. 135 shows an example circuit diagram illustrating several features about a CQM controller design for how contact quality monitoring may be used to identify a return pad, in accordance with at least one aspect of the present disclosure.

Figure 136:
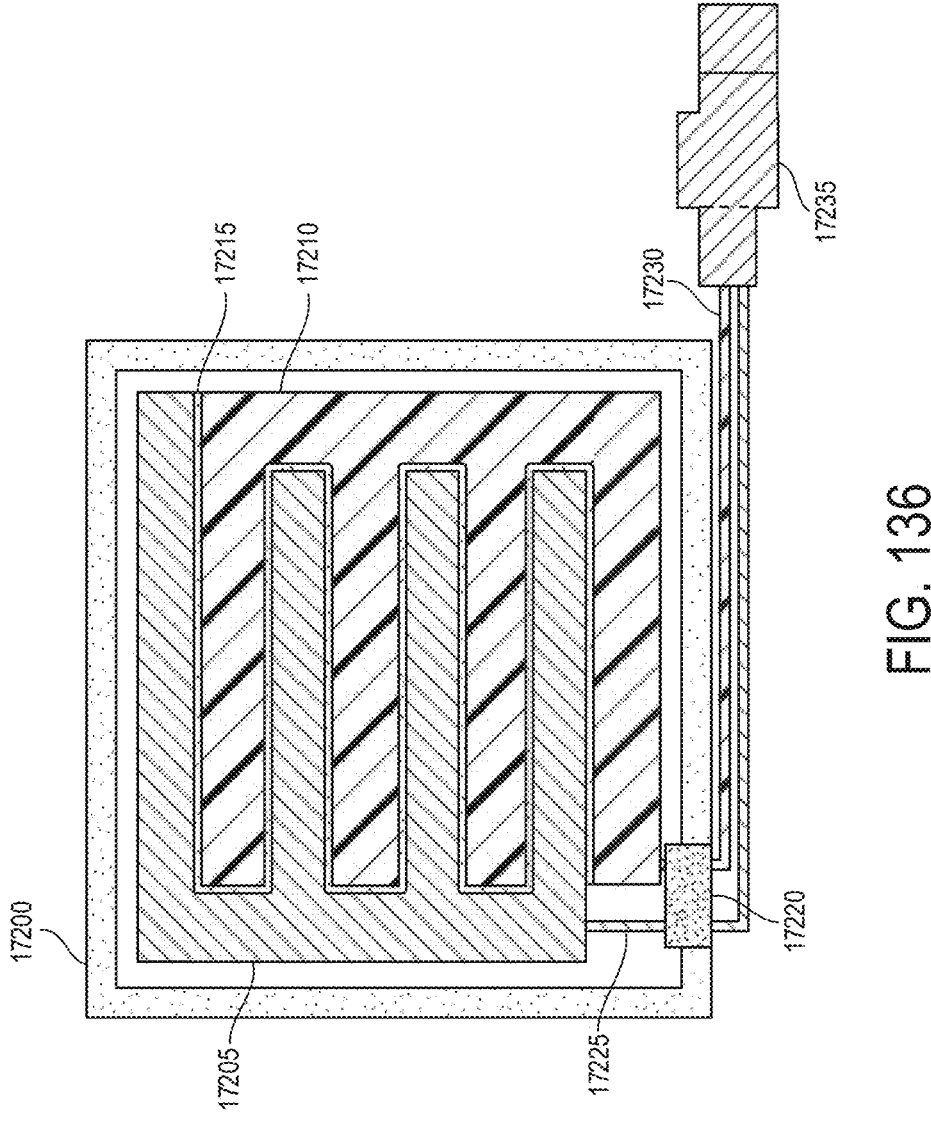

FIG. 136 shows an example design layout of a return pad configured to facilitate its identification using a pre-configured non-zero impedance, in accordance with at least one aspect of the present disclosure.

Figure 121:
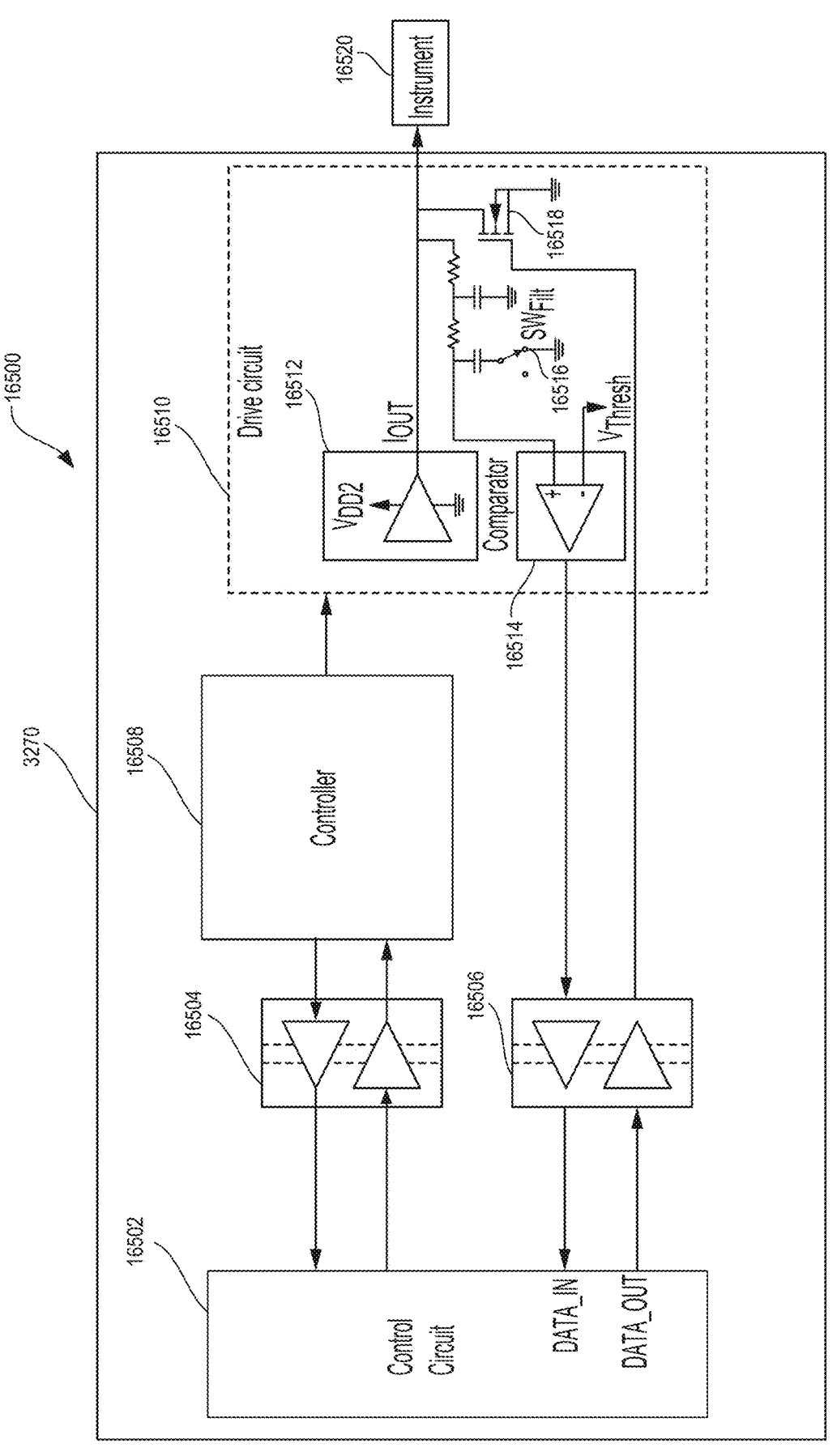
FIG. 121 is a schematic diagram of a communication circuit including a configurable current source circuit to implement multiple communication protocols, in accordance with at least one aspect of the present disclosure.
Figure 137:
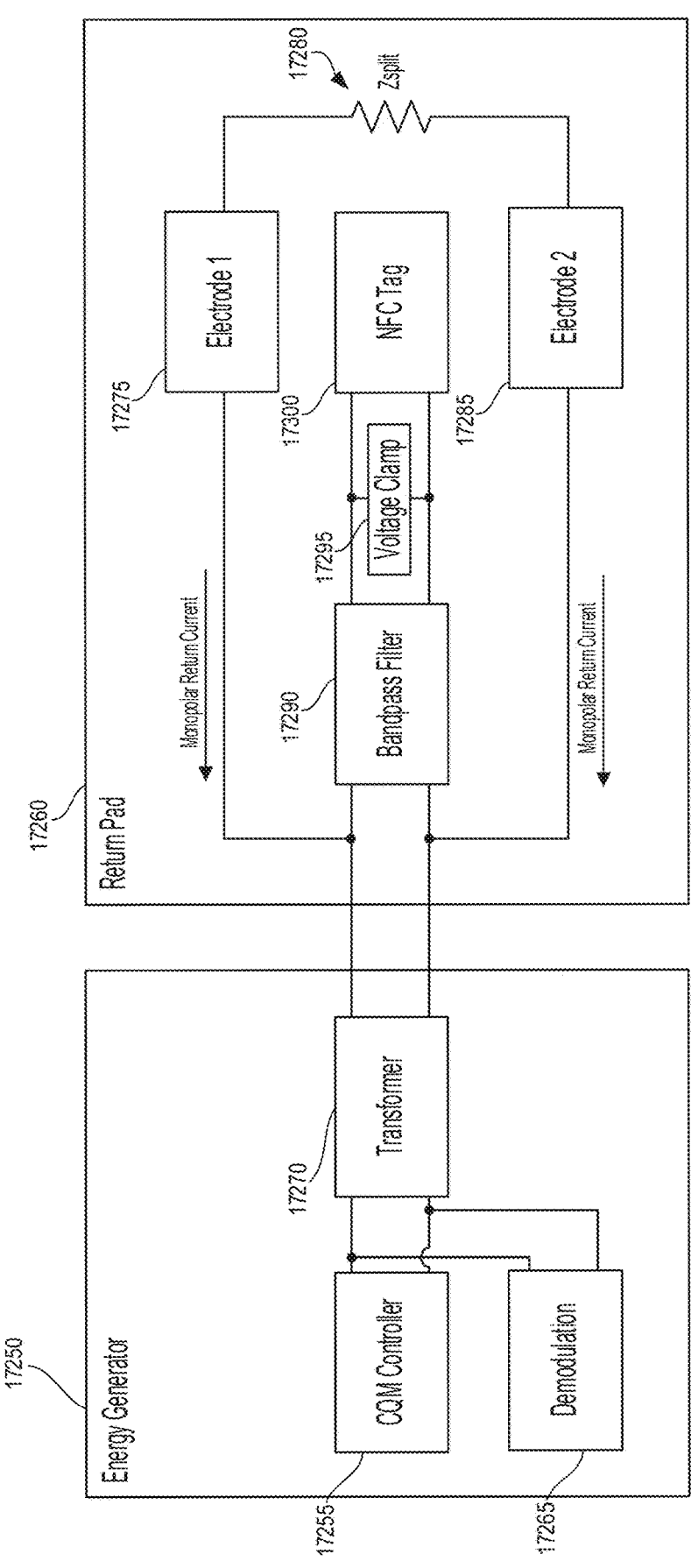

FIG. 137 shows a block diagram with structures similar to FIG. 121 that also include means for identifying the return pad using NFC signals, in accordance with at least one aspect of the present disclosure.

Figure 138:
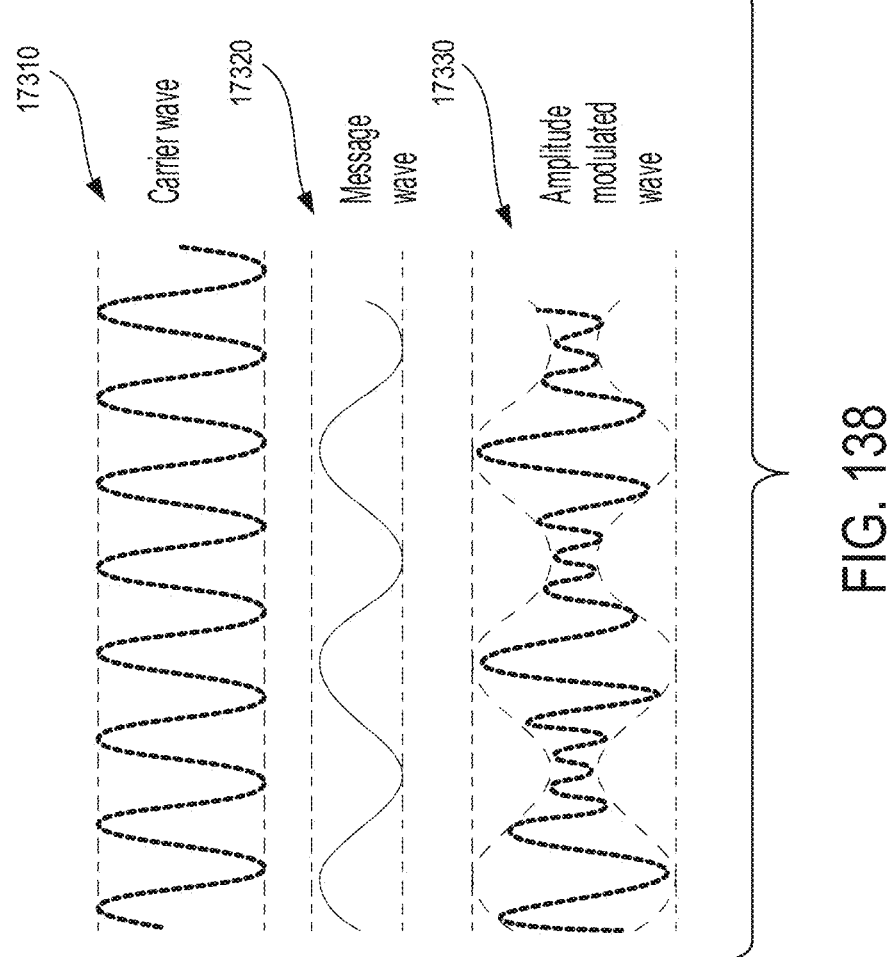

FIG. 138 an example of how two signals may be combined to be processed by the CQM controller, in accordance with at least one aspect of the present disclosure.

FIG. 139 provides an example designation of types of return pads that may be categorized based on different impedance measurements, in accordance with at least one aspect of the present disclosure.

Figure 140:

FIG. 140 shows an example time series of a message channel used for time-domain multiplexing the different types of signals between the energy generator and the return pad, in accordance with at least one aspect of the present disclosure.

Figure 141:
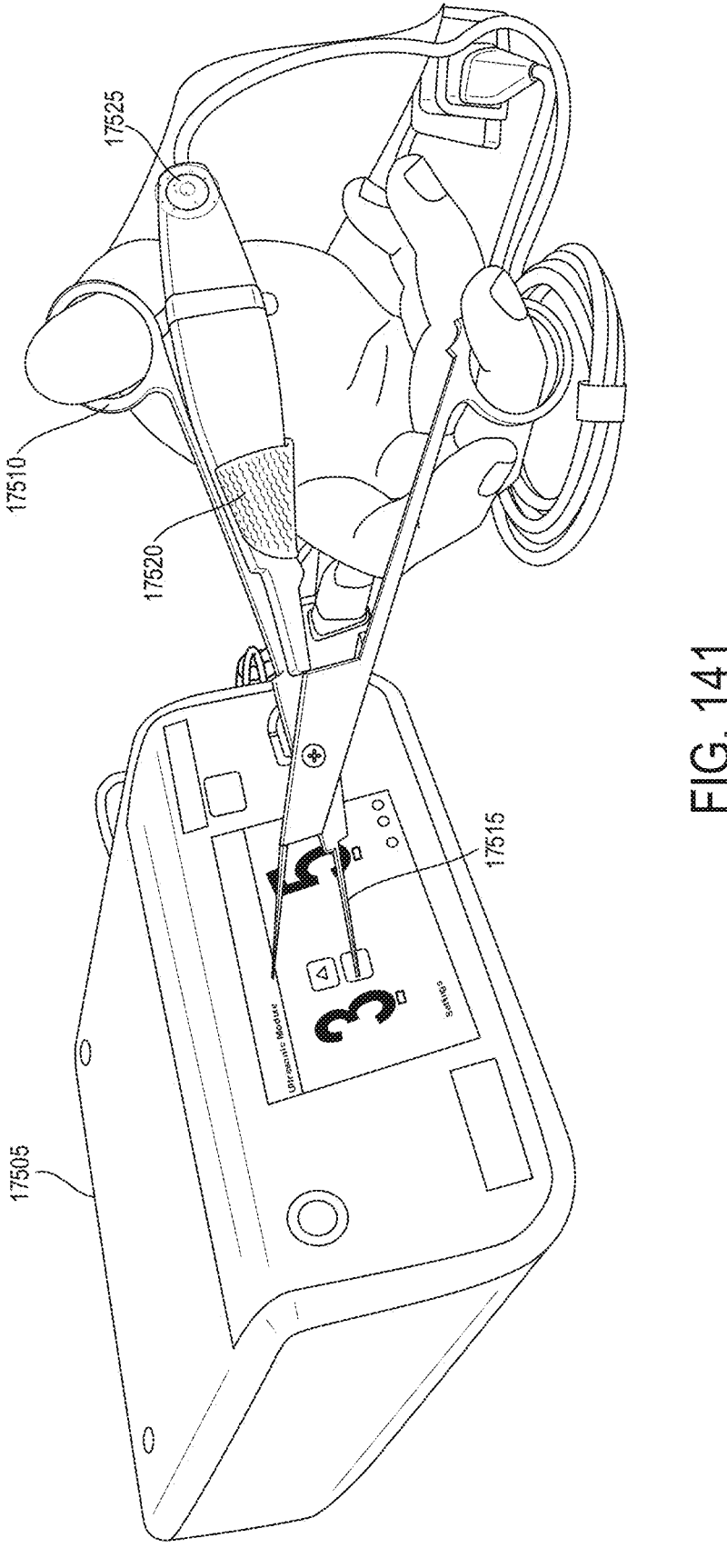

FIG. 141 shows an illustration of an example implementation of automatic ultrasonic activation of a surgical device, in accordance with at least one aspect of the present disclosure.

Figure 142:
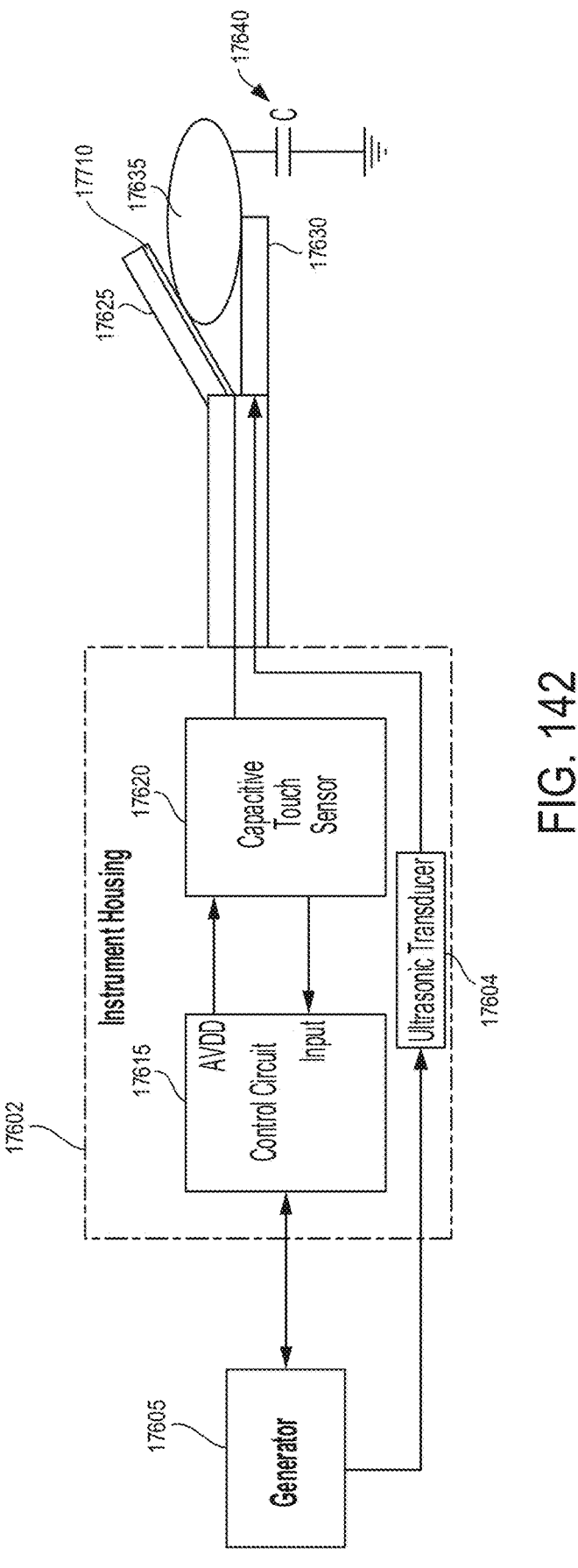

FIG. 142 shows a block diagram illustration of various components of an instrument with automatic activation capabilities using a capacitive touch sensor, in accordance with at least one aspect of the present disclosure.

Figure 143:
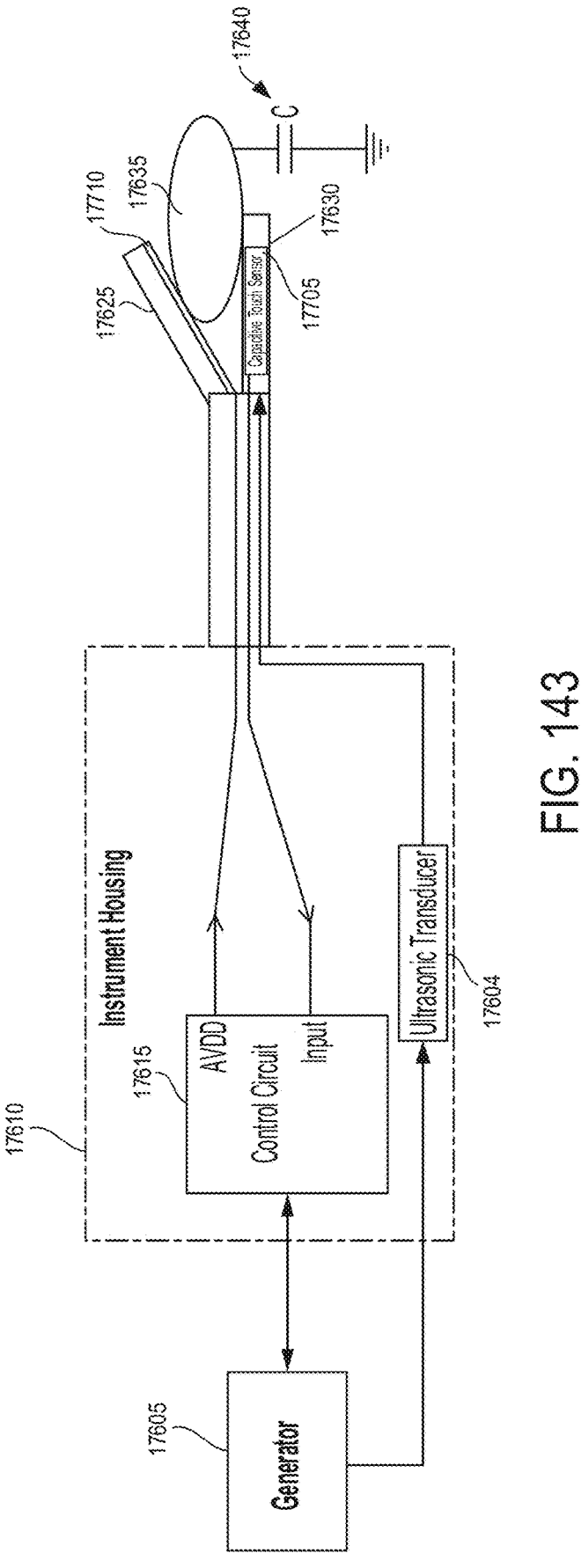

FIG. 143 shows another variant of the instrument having automatic ultrasonic activation with the capacitive touch sensor positioned at the end effector, in accordance with at least one aspect of the present disclosure.

Figure 144:
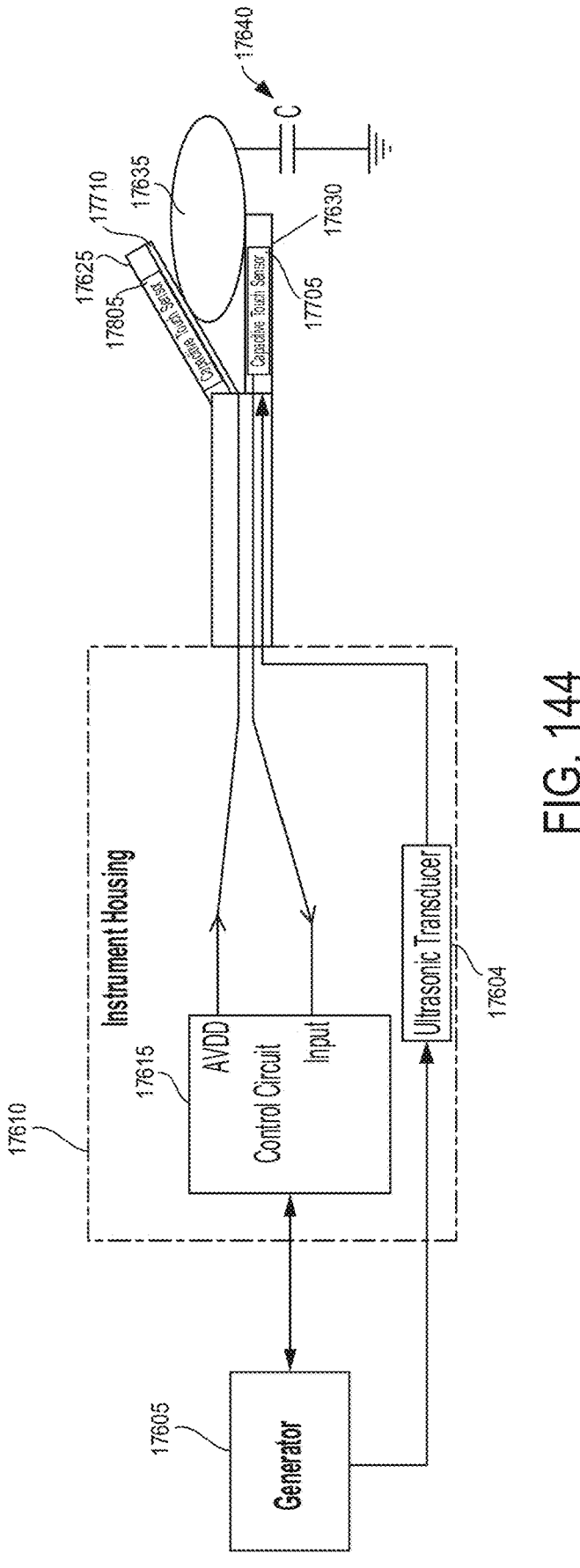

FIG. 144 shows in another variant of the surgical instrument, a pair of capacitive touch sensors configured to register some capacitive reading simultaneously in order for the therapeutic energy to automatically activate, in accordance with at least one aspect of the present disclosure.

Figure 145:
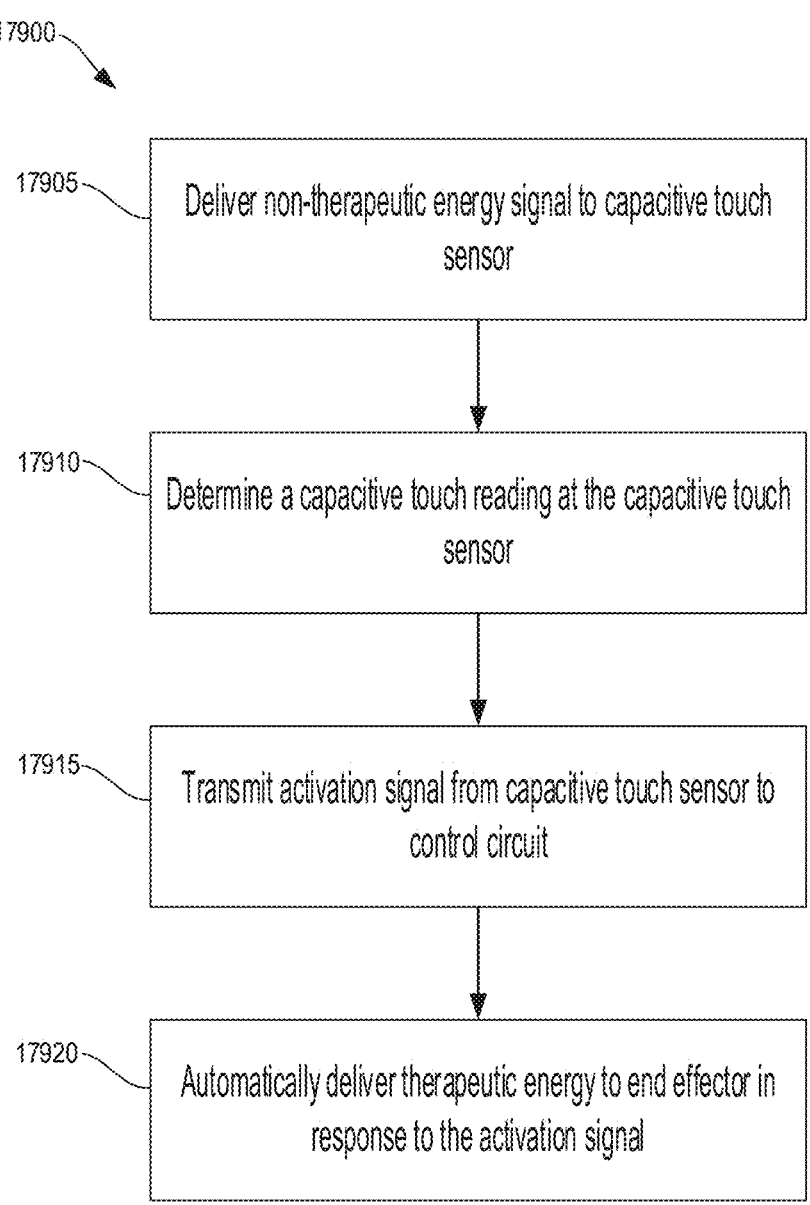

FIG. 145 is a logic diagram of a process depicting a control program or a logic configuration for automatically activating therapeutic ultrasonic energy by an instrument, in accordance with at least one aspect of the present disclosure.

Figure 146:
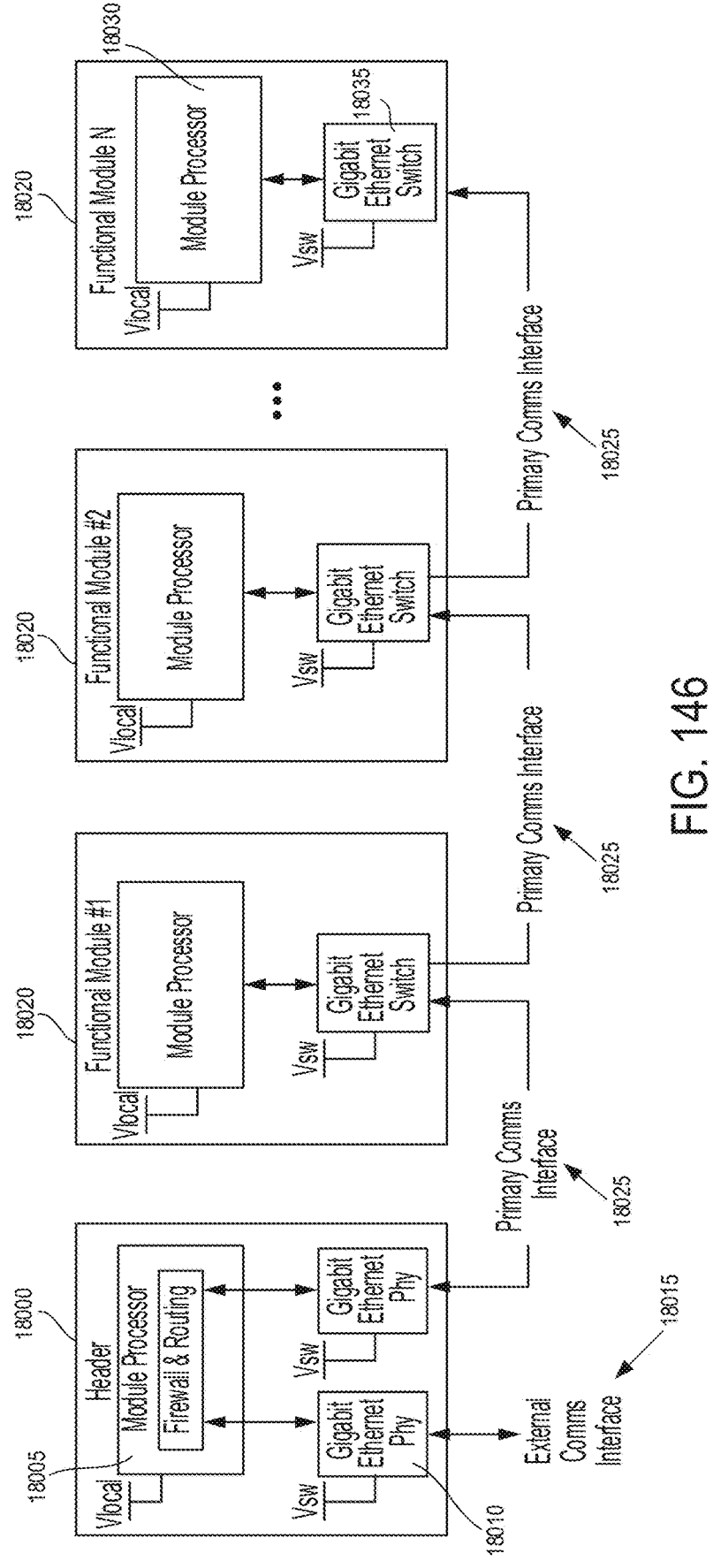

FIG. 146 shows an example block diagram of multiple modules that may be connected together that include communications interfaces that allow for coordinated energy output between multiple modules, in accordance with at least one aspect of the present disclosure.

Figure 147A:
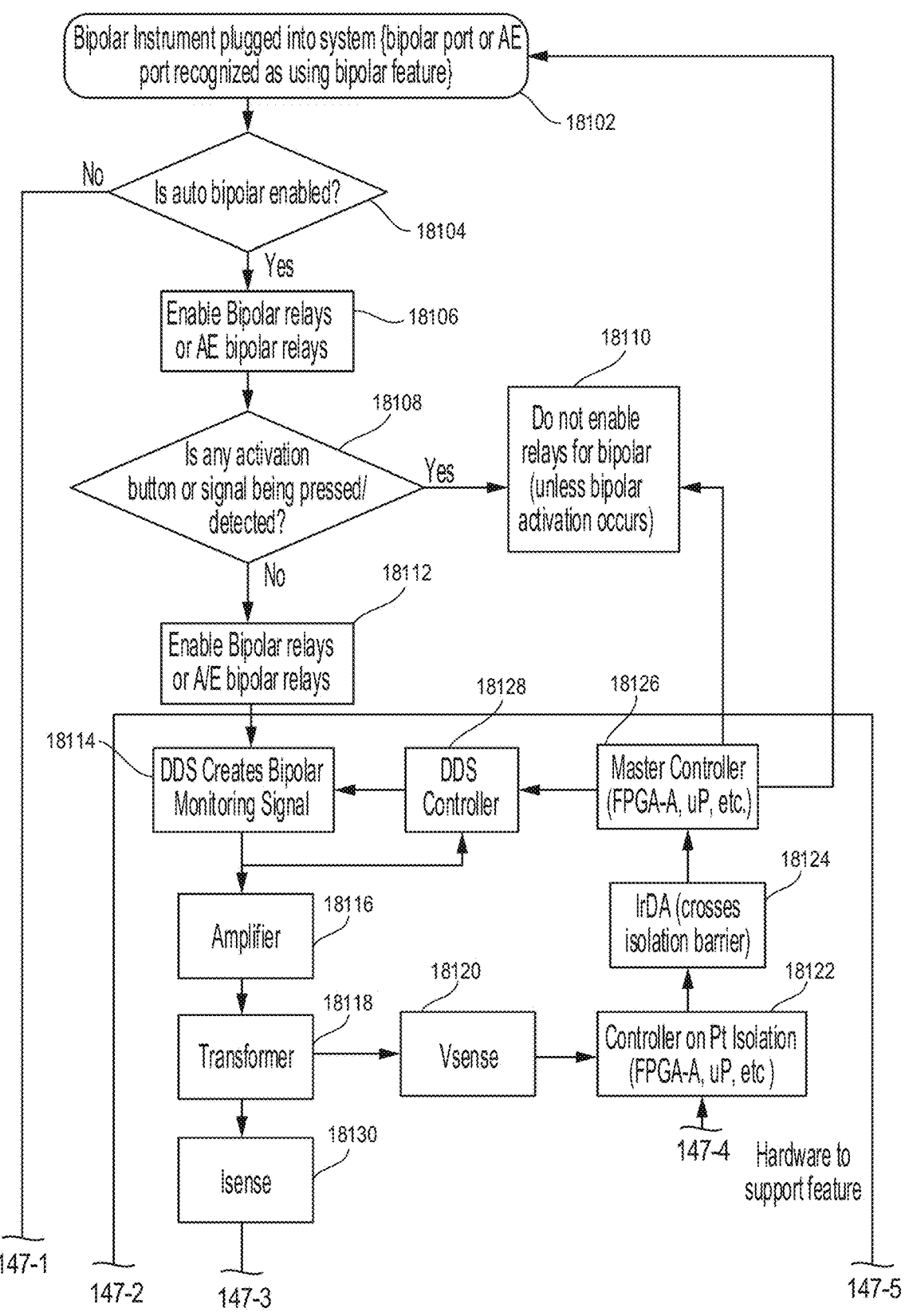
Figure 147B:
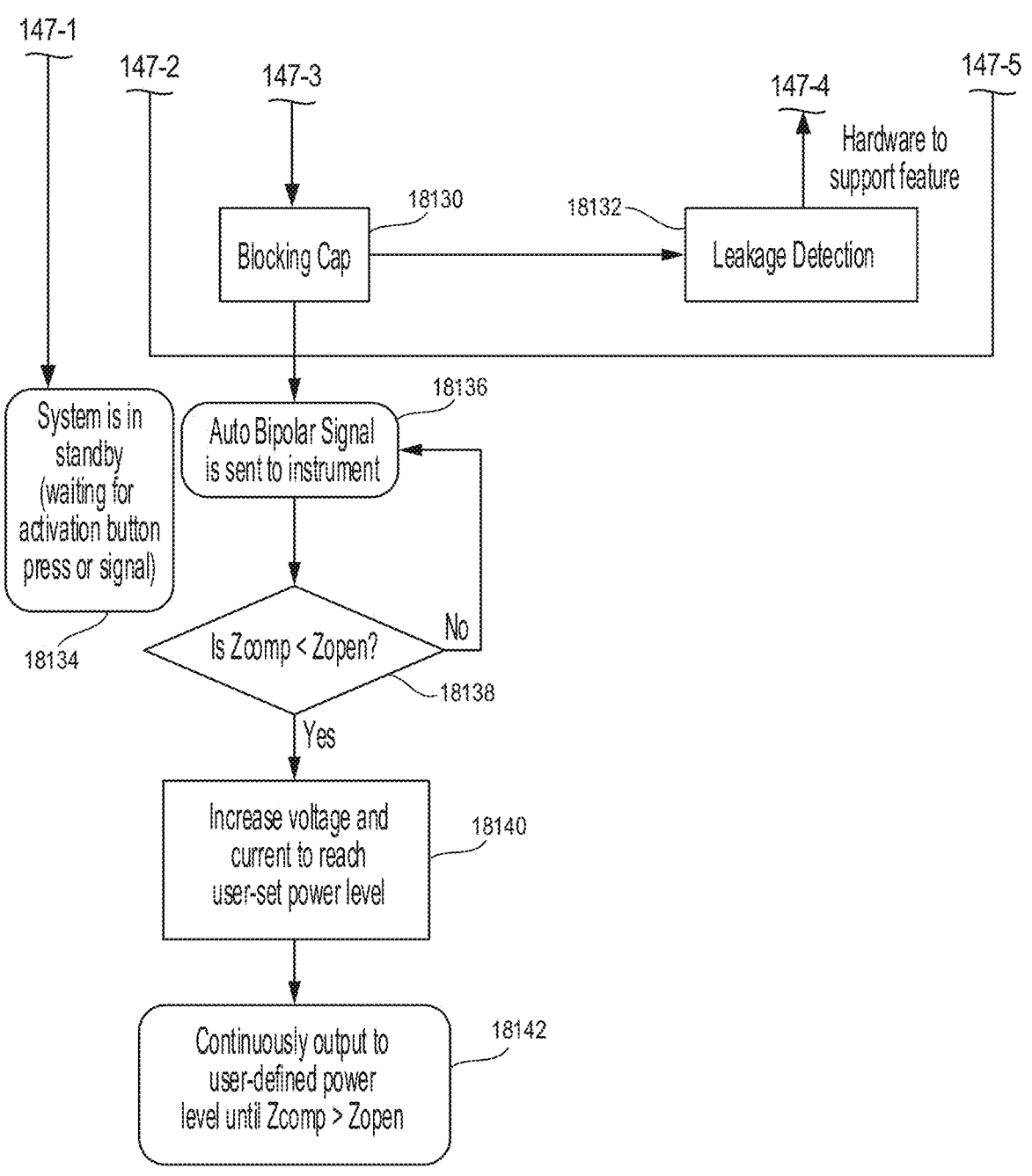

FIGS. 147A and 147B show an example logic diagram of a process depicting a control program or a logic configuration for automatically activating a bipolar surgical system in one or more of the modular systems using the Data Distribution Service standard, in accordance with at least one aspect of the present disclosure.

Figure 148A:
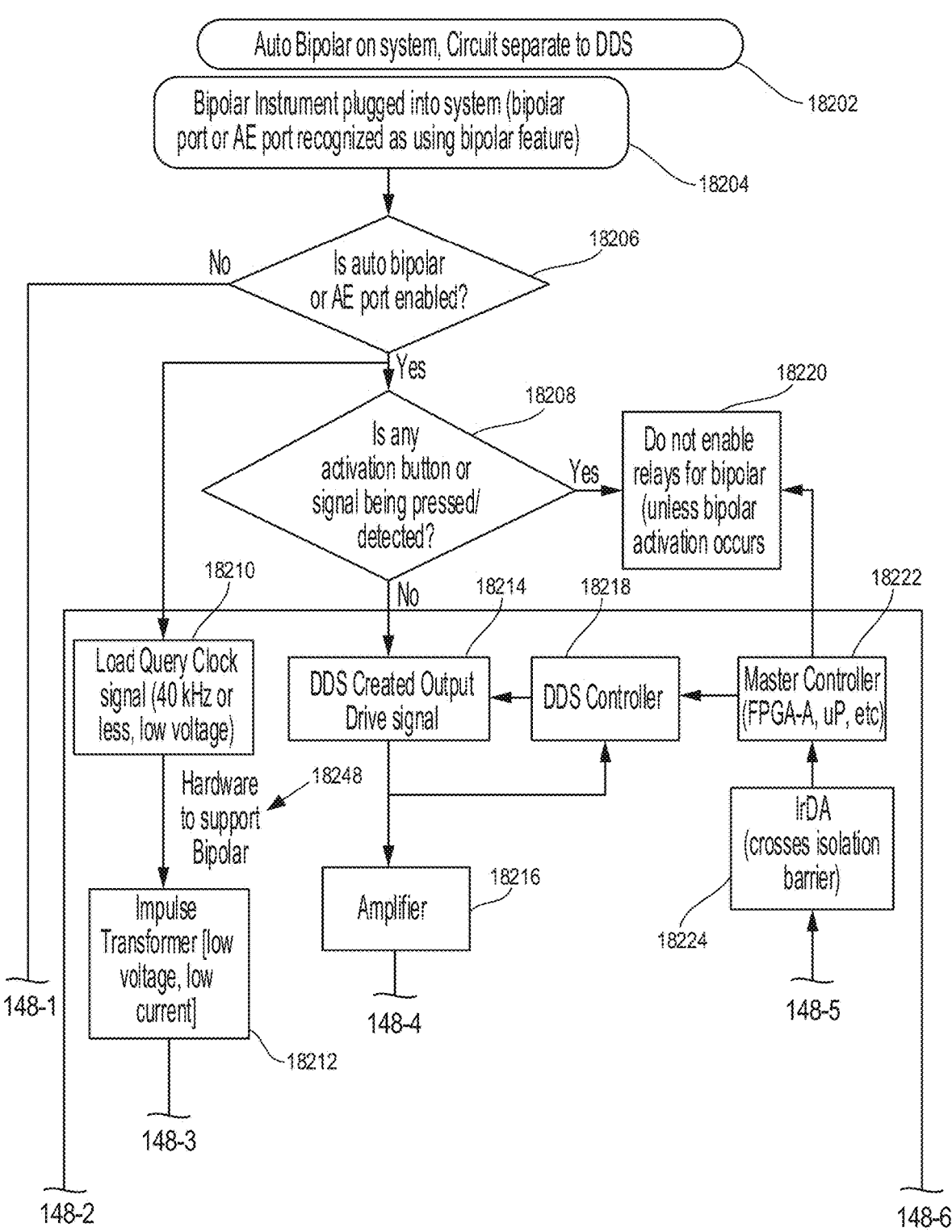
Figure 148B:
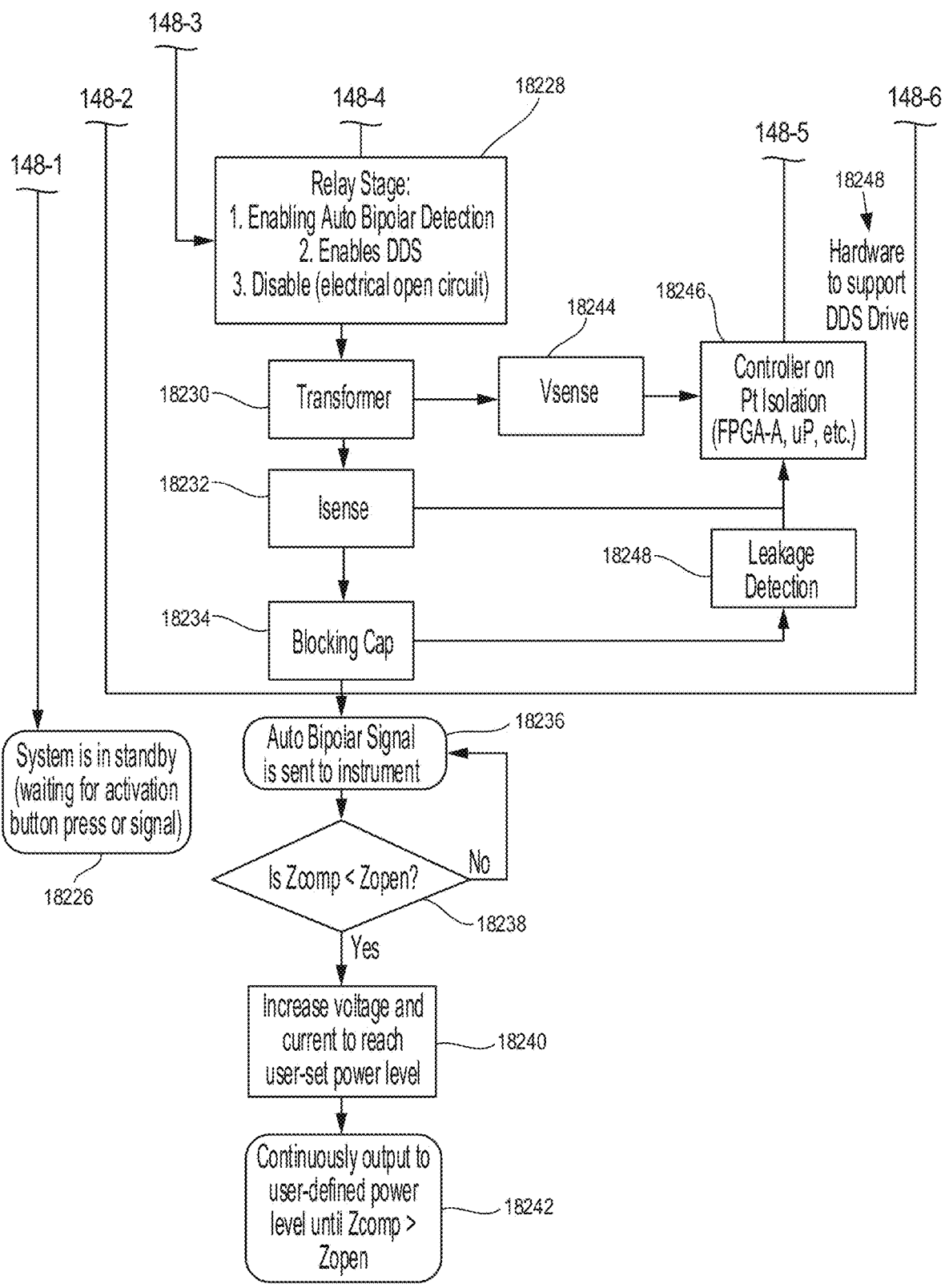

FIGS. 148A and 148B show an example logic diagram of a process depicting a control program or a logic configuration for automatically activating a bipolar surgical system in one or more of the modular systems when hardware to implement the Data Distribution Service is separate from the overall system, in accordance with at least one aspect of the present disclosure.

Figure 149:
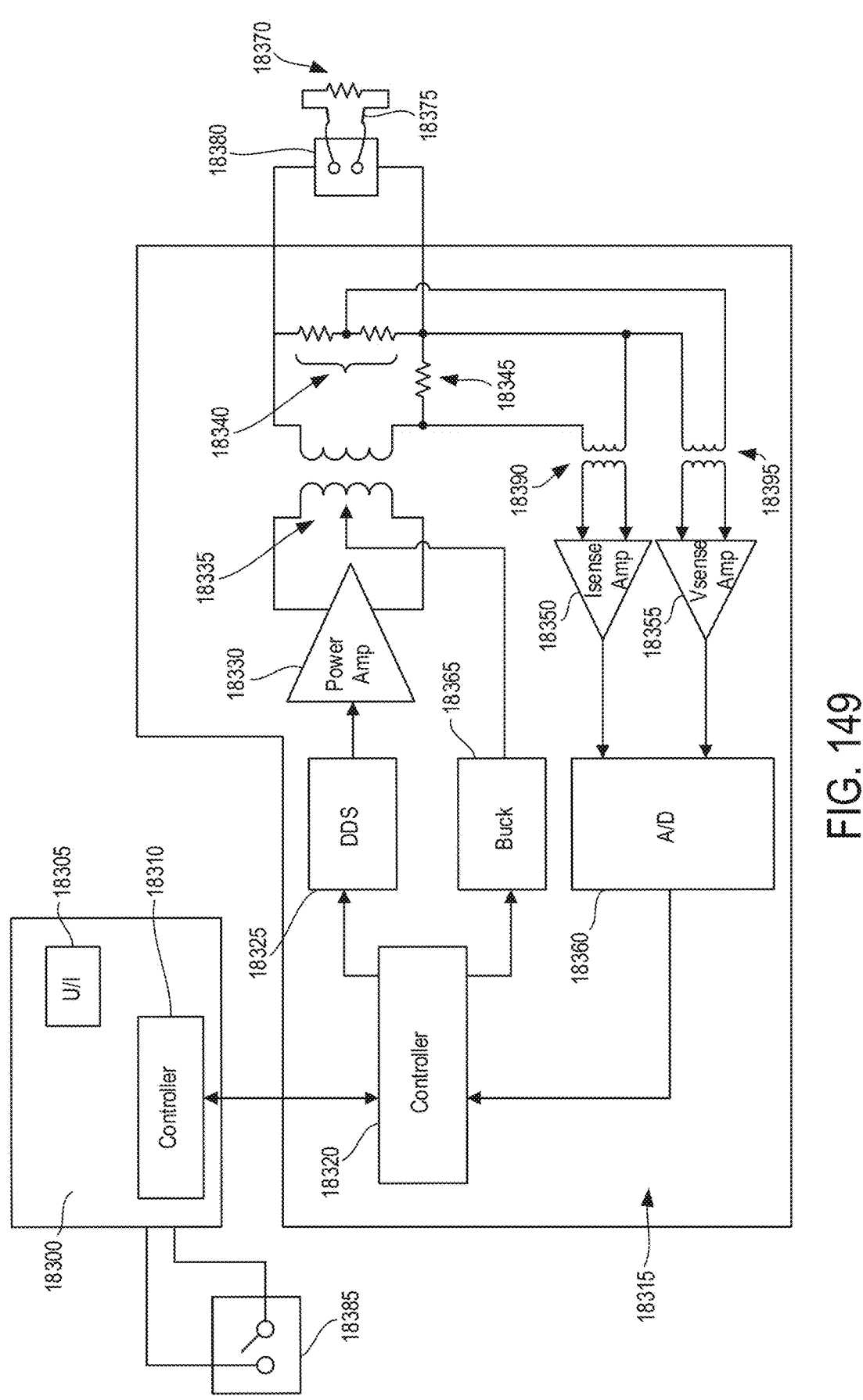

FIG. 149 shows an example diagram of circuit components in a system for conducting automatic activation of a bipolar instrument, in accordance with at least one aspect of the present disclosure.

Figure 150:
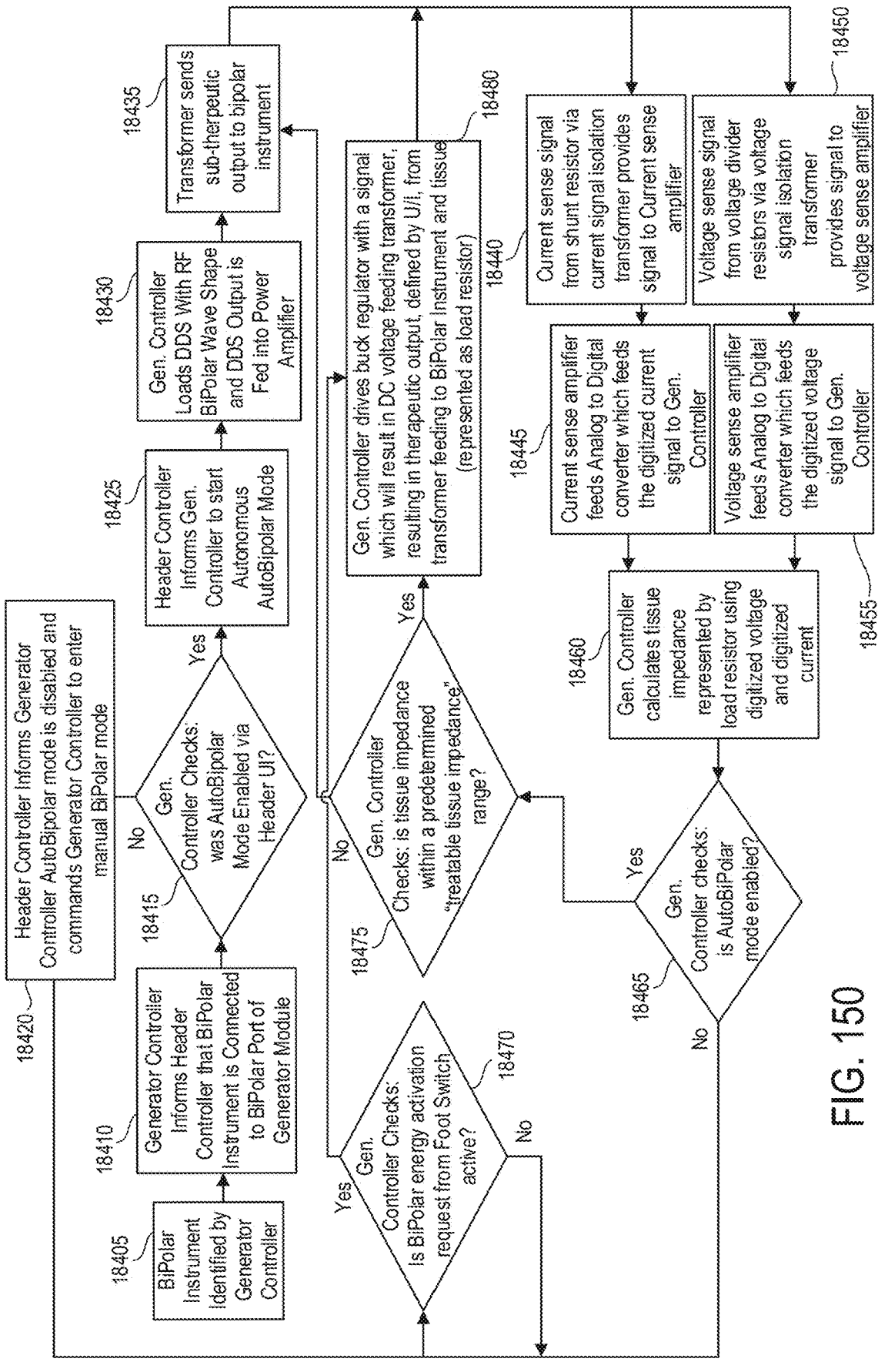

FIG. 150 shows a logic diagram of a process depicting a control program or a logic configuration for conducting automatic bipolar activation in a bipolar instrument, in accordance with at least one aspect of the present disclosure.

Figure 151:
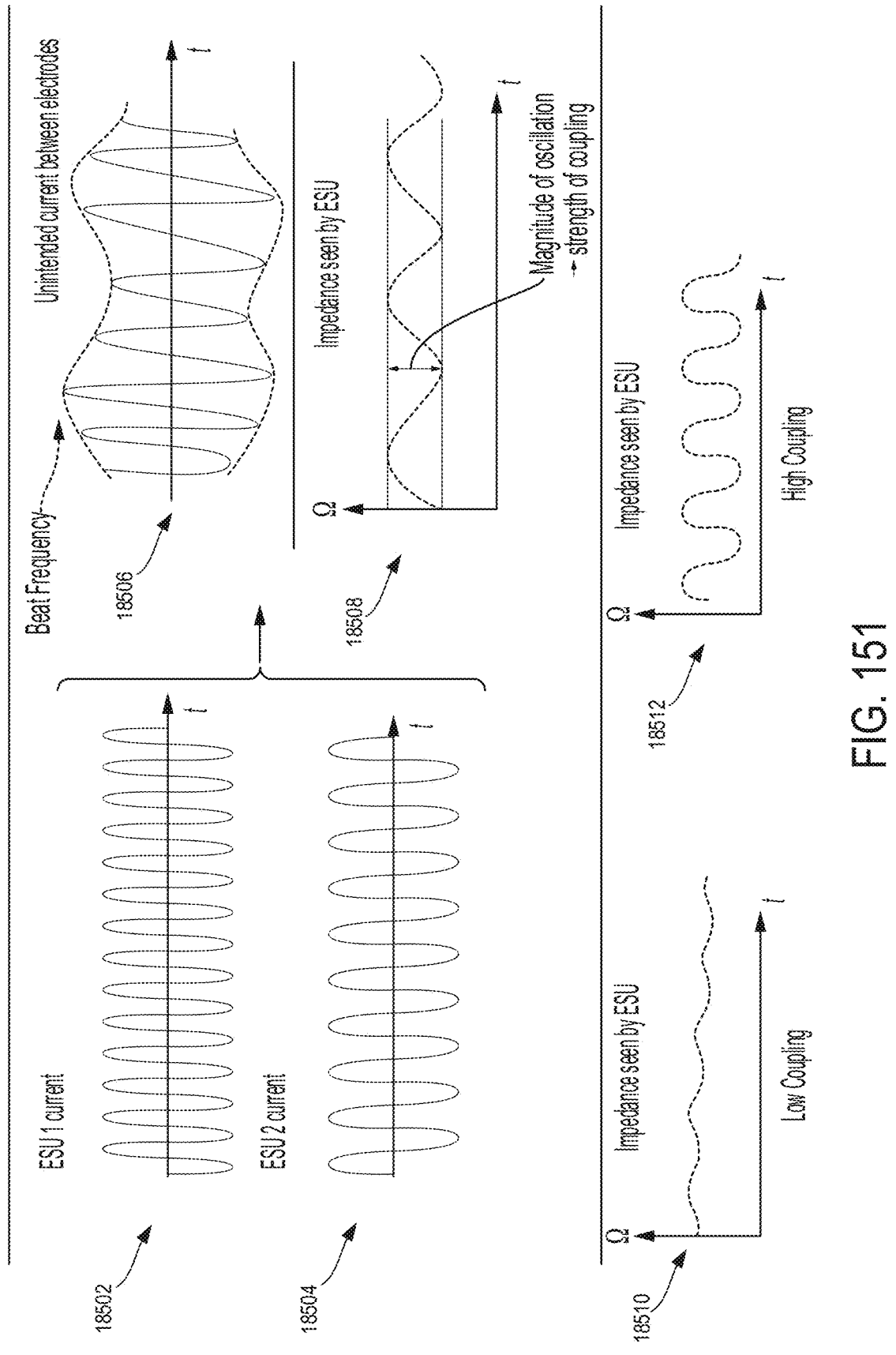

FIG. 151 shows a set of graphs that present one problem with utilizing two monopolar surgical instruments on the same patient, in accordance with at least one aspect of the present disclosure.

Figure 152:
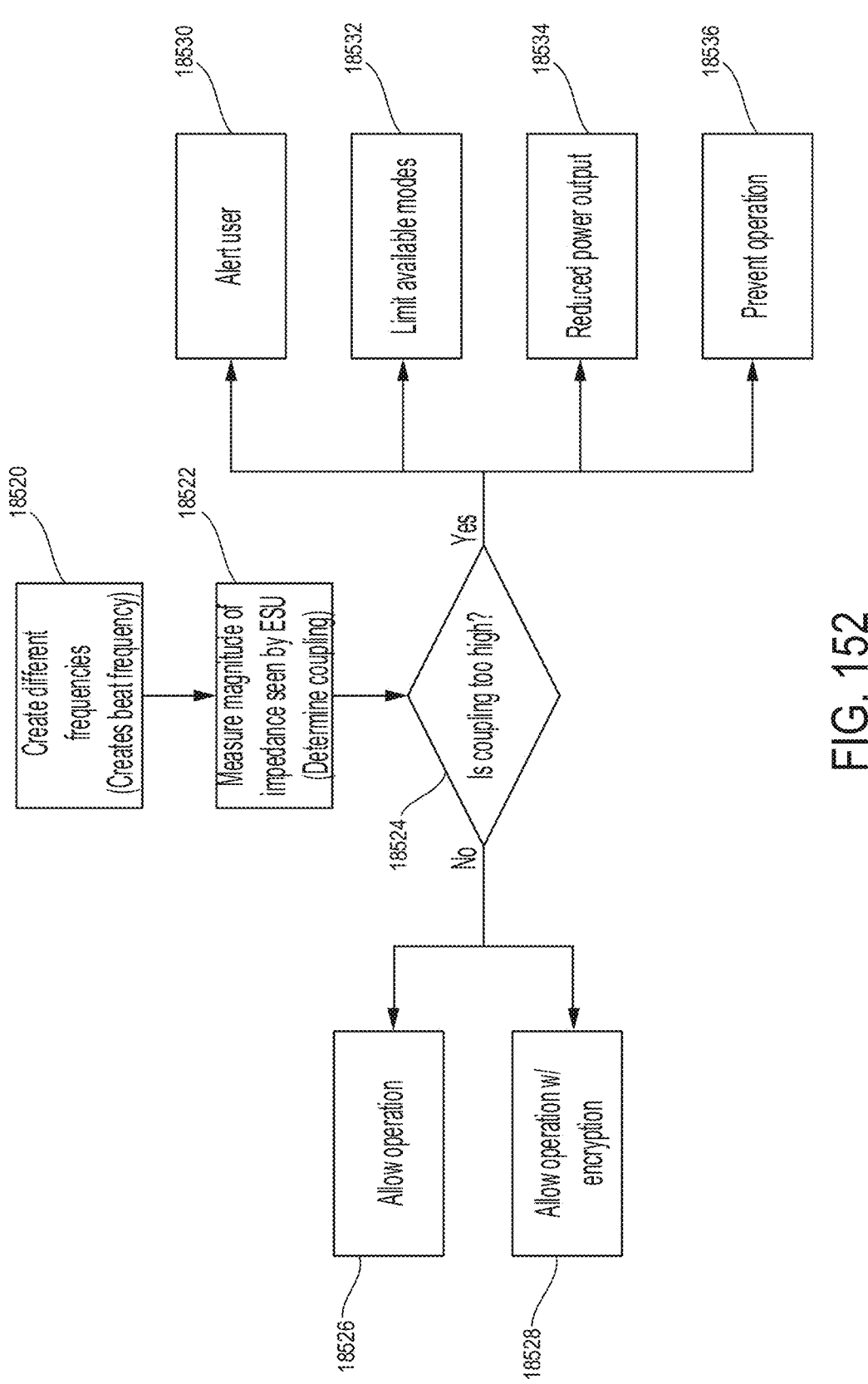

FIG. 152 shows an example logic diagram of a process depicting a control program or a logic configuration for providing a high level algorithm that may be performed by a system including one or more generators and a control circuit in communication with two electrosurgical units (ESUs), in accordance with at least one aspect of the present disclosure.

Figure 153:
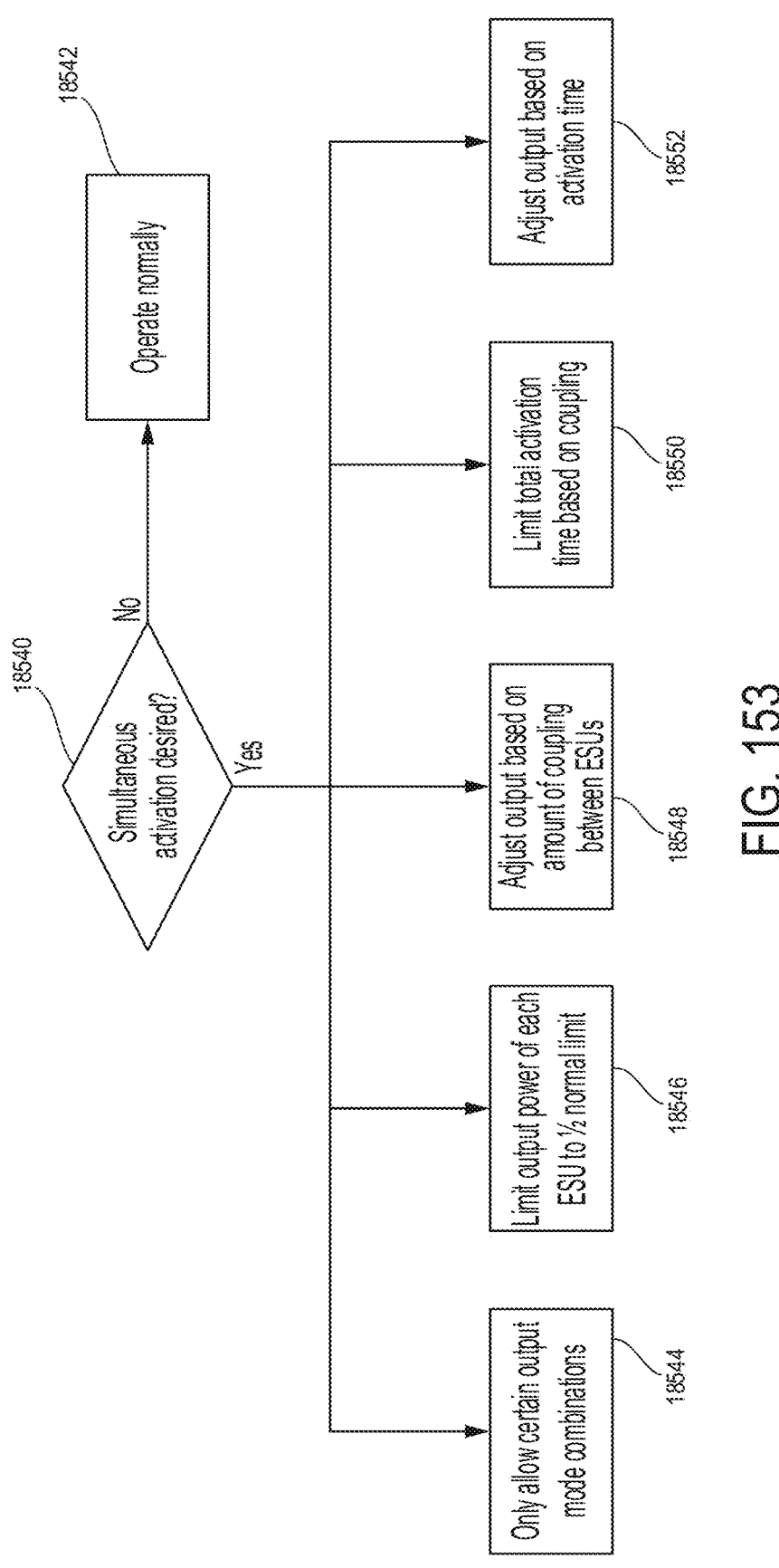

FIG. 153 shows a high level logic diagram of a process depicting a control program or a logic configuration for what a control circuit may analyze through when operations may call for simultaneous operation of two instruments, in accordance with at least one aspect of the present disclosure.

Figure 154:
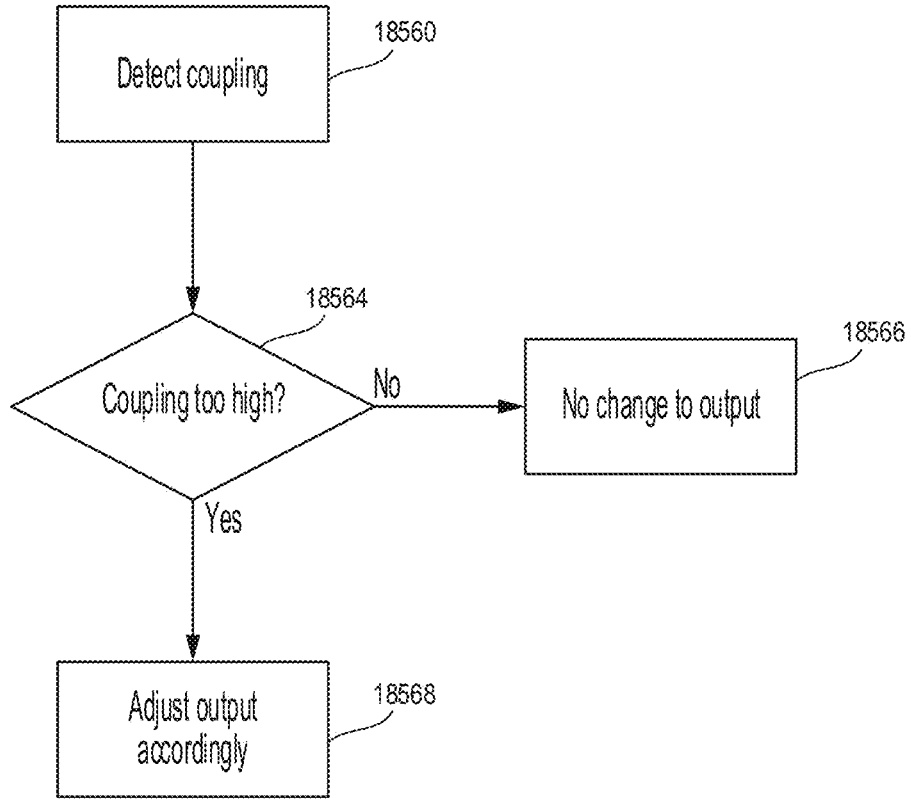

FIG. 154 shows a more detailed logic diagram of a process depicting a control program or a logic configuration for how a control circuit may adjust the output between two ESUs to account for simultaneous activation of the two ESUs, in accordance with at least one aspect of the present disclosure.

Figure 155:
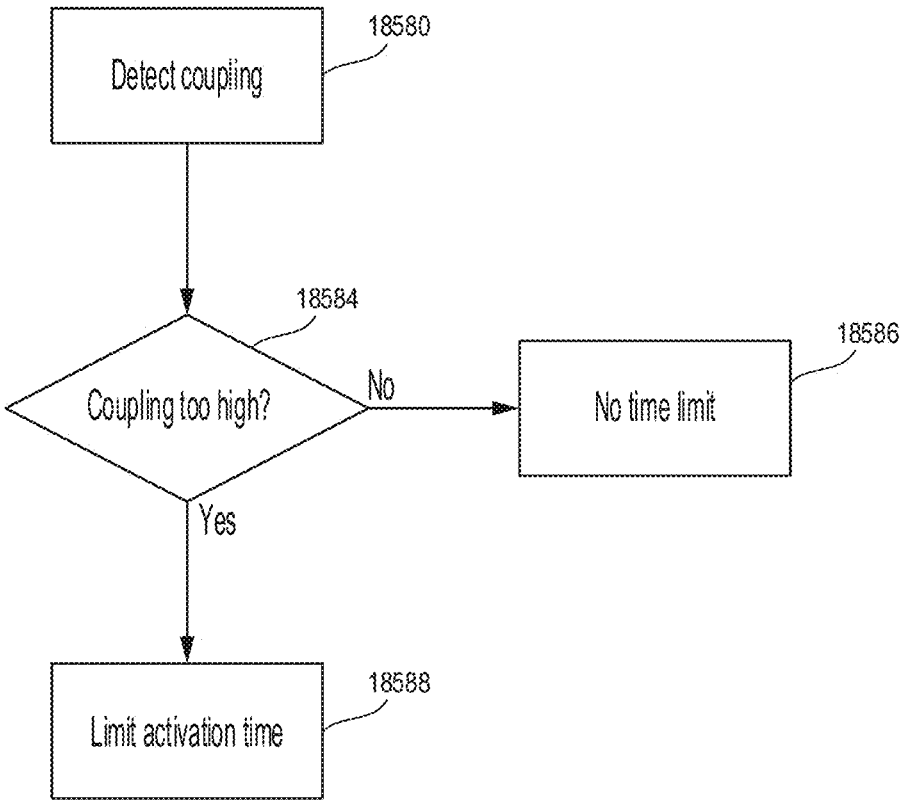

FIG. 155 shows a more detailed logic diagram of a process depicting a control program or a logic configuration for how a control circuit may adjust the activation time of one or more ESUs to account for simultaneous activation of the two ESUs, in accordance with at least one aspect of the present disclosure.

Figure 156:
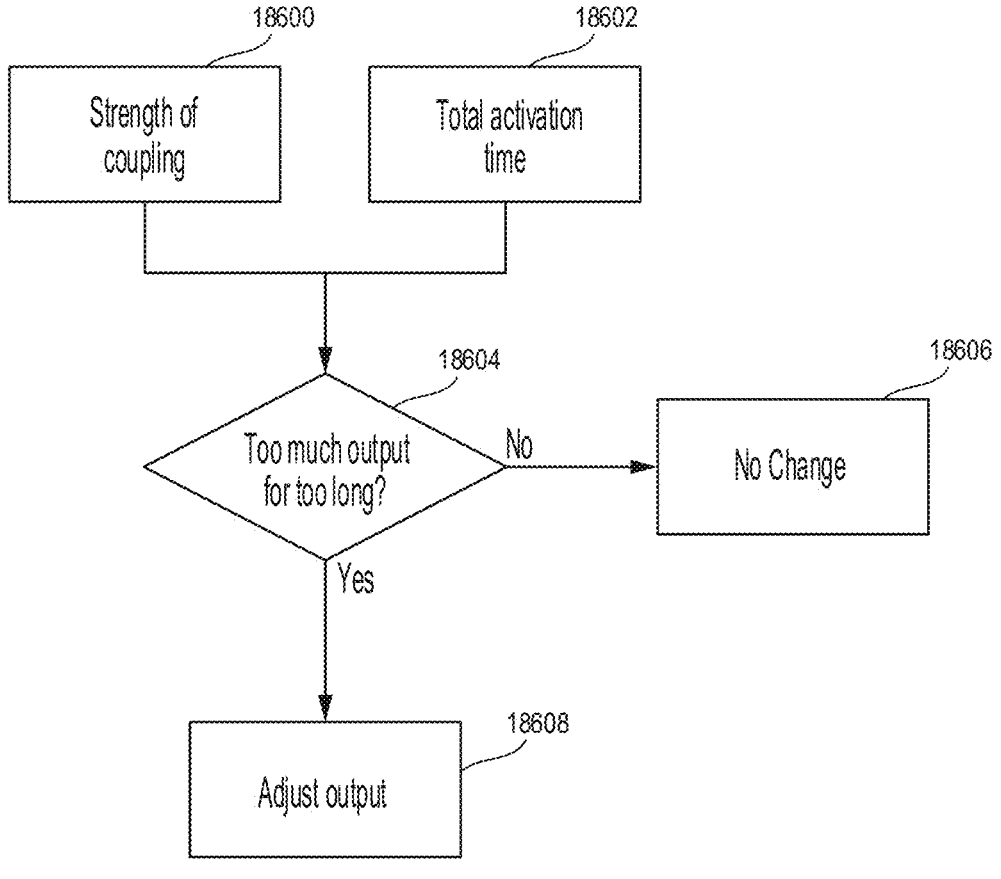

FIG. 156 shows a more detailed logic diagram of a process depicting a control program or a logic configuration for how a control circuit may adjust the output of one or more ESUs based on current activation time to account for simultaneous activation of the two ESUs, in accordance with at least one aspect of the present disclosure.

Figure 157:
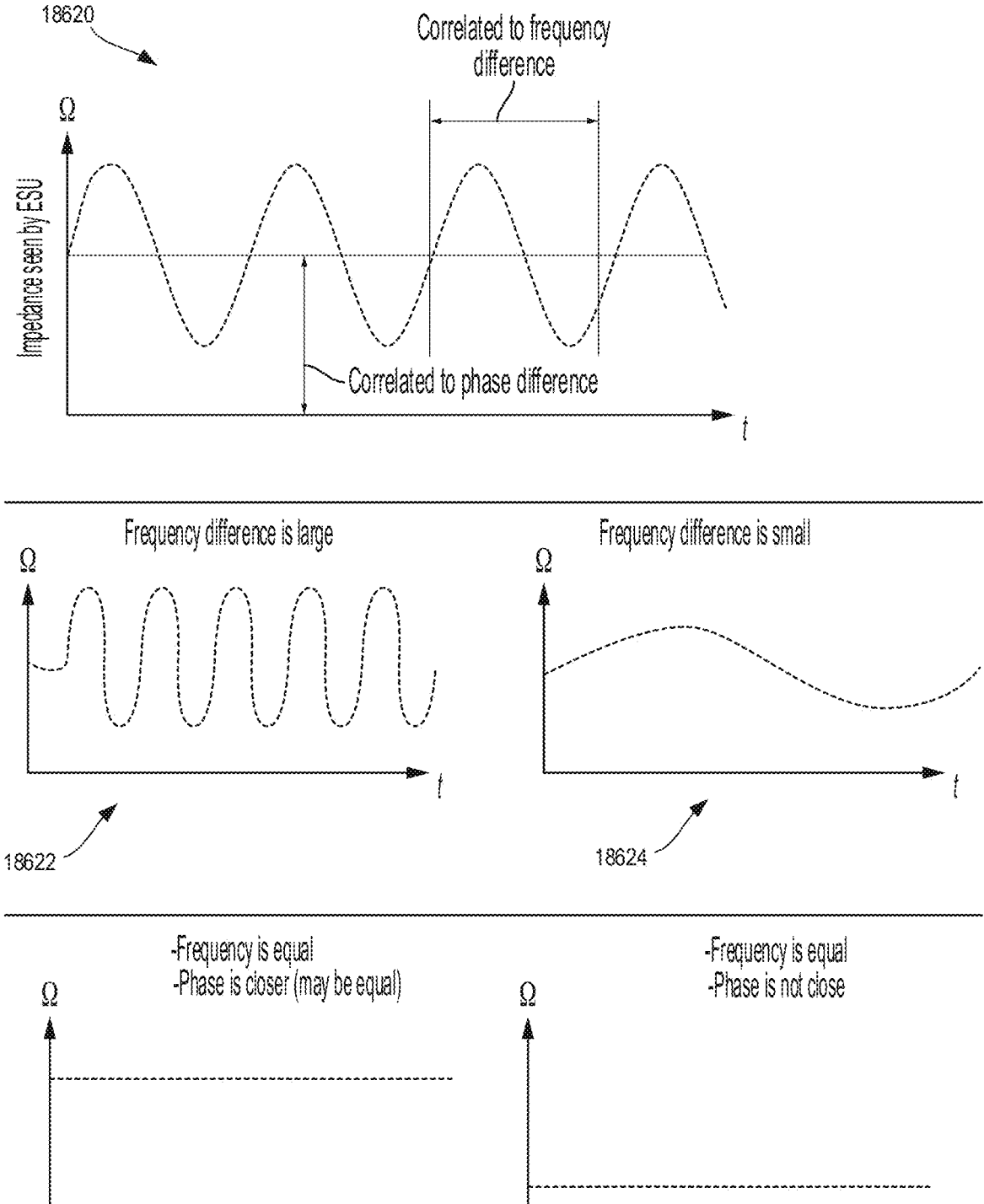

FIG. 157 shows some example graphs that illustrate what synchronizing corrections of one ESU to another may look like conceptually, in accordance with at least one aspect of the present disclosure.

FIG. 158 shows example logic diagrams of a process depicting a control program or a logic configuration for reflecting how a control circuit may synchronize frequencies between two ESUs, in accordance with at least one aspect of the present disclosure.

FIG. 159 shows example logic diagrams of a process depicting a control program or a logic configuration for reflecting how a control circuit may synchronize the phases between two ESUs, in accordance with at least one aspect of the present disclosure.

FIGS. 160A-160D show example configurations for how two instruments, ESU 1 and ESU 2, may be interrelated to participate in a simultaneous operation on a patient and be in position to be compared against one another for synchronization, in accordance with at least one aspect of the present disclosure.

Figure 161:
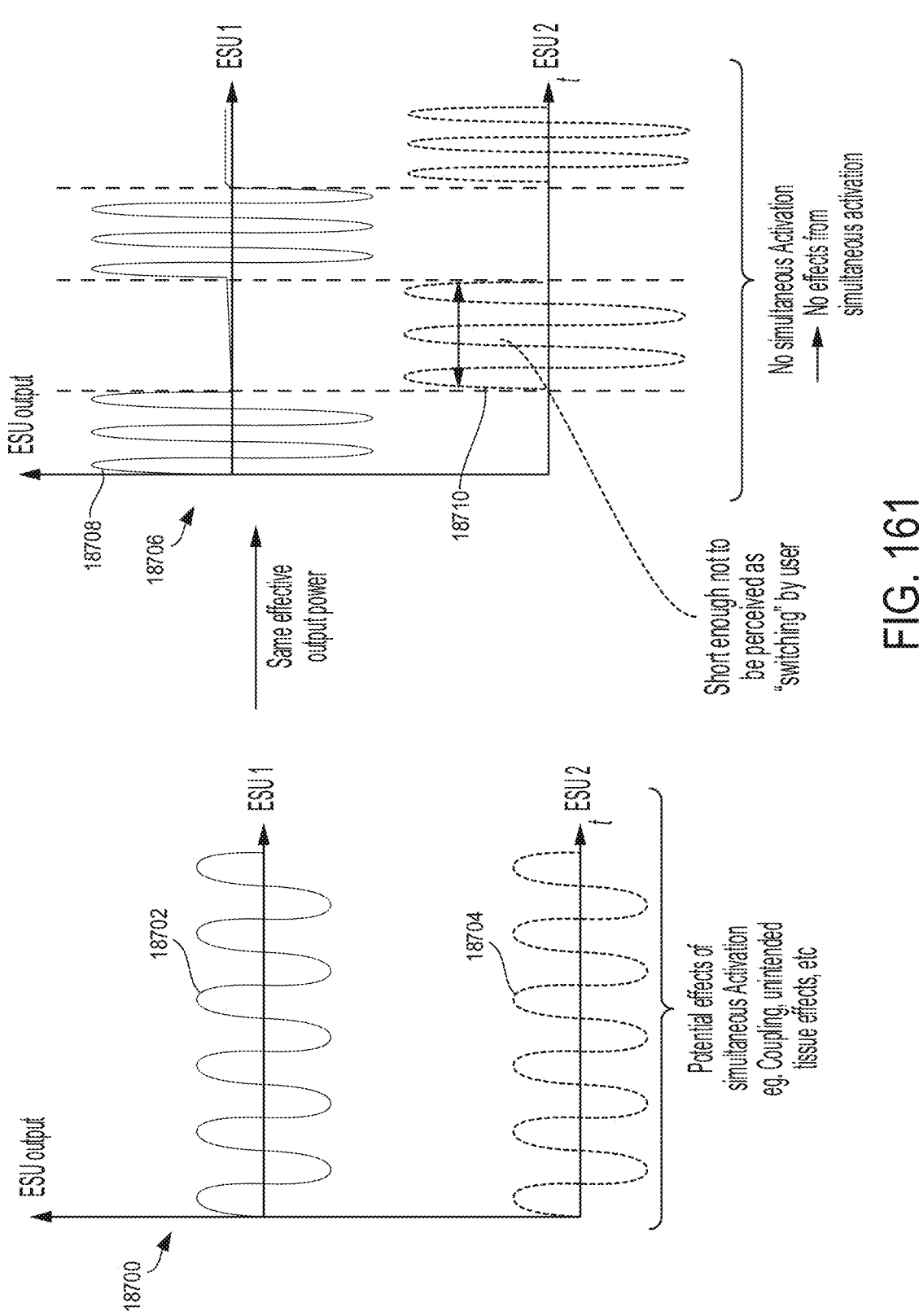

FIG. 161 shows how an alternative adjustment for handing simultaneous outputs may include sending both signals through a duty cycle schedule, in accordance with at least one aspect of the present disclosure.

Figure 162:
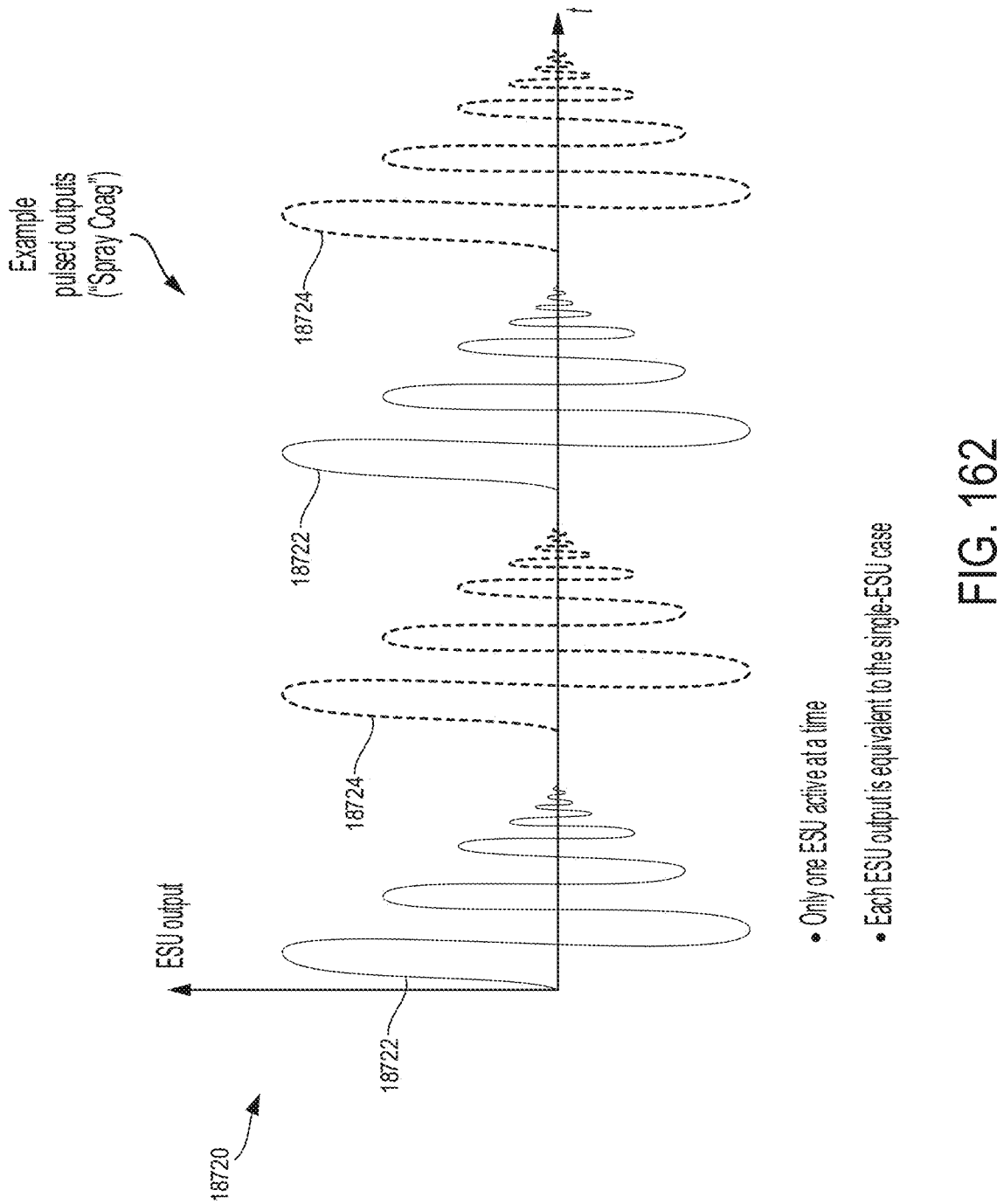

FIG. 162 show a variant of the duty cycle methodology that includes transmitting pulsed outputs in alternating fashion, in accordance with at least one aspect of the present disclosure.

Figure 163:
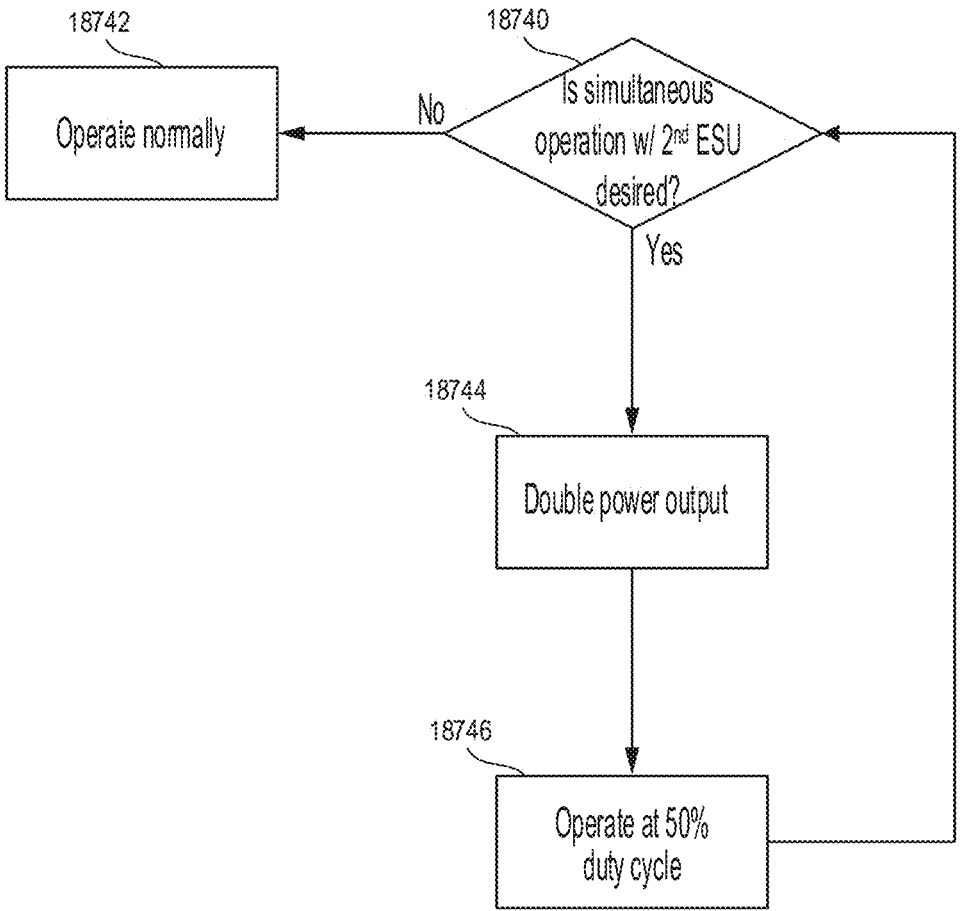

FIG. 163 shows a logic diagram of a process depicting a control program or a logic configuration that expresses the methodology for performing duty cycling as a way to address simultaneous operation of two or more instruments, in accordance with at least one aspect of the present disclosure.

Figure 164:
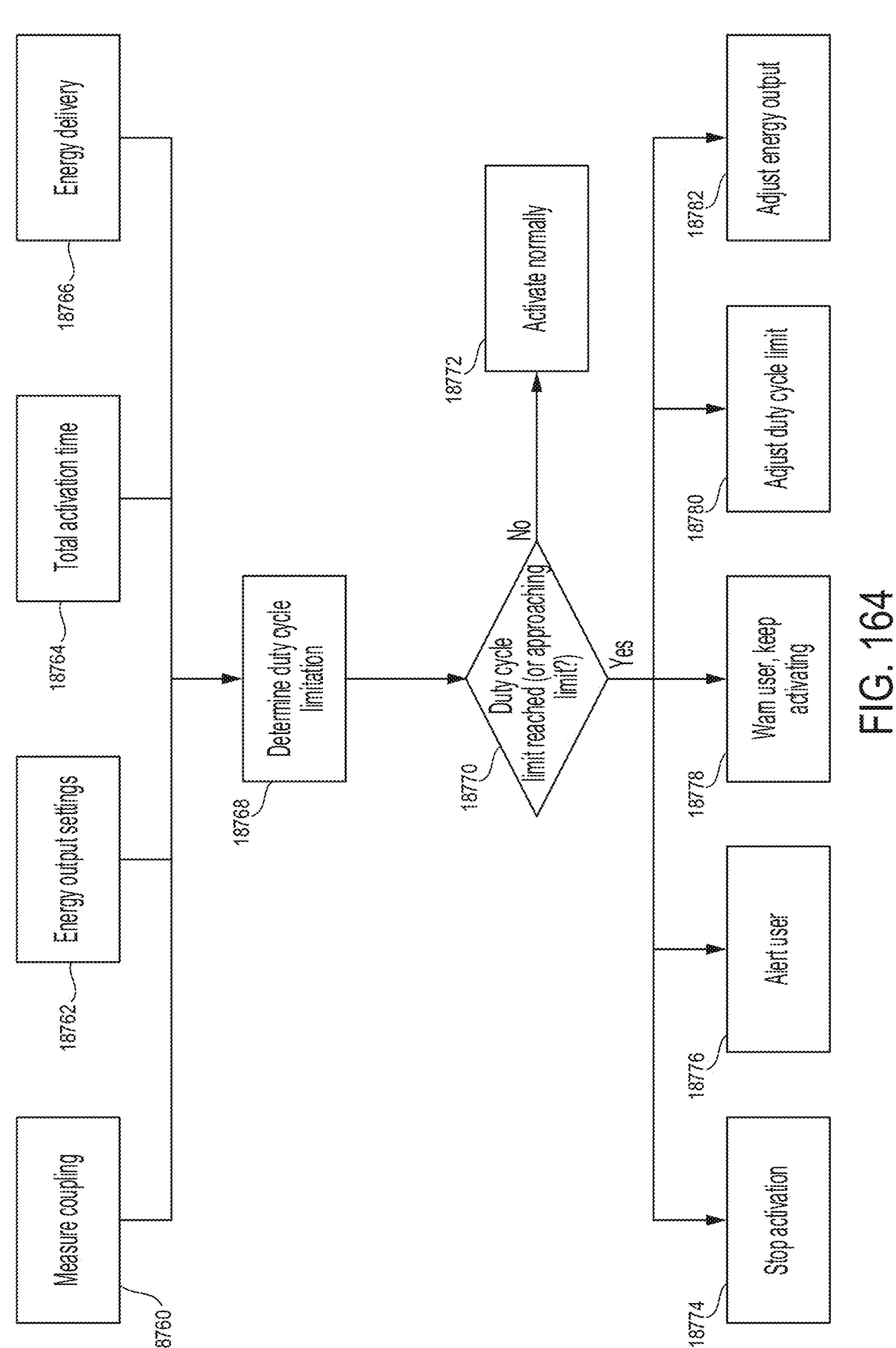

FIG. 164 shows a more complex logic diagram of a process depicting a control program or a logic configuration for how a control circuit may conduct duty cycling to address simultaneous energy outputs of two or more electrosurgical units, in accordance with at least one aspect of the present disclosure.

Figure 165:
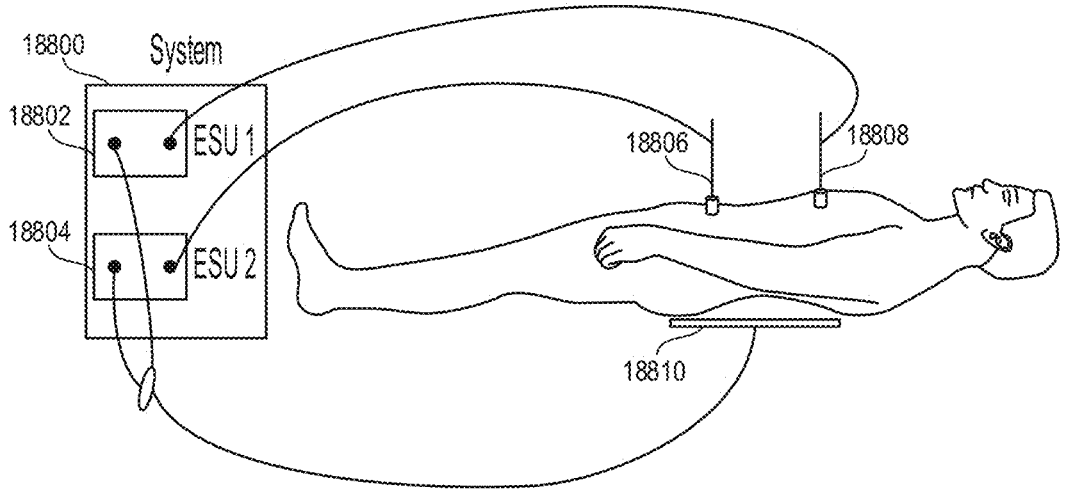

FIG. 165 shows a system for handling simultaneous activation of instruments may include a return pad and system in the event the two instruments are part of a monopolar system, in accordance with at least one aspect of the present disclosure.

Figure 166A:
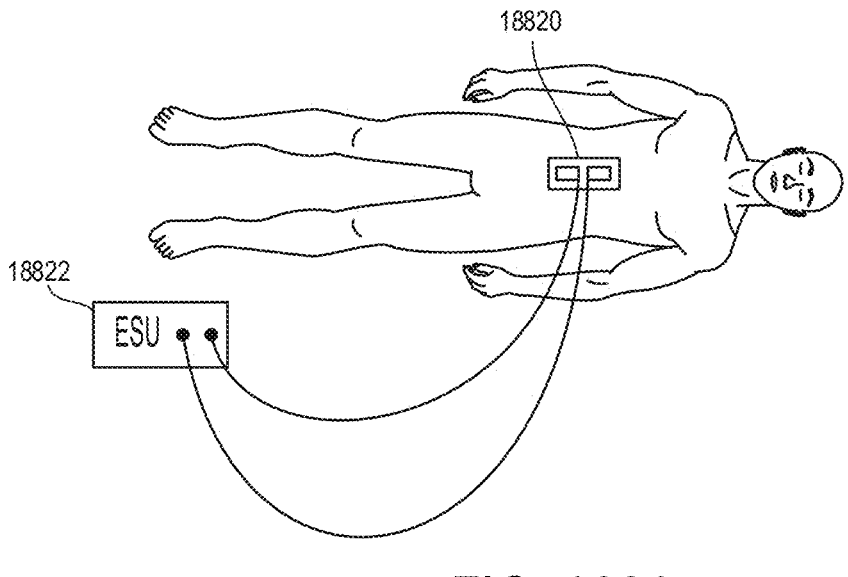
Figure 166B:
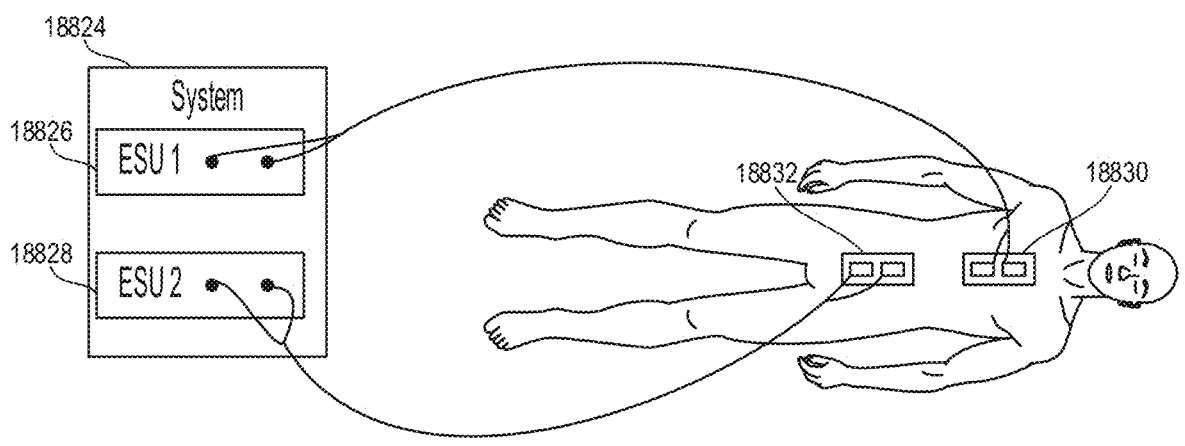

FIGS. 166A-166B show how the system may include a contact quality monitoring (CQM) configuration to not only perform CQM but to also be used in providing an interface between the two ESUs for use in coordinating simultaneous activation, consistent with the descriptions above involving CQM, in accordance with at least one aspect of the present disclosure.

Figure 167:
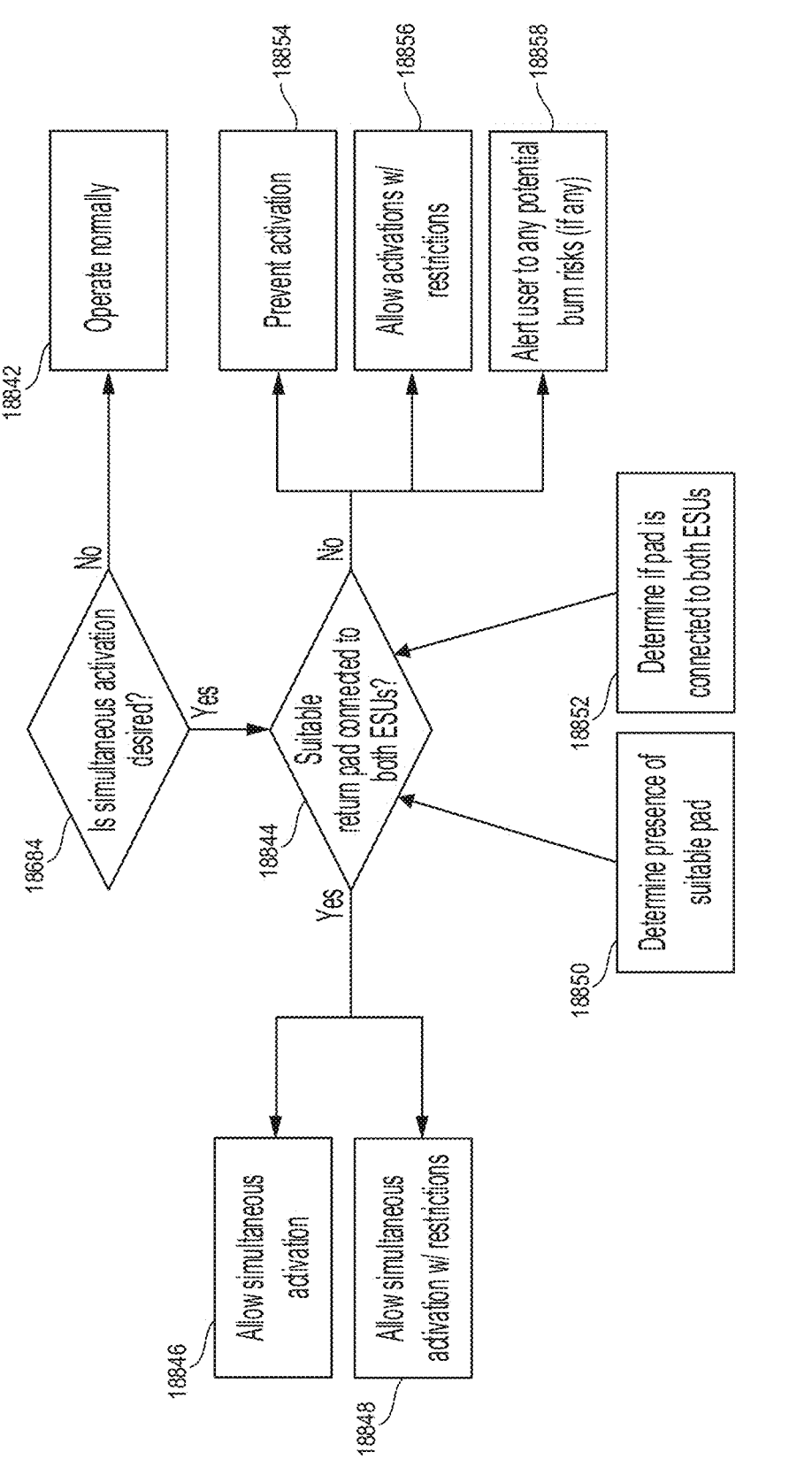

FIG. 167 show an example methodology for utilizing one or more return pads to handle simultaneous activation of monopolar electrosurgical instruments, in accordance with at least one aspect of the present disclosure.

Figure 168:
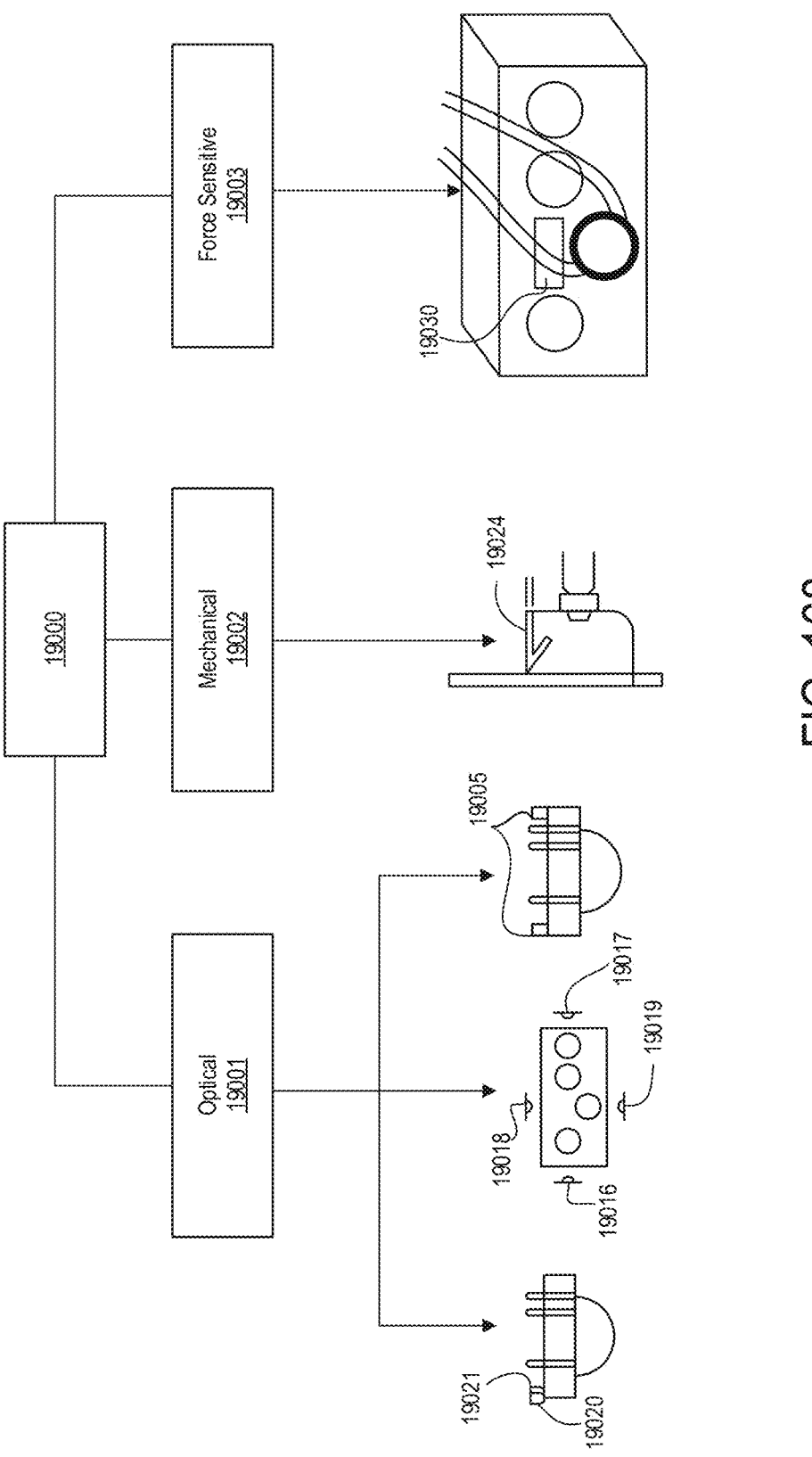

FIG. 168 is a block diagram of an energy module including multiple ports configured to detect presence of a connector in accordance with at least one aspect of the present disclosure.

Figure 169:
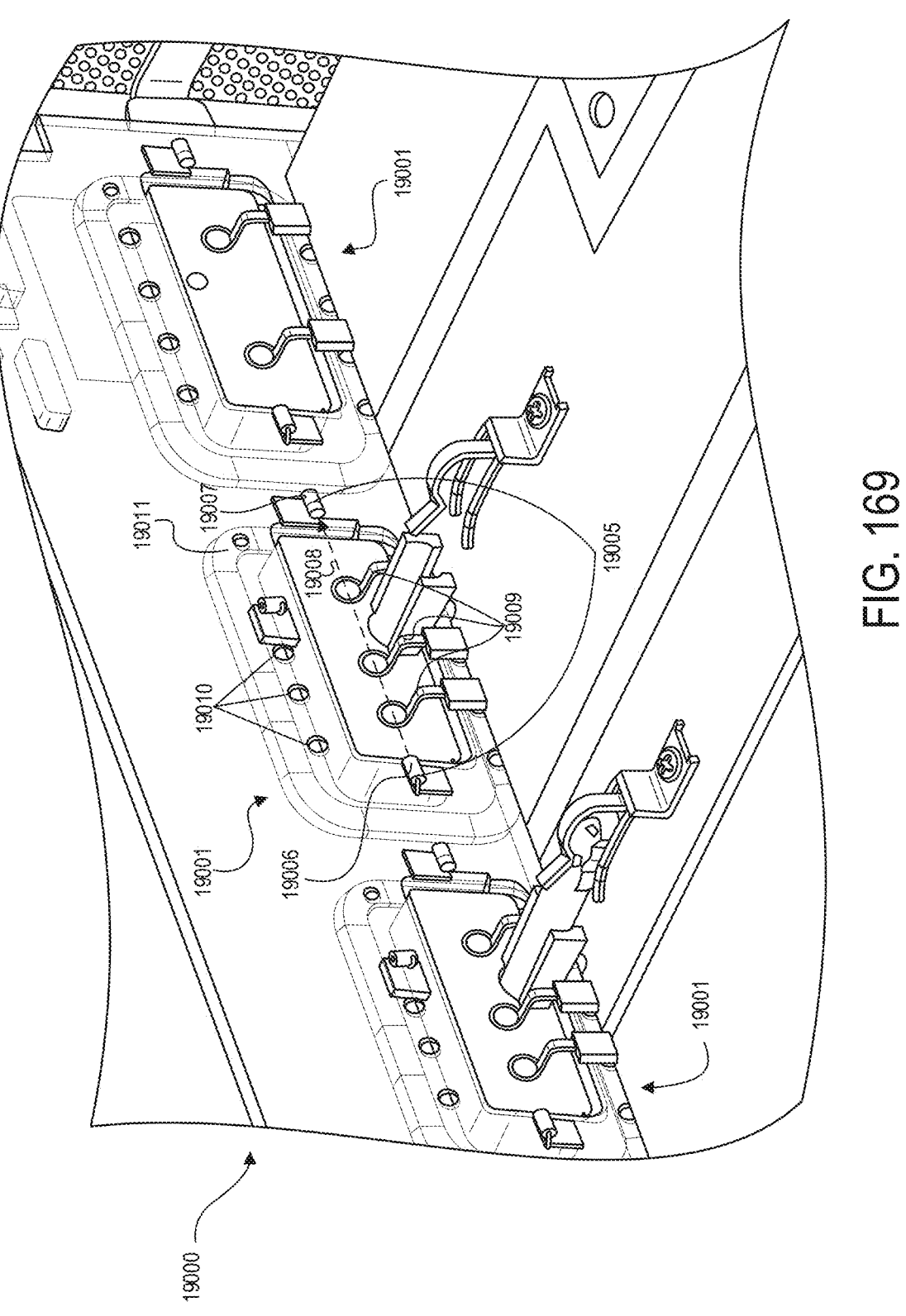

FIG. 169 is a perspective view of an optical sensing port in accordance with at least one aspect of the present disclosure.

Figure 170:
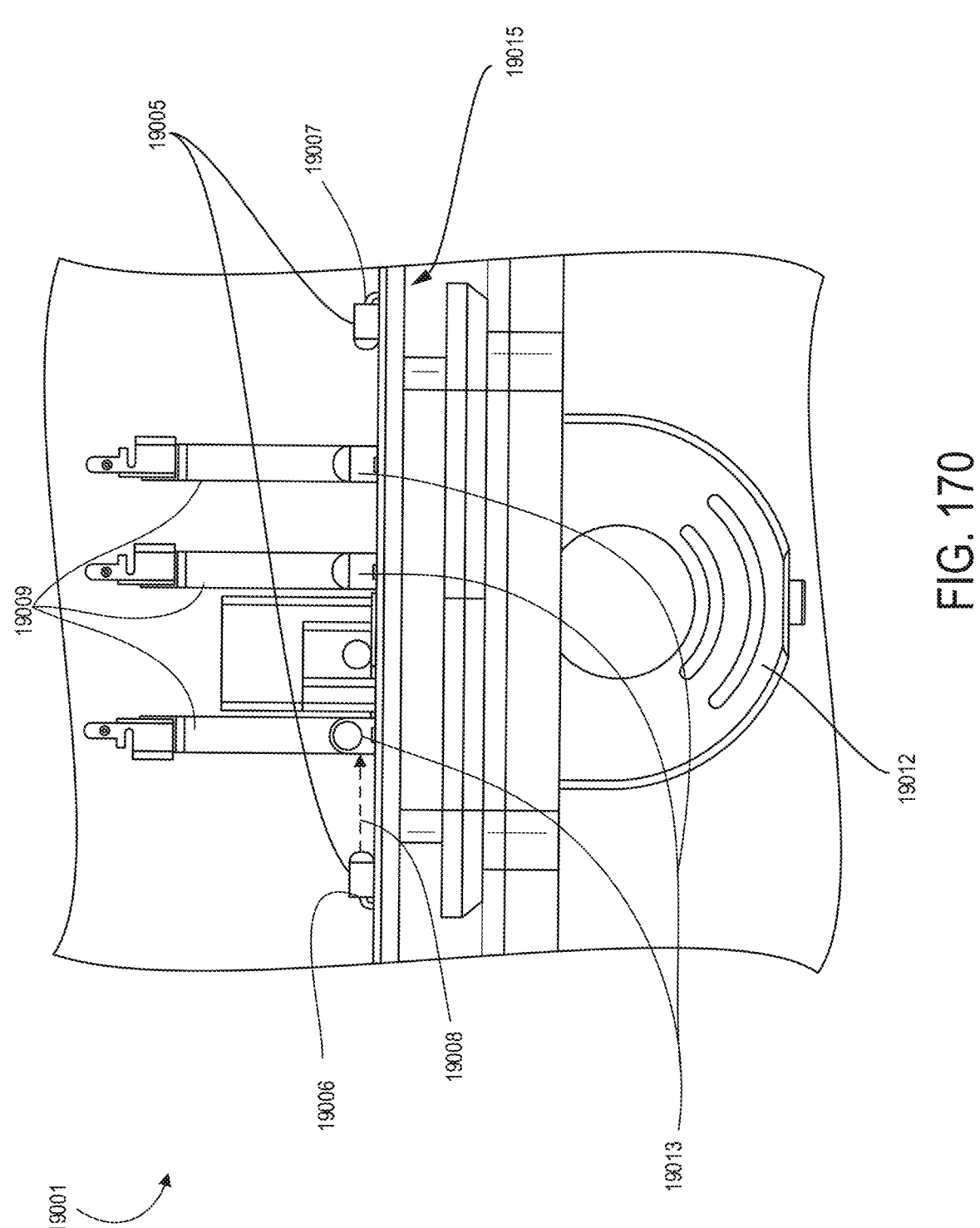

FIG. 170 is a top view of the optical sensing port of FIG. 169 in accordance with at least one aspect of the present disclosure.

Figure 171:
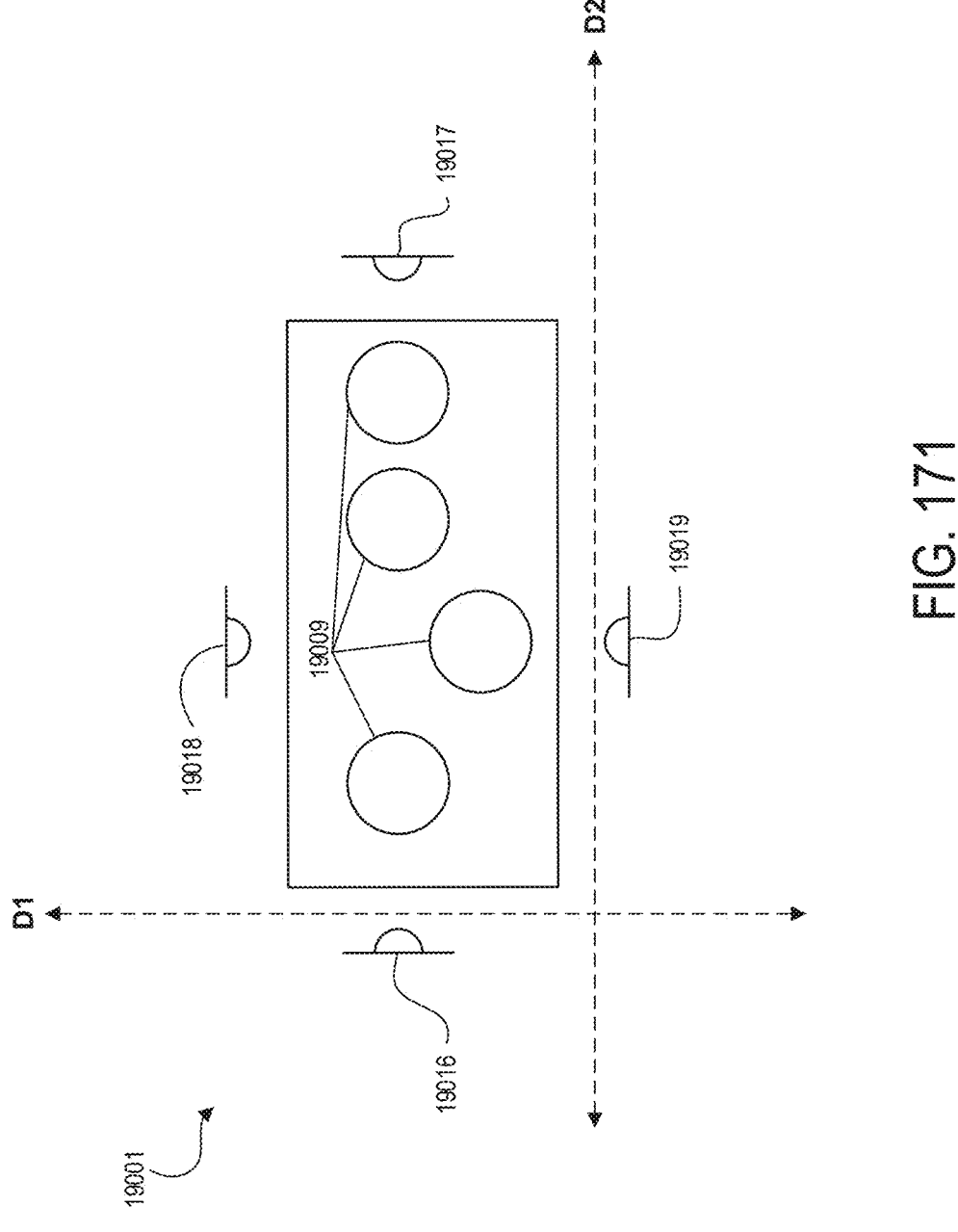

FIG. 171 is a front view of an optical sensing port in accordance with at least one aspect of the present disclosure.

Figure 172:
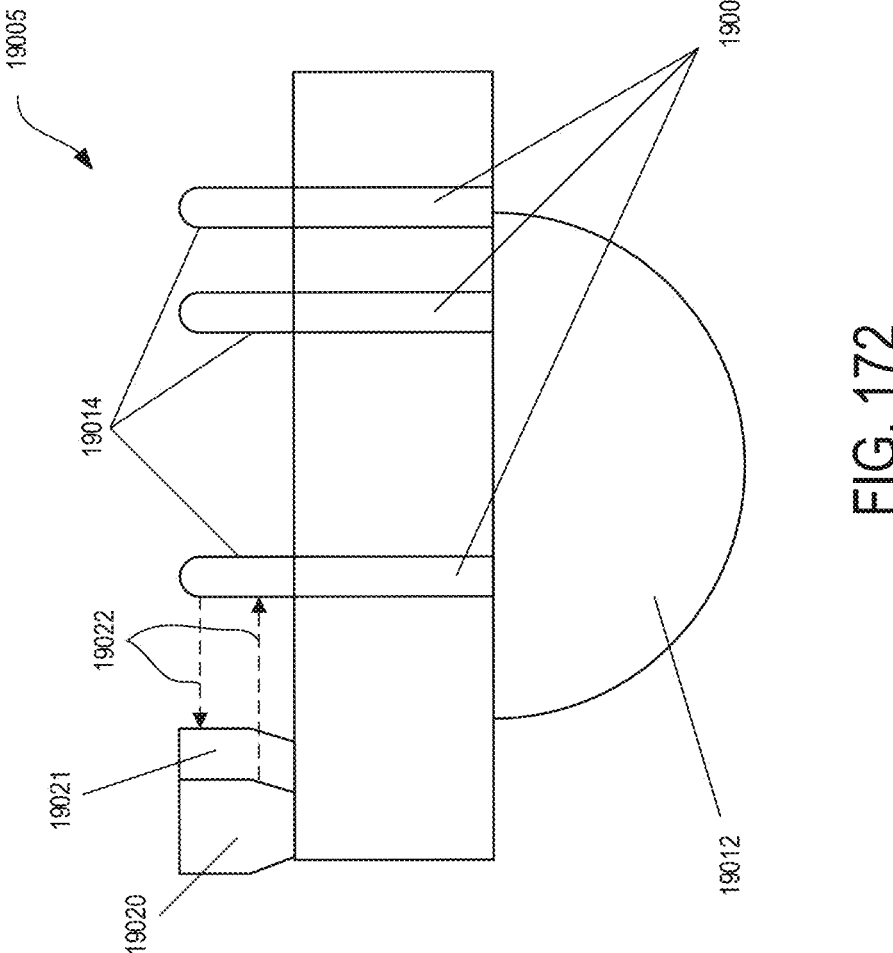

FIG. 172 is a top view of an optical sensing port depicted in accordance with at least one aspect of the present disclosure.

Figure 173A:
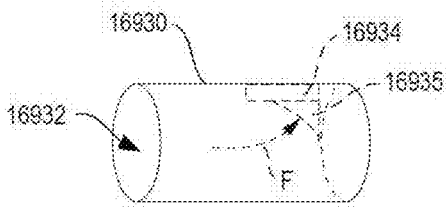
Figure 173B:
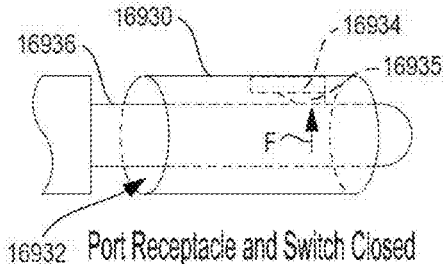

FIGS. 173A-173B illustrate a mechanical sensing port receptacle comprising a depressible switch, in accordance with at least one aspect of the present disclosure, where FIG. 173A depicts the depressible switch in an open configuration and FIG. 173B depicts the depressible switch in a closed configuration.

Figure 174A:
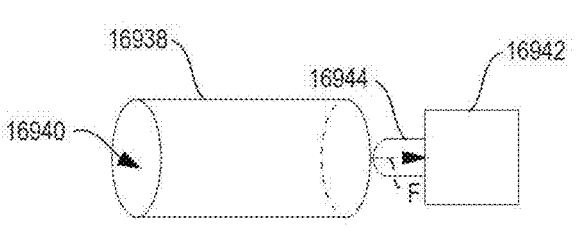
Figure 174B:
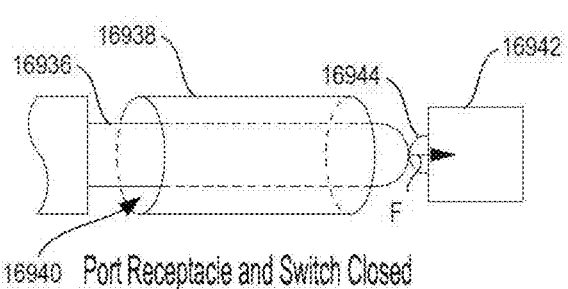

FIGS. 174A-174B illustrate a mechanical sensing port receptacle comprising a push button switch, in accordance with at least one aspect of the present disclosure, where FIG. 174A depicts the push button switch in an open configuration and FIG. 174B depicts the push button switch in a closed configuration.

Figure 175A:
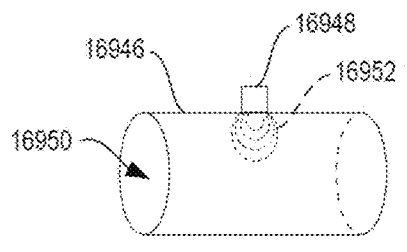
Figure 175B:
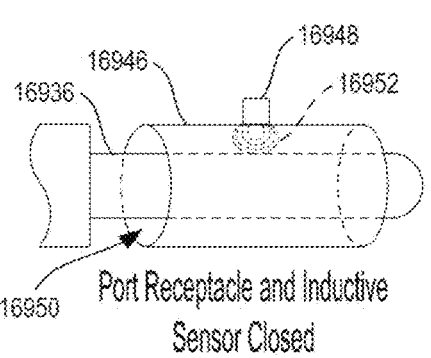

FIGS. 175A-175B illustrate an electrical sensing port receptacle comprising a non-contact proximity switch, in accordance with at least one aspect of the present disclosure, where FIG. 175A depicts the non-contact proximity switch in an open configuration and FIG. 175B depicts the non-contact proximity switch in a closed configuration.

Figure 176:
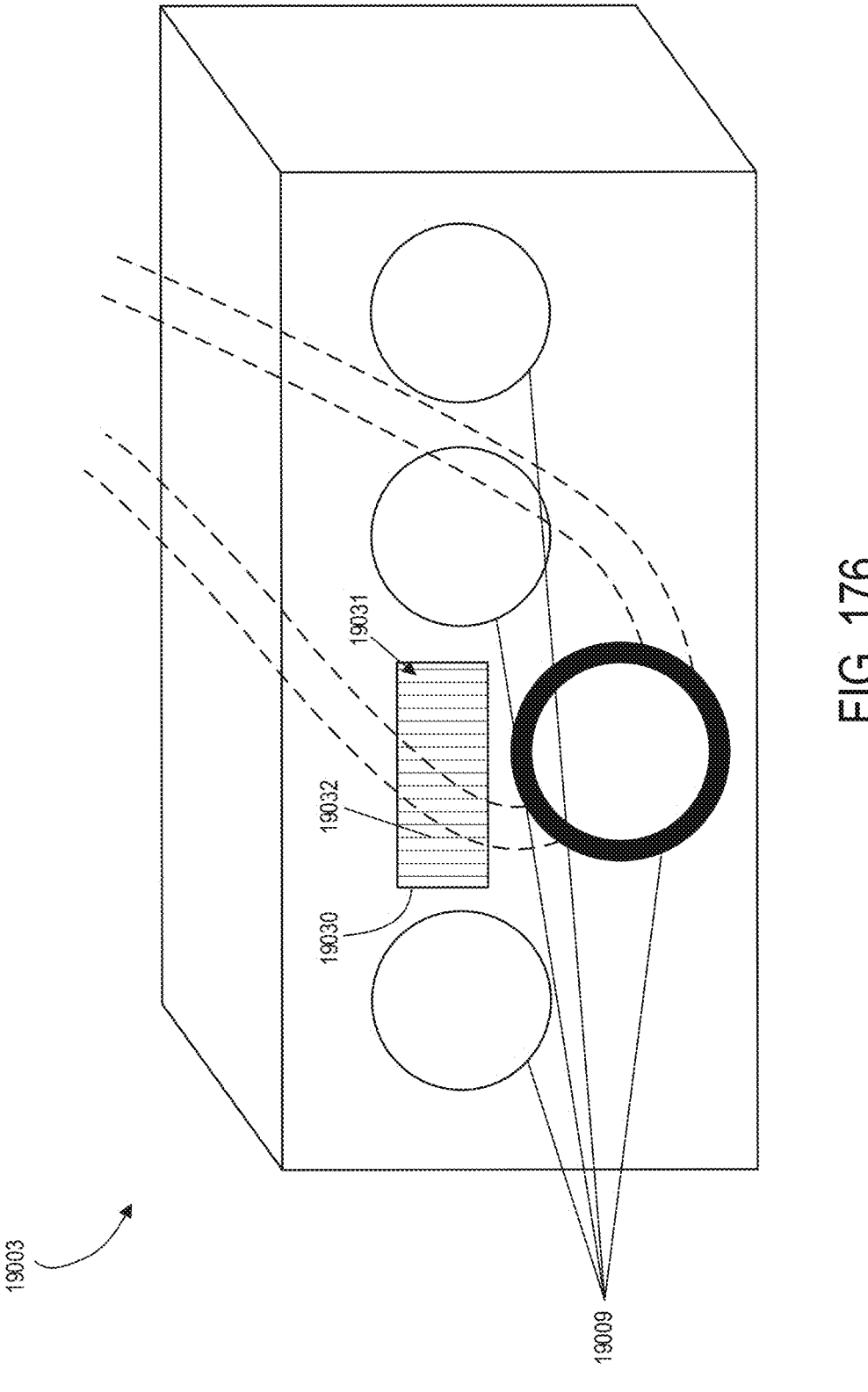

FIG. 176 is a perspective view of a force sensing port in accordance with at least one aspect of the present disclosure.

Figure 177:
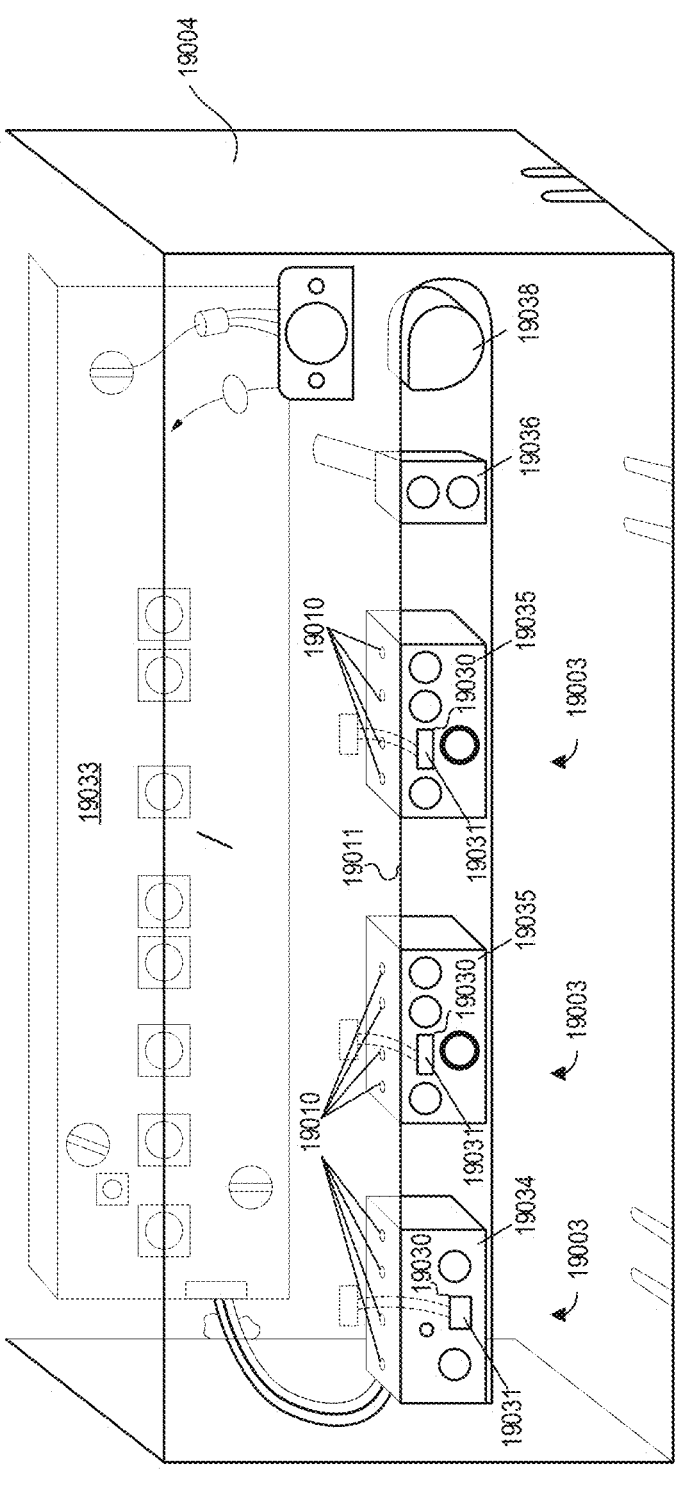

FIG. 177 is a perspective view of an electrosurgical generator in accordance with at least one aspect of the present disclosure.

Figure 178:
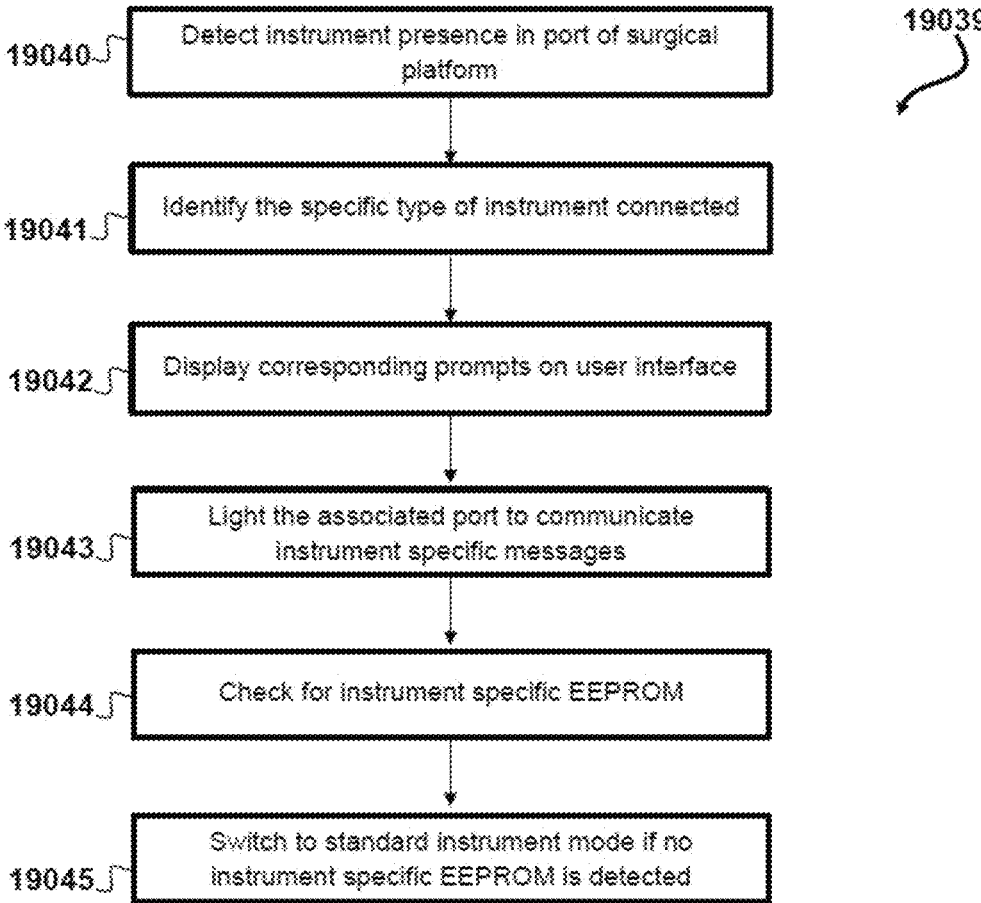

FIG. 178 is a logic diagram of a process depicting a control program or a logic configuration for detecting, identifying, and managing instruments connected to ports of a energy module in accordance with at least one aspect of the present disclosure.

Figures 179A, 179B, 179C, 179D, 179E:
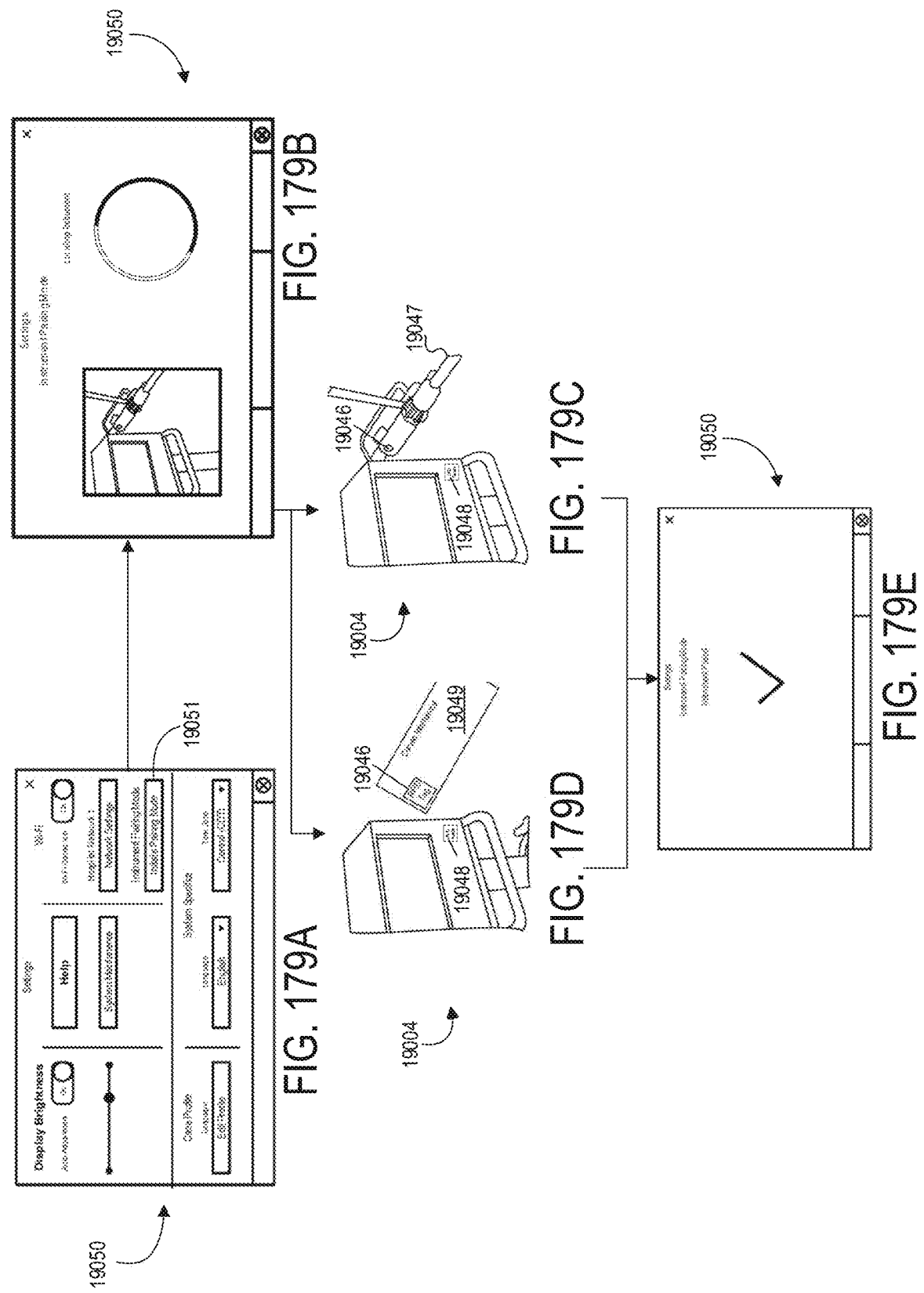

FIGS. 179A-179E is a block diagram of a system for detecting instruments connected to an energy module using radio frequency identification (RFID) circuits in accordance with at least one aspect of the present disclosure, where:

FIG. 179A illustrates a user initiated detection sequence via a display of a user interface of the RFID enabled energy module by selecting a pairing mode option;

FIG. 179B illustrates selecting a pairing mode option to transition the user interface to another display to prompts the user to pair a device;

FIG. 179C illustrates an RFID circuit affixed to an RFID enabled instrument and an RFID scanner affixed to an RFID enabled energy module;

FIG. 179D illustrates an RFID circuit that could be affixed to inventory management paperwork associated with the instrument; and FIG. 179E illustrates a visual confirmation provided by the RFID enabled energy module that the RFID enabled instrument has been successfully detected by and paired to the RFID enabled energy module.

Figures 180A, 180B, 180C, 180D, 180E:
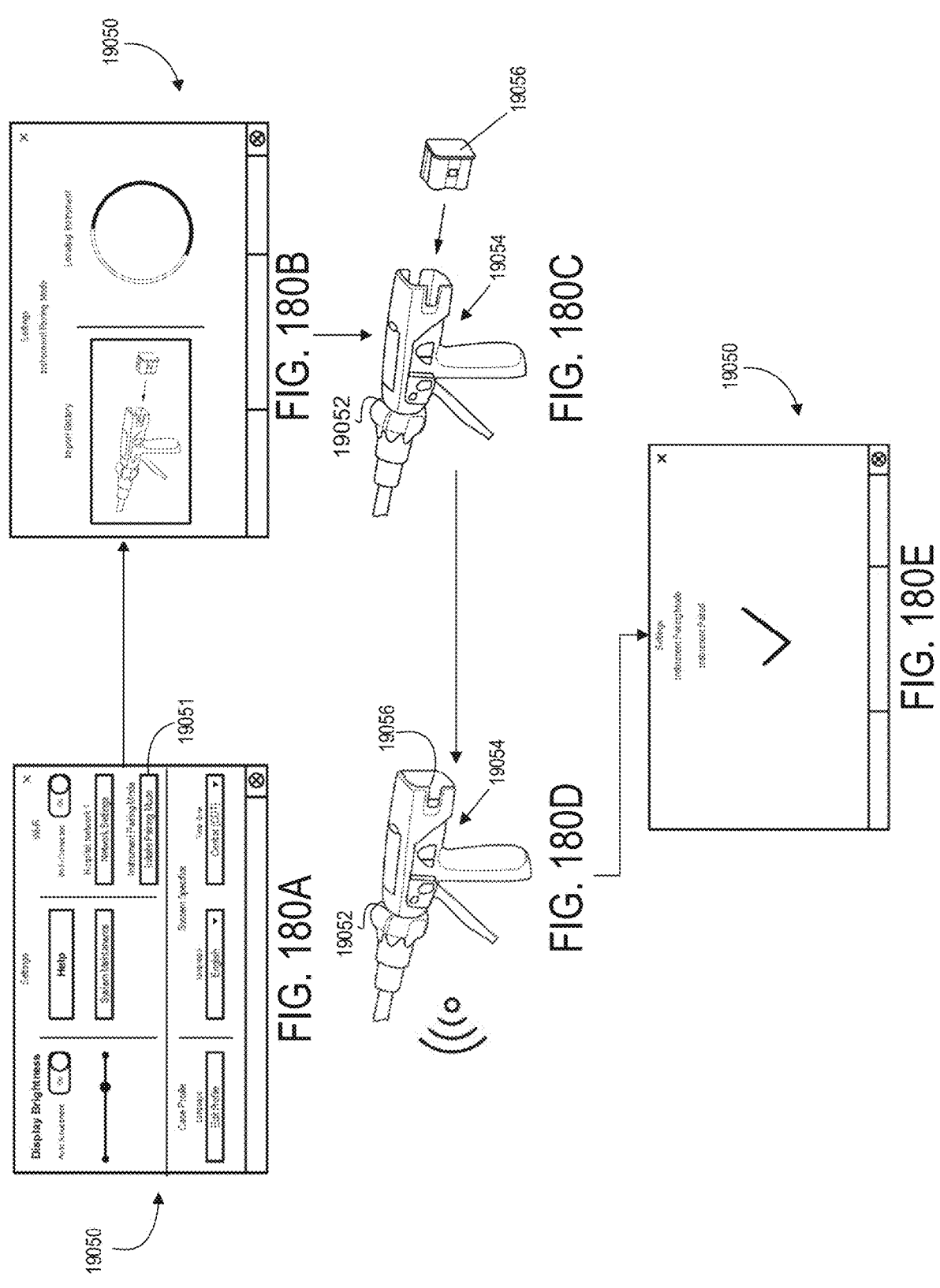

FIGS. 180A-180E is a block diagram of a system for detecting instruments connected to a energy module using a battery installation process in accordance with at least one aspect of the present disclosure, where:

FIG. 180A illustrates a user initiates detection sequence via a user interface of a wirelessly enabled energy module by selecting a pairing mode option;

FIG. 180B illustrates selection of the pairing mode option commencing the process of pairing;

FIG. 180C illustrates the user installing a removable battery into the cavity of the wirelessly enabled having initiated the pairing mode;

FIG. 180D illustrates electrical communication established and the wireless communication module activated when the battery is installed;

FIG. 180E illustrates a user interface of the wirelessly enabled energy module to provide a visual confirmation that the wirelessly enabled instrument has been successfully detected by and paired to the wirelessly enabled energy module.

Figure 181:
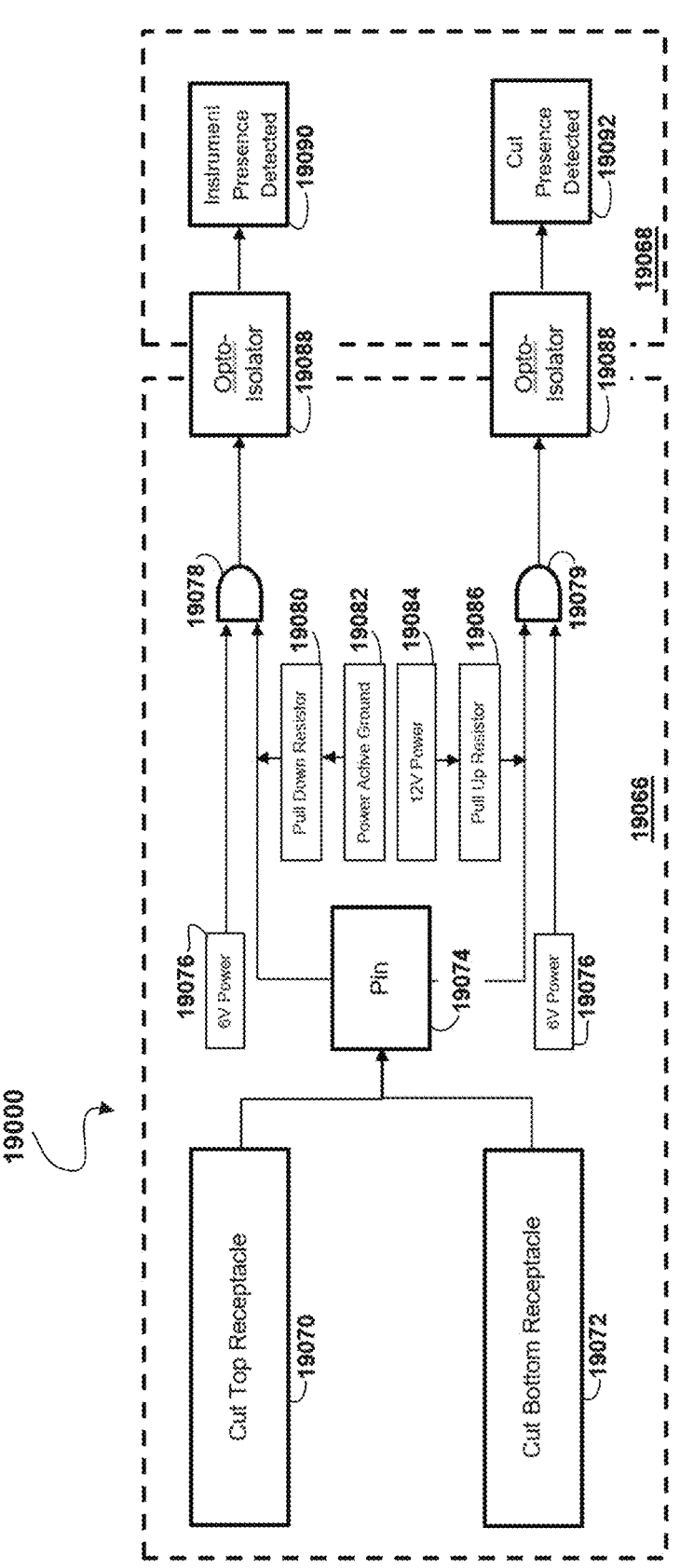

FIG. 181 is a block diagram of an electrical circuit configured to detect whether an instrument is connected to an energy module in accordance with at least one aspect of the present disclosure.

Figure 182:
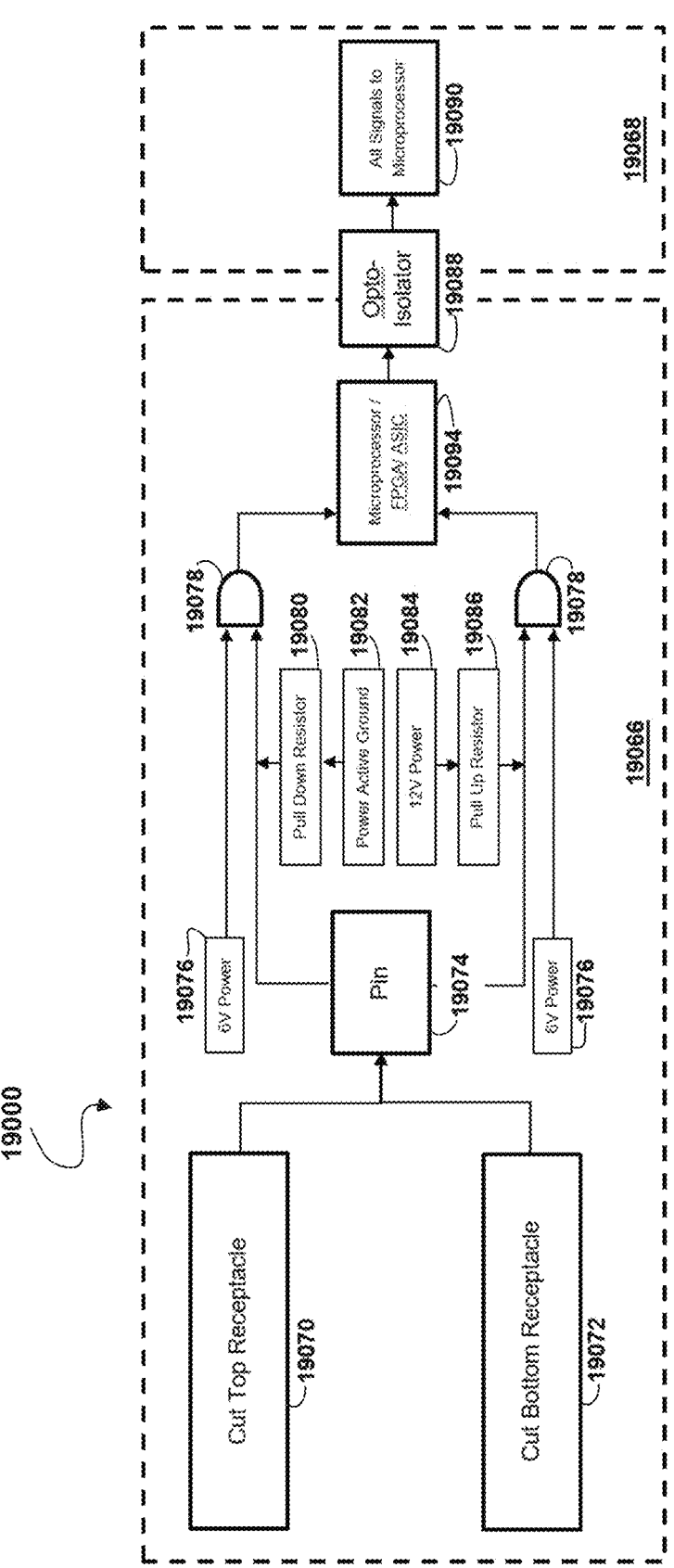

FIG. 182 is a block diagram of an electrical circuit configured to detect whether an instrument is connected to an energy module in accordance with at least one aspect of the present disclosure.

Figure 183:
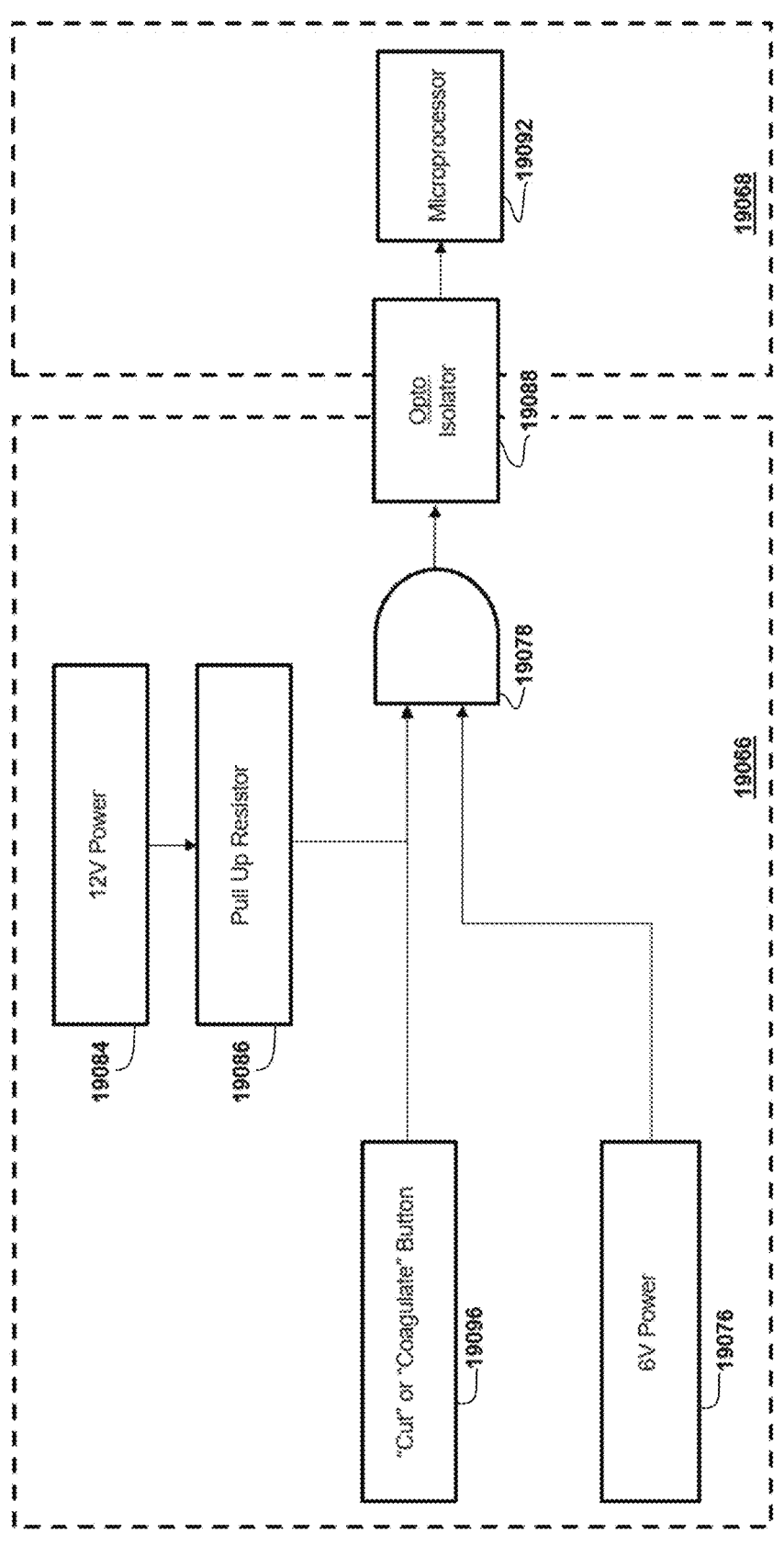

FIG. 183 is a block diagram of an electrical circuit configured to detect whether an instrument is connected to an energy module in accordance with at least one aspect of the present disclosure.

Figure 184:
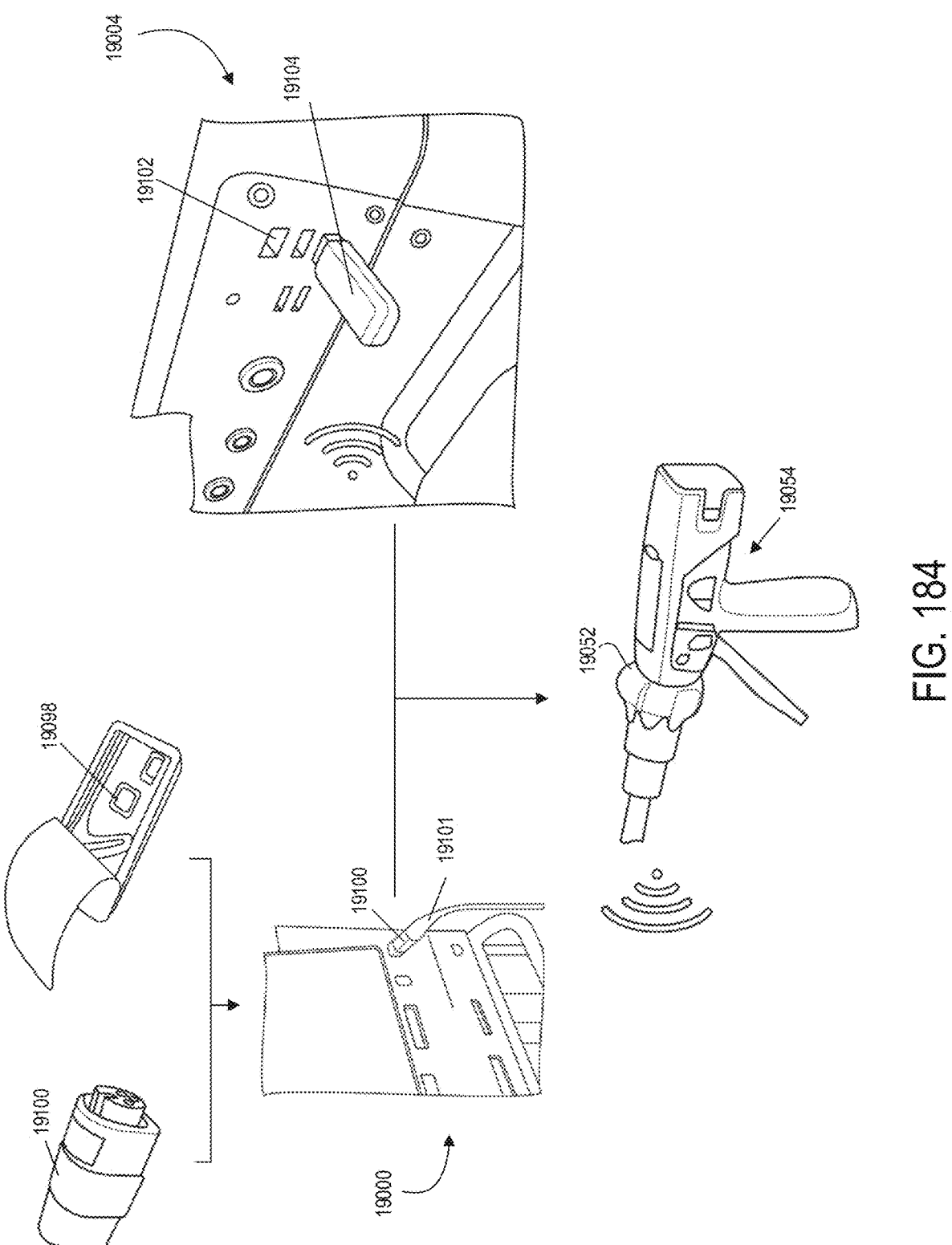

FIG. 184 is a block diagram of a system for detecting instruments to an energy module using a wireless capital equipment key in accordance with at least one aspect of the present disclosure.

Figure 185:
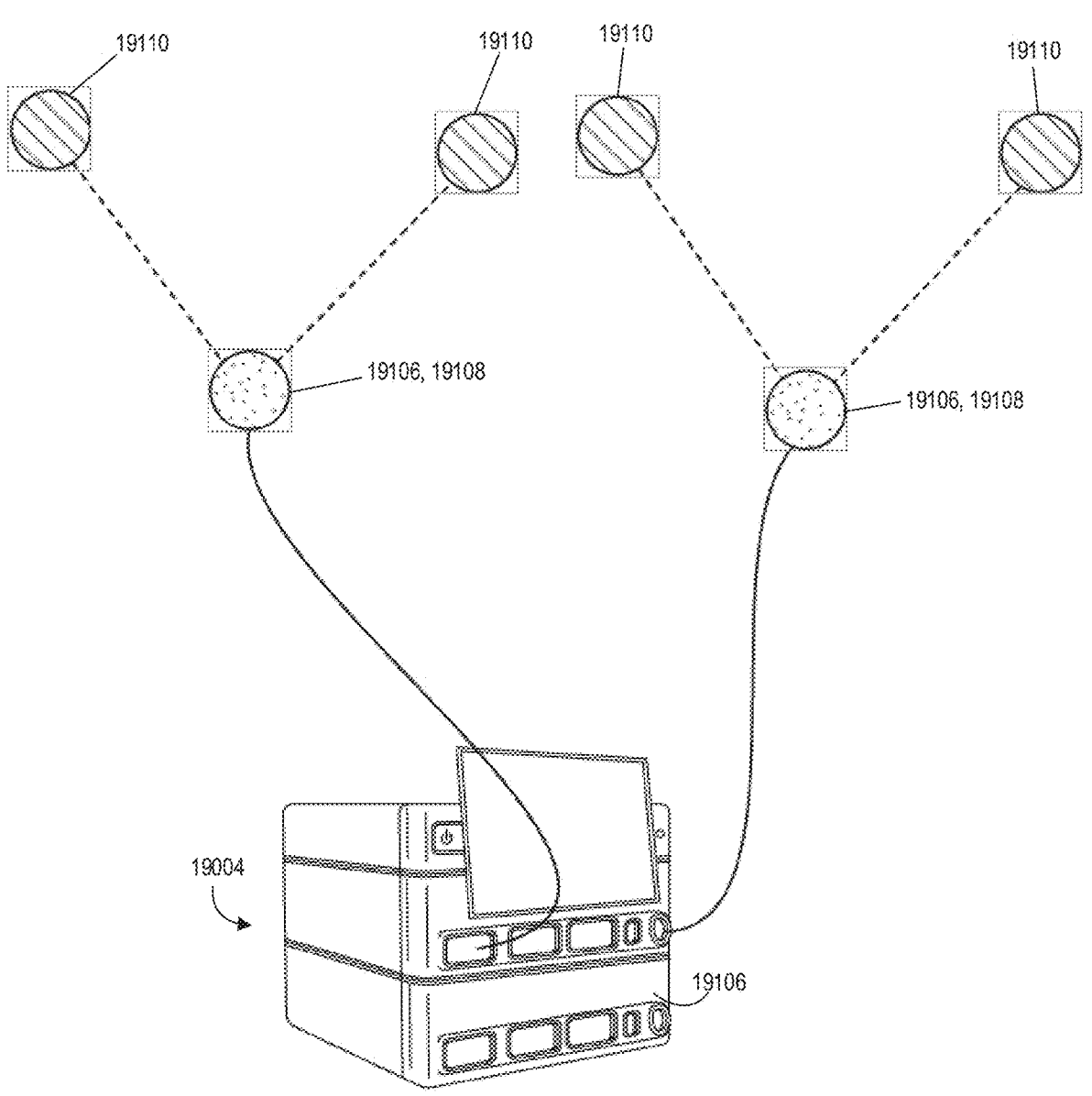

FIG. 185 is a block diagram of a system for detecting instruments to an energy module using a wireless mesh network in accordance with at least one aspect of the present disclosure.

Figure 186:
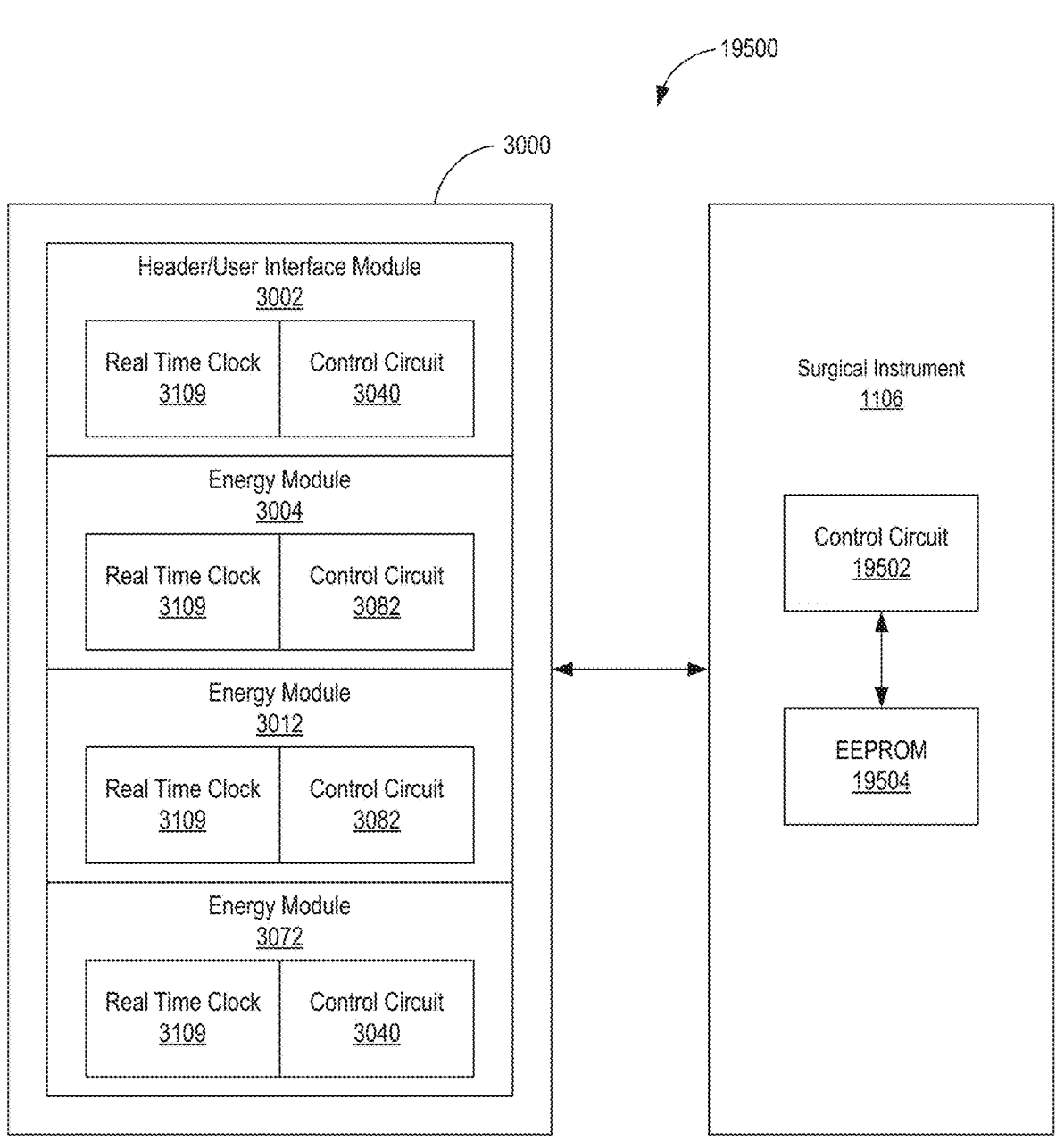

FIG. 186 illustrates a real time instrument tracking system, in accordance with at least one aspect of the present disclosure.

Figure 187:
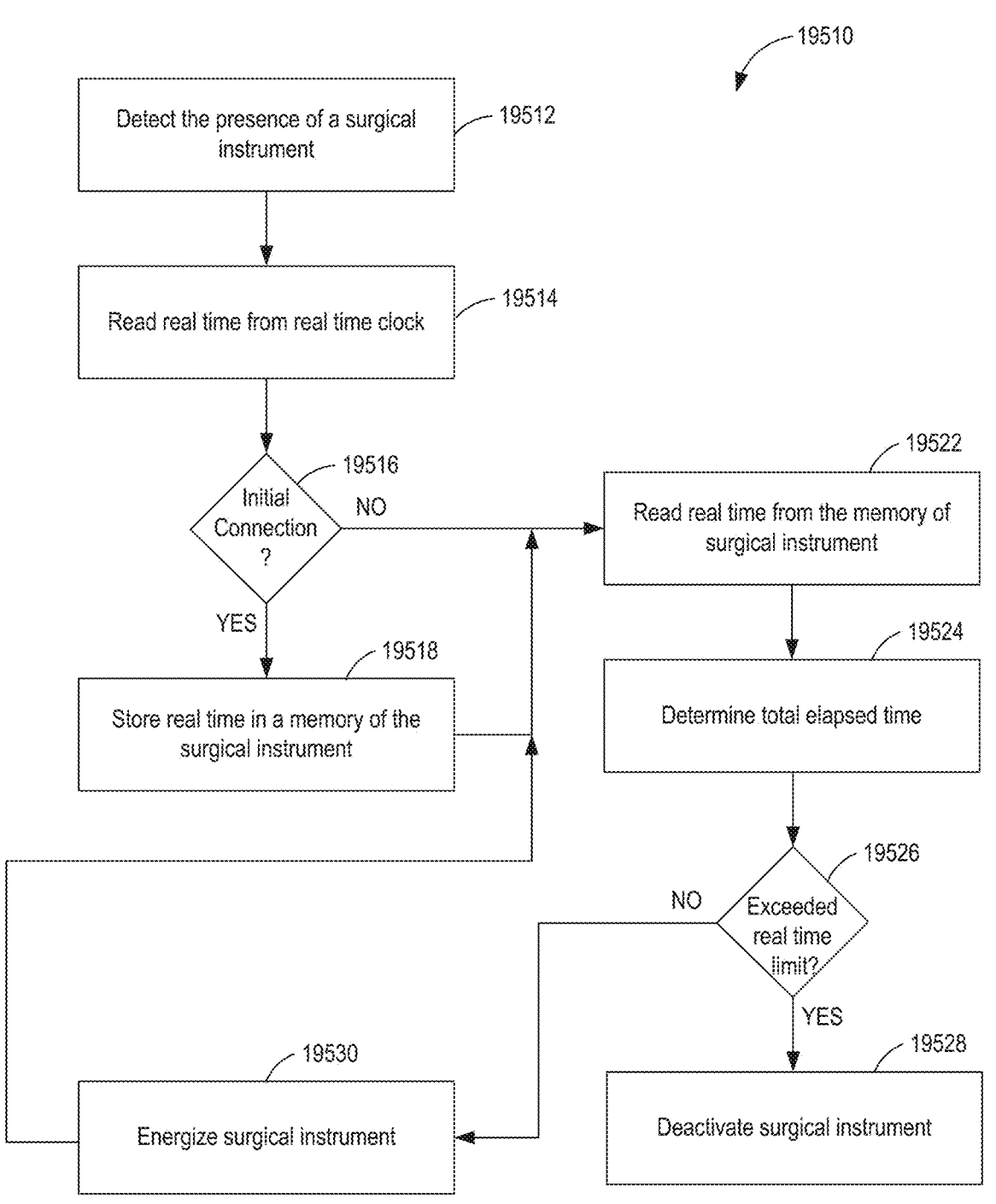
Figure 188:
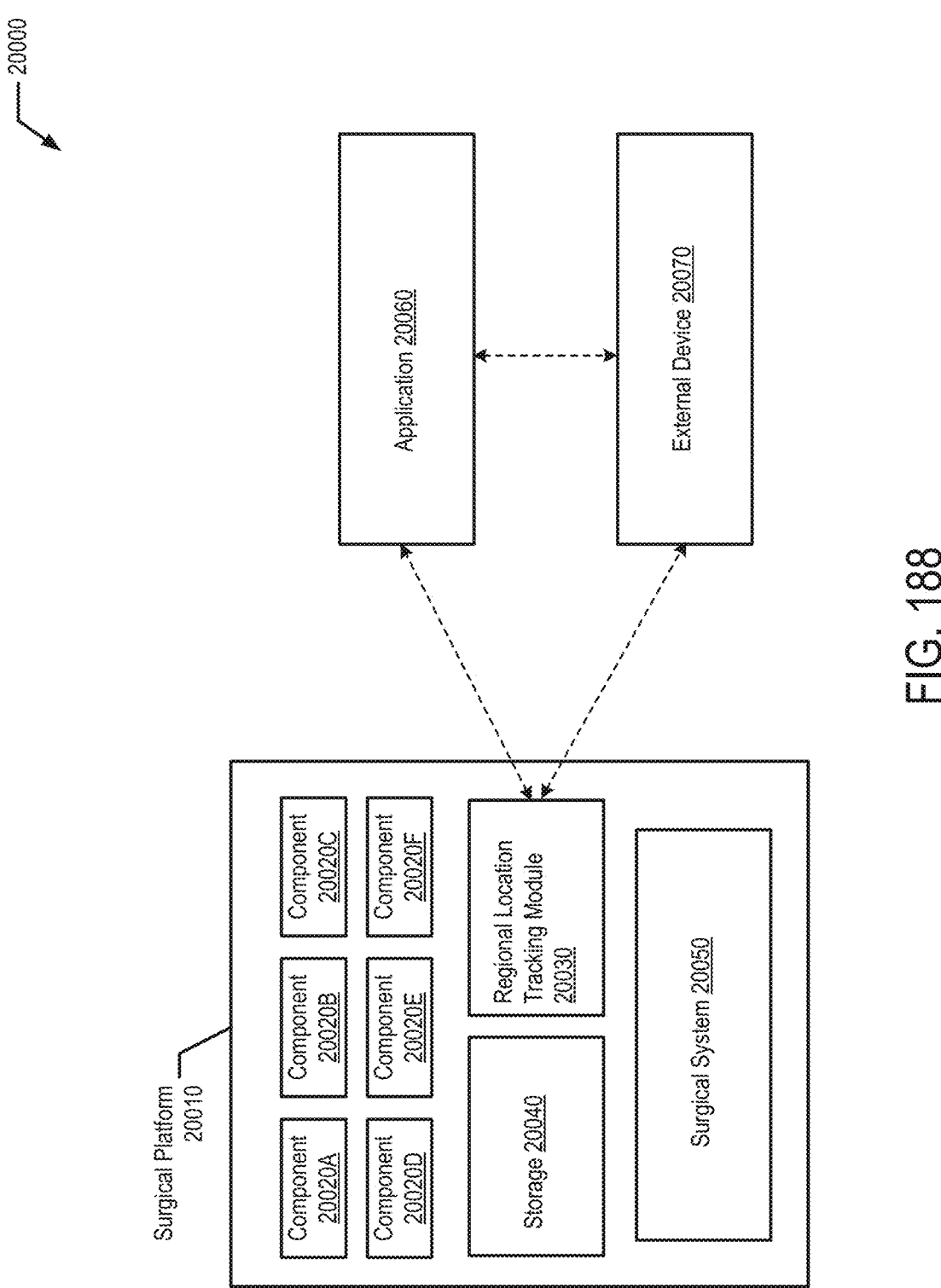

FIG. 187 is a logic diagram of a process depicting a control program or a logic configuration for tracking instruments in real time, in accordance with at least one aspect of the FIG. 188 is a schematic diagram of a system including a surgical platform, an application, and an external device, in accordance with at least one aspect of the present disclosure.

Figure 189:
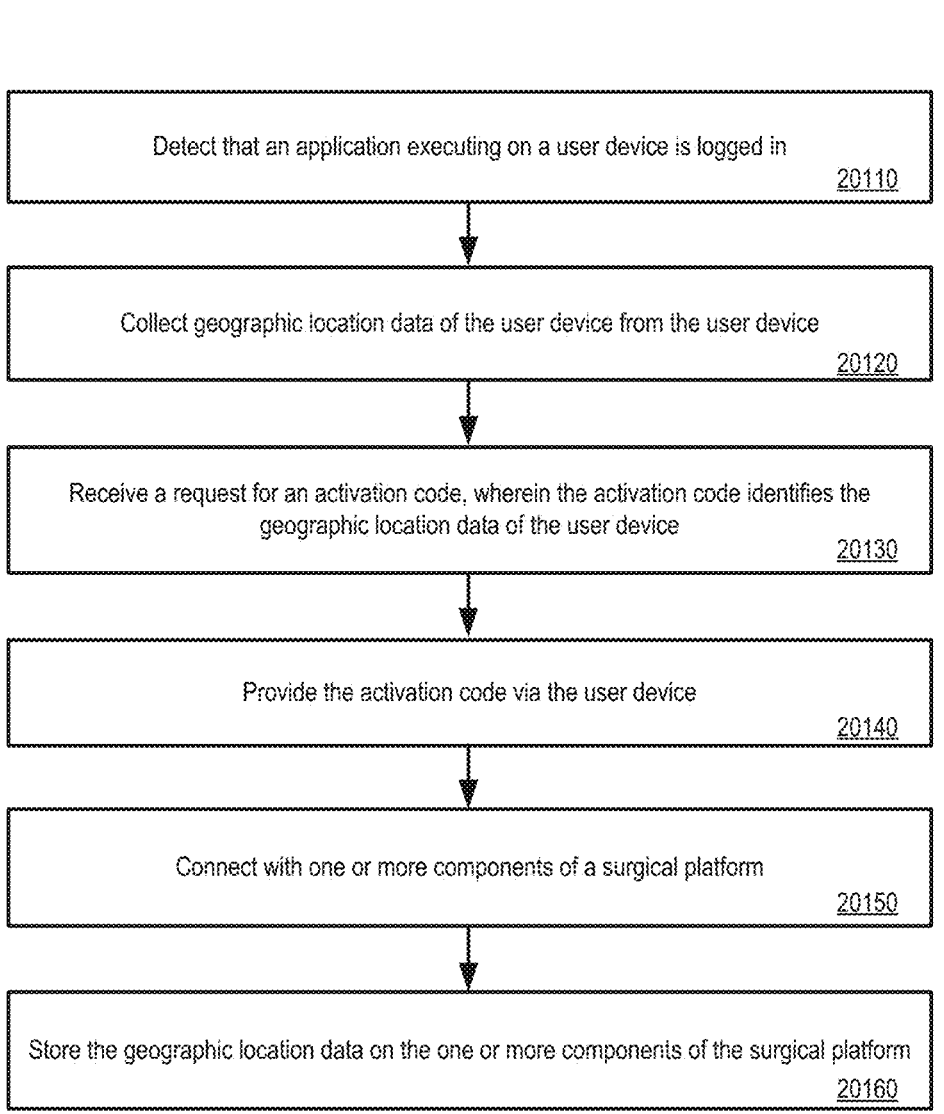

FIG. 189 is a logic diagram of a process depicting a control program or a logic configuration for determining a geographical location of one or more components of a surgical platform, in accordance with at least one aspect of the present disclosure.

FIG. 190 is a logic diagram of a process depicting a control program or a logic configuration for upgrading software logic for one or more components of a surgical platform based on a geographical location of the one or more components, in accordance with at least one aspect of the present disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Applicant of the present application owns the following U.S. Patent Applications filed on Sep. 5, 2019, the disclosure of each of which is herein incorporated by reference in its entirety:

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,144, titled METHOD FOR CONTROLLING A MODULAR ENERGY SYSTEM USER INTERFACE, now U.S. Pat. No. 11,471,206;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Pat. No. 11,218,822;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Pat. No. 11,350,978;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Pat. No. 11,510,720;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29,704,610, titled ENERGY MODULE, now U.S. Design Pat. No. D928,725;

U.S. Design patent application Ser. No. 29/704,614, titled ENERGY MODULE MONOPOLAR PORT WITH FOURTH SOCKET AMONG THREE OTHER SOCKETS, now U.S. Design Pat. No. D928,726;

U.S. Design patent application Ser. No. 29/704,616, titled BACKPLANE CONNECTOR FOR ENERGY MODULE, now U.S. Design Pat. No. D924,139; and U.S. Design patent application Ser. No. 29/704,617, titled ALERT SCREEN FOR ENERGY MODULE, now U.S. Design Pat. No. D939,545.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Figure 1:
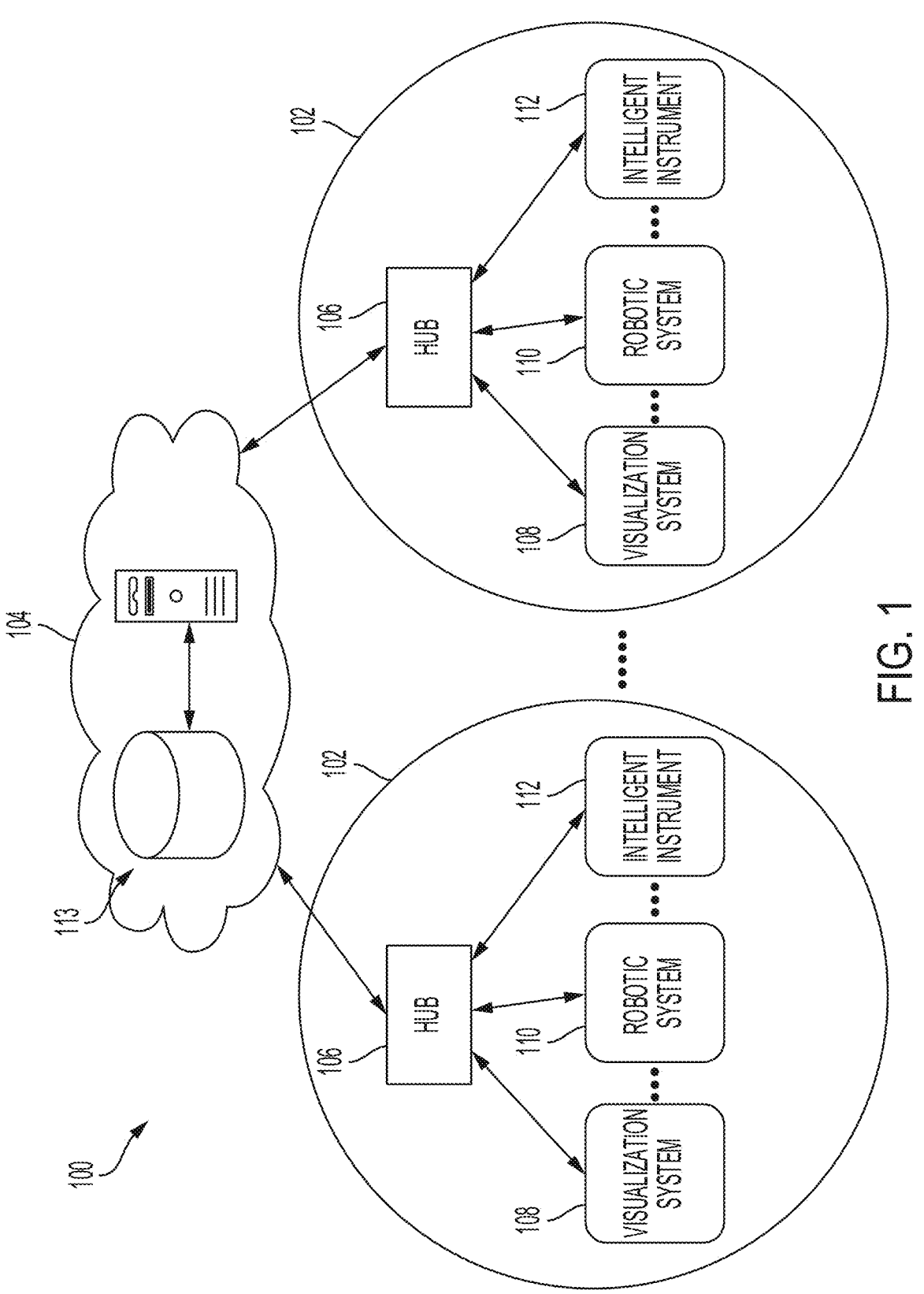
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
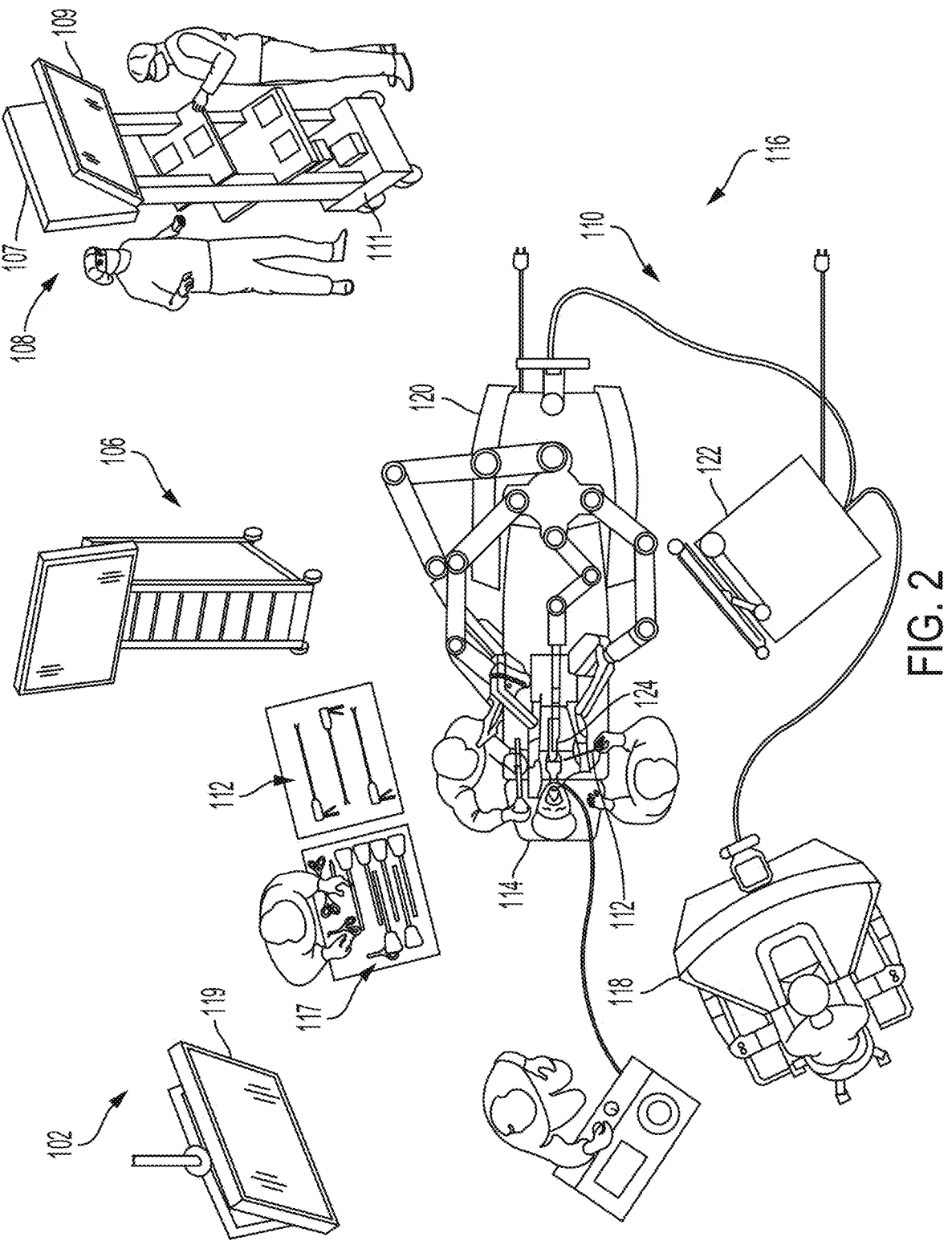
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
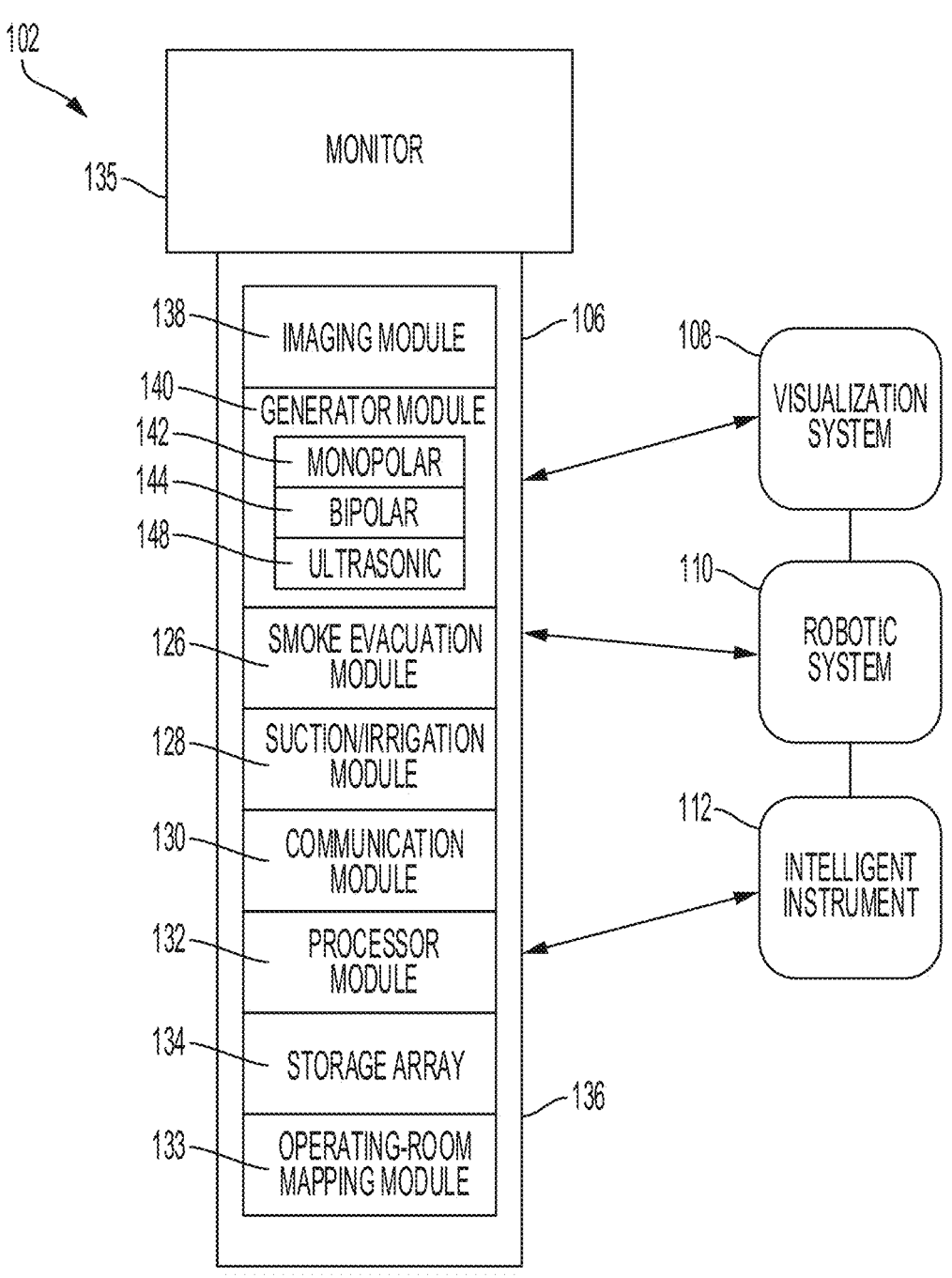
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 4:
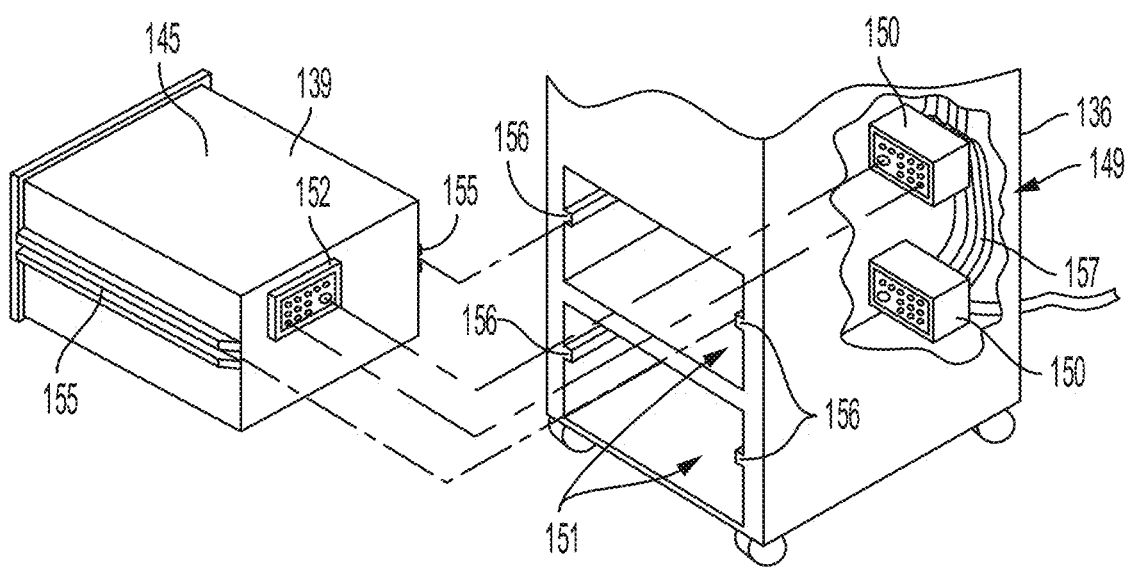
FIG. 4 is a partial perspective view of a surgical hub enclosure, and of a combo generator module slidably receivable in a drawer of the surgical hub enclosure, in accordance with at least one aspect of the present disclosure.
Figure 5:
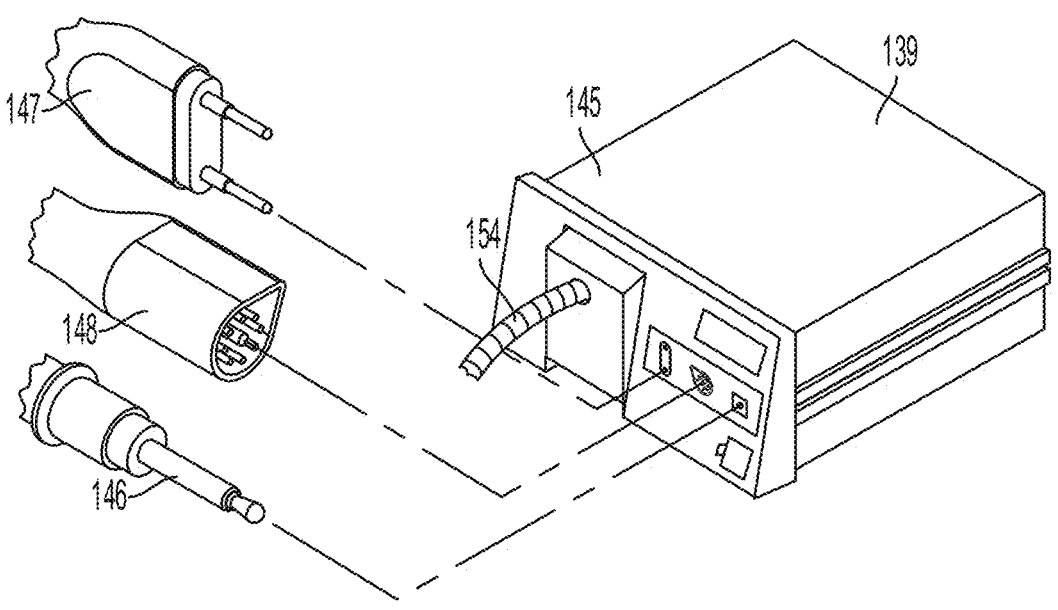
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
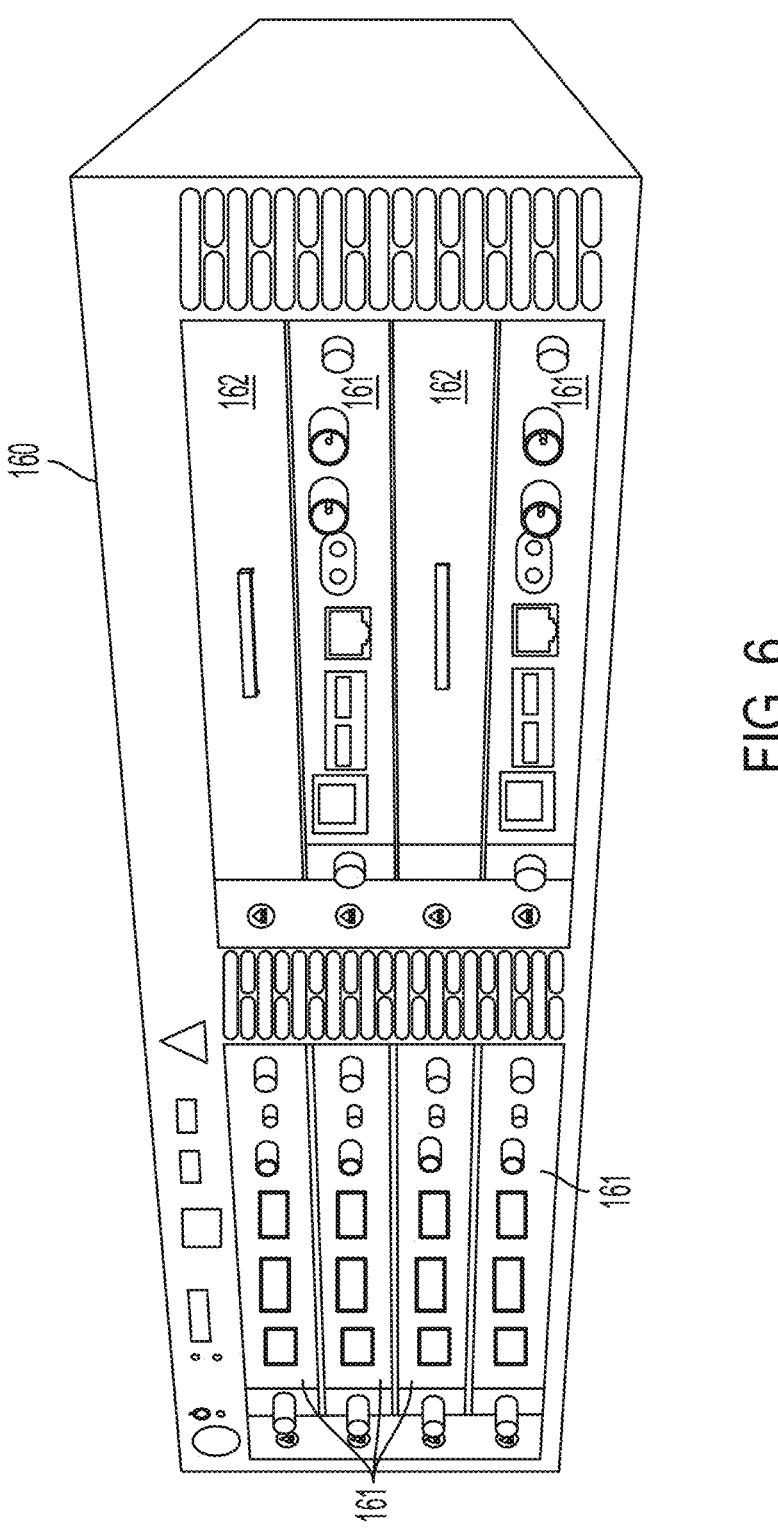
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
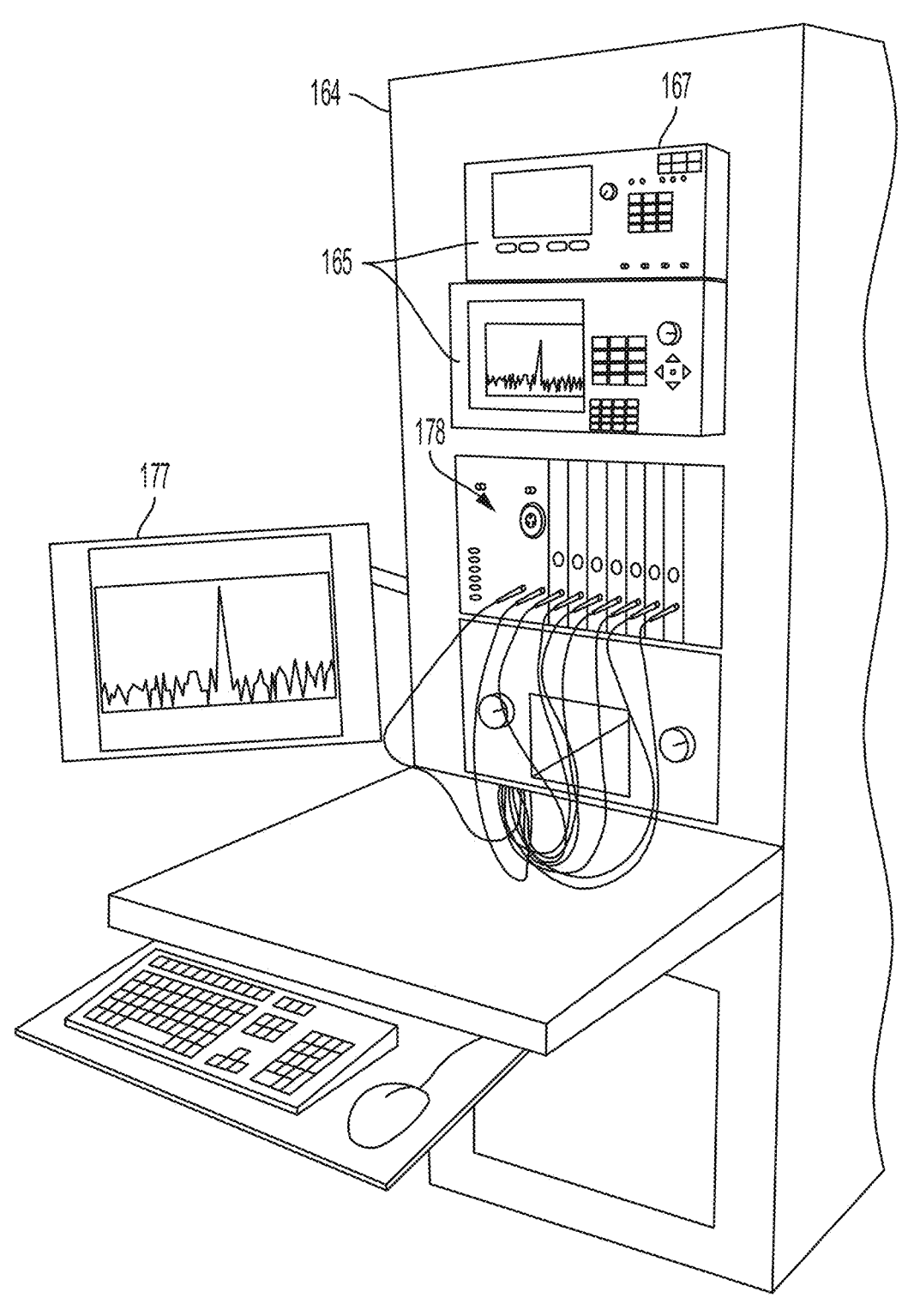
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
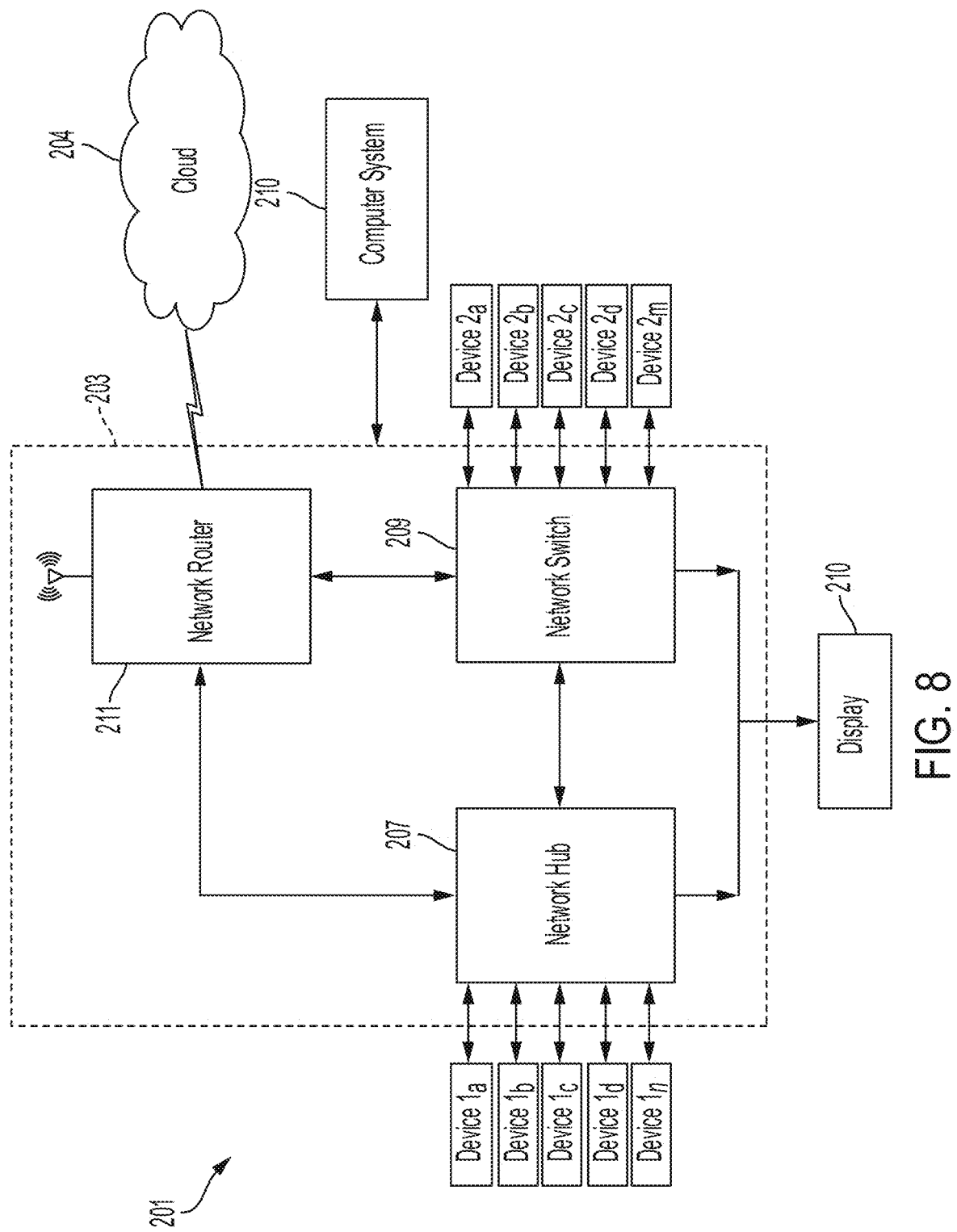
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
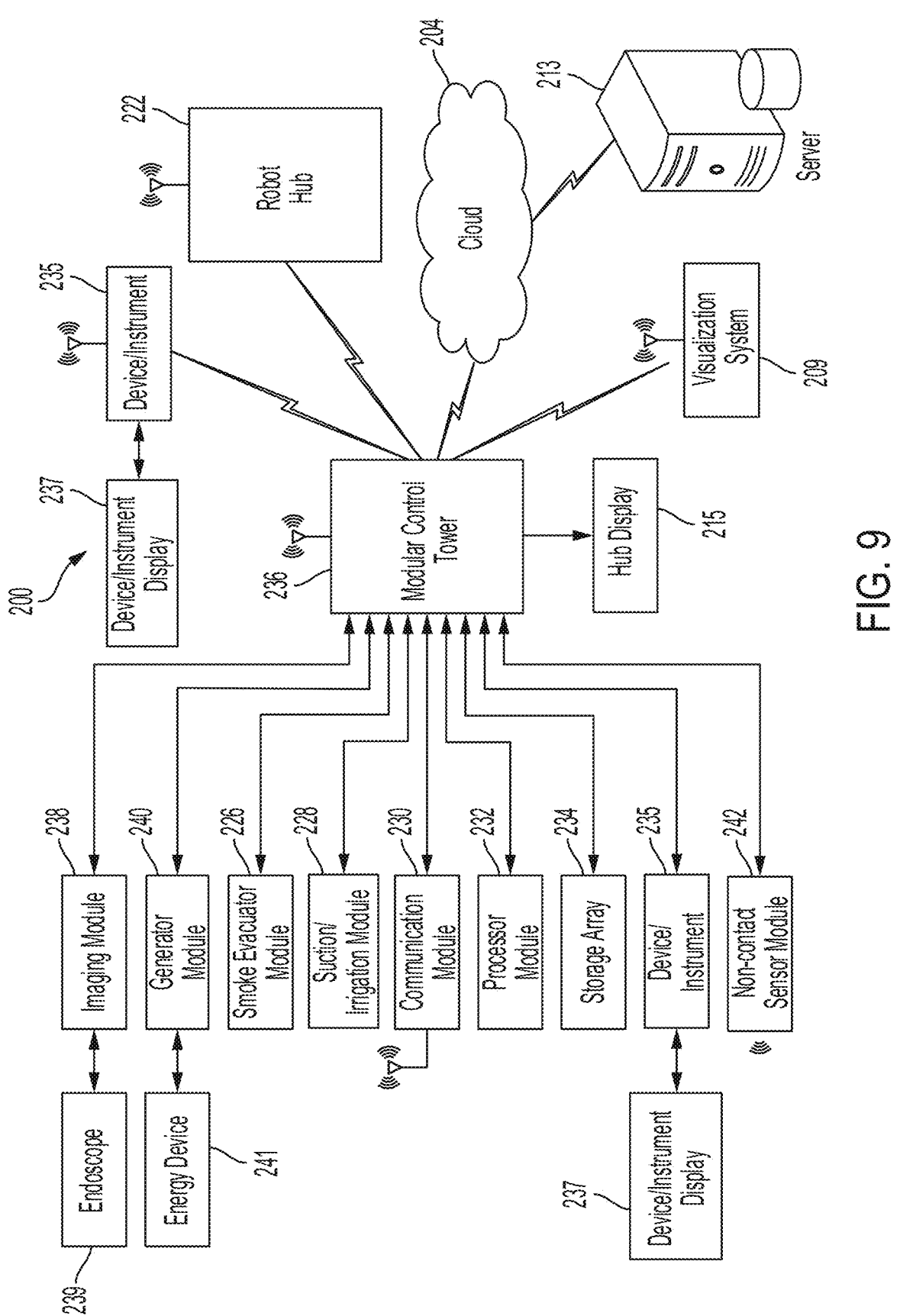
FIG. 9 illustrates a computer-implemented interactive surgical system, in accordance with at least one aspect of the present disclosure.
Figure 10:
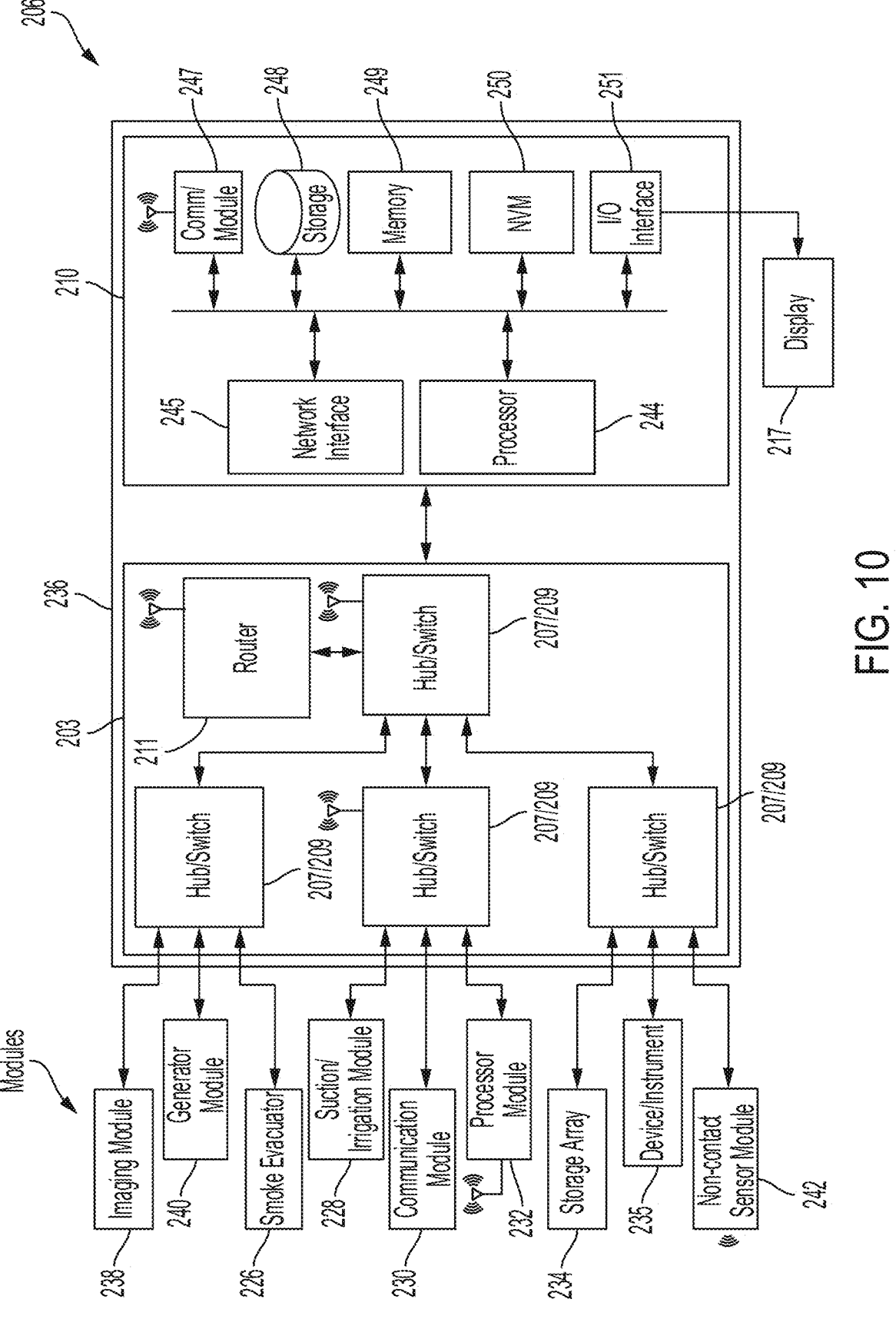
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
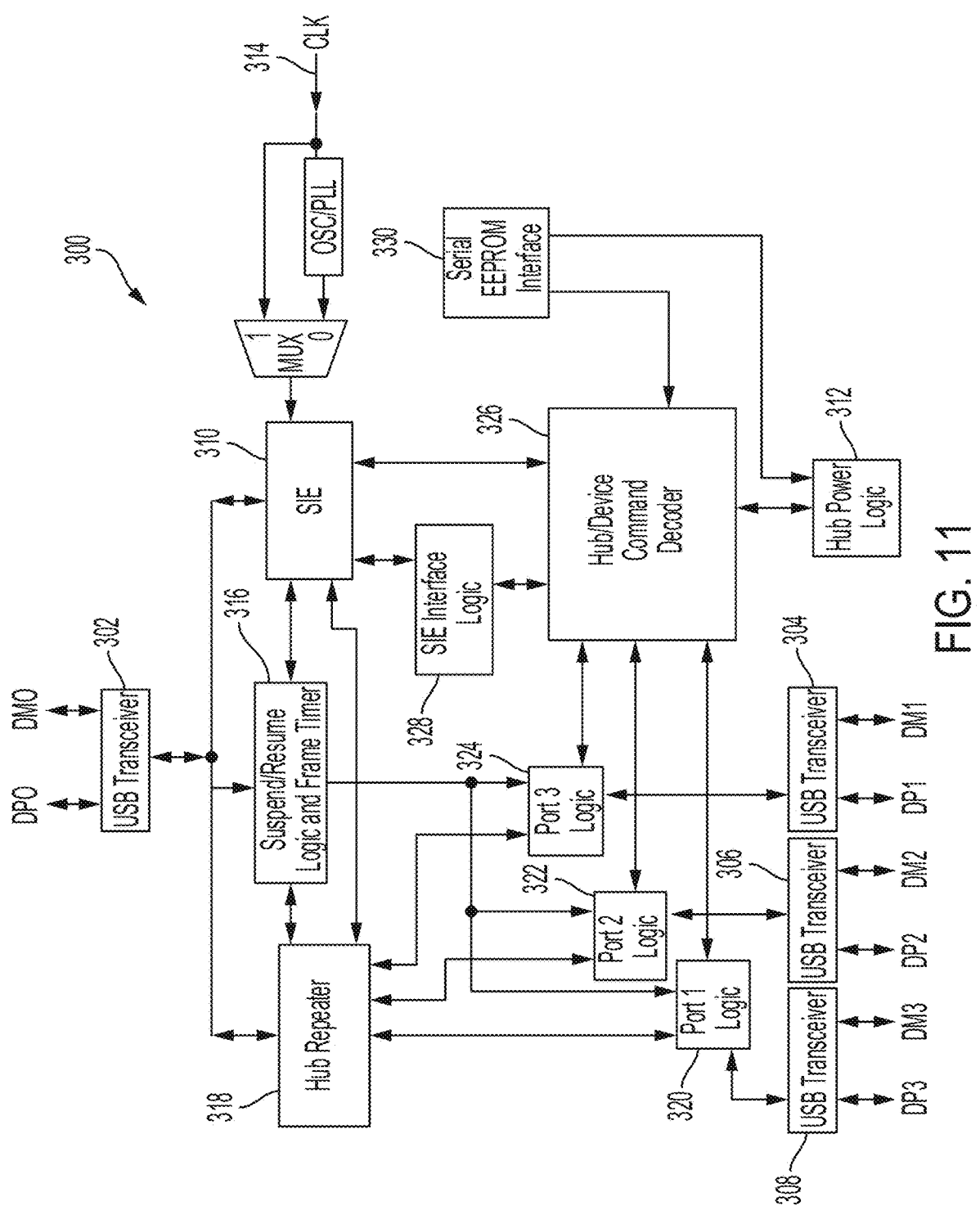
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
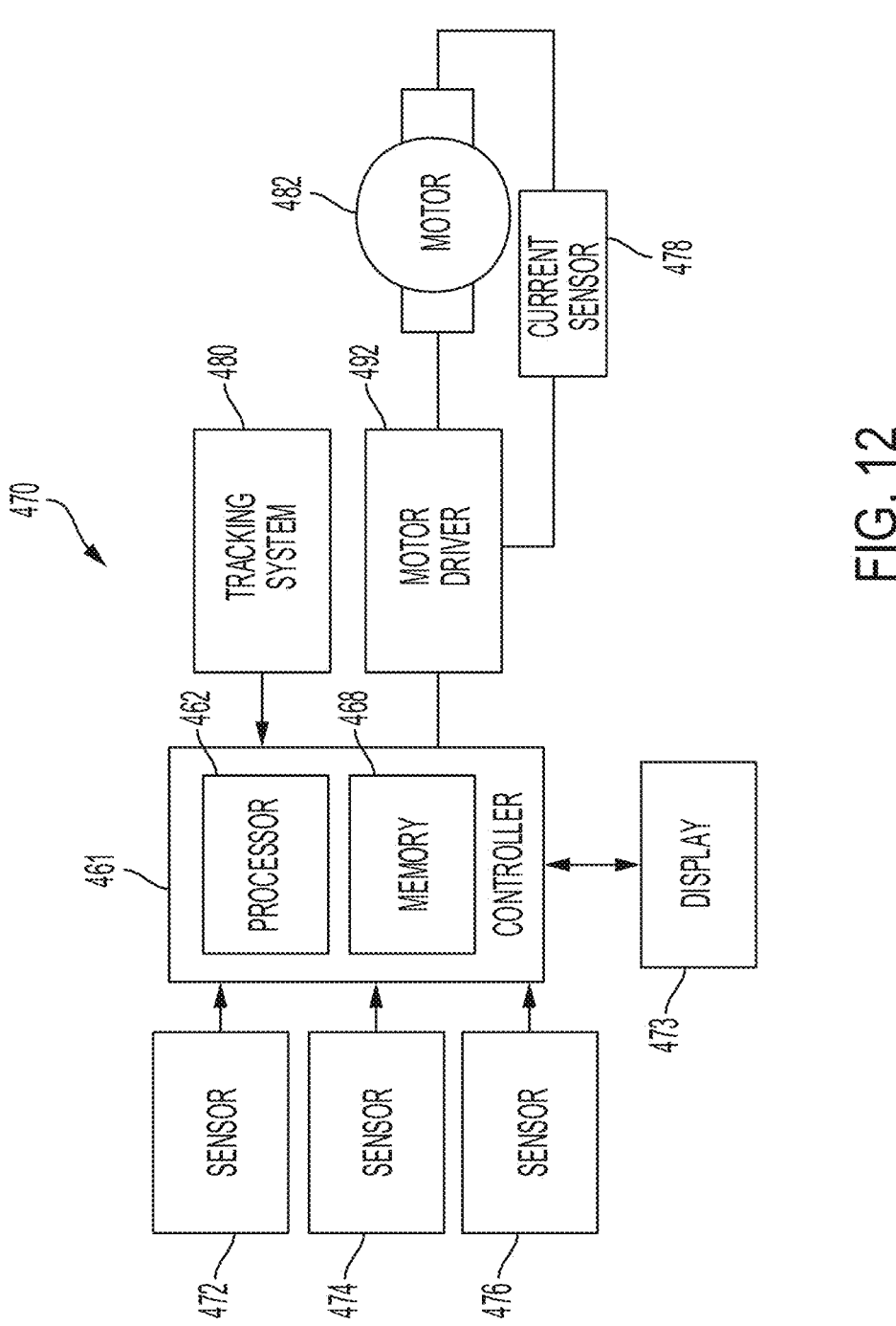
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member. In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+ \ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertia, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
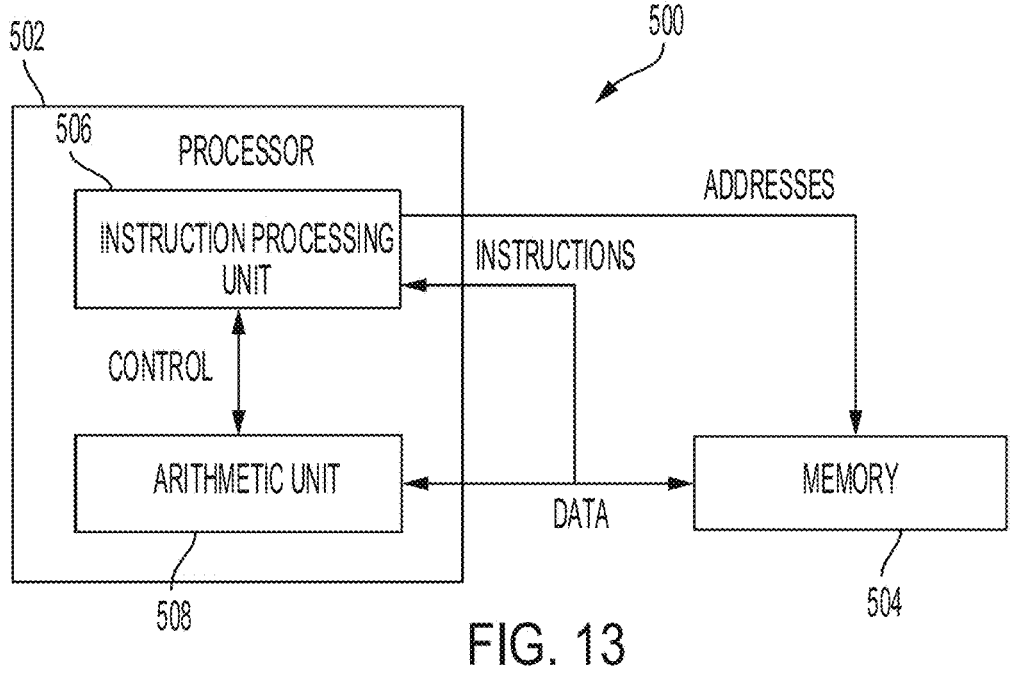
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
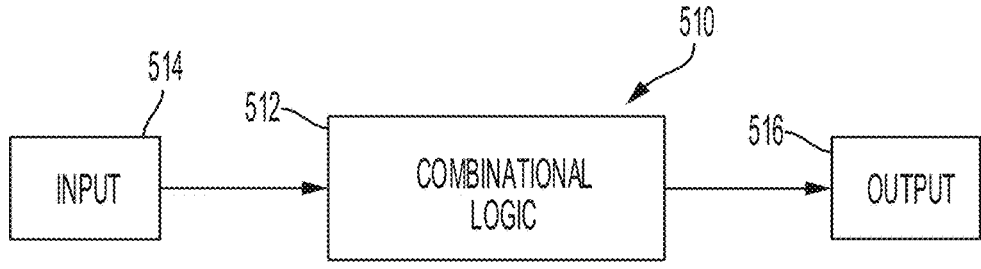
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
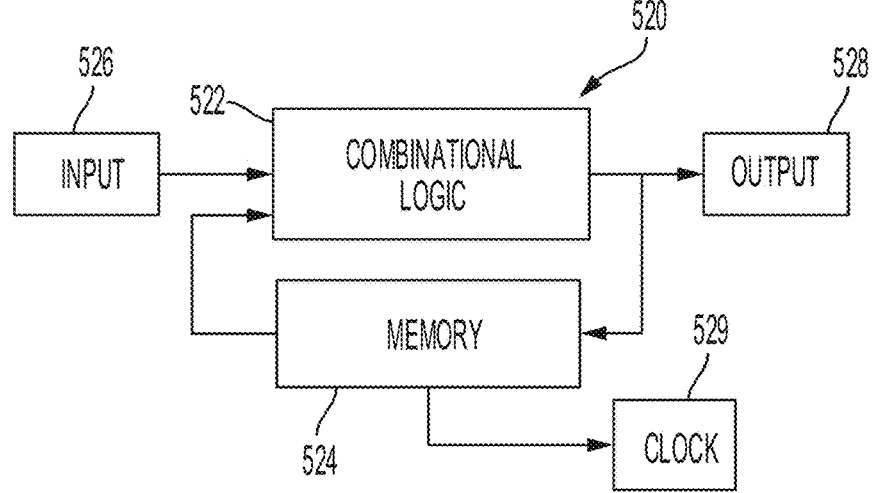
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
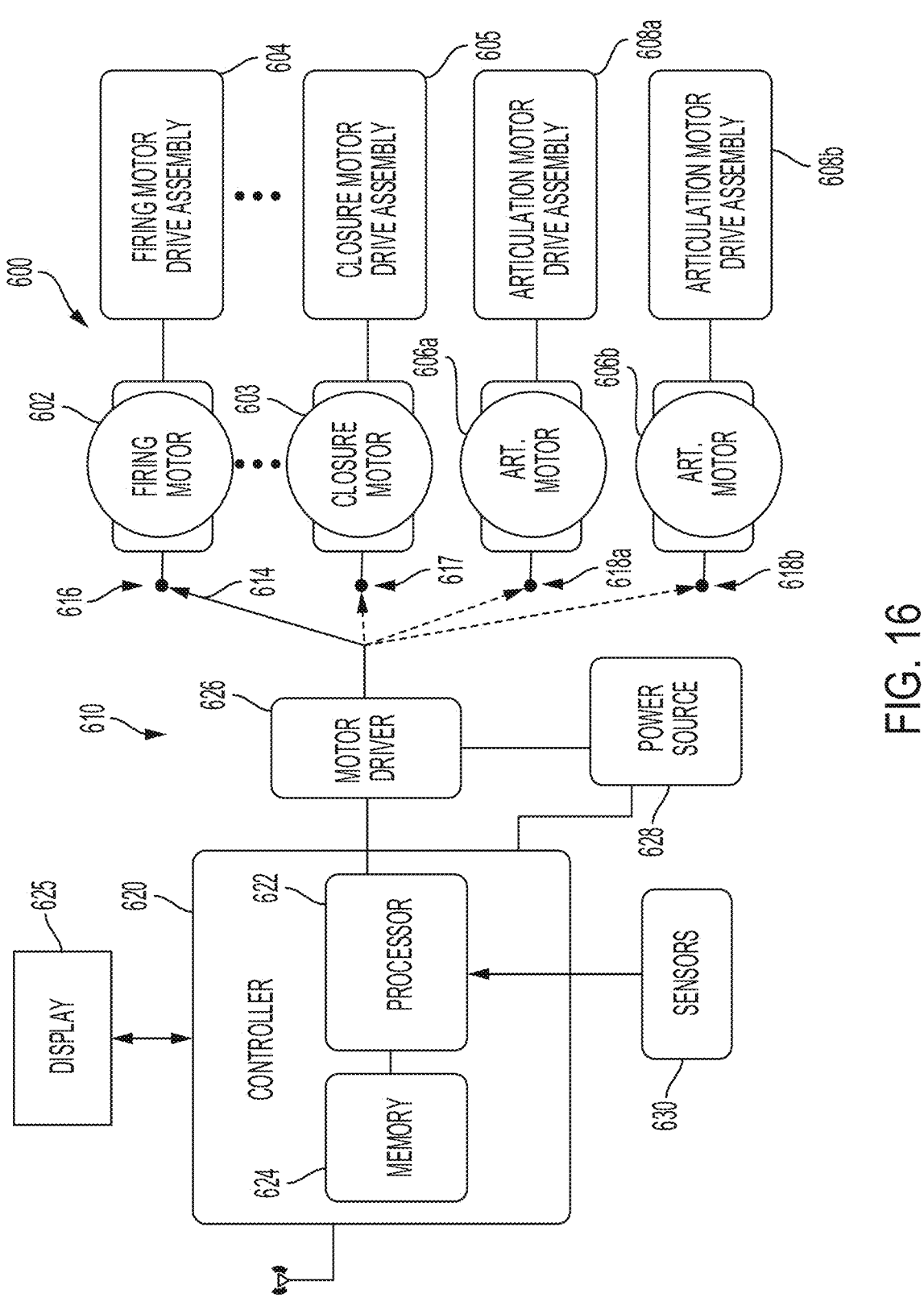
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
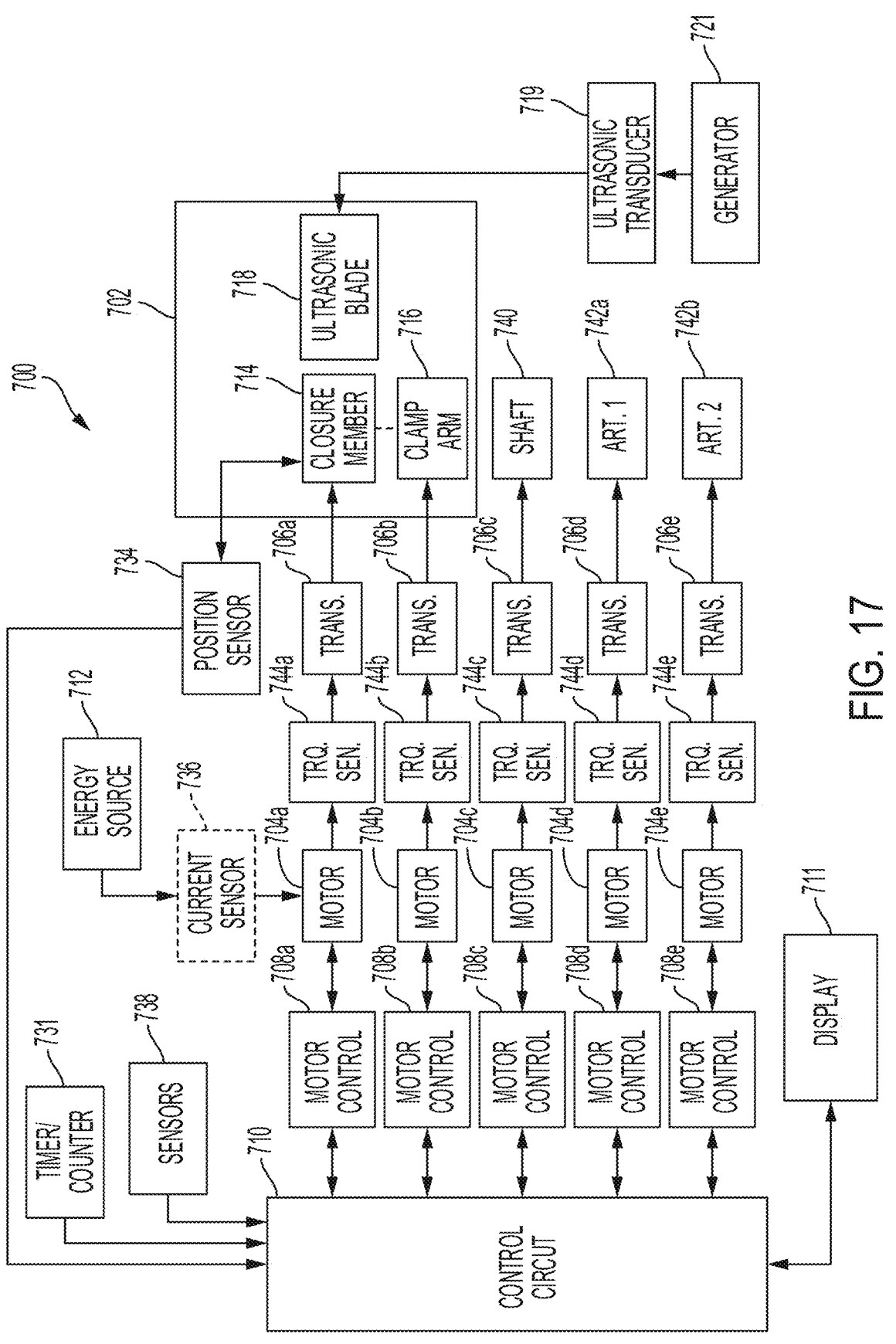
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742*a*, 742*b*.

In one aspect, the control circuit 710 may generate motor set point signals. The motor set point signals may be provided to various motor controllers 708*a*-708*e*. The motor controllers 708*a*-708*e* may comprise one or more circuits configured to provide motor drive signals to the motors 704*a*-704*e* to drive the motors 704*a*-704*e* as described herein. In some examples, the motors 704*a*-704*e* may be brushed DC electric motors. For example, the velocity of the motors 704*a*-704*e* may be proportional to the respective motor drive signals. In some examples, the motors 704*a*-704*e* may be brushless DC electric motors, and the respective motor drive signals may comprise a PWM signal provided to one or more stator windings of the motors 704*a*-704*e*. Also, in some examples, the motor controllers 708*a*-708*e* may be omitted and the control circuit 710 may generate the motor drive signals directly.

In one aspect, the control circuit 710 may initially operate each of the motors 704*a*-704*e* in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704*a*-704*e* during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704*a*-704*e* based on translation data describing a position of the displacement member in a closed-loop manner to translate the displacement member at a constant velocity.

In one aspect, the motors 704*a*-704*e* may receive power from an energy source 712. The energy source 712 may be a DC power supply driven by a main alternating current power source, a battery, a super capacitor, or any other suitable energy source. The motors 704*a*-704*e* may be mechanically coupled to individual movable mechanical elements such as the closure member 714, clamp arm 716, shaft 740, articulation 742*a*, and articulation 742*b* via respective transmissions 706*a*-706*e*. The transmissions 706*a*-706*e* may include one or more gears or other linkage components to couple the motors 704*a*-704*e* to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704*a*-704*e* is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704*a*-704*e* include a torque sensor 744*a*-744*e* to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708*a*, which provides a drive signal to the motor 704*a*. The output shaft of the motor 704*a* is coupled to a torque sensor 744*a*. The torque sensor 744*a* is coupled to a transmission 706*a* which is coupled to the closure member 714. The transmission 706*a* comprises movable mechanical elements such as rotating elements and a firing member to control the movement of the closure member 714 distally and proximally along a longitudinal axis of the end effector 702. In one aspect, the motor 704*a* may be coupled to the knife gear assembly, which includes a knife gear reduction set that includes a first knife drive gear and a second knife drive gear. A torque sensor 744*a* provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708b. In response to the closure signal, the motor 704b advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
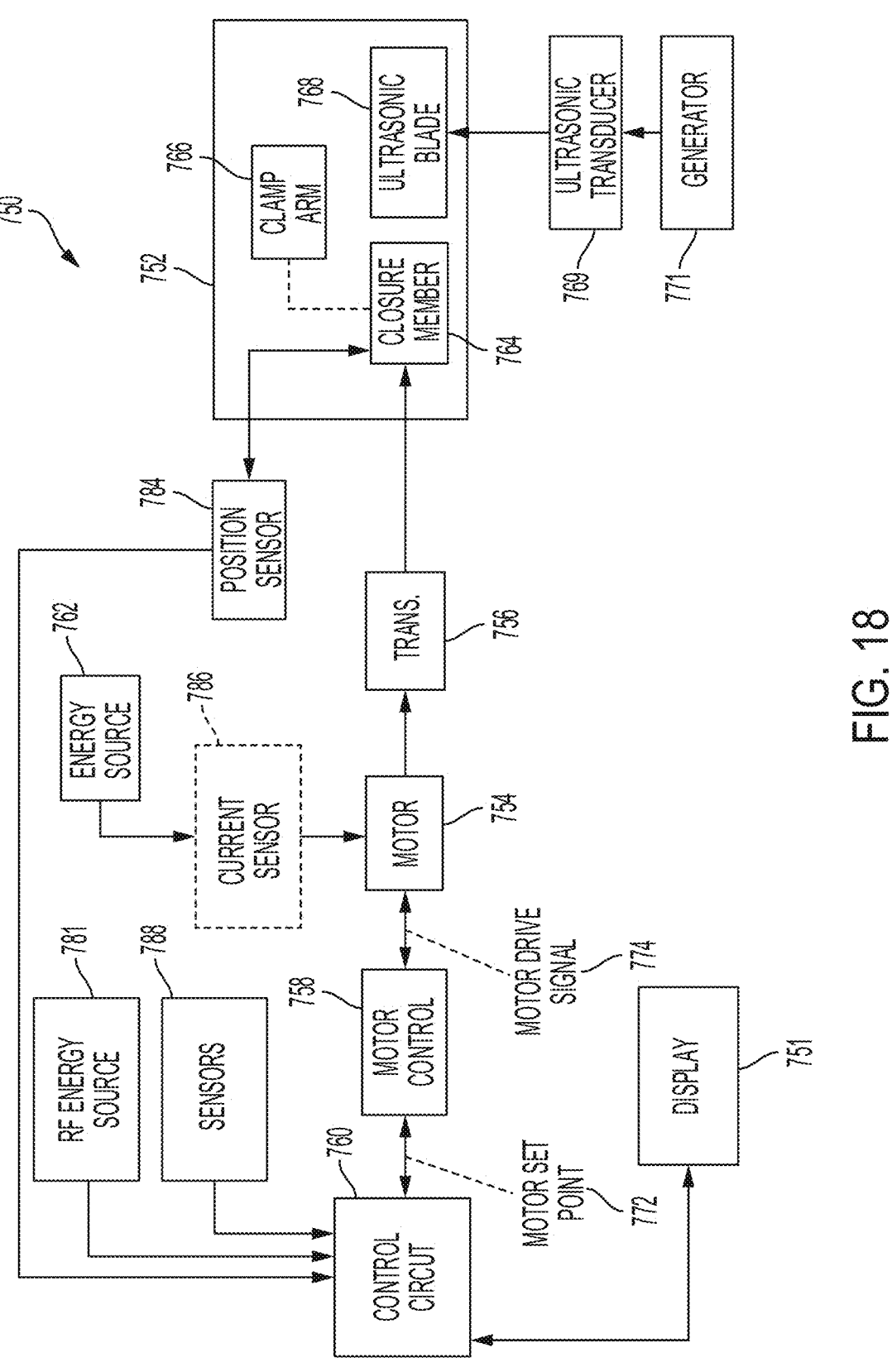
FIG. 18 illustrates a block diagram of a surgical instrument programmed to control the distal translation of a displacement member, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
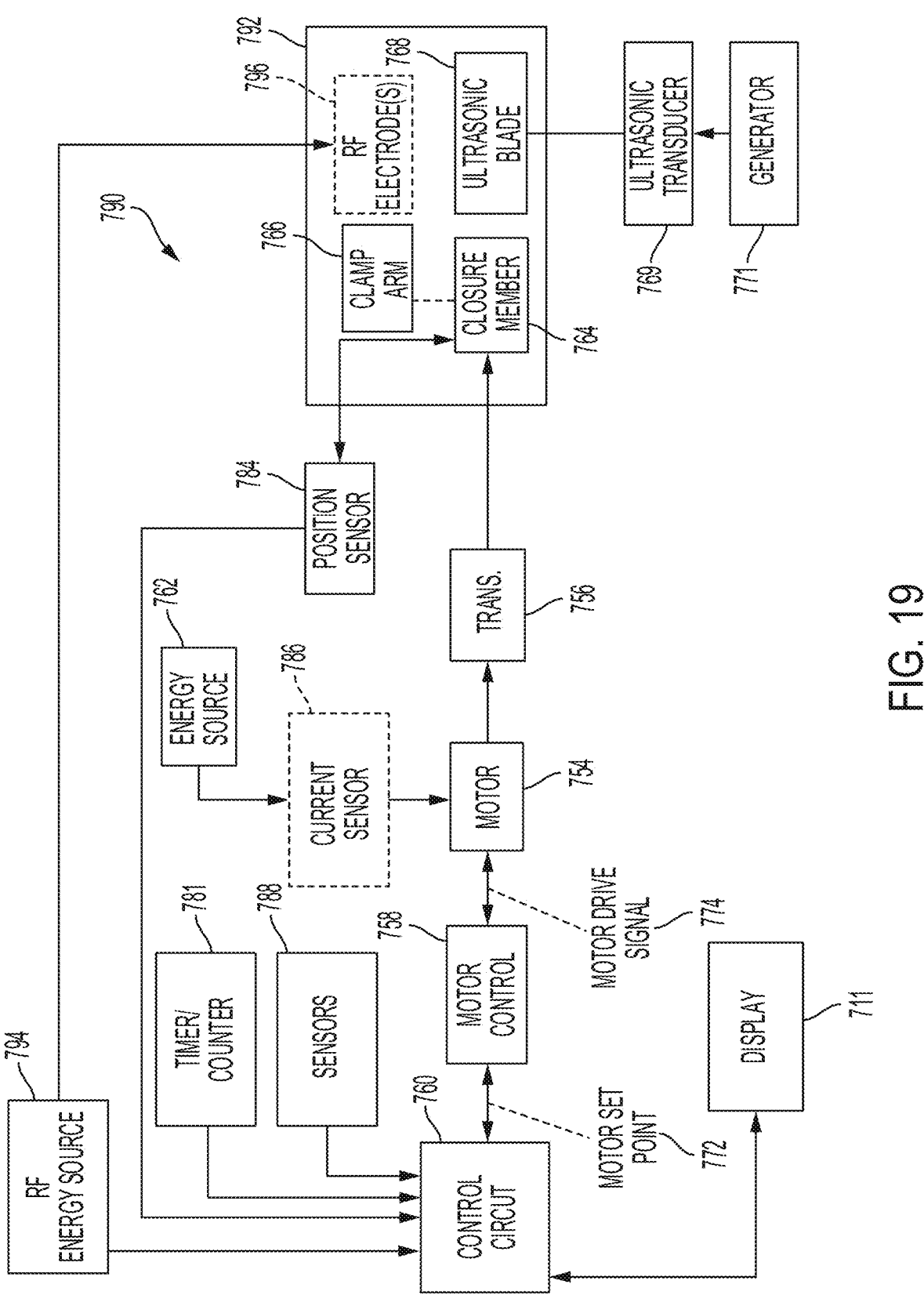
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOS-FET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 12-19, for example. Accordingly, the following description of adaptive ultrasonic blade control algorithms should be read in conjunction with FIGS. 12-19 and the description associated therewith.

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 20:
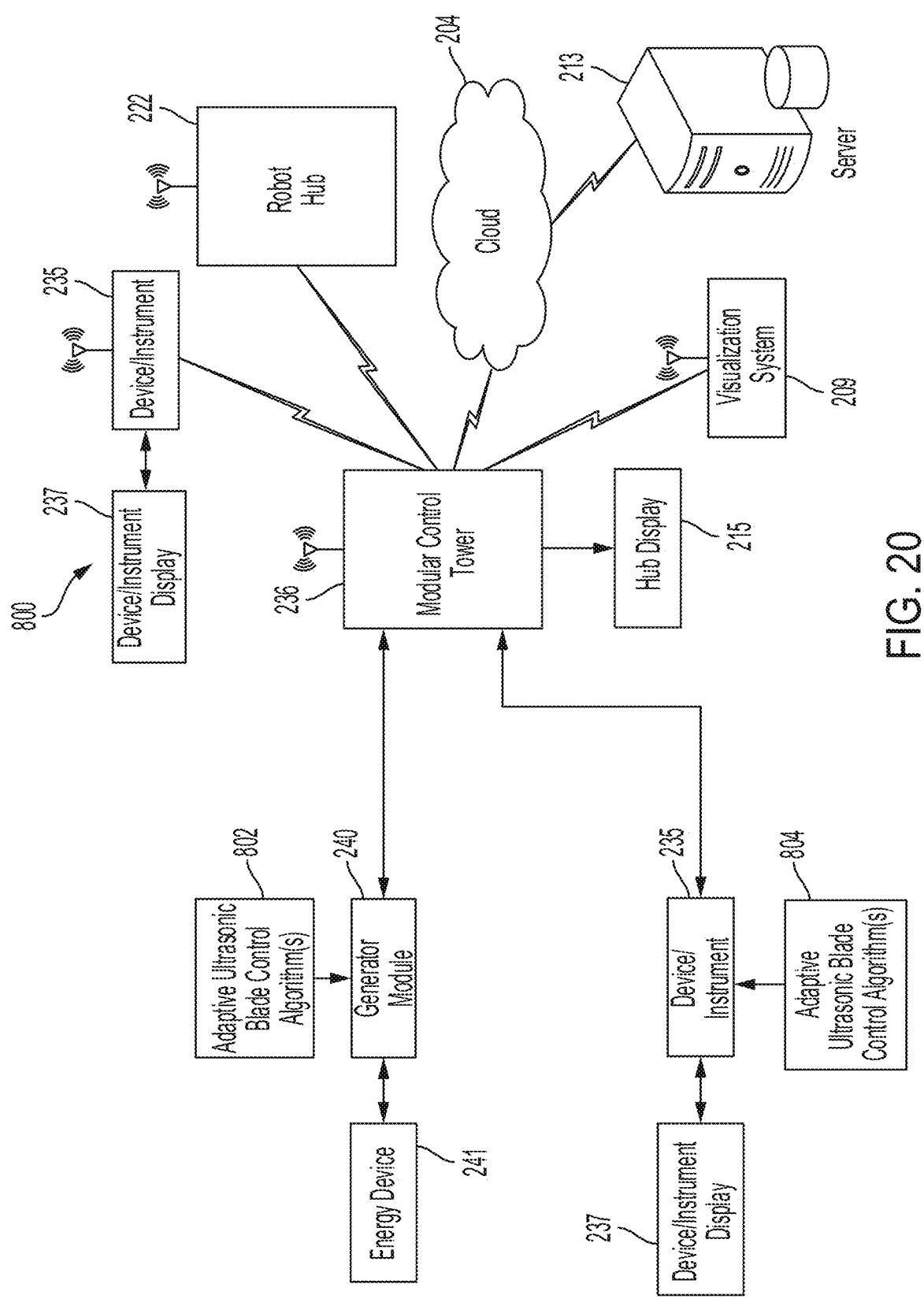
FIG. 20 is a system configured to execute adaptive ultrasonic blade control algorithms in a surgical data network comprising a modular communication hub, in accordance with at least one aspect of the present disclosure.

FIG. 20 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802. In another aspect, the device/instrument 235 is configured to execute the adaptive ultrasonic blade control algorithm(s) 804. In another aspect, both the generator module 240 and the device/instrument 235 are configured to execute the adaptive ultrasonic blade control algorithms 802, 804.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-22.

The generator module 240 or the device/instrument 235 or both are coupled the modular control tower 236 connected to multiple operating theater devices such as, for example, intelligent surgical instruments, robots, and other computerized devices located in the operating theater, as described with reference to FIGS. 8-11, for example.

Figure 21:
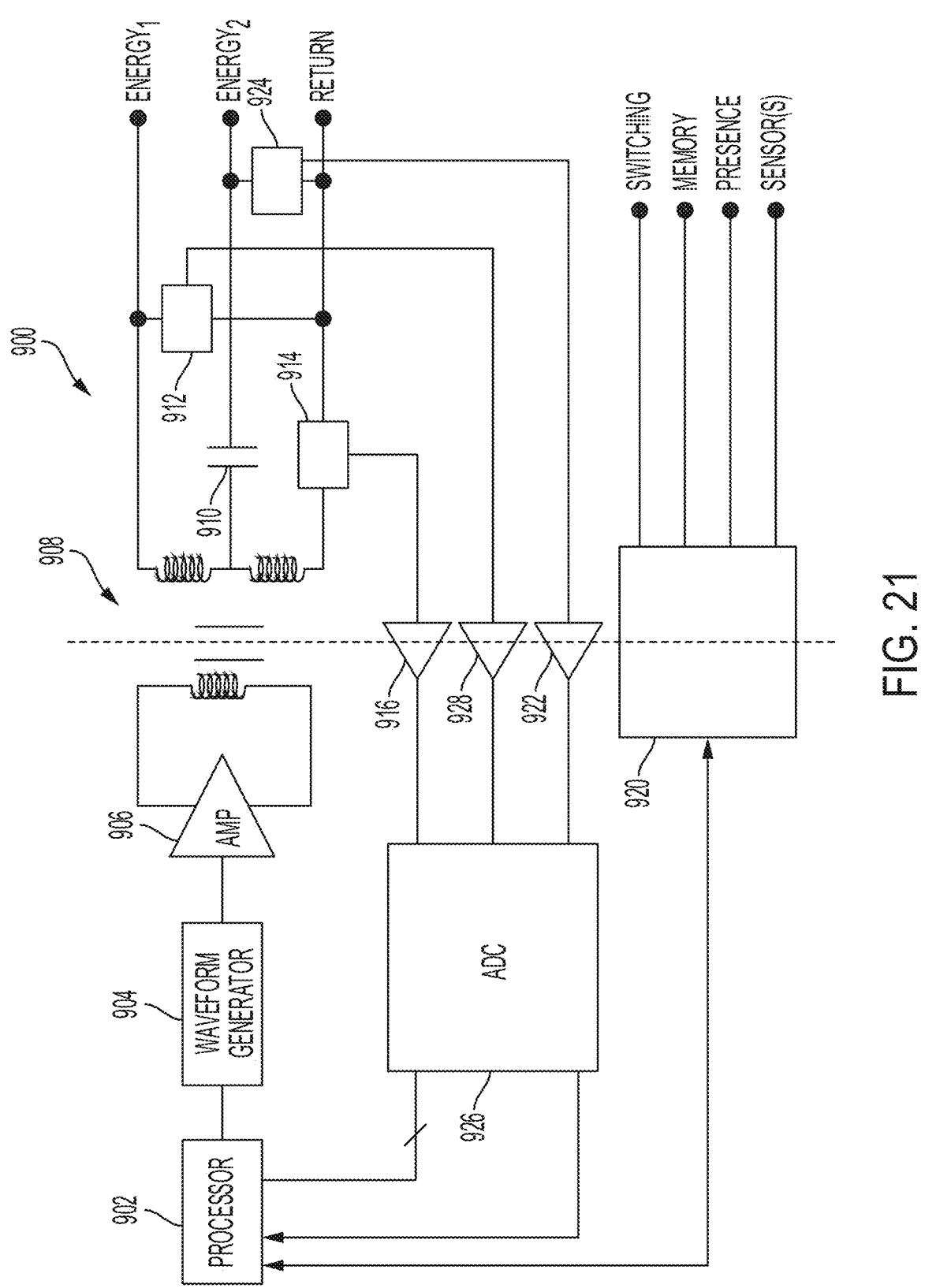
FIG. 21 illustrates an example of a generator, in accordance with at least one aspect of the present disclosure.

FIG. 21 illustrates an example of a generator 900, which is one form of a generator configured to couple to an ultrasonic instrument and further configured to execute adaptive ultrasonic blade control algorithms in a surgical data network comprising a modular communication hub as shown in FIG. 20. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY$_1$ and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be ultrasonic energy and the second energy modality ENERGY$_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 21. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 22:
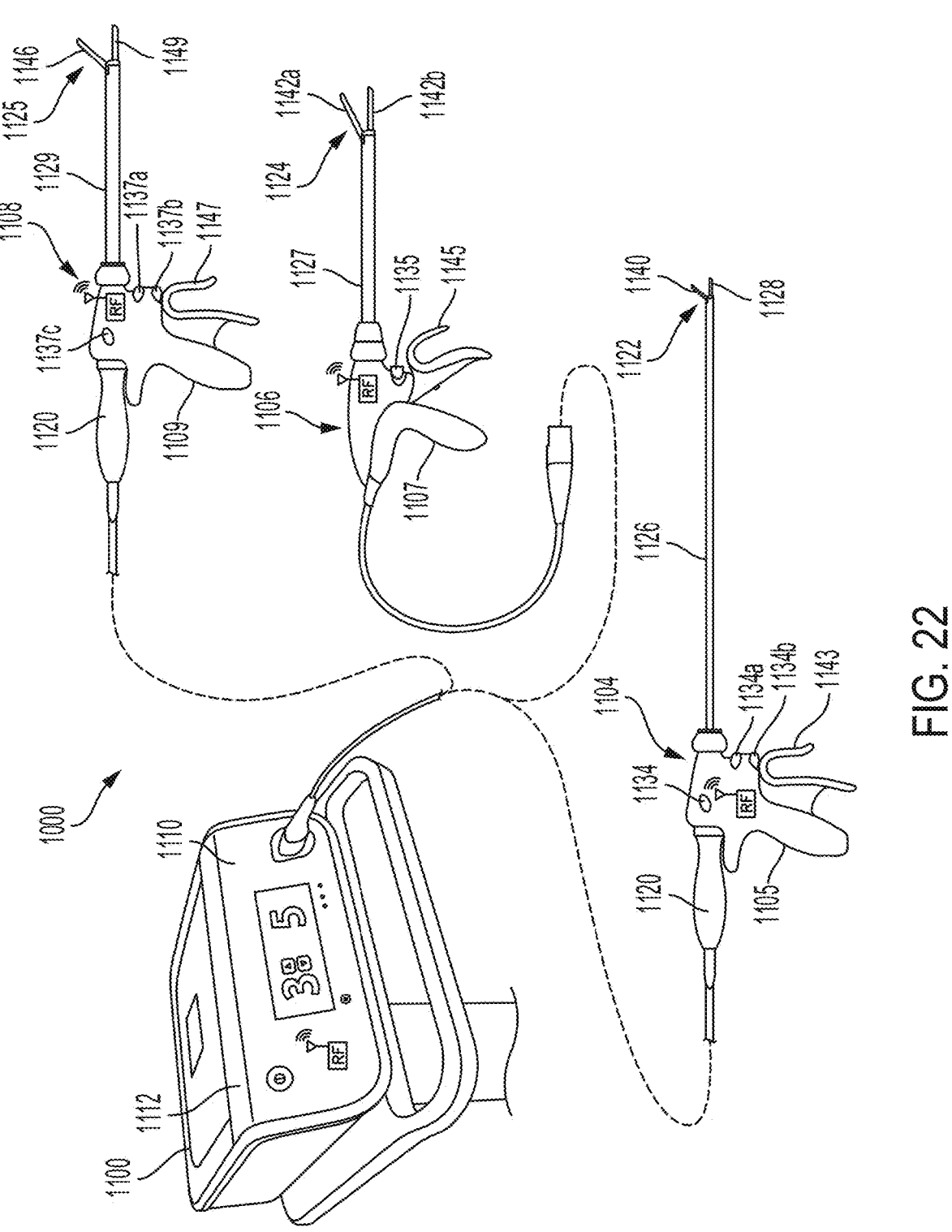
FIG. 22 is a surgical system comprising a generator and various surgical instruments usable therewith, in accordance with at least one aspect of the present disclosure.

FIG. 22 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 22 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 22 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 23:
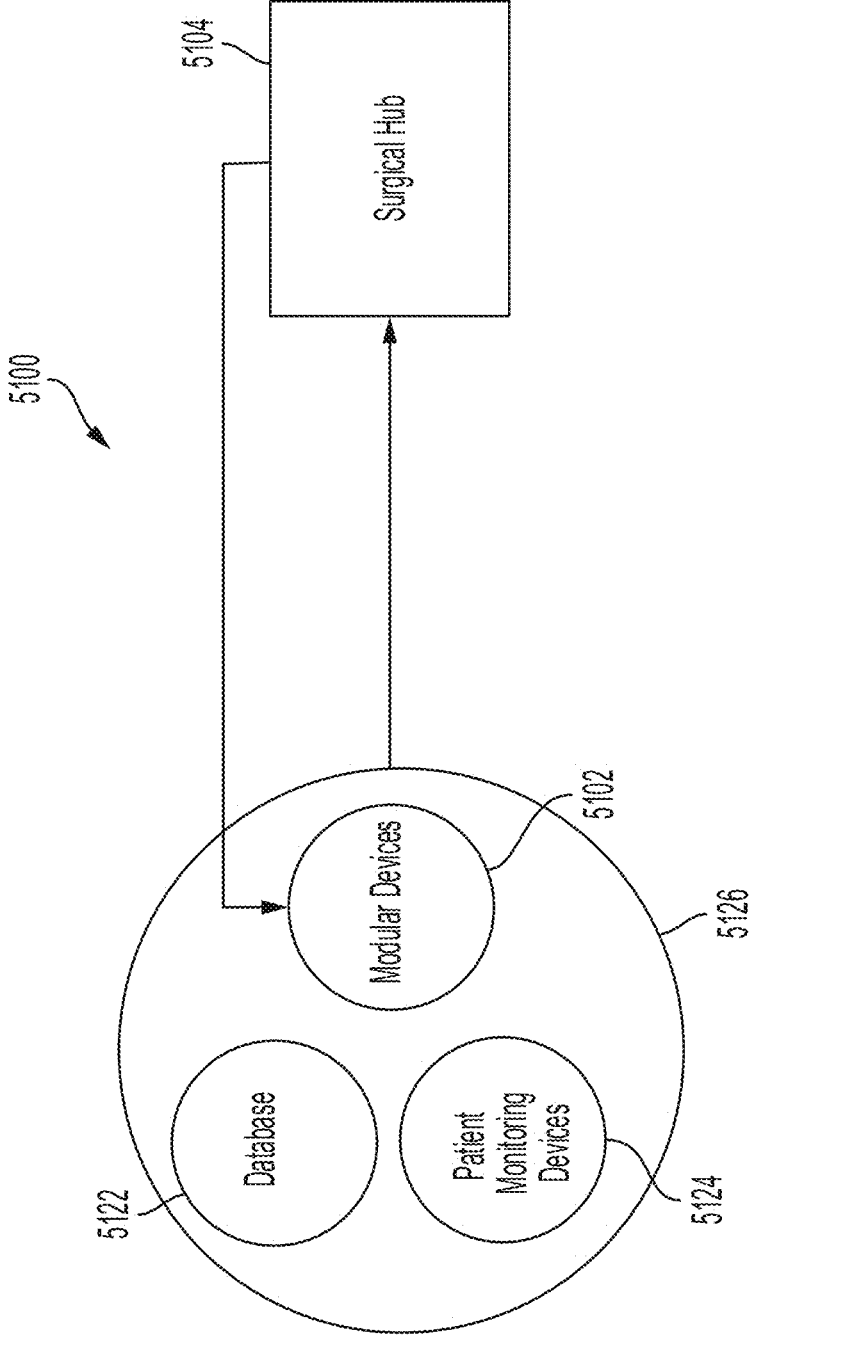
FIG. 23 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 23 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by a scanner, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-11, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 24-30. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIGS. 3 and 4. The modular energy system 2000 can also include a variety of different components or accessories that are also connectable to or otherwise associatable with the modules 2001. In another aspect, the modular energy system 2000 can be embodied as a generator module 140, 240 (FIGS. 3 and 10) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 24:
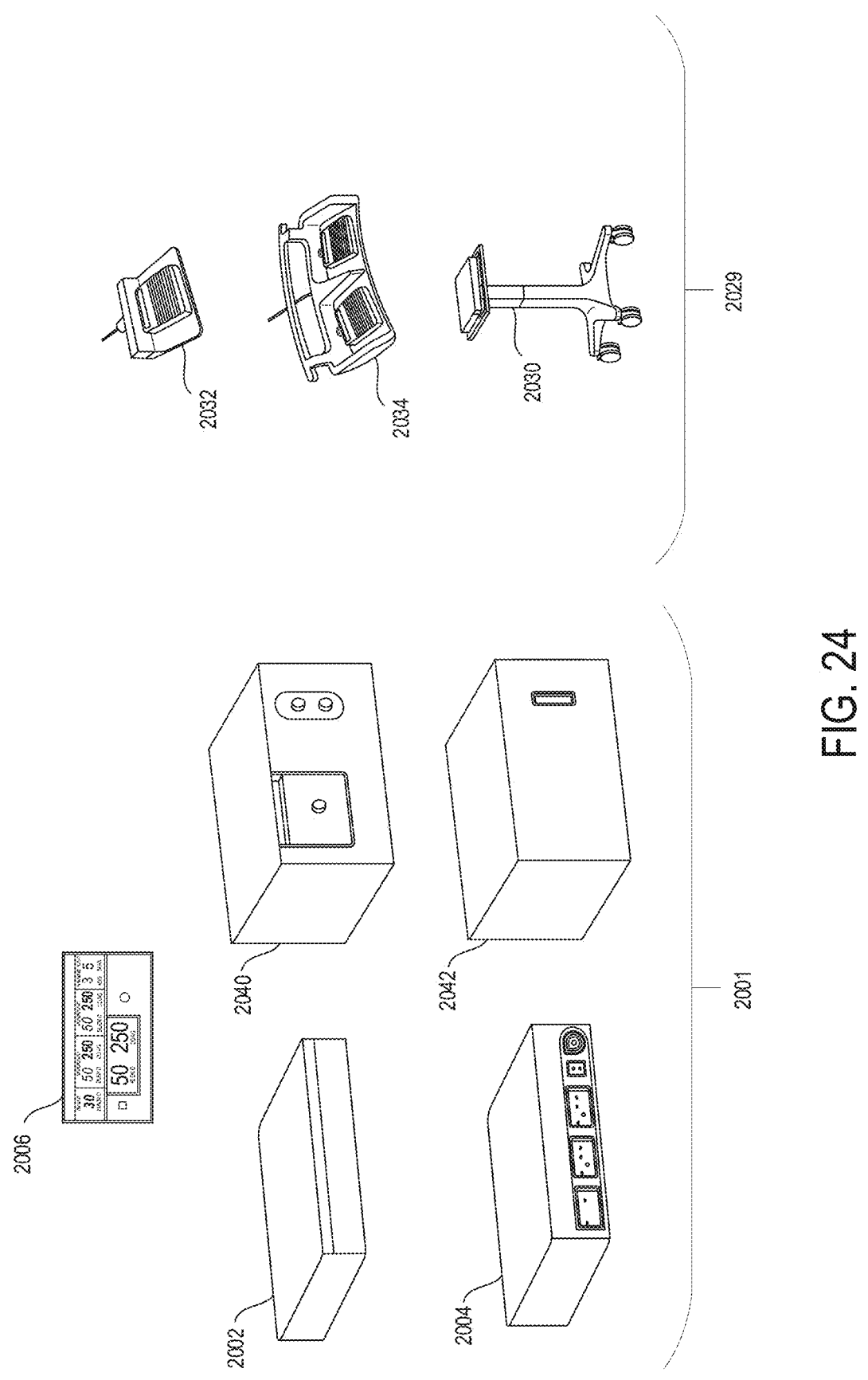
FIG. 24 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 24. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140, 240 (FIGS. 3 and 10), can be configured to generate one or multiple energy modalities for driving electrosurgical and/or ultrasonic surgical instruments connected thereto, such as is described above in connection with the generator 900 illustrated in FIG. 21. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-11.

Figure 25B:
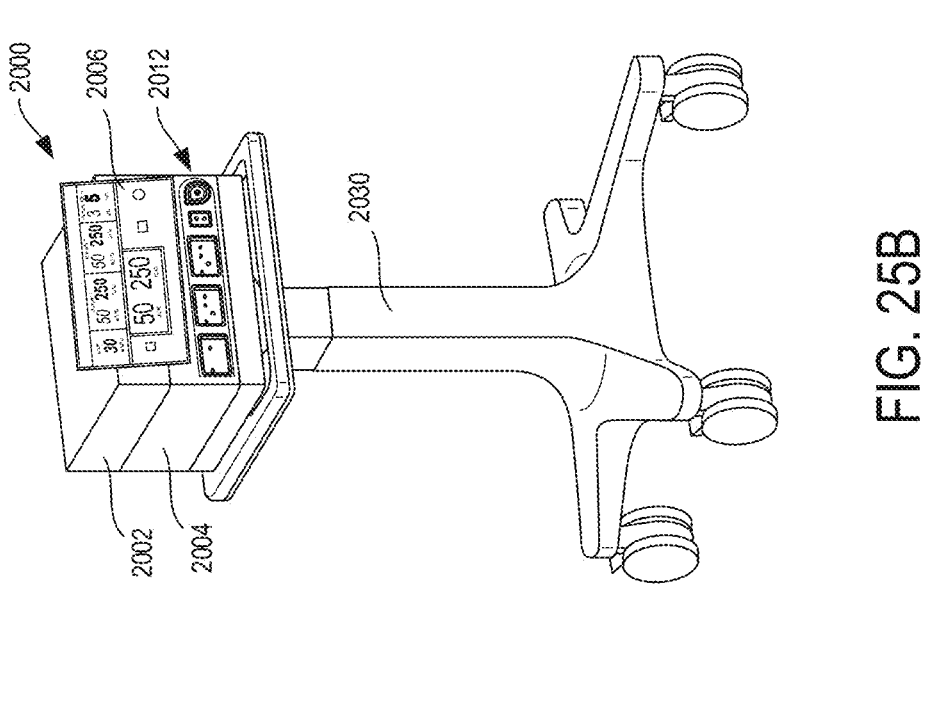
FIG. 25B is the modular energy system shown in FIG. 25A mounted to a cart, in accordance with at least one aspect of the present disclosure.
Figure 25A:
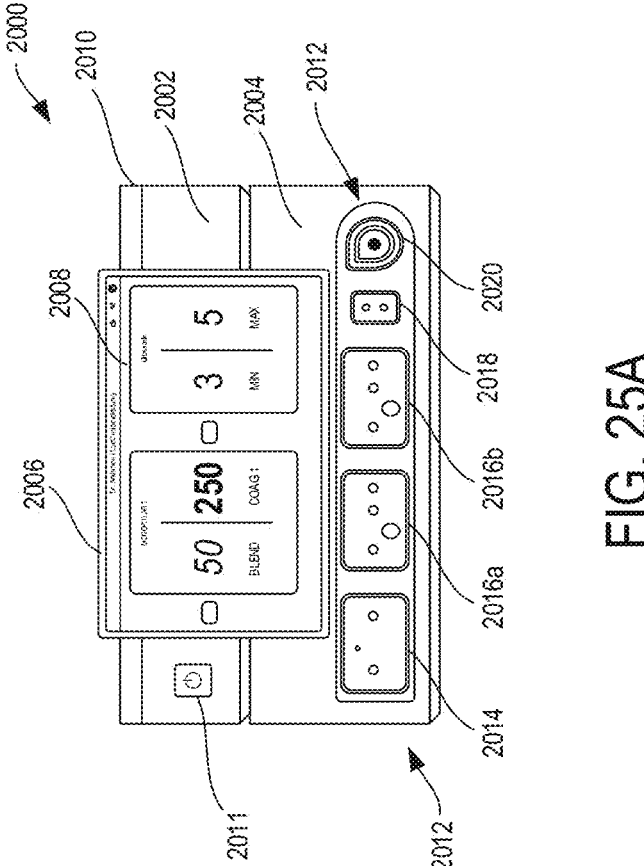
FIG. 25A is a first illustrative modular energy system configuration including a header module and a display screen that renders a graphical user interface (GUI) for relaying information regarding modules connected to the header module, in accordance with at least one aspect of the present disclosure.
Figure 29:
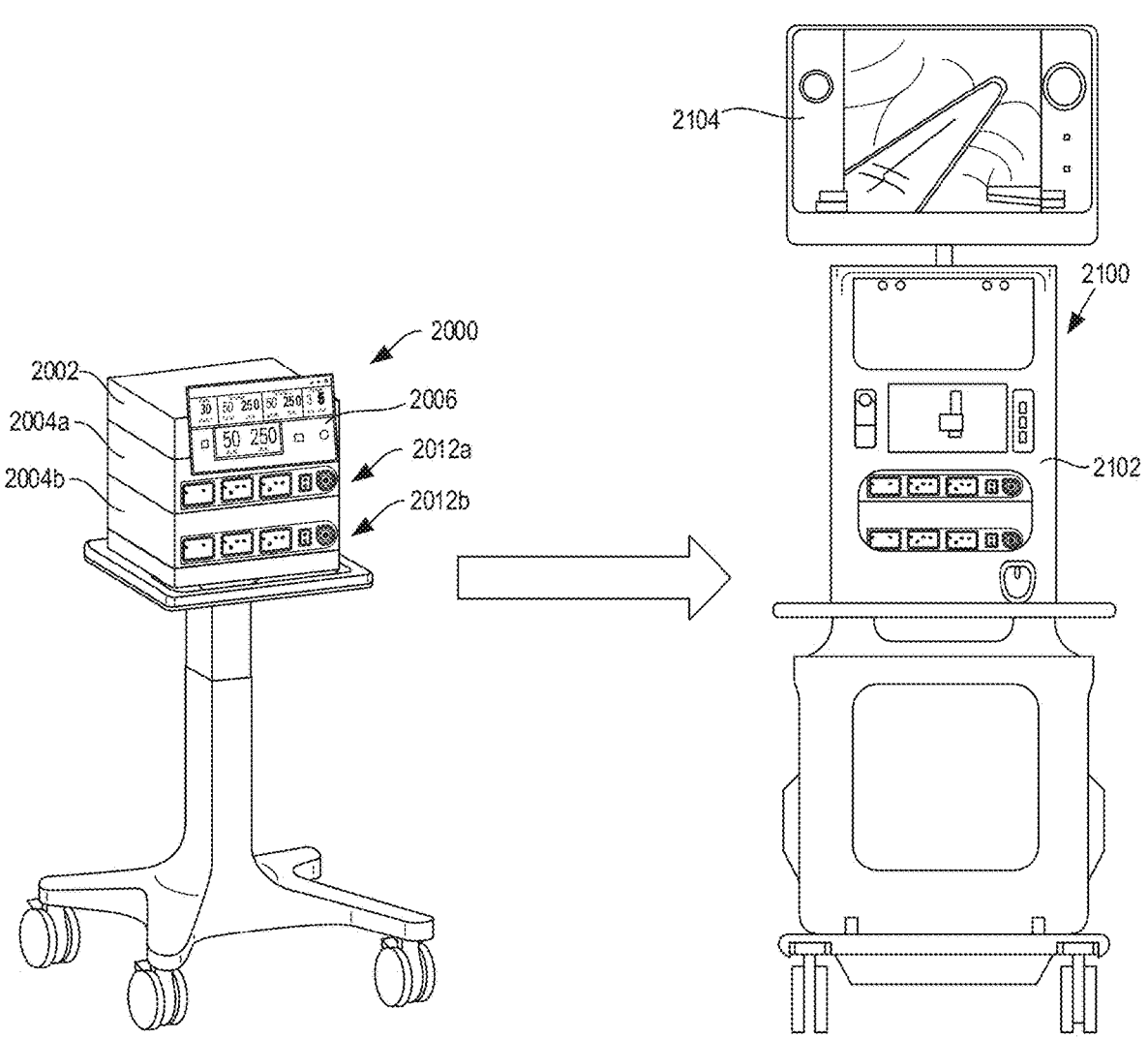
FIG. 29 is a diagram of a modular energy system including communicably connectable surgical platforms, in accordance with at least one aspect of the present disclosure.

Referring now to FIG. 25A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 30. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 29. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 25A, the energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 25A and 25B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 26A:
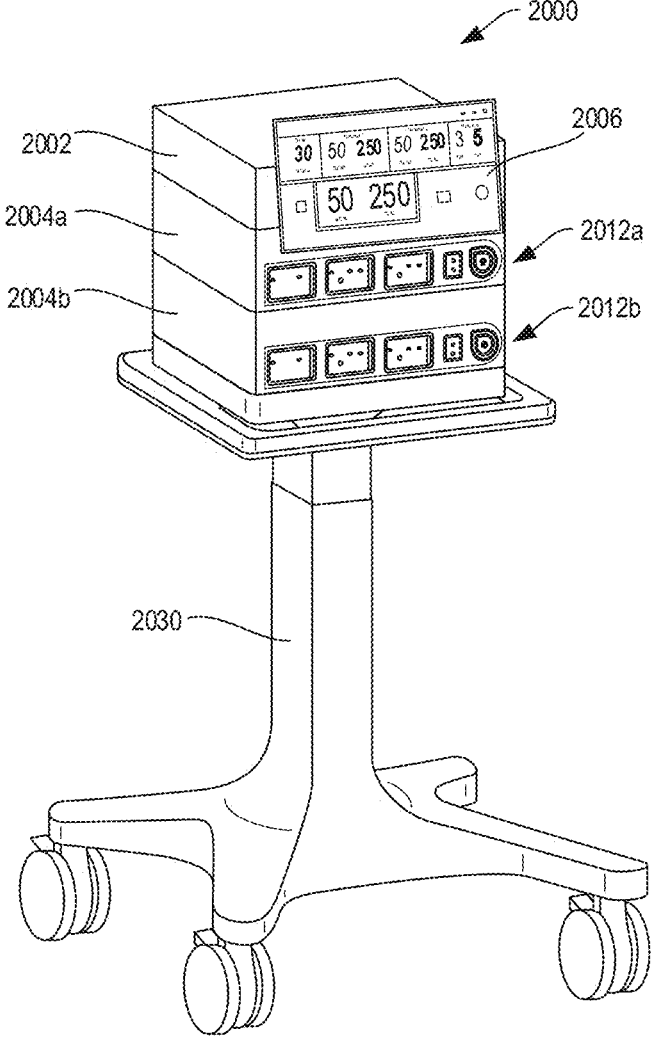
FIG. 26A is a second illustrative modular energy system configuration including a header module, a display screen, an energy module, and an expanded energy module connected together and mounted to a cart, in accordance with at least one aspect of the present disclosure.
Figure 26B:
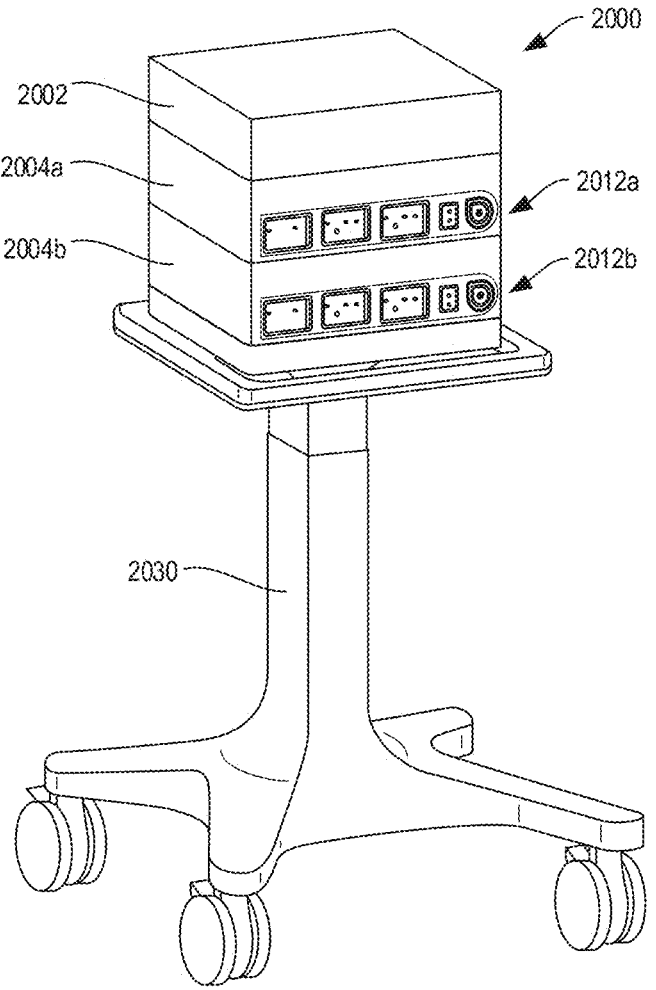
FIG. 26B is a third illustrative modular energy system configuration that is similar to the second configuration shown in FIG. 25A, except that the header module lacks a display screen, in accordance with at least one aspect of the present disclosure.

FIG. 26A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 26B illustrates a third illustrative configuration that is similar to the second configuration, except that the header module 2002 lacks a display screen 2006. This configuration can be suitable for robotic surgical applications or mobile display applications, as noted above.

Figure 27:
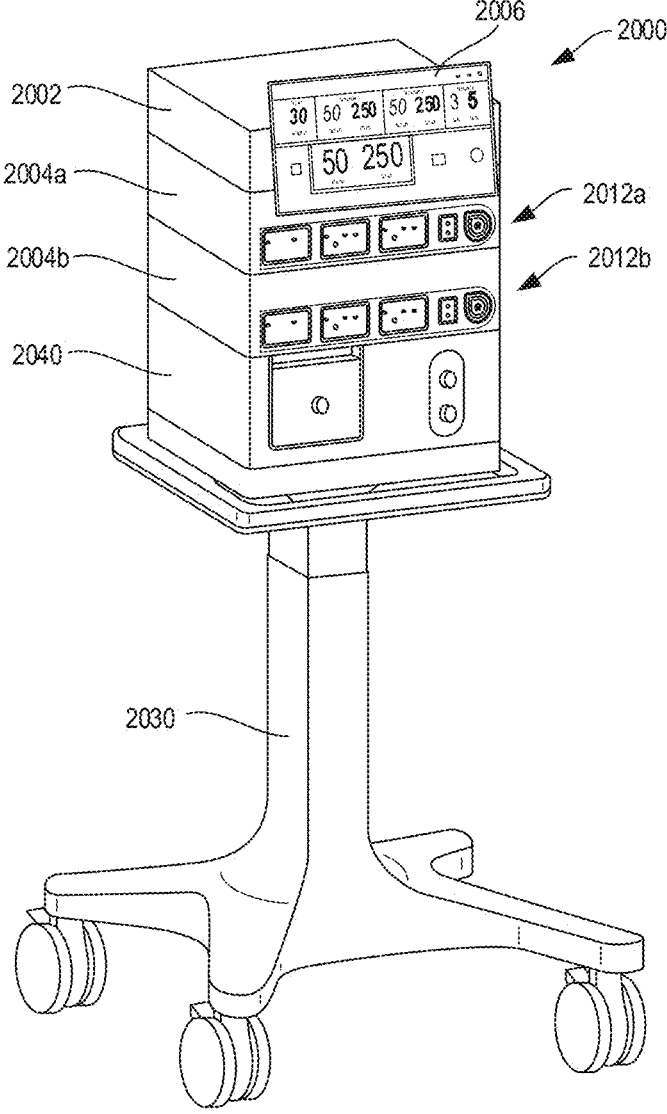
FIG. 27 is a fourth illustrative modular energy system configuration including a header module, a display screen, an energy module, ae expanded energy module, and a technology module connected together and mounted to a cart, in accordance with at least one aspect of the present disclosure.

FIG. 27 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 28:
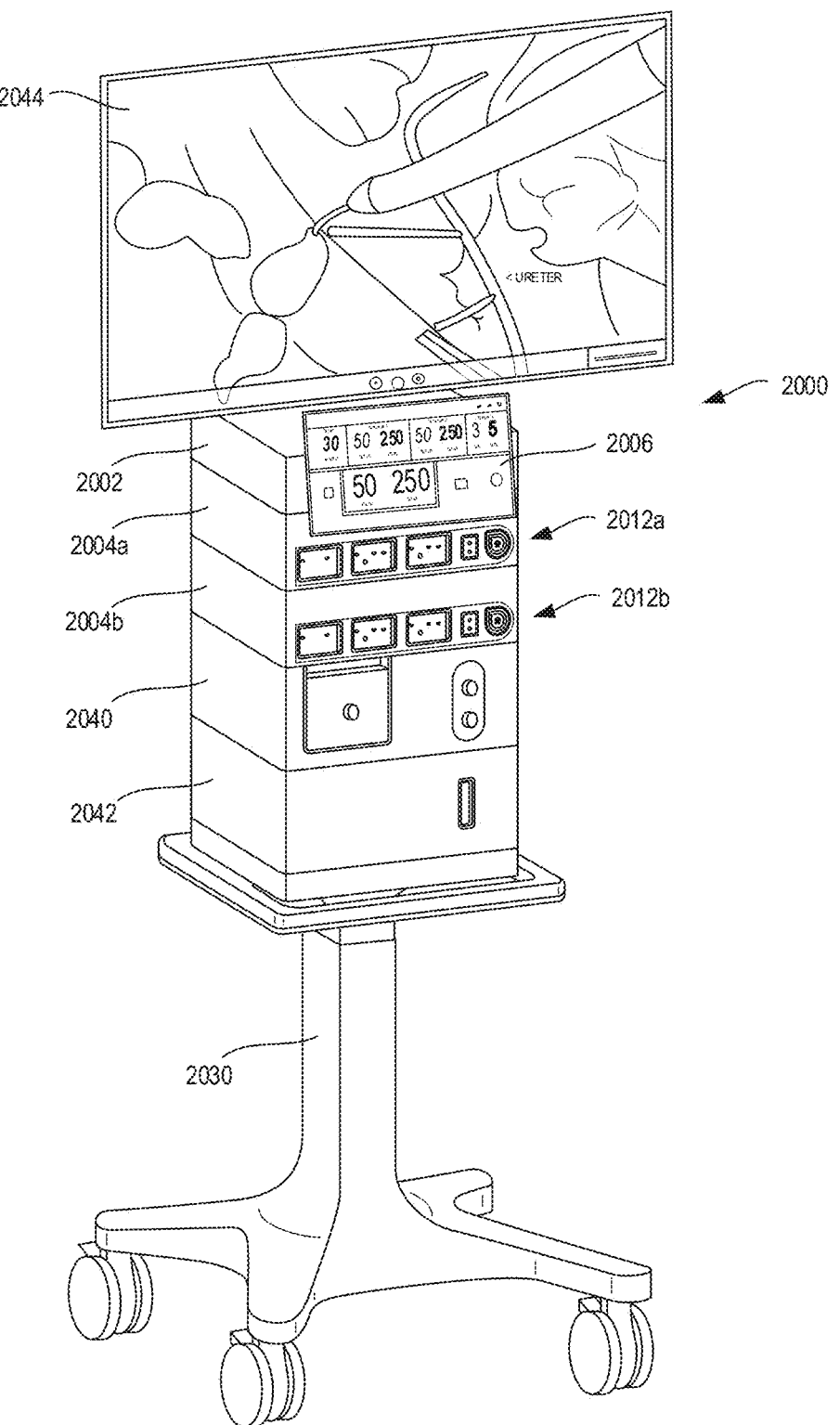
FIG. 28 is a fifth illustrative modular energy system configuration including a header module, a display screen, an energy module, an expanded energy module, a technology module, and a visualization module connected together and mounted to a cart, in accordance with at least one aspect of the present disclosure.

FIG. 28 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 25A-29 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 29. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 30:
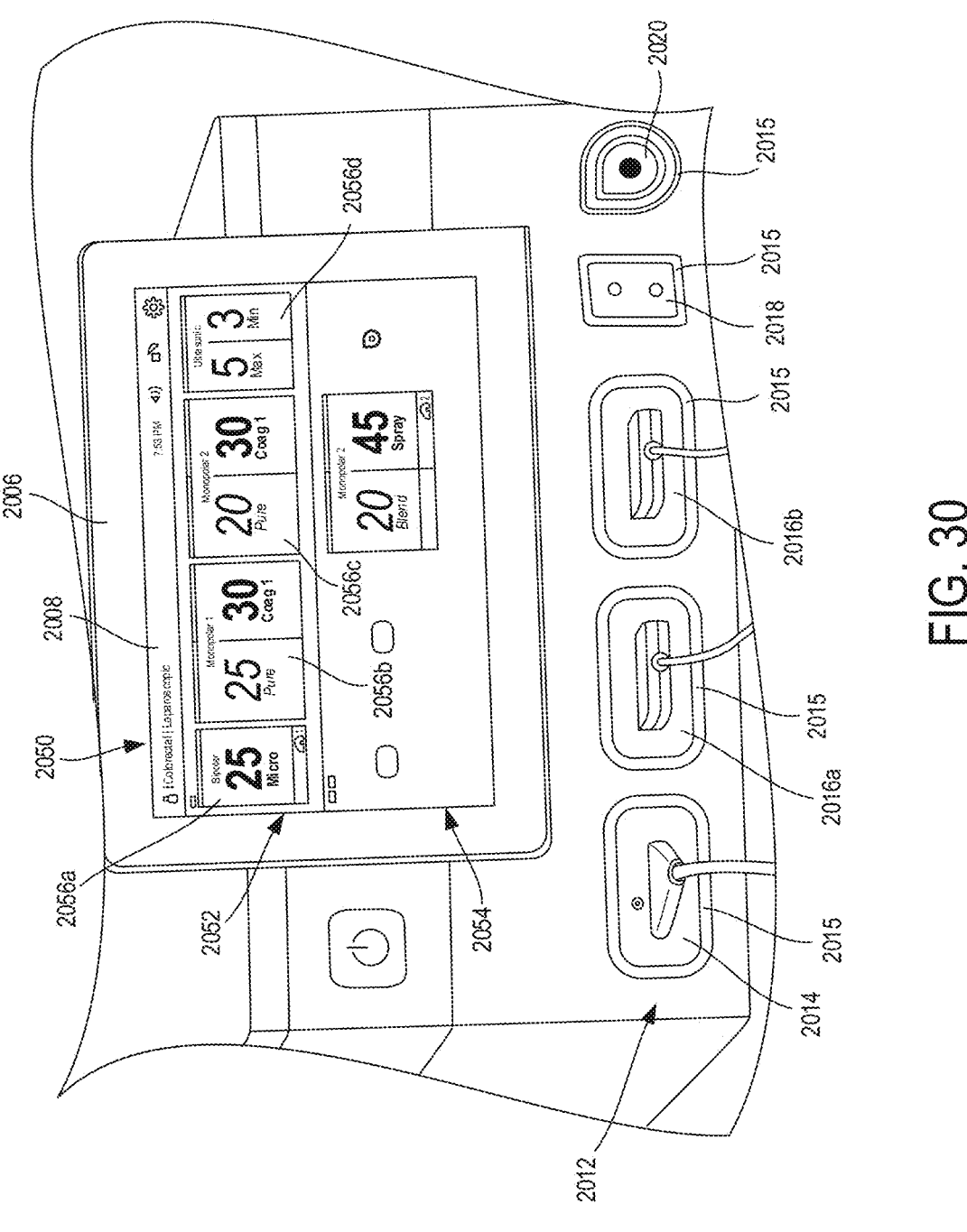
FIG. 30 is a perspective view of a header module of a modular energy system including a user interface, in accordance with at least one aspect of the present disclosure.

Referring now to FIG. 30, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 30, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the activation of each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 31:
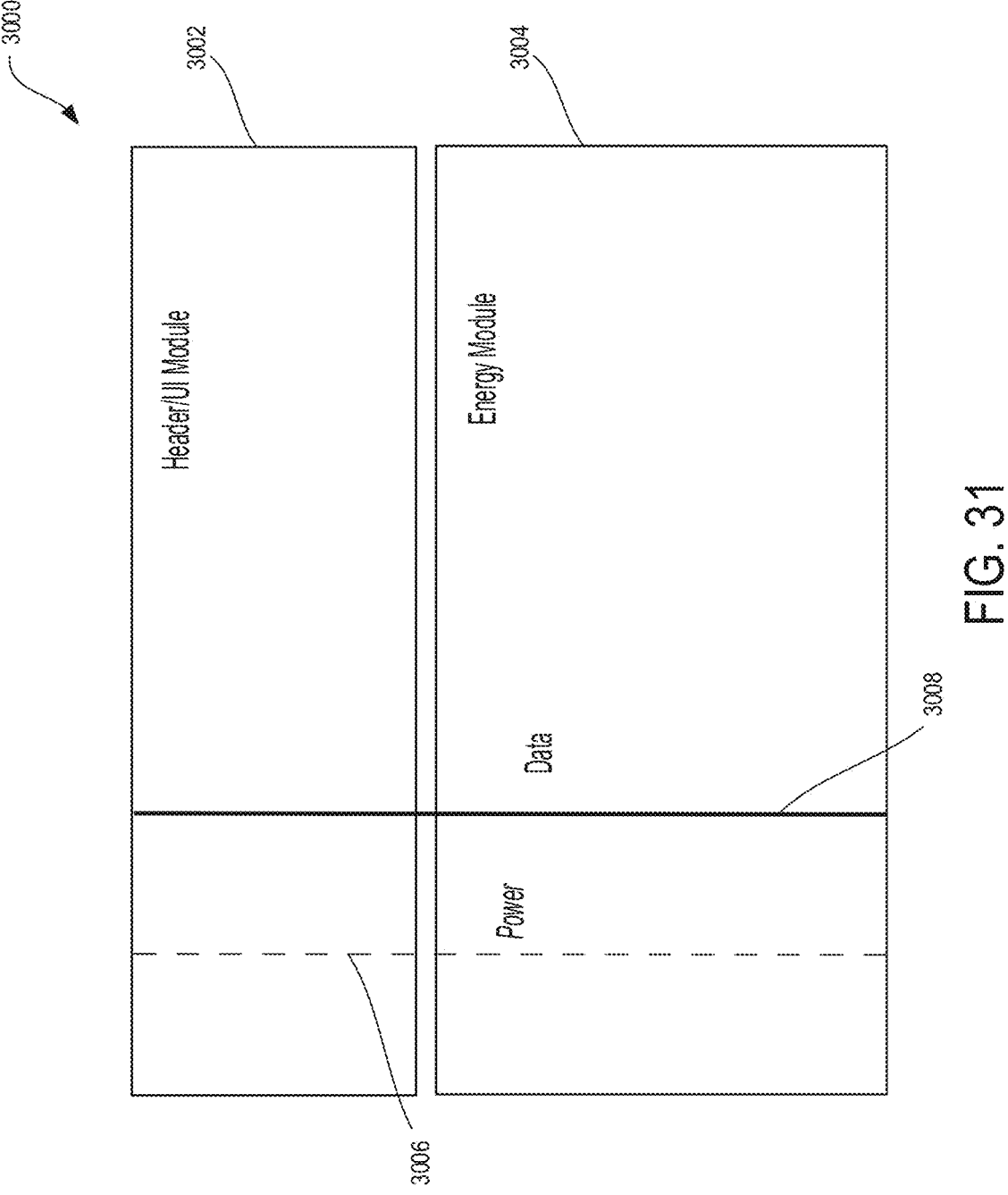
FIG. 31 is a block diagram of a stand-alone hub configuration of a modular energy system, in accordance with at least one aspect of the present disclosure.
Figure 32:
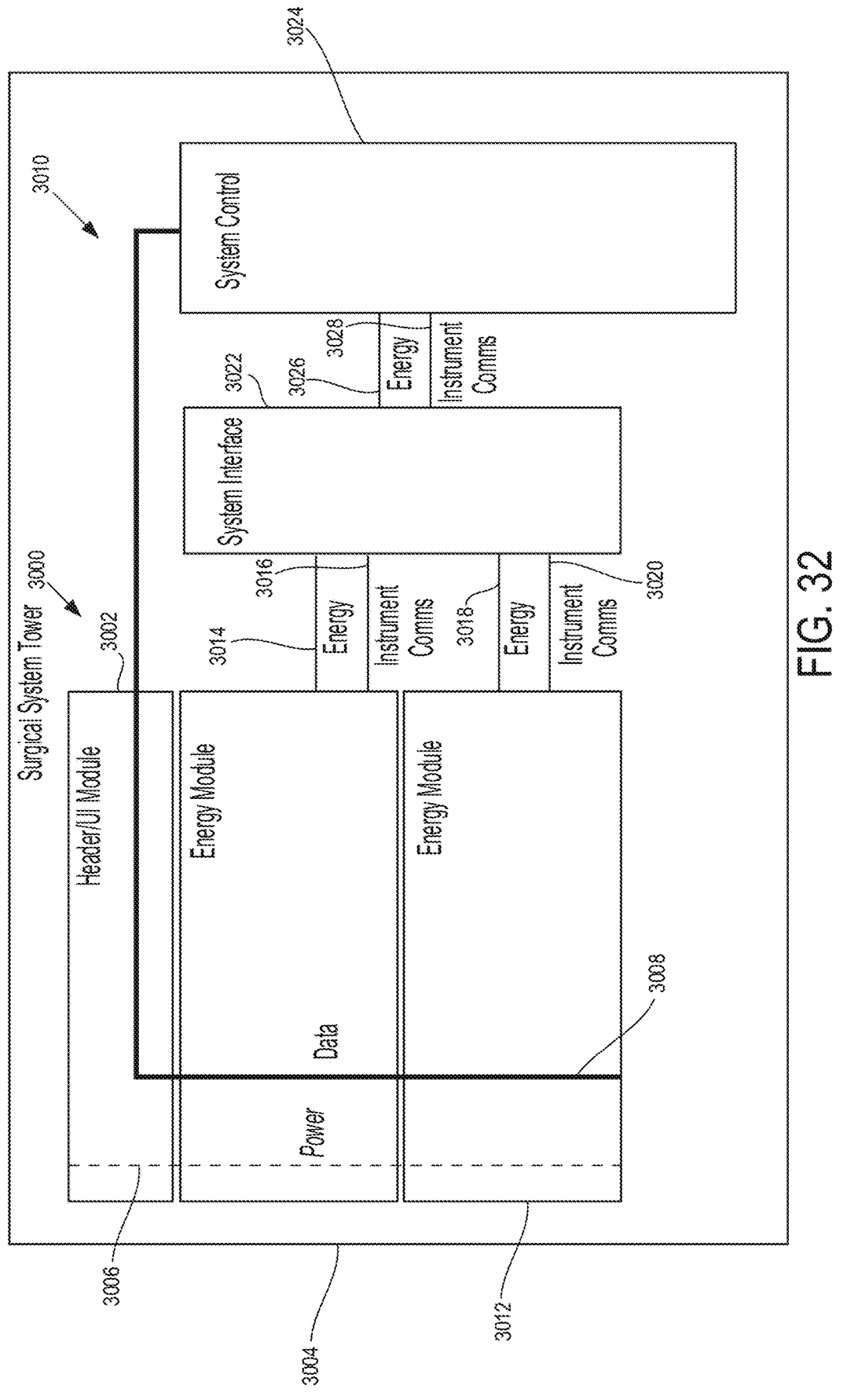
FIG. 32 is a block diagram of a hub configuration of a modular energy system integrated with a surgical control system, in accordance with at least one aspect of the present disclosure.

FIG. 31 is a block diagram of a stand-alone hub configuration of a modular energy system 3000, in accordance with at least one aspect of the present disclosure and FIG. 32 is a block diagram of a hub configuration of a modular energy system 3000 integrated with a surgical control system 3010, in accordance with at least one aspect of the present disclosure. As depicted in FIGS. 31 and 32, the modular energy system 3000 can be either utilized as stand-alone units or integrated with a surgical control system 3010 that controls and/or receives data from one or more surgical hub units. In the examples illustrated in FIGS. 31 and 32, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 31, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 32, a surgical hub configuration includes a modular energy system 3000 integrated with a control system 3010 and an interface system 3022 for managing, among other things, data and power transmission to and/or from the modular energy system 3000. The modular energy system depicted in FIG. 32 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

As described in more detail hereinbelow, the energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 33:
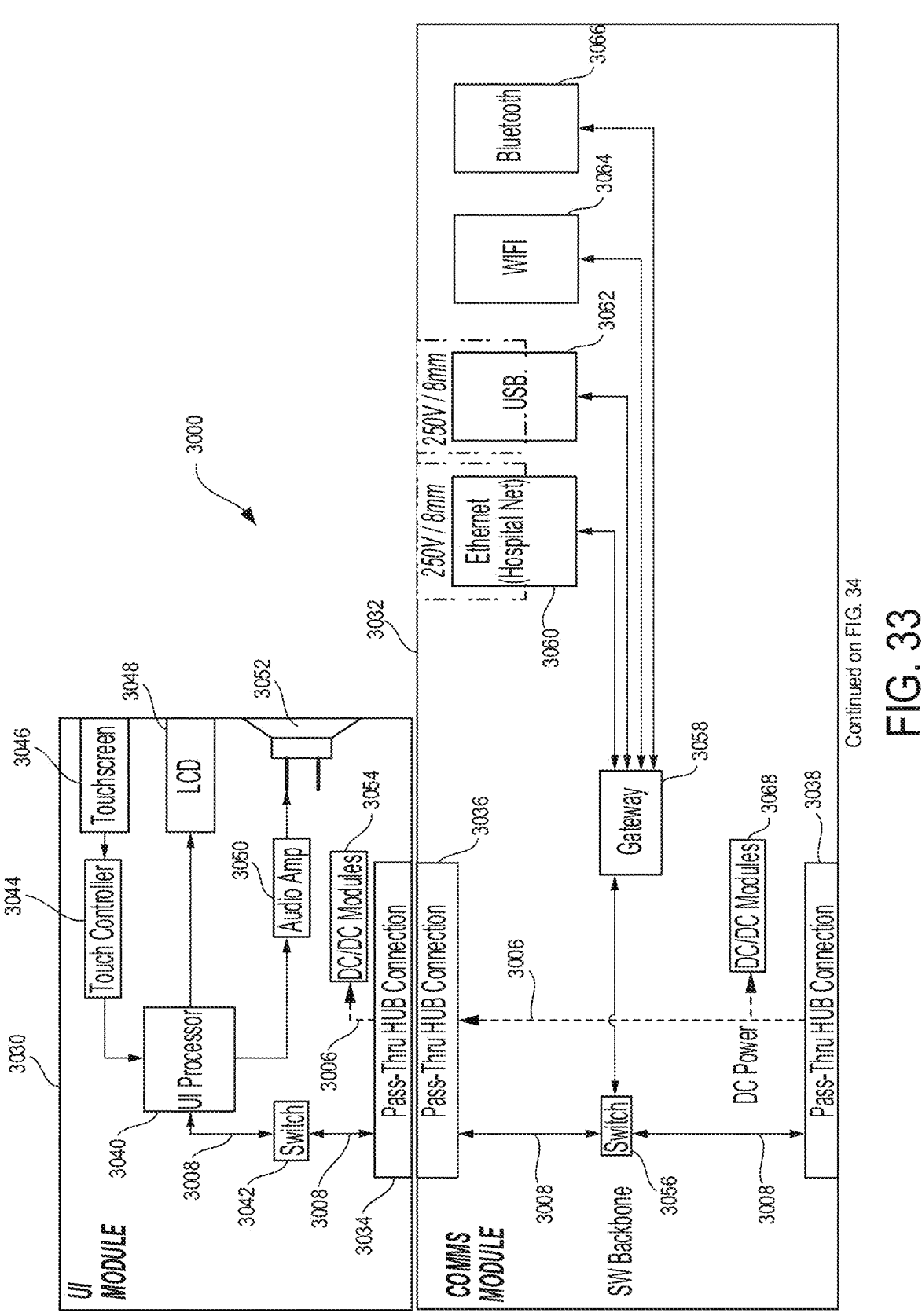
FIG. 33 is a block diagram of a user interface module coupled to a communications module of a modular energy system, in accordance with at least one aspect of the present disclosure.
Figure 34:
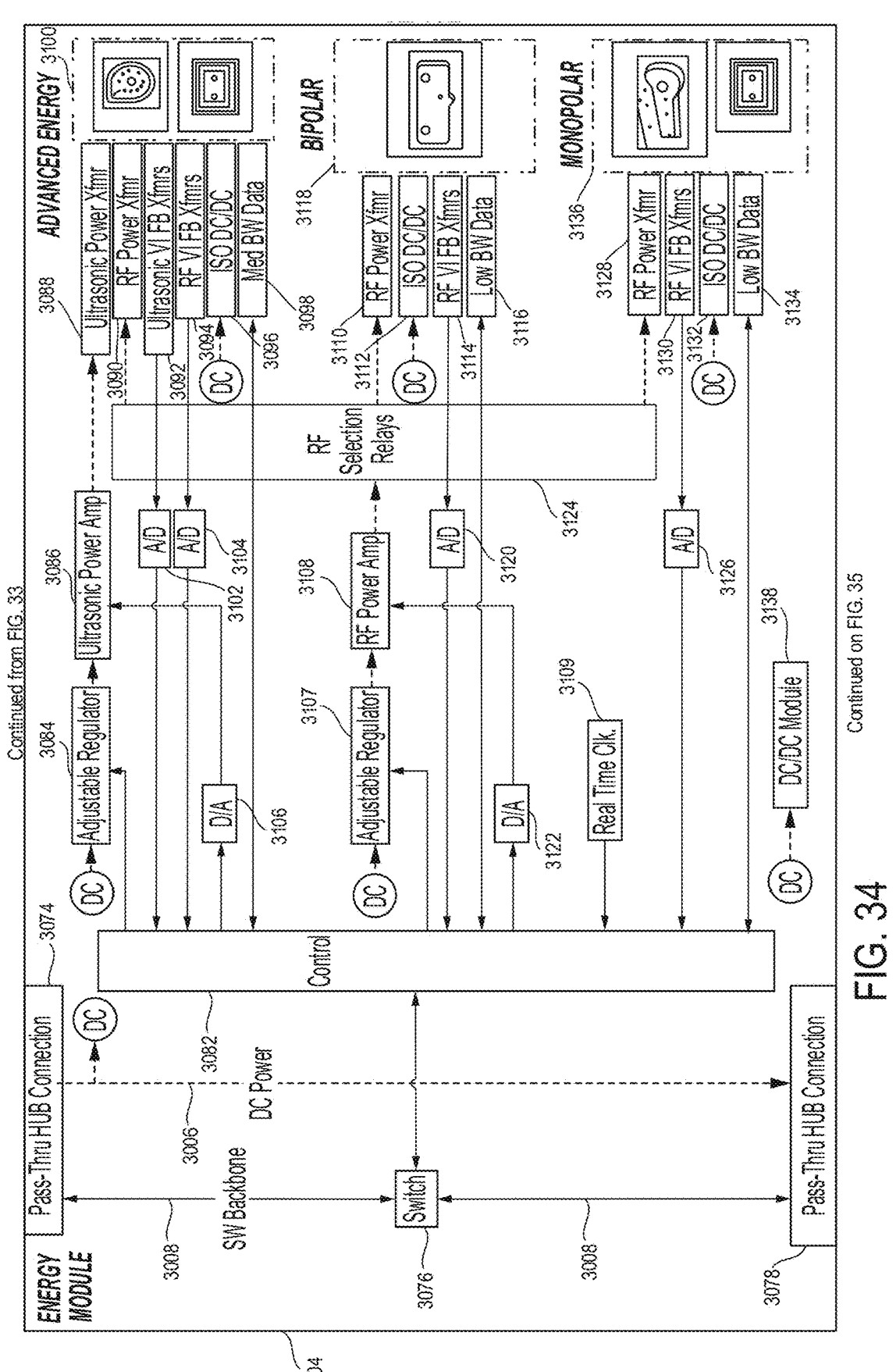
FIG. 34 is a block diagram of an energy module of a modular energy system, in accordance with at least one aspect of the present disclosure.
Figure 35A:
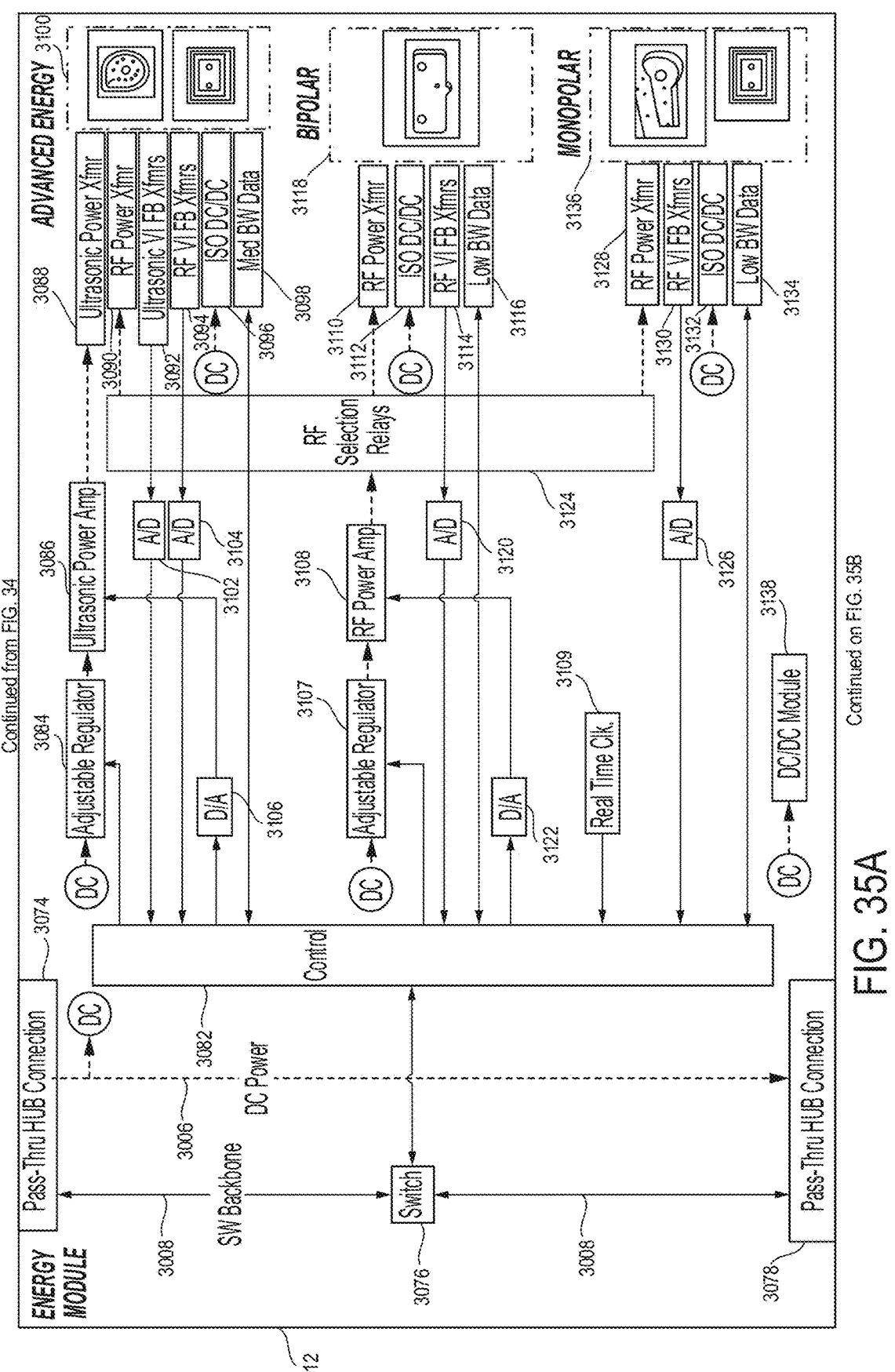
FIGS. 35A and 35B illustrate a block diagram of an energy module coupled to a header module of a modular energy system, in accordance with at least one aspect of the present disclosure.
Figure 35B:
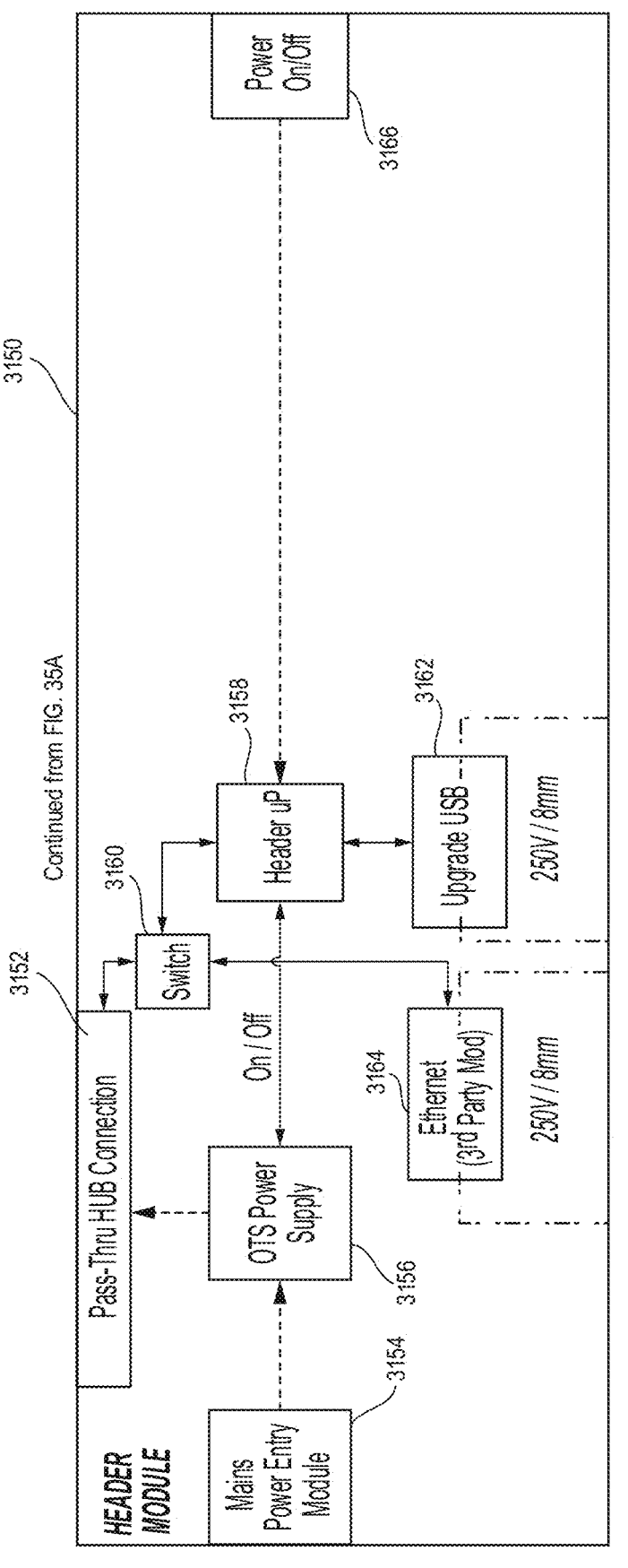

FIGS. 33-35 are block diagrams of various modular energy systems connected together to form a hub, in accordance with at least one aspect of the present disclosure. FIGS. 33-35 depict various diagrams (e.g., circuit or control diagrams) of hub modules. The modular energy system 3000 includes multiple energy modules 3004 (FIG. 34), 3012 (FIG. 35), a header module 3150 (FIG. 35), a UI module 3030 (FIG. 33), and a communications module 3032 (FIG. 33), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 33, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 35) and may be communicatively coupled to the header module

3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 33, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 36A:
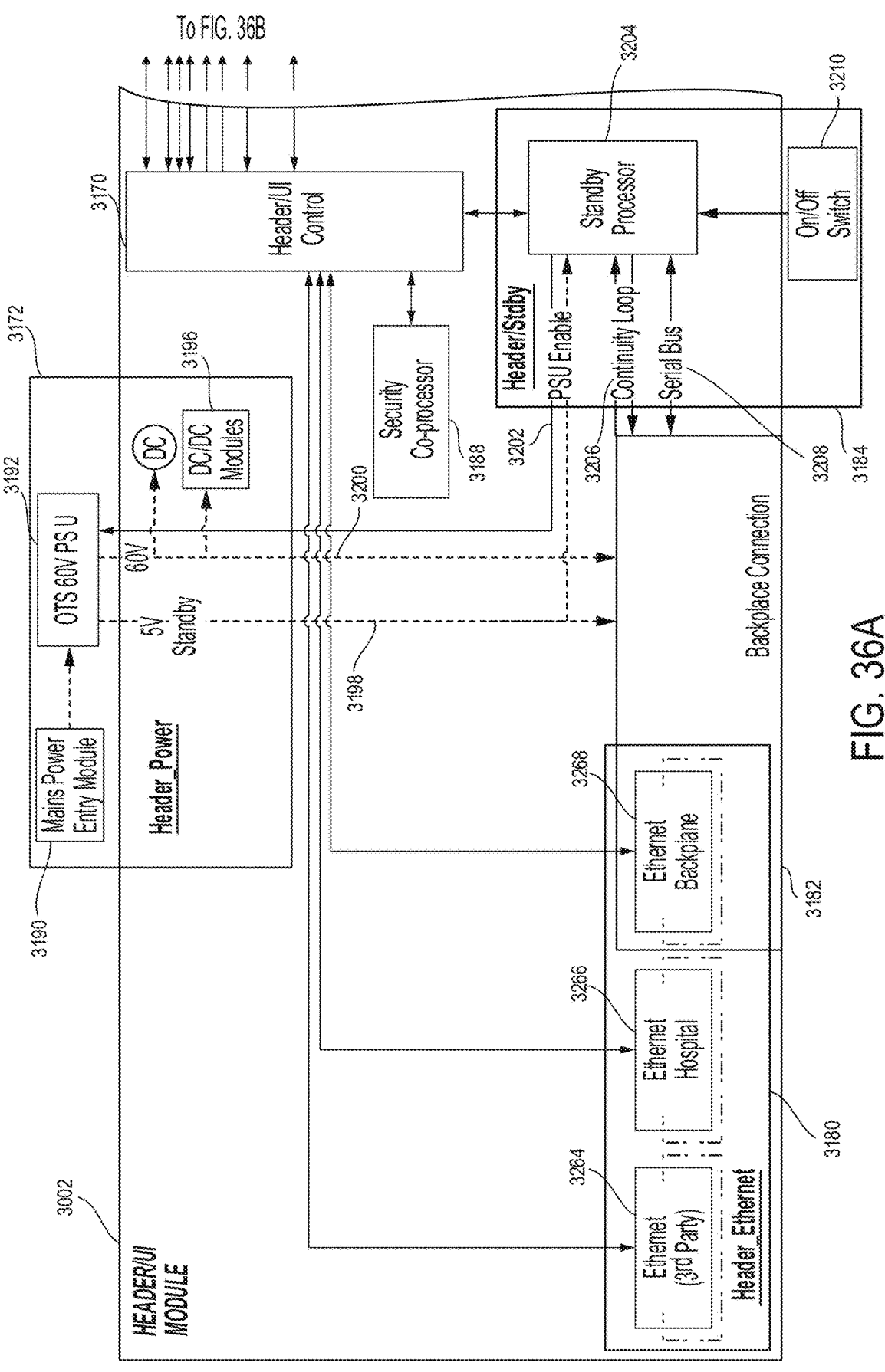
FIGS. 36A and 36B illustrate a block diagram of a header/user interface (UI) module of a modular energy system for a hub, such as the header module depicted in FIG. 33, in accordance with at least one aspect of the present disclosure.

In some aspects, all of the modules (i.e., detachable hardware) are controlled by a single UI module 3030 that is disposed on or integral to a header module. FIG. 35 shows a stand alone header module 3150 to which the UI module 3030 can be attached. FIGS. 31, 32, and 36 show an integrated header/UI Module 3002. Returning now to FIG. 33, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 34, there is shown a block diagram of an energy module 3004, in accordance with at least one aspect of the present disclosure. The communications module 3032 (FIG. 33) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 35, via a second pass-through hub connector 3078. Turning back to FIG. 34, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 35 is a block diagram of a second energy module 3012 coupled to a header module 3150, in accordance with at least one aspect of the present disclosure. The first energy module 3004 shown in FIG. 34 is coupled to the second energy module 3012 shown in FIG. 35 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 35. In another aspect, the second energy module 2012 can be a different energy module compared to the first energy module, such as an energy module illustrated in FIG. 37, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 36 is a block diagram of a header/user interface (UI) module 3002 for a hub, such as the header module depicted in FIG. 33, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security coprocessor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument(s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 37:
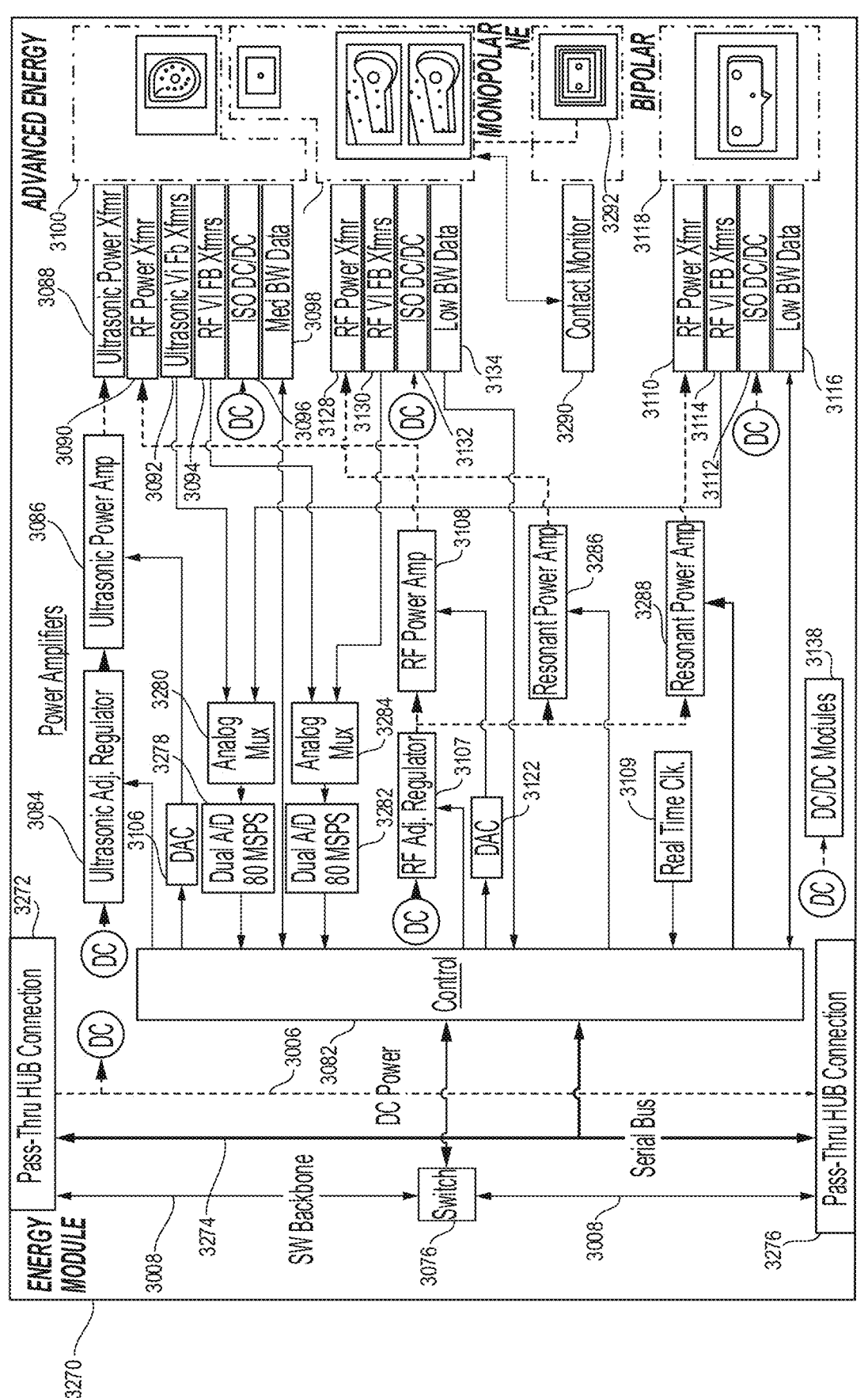
FIG. 37 is a block diagram of an energy module for a hub, such as the energy module depicted in FIGS. 31-36B, in accordance with at least one aspect of the present disclosure.

FIG. 37 is a block diagram of an energy module 3270 for a hub, such as the energy module depicted in FIGS. 31, 32, 34, and 35, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 34 and 35, the energy module 3270 does not include RF selection relays configured to receive an RF output signal from the adjustable buck regulator 3107. In addition, unlike the energy modules 3004, 3012 shown and described in FIGS. 34 and 35, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 31-37, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 31-37, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 31-37, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled and set to a high impedance state.

In one aspect, with reference to FIGS. 31-37, the modules of the modular energy system 3000 can include an amplifier pulse/stimulation/auxiliary DC amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular surgical system comprises a header module and one or more functional or surgical modules. In various instances, the modular surgical system is a modular energy system. In various instances, the surgical modules include energy modules, communication modules, user interface modules; however, the surgical modules are envisioned to be any suitable type of functional or surgical module for use with the modular surgical system.

Modular surgical system offers many advantages in a surgical procedure, as described above in connection with the modular energy systems 2000 (FIG. 24-30), 3000 (FIG. 31, 32). However, cable management and setup/teardown time can be a significant deterrent. Various embodiments of the present disclosure provide a modular surgical system with a single power cable and a single power switch to control startup and shutdown of the entire modular surgical system, which obviated the need to individually activate and deactivate each individual module from which the modular surgical system is constructed. Also, various embodiments of the present disclosure provide a modular surgical system with power management schemes that facilitate a safe and, in some instances, concurrent delivery of power to the modules of a modular surgical system.

Figure 38:
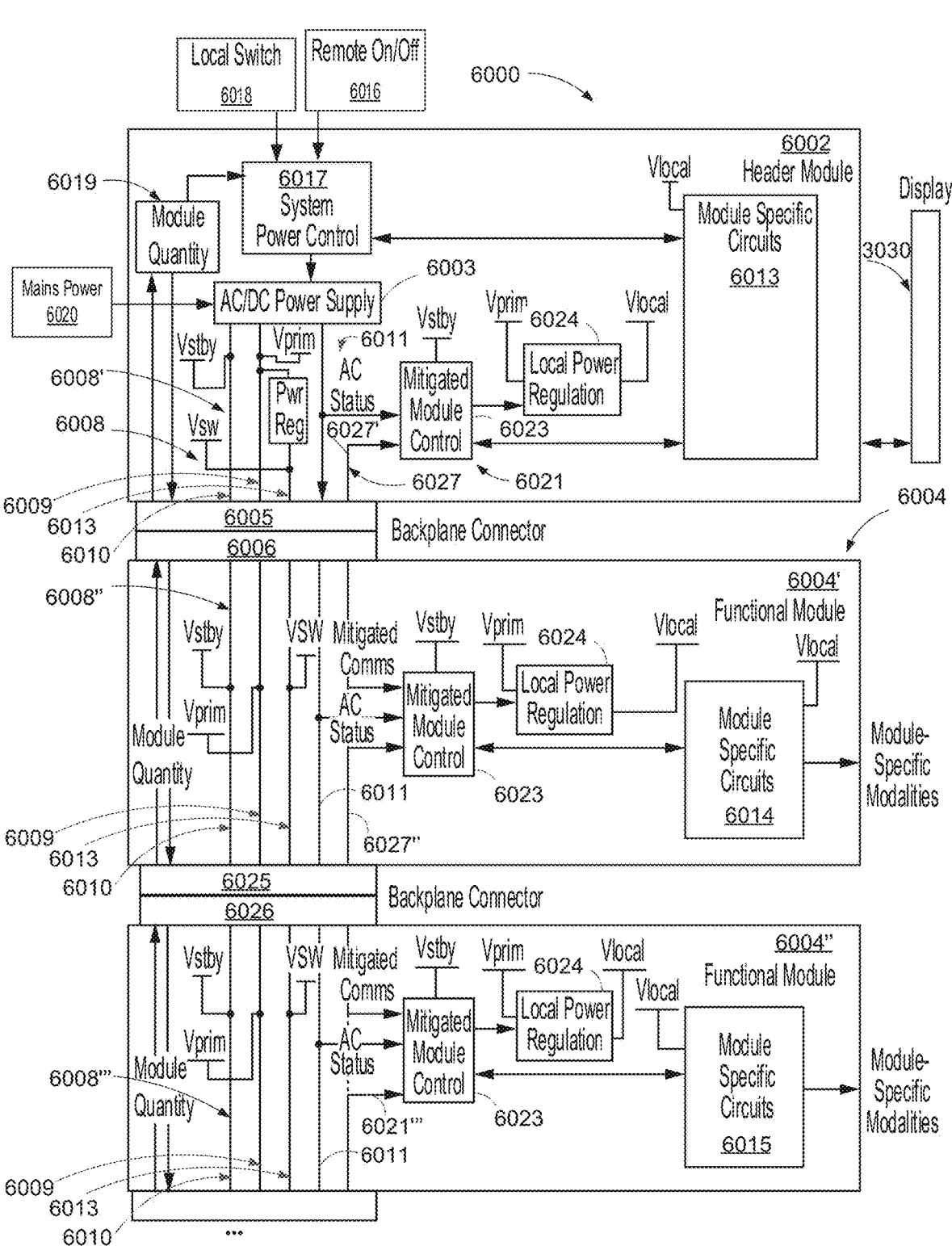
FIG. 38 is a schematic diagram of a modular surgical system stack illustrating a power backplane, in accordance with at least one aspect of the present disclosure.

In various aspects, as illustrated in FIG. 38, a modular surgical system 6000 that is similar in many respects to the modular surgical systems 2000 (FIG. 24-30), 3000 (FIG. 31, 32). For the sake of brevity, various details of the modular surgical system 6000, which are similar to the modular surgical system 2000 and/or the modular surgical system 3000, are not repeated herein.

The modular surgical system 6000 comprises a header module 6002 and an "N" number of surgical modules 6004, where "N" is an integer greater than or equal to one. In various examples, the modular surgical system 6000 includes a UI module such as, for example, the UI module 3030 and/or a communication module such as, for example, the communication module 3032. Furthermore, pass-through hub connectors couple individual modules to one another in a stack configuration. In the example of 38, the header module 6002 is coupled to a surgical module 6004 via pass-through hub connectors 6005, 6006.

The modular surgical system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 38 demonstrates three separate power domains on the power backplane 6008: a primary power domain 6009, a standby power domain 6010, and an Ethernet switch power domain 6013.

In the example illustrated in FIG. 38, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various embodiments, the primary power domain 6009 is controlled by the header module 6002. In certain instances, as illustrated in FIG. 38, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 39:
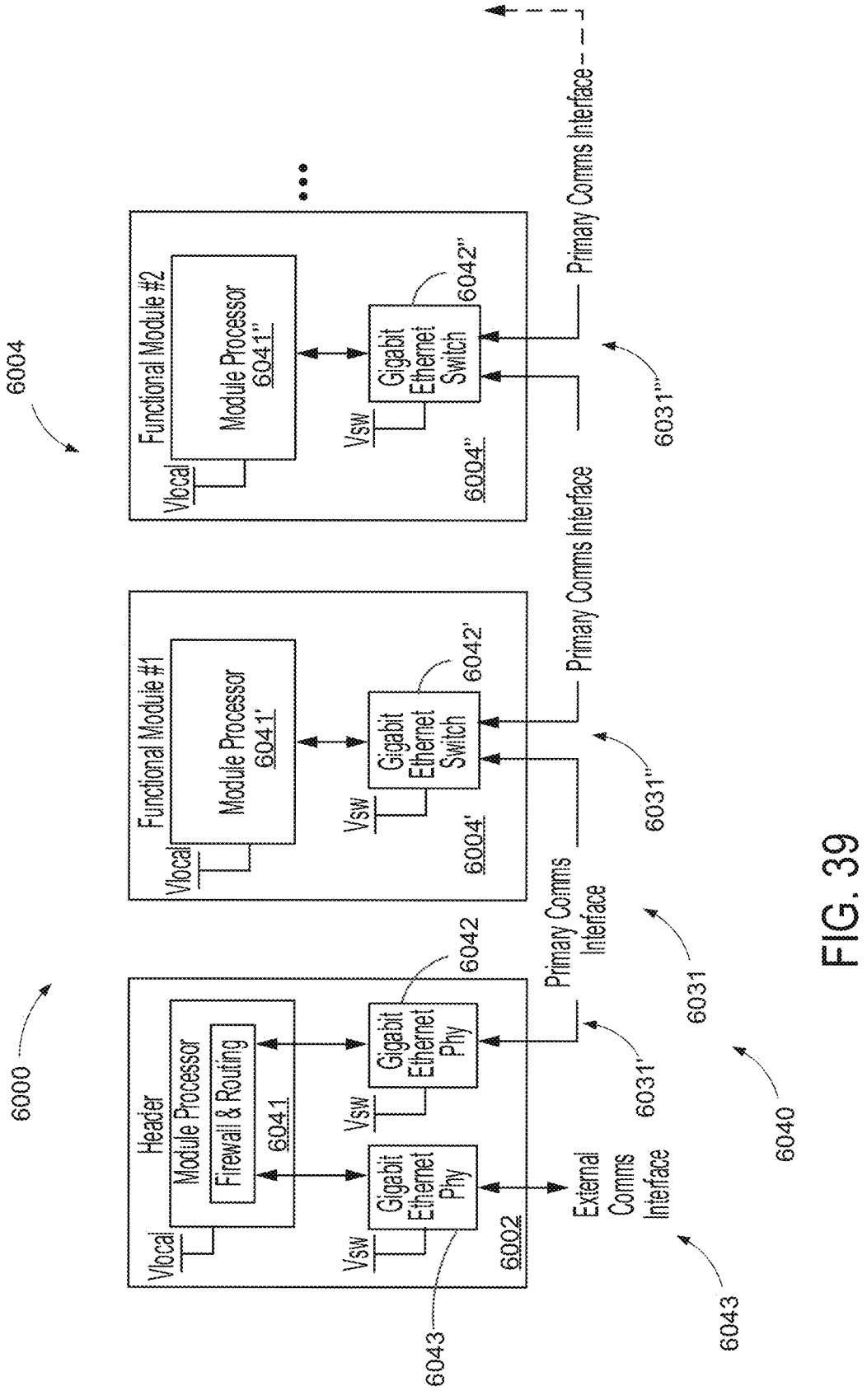
FIG. 39 is a schematic diagram of a modular surgical system, in accordance with at least one aspect of the present disclosure.

In various aspects, as illustrated in FIG. 39, the modules of the modular surgical system 6000 can be communicably coupled to the header module 6002 and/or to each other via a communication (Serial bus/Ethernet) interface 6040 such that data or other information is shared by and between the modules of which the modular surgical system is constructed. An Ethernet switch domain 6013 can be derived from the primary power domain 6009, for example. The Ethernet switch power domain 6013 is segregated into a separate power domain, so that the primary communications interface 6040 will remain alive when local power to a module is removed, which is configured to power Ethernet switches within each of the modules in the stack configuration. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular surgical system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 38, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 38, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular surgical system 6000. This arrangement further reduces the number of cords required for proper operation of the modular surgical system 6000, which can reduce clutter and footprint in the operating room.

Accordingly, a surgical instrument connected to surgical modules 6004 of a modular surgical system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular surgical system 6000. In the example of FIG. 38, the header module 6002 houses a power backplane segment 6008', the first surgical module 6004' houses a power backplane segment 6008", and the second surgical module 6004" houses a power backplane segment 6008". The power backplane segment 6008' is detachably coupled to the power backplane segment 6008" in the stack configuration. Further, the power backplane 6008" is detachably coupled to the power backplane segment 6008''' in the stack configuration. Accordingly, energy flows from the AC/DC power supply 6003 to the power backplane segment 6008', then to the power backplane segment 6008", and then to the power backplane segment 6008'''.

In the example of FIG. 38, the power backplane segment 6008' is detachably connected to the power backplane segment 6008" via pass-through hub connectors 6005, 6006 in the stack configuration. Further, the power backplane segment 6008" is detachably connected to the power backplane segment 6008''' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008' from the power backplane segment 6008". However, the connection between the power backplane segment 6008" and the power backplane segment 6008''' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 38, each of the modules 6002, 6004 includes a mitigated module control 6023 configured to determine an AC status based on an AC status of the AC/DC power supply 6003 based on an AC status signal 6011 transmitted to the mitigated module controls 6023 of the modules of the modular surgical system 6000. The mitigated module controls 6023 are coupled to corresponding local power regulation modules 6024 that are configured to regulate power based on input from the mitigated module controls 6023, which can be indicative of the AC status received by the mitigated module controls 6023, for each of the surgical modules.

The modular surgical system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular surgical system 6000. In the example of FIG. 38, the header module 6002 houses a communication backplane segment 6027', the first surgical module 6004' houses a communication backplane segment 6027", and the second surgical module 6004" houses a communication backplane segment 6027'''. The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 38 depicts a modular surgical system 6000 includes a header module 6002 and two surgical modules 6004' 6004", this is not limiting. Modular surgical systems with more or less surgical modules are contemplated by the present disclosure. In some aspects, the modular surgical system 6000 includes other modules such as, for example, the communications module 3032 (FIG. 33). In some aspects, the header module 6502 supports a display screen such as, for example, the display 2006 (FIG. 25A) that renders a GUI such as, for example, the GUI 2008 for relaying information regarding the modules connected to the header module 6002. As described in greater detail in connection with the example of FIG. 33, in some aspects, the GUI 2008 of the display screen 2006 can provide a consolidated point of control all of the modules making up the particular configuration of a modular surgical system.

FIG. 39 depicts a simplified schematic diagram of the modular surgical system 6000, which illustrates a primary communications interface 6040 between the header module 6002 and the surgical modules 6004. The primary communications interface 6040 communicably connects module processors 6041, 6041", 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, t the primary communications interface 6040 is configured to establish a one-way communication pathway between neighboring modules.

Furthermore, the primary communications interface 6040 includes a segmented communication backplane 6031, which is similar in many respects to the segmented power backplane 8006. Communication between the header module 6002 and the surgical modules 6004 can be achieved through the segmented communication backplane 6031 defined through the modular surgical system 6000. In the example of FIG. 39, the header module 6002 houses a communication backplane segment 6031', the first surgical module 6004' houses a communication backplane segment 6031", and the second surgical module 6004" houses a communication backplane segment 6031'''. The communication backplane segment 6031' is detachably coupled to the communication backplane segment 6031" in the stack configuration via the pass-through hub connectors 6005, 6006.

Further, the communication backplane 6031" is detachably coupled to the communication backplane segment 6031" in the stack configuration via the pass-through hub connectors 6025, 6026.

In at least one example, as illustrated in FIG. 39, the primary communications interface 6040 is implemented using the DDS framework running on a Gigabit Ethernet interface. The module processors 6041, 6041', 6041" are connected to Gigabit Ethernet Switches 6042, 6042', 6042". In the example of FIG. 39, the segmented communication backplane 6031 connects the Gigabit Ethernet Switches 6042 of the neighboring modules.

In various aspects, as illustrated in FIG. 39, the header module 6002 includes a separate Gigabit Ethernet Switch 6043 for an external communications interface 6043 with the processor module 6041 of the header module 6002. In at least one example, the processor module 6041 of the header module 6002 handles firewalls and information routing.

Figure 41:
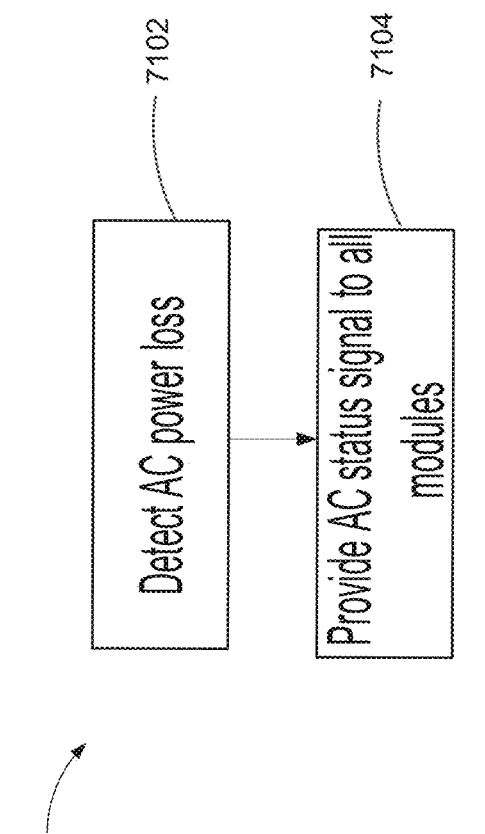
FIG. 41 is a logic flow diagram of a process depicting a control program or a logic configuration for managing a power failure among surgical modules of a modular surgical system, in accordance with at least one aspect of the present disclosure.

Referring to FIGS. 38 and 41, the AC/DC power supply 6003 may provide 7104 an AC Status signal 6011 that indicates a loss of AC power supplied by the AC/DC power supply 6003. The AC status signal 6011 can be provided 7104 to all the modules of the modular surgical system 6000 via the segmented power backplane 6008 to allow each module as much time as possible for a graceful shutdown, before primary output power is lost. The AC status signal 6011 can be received by a mitigated module control 6023 at each of the modules of the modular surgical system 6000, which is in communication with the module specific circuits 6013, 6014, 6015, for example. In various examples, the system power control 6017 can be configured to detect 7102 AC power loss. In at least one example, the AC power loss is detected via one or more suitable sensors.

Referring to FIGS. 38 and 39, to ensure that a local power failure in one of the modules of the modular surgical system 6000 does not disable the entire power bus, the primary power input to all modules can be fused. Further, Ethernet switch power is segregated into a separate power domain 6013 so that the primary communications interface 6040 remains alive when local power to a module is removed. In other words, primary power can be removes and/or diverted from a surgical module without losing its ability to communicate with other surgical modules 6004 and/or the header module 6002.

Figure 40:
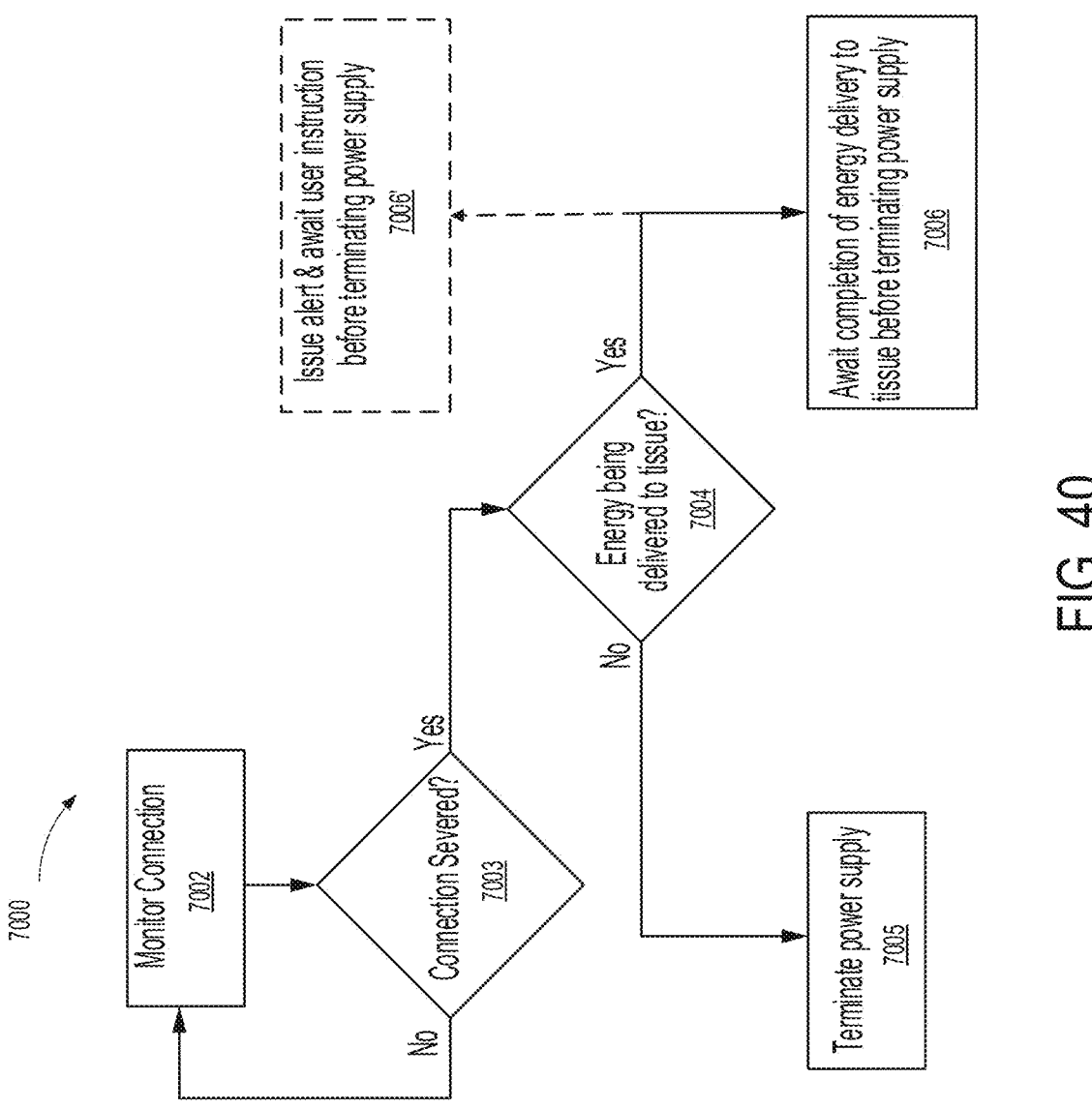
FIG. 40 is a logic flow diagram of a process depicting a control program or a logic configuration for managing power distribution among surgical modules of a modular surgical system, in accordance with at least one aspect of the present disclosure.

FIG. 40 is a logic flow diagram of a process 7000 depicting a control program or a logic configuration for managing power distribution among surgical modules of a modular surgical system such as, for example, the modular surgical system 6000. In at least one example, the process 7000 of FIG. 40 is executed by a module detection circuit 6019 (FIG. 38), which is in communication with the system power control 6017 of the header module 6017. In various examples, the system power control 6017 includes a processor 502 and a memory 504 storing a set of computer-executable instructions that, when executed by the processor 502, cause the processor 502 to perform the process 7000. Although the process 7000, and various other processes of the present disclosure, are described as being executed by a processor, this is merely for brevity, and it should be understood that the processes of the present disclosure can be executed by other suitable circuitry and various suitable systems described by the present disclosure such as, for example, the combinational logic circuit 510 (FIG. 14) or the sequential logic circuit 520 (FIG. 15).

The process 7000 monitors 7002 connections or contact points between modules of the modular surgical system 6000. In at least on example, any suitable sensors such as, for example, suitable pressure, contact, and/or or proximity sensors can be employed by the module detection circuit 6019, for example, to detect addition and/or removal of surgical modules to the modular surgical system 6000 and/or monitor surgical module-to-surgical module and/or surgical module-to-header/footer module connections or contact points. In at least one example, the system power control 6017 is configured to receive input from a module detection circuit 6019 indicative of whether one or more of the surgical module-to-surgical module and/or surgical module-to-header module connections are severed 7003. The module detection circuit 6019 extends through the header module 6002 and surgical modules 6004 of the modular surgical system 6000 in the stack configuration, as illustrated in FIG. 38, and can include, for example, one or more sensors for detecting addition and/or removal of surgical modules to the modular surgical system 6000 and/or monitoring the surgical module-to-surgical module and/or surgical module-to-header module connections.

In at least one example, one or more pressure sensors can be positioned on a bottom and/or top surface of the modules. Each of the pressure sensors is operable to sense pressure, such as by converting a physical deflection into an electrical signal, and thereby provide pressure data. A circuit such as, for example, the module detection circuit 6019 can detect whether modules of a modular surgical system are properly stacked based on pressure data generated by the pressure sensors. To distinguish pressure data caused by abutting against a working surface from pressure data caused by abutting against another module, the pressure sensor(s) can be placed on depressed portions, or ridges, in bottom surfaces of the modules. Corresponding raised portions, or protrusions, on top surfaces of the module are configured to engage the pressure sensors of the depressed portions when the modules are properly stacked in a stack configuration yielding unique pressure data that can signify a proper connection between two surgical modules or a surgical module and header/footer module. In at least one alternative example, the pressure sensor(s) can be placed on the raised portions instead of the depressed portions. The pressure sensors comprise any suitable type(s) of pressure sensors, including but not limited to piezoresistive, capacitive, strain gauges, or any other suitable sensor type, including combinations thereof.

In at least one example, a Hall-effect sensor or any suitable transducer that varies its output voltage in response to a magnetic field, can be employed by the module detection circuit 6019 to detect addition and/or removal of surgical modules to the modular surgical system 6000 and/or monitor surgical module-to-surgical module and/or surgical module-to-header/footer module connections. Hall-effect sensors and corresponding magnets can be installed onto the housings of modules of a modular surgical system 6000 to trigger hall-effect sensors in a connected configuration.

The module detection circuit 6019 can be implemented as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION, U.S. patent application Ser. No. 16/562,234, titled MODULAR SURGICAL ENERGY SYSTEM WITH MODULE POSITIONAL AWARENESS SENSING WITH TIME COUNTER, and U.S. patent application Ser. No. 16/562,234, titled MODULAR SURGICAL ENERGY SYSTEM WITH MODULE POSITIONAL AWARENESS WITH DIGITAL LOGIC, which are incorporated by reference herein in their entireties.

In various aspects, if the header module 6002 determines 7003 that one or more of the connections is severed 7003, the header module 6002 may further determine 7004 whether therapeutic energy is being delivered to the tissue prior to taking actions to mitigate the severed connection(s). If the header module 6002 determines 7004 that no therapeutic energy is being delivered to tissue, the header module 6002 can cause the system power control 6017 to terminate 7005 power supply to the surgical modules of the modular surgical system 6000. In one example, the header module 6002 may terminate all power supply to the surgical modules. In another example, the header module 6002 may terminate the primary power supply while maintaining the communication and/or standby power supplies.

If, however, the header module 6002 determines 7004 that therapeutic energy is being delivered to tissue by a surgical instrument or tool, the header module 6002 may maintain 7006 the primary power supply until the therapeutic energy delivery to tissue is completed. Alternatively, the header module 6002 may issue an alert 7006' and await user instructions before terminating the primary power supply In at least one example, the alert can be issued through the UI module 3030 (FIG. 33). In various examples, the header module 6002 may select to override or inhibit a power off command, resulting from a detected severed connection, if a surgical module in the stack is performing a therapeutic function at the time of a power off command.

In at least one example, the header module 6002 may query local control circuits (e.g. local control circuits 6013, 6014, 6015) of the surgical modules of the modular surgical system 6000 to determine 7004 whether therapeutic energy is being delivered to the tissue. In at least one example, the header module 6002 may query a surgical module status database stored in any suitable storage medium to determine 7004 whether therapeutic energy is being delivered to the tissue. The queried information may include status, type, energy modality, and/or number of surgical instruments delivering therapeutic energy to the tissue.

Further, the Header module 6002 may query local control circuits (e.g. local control circuits 6013, 6014, 6015) of the surgical modules of the modular surgical system 6000 through the communication backplane 6031 (FIG. 39), for example, to determine the number of surgical modules in the stack configuration. In at least one example, the header module 6002 may query a surgical module status database stored in any suitable storage medium to determine the number of surgical modules in the stack configuration. The header module 6002 may further compare the queried information to the number of surgical modules detected by the module detection circuit 6019 to update the database.

In at least one example, a modular surgical system 6000, which includes a header module 6002 and two surgical modules 6004', 6004", can implement the process 7000 to address a severed connection between the first surgical module 6004' and the second surgical module 6004" while therapeutic energy generated by the first surgical module 6004' is being delivered to tissue via a surgical instrument coupled to one of the ports of the first surgical module 6004'. Since the first surgical module 6004' is stacked between the header module 6002 and the second surgical module 6004", the severed connection occurred downstream from where therapeutic energy is being delivered to tissue by the surgical instrument through the first surgical module 6004'. Accordingly, the process 7000 maintains primary power supply to the first surgical module 6004' until therapeutic energy application to tissue is completed. In at least one alternative example, as illustrated in FIG. 40, the process 7000 may issue an alert 7006' and await user instructions before terminating the primary power supply.

In at least one example, the header module 6003 determines that therapeutic energy is being delivered to tissue through a feedback input from the first surgical module 6004'. The header module 6003 may query local control circuit 6014 of the surgical modules of the modular surgical system 6000 to determine 7004 whether therapeutic energy is being delivered to the tissue.

The modular surgical system 6000 permits a user to add or remove modules to adapt the modular surgical system 6000 to a surgical procedure, for example. The power budget of a modular surgical system 6000 varies based on the number of surgical modules 6004 present in the stack. Consequently, the power budget of the modular surgical systems disclosed herein is actively and adaptively managed to ensure that the stack as a whole does not consume more than the rated power.

In various examples, the header module 6002 can be configured to determine the number of surgical modules 6004 present in the stack configuration of the modular surgical system 6000, and allocate power to each of the surgical modules 6004 based on the determined number of surgical modules 6004 present in the stack configuration. In at least one example, a suitable circuit, which employs digital logic or a time counter for example, can be employed by the header module 6002 to determine the number and/or position of surgical modules 6004 present in the stack configuration. In another example, user input is solicited to determine or to confirm the number of surgical modules 6004 present in the stack configuration. This arrangement allows the modular surgical system 6000 to handle situations where surgical modules 6004 are added or removed by a user. In at least one example, the header module 6002 can infer the number of surgical modules 6004 present in the stack configuration based on the type of surgical procedure being performed, which can be ascertained from user-input, for example. In various aspects, a look-up table or a database of surgical procedure types and their surgical module requirements can be stored in a local memory or a remote server 113 on a cloud, and can be queried by the header module 6002 to determine the number of surgical modules 6004 present in the stack configuration based on the type of surgical procedure being performed.

As described above in greater detail in connection with FIGS. 24-30, a surgical module such as, for example, the surgical module 2004 can include a port assembly 2012 including a number of different ports configured to deliver different energy modalities to corresponding surgical instruments that are connectable thereto. Accordingly, the power requirements of a surgical module varies, at least in part, based on the types, energy modalities, and/or number of surgical instruments connected thereto. In various aspects, connecting or disconnecting a surgical instrument to one of the ports of the port assembly 2012 of a surgical module in a stack configuration causes the header module 6002 to reassess energy allocations to the surgical modules in the stack configuration, and can trigger an adjustment of the power allocations to the surgical modules.

In at least one example, referring primarily to FIG. 38, connecting a surgical instrument to the port assembly of the first surgical module 6004' causes the header module 6002 to increase a previously determined power allocation to the first surgical module 6004' and, consequently, decrease a previously determined power allocation to the second surgical module 6004' to free power for the additional power allocation to the first surgical module 6004'.

In various examples, as described above, a power alloca-
tion adjustment event can be triggered by connecting or
disconnecting a surgical instrument to a port of the port
assembly 2012. In at least one example, any suitable sensors
such as, for example, suitable pressure, contact, and/or or
proximity sensors can be employed by the header module
6003 to monitor the ports of the port assembly 2012 for a
power-allocation adjustment triggering event. In other
examples, the power-allocation adjustment triggering event
can be the activation of a connected surgical instrument
and/or a user-input through the UI module 3030 such as, for
example, a selection of a surgical instrument setting such as,
for example, an energy setting.

In various aspects, the modular surgical system 6000
actively and adaptively manages the power budget through
an ongoing negotiation between the functional surgical
modules 6004 and the header module 6002 to determine
how much power is allocated to each of the surgical modules
6004. Various processes are disclosed herein for active
power management of the modular surgical system. In at
least one example, such processes can be executed by a
control circuit of the modular surgical system such as, for
example, the control circuit 500 (FIG. 13).

In various examples, a power-allocation adjustment trig-
gering event can cause the header module 6002 to apply
restricted power level settings to one or more of functional
modalities of one or more of the surgical modules. In various
examples, a power-allocation adjustment triggering event
can cause the header module 6002 to prevent simultaneous
activation of certain functional modalities of one or more of
the surgical modules at certain power settings. In various
examples, the header module 6002 can disable or deactivate
a module if it is not needed for a particular surgical proce-
dure.

When conflict arises in the power budget negotiations
between the modules of a modular surgical system 6000, the
header module 6002 can attempt to resolve the conflict or,
alternatively, prompt a user to resolve the conflict through
the UI 3030, for example. In various aspects, the power
budget negotiation will be made transparent to the user. In
certain aspects, the user can be notified of a limitation
imposed by the header module 6002. Following the power
budget negotiation, each module is responsible for monitor-
ing its own input power and ensuring that it stays under
predetermined limits. Further, each module implements its
own mitigations to address a situation where the input power
budgeted for the module is exceeded.

Figure 42A:
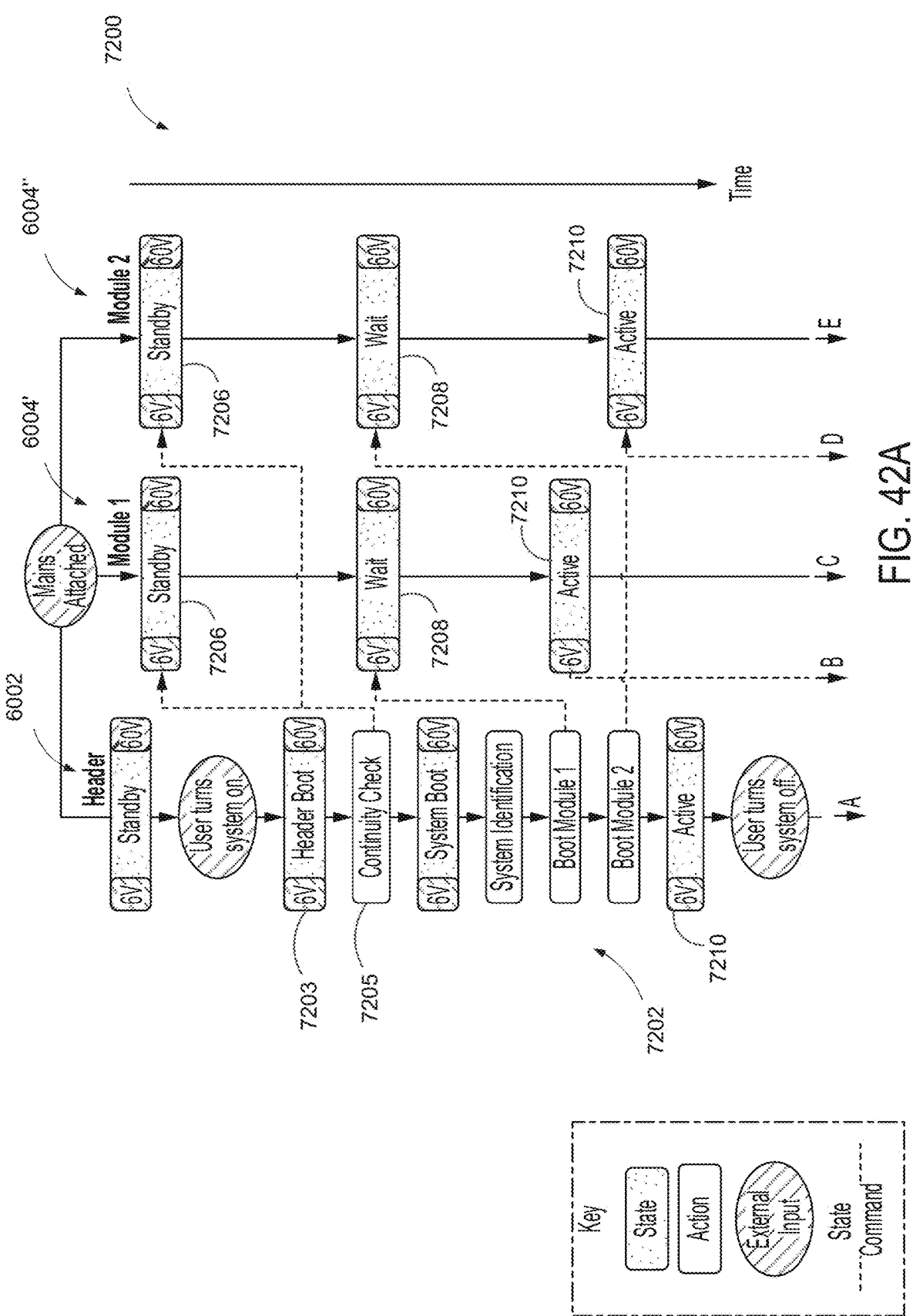
FIGS. 42A and 42B illustrate power up and power down sequences for a modular surgical system, in accordance with at least one aspect of the present disclosure.
Figure 42B:
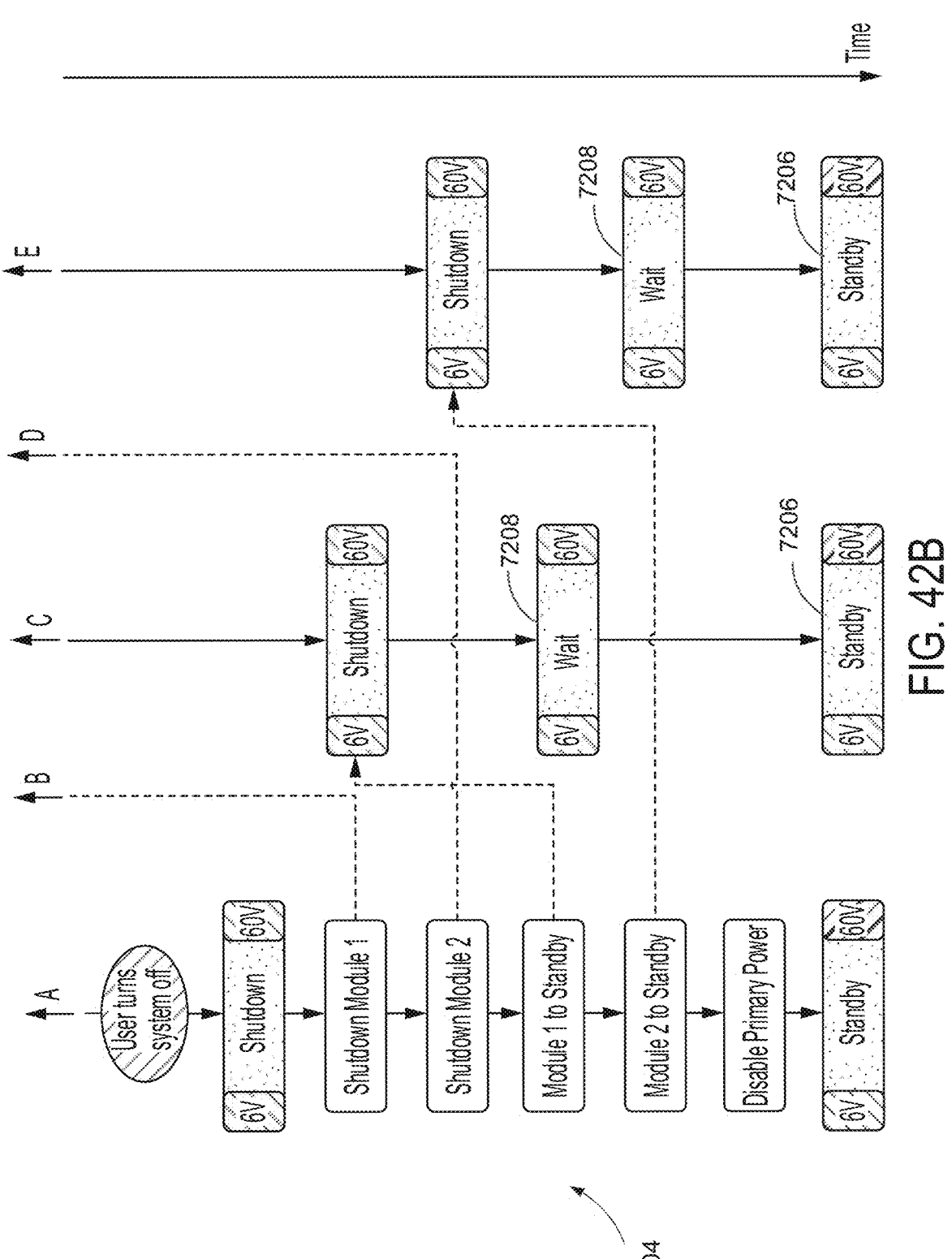

Referring primarily to FIGS. 42A and 42B, an example
power up and power down sequence 7200 of a modular
surgical system 6000 is depicted. The modular surgical
system 6000 of FIGS. 42A and 42B includes a header
module 6002 arranged in a stack configuration with a first
surgical module 6004' and a second surgical module 6004".
FIGS. 42A and 42B detail four unique power states or modes
that modular surgical system 6000 may transition through
during the power up sequence 7202 and/or power down
sequence 7204.

Initially, the header module 6002 is shown in a standby
mode 7206. The primary power and Communications are
disabled in the standby mode 7260. The surgical modules
6004 await for commands from the Header module 6002 to
transition from a standby mode 7206 to a wait mode 7208.
Primary power and communications are enabled in the wait
mode 7208, but the modules consume minimal power as
only limited tasks are available in the wait mode 7208 such
as, for example, system initialization, authentication, and/or
module discovery. In contrast, the primary module functions, for example energy delivery on a surgical module, are
disabled in the wait mode 7208. Accordingly, the surgical
modules 6004 in the stack configuration is incapable of
delivering therapeutic energy in the wait mode 7208.

Further to the above, the header module 6002, while in the
standby mode 7206, is capable of receiving local 6018 (FIG.
38) and/or remote on/off 6016 (FIG. 38) detection com-
mands. Upon receiving a booting command, the primary
power is enabled and a main processor 6041 of the header
module 6002 begins a boot sequence 7203. Then a module
detection check 7205 is performed using the module detec-
tion circuit 6019, for example.

Due to the modular nature of the modular surgical system
6000, a module detection check 7205 is performed to ensure
proper connections are achieved between the modules in the
stack. If the module detection check is passed, the seg-
mented power backplane 6008 of the stack is enabled at 60
volts, for example. If, however, the stack fails the module
detection check 7205, an error message indicative of the
failure can be provided through the user interface 3030 of
the header module 6002, for example. Instructions as to the
reason for the failure, and how to address it, can also be
provided.

In various aspects, once the header module 6002 and the
user interface 3030 are in active mode 7210, the remaining
modules are then brought to an active mode 7210. The
header module 6002 may query module types, versions,
locations over Data Distribution Services (hereinafter
"DDS") framework that may run on a Gigabit Ethernet
interface. Once an active mode of the modular surgical
system 6000 is achieved, a user may be prompted through
the user interface 3030 that the modular surgical system
6000 is ready for use in a surgical procedure.

Like the power up sequence, the power down sequence
7204 can be triggered by a local 6018 and/or remote on/off
6016 command. In the power down sequence 7204, the
modules primary functions are disabled, primary power
consumption is reduced, and/or priority tasks (write logs,
complete data transfers, etc.) are completed, ultimately
causing the power level to be sufficiently reduced to match
the wait mode 7208.

The modular surgical systems of the present disclosure
such as, for example, the modular surgical system 6000 are
assembled or modified by an end user either prior to or
during a surgical procedure. Accordingly, various assembly
and disassembly steps are performed on the modular surgi-
cal systems by someone other than the manufacturer. Many
advantages are gained by such modularity, which also intro-
duces potential failures. To protect against the potential
failures, the modular surgical systems of the present disclo-
sure are equipped with various mechanisms for fault isola-
tion and minimization of single point failures. In addition,
the modular surgical systems include various mechanisms
for awareness of the quantity, type, and/or position of
modules in the stack prior to and/or during application of
power.

In at least one example, as illustrated in FIG. 38, the
modular surgical system 6000 includes a mitigated commu-
nications interface 6021 between the modules in the stack.
To enable fault isolation and minimization of single point
failures, the mitigated communications interface 6021 is
powered from the standby output of the AC/DC power
supply 6003, allowing the mitigated communications inter-
face 6021 to be alive when primary power is removed, or in
the event of a local power failure in a module in the stack.
Furthermore, the mitigated communications interface 6021
is implemented in a separate controller 6023 from the primary communications interface 6040 to ensure that a failure in the primary controller 6041, 6041', 6041" for a module 6002, 6004" 6004", respectively, does not impact the mitigated communications interface 6021.

In various aspects, the Header module 6002 is configured to detect a failure in the modular surgical system 6000 by measuring the total current draw on the primary power domain 6009, and comparing the measured total current draw to the total system input current. If the total system input current is exceeded, the header module 6002 determines that a failure in the modular surgical system 6000 is detected, and can take steps to mitigate the failure, as described elsewhere herein in greater detail.

Further to the above, the mitigated communications interface 6021 could be implemented in either hardware or software. In at least one example, the mitigated communications interface 6021 is implemented as a serial bus or as a command/status shift register, with data/clock/latch signals. The serial bus interface could be either point-to-point or multi-drop. In various examples, as illustrated in FIG. 38, the mitigated communications interface 6021 is implemented in a segmented backplane 6027 connecting the mitigated module controls 6023 of the individual modules of the modular surgical system 6000.

In various aspects, the mitigated communications interface 6021 can facilitate communication between modules in the event of a failure of the primary communications interface 6040. The mitigated communications interface 6021 can also determine the quantity and type(s) of modules in the stack prior to application of power, enabling a stable, predictable power on sequence. Furthermore, module resets, module local power control, and/or module local power sequencing, if necessary, can be facilitated by the mitigated communications interface 6021. In certain examples, the mitigated Communications interface 6021 can be used to put a module into a reset and/or local power down state to isolate failures in a particular module from the rest of the stack.

In various aspects, the header module 6002 is configured to control the local power to each of the surgical modules in a stack via commands on the mitigated communications interface 6021. The Modules can be in one of a number of example power modes. In an off mode, a standby power is available, while the primary backplane power (e.g. 60V) is disabled. In the off mode, the header module 6002 is capable of identifying the presence and/or type of modules connected in the stack, for example.

Further to the above, the standby power is also available in the standby mode. In addition, the primary backplane power (e.g. 60V) is enabled in the standby mode. In contrast, a module secondary power is disabled in the standby mode. The header module 6002 may identify the presence and type of modules in the stack in the standby mode. In addition to the off and standby modes, a sleep mode can also be available, as discussed in connection with FIGS. 42A and 42B. In the sleep mode, the standby power and the backplane power (e.g. 60V) are enabled and module detection check through the module detection circuit 6019 is active. In contrast, all functionality not critical to module detection check, wake detection, module identification, and/or communication between modules is disabled. Further, a wake or active mode is also available. In the active mode, the standby power and the backplane (e.g. 60V) power are enabled and module detection check is active. Further, a module in the active mode participates in all backplane communications.

As discussed above, the one or more modules can be connected together in a variety of different stacked configurations to form various modular surgical system configurations. The stacked configuration of the modules effectively reduces the footprint needed for the modules in the operating room.

Figure 43A:
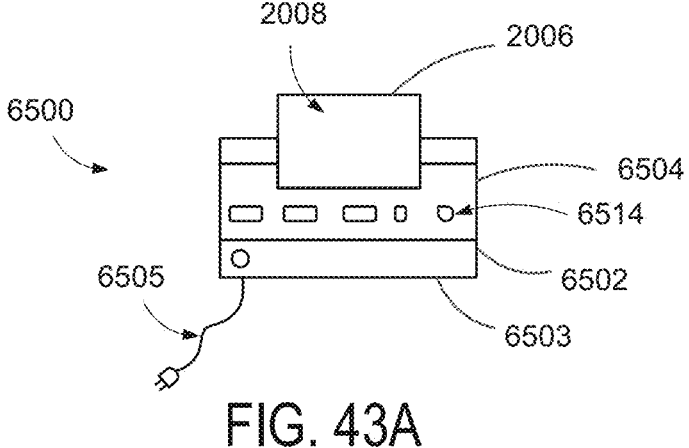
FIG. 43A illustrates a modular surgical system including a header module, a surgical module, and a footer module, in accordance with at least one aspect of the present disclosure.

Referring to FIG. 43A, an alternative modular surgical system 6500 is shown. The modular surgical system 6500 is similar in many respects to other modular surgical systems described elsewhere such as, for example, the modular surgical systems 2000, 6000. However, unlike the modular surgical system 6000, the modular surgical system 6500 includes a header module with a power supply that provides power to surgical modules stacked on top of the header module. Accordingly, the header module of the modular surgical system 6500 is referred to herein as a footer module 6502. Further, one or more surgical modules 6504 are configured to be stacked on top of the footer module 6502.

In some aspects, the modular surgical system 6500 further includes a display screen 6506 that renders a GUI 6508, as described in greater detail below. The positioning of the footer module 6502 beneath the other modules of the modular surgical system 6500 in the stack configuration improves weight distribution of the stack and increases its resistance to external forces when placed upon a work surface, thereby reducing the susceptibility of the stack to being tipped over during use.

As discussed above, it is desirable to reduce the number of cords for a modular surgical system by using a single AC/DC power for the entire system. The footer module 6502 of the modular surgical system 6500 comprises an enclosure or housing 6503 that is configured to be placed upon a work surface, such as a table or cart. The footer module 6502 of the modular surgical system 6500 provides the main AC/DC power supply for the entire system. The footer module 6502 includes a power cord 6505 that is configured to connect to an AC source. The footer module 6502 also includes an AC to DC converter, which is configured to convert the AC current from the AC source to DC voltage for the modules in the modular surgical system.

Like the header module 6002 of the modular surgical system 600, the footer module 6502 of the modular surgical system 6500 provides the main AC/DC power supply for the entire system. The footer module 6502 includes a power cord 6505 that is configured to connect to an AC source. The footer module 6502 also includes an AC to DC converter, which is configured to convert the AC current from the AC source to DC voltage for the modules in the modular surgical system 6500. Further, the footer module can include a power button, which can be used to turn the system on and off, without the need for unplugging and re-plugging the power cord 6505 with each use. The modular surgical system 6500 further includes a surgical module 6504 stacked above the footer module 6502. The surgical module 6504 is configured to support the delivery of energy to instruments that are attached thereto. The surgical module is able to deliver the energy in a multitude of modalities, such as ultrasonic, ABP, monopolar, and bipolar, for example.

Also, like the modular surgical system 6000, the modular surgical system 6500 includes a segmented power backplane similar in many respects to the segmented power backplane 6008 and, in some aspects, a segmented communication back plane similar in many respects to the segmented communication backplane 6021. The segmented power and/or communication backplanes couple the footer module 6502 to other modules of the modular surgical system 6500 in the stack configuration such as, for example, the surgical module 6504. This arrangement allows the footer module 6502 to distribute the DC voltage to the other modules in the system, thereby providing the system with a single energy source for the entire stack.

In some aspects, the modular surgical system 6500 includes a display screen 2006 that renders a GUI 2008 for relaying information regarding the modules 2001 connected to the footer module 6502. In some aspects, the GUI 2008 of the display screen 2006 can provide a consolidated point of control all of the modules making up the particular configuration of the modular surgical system 6500. Various aspects of the GUI 2008 are discussed in fuller detail below in connection with FIG. 30. In alternative aspects, the modular surgical system 6500 can lack the display screen 2006 or the display screen 2006 can be detachably connected to the housing of one of the modules of the modular surgical system 6500.

Figure 43B:
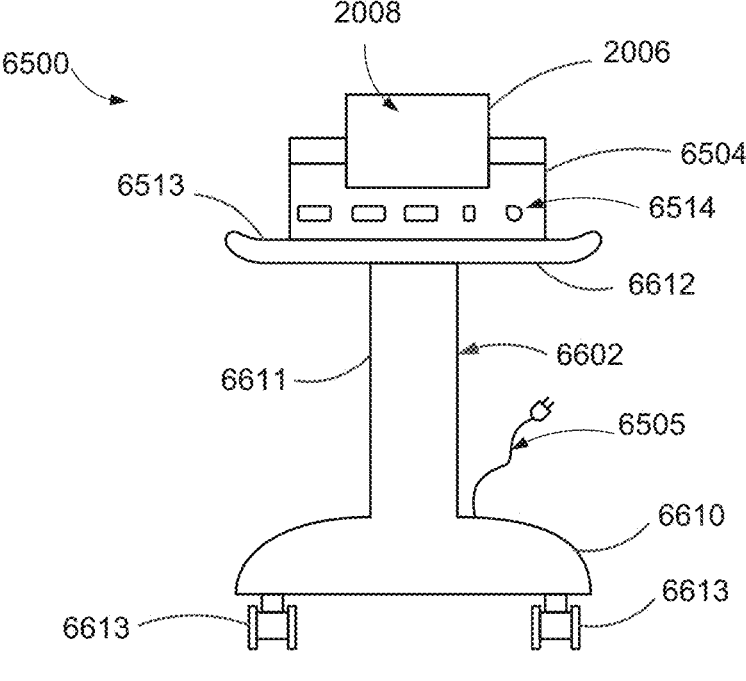
FIG. 43B illustrates a modular surgical system including a header module and a surgical module, the modular surgical system being seated on a footer module cart, in accordance with at least one aspect of the present disclosure.

Referring now to FIG. 43B, an alternative modular surgical system 6600 is depicted in a stack configuration. The modular surgical system 6600 is similar in many respects to the modular surgical system 6500; however, the modular surgical system 6600 includes a footer module 6602 that is integrated into a cart or any other suitable mobile configuration. This design allows the user to reposition the modular surgical system 6600 by rolling the footer module 6602 into its desired location without needing to pick up the modules from the stack. Like the footer module 6502, the footer module 6602 includes a power cord, which can be plugged into an AC source to receive power, which can then be converted to DC power for the modular surgical system 6600 by way of an AC to DC converter, for example.

The footer module 6600 includes a base 6610, a column 6611 extending from the base 6610, and a tray 6612 configured to support, and detachably connect the footer module 6602 to one or more surgical modules 6504 in a stack configuration. In at least one example, the height of the column 6611 can be adjusted by any suitable mechanism to raise or lower the tray 6612. In at least one example, various components of the footer module 6602 can be housed in the base 6610 to improve weight distribution of the stack and increase its resistance to external forces, and reduce the susceptibility of the stack to being tipped over during use.

In various aspects, the modular surgical system 6600 includes one or more of the surgical modules 6504 and/or the display screen 2006. The description of such components is not repeated herein for brevity.

In various aspects, the tray 6612 is detachably coupled to a surgical module 6504 via pass-through hub connectors. Further, like the modular surgical systems 6000, 6500, the modular surgical system 6600 includes a segmented power backplane similar in many respects to the segmented power backplane 6008 and, in some aspects, a segmented communication back plane similar in many respects to the segmented communication backplane 6021. The segmented power and/or communication backplanes couple the footer module 6602 to other modules of the modular surgical system 6600 in the stack configuration such as, for example, the surgical module 6504. This arrangement allows the footer module 6502 to distribute the DC voltage to the other modules in the system, thereby providing the system with a single energy source for the entire stack.

In various aspects, an address such as, for example, 3-bit address which is unique to each module in the stack configuration, is automatically generated in hardware at power-up. The address provides each module with its physical location within the stack configuration as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION, U.S. patent application Ser. No. 16/562,234, titled MODULAR SURGICAL ENERGY SYSTEM WITH MODULE POSITIONAL AWARENESS SENSING WITH TIME COUNTER, and U.S. patent application Ser. No. 16/562,243, titled MODULAR SURGICAL ENERGY SYSTEM WITH MODULE POSITIONAL AWARENESS WITH DIGITAL LOGIC, which are incorporated by reference herein in their entireties.

As described in greater detail herein, a modular surgical system comprises a header module and one or more functional or surgical modules. In various instances, the modular surgical system is a modular energy system. In various instances, the surgical modules include energy modules, communication modules, and/or user interface modules; however, the surgical modules are envisioned to be any suitable type of functional or surgical module for use with the modular surgical system.

The header module is configured to control the system-wide settings of each module/component connected thereto. In order to effectively control the modules, it is important for the header module to know and/or be aware of the physical location of each module in the system. In various instances, the physical location of each connected module is recognized and/or determined by the header module so that user interface content for each module can be arranged with a 1:1 association to the physical location of each module. In various instances, the physical location of each connected module is recognized by the header module so that a unique address can be assigned to each module. Assignment of a unique address allows the module to be used with a mitigated communication bus.

Figure 44:
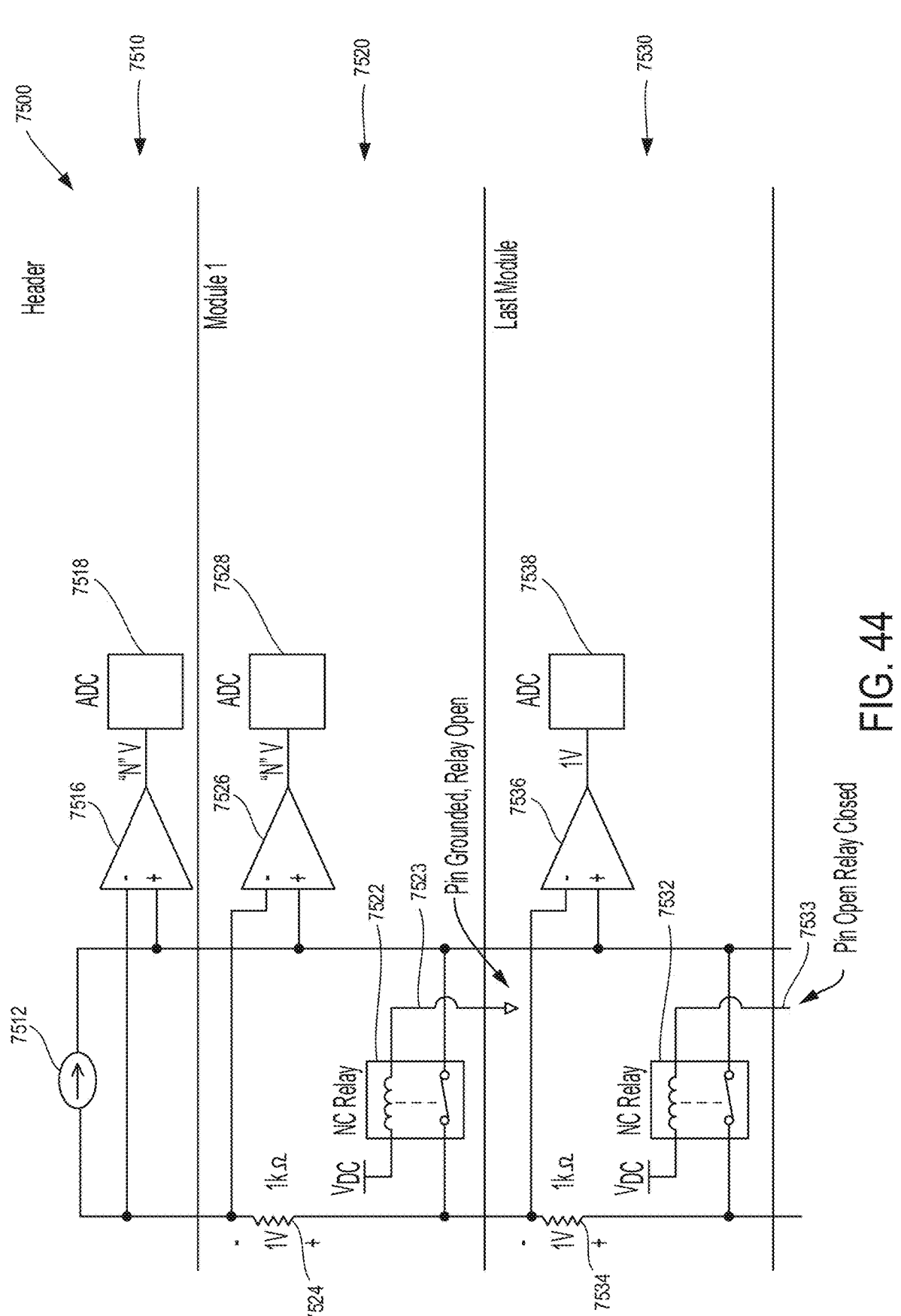
FIG. 44 is a module identification circuit of a modular surgical system, in accordance with at least one aspect of the present disclosure.

FIG. 44 illustrates a modular identification circuit 7500 of a modular surgical system, or a modular energy system. Among other things, the modular identification circuit 7500 is utilized to identify the physical location of one or more modules within a stack configuration of the modular surgical system. In various instances, the modular identification circuit 7500 is configured to detect the total number of modules present within the stack configuration. As shown in FIG. 44, the modular surgical system comprises a header module 7510, a first module 7520, and a second, or last, module 7530. The header module 7510 comprises a current source 7512. A current loop extends from the header module 7510 through each module of the modular surgical system, ultimately returning to the header module 7510. In order for the current to travel through each module of the modular surgical system, each module must be appropriately connected to the modular surgical system and/or each module must be functional.

The header module 7510 is stacked at a top position of the modular surgical system as shown in FIG. 44. A first module 7520 is shown stacked below the header module 7510 in an adjacent position. A second, or last, module 7530 is shown stacked below the first module 7520. In other words, the modular surgical system depicted in FIG. 44 comprises a stack configuration (from top to bottom) of: the header module 7510; the first module 7520; and the last module 7530.

The first module 7520 comprises a first pin 7523 and a normally-closed (NC) relay 7522. The NC relay 7522 is configurable in an open state and a closed state. When the first module 7520 is the only modular component connected to the header module 7510 and/or the first module 7520 is located at bottom-most position within the stack configuration, the first pin 7523 is open and the relay 7522 is closed. In such instances, the current runs from the header module 7510 though the first module 7520 and back to the header module 7510. In various instances, the first pin 7523 is open and the relay 7522 is closed when the first module 7520 is located at bottom-most position within the stack configuration. For example, the first module 7520 could be the only modular component connected to the header module 7510 and/or one or more modules can be positioned between the first module 7520 and the header module 7510.

The second, or last, module 7530 comprises a second pin 7233 and a normally-closed (NC) relay 7532. The NC relay 7532 is configurable in an open state and a closed state. When the second module 7530 is the only modular component connected to the header module 7510, the second pin 7533 is open and the relay 7532 is closed. In such instances, the current runs from the header module 7510 though the second module 7530 and back to the header module 7510. In various instances, such as shown in FIG. 44, the modular surgical system comprises a modular component, such as the first module 7520, positioned in between the second module 7530 and the header module 7510. The connection between the first module 7520 and the second module 7530 causes the first pin 7523 of the first module 7520 to be grounded and causes the NC relay 7522 to be in an open state. As the second module 7530 does not comprise any additional modular components connected and/or positioned underneath the second module 7530 in the stack configuration, the second pin 7233 is in the closed state. In such instances, the current runs from the header module 7510 through the first module 7520, from the first module 7520 through the second module 7520, from the second module 7520 back through the first module 7520, and from the first module 7520 back to the header module 7510.

The relay of the bottom functional modules is closed because its pin is open. In contrast, the relay of an intermediate functional module is open because its pin is grounded in a lower module chassis.

Each module adds series resistance to the current loop, creating a voltage divider. The first module 7520 comprises a first resistor 7524, and the second module 7530 comprises a second resistor 7534. The first resistor 7524 and the second resistor 7534 are placed in series with the current source 7512 of the header module 7510. By placing the resistors 7524, 7534 in series with the current source 7512, a voltage divider is created. The header module 7510 is configured to measure the total resistance in the loop to determine the total number of modules in the stack configuration and/or the modular surgical system.

By measuring the total voltage drop between the input and the output of the current source 7512, the header module 7510 is configured to detect the total number of modules present within the stack configuration. For example, the resistors 7524, 7534 have a resistance of 1 ohm. If the header module 7510 detects a total voltage drop of 1V, only 1 module is present and/or appropriately connected within the stack configuration. If the header module 7510 detects a total voltage drop of 2V, 2 modules are present and/or appropriately connected within the stack configuration. Such an ability of the header module 7510 provides a mitigation strategy, by providing the header module 7510 with a secondary means for detecting module quantity outside of a primary communication bus, such as, for example, an Ethernet cable.

Each module within the stack configuration is configured to measure the voltage from the current source 7512 of the header module 7510 to the low side of the module's resistor in the loop. By measuring the voltage drop between the current source 7512 of the header module 7510 and the low side of the module resistor, a module may detect its own physical position within the stack configuration. The header module comprises a differential amplifier 7516 and an analog to digital converter (ADC) 7518. The first module 7520 further comprises a differential amplifier 7526 and an ADC 7528. The second module 7530 further comprises a differential amplifier 7536 and an ADC 7538. It is envisioned that each module within the modular surgical system comprises a differential amplifier and an ADC for determining the voltage value at each of the modules. In the first module 7520, the differential amplifier 7526 is connected to a high side of the module 7520, which is a position in the module 7520 before the current passes through the resistor 7524. The differential amplifier 7526 is also connected to a low side of the module 7520, which is a position after the current has passed through the resistor 7524. The voltage drop between the header current source 7512 and the low side of the resistor 7524 is measured by the differential amplifier 7526 and is then passed to the ADC 7528. The ADC 7528 then uses this voltage drop to determine a physical location of the module 7520 within the stack configuration.

In a similar manner, the differential amplifier 7536 is connected to a high side of the second module 7530, which is a position in the module 7530 before the current passes through the resistor 7534. The differential amplifier 7536 is also connected to a low side of the module 7530, which is a position after the current has passed through the resistor 7534. The voltage drop between the header current source 7512 and the low side of the resistor 7534 is measured by the differential amplifier 7536 and is then passed to the ADC 7538. The ADC 7538 then uses this voltage drop to determine a physical location of the module 7530 within the stack configuration.

In the modular identification circuit 7500 illustrated in FIG. 44, the header module 7510 comprises a 1 mA current source 7512. The header module is stacked on top of a first module 7520 and a second module 7530. As described above the first module 7520 comprises a 1kΩ resistor 7524, a differential amplifier 7526, and an ADC 7528. The second module 7530 comprises a 1kΩ resistor 7534, a differential amplifier 7536, and an ADC 7538. While a 1 mA current source 7512 and 1kΩ resistors 7524, 7534 are shown, it is envisioned that any suitable combination of current sources and resistors can be used.

The 1 mA current flows from the header module 7510 through the modules stacked therebelow. As discussed above, the high side of the differential amplifiers of the modules measure the voltage before the current passes through the resistor. The current from the header module 7510 flows through the high side of all of the differential amplifiers 7526, 7536 of the modules stack therebelow. Once the current reaches the last module of the stack configuration, the current begins to flow back toward the header module. For example, in FIG. 44, once the 1 mA current reaches the second module 7530, the 1 mA current begins flowing back toward the header module 7510.

As the current flows back toward the header module 7510, the 1 mA current passes across the 1kΩ resistor 7534 of the second module 7530, which results in a 1V voltage drop between the header current source 7512 and the resistor 7534. The differential amplifier 7536 of the second module 7530 is configured to measure this 1V voltage drop and determine a 1V voltage differential between the header current source 7512 and the low side of the resistor 7534 of the second module 7530. The differential amplifier 7536 can then transmit a signal corresponding to this voltage differential to the ADC 7538, which can interpret this signal and assign a corresponding address to the second module 7530. In the illustrated example, the 1V voltage differential signal is converted to a digital reading by the ADC 7538. The digital reading is interpreted by a controller that assigns a corresponding and/or unique address to the second module 7530. The assigned address corresponds to a physical location of the second module 7530 within the stack configuration with respect to the header module 7510.

After the current passes through the resistor 7534 of the second module 7530 of the module stack, the current continues to flow back toward the header module 7510. As the current flows from the second module 7530 toward the header module 7510, the 1 mA current passes across the 1kΩ resistor 7524 of the first module 7520. The differential amplifier 7526 of the first module 7520 is configured to measure this voltage drop and determine a 2V voltage differential between the header current source 7512 and the low side of the resistor 7524 of the first module 7520. The differential amplifier 7526 can then transmit a signal corresponding to this voltage differential to the ADC 7528, which can interpret this signal and assign a corresponding address to the first module 7520. In the illustrated example, the 2V voltage differential signal is converted to a digital reading by the ADC 7528. The digital reading is interpreted by a controller that assigns a corresponding and/or unique address to the first module 7520. The assigned address corresponds to a physical location of the first module 7520 within the stack configuration with respect to the header module 7510.

In instances where additional modular components are positioned between the second module 7530 and the header module 7510, each differential amplifier and ADC of the remaining modules are configured to measure the voltage drop across its respective module resistors and assign corresponding "N" addresses until the current returns to the header module. An address is not assigned to the header module.

The circuit illustrates a header module stack at the top position of the modular energy system configuration. In the example circuit, "N" modules are shown stack below the header module, where "N" represents any positive integer. While the example circuit illustrates two modules stack below the header module, more or fewer modules can be used.

In various instances, the module positioned at the bottom of the stack configuration is assigned an address "1" based on the detected voltage drop between the header current source and the low side of the module resistor. The next module measures a voltage drop of 2V and is assigned address "2", for example. The "Nth" module measures "N" V, and is assigned address N. In various aspects, the header module comprises a memory storing information indicating that the address "1" corresponds to a module at the bottom of the stack, and the module with the address "N" is on the top of the stack, wherein the bottom of the stack is furthest away from the header module, and wherein the top of the stack is closest to the header module.

As discussed in greater detail herein, in various instances, the modular surgical system further comprises a display screen, such as, for example, the display screen 2006. The display screen renders a graphical user interface for relaying information regarding the modules connected to the header module. In various instances, the display is configured to visually represent and/or communicate the determined physical location of each modular component within the stack configuration of the modular surgical system.

As described in greater detail herein, a modular surgical system comprises a header module, to control the system-wide settings of each module/component connected thereto. The header module can facilitate power transmission between the modules in the system. However, it is desirable for the header module to be able to verify the integrity of the connections between the one or more modules prior to applying power to the system.

Figure 45:
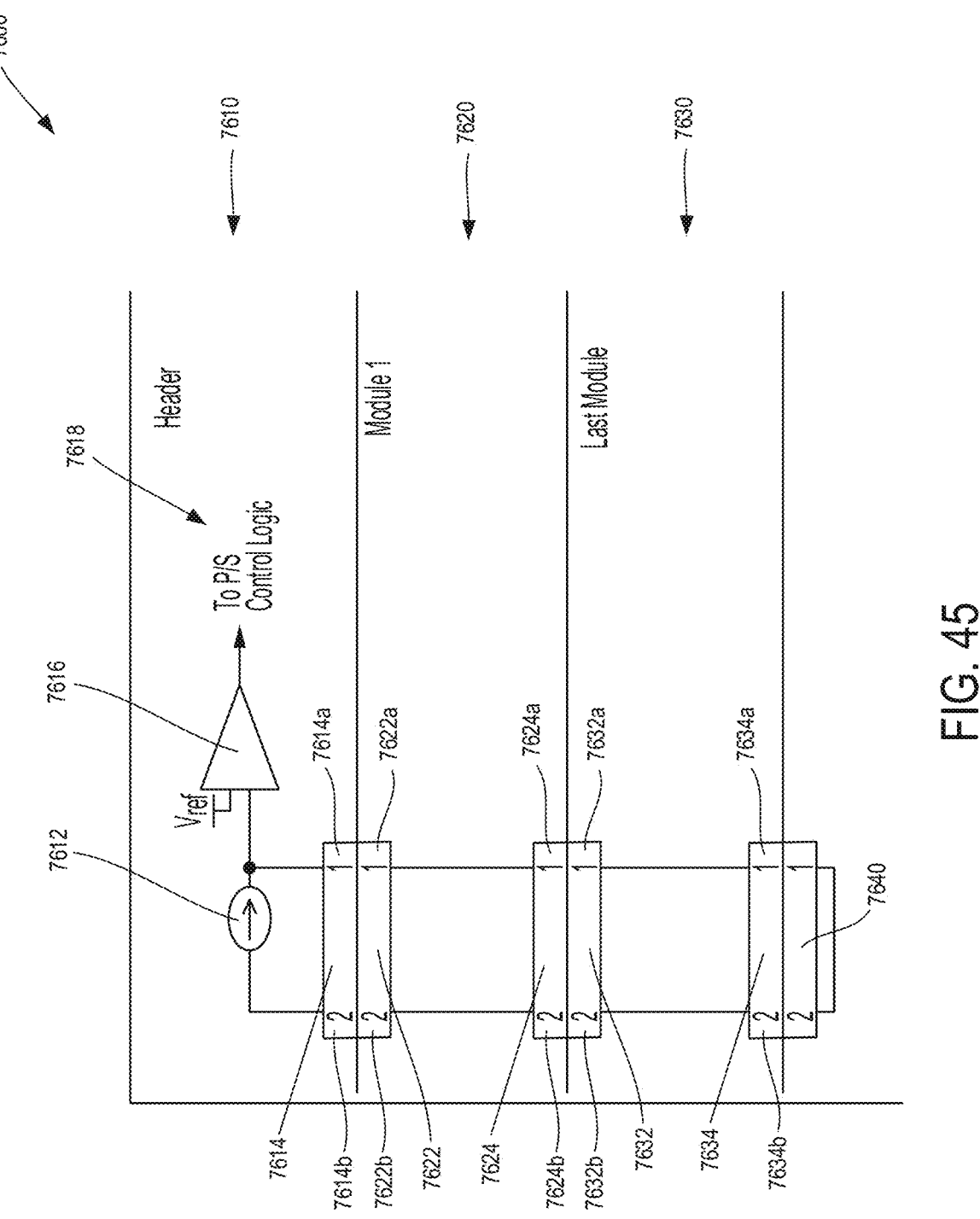
FIG. 45 is a connection integrity circuit of a modular surgical system, in accordance with at least one aspect of the present disclosure.

Referring now to FIG. 45, a connection integrity circuit 7600 a modular surgical system, or a modular energy system, is shown. The connection integrity circuit 7600 causes a header module 7610 to detect an open circuit (no voltage difference across a current source) when: (1) there are no modules connected to the header module 7610; (2) there is a broken pin and/or a broken connection on one of the modules connected downstream; and/or (3) there is a faulty relay in the last module. The modular surgical system comprises a header module 7610 and two modules stack therebelow. The two modules comprise a first module 7620 and a second module 7630. While the illustrated circuit 7600 depicts two modules connected with the header module 7610, any suitable number of modules can be used and/or connected.

The header module 7610 is connected to a first module 7620 by way of a bridge connector. The input bridge connector 7622 of the first module 7620 comprises a first pin 7622a and a second pin 7622b. The first pin 7622a and the second pin 7622b of the input bridge connector 7622 are configured to connect to a corresponding first pin 7614a and second pin 7614b in an output bridge connector 7614 of the header module 7610. In addition, the first module 7610 comprises an output bridge connector 7624 comprising a first pin 7624a and a second pin 7624b. The first and second pins 7624a, 7624b of the output bridge connector 7624 of the first module 7620 are configured to respectively connect to a first pin 7632a and a second pin 7632b of an input bridge connector 7632 of the next module in the stack, i.e., the second module 7630. The second module 7630, similar to the first module 7620, comprises an output bridge connector 7634 that comprises first and second pins 7634a, 7634b. As the second module 7630 is the last module in the depicted stack, a shorting plug 7640 connects the first and second pins 7634a, 7634b of the output bridge connector 7634, thereby completing the circuit.

In order to verify the integrity of the connections of the modules with the header module 7610, a continuity loop is utilized. The header module 7610 comprises a current source 7612, which is configured to pass a current through the first pins 7614a, 7624a, 7634a of the modules in the stack and return the current to the header module 7610 through the second pins 7634b, 7624b, 7614b of the modules in the stack. The continuity loop allows the header module 7610 to detect a high resistance and/or an open connection in one of the module-to-module bridge connectors 7614, 7622, 7624, 7632, 7634.

In various instances, the connection integrity circuit 7600 comprises an operational amplifier 7616. The voltage output of the operational amplifier 7616 can be indicative of the integrity of the connection to all modules in its stack. In at least one example, an analogue to digital converter ("ADC") 7618 can convert the voltage output of the operational amplifier 7616 into digital readings indicative of the integrity of the connection(s). The digital readings can be communicated to a controller that may issue an alert and/or disable power supply, for example, if the controller determines that the integrity of the connection is compromised. The alert can be issued through a user interface of the header module 7610 and can include instructions of how to properly connect the assembly of the stack, for example.

In various instances, the connection integrity circuit 7600 is configured to generate a first output indicative an uncompromised electrical connection to the modules in the stack. The connection integrity circuit 7600 is further configured to generate a second output, different than the first output, indicative of a compromised electrical connection between one or more modules in the stack.

Figure 46:
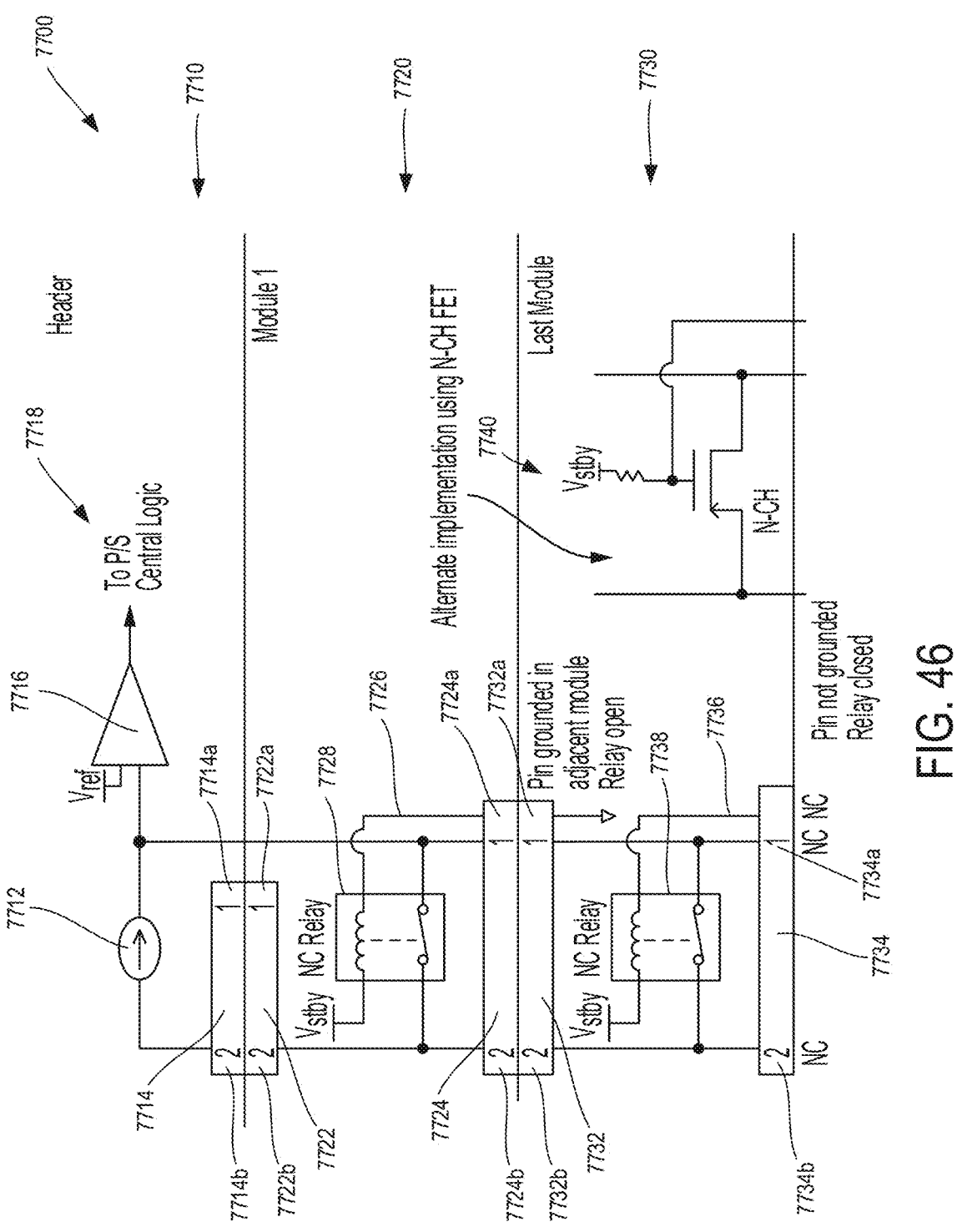
FIG. 46 is a connection integrity circuit of a modular surgical system, in accordance with at least one aspect of the present disclosure.

As discussed above, the connection integrity circuit 7600 of FIG. 45 comprises a shorting plug 7640 attached to the first and second pins 7634a, 7634b of the second module 7630 to complete the circuit. Referring now to FIG. 46, a connection integrity circuit 7700 is shown that does not require a shorting plug. The circuit 7700 is similar to the circuit 7600 shown and described in FIG. 45 in that there is, among other things, a header module 7710 comprising a current source 7712, a first module 7720, and a second module 7730. As discussed above, while two modules are depicted in connection with the header module, any suitable number of modules can be used and/or connected.

The header module 7710 is connected to the first module 7720 by way of a bridge connector. An input bridge connector 7722 of the first module 7720 comprises a first pin 7722a and a second pin 7722b. The first pin 7722a and the second pin 7722b of the input bridge connector 7722 are configured to connect to a corresponding first pin 7714a and second pin 7714b in an output bridge connector 7714 of the header module 7710. In addition, the first module 7710 comprises an output bridge connector 7724 comprising a first pin 7724a and a second pin 7724b. The first and second pins 7724a, 7724b of the output bridge connector 7724 of the first module 7720 are configured to respectively connect to a first pin 7732a and a second pin 7732b of an input bridge connector 7732 of the next module in the stack, i.e., the second module 7730. The second module 7730, similar to the first module 7720, comprises an output bridge connector 7734 that comprises first and second pins 7734a, 7734b.

In order to verify the integrity of the connections of the modules with the header module 7710, a continuity loop is utilized. The header module 7710 comprises a current source 7712, which is configured to pass a current through the first pins 7714a, 7724a, 7734a of the modules in the stack and return the current to the header module 7710 through the second pins 7734b, 7724b, 7714b of the modules in the stack. The continuity loop allows the header module 7610 to detect a high resistance and/or an open connection in one of the module-to-module bridge connectors 7714, 7722, 7724, 7732, 7734.

As illustrated in FIG. 46, instead of connecting a shorting plug to the first and second pins 7734a, 7734b of the second module 7730, an NC relay can be incorporated into each module. More specifically, the first module 7720 comprises a NC relay 7728 and the second module 7730 comprises a NC relay 7738. The NC relays are normally closed; however, the NC relays are driven open when a pin in the adjacent module is pulled down to ground. Thus, in the depicted circuit, an NC relay is driven open in all modules except the last module, as the control pin is not pulled to ground. In various instances, the NC relays 7728, 7738 can be replaced by an N-Channel MOSFET 7740.

One of the limitations of the NC relay/FET solution is that the control of the relay relies on a connection being made in the same connector interface that is being checked for continuity on other pins. Accordingly, various alternative connection integrity circuits are presented, which control the relay using different mechanisms of detecting whether a module is the last/bottom module in the stack.

In various instances, the bottom module can be detected by a Hall Effect sensor. A magnet is placed on or near a top surface of the functional modules, and a Hall Effect sensor is placed on or near the bottom surface of the functional modules. The Hall Effect sensor of an upper module will detect the magnet of a lower adjacent module in the stack configuration. Since the bottom module in a stack is not followed by a lower module, its Hall Effect sensor will not detect a magnet. The absence of a magnet indicates the absence of a lower module. Signals from a Hall Effect sensor of a functional module can be analyzed by a control circuit to determine whether the module is the bottom module in the stack.

In various instances, the bottom module can be detected by any suitable type of near field communication. A tag is placed on or near a top surface of the functional modules, and a tag reader is placed on or near the bottom surface of the functional modules. The tag reader of an upper module will detect the tag of a lower adjacent module in the stack configuration. Since the bottom module in a stack is not followed by a lower module, its tag reader will not detect a tag. The absence of a tag indicates the absence of a lower module. Signals from a tag reader of a functional module can be analyzed by a control circuit to determine whether the module is the bottom module in the stack.

In various instances, a mechanical switch in the upper module can be tripped by a feature in the lower module. Accordingly, an un-tripped switch is indicative of the last/bottom module in the stack.

In various instances, an optical sensor in the upper module can be tripped by a feature in a lower module. Accordingly, an un-tripped optical sensor is indicative of the last/bottom module in the stack.

Figure 47:
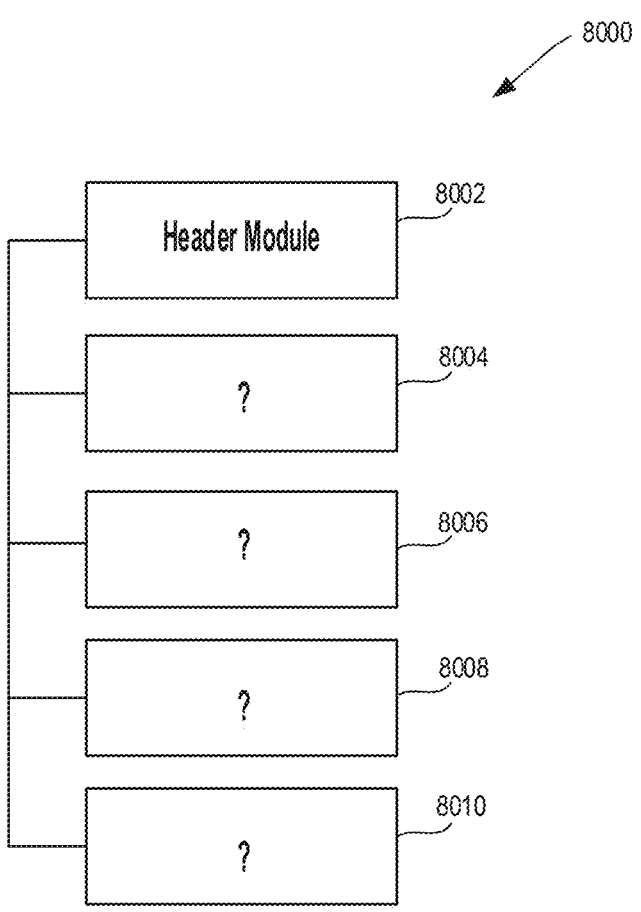
FIG. 47 is a schematic diagram of a modular energy system, in accordance with at least one aspect of the present disclosure.

As discussed above, the one or more modules can be connected to a header module, such as header module 2002, in a variety of different stacked configurations to form various modular energy system configurations, such as modular energy system 2000. For example, as illustrated in FIG. 47, a modular energy system 8000 can include a header module 8002 connected to a top module 8004, a bottom module 8010, and two intermediate modules 8006, 8006. In certain instances, the header module 8002 requires the physical location of the modules in its stack so that user interface content from a GUI, such as GUI 2008, for each module can be arranged with a 1:1 association to the physical location of each module. In certain instances, the header module requires the physical location of each module in the stack so that an address can be assigned, and so that the module can be used with a mitigated communications bus, such as data bus 3008. In various examples, the header modular identifies the physical location of each module and assigns an address by way of an analog signal, such as in U.S. patent application Ser. No. 16/562,212, or a digital signal, such as in U.S. patent application Ser. No. 16/562,243, both of which are incorporated by reference in their entireties. In other examples, as described below, the header module identifies the physical location of each module and assigns an address with a clock pulse signal. Positional awareness of the modules 8004, 8006, 8008, 8010 with respect to the header module 8002 and/or with respect to each other facilitates a proper interaction between the modules 8004, 8006, 8008, 8010 and the header module 8002.

In various aspects, to avoid a faulty start of a modular energy system, it is desirable to perform at least an initial determination of the physical positions of the modules in a stack at low power and without aid or support from the processors of the modules in the stack. The present disclosure provides a reliable mechanism for identification of the physical positions of the modules in a stack, which does not require primary or intensive backplane (serial bus/Ethernet) communication to identify the modules.

Figure 48:
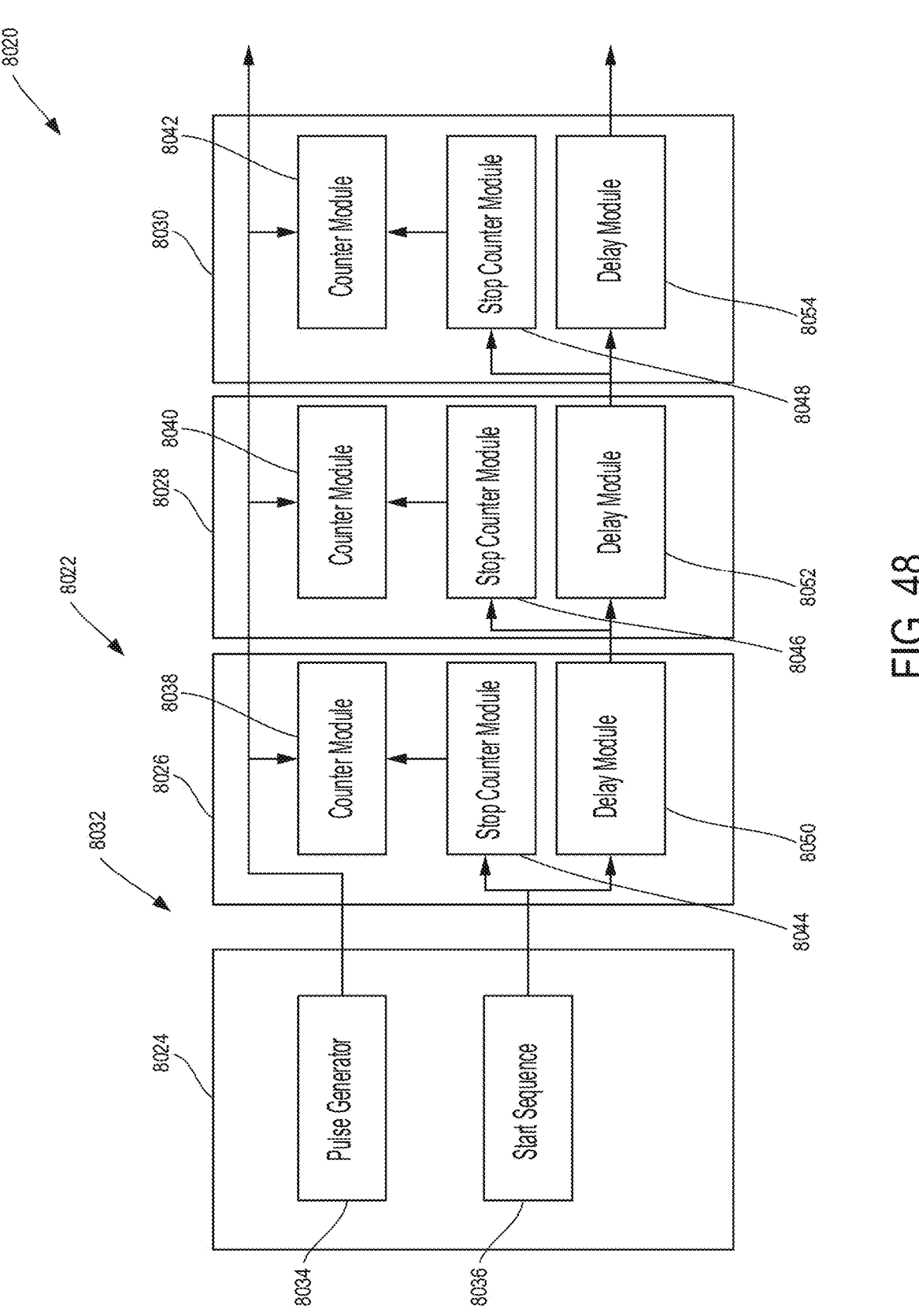
FIG. 48 is a schematic diagram of an identification circuit for determining physical locations of modules in a modular energy system utilizing a timing signal or clock pulses, in accordance with at least one aspect of the present disclosure.

Referring to FIG. 48, a modular energy system 8020 can include an identification circuit 8022, which is employed by a header module 8024 to determine the physical position of modules, such as modules 8026, 8028, 8030, within the modular energy system 8020. While three modules 8026, 8028, 8030 are shown and described, any more or less modules can be used. The identification circuit 8022 defines a communication interface 8032 configured to electrically couple the modules 8026, 8028, 8030 to the header module 8024 and/or to one other. The communication interface 8032 can, for example, be implemented by a separate communication bus (e.g. Ethernet, serial bus, LIN, etc.), which can be defined by detachably couplable communication backplane segments of the individual modules. In at least one example, the communication interface 8032 is a two-wire interface.

The header module 8024 can use the communication interface 8032 to interact with the modules 8026, 8028, 8030 to identify and determine the physical position of the modules 8026, 8028, 8030 within the modular energy system 8020. Additionally, or alternatively, the modules 8026, 8028, 8030 can utilize the communication interface 8032 to interact with one another to exchange addresses and/or other relevant information, independently from the header module 8024. In one embodiment, the physical position of the modules 8026, 8028, 8030 can be a physical position relative to the header module 8024. In another embodiment, the physical position can be a physical position relative to a module other than the header module 8024. In at least one example, the identification circuit 8022 does not require software to perform the identification of the modules 8026, 8028, 8030.

In one embodiment, the header module 8024 can include a pulse generator module 8034 and a start sequence module 8036. The pulse generator module 8034 can be configured to generate a timing signal or clock pulses that can be synchronously transmitted to each of the modules 8026, 8028, 8030 in the modular energy system 8020 by way of the communication interface 8032. The start sequence module 8036 can configured to generate a sequence signal that can be transmitted to the first module in the modular energy system 8020, such as module 8026, by way of the communication interface 8032.

Each of the modules 8026, 8028, 8030 in the modular energy system 8020 can include a counter module 8038, 8040, 8042, a stop-counter module 8044, 8046, 8048, and a delay module 8050, 8052, 8054, respectively. When the header module 8024 is electrically coupled to the modules 8026, 8028, 8030 in the modular energy system 8020 by way of the communication interface 8032, the pulse generator module 8034 can be configured to electrically couple to each of the counter modules 8038, 8040, 8042. This configuration can allow a timing signal or clock pulses from the pulse generator module 8034 to be received by each of the counter modules 8038, 8040, 8042 at substantially the same time. When the header module 8024 is electrically coupled to the modules 8026, 8028, 8030 in the modular energy system 8020 by way of the communication interface 8032, the start sequence module 8036 can be configured to electrically couple to the stop-counter module 8044 and the delay module 8050 of the first module 8026. This configuration can allow a sequence signal from the start sequence module

8034 to be only be received by the stop-counter module 8044 and the delay module 8050 of the first module 8026.

Each of the delay modules can be configured to couple to the subsequent stop-counter module and delay module in the modular energy system 8020. In this configuration, a sequence signal for each stop-counter module and delay module, after the first module, can be received from the previous delay module. In one example, the delay module 8050 is configured to couple to the stop-counter module 8046 and delay module 8052 of the second module 8028 and provide a sequence signal thereto. In a second example, the delay module 8052 is configured to couple to the stop-counter module 8048 and delay module 8054 of the third module 8030 and provide a sequence signal thereto.

To perform the identification process, each of the counter modules 8038, 8040, 8042 can be configured to initiate at count 0. A timing signal comprising a first pulse train can be transmitted from the pulse generator module 8034 to each counter module 8038, 8040, 8042 through the communication interface 8032. Upon reception of a first pulse from the pulse generator module 8034, each counter module 8038, 8040, 8042 can be configured to increment. In one example, a first pulse can be configured to increment each counter module 8038, 8040, 8042 to 1. Subsequent pulses from the pulse generator module 8034 can cause the counter modules 8038, 8040, 8042 to further increment and count the number of pulses received from the pulse generator module 8034.

At substantially the same time as the first pulse from the pulse generator module 8034, a sequence signal can be transmitted from the start sequence module 8036 to the stop-counter module 8044 and the delay module 8050 through the communication interface 8032. In at least one other embodiment, the start sequence module 8036 can be configured to transmit the sequence signal at a time after the first pulse from the pulse generator 8034, but before a second pulse from the pulse generator 8034. Upon reception of the sequence signal from the start sequence module 8036, the stop-counter module 8044 can be configured to deliver a stop signal to the counter module 8038 to stop the counter module 8038 from further incrementing. The final increment at which the counter module 8038 is at upon reception of the stop signal from the stop-counter module 8044 can be locked in and stored in the counter module 8038, such as in a memory. A module ID number can be assigned to the first module 8026 based on the final increment count.

In one embodiment, the pulse generator module 8034 can transmit a first pulse to the counter module 8038 at substantially the same time that the start sequence module 8036 transmits a sequence signal to the stop-counter module 8044, which then sends a stop signal to the counter module 8038. The counter modules can be configured to process and interpret near simultaneous increment signals and a stop signal. In one example, the counter module 8038 can give priority to the stop signal, at a rising edge of a pulse from the pulse generator module 8034, stopping count at 0. In a second example, the counter module 8038 can give priority to the increment signal and increment to 1 at a rising edge of a pulse from the pulse generator module 8034. In one embodiment where the stop signal is given priority over the increment signal, the counter module 8038 can be finalized before receiving the first pulse from the pulse generator module 8034. In this embodiment, the counter module 8038 has not incremented beyond 0 when it has finalized. This 0 value can be used to provide a module ID number to the module. In one example, the final increment number can be the module ID number. In the example described above where counter module 8038 has finalized at 0, the first module 8026 can be assigned module ID number 0. The module ID number can be used to indicate the physical position of the module within the modular energy system 8020.

Continuing from above, upon reception of the sequence signal from the start sequence module 8036, the delay module 8050 can be configured to delay the sequence signal from the start sequence module 8036 by a predetermined time delay, which can be, for example, one pulse. In at least one example, the one pulse delay can be substantially the same as the period of the pulses generated by the pulse generator module 8034. In at least one example, the predetermined time delay is measured in number of timing-signal pulses.

After the one pulse delay, the delay module 8050 can be configured to transmit a sequence signal to the stop-counter module 8046 and the delay module 8052 of the second module 8040. Similar to above, the stop-counter module 8046 can be configured to transmit a stop signal to the counter module 8040 upon reception of the sequence signal from the delay module 8050. The stop signal from the stop-counter module 8046 can be configured to stop the counter module 8040 from further incrementing and lock in the final increment count. As the stop signal from the stop-counter module 8046 was delayed one pulse by the delay module 8050, the counter module 8040 can at least be allowed to increment in response to the first pulse from the pulse generator module 8034. In one embodiment, the counter module 8040 can increment to 1 before the stop-counter module 8046 transmits a stop signal to the counter module 8040. In one example where the stop signal is given priority over a pulse from the pulse generator module 8034, the final increment on counter module 8040 can be 1, which can be used to assign a module ID number 1 to the module 8028.

Accordingly, the identification circuit formed by the stack is capable of determining the position of each of the modules in the stack and assigning a unique identifier to each module using only two backplane signals in a low power setting without aid or support from the primary processors of the modules. The number of modules identifiable using the identification circuit is limited only by the pulse-counters count.

In some aspects, the header module 8024 can include or support a display, such as display 2006. After the identification process, the modules 8026, 8028, 8030 can be configured to determine their own module ID number without involvement from the header module 8024. This can allow the modules 8026, 8028, 8030 to act on information without header module 8024 involvement, such as setting up the modules' communication addresses for other communication buses. In another embodiment, the header module 8024 can be configured to receive the module ID numbers from the modules 8026, 8028, 8030. In one example, the header module 8024 can be configured to receive the module ID number through the communication interface 8032. The header module 8024 can be configured to interpret the module ID numbers and provide a visual representation of the modules 8026, 8028, 8030 on the display in relative position representing their physical position in the modular energy system 8020. The display can provide information about the modules 8026, 8028, 8030, such as the type of module, status of module, availability of the module, health of module, etc. A user can select one of the modules from the display, such as with a touchscreen, in order to provide instructions to the module by way of a user interface.

Figure 49:
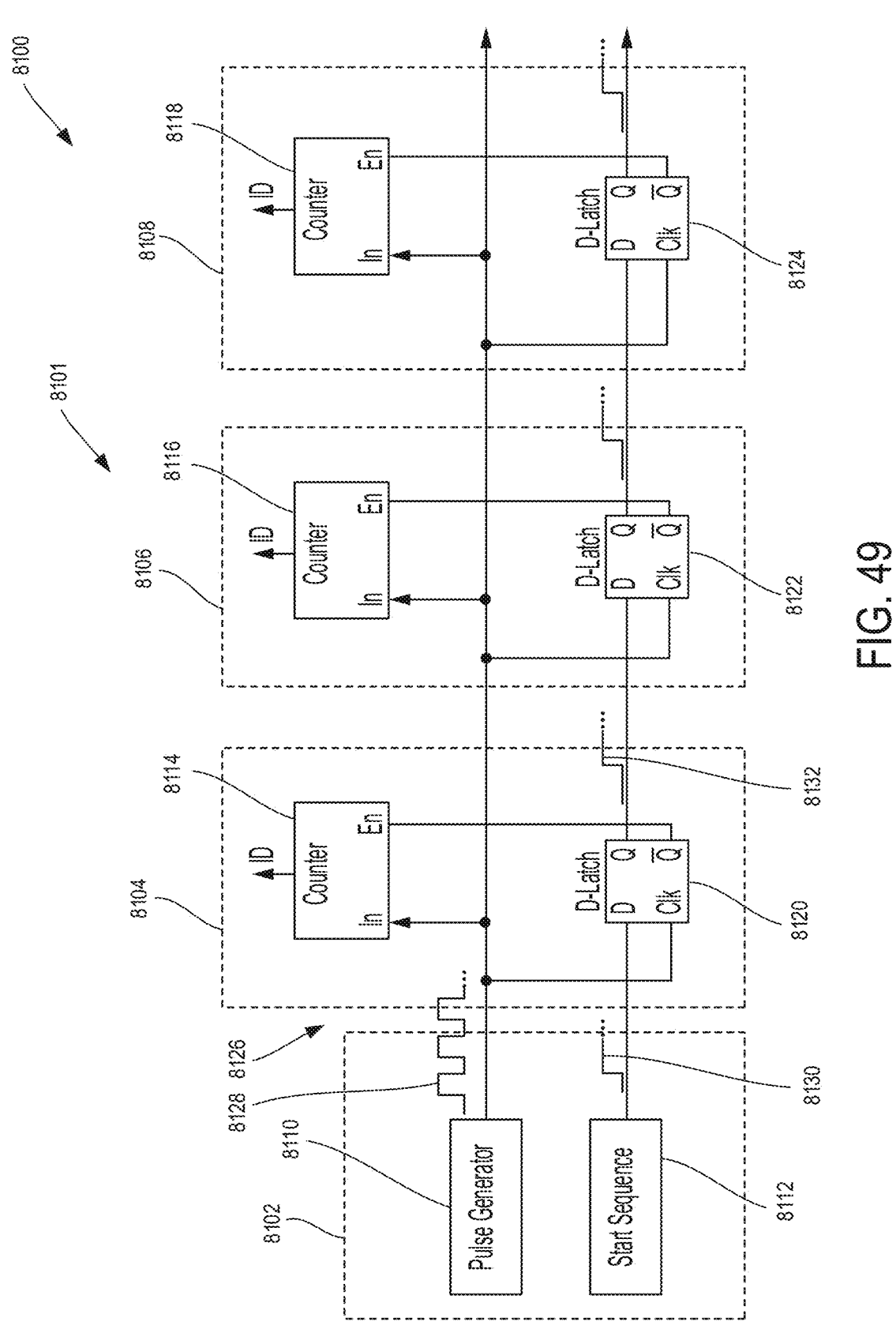
FIG. 49 is a schematic diagram of another identification circuit for determining physical locations of modules in a modular energy system utilizing a timing signal or clock pulses, in accordance with at least one aspect of the present disclosure.

Referring now to FIG. 49, another embodiment of a modular energy system 8100 is shown that can assign a unique identifier to each module in a modular energy system using only two backplane signals in a low power setting. The modular energy system 8100 can include an identification circuit 8101 that can be employed by a header module 8102 to determine the physical position of modules, such as modules 8104, 8106, 8108, within the modular energy system 8100. While three modules 8104, 8106, 8108 are shown and described, any more or less modules can be utilized. The identification circuit 8101 defines a communication interface 8126 configured to electrically couple the modules 8104, 8106, 8108 to the header module 8102 and/or to one another. The communication interface 8126 can, for example, be implemented by a separate communication bus (e.g. Ethernet, serial bus, LIN, etc.), which can be defined by detachably couplable communication backplane segments of the individual modules. In at least one example, the communication interface 8126 is a two-wire interface. The header module 8102 can be configured to use the two-wire interface 8126 to interact with the modules 8104, 8106, 8108 to identify and determine the physical position of the modules 8104, 8106, 8108 within the modular energy system 8100. Additionally, or alternatively, the modules 8104, 8106, 8108 can utilize the communication interface 8126 to interact with one another to exchange addresses and/or other relevant information, independently from the header module 8102. In a first embodiment, the physical position of the modules can be a physical position relative to the header module 8102. In a second embodiment, the physical position can be a physical position relative to a module other than the header module 8102. In at least one example, the identification circuit 8101 does not require software to perform the identification of the modules.

In one embodiment, the header module 8102 can include a pulse generator module 8110 and a start sequence module 8112. The pulse generator module 8034 can be configured to generate a timing signal or clock pulses 8128 to each of the modules 8104, 8106, 8108 in the modular energy system 8100 by way of the communication interface 8126. The start sequence module 8112 can be configured to generate a data signal 8130 to the first module in the modular energy system 8100, such as module 8104, by way of the communication interface 8126.

Each of the modules 8104, 8106, 8108 in the modular energy system 8100 can include a counter module 8114, 8116, 8118. Each of the counter modules 8114, 8116, 8118 can include a first input (In) and a second input (En). The counter modules 8114, 8116, 8118 can be configured to receive a timing signal or clock pulses, such as clock pulses 8128, at the first inputs. Upon reception of a first pulse from a clock pulse, the counter modules 8114, 8116, 8118 can be configured to initiate at 0. Upon reception of additional clock pulses, the counter modules 8114, 8116, 8118 can be configured to increment and count additional clock pulses received from the pulse generator module 8110 after the first clock pulse. In at least one other embodiment, the counter modules 8114, 8116, 8118 can be configured to initiate at 0 prior to receiving a first pulse from the pulse generator module 8110 such that a first pulse from the pulse generator module 8110 increments the counter modules 8114, 8116, 8118.

The counter modules 8114, 8116, 8118 can be configured to stop incrementing upon receiving a disabling signal at the second input. In one example, the disabling signal can be a falling edge of a signal received at the second input. In one example, the disabling signal can be a rising edge of a signal received at the second input. The final increment value of a counter module after reception of a disabling signal at the second input can be used to assign a module ID number to the respective module. The module ID number can be based on the final increment count and can correspond to a physical location of the module in the modular energy system 8100. In one example, the first module 8104 can receive a first clock pulse from the pulse generator 8110. The counter module 8114 can be configured to initiate at 0 upon reception of the first clock pulse. The counter module 8114 can then receive a disable signal at the second input of the counter module 8114 before reception of a second clock pulse from the pulse generator 8110, which can cause the counter module 8114 to finalize at the count 0. This 0 count can be used to assign the first module 8104 with a module ID number. In one example, the module ID number can be module Address 0 based on the 0 count, which can indicate that the first module 8104 is the first module in the modular system 8100 relative to the header module 8102.

Each of the modules 8104, 8106, 8108 in the modular energy system 8100 can further include a D-latch flip-flop 8120, 8122, 8124. Each of the flip-flops 8120, 8122, 8124 can be configured to receive a timing signal or clock pulses at the clock inputs (CLK) from a clock pulse source, such as the pulse generator module 8110. The flip-flops 8120, 8122, 8124 can be configured in a series configuration. In one example, the first flip-flop after the header module 8102, such as flip-flop 8120, can be configured to receive a data signal from a data source, such as a data signal 8130 from the start sequence module 8112, at the data input (D). The subsequent flip-flops after the first flip-flop can be configured to receive a data signal from the Q output of the proceeding flip-flop in the modular energy system 8100. In one example, flip-flop 8122 can be configured to receive a data signal 8132 from the Q output of flip-flop 8120. The flip-flops can further be configured to couple the Q⁻ outputs to the second inputs of the counter modules. In one example, the Q⁻ output of flip-flop 8120 can be configured to couple to the second input of the first counter module 8114.

In one example, flip-flop 8120 can be in the Q⁻ output state, where the data input signal 8130 from the start sequence module 8112 can be transmitted to the second input of the first counter module 8114. Upon reception of a clock signal from the pulse generator module 8110, the flip-flop 8120 can be configured to transition from the Q⁻ output state to the Q output state. The loss of the data input signal 8130 at the second input of the counter module 8114 (disabled low signal) can cause the counter module 8114 to stop incrementing. Further, the transition from the Q⁻ output state to the Q output state can cause flip-flop 8120 to transmit the data signal 8132 to the data input of flop-flop 8122.

To perform the identification process, a clock signal 8128 can be transmitted from the pulse generator module 8110 to each of the counter modules 8114, 8116, 8118 through the communication interface 8126. The first pulse from the clock signal 8128 can cause each of the counter modules 8114, 8116, 8118 to initiate at 0. Further, the clock signal can be transmitted to each of the clock inputs of the flip-flops 8120, 8122, 8124.

At a time after the rising edge of the first pulse from the clock signal 8128, the start sequence module 8112 can be configured to transmit a data signal 8130 to flip-flop 8120 by way of the communication interface 8126. In one example, the start sequence module 8112 can transmit the data signal 8130 during the falling edge of the first pulse from the clock signal 8128. Upon reception of the data signal 8130 from the start sequence module 8112, the flip-flop 8120 can be configured to transmit a signal from the Q⁻ output to the second input of the counter module 8114.

At the rising edge of a second pulse from the clock signal 8128, each of the counter modules 8114, 8116, 8118 can be configured to increment. At substantially the same time, the flip-flop 8120 can be configured to receive the second pulse at the clock input of flip-flop 8120 and transition from the Q⁻ output state to the Q output state. Transitioning from the Q⁻ output state to the Q output state removes the data signal from the second input of the counter module 8114, which can be a disabling signal for counter module 8114. The disabling signal can cause the counter module 8114 to stop incrementing and finalize. In one example, the counter modules can be configured to process and interpret near simultaneous increment signals and disabling signals. In one example, the counter module can give priority to the disabling signal, at a rising edge pulse from the clock signal 8128, at a rising edge of a pulse from the pulse generator module 8034, stopping count at 0. In a second example, the counter module can give priority to the increment signal and increment to 1 at a rising edge pulse from the clock signal 8128. In the above described example where the counter module 8114 gives priority to the stop incrementing signal, the counter module 8114 is disabled at 0 before incrementing to 1. In one aspect, the counter module 8114 can assign a module ID number to the first module 8104 based on the final increment value. In one example, the first module 8104 can be assigned module ID number 0.

Further to the above, after flip-flop 8120 receives the second pulse at the clock input and transitions from the Q⁻ output state to the Q output state, a data signal 8132 from the Q output of the flip-flop 8120 can be transmitted to the data input of flip-flop 8122. Flip-flop 8122 can be configured such that the data signal 8132 is transmitted from the Q⁻ output to the second input of the counter module 8116.

At the rising edge of a third pulse from the clock signal 8128, each of the non-disabled counter modules 8116, 8118 can be configured to further increment. At substantially the same time, flip-flop 8122 can be configured to receive the third pulse at the clock input and transition from the Q⁻ output state to the Q output state. Similar to above, transitioning from the Q⁻ output state to the Q output state can remove the data signal 8132 from the second input of the counter module 8116, which can cause the counter module 8116 to stop incrementing. In one example where the counter module 8116 gives priority to the stop incrementing signal, the counter module 8116 can be disabled at 1 before incrementing to 2. In one aspect, the counter module 8116 can assign a module ID number to the second module 8106 based on the final increment value. In one example, the second module 8106 can be assigned module ID number 1.

The above-described process can occur for each module in the modular energy system 8100 until each of the counter modules have been disabled and a final counter value has been determined. Each of the counter modules can output this value a control circuit, control logic, microprocessor, microcontroller, logic, or FPGA, or various combinations thereof, as an example, which can assign each module a module ID number based on the final counter value from its respective counter. In a separate embodiment, the counter modules can include a memory and the module ID number can be stored therein. This module ID number can correspond to a physical location of the module within the modular energy system 8100 relative to the header module.

Accordingly, the identification circuit formed by the stack is capable of determining the position of each of the modules in the stack and assigning a unique identifier to each module using only two backplane signals in a low power setting without aid or support from the processors of the modules. The number of modules identifiable using the identification circuit is limited only by the pulse-counters count.

In some aspects, the header module 8102 can include or support a display, such as display 2006. After the identification process, the header module 8102 can be configured to receive the module ID numbers from the modules 8104, 8106, 8108. In one example, the header module 8024 can be configured to receive the module ID number through the communication interface 8126. The header module 8102 can be configured to interpret the module ID numbers and provide a visual representation of the modules 8104, 8106, 8108 on the display in relative position representing their physical position in the modular energy system 8100. The display can provide information about the modules 8104, 8106, 8108, such as the type of module, status of module, availability of the module, health of module, etc. A user can select one of the modules from the display, such as with a touchscreen, in order to provide instructions to the module by way of a user interface.

In some aspects, the above-described embodiments represent ways to determine a physical position of modules in a modular energy system by implementing counter modules to incrementally count the number of pulses received before a stop signal disables the counter modules. The number of pulses can be utilized to assign a module ID number to the modules based on the incremental count. In other aspects, it can be possible to determine a physical position of modules in a modular energy system by utilizing a timer module and a single clock pulse. In one instance, the timer modules can be configured to measure an elapsed time between a first signal at a first input, in which the timer module can be configured to initiate a timer, and a second signal at a second input, in which the timer module can be configured to disable the timer. The timer modules can utilized the elapsed time to assign a module ID number to the modules based on the final timer count.

Figure 50:
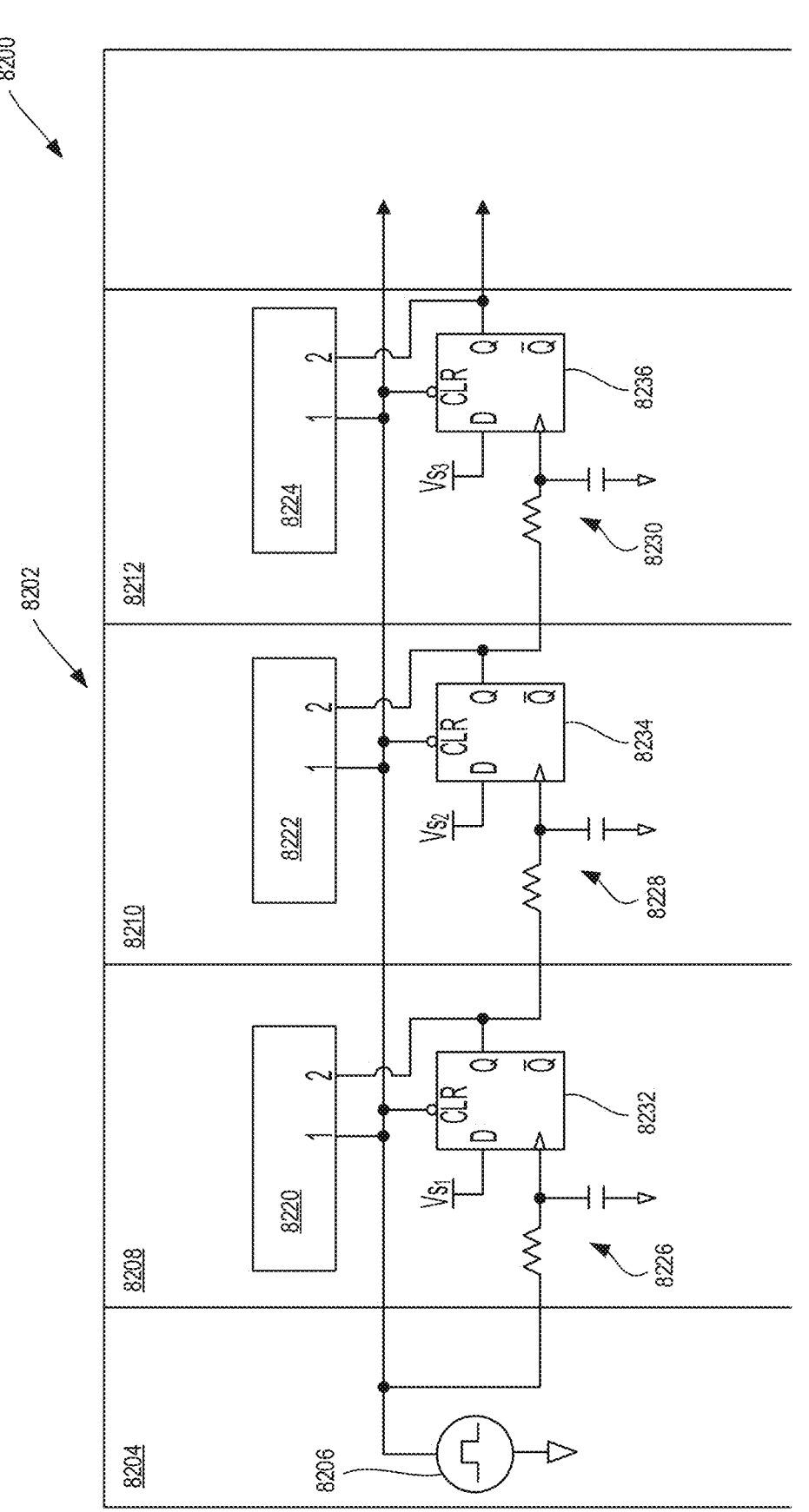
FIG. 50 is a schematic diagram of another identification circuit for determining physical locations of modules in a modular energy system utilizing a single clock pulse, in accordance with at least one aspect of the present disclosure.

Referring now to FIG. 50, an example module position-identification circuit 8202 for determining the position of modules in stacked modular energy system 8200 using a timer module is shown. The stacked modular energy system 8200 can include a header module 8204 that can include a clock pulse generator 8206 configured to produce a clock pulse signal. The stacked modular energy system 8200 can further include any number of modules coupled with the header module 8204. In one embodiment, as is illustrated in FIG. 50, the stacked modular energy system 8200 can include a first module 8208, a second module 8210, a third module 8212, coupled with the header module 8204. In one embodiment, each of the modules 8208, 8210, 8212 can include a timer module 8220, 8222, 8224, an RC delay circuit 8226, 8228, 8230, and a D-type flip-flop 8232, 8234, 8236. The timer module could be any one of a control circuit, control logic, microprocessor, microcontroller, logic, or FPGA, or various combinations thereof.

Each timer module 8220, 8222, 8224 of the stacked modular configuration 8200 can include two input pins, which are identified as "1" and "2" on each timer module, respectively. The first pin of each timer module 8220, 8222, 8224 can be electrically connected with the clock pulse generator 8206 of the header module 8204. The clock pulse generator 8206 can be configured to generate a clock pulse that can be synchronously received by each of the timer modules 8220, 8222, 8224 at the first pins. The first input pins of the timer modules 8220, 8222, 8224 can be configured to receive a rising edge of the clock pulse signal from the clock pulse generator 8206 and begin a timer. The timer modules 8220, 8222, 8224 can be configured to measure the amount of time it takes to receive a signal at their respective second input pins after receiving the rising edge of the clock pulse at the first input pins. In addition, the clock signal from the clock pulse generator can be transmitted to a clear state input (CLR) on each flip-flop 8232, 8234, 8236. In at least one example, the falling edge or low side of the clock signal transmitted to the clear state input can reset the flip-flops 8232, 8234, 8236 to a reset state, which will be described in more detail below.

The electrical output from the clock pulse generator 8206 of the header module 8204 can be branched such that a clock pulse signal can be transmitted to an RC delay circuit 8226 of the first module 8208. The RC delay circuit 8226 can be configured such that the clock pulse received by the RC delay circuit 8226 is delayed from being transmitted to the flip-flop 8232 of the first module 8208 by a predetermined amount of time. In one example, the delay can be 1 ms. In a second example, the delay can be more or less than 1 ms. The delay from the RC delay circuit 8226 can be configured to create a first delayed clock signal.

After the RC delay circuit 8226 of the first module 8208, the first delayed clock signal is configured to be transmitted to the flip-flop 8232 of the first module 8208. When the first delayed clock signal from the RC delay circuit 8226 is transmitted to the clock input of the flip-flop 8232, the flip-flop 8232 is configured to transition from a Q initial output state to a Q output state. The Q output of flip-flop 8232 can configured to transmit a supply voltage $V_{s1}$ at the data input D of the flip-flop 8232 through the Q output. The output of the Q output of flip-flop 8232 can be branched such that the Q output signal can be transmitted to the second input pin of the timer module 8220 and an RC delay circuit 8228 of the second module 8210.

When the flip-flop 8232 of the first module 8208 transitions from the $Q^-$ initial output state to the Q output state, $V_{s1}$ can be transmitted to the second input pin of the timer module 8220. The $V_{s1}$ signal is configured to be received by the second input pin of the timer module 8220 at a time after the timer module 8220 receives the clock signal from the clock pulse generator 8206. The timer module 8220 can be configured to compute the time difference between the two signals, such as by a timer. The timer module 8220 can be configured to interpret this time difference and assign a corresponding module ID to the module 8208 based on this time difference. This module ID can correspond to a physical location of the module 8208 in the stacked modular energy system 8200.

In one example, the RC delay circuit 8226 can be set to delay the initial clock pulse by 1 ms. The first pin of the timer module 8220 can receive the initial clock pulse from the clock pulse generator 8206 at approximately 0 seconds and the second pin of the timer module 8220 can receive the $V_{s1}$ signal from the flip-flop 8232 at approximately 1 ms. As a result, the timer module 8220 can compute the time difference between the two pins as approximately 1 ms and assign a modular identifying address based on the timing difference between the two signals. The timer module 8220 can assign the first module 8208 Address 1, as an example, which can correspond to the first module after the header module 8204 in the modular energy system 8200.

Further to the above, the $V_{s1}$ signal from the flip-flop 8232 of the first module 8210 can be configured to be transmitted to the RC delay circuit 8228 of the second module 8210. Similar to above, the RC delay circuit 8228 of the second module 8210 can be configured to delay the $V_{s1}$ signal to the flip-flop 8234, creating a second delayed clock signal. In one example, the RC delay circuit 8228 can delay the $V_{s1}$ signal by the same time as the first RC delay circuit 8226. The second delayed clock signal can be transmitted to the clock input of the flip-flop 8234 of the second module 8210. The flip-flop 8234 of the second module 8210 can be configured to transition from a Q initial output state to a Q output state and output a $V_{s2}$ supply signal at the data input to the Q output. The flip-flop 8234 of the second module 8210 can be configured to transmit the $V_{s2}$ signal to the second input pin of the timer module 8222 and an RC delay circuit 8230 of the third module 8212. As the $V_{s2}$ signal at the second input pin of the timer module 8222 is delayed compared to the initial clock signal from the clock pulse generator 8206, the timer module 8222 can interpret this time difference value and use the value to assign a module ID to the second module 8210. This module ID can correspond to a physical location of the second module 8210 in the stacked modular energy system 8200. In one example, the clock signal at the second input pin the second timer module 8222 can be delayed by 2 ms as a result of a 1 ms delay at both the first RC delay circuit 8226 and the second RC delay circuit 8228. In this example, the 2 ms delay interpreted by the timer module 8222 can result in the second module 8210 being assigned Address 2, as an example.

The second delayed clock signal from the flip-flop 8234 of the second module 8210, as described above, can be transmitted to the third module 8212 in the modular energy system 8200. The above-described process can occur until each of the timer modules have assigned their respective modules a module ID number. The time delay due to the RC delay circuit allows the timer modules of each of the modules to determine their physical location relative to the header module. The timer modules can continue to assign addresses until the last module in the system is reached. After each module has been assigned a module ID, the falling edge of the clock pulse from the clock pulse generator 8206 can be configured to be received at the clear input states of each flip-flop to transition each flip-flop in the modular energy system 8200 back to a reset state. In at least one example, the falling edge of the initial clock signal can be configured to transition each flip-flop from the Q output state to the Q⁻ output state. In at least one example, the initial pulse signal from the clock pulse generator is made sufficiently large to exceed the sum of all the delays in the modular energy system to ensure that the flip-flops are not reset before all of the modules have been assigned a module ID number.

In some aspects, the header module 8204 can include or support a display, such as display 2006. After the identification process, the header module 8204 can be configured to receive the module ID numbers from the modules 8208, 8210, 8212. The header module 8204 can be configured to interpret the module ID numbers and provide a visual representation of the modules 8208, 8210, 8212 on the display in relative position representing their physical position in the modular energy system 8100. The display can provide information about the modules 8208, 8210, 8212, such as the type of module, status of module, availability of the module, health of module, etc. A user can select one of the modules from the display, such as with a touchscreen, in order to provide instructions to the module by way of a user interface.

Figure 51:
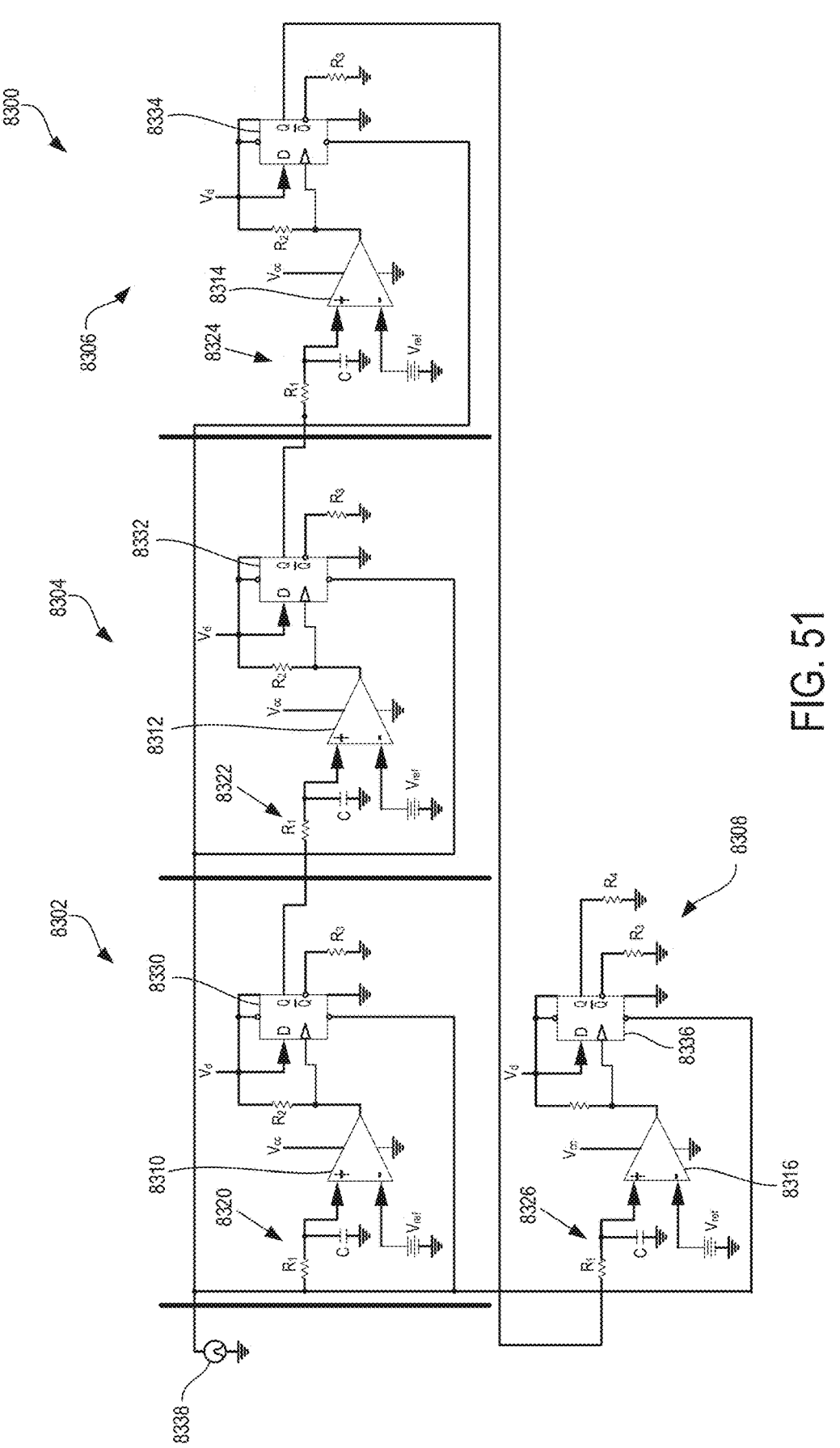
FIG. 51 is a wire diagram of an example circuit of the identification circuit of FIG. 50, in accordance with at least one aspect of the present disclosure.

Depending on the logic family selected for implementation of the circuit described above, it may be necessary to insert a comparator, Schmitt-Trigger style buffer, or other equivalent circuits in order to provide a fast-rising edge at the clock input of the flip-flops. As can be seen in FIG. 51, a schematic of a stacked modular configuration 8300 is illustrated that can include four modules 8302, 8304, 8306, 8308 and a clock pulse generator 8338. The clock pulse generator 8338 can be a part of a header module, for example. Each module can include a comparator 8310, 8312, 8314, 8316, an RC delay circuit 8320, 8322, 8324, 8326, and a flip-flop 8330, 8332, 8334, 8336. The comparators 8310, 8312, 8314, 8316 can be placed in between RC delay circuits 8320, 8322, 8324, 8326 and the clock signal inputs of the flip-flops 8330, 8332, 8334, 8336. The comparators can be provided with a supply voltage $V_{cc}$ and be configured to compare the output voltage of the RC delay circuits against a reference voltage $V_{ref}$. In one embodiment, when the output of the RC delay circuit exceeds the reference voltage $V_{ref}$, the comparators can transmit the supply voltage $V_{cc}$ to the clock input of the flip-flops.

Figure 52:
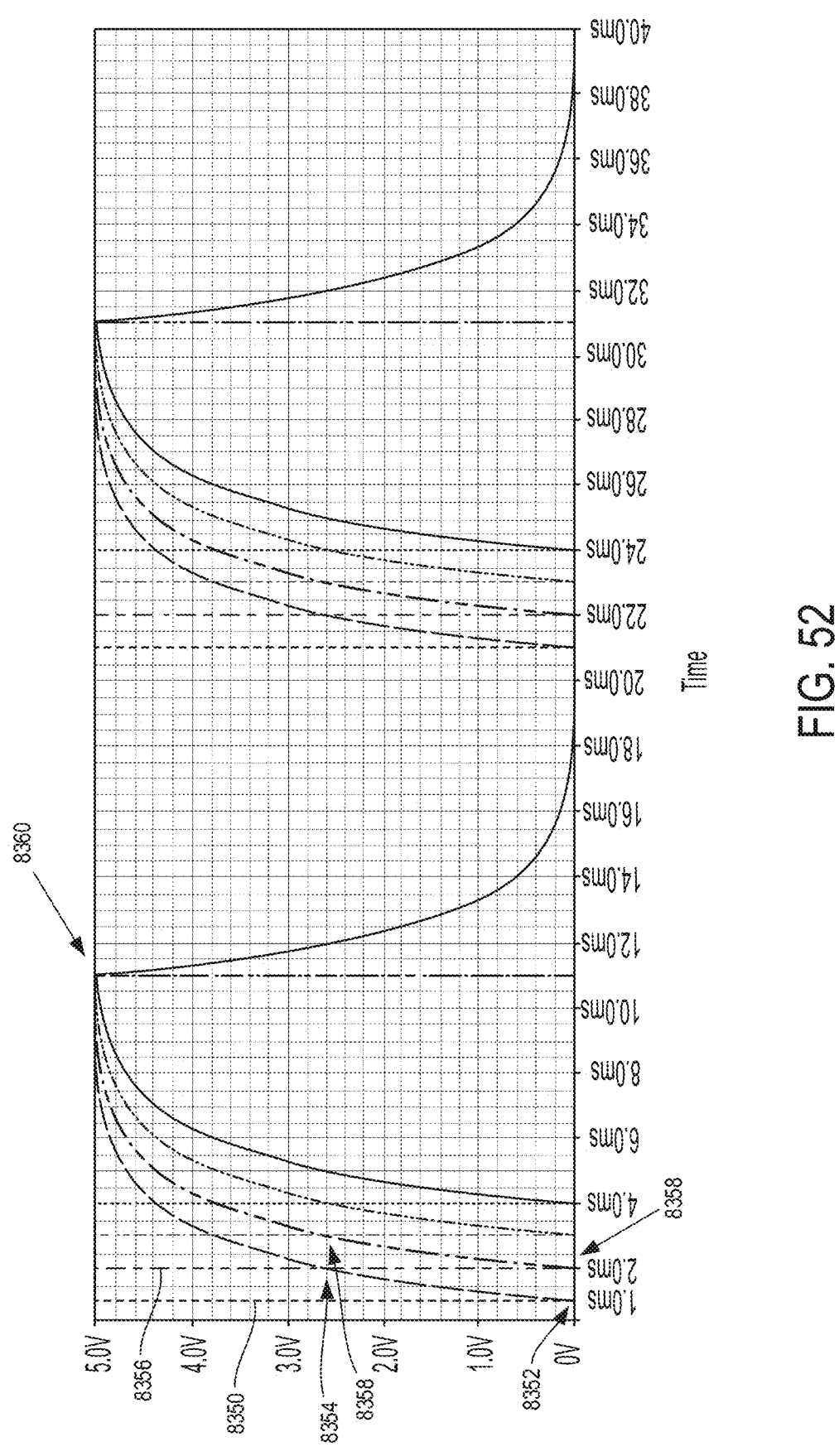
FIG. 52 illustrates simulation results of the example circuit of FIG. 51, in accordance with at least one aspect of the present disclosure.

Referring now to FIG. 52, simulation results for the above-described circuit can be seen. For the simulation, $V_{cc}$ and $V_d$ were selected to be 5V, $V_{ref}$ was selected to be 2.5V, C was selected to be 0.1 pF, R1 was selected to be 14.4kΩ, R2 was selected to be 1KΩ, and R3 and R4 were selected to be 10MΩ.

At 1 ms, the clock pulse generator 8338 provides an initial clock pulse signal 8350 to the RC delay circuit 8320 of the first module 8302. The RC delay circuit 8320 begins to charge 8352 and outputs a signal to the comparator 8310. Once the RC delay circuit 8320 has charged to provide an output voltage signal that exceeds the reference voltage $V_{ref}$ of the comparator 8310, the comparator 8310 outputs the supply voltage $V_{cc}$ to the flip-flop 8330. Based on the above provided values, the RC delay circuit 8320 exceeds the reference voltage $V_{ref}$ approximately 1 ms after receiving the rising edge of the initial clock signal from the clock pulse generator 8338, which can be seen at 8354.

After the comparator 8310 of the first module 8302 outputs the supply voltage $V_{cc}$ to the flip-flop 8330, the flip-flop 8330 transitions from the Q⁻ output state to the Q output state and transmits a data signal $V_d$ 8356 to the RC delay circuit 8322 of the second module 8304, which begins to charge 8358 the RC delay circuit 8322. Similar to what was described above, the RC delay circuit 8322 begins to charge 8358 and outputs a signal to the comparator 8312. Once the RC delay circuit 8322 has charged to provide an output voltage signal that exceeds the reference voltage $V_{ref}$ of the comparator 8312, the comparator outputs the supply voltage $V_{cc}$ to the flip-flop 8332. Based on the above provided values, the RC delay circuit 8322 exceeds the reference voltage approximately 2 ms after the initial clock pulse signal, which can be seen at 8358.

The above-described process occurs for each module in the modular stack 8300 until the falling edge of the initial clock pulse signal from the clock pulse generator 8338 occurs, which can be seen at 8360. At the falling edge of the initial clock pulse signal, each flip-flop 8330, 8332, 8334, 8336 can be transitioned back to a cleared state by way of the clear inputs of the flip-flops, as described above. In one example, the clock pulse signal can be sufficiently set so that each module in the modular stack will receive a delayed signal before the flip-flops are returned to a clear state. In one embodiment, the flip-flops can transition from the Q output state to the Q⁻ output state upon receiving the falling edge of the clock pulse. After the RC delay circuits have been sufficiently discharged, the identification process can be completed again.

As described in greater detail herein, a modular surgical system comprises a header module and one or more functional or surgical modules. In various instances, the modular surgical system is a modular energy system. In various instances, the surgical modules include energy modules, communication modules, user interface modules; however, the surgical modules are envisioned to be any suitable type of functional or surgical module for use with the modular surgical system.

One or more surgical modules of a modular surgical system can be connected to a header module in a variety of different stacked configurations. To function properly, a modular surgical system needs to determine the physical location of the modules in its stack. Positional awareness of the modules with respect to the header module and/or with respect to each other facilitates a proper interaction between the modules and the header module, and allows a UI module such as, for example, the UI module 3030 (FIG. 33) to provide a visual representation of the modules where each module is arranged with a 1:1 association to its physical location. In certain instances, the physical location of a module in the stack configuration is associated with, or corresponds to, a unique address (e.g. a unique bit pattern) that identifies the module, and facilitates proper communication with the header module and/or other modules in the stack configuration.

In various examples, the physical location of each module is identified and/or an address is assigned to it by way of an analog signal or a clock pulse signal, as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION and U.S. patent application Ser. No. 16/562,234, titled MODULAR SURGICAL ENERGY SYSTEM WITH MODULE POSITIONAL AWARENESS SENSING WITH TIME COUNTER, which are incorporated by reference herein in their entireties.

In various aspects, to avoid a faulty start of a modular surgical system, it is desirable to perform at least an initial determination of the physical positions of the modules in the stack. The present disclosure provides reliable mechanisms for identification of the physical positions of the modules in a stack.

In various aspects, the Header module of a modular surgical system is configured to interact with the modules in a stack configuration via unique addresses, associated with each of the modules, which are based on the physical location of the modules in the stack configuration. Accordingly, a user can stack identical modules in any desirable stack configuration, or change an existing stack configuration, without having to manually provide the physical positions of the modules to the header module. Instead, each module is able to identify its own position in the stack configuration, and a unique address associated with such position. The header module is then able to deduce the relative positions of the modules, and the number of modules, in the stack configuration according to whether the header module is able to successfully communicate with such addresses.

For example, if the header module is able to establish a successful communication with a surgical module using an address associated with a first position in the stack configuration, the header module deduces the presence of a surgical module in the first position, and that at least one surgical module is in the stack configuration. If the header module is able to establish a successful communication with a surgical module using an address associated with a second position in the stack configuration, the header module deduces the presence of a surgical module in the second position, and that at least two surgical modules are in the stack configuration. If the header module is able to establish a successful communication with a surgical module using an address associated with a third position in the stack configuration, the header module deduces the presence of a surgical module in the third position, and that at least three surgical modules are in the stack configuration. In various examples, such communication attempts are carried out by a communication interface that uses any suitable communication means (e.g., a LIN or Ethernet network).

Accordingly, a user can stack identical modules in any desirable stack configuration, and depending on their positions in the stack configuration, unique addresses are generated for each of the identical modules. In various aspects, the unique addresses and their corresponding physical positions are stored in any suitable storage medium, in the form of a look-up table or database, for example, and are accessible by a processor of the header module.

Figure 53:
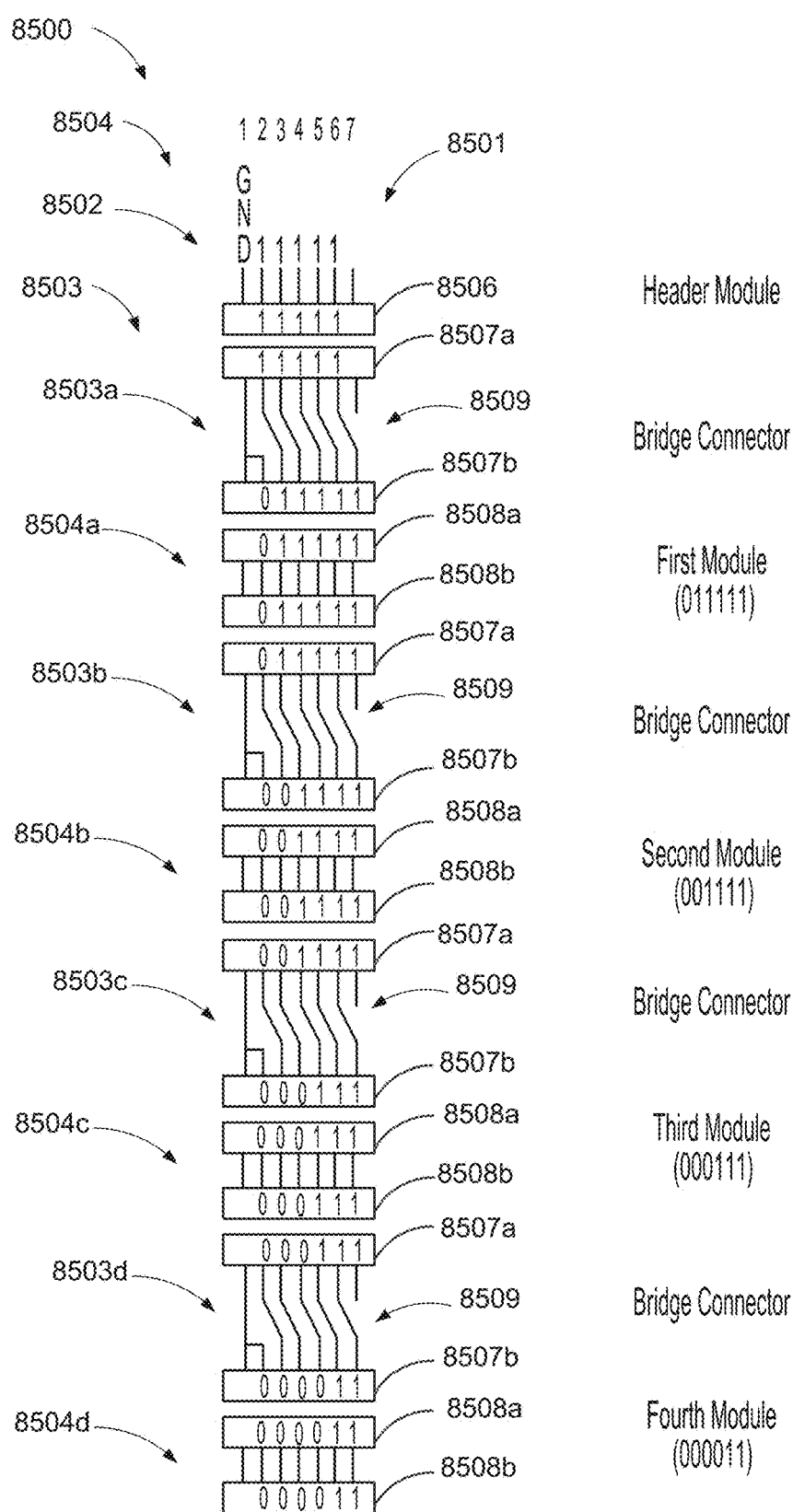
FIG. 53 illustrates a simplified schematic diagram of a positional awareness circuit of a modular energy system, in accordance with at least one embodiment of the present disclosure.

FIG. 53 illustrates a simplified schematic diagram of a positional awareness circuit 8501 of a modular surgical system 8500, which is configured to identify relative positions of surgical modules in a stack configuration of the modular surgical system 8500, and produce unique addresses for each of the surgical modules, as described above. Like other modular surgical systems described elsewhere herein, the modular surgical system 8500 includes a header module 8502 configured to be arranged in a stack configuration with one or more surgical modules 8504. In the example of FIG. 53, the modular surgical system 8500 includes four surgical modules 8504a, 8504b, 8504c, 8504d, which are collectively referred to herein as surgical modules 8504. However, this number of surgical modules is not limiting. In other examples, a modular surgical system 8500 can include more or less than four surgical modules in a stack configuration.

Further, the modular surgical system 8500 also includes a number of backplane connectors 8503 configured to connect consecutive modules in the stack configuration. For example, a backplane connector 8503a connects the header module 8502 and the surgical module 8504a, a backplane connector 8503b connects the surgical module 8504a and the surgical module 8504b, a backplane connector 8503c connects the surgical module 8504b and the surgical module 8504c, and a backplane connector 8503d connects the surgical module 8504c and the surgical module 8504d. The positional awareness circuit 8501 employs a shifting bit pattern, defined by the backplane connectors 8503, to identify the number of surgical modules 8504 and/or the position of each of the surgical modules 8504 in the stack configuration.

Each of the surgical modules 8504 in the stack configuration of the modular surgical system 8500 is identifiable by a unique bit pattern produced by preceding backplane connector(s) 8503 in the stack configuration. Each backplane connector connecting a directly-upstream surgical module and a directly-downstream surgical module in the stack configuration yields a bit pattern, shifted to the right by one position from the bit pattern of the directly-upstream surgical module, which is configured to identify the directly-downstream surgical module.

Each of the backplane connectors 8503 includes a top or first coupling portion 8507a and a bottom or second coupling portion 8507b. Conductor elements extend between the first coupling portion 8507a and the second coupling portion 8507b defining a conductor layout 8509 that yields the shifting bit pattern of the positional awareness circuit 8501. A left-most conductor element extends from a 1st position of the first coupling portion 8507*a* to a 1st position of the second coupling portion 8507*b*. The left-most conductor comprises a split that extends to the 2nd position of the second coupling portion 8507*b*. The left-most conductor is a common ground reference for transmitted logic signals, and may be utilized in performing other functions.

The shifting bit pattern of the positional awareness circuit 8501 is achieved using conductor elements, without active components. In various aspects, the conductor layout 8509 includes a plurality of shifting conductor elements. In the example illustrated in FIG. 53, the conductor layout 8509 further includes a conductor element that extends from a 2nd position of the first coupling portion 8507*a* to a 3rd position of the second coupling portion 8507*b*. Similarly, a conductor element extends from a 3rd position of the first coupling portion 8507*a* to a 4th position of the second coupling portion 8507*b*. Similarly, a conductor element extends from a 4th position of the first coupling portion 8507*a* to a 5th position of the second coupling portion 8507*b*. Similarly, a conductor element extends from a 5th position of the first coupling portion 8507*a* to a 6th position of the second coupling portion 8507*b*. Similarly, a conductor element extends from a 6th position of the first coupling portion 8507*a* to a 7th position of the second coupling portion 8507*b*.

As illustrated in FIG. 53, backplane connectors 8503 with the conductor layout 8509 yield different, unique, bit patterns depending on the position of such backplane connectors 8503 in the stack configuration. The first or top backplane connector 8503*a*, which extends between a coupling portion 8506 of the header module 8502 and the first coupling portion 8508*a* of the surgical module 8504*a*, yields a bit pattern "011111" that identifies the surgical module 8504*a* as the first surgical module in the stack configuration of the modular surgical system 8500. Notably, any surgical module positioned directly below the header module, and in connection with the backplane connector 8503*a*, will be assigned the bit pattern "011111". Accordingly, the header module 8502 is able to deduce that the surgical module 8504*a* is the first surgical module in the stack configuration of the modular surgical system 8500, and that it is situated directly below the header module 8502, from successful communication with the surgical module 8504*a* using the bit pattern "011111".

Further to the above, the backplane connector 8503*b*, which extends between the second coupling portion 8508*b* of the first surgical module 8504*a* and the first coupling portion 8508*a* of the surgical module 8504*b*, yields a bit pattern "001111" that identifies the surgical module 8504*b* as the second surgical module in the stack configuration of the modular surgical system 8500. Notably, any surgical module positioned directly below the first surgical module 8504*a*, and in connection with the backplane connector 8503*b*, will be assigned the bit pattern "001111". Accordingly, the header module 8502 is able to deduce that the surgical module 8504*b* is the second surgical module in the stack configuration of the modular surgical system 8500, and that it is situated directly below the surgical module 8504*a*, from successful communication with the surgical module 8504*b* using the bit pattern "001111". Similarly, the header module 8502 is able to deduce that the surgical modules 8504*c*, 8504*d* are the third and fourth surgical modules in the stack configuration of the modular surgical system 8500 from successful communication with the surgical modules 8504*c* 8504*d* using the bit patterns "000111" and "000011", respectively, which are produced by the backplane connectors 8503*c*, 8503*d*, respectively.

In various instances, the backplane connectors 8503 are integrated with their respective directly-upstream modules in the stack configuration, and are detachably couplable to their respective directly-downstream modules in the stack configuration. For example, the backplane connector 8503*a* can be integrated with the header module 8502, and can be detachably couplable to the surgical module 8504*a*. Likewise, the backplane connector 8503*b* can be integrated with the surgical module 8504*a*, and can be detachably couplable to the surgical module 8504*b*. Similarly, the backplane connector 8503*c* can be integrated with the surgical module 8504*b*, and can be detachably couplable to the surgical module 8504*c*. Also, the backplane connector 8503*d* can be integrated with the surgical module 8504*c*, and can be detachably couplable to the surgical module 8504*d*. Alternatively, in other instances, the backplane connectors 8503 can be integrated with their respective directly-downstream modules in the stack configuration, and can be detachably couplable to their respective directly-upstream modules in the stack configuration. Alternatively, in certain instances, the backplane connectors 8503 can be independent components that are detachably couplable to their respective directly-upstream and directly-downstream modules in the stack configuration.

In various aspects, the header module 8502 employs a look-up table or a database, which can be stored in any suitable storage medium to correlate the bit patterns "011111", "001111", "000111", and "000011", with a first position, second position, third position, and fourth position, respectively, below the header module 8502, respectively, in the stack configuration. Accordingly, the header module 8502 can deduce whether a surgical module occupies a position in the stack configuration of the modular surgical system 8500 by querying the look-up table or database for the address associated with the position, and attempting to communicate using the address. If a successful communication with a surgical module is achieved, the header module 8502 concludes that the surgical module is located at the position associated with the address that caused the successful communication. Further, the header module 8502 can deduce that the number of modules in the stack configuration is at least the number that corresponds to the ranking of the position. For example, the header module 8502 can deduce that the surgical module 8504*c* occupies the third position in the stack configuration of the modular surgical system 8500 by querying the look-up table or database for the address associated with the third position, which is the bit pattern "000111," and performing a successful communication using the address. If a successful communication with a surgical module is achieved, the header module 8502 concludes that the surgical module 8504*c* is located at the third position. Further, the header module 8502 can deduce that the number of modules in the stack configuration is at least the three. Similar conclusions can be made regarding the surgical modules in the first, second, and fourth positions.

In the example embodiment illustrated in FIG. 53, the header module 8502 is configured to deduce the number and relative position of the modules in a stack configuration of the modular surgical system 8500 using the shifting bit pattern produced by the backplane connectors 8503. It is, however, understood that various other suitable backplane connectors and shifting bit patterns can be equally employed by the header module 8502 to deduce the number and relative position of the modules in a stack configuration of the modular surgical system 8500. Further, the shifting bit pattern need not be produced by the backplane connectors. In various examples, as illustrated in FIG. 54, a shifting bit pattern for identification of the number and relative position of the modules in a stack configuration can be produced by the modules themselves.

Figure 54:
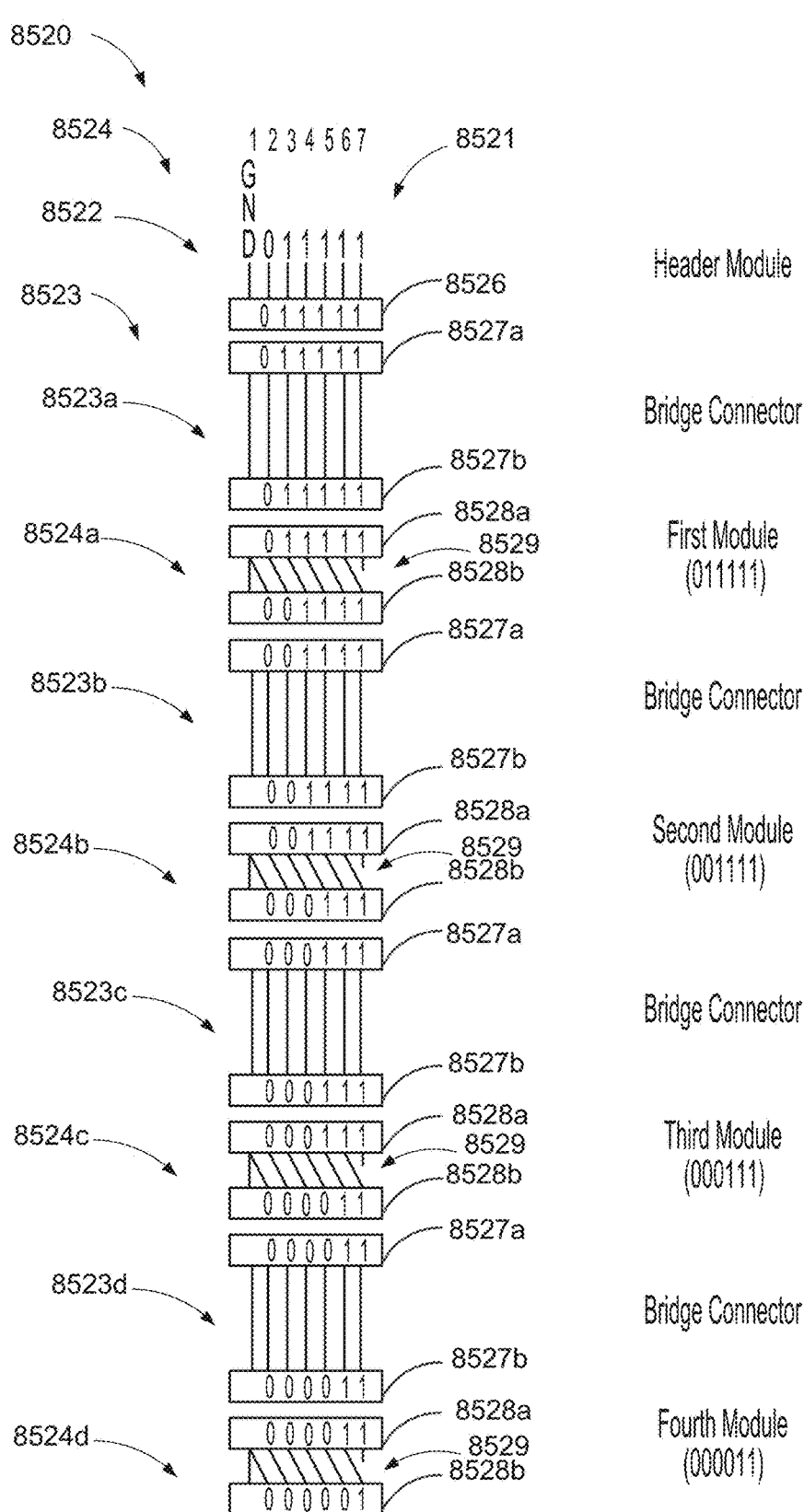
FIG. 54 illustrates a simplified schematic diagram of a positional awareness circuit of a modular energy system, in accordance with at least one embodiment of the present disclosure.

FIG. 54 illustrates a simplified schematic diagram of a positional awareness circuit 8521 of a modular surgical system 8520, which is configured to identify relative positions of surgical modules in a stack configuration of the modular surgical system 8520, and produce unique addresses for each of the surgical modules, as described above. The modular surgical system 8520 is similar in many respects to other modular surgical systems disclosed elsewhere herein such as, for example, the modular surgical system 8500. Like the modular surgical system 8500, the modular surgical system 8520 includes a header module 8522 configured to be arranged in a stack configuration with one or more surgical modules 8524. In the example of FIG. 54, the modular surgical system 8520 includes four surgical modules 8524a, 8524b, 8524c, 8524d, which are collectively referred to herein as surgical modules 8524. However, this number of surgical modules is not limiting. In other examples, a modular surgical system 8520 can include more or less than four surgical modules in a stack configuration.

Further, the modular surgical system 8520 also includes a number of backplane connectors 8523 configured to connect consecutive modules in the stack configuration. For example, a backplane connector 8523a connects the header module 8522 and the surgical module 8524a, a backplane connector 8523b connects the surgical module 8524a and the surgical module 8524b, a backplane connector 8523c connects the surgical module 8524b and the surgical module 8524c, and a backplane connector 8523d connects the surgical module 8524c and the surgical module 8524d. The positional awareness circuit 8521 employs a shifting bit pattern, defined by the surgical modules 8524, to identify the number of surgical modules 8524 and/or the position of each of the surgical modules 8524 in the stack configuration.

Each of the surgical modules 8524 in the stack configuration of the modular surgical system 8520 is identifiable by a unique bit pattern produced by preceding surgical module(s) in the stack configuration. Each new surgical module added to the bottom of a preceding surgical module in the stack configuration is configured to receive a new bit pattern, shifted to the right by one position from the bit pattern of the preceding surgical module. The new bit pattern is configured to identify the newly added surgical module, and is produced by the preceding surgical module(s) in the stack configuration.

Each of the surgical modules 8524 includes a top or first coupling portion 8528a and a bottom or second coupling portion 8528b. Conductor elements extend between the first coupling portion 8528a and the second coupling portion 8528b defining a conductor layout 8529 that yields the shifting bit pattern of the positional awareness circuit 8521. A left-most conductor element extends from a 1st position of the first coupling portion 8528a to a 1st position of the second coupling portion 8528b. The left-most conductor comprises a split that extends to the 2nd position of the second coupling portion 8528b. The left-most conductor is a common ground reference for transmitted logic signals, and may be utilized in performing other functions.

Like the shifting bit pattern of the positional awareness circuit 8501, the shifting bit pattern of the positional awareness circuit 8521 is achieved using conductor elements, without active components. In various aspects, the conductor layout 8529 includes a plurality of shifting conductor elements. In the example illustrated in FIG. 54, the conductor layout 8529 further includes a conductor element that extends from a 2nd position of the first coupling portion 8528a to a 3rd position of the second coupling portion 8528b. Similarly, a conductor element extends from a 3rd position of the first coupling portion 8528a to a 4th position of the second coupling portion 8528b. Similarly, a conductor element extends from a 4th position of the first coupling portion 8528a to a 5th position of the second coupling portion 8528b. Similarly, a conductor element extends from a 5th position of the first coupling portion 8528a to a 6th position of the second coupling portion 8528b. Similarly, a conductor element extends from a 6th position of the first coupling portion 8528a to a 7th position of the second coupling portion 8528b.

As illustrated in FIG. 54, the surgical modules 8524 with the conductor layout 8529 yield different, unique, bit patterns depending on the position of such surgical modules 8524 in the stack configuration, which are configured to identify their respective following surgical modules in the stack configuration. The first surgical module 8524a received its identifying bit pattern "011111" from the header module 8522. Notably, any surgical module positioned directly below the header module, and in connection with the backplane connector 8523a, will be assigned the bit pattern "011111". Accordingly, the header module 8522 is able to deduce that the surgical module 8524a is the first surgical module in the stack configuration of the modular surgical system 8520, situated directly below the header module 8522, from successful communication with the surgical module 8524a using the bit pattern "011111".

Further, the conductor layout of the surgical module 8524a, yields a bit pattern "001111" that identifies the surgical module 8524b as the second surgical module in the stack configuration of the modular surgical system 8520. Notably, any surgical module in a second position below a header module 8522 will be assigned the bit pattern "001111".

Accordingly, the header module 8522 is able to deduce that the surgical module 8524b is the second surgical module in the stack configuration of the modular surgical system 8520, and that it is situated directly below the surgical module 8524a, from successful communication with the surgical module 8524b using the bit pattern "001111". Similarly, the header module 8522 is able to deduce that the surgical modules 8524c, 8524d are the third and fourth surgical modules in the stack configuration of the modular surgical system 8520 from successful communication with the surgical modules 8524c 8524d using the bit patterns "000111" and "000011", respectively, which are produced by the surgical modules 8524b, 8524c, respectively.

In various aspects, the header module 8522 employs a look-up table or a database, which can be stored in any suitable storage medium to correlate the bit patterns "011111", "001111", "000111", and "000011", with a first position, second position, third position, and fourth position, respectively, below the header module 8522, respectively, in the stack configuration. Accordingly, the header module 8522 can deduce whether a surgical module occupies a position in the stack configuration of the modular surgical system 8520 by querying the look-up table or database for the address associated with the position, and attempting to communicate using the address. If a successful communication with a surgical module is achieved, the header module 8522 concludes that the surgical module is located at the position associated with the address that caused the successful communication. Further, the header module 8522 can deduce that the number of modules in the stack configuration is at least the number that corresponds to the ranking of the position. For example, the header module 8522 can deduce that the surgical module 8524c occupies the third position in the stack configuration of the modular surgical system 8520 by querying the look-up table or database for the address associated with the third position, which is the bit pattern "000111," and performing a successful communication using the address. If a successful communication with a surgical module is achieved, the header module 8522 concludes that the surgical module 8524c is located at the third position. Further, the header module 8522 can deduce that the number of modules in the stack configuration is at least the three. Similar conclusions can be made regarding the surgical modules in the first, second, and fourth positions.

In the example embodiments illustrated in FIGS. 53 and 54, the header module 8522 is configured to deduce the number and relative position of the modules in a stack configuration of the modular surgical system using a shifting bit pattern. This, however, is not limiting. In other examples, as illustrated in FIGS. 55 and 56, a rotating bit pattern can be employed to identify the number and relative position of the modules in a stack configuration of a modular surgical system.

Figure 55:
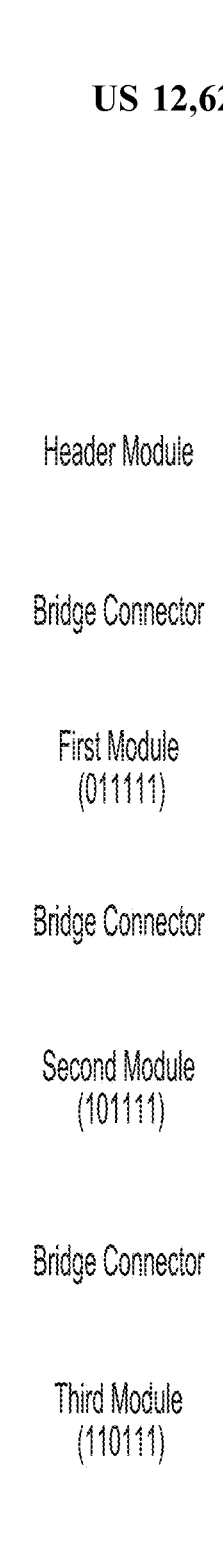
FIG. 55 illustrates a simplified schematic diagram of a positional awareness circuit of a modular energy system, in accordance with at least one embodiment of the present disclosure.
Figure 56:
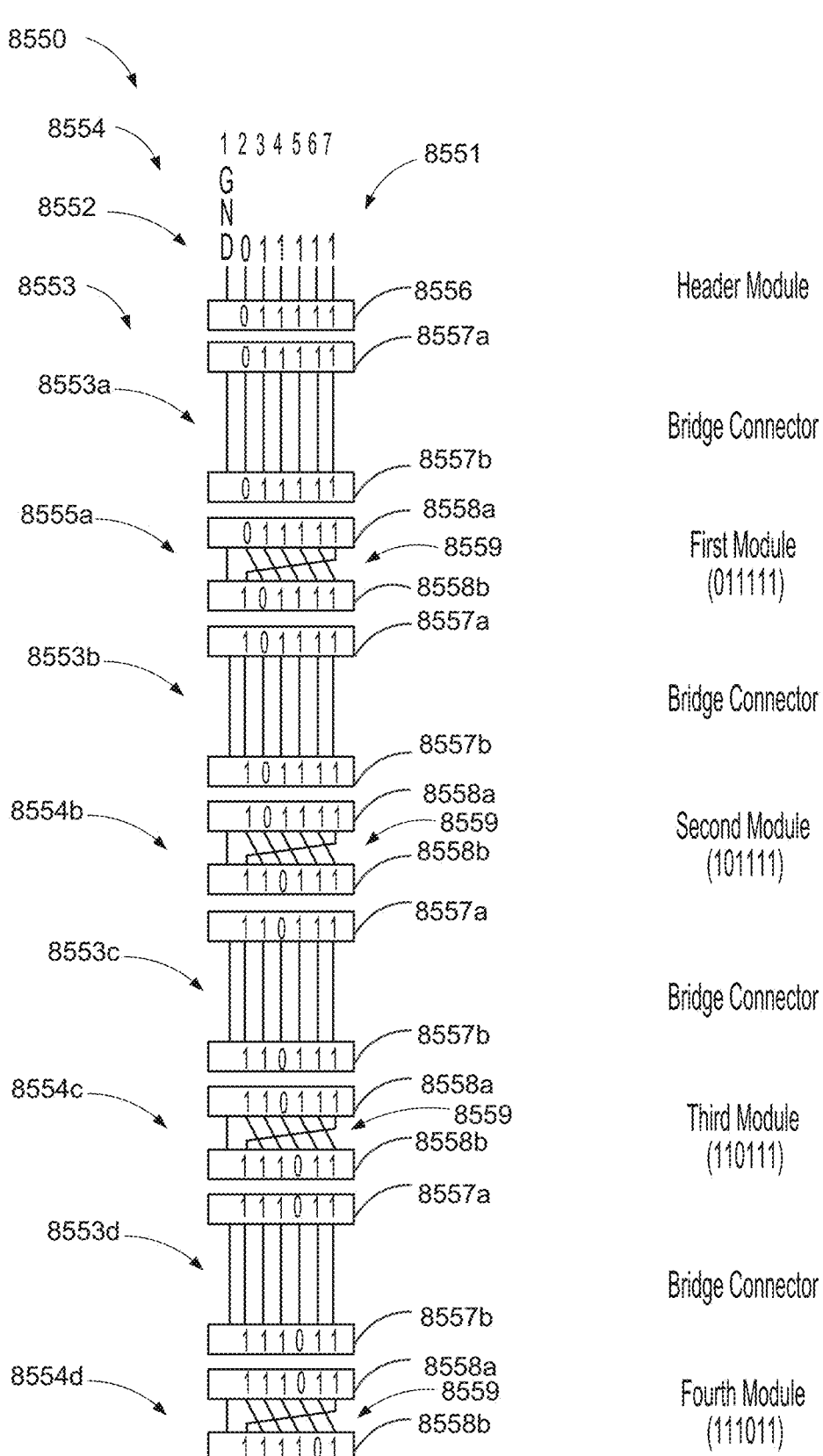
FIG. 56 illustrates a simplified schematic diagram of a positional awareness circuit of a modular energy system, in accordance with at least one embodiment of the present disclosure.

FIG. 55 illustrates a simplified schematic diagram of a positional awareness circuit 8541 of a modular surgical system 8540, which is configured to identify relative positions of surgical modules in a stack configuration of the modular surgical system 8500, and produce unique addresses for each of the surgical modules, as described above. Like other modular surgical systems described elsewhere herein, the modular surgical system 8540 includes a header module 8542 configured to be arranged in a stack configuration with one or more surgical modules 8544. In the example of FIG. 55, the modular surgical system 8540 includes four surgical modules 8544a, 8544b, 8544c, 8544d, which are collectively referred to herein as surgical modules 8544. However, this number of surgical modules is not limiting. In other examples, a modular surgical system 8540 can include more or less than four surgical modules in a stack configuration.

Further, the modular surgical system 8540 also includes a number of backplane connectors 8543 configured to connect consecutive modules in the stack configuration. For example, a backplane connector 8543a connects the header module 8542 and the surgical module 8544a, a backplane connector 8543b connects the surgical module 8544a and the surgical module 8544b, a backplane connector 8543c connects the surgical module 8544b and the surgical module 8544c, and a backplane connector 8543d connects the surgical module 8544c and the surgical module 8544d. The positional awareness circuit 8541 employs a rotating bit pattern, defined by the backplane connectors 8543, to identify the number of surgical modules 8544 and/or the position of each of the surgical modules 8544 in the stack configuration.

Each of the surgical modules 8544 in the stack configuration of the modular surgical system 8540 is identifiable by a unique bit pattern produced by preceding backplane connector(s) 8543 in the stack configuration. Each backplane connector connecting a directly-upstream surgical module and a directly-downstream surgical module in the stack configuration yields a bit pattern that is different than the bit pattern identifying the directly-upstream surgical module, and is configured to identify the directly-downstream surgical module.

Each of the backplane connectors 8543 includes a top or first coupling portion 8547a and a bottom or second coupling portion 8547b. Conductor elements extend between the first coupling portion 8547a and the second coupling portion 8547b defining a conductor layout 8549 that yields the rotating bit pattern of the positional awareness circuit 8541. A left-most conductor element extends from a 1st position of the first coupling portion 8547a to a 1st position of the second coupling portion 8547b. The left-most conductor is a common ground reference for transmitted logic signals, and may be utilized in performing other functions.

The rotating bit pattern of the positional awareness circuit 8541 is achieved using conductor elements, without active components. In various aspects, the conductor layout 8529 includes a plurality of shifting conductor elements, and a rotating conductor element. In the example illustrated in FIG. 55, the conductor layout 8549 further includes a conductor element that extends from a 2nd position of the first coupling portion 8547a to a 3rd position of the second coupling portion 8547b. Similarly, a conductor element extends from a 3rd position of the first coupling portion 8547a to a 4th position of the second coupling portion 8547b. Similarly, a conductor element extends from a 4th position of the first coupling portion 8547a to a 5th position of the second coupling portion 8547b. Similarly, a conductor element extends from a 5th position of the first coupling portion 8547a to a 6th position of the second coupling portion 8547b. Similarly, a conductor element extends from a 6th position of the first coupling portion 8547a to a 7th position of the second coupling portion 8547b. Finally, a conductor element extends, in a rotating fashion, from a 7th position of the first coupling portion 8547a to a 2nd position of the second coupling portion 8547b, facilitating the rotation of the rotating bit pattern.

As illustrated in FIG. 55, backplane connectors 8543 with the conductor layout 8549 yield different, unique, bit patterns depending on the position of such backplane connectors 8543 in the stack configuration. The first or top backplane connector 8543a, which extends between a coupling portion 8546 of the header module 8542 and the first coupling portion 8548a of the surgical module 8544a, yields a bit pattern "011111" that identifies the surgical module 8544a as the first surgical module in the stack configuration of the modular surgical system 8540. Notably, any surgical module positioned directly below the header module 8542, and in connection with the backplane connector 8543a, will be assigned the bit pattern "011111". Accordingly, the header module 8542 is able to deduce that the surgical module 8544a is the first surgical module in the stack configuration of the modular surgical system 8540, situated directly below the header module 8542, from successful communication with the surgical module 8544a using the bit pattern "011111".

Further to the above, the backplane connector 8543b, which extends between the second coupling portion 8548b of the first surgical module 8544a and the first coupling portion 8548a of the surgical module 8544b, yields a bit pattern "101111" that identifies the surgical module 8544b as the second surgical module in the stack configuration of the modular surgical system 8540. Notably, any surgical module positioned directly below the first surgical module 8544a, and in connection with the backplane connector 8543b, will be assigned the bit pattern "101111".

Accordingly, the header module 8542 is able to deduce that the surgical module 8544*b* is the second surgical module in the stack configuration of the modular surgical system 8540, and that it is situated directly below the surgical module 8544*a*, from successful communication with the surgical module 8544*b* using the bit pattern "101111". Similarly, the header module 8542 is able to deduce that the surgical modules 8544*c*, 8544*d* are the third and fourth surgical modules in the stack configuration of the modular surgical system 8540 from successful communication with the surgical modules 8544*c* 8544*d* using the bit patterns "110111" and "111011", respectively, which are produced by the backplane connectors 8543*c*, 8543*d*, respectively In various aspects, the header module 8542 employs a look-up table or a database, which can be stored in any suitable storage medium to correlate the bit patterns "011111", "101111", "110111", and "111011", with a first position, second position, third position, and fourth position, respectively, below the header module 8542, respectively, in the stack configuration. Accordingly, the header module 8542 can deduce whether a surgical module occupies a position in the stack configuration of the modular surgical system 8540 by querying the look-up table or database for the address associated with the position, and attempting to communicate using the address. If a successful communication with a surgical module is achieved, the header module 8542 concludes that the surgical module is located at the position associated with the address that caused the successful communication. Further, the header module 8542 can deduce that the number of modules in the stack configuration is at least the number that corresponds to the ranking of the position. For example, the header module 8542 can deduce that the surgical module 8544*c* occupies the third position in the stack configuration of the modular surgical system 8540 by querying the look-up table or database for the address associated with the third position, which is the bit pattern "110111," and performing a successful communication using the address. If a successful communication with a surgical module is achieved, the header module 8542 concludes that the surgical module 8544*c* is located at the third position. Further, the header module 8542 can deduce that the number of modules in the stack configuration is at least the three. Similar conclusions can be made regarding the surgical modules in the first, second, and fourth positions.

In various instances, the backplane connectors 8543 are integrated with their respective directly-upstream modules in the stack configuration, and are detachably couplable to their respective directly-downstream modules in the stack configuration. For example, the backplane connector 8543*a* can be integrated with the header module 8542, and can be detachably couplable to the surgical module 8544*a*. Likewise, the backplane connector 8543*b* can be integrated with the surgical module 8544*a*, and can be detachably couplable to the surgical module 8544*b*. Similarly, the backplane connector 8543*c* can be integrated with the surgical module 8544*b*, and can be detachably couplable to the surgical module 8544*c*. Also, the backplane connector 8543*d* can be integrated with the surgical module 8544*c*, and can be detachably couplable to the surgical module 8544*d*. Alternatively, in other instances, the backplane connectors 8543 can be integrated with their respective directly-downstream modules in the stack configuration, and can be detachably couplable to their respective directly-upstream modules in the stack configuration. Alternatively, in certain instances, the backplane connectors 8543 can be independent components that are detachably couplable to their respective directly-upstream and directly-downstream modules in the stack configuration.

In the example embodiment illustrated in FIG. 55, the header module 8542 is configured to identify the number and relative position of the modules in a stack configuration of the modular surgical system 8540 using the rotating bit pattern produced by the backplane connectors 8543. It is, however, understood that various other suitable backplane connectors and rotating bit patterns can be equally employed by the header module 8502 to identify the number and relative position of the modules in a stack configuration of the modular surgical system 8540. Further, the rotating bit pattern need not be produced by the backplane connectors. In various examples, as illustrated in FIG. 56, a rotating bit pattern for identification of the number and relative position of the modules in a stack configuration can be produced by the modules themselves.

FIG. 56 illustrates a simplified schematic diagram of a positional awareness circuit 8551 of a modular surgical system 8550, which is configured to identify relative positions of surgical modules in a stack configuration of the modular surgical system 8500, and produce unique addresses for each of the surgical modules, as described above. The modular surgical system 8550 is similar in many respects to other modular surgical systems disclosed elsewhere herein such as, for example, the modular surgical system 8500. Like the modular surgical system 8500, the modular surgical system 8550 includes a header module 8552 configured to be arranged in a stack configuration with one or more surgical modules 8554. In the example of FIG. 56, the modular surgical system 8550 includes four surgical modules 8554*a*, 8554*b*, 8554*c*, 8554*d*, which are collectively referred to herein as surgical modules 8554. However, this number of surgical modules is not limiting. In other examples, a modular surgical system 8550 can include more or less than four surgical modules in a stack configuration.

Further, the modular surgical system 8550 also includes a number of backplane connectors 8553 configured to connect consecutive modules in the stack configuration. For example, a backplane connector 8553*a* connects the header module 8552 and the surgical module 8554*a*, a backplane connector 8553*b* connects the surgical module 8554*a* and the surgical module 8554*b*, a backplane connector 8553*c* connects the surgical module 8554*b* and the surgical module 8554*c*, and a backplane connector 8553*d* connects the surgical module 8554*c* and the surgical module 8554*d*. The positional awareness circuit 8551 employs a rotating bit pattern, defined by the surgical modules 8554, to identify the number of surgical modules 8554 and/or the position of each of the surgical modules 8554 in the stack configuration.

Each of the surgical modules 8554 in the stack configuration of the modular surgical system 8550 is identifiable by a unique bit pattern produced by a directly preceding surgical module in the stack configuration. Each new surgical module added to the bottom of a preceding surgical module in the stack configuration is configured to receive a new bit pattern configured to identify the newly added energy, and is produced by the directly surgical module in the stack configuration.

Each of the surgical modules 8554 includes a top or first coupling portion 8558*a* and a bottom or second coupling portion 8558*b*. Conductor elements extend between the first coupling portion 8558*a* and the second coupling portion 8558*b* defining a conductor layout 8559 that yields the rotating bit pattern of the positional awareness circuit 8551. A left-most conductor element extends from a 1st position of the first coupling portion 8558*a* to a 1st position of the second coupling portion 8558*b*. The left-most conductor comprises a split that extends to the 2nd position of the second coupling portion 8558*b*. The left-most conductor is a common ground reference for transmitted logic signals, and may be utilized in performing other functions.

Like the shifting bit pattern of the positional awareness circuit 8541, the rotating bit pattern of the positional awareness circuit 8551 is achieved using conductor elements, without active components. In various aspects, the conductor layout 8529 includes a plurality of shifting conductor elements, and a rotating conductor element. In the example illustrated in FIG. 56, the conductor layout 8559 further includes a conductor element that extends from a 2nd position of the first coupling portion 8558*a* to a 3rd position of the second coupling portion 8558*b*. Similarly, a conductor element extends from a 3rd position of the first coupling portion 8558*a* to a 4th position of the second coupling portion 8558*b*. Similarly, a conductor element extends from a 4th position of the first coupling portion 8558*a* to a 5th position of the second coupling portion 8558*b*. Similarly, a conductor element extends from a 5th position of the first coupling portion 8558*a* to a 6th position of the second coupling portion 8558*b*. Similarly, a conductor element extends from a 6th position of the first coupling portion 8558*a* to a 7th position of the second coupling portion 8558*b*. Finally, a conductor element extends, in a rotating fashion, from a 7th position of the first coupling portion 8558*a* to a 2nd position of the second coupling portion 8558*b*, facilitating the rotation of the rotating bit pattern.

As illustrated in FIG. 56, the surgical modules 8554 with the conductor layout 8559 yield different, unique, bit patterns depending on the position of such surgical modules 8554 in the stack configuration, which are configured to identify their respective following surgical modules in the stack configuration. The first surgical module 8554*a* received its identifying bit pattern "011111" from the header module 8552. Notably, any surgical module positioned directly below the header module, and in connection with the backplane connector 8553*a*, will be assigned the bit pattern "011111". Accordingly, the header module 8552 is able to deduce that the surgical module 8554*a* is the first surgical module in the stack configuration of the modular surgical system 8550, situated directly below the header module 8552, from successful communication with the surgical module 8554*a* using the bit pattern "011111".

Further, the conductor layout of the surgical module 8554*a*, yields a bit pattern "101111" that identifies the surgical module 8554*b* as the second surgical module in the stack configuration of the modular surgical system 8550. Notably, any surgical module in a second position below a header module 8552 will be assigned the bit pattern "101111". Accordingly, the header module 8552 is able to deduce that the surgical module 8554*b* is the second surgical module in the stack configuration of the modular surgical system 8550, and that it is situated directly below the surgical module 8554*a*, from successful communication with the surgical module 8554*b* using the bit pattern "101111". Similarly, the header module 8552 is able to deduce that the surgical modules 8554*c*, 8554*d* are the third and fourth surgical modules in the stack configuration of the modular surgical system 8550 from successful communication with the surgical modules 8554*c* 8554*d* using the bit patterns "110111" and "111011", respectively, which are produced by the surgical modules 8554*b*, 8554*c*, respectively.

In various aspects, the header module 8552 employs a look-up table or a database, which can be stored in any suitable storage medium to correlate the bit patterns "011111", "101111", "110111", and "111011", with a first position, second position, third position, and fourth position, respectively, below the header module 8552, respectively, in the stack configuration. Accordingly, the header module 8552 can deduce whether a surgical module occupies a position in the stack configuration of the modular surgical system 8550 by querying the look-up table or database for the address associated with the position, and attempting to communicate using the address. If a successful communication with a surgical module is achieved, the header module 8552 concludes that the surgical module is located at the position associated with the address that caused the successful communication. Further, the header module 8552 can deduce that the number of modules in the stack configuration is at least the number that corresponds to the ranking of the position. For example, the header module 8552 can deduce that the surgical module 8554*c* occupies the third position in the stack configuration of the modular surgical system 8550 by querying the look-up table or database for the address associated with the third position, which is the bit pattern "110111," and performing a successful communication using the address. If a successful communication with a surgical module is achieved, the header module 8552 concludes that the surgical module 8554*c* is located at the third position. Further, the header module 8552 can deduce that the number of modules in the stack configuration is at least the three. Similar conclusions can be made regarding the surgical modules in the first, second, and fourth positions.

Referring to FIGS. 53-56, the modular surgical systems 8500, 8520, 8540, 8550 comprise positional awareness circuits 8501, 8521, 8541, 8551 that can be configured to support identification of a maximum number of surgical modules permissible in their the stack configurations. By choosing the number of shifted (or rotated) lines of the conductor layout to be one more than the maximum number of surgical modules allowed in the stack, the surgical module added to the stack that exceeds the maximum permissible number of shifted (or rotated) lines will see a zero on the right-most conductor (the sixth data conductor in the example embodiments shown in FIGS. 53-56, which are sized for a maximum of five modules in the stack). In other examples, however, it is foreseeable that a modular surgical system can include a positional awareness circuit configured to support a maximum of more or less than five surgical modules. In at least one example, by providing an additional sense line or conductor element 8511, as illustrated in FIG. 57 with respect to a positional awareness circuit 8501' of a modular surgical system 8500', to each of the positional awareness circuits 8501, 8521, 8541, 8551, all modules, including the header module, of the modular surgical systems 8500, 8520, 8540, 8550 are able to detect a module limit-exceeded status.

Figure 57:
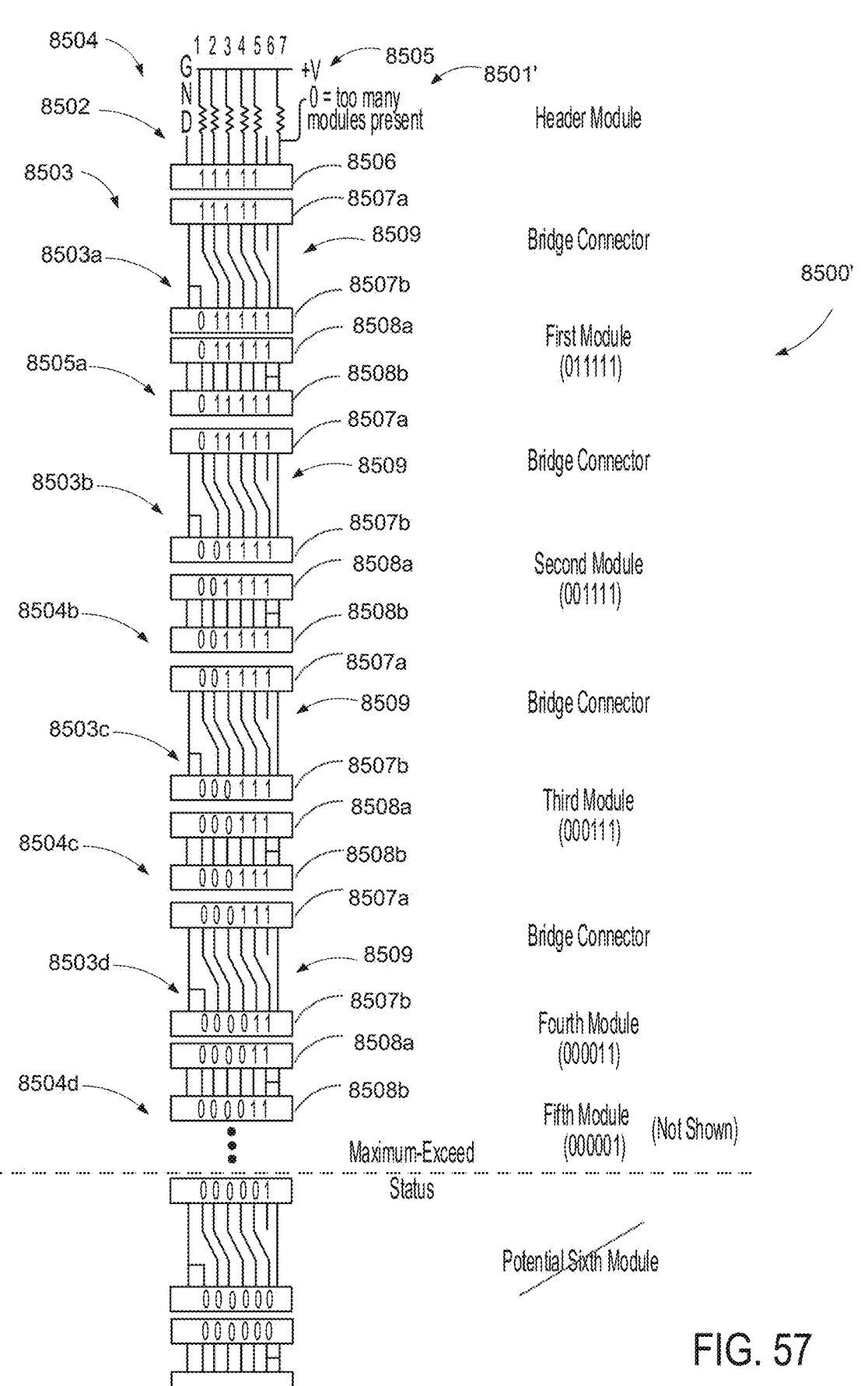
FIG. 57 illustrates a simplified schematic diagram of a positional awareness circuit of a modular energy system, in accordance with at least one embodiment of the present disclosure.

FIG. 57 illustrates a simplified schematic diagram of a positional awareness circuit 8501' of a modular surgical system 8500', which is configured to identify relative positions of surgical modules in a stack configuration of the modular surgical system 8500, and produce unique addresses for each of the surgical modules, as described above. The modular surgical system 8500' is similar in many respects to other modular surgical systems disclosed elsewhere herein such as, for example, the modular surgical system 8500. Like the modular surgical system 8500, the modular surgical system 8500' includes a header module

8502 configured to be arranged in a stack configuration with one or more surgical modules 8504'. In the example of FIG. 57, the modular surgical system 8500' includes four surgical modules 8504a, 8504b, 8504c, 8504d, which are collectively referred to herein as surgical modules 8504'. However, this number of surgical modules is not limiting. In other examples, a modular surgical system 8500 can include more or less than four surgical modules in a stack configuration.

Further to the above, the positional awareness circuit 8501' of the modular surgical system 8500' includes a segmented conductor that defines an additional sense line 8511 that can be extended through all the modules and backplane connectors of the modular surgical system 8500' in the stack configuration, as illustrated in FIG. 57. The sense line 8511 is employed to detect a module limit-exceeded status. As illustrated in FIG. 57, all lines of the modular surgical system 8500' are pulled high through resistors 8505. During operation all the lines are shorted low if module limit-exceeded status is triggered. The voltage across the resistors 8505 can be monitored by the header module 8602 to detect the module limit-exceeded status. In the example of FIG. 57, attaching a sixth module to the stack configuration of the modular surgical system 8500' is impermissible because it exceeds the maximum limit of permissible modules. The header module 8502 is able to detect a maximum-exceeded status when a user attempts to attach a sixth module by monitoring the resistors 8505 for a transition from high to low.

Figure 58:
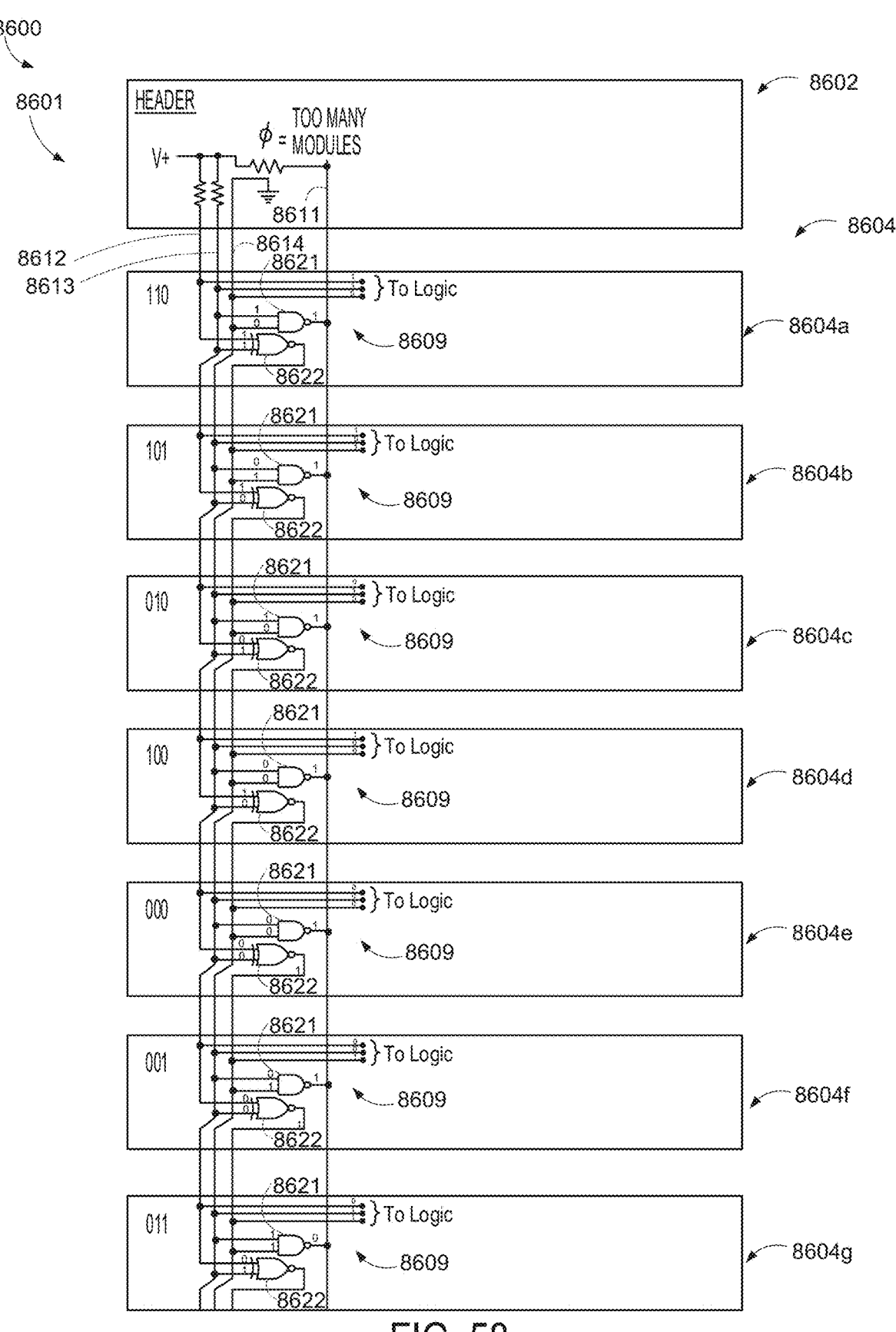
FIG. 58 illustrates a simplified schematic diagram of a positional awareness circuit of a modular energy system, in accordance with at least one embodiment of the present disclosure.

The conductor layouts of the surgical modules 8504' of the modular surgical system 8500' are slightly modified from their counterparts in the modular surgical system 8500 to include an H-bridge between the sense line conductors and the sixth line conductors positioned next to the sense line conductors, as illustrated in FIG. 58. The H-bridge shorts the sense line when a surgical module is added to the stack configuration beyond the maximum number of permissible surgical modules, thereby triggering the maximum-exceeded status. In the example of FIG. 57, adding a sixth surgical module to the stack configuration exceeds the maximum number of permissible surgical modules, which triggers the maximum-exceeded status by shorting all the data lines. In response, in certain instances, the header module 8602, may cause an alert to be issued through the UI module 3030 (FIG. 33), for example.

In various aspects, other modular surgical systems of the present disclosure such as, for example, the modular surgical systems 8500, 8510, 8520, 8540, 8550 can be modified to include a sense line, as discussed above.

The modular surgical systems of FIGS. 53-57 are configured to identify the position and number of surgical modules in their respective stack configuration using inactive-state components. In alternative embodiments, however, active-state components can be employed instead of the inactive-state components to identify the position and number of surgical modules in a stack configuration. For example, FIG. 58 illustrates a modular surgical system 8600 that relies on a logic gate configuration 8609 to identify the position and number of surgical modules in its stack configuration.

FIG. 58 illustrates a simplified schematic diagram of a positional awareness circuit 8601 of the modular surgical system 8600, which is configured to identify relative positions of surgical modules in a stack configuration of the modular surgical system 8500, and produce unique addresses for each of the surgical modules, as described above. The modular surgical system 8600 is similar in many respects to other modular surgical systems disclosed elsewhere herein such as, for example, the modular surgical system 8500. Like the modular surgical system 8500, the modular surgical system 8600 includes a header module 8602 configured to be arranged in a stack configuration with one or more surgical modules 8604. In the example of FIG. 58, the modular surgical system 8600 includes seven surgical modules 8604a, 8604b, 8604c, 8604d, 8604e, 8604f, 8604g which are collectively referred to herein as surgical modules 8604. However, this number of surgical modules is not limiting. In other examples, a modular surgical system 8600 can include more or less than seven surgical modules in a stack configuration.

Each of the surgical modules 8604 includes a logic gate configuration 8609 that yields a different bit pattern depending on the position of its surgical module below the header module 8602 in the stack configuration. In the example of FIG. 58, the first position below the header module 8602 corresponds to a bit pattern "110", the second position below the header module 8602 corresponds to a bit pattern "101", the third position below the header module 8602 corresponds to a bit pattern "010", the fourth position below the header module 8602 corresponds to a bit pattern "100", the fifth position below the header module 8602 corresponds to a bit pattern "000", the sixth position below the header module 8602 corresponds to a bit pattern "001", and the seventh position below the header module 8602 corresponds to a bit pattern "011". Although the logic gate configuration of the surgical modules 8604 is a three-bit sequence, this is not limiting. Modular surgical systems with logic gate configurations comprising more or less than three bits are contemplated by the present disclosure.

In the example illustrated in FIG. 58, one logic gate configuration is repeated in all the surgical modules 8604 in the stack configuration. Each logic gate configuration 8609, however, yields a unique bit pattern depending on the position of its surgical module in the stack configuration, as discussed above.

Further, the logic gate configurations 8609 include NAND gates 8621 and EXNOR gates 8622. The NAND gates 8621 comprise outputs that are coupled to the sense line 8611. In the example of FIG. 58, the positional awareness circuit 8601 is designed to yield a high output for all NAND gates 8621 of all the surgical modules 8604 in the stack configuration that are at or below a maximum number (e.g. six) of permissible surgical modules. The NAND gates 8621 of the surgical modules 8604a, 8604b, 8604c, 8604d, 8604e, 8604f, which are at or below the maximum permissible number of surgical modules for 8600, yield high outputs before attachment of the surgical module 8604g. Upon attachment of the surgical module 8604g in a seventh position in the stack configuration, the NAND gate 8621 of the surgical module 8604g yields a low output because the surgical module 8604g causes the number of surgical modules 8604 in the stack configuration to be greater than the maximum permissible number (e.g. six) of surgical modules for 8600. The low output is detectable by the header module 8602 as being indicative of a module maximum-exceeded status. In at least one example, the header module 8602 monitors the sense line 8611 to determine if a module-exceeded status is triggered.

In addition to the NAND gates 8621, the logic gate configurations 8609 include EXNOR gates 8622 that are arranged with the NAND gates 8621 to set the maximum permissible number of surgical modules in the stack configuration of the module surgical system 8600. In the example of FIG. 58, the positional awareness circuit 8601 of the modular surgical system 8600 is designed to limit the maximum permissible number of surgical modules in the stack configuration to six. Accordingly, the addition of a seventh surgical module 8604g to the stack configuration already comprising the surgical modules 8604a, 8604b, 8604c, 8604d, 8604e, 8604f yields a maximum-exceeded signal or status that alerts the header module 8602 to the attachment of a surgical module that exceeds the maximum permissible number of surgical modules in the stack configuration. In response, the header module 8602 may alert a user through the UI module 3030 (FIG. 33), for example, that the surgical module 8604g exceeds the maximum permissible number of surgical modules in the stack configuration and/or instruct the user to remove the surgical module 8604g from the stack configuration.

In some aspects, the header modules described herein can include or support a display, such as display 3046 of the UI module 3030. The header modules can be configured to provide a visual representation of the modules in their stack configuration on the display in relative position representing their physical position in their respective modular surgical systems. The display can provide information about the modules, such as the type of module, status of module, availability of the module, health of module, etc. A user can select one of the modules from the display, such as with a touchscreen, in order to provide instructions to the module by way of a user interface.

Energy Module Hardware

Some surgical procedures require the use of multiple different types of energy modalities. One option is to utilize multiple different surgical systems that are each configured to deliver one type of energy modality and switch between the surgical systems as needed during the course of the surgical procedure. However, in addition to the general convenience of having multiple different energy modalities available through a single system, a surgical system that is configured to deliver combinations of different energy modalities can provide a number of benefits and improved functionality over surgical systems that are configured to deliver a singular energy modality. For example, simultaneously delivering combinations of energy modalities can provide improved tissue coagulation as compared to a single energy modality. As another example, monopolar surgical systems can have issues with tissue adherence to the tip of the monopolar electrosurgical instrument. However, a surgical system configured to deliver both monopolar and ultrasonic energy can reduce tissue adherence to the surgical instrument when delivering monopolar energy by vibrating the end effector as energy is delivered. As yet another example, a surgical system configured to deliver monopolar energy in addition to other energy modalities can allow for the monopolar energy to be utilized as a supplement for the system's other energy modality, which can be useful for "touch up" coagulation. Accordingly, in various aspects, a surgical system configured to deliver multiple energy modalities can be configured to deliver bipolar, monopolar, and/or ultrasonic energy. Surgical systems that are configured to deliver combinations of energy modalities can further include a surgical generator or energy module that can deliver multiple energy modalities to the surgical instrument via a single port, thereby allowing a single surgical instrument to simultaneously or alternatively utilize the different energy modalities.

In various aspects, the present disclosure provides an amplifier circuit and port arrangement within a single energy module configured to deliver signals to surgical devices. The port is coupled to two separate monopolar energy sources, one bipolar energy source, and one advanced energy source, which includes, bipolar energy mode, monopolar energy mode, and ultrasonic energy mode. In a further aspect, the present disclosure provides an energy source connector that includes a pin arrangement configured to deliver bipolar energy, monopolar energy, and ultrasonic energy, where the monopolar pin has a different pin size and spacing from the other pins to prevent electrical arcing and shorting between pins. In yet a further aspect, the present disclosure provides a leakage current detection circuit on each port on an energy source to monitor for stray energy, which can be used to shut off an unwanted energy path.

Figure 59:
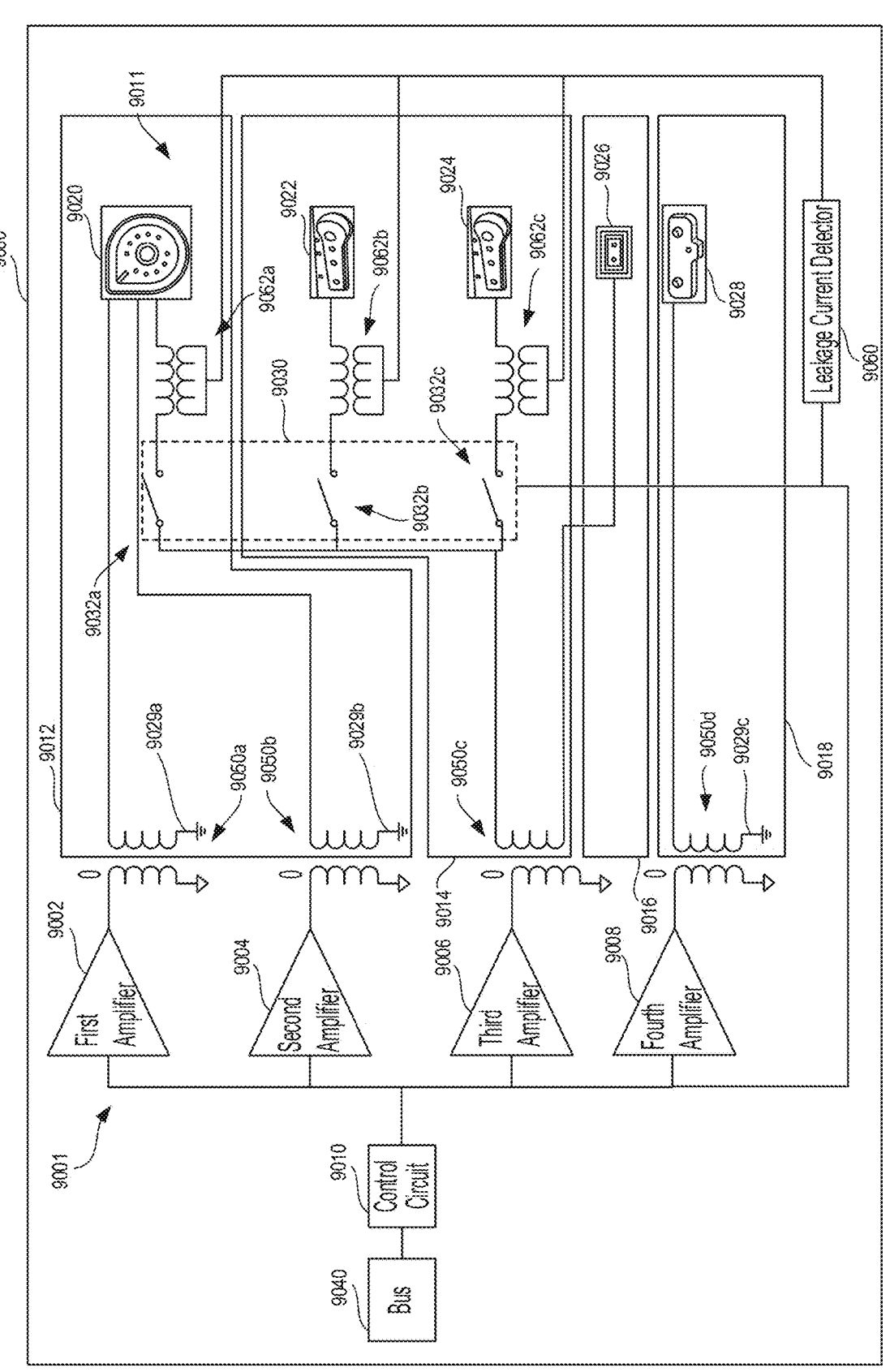
FIG. 59 is a block diagram of an energy module circuit, in accordance with at least one aspect of the present disclosure.

As described above in connection with FIGS. 21, 22, 24-30, and 33-37, an energy module 2004 can be configured to provide a variety of different energy modalities. For example, FIG. 59 is a block diagram of an energy module circuit 9000 for an energy module 2004 that is configured to deliver multiple energy modalities to a surgical instrument connected to the energy module 2004. The energy module circuit 9000 includes an energy drive assembly 9001 that is configured to generate the electrical signals for driving the various energy modalities applied by the surgical instrument connected to the energy module 2004. The energy drive assembly 9001 can include various circuitry and/or other hardware components for generating, controlling, and delivering drive signals for driving monopolar electrosurgical energy, bipolar electrosurgical energy, ultrasonic energy, or other energy modalities, and combinations thereof, at a surgical instrument coupled to the energy module 2004. In this particular example, the energy drive assembly 9001 includes a first amplifier 9002 configured to drive a first energy modality, a second amplifier 9004 configured to drive a second energy modality, a third amplifier 9006 configured to drive a third energy modality, and a fourth amplifier 9008 configured to drive a fourth energy modality. The amplifiers 9002, 9004, 9006, 9008 can be configured to drive the same or different energy modalities. The various amplifiers 9002, 9004, 9006, 9008 can include an ultrasonic amplifier capable of generating arbitrary waveforms to drive ultrasonic transducers at low total harmonic distortion (THD) levels and/or a bipolar and/or monopolar electrosurgical amplifier capable of generating arbitrary waveforms to drive RF loads at a range of output frequencies. The waveforms generated by the various amplifier types can also be referred to as "drive signals" for the different energy modality types. Further, such amplifiers can include linear or resonant amplifiers. In one particular implementation of the energy module circuit 9000, the first amplifier 9002 can include an ultrasonic amplifier, the second amplifier 9004 can include a bipolar electrosurgical amplifier, the third amplifier 9006 can include a monopolar electrosurgical amplifier, and the fourth amplifier 9008 can include another bipolar electrosurgical amplifier. However, the energy drive assembly 9001 can include other numbers and combinations of amplifiers, such as with the energy module 3004 shown in FIG. 34, for example. Further, the energy drive assembly 9001 can include a variety of other circuit components, such as is described in connection with the energy modules 3004, 3270 shown in FIGS. 34, 35, and 37.

The energy module circuit 9000 further includes a receptacle or port assembly 9011 that is electrically coupled to the energy drive assembly 9001. In this particular example, the port assembly 9011 includes a first port 9020, a second port 9022, a third port 9024, a fourth port 9026, and a fifth port 9028. The ports 9020, 9022, 9024, 9026, 9028 (which can also be referred to as receptacles) can be configured to, for example, receive or engage with corresponding connectors associated with surgical instruments (or cables to which the surgical instruments are connected) or connectors for an energy module/surgical system accessory (e.g., a monopolar return pad). In this particular example, the first port 9020 is electrically coupled or couplable to each of the first amplifier 9002, the second amplifier 9004, and the third amplifier 9006 and is thus capable of delivering up to three different energy modalities, one of which is driven by each of the respective amplifiers 9002, 9004, 9006. The second port 9022 and the third port 9024 are each electrically coupled to the third amplifier 9006 and are thus capable of delivering the same energy modality driven therefrom. The fourth port 9026 is electrically coupled to an electrical ground for the third amplifier 9006 and thus serves as an electrical return path for the energy modality driven by the third amplifier 9006 through at least one of the first, second, or third ports 9020, 9022, 9024. For example, the fourth port 9026 can serve as a connection point for a monopolar return pad for aspects where the third amplifier 9006 is a monopolar amplifier (as a monopolar electrosurgical instrument, as opposed to a bipolar electrosurgical instrument, must be used in connection with a monopolar return pad). The fifth port 9028 is electrically coupled to the fourth amplifier 9008 and is thus capable of delivering an energy modality driven therefrom.

In one aspect, the energy module circuit 9000 can be divided into a multiple isolated circuit portions or stages. Each of the circuit portions can be electrically isolated from the other circuit portions for safety purposes and compliance with electrosurgical generator technical standards, such as IEC 60601. Each of the isolated circuit portions can be coupled to the energy drive assembly 9001 via one or more isolation transformers. An isolation transformer is utilized to transfer electrical power from a source of AC power to a recipient device, in this case, the isolated circuit portions, while isolating the recipient device from the power source. Further, the isolated circuit portions can include one or more local grounds for electrically isolating the components of the energy drive assembly 9001 corresponding to that circuit portion from the components corresponding to the other circuit portions. Accordingly, each of the circuit portions are electrically isolated from each other. In the particular implementation illustrated in FIG. 59, the energy module circuit 9000 includes a first isolated circuit portion 9012 corresponding to the first port 9020, a second isolated circuit portion 9014 corresponding to the second and third ports 9022, 9024, a third isolated circuit portion 9016 corresponding to the fourth port 9026, and a fourth isolated circuit portion 9018 corresponding to the fifth port 9028. The first isolated circuit portion 9012 is coupled to the first and second amplifiers 9002, 9004 via a first isolation transformer 9050*a* and a second isolation transformer 9050*b*, respectively. The first isolated circuit portion 9012 is further couplable to the third amplifier 9006, through the switch assembly 9030, via a third isolation transformer 9050*c*. The second isolated circuit portion 9014 is coupled to the third amplifier 9006 via the third isolation transformer 9050*c*. The third isolated circuit portion 9016 is coupled to the return terminal of the third isolation transformer 9050*c*. Lastly, the fourth isolated circuit portion 9018 is coupled to the fourth amplifier 9008 via a fourth isolation transformer 9050*d*. Further, the first isolated circuit portion 9012 includes a first isolated local ground 9029*a* and a second isolated local ground 9029*b* for the first isolation transformer 9050*a* and the second isolation transformer 9050*b*, respectively. The fourth isolated circuit portion 9018 includes a third isolated local ground 9029*c* for the fourth isolation transformer 9050*d*. The third isolated circuit portion 9016 is electrically isolated from the other circuit portions 9012, 9014, 9018 via the connection between the fourth port 9026 and the return terminal of the third isolation transformer 9050*c*. The fourth port 9026 can likewise, in part, serve the electrical isolation of the first isolated circuit portion 9012 when the first switch 9032*a* is in its closed state and the first port 9020 is coupled to the third amplifier 9006 through the third isolation transformer 9050*c*. In addition to generally seeking to comply with applicable technical standards, dividing the energy module circuit 9000 into multiple isolated circuit portions 9012, 9014, 9016, 9018 in this manner ensures that surgical components that are intended to come into contact with patients are not inadvertently energized when other components or circuits are energized, which, in turn, promotes patient and operator safety.

It should be noted that the particular implementation of the energy module circuit 9000 illustrated in FIG. 59 for an energy module 3004 is only provided for illustrative purposes. Various other arrangements or combinations of amplifiers 9002, 9004, 9006, 9008 within the energy drive assembly 9001, isolated circuit portions 9012, 9014, 9016, 9018, and/or ports 9020, 9022, 9024, 9026, 9028 are within the scope of the present disclosure, including different numbers or amplifiers 9002, 9004, 9006, 9008 or amplifiers 9002, 9004, 9006, 9008 that drive different combinations of energy modalities, isolated circuit portions 9012, 9014, 9016, 9018 that include different combinations of components or are otherwise arranged in different manners, and so on.

As described above, in one aspect, the energy module circuit 9000 can include a circuit (e.g., the first isolated circuit portion 9012 and/or other associated components, such as the first, second, and third amplifiers 9002, 9004, 9006) that is configured to deliver multiple different energy modalities to a surgical instrument connected to the port (e.g., the first port 9020) associated with the particular circuit. In one aspect, a surgical instrument receiving multiple energy drive signals can be configured to simultaneously or individually apply the driven energy modalities to tissue. In another aspect, such a surgical instrument can be configured to utilize one or more of the driven energy modalities for non-tissue treatment purposes, such as sensing or for driving secondary functions of the surgical instrument. For example, a drive signal from a bipolar amplifier (e.g., the second amplifier 9004) can be driven at nontherapeutic frequencies (i.e., below the minimum frequency necessary to induce treatment effects in tissue to which the signal is applied) for sensing various tissue properties, such as tissue thickness or tissue type. As another signal, a drive signal from an ultrasonic amplifier (e.g., the first amplifier 9002) can be driven at nontherapeutic frequencies to vibrate an end effector to prevent tissue adhesion thereto as monopolar or bipolar energy is applied to tissue to prevent tissue adhesion to the end effector. In yet another aspect, energy module drive signals can be utilized to power secondary or nontherapeutic components of connected surgical instruments, as is described herebelow.

Figure 60:
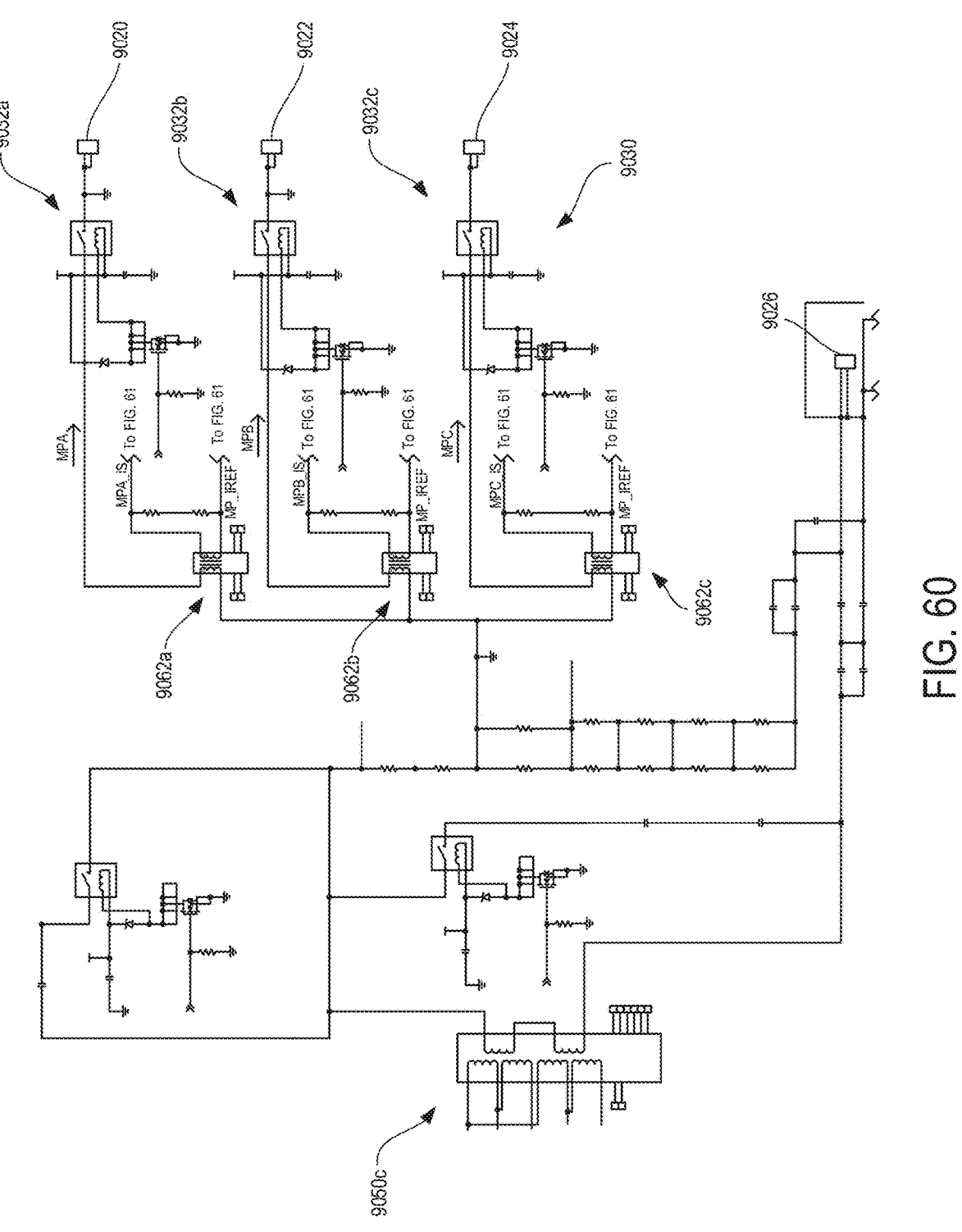
FIG. 60 is a diagram of an energy module circuit, in accordance with at least one aspect of the present disclosure.

Because of the significant number of hardware components required by the energy modules 2004 described herein for driving all of the various combinations of energy modalities, it would generally be desirable to utilize hardware components for multiple different purposes within the energy modules 2004 in order to minimize the hardware footprint of the energy modules 2004. In one aspect, one or more amplifiers of the energy driver assembly 9001 can be interchangeably couplable to one or more ports of the port assembly 9011 via a switch assembly 9030. In this particular example, the third amplifier 9006 is interchangeably couplable to each of the first port 9020, the second port 9022, and the third port 9024 via the switch assembly 9030. The switch assembly 9030 includes a first switch 9032a for coupling the third amplifier 9006 to the first port 9020, a second switch 9032b for coupling the third amplifier 9006 to the second port 9022, and a third switch 9032c for coupling the third amplifier 9006 to the third port 9024. Each of the switches 9032a, 9032b, 9032c can be transitioned between an open position/state in which the third amplifier 9006 is decoupled from the respective port 9020, 9022, 9024 and a closed position/state in which the third amplifier 9006 is coupled to the respective port 9020, 9022, 9024. Accordingly, the third amplifier 9006 can be configured to generate an electrical drive signal for driving its respective energy modality, which can be provided to a surgical instrument through the first port 9020, the second port 9022, and/or the third port 9024 according to which of the respective switches 9032a, 9032b, 9032c is in its closed position or state. In various aspects, the switch assembly 9030 can be controlled by a control circuit 9010, which is described further below, to selectively control which of the ports 9020, 9022, 9024 the third amplifier 9006 is coupled to. Further, FIG. 60 illustrates a circuit diagram providing additional detail regarding the circuit architecture of the third amplifier 9006 and the switch assembly 9030. Utilizing a switching assembly 9030 to interchangeably connect an amplifier from the energy driver assembly 9001 to multiple ports utilizing the same energy modality, as opposed to dedicating a unique amplifier configured to drive the appropriate energy modality to each port, simplifies the internal structure of the energy module 3004 by reusing the third amplifier 9006 across multiple ports. Reusing the third amplifier 9006, in turn, reduces cost and saves space within the energy module 3004. Further, the illustrated circuit architecture eliminates the need for relays to be integrated within the circuit pathway for the neutral electrode port (i.e., the fourth port 9026 in the particular example illustrated in FIG. 59) because a single neutral electrode pathway can be dedicated to the monopolar energy-providing third amplifier 9006.

Figure 61:
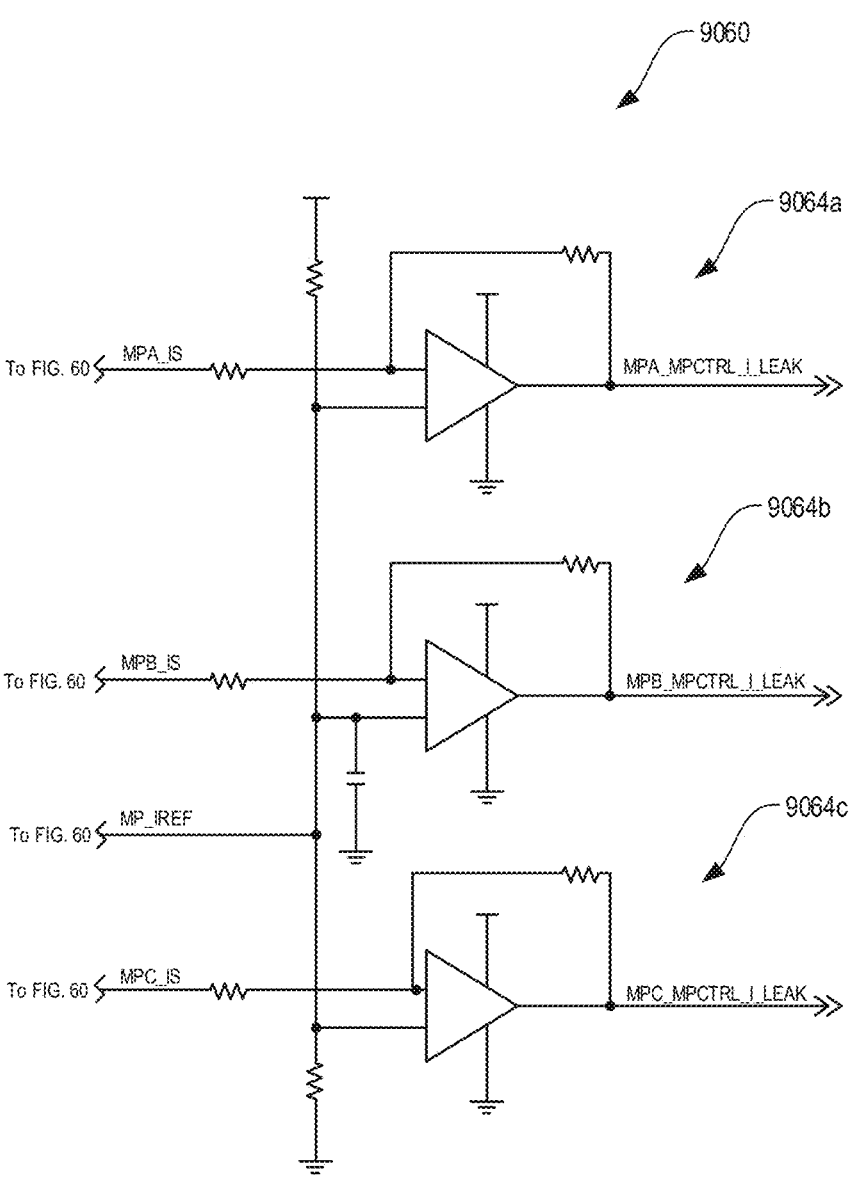
FIG. 61 is a diagram of a leakage current detector circuit, in accordance with at least one aspect of the present disclosure.

For operator and patient safety purposes, it is desirable for surgical generator/energy systems having multiple monopolar ports (such as with the energy module 3004 described above) to include systems to ensure that the monopolar energy is only driven to the intended monopolar port/instrument. In one aspect, the energy module circuit 9000 can further include a leakage current detector circuit 9060 coupled to each of the ports 9020, 9022, 9024 to which the switch assembly 9030 is configured to interchangeably couple the third amplifier 9006 (which, in the example described above, is configured to provide a monopolar drive signal). The leakage current detector circuit 9060 can be embodied as one or multiple circuit portions that are included within or coupled to the electrical pathways for the ports 9020, 9022, 9024. The leakage current detector circuit 9060 can be configured to determine whether monopolar energy/drive signal is being inadvertently transmitted from the third amplifier 9006 to the respective port 9020, 9022, 9024. In one aspect, the leakage current detector circuit 9060 can be coupled to each pathway for the first, second, and third pots 9020, 9022, 9024 via a respective current sensing transformer 9062a, 9062b, 9062c. As can be seen in FIG. 61, the leakage current detector circuit 9060 can receive as input a first sensed electrical current (MPA_IS) corresponding to the monopolar output current (MPA) transmitted to the first port 9020, a second sensed electrical current (MPB_IS) corresponding to the monopolar output current (MPB) transmitted to the second port 9022, a third sensed electrical current (MPC_IS) corresponding to the monopolar output current (MPC) transmitted to the third port 9024, and a reference current (MP_IREF). The leakage current detector circuit 9060 can further include a pass/fail comparator 9064a, 9064b, 9064c for each of the current sensing transformer 9062a, 9062b, 9062c. Each of the pass/fail comparators 9064a, 9064b, 9064c is configured to change its output state according to whether it senses a monopolar output. The output of the leakage current detector circuit 9060 can include one or more signals (labeled: MPA_MPCTRL_I_LEAK, MPB_MPCTRL_I_LEAK, and MPC_MPCTRL_I_LEAK) that are output by the pass/fail comparator 9064a, 9064b, 9064c according to their states. The output signals can each indicate whether the port 9020, 9022, 9024 to which the output signal corresponds is receiving monopolar output (i.e., a monopolar drive signal), which can in turn be utilized to determine whether any of the ports 9020, 9022, 9024 are inadvertently receiving monopolar output. These output signals from the comparators 9064a, 9064b, 9064c can be communicated to the control circuit 9010, which can then control the third amplifier 9006 and/or switch assembly 9030 based upon whether leakage current is detected. For example, when a leakage current is detected, the control circuit 9010 can cause the third amplifier 9006 to cease outputting the drive signal. As another example, when a leakage current is detected, the control circuit 9010 can cause the switch assembly 9030 to transition the appropriate switch 9032a, 9032b, 9032c to its closed position/state to halt the unintended delivery of the drive signal to the port 9020, 9022, 9024 at which the leakage current was detected.

As noted above, the energy module circuit 9000 can further include a control circuit 9010 that is communicably coupled to the energy drive assembly 9001, the switch assembly 9030, and/or the leakage current detector circuit 9060. The control circuit 9010 can further be communicably coupled to a bus 9040 for transmitting and receiving information/signals to and from other modules with a modular energy system 3000 (FIGS. 31-37) or external systems, as is described in FIG. 34. In one aspect, the control circuit 9010 can include the controller 3082 described in connection with FIGS. 33-37. The control circuit 9010 can further be configured to execute various algorithms or processes for controlling the energy module 3004.

Figure 62:
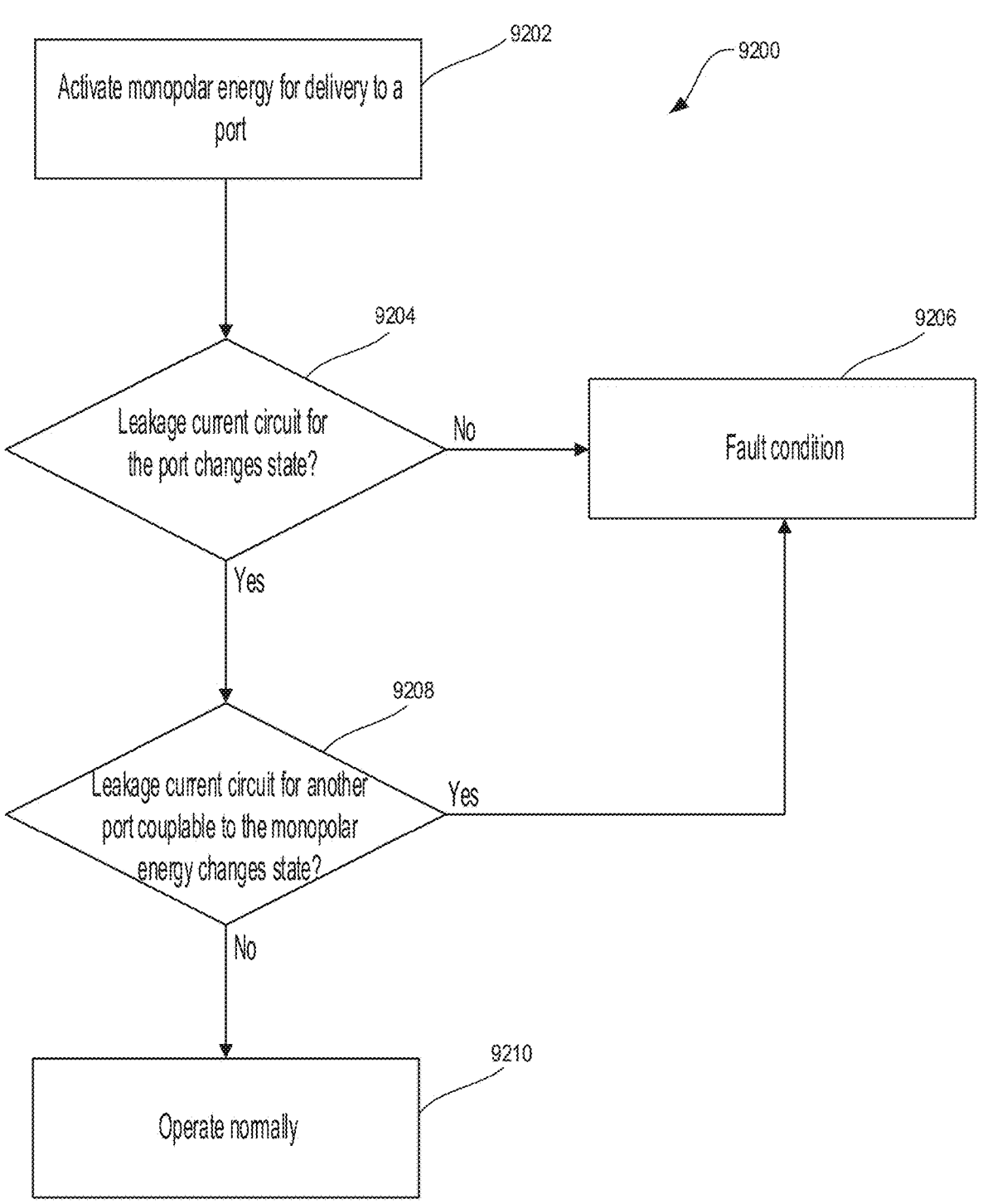
FIG. 62 is a logic flow diagram of a process for monitoring an energy module circuit for monopolar leakage current, in accordance with at least one aspect of the present disclosure.

In one aspect, the control circuit 9010 can be configured to monitor the energy module circuit 9000 to determine when monopolar energy is inadvertently being applied to one or more ports of the energy module 3004. For example, the control circuit 9010 can be configured to execute the process 9200 illustrated in FIG. 62. The process 9200 can be embodied as, for example, instructions stored in a memory coupled to the control circuit 9010 that, when executed by the control circuit 9010, cause the control circuit 9010 to perform the enumerated steps of the process 9200. In the following description of the process 9200, reference should also be made to FIGS. 59-61.

Accordingly, the control circuit 9010 executing the process 9200 activates 9202 monopolar energy for delivery to one of the ports of the port assembly 9011. For example, the control circuit 9010 can cause a monopolar amplifier of the energy module 3004 (e.g., the third amplifier 9006) to generate a monopolar electrosurgical drive signal, which is delivered by the isolation transformer 9050c to the patient-isolated side of the energy module circuit 9000, then through the switch assembly 9030 to one of the ports 9020, 9022, 9024.

Accordingly, the control circuit 9010 determines 9204 whether the port to which the monopolar electrosurgical drive signal is intended to be driven changes state. As discussed above, in one aspect, the control circuit 9010 can receive a signal from the comparators 9064a, 9064b, 9064c of the leakage current detector circuit 9060 corresponding to the intended port. If the received signal indicates that energy is not being applied to the intended port, then the process 9200 can proceed along the NO branch and the control circuit 9010 determines 9206 that a fault condition has occurred because the port that is intended to be energized is not in fact being energized. If the received signal indicates that energy is being applied to the intended port, then the process 9200 can proceed along the YES branch and the control circuit 9010 determines 9208 whether another port configured to delivery monopolar energy has changed state. In other words, the control circuit 9010 determines 9208 whether the ports couplable to the monopolar amplifier via the switch assembly 9030, other than the intended port, are being energized by the monopolar amplifier. As discussed above, the control circuit 9010 can likewise receive signals from the comparators 9064a, 9064b, 9064c of the leakage current detector circuit 9060 that correspond to the other ports coupled to the switch assembly 9030. If the received signal(s) indicate(s) that energy is being applied to the other ports, then the process 9200 can proceed along the YES branch and the control circuit 9010 determines 9206 that a fault condition has occurred because at least one port is being inadvertently energized with monopolar energy. If the received signal(s) indicate(s) that energy is not being applied to the other ports, then the process 9200 can proceed along the NO branch and the control circuit 9010 determines 9210 that the energy module 3004 is operating normally.

In the event that the control circuit 9010 executing the process 9200 determines 9206 that a fault condition has occurred, the control circuit 9010 can take a variety of different actions, including providing an alert to the user (e.g., via the display 2006 in FIGS. 24-30) or deactivating the energy drive assembly 9001 or a component thereof (e.g., the monopolar amplifier).

In other aspects, a control circuit 9010 can be configured to control the energy module 3004 in a variety of other ways. For example, a control circuit 9010 can be configured to control the power level of or waveform generated by the energy drive assembly 9001, the switch assembly 9030 to selectively couple or decouple the monopolar amplifier to one or more ports, and/or various other components of the energy module 3004 based on sensed parameters.

As noted above, the energy module circuit 9000 can be delineated into multiple isolated circuit portions 9012, 9014, 9016, 9018. Further, the first and second isolated circuit portions 9012, 9014 could, via the switch assembly 9030, potentially be both coupled to the same amplifier (i.e., the third amplifier 9006). As the isolated circuit portions 9012, 9014, 9016, 9018 are intended to be electrically isolated from each other, it can be beneficial to ensure that only one of the first and second isolated circuit portions 9012, 9014 is coupled to the third amplifier 9006 at any given time. In one aspect, the control circuit 9010 can be configured to control the relay 9030 such that only one of the first and second isolated circuit portions 9012, 9014 is coupled to the third amplifier 9006 at any given time. For example, the control circuit 9010 can be configured to detect the position/state of each of the switches 9032a, 9032b, 9032c. If the control circuit 9010 determines that the first switch 9032a has transitioned from its open position/state to its closed position/state, then in response, the control circuit 9010 can control the switch assembly 9030 to transition the second and third switches 9032b, 9032c to their open position/state. Correspondingly, if the control circuit 9010 determines that at least one of the second or third switches 9032b, 9032c has transitioned from its open position/state to its closed position/state, then in response, the control circuit 9010 can control the switch assembly 9030 to transition the first switch 9032a to its open position/state. As another example, the control circuit 9010 can monitor the leakage current detector circuit 9060 to determine which ports are receiving monopolar output, as is described above, and then control the relay assembly 9030 accordingly to ensure that only the first port 9020 or the second and third ports 9022, 9024 are coupled to the third amplifier 9006.

Figure 63:
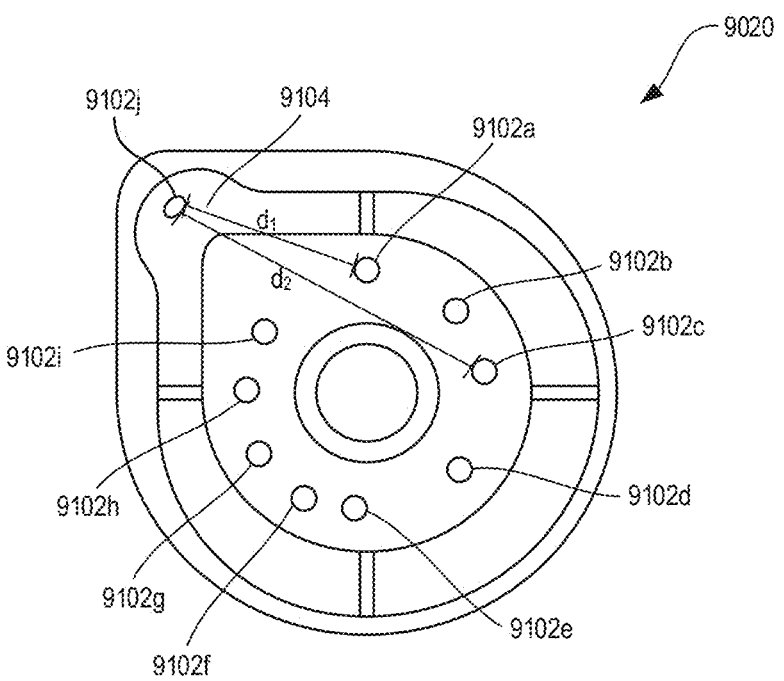
FIG. 63 is a view of an electrical connector port configured to deliver multiple energy modalities, in accordance with at least one aspect of the present disclosure.

As described in various aspects above, the first port 9020 can be configured to deliver a combination of different energy modalities. Accordingly, as illustrated in FIG. 63, the first port 9020 can include a pin arrangement comprising a number of electrical pins or contacts 9102a-j that are positioned to engage with corresponding electrical pins or contacts of a connector that is configured to engage with the port 9020. The electrical contacts 9102a-j are configured to relay the drive signals generated by the energy module 3004 and/or support sensing and communications between the surgical instrument and the energy module 3004. In one aspect, the port 9020 can include an electrical contact that is dedicated to each of the energy modalities that the port 9020 is configured to deliver to a surgical instrument connected thereto. For example, a first contact 9102a can be configured to deliver an ultrasonic drive signal, a second contact 9102c can be configured to deliver a bipolar electrosurgical drive signal, and a third contact 9102j can be configured to deliver a monopolar electrosurgical drive signal to a connected surgical instrument. In various aspects, the first contact 9102a, second contact 9102c, and third contact 9102j can be arranged to prevent electrical interference between the contacts 9102a, 9102c, 9102j. In one aspect, the third contact 9102j can be offset or spaced away from the first and second contacts 9102a, 9102c by a distance sufficient to prevent electrical arcing and shorting that could be caused by the high-voltage, high-crest factor monopolar drive signal. For example, the third contact 9102j can be positioned a distance $d_1$ from the first contact 9102a and a distance $d_2$ from the second contact 9102c. The distances $d_1$ and $d_2$ can be selected to be at least the minimum necessary distances required to prevent electrical arcing and shorting between the contacts 9102a, 9102c, 9102j and/or comply with relevant safety/technical standards, such as IEC 60601.

Surgical Instrument Circuitry

Some electrosurgical instruments may require a large amount of direct current (DC) power for powering particular components or performing particular functions. For example, a surgical instrument may include one or more motors to control articulation, clamp force, blade firing, and other parameters of the instrument. As another example, a surgical instrument may include a high-power light-emitting diode (LED) used to illuminate the body cavity. However, some interfaces between a surgical generator (e.g., an energy module) and the electrosurgical and/or ultrasonic instruments may not support this type of high-power DC output.

In various aspects, the present disclosure provides an electrical energy source configured to deliver energy in two patient domains through the same connector to avoid one powered "hot" device out of two coupled to the same connector. For example, this situation may arise if a device includes two end-effectors extending from a single connector. In this environment, the present disclosure provides isolation techniques that can be employed to deliver a flexible auxiliary power supply for an energy device. The present disclosure further provides various circuits configured to enable delivery of energy from the same port in two patient domains, and to deactivate one of two devices from that port.

In one general aspect, the present disclosure provides a surgical generator (e.g., an energy module) connectable to a surgical instrument. The surgical instrument comprises an end effector to deliver energy to a tissue, the surgical energy module comprising a first high power amplifier, a second high power amplifier, and a control circuit coupled to the first high power amplifier and the second high power amplifier. The control circuit configured to cause the first high power amplifier to power the end effector to deliver energy to the tissue and cause the second high power amplifier to power a secondary function of the surgical instrument.

In another general aspect, the present disclosure provides a surgical energy module connectable to a surgical instrument. The surgical energy module comprises a first circuit configured to provide ultrasonic energy to the surgical instrument, a second circuit configured to provide bipolar electrosurgical energy to the surgical instrument, and a third circuit configured to provide monopolar electrosurgical energy to the surgical instrument. The first circuit, the second circuit, and the third circuit are electrically isolated from each other.

Figure 64:
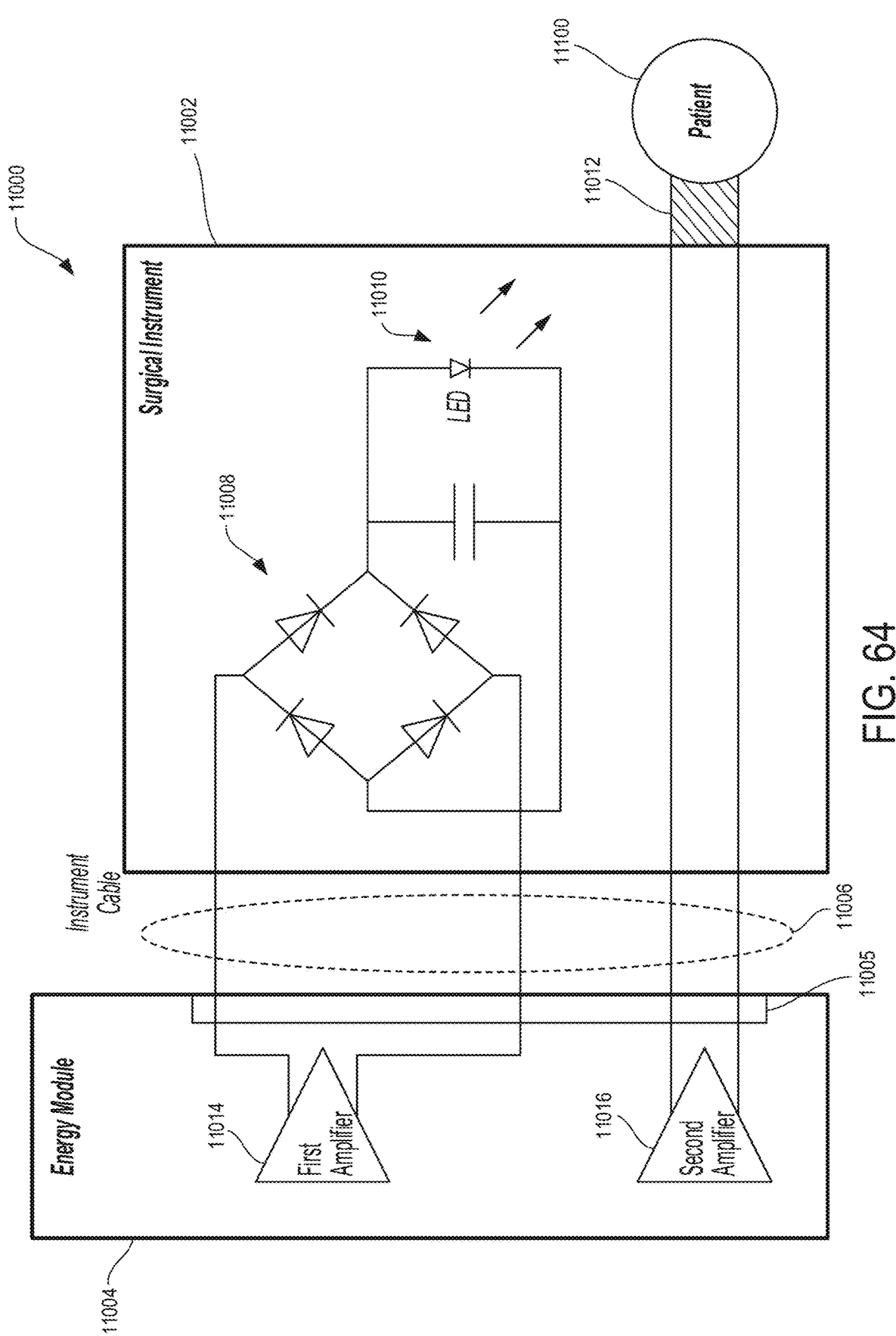
FIG. 64 is a block diagram of a surgical system, in accordance with at least one aspect of the present disclosure.

FIG. 64 is a block diagram of a surgical system 11000 including a surgical instrument 11002 connected to an energy module 11004, such as the various energy modules described in connection with FIGS. 24-37, via a cable assembly 11006. As described above in fuller detail with respect to FIGS. 31-37, the energy module 11004 can be configured to provide multiple different energy modality output or drive signals to a surgical instrument 11002 via a single receptacle 11005, such as the advanced energy receptacle 3100 illustrated in FIGS. 34 and 35. In particular, the energy module 11004 can include various amplifiers 11014, 11016 and associated circuit components for generating drive signals to drive an energy modality deliverable by a connected surgical instrument 11002 for cutting, coagulating, or otherwise therapeutically treating tissue. The generated drive signals can have different frequency ranges according to the energy modality type that the drive signal drives. In one implementation of the energy module 11004, the first amplifier 11014 can include an ultrasonic amplifier and the second amplifier 11016 can include a bipolar or monopolar electrosurgical amplifier. Accordingly, the first amplifier 11014 can be configured to generate an AC drive signal configured to actuate an ultrasonic transducer for driving an ultrasonic blade of the surgical instrument 11002, as described in connection with FIGS. 17 and 18. Accordingly, the second amplifier 11016 can be configured to generate an AC drive signal configured to cause electrodes of the surgical instrument 11002 to deliver electrosurgical RF current to captured tissue, as described in connection with FIG. 19. Additional detail regarding energy module/generator circuit configurations for delivering various combinations of energy modalities can be found in herein.

Although various energy modules 11004 described herein can include multiple amplifier types for driving different energy modalities, not all surgical instruments 11002 connectable to the energy modules 11004 may require the use of the available energy modalities for treating tissue. Accordingly, one or more of the amplifiers may be unused for particular types of surgical instruments 11002. For example, when a bipolar electrosurgical instrument is connected to the energy module 11004, the bipolar amplifier (e.g., the second amplifier 11016) may be utilized for tissue treatment, but the ultrasonic amplifier (e.g., the first amplifier 11014) may be unused for tissue treatment. Such energy modules 11004 present a unique advantage in such situations where the surgical instrument 11002 connected to the energy module 11004 does not require the use of each of the amplifiers at any given time during a surgical procedure. Namely, the one or more amplifiers that are not presently in use for therapeutically treating tissue can be utilized by the surgical instrument 11002 as secondary power sources for powering other components and/or functions of the surgical instrument 11002.

In one aspect, a surgical instrument 11002 can be configured to utilize drive signals provided from the energy module 11004 to alternatively drive or power non-therapeutic energy application functions or components of the surgical instrument 11002. For example, the surgical instrument 11002 may be configured to utilize an energy modality that is driven by the second amplifier 11016 (e.g., RF electrosurgical energy) but not an energy modality that is driven by the first amplifier 11014 (e.g., ultrasonic energy). In one aspect, the surgical instrument 11002 can include circuitry configured to utilize the amplifier(s) driving energy modalities that the surgical instrument 11002 is not configured to deliver as a DC power source. In the illustrated aspect, the surgical instrument 11002 includes a rectifier 11008 (e.g., a full-wave rectifier) that is configured to convert the AC drive generated by the first amplifier 11014 into an output DC voltage. The surgical instrument 11002 can include various additional hardware and/or software (e.g., a filter or a voltage regulator) for processing or smoothing the output of the rectifier 11008. The output DC voltage can then be utilized to power various components or functions of the surgical instrument 11002, such as a light source 11010 (e.g., an LED). The light source 11010 can be positioned on the surgical instrument 11002 for illuminating the body cavity of the patent on which the surgical procedure is being performed, for example. In various aspects, the converted drive signal can be utilized to provide auxiliary power to the surgical instrument 11002 for a variety of different applications, including nerve stimulation (e.g., powering a waveform generator configured to generate signals of a predetermined frequency for stimulating nerves), powering electromechanical components of the surgical instrument 11002 (e.g., a motor) or other loads associated with the surgical instrument 11002 (e.g., a light source 11010), powering a processor or control circuit implementing various control algorithms, powering sensors for detecting various parameters (e.g., tissue impedance, temperature, 3D acceleration, clamp arm gap, clamp force, tissue type identification, or critical structure identification), and/or charging a battery of the surgical instrument 11002. In such aspects, the components and/or functions powered by the output DC voltage may be controlled simultaneously with energy delivery by the surgical instrument 11002 driven by the other drive signals generated by the energy module 11004 (e.g., controlling the clamp arm force or controlling the tissue gap as the tissue is therapeutically treated). The remaining amplifiers of the energy module 11004 to which the surgical instrument 11002 is electrically coupled through the connection to the receptacle 11005, such as the second amplifier 11016 in the particular implementation in FIG. 64, can be utilized as normal to deliver the driven energy modality through the end effector 11012 to therapeutically treat tissue of the patient 11100 during a surgical procedure.

In an alternative aspect, the cable assembly 11006, rather than the surgical instrument 11002, can include circuitry disposed therein that is configured to convert drive signals provided from the energy module 11004 to an alternative form suitable for driving or powering non-therapeutic energy application functions or components of the surgical instrument 11002. For example, the cable assembly 11006 can include a rectifier 11008 that is configured to convert the AC drive generated by the first amplifier 11014 into an output DC voltage. Accordingly, the cable assembly 11006 can receive drive signals generated by the energy module 11004 through its connection to the receptacle 11005, convert one or more of the drive signals into an output DC voltage, and then provide the output DC voltage to the surgical instrument 11002 to which it is connected for various applications, which are described above.

Although FIG. 64 depicts the surgical instrument 11002 as including a single rectifier 11008, the surgical instrument 11002 and/or cable assembly 11006 can, in one aspect, include multiple rectifiers for converting multiple different drive signals generated by the energy module 11004 into DC output voltages. These DC outputs voltages can power the same or different components and/or functions of the surgical instrument 11002. Further, the multiple rectifiers can be configured to convert the same or different drive signals generated by the energy module 11004. For example, the surgical instrument 11002 and/or cable assembly 11006 can include a first rectifier configured to convert a first drive signal generated by the first amplifier 11014 to a first output DC voltage and a second rectifier configured to convert a second drive signal generated by the second amplifier 11016 to a second output DC voltage. The surgical instrument 11002 can be configured to utilize the first and second output DC voltages to power the same or different components of the surgical instrument 11002.

In some aspects, the surgical instrument 11002 may be configured to utilize only one or less than all of the energy modalities that the energy module 11004 is configured to drive through the receptacle 11005. For example, the surgical instrument 11002 illustrated in FIG. 59 may only be configured to utilize the energy modality driven by the drive signal from the second amplifier 11016, despite the fact that the energy module 11004 is also capable of driving a second energy modality via the drive signal from the first amplifier 11014. In one particular implementation, the surgical instrument 11002 may be configured to only deliver bipolar electrosurgical energy driven by the second amplifier 11016, despite the fact that the energy module 11004 is also configured to deliver ultrasonic energy by the first amplifier 11014 through the receptacle 11005, for example. In such aspects, the surgical instrument 11002 and/or cable assembly 11006 can be configured to automatically or inherently convert the unused drive signal(s) to DC output voltage(s). In other aspects, the surgical instrument 11002 and/or cable assembly 11006 can further be configured to selectively convert the drive signal(s) generated from one or multiple amplifiers 11014, 11016 of the energy module 11004 based upon whether the surgical instrument 11002 is actively applying the particular energy modalities. For example, the surgical instrument 11002 can include a control circuit, such as a microcontroller 461 (FIG. 12), that is configured to determine whether an energy modality driven by one of the amplifiers 11014, 11016 of the energy module 11004 is actively being utilized or delivered by the surgical instrument 11002 (e.g., being applied through the end effector 11012 to therapeutically treat tissue of the patient 11100). If the energy modality is not actively being utilized by the surgical instrument 11002, the control circuit can be configured to reroute the drive signal received from the particular amplifier (e.g., the first amplifier 11014) to a rectifier (e.g., the rectifier 11008) to convert the drive signal to a DC output voltage for powering an alternative component and/or function of the surgical instrument 11002. The control circuit can be further configured to reverse the rerouting of the drive signal through the rectifier and, once again, drive the energy modality in response to sensed conditions and/or controls by the user or an external system. In this way, the surgical instrument 11002 can be configured to dynamically reroute unused energy supplied by the energy module 11004 depending on which particular energy modalities are in use at any given time.

Energy Module Electrical Grounding

In various aspects, an end user is permitted to assemble any suitable number of modules into a variety of different stacked configurations that support electrical energy flow therebetween. The modular energy system is assembled or is modified by an end user either prior to or during a surgical procedure. Since the manufacturer is not involved with the final assembly of a modular energy system, suitable precautions are taken to ensure proper electrical grounding of an assembled modular energy system and/or alignment of modules within the modular energy system.

In various aspects, accessible metal in the modular energy system is either protectively earthed or separated from live circuits to ensure user safety. This requirement is especially necessary in instances where secondary circuits are referenced to module chassis ground. Further, the protective earth connections between the modules of a modular energy system must meet the stringent International Electrotechnical Commission ("IEC") 60601 maximum impedance requirements.

In one general aspect, the present disclosure provides a grounding arrangement for a modular energy system comprising an independent bridge connector between the modules of the modular energy system and grounds that come into contact with each other prior to the bridge connection.

In another general aspect, the present disclosure provides a surgical system that comprises a first surgical module and a second surgical module. The first surgical module comprises a first enclosure comprising a bottom surface, a grounding foot extending from the bottom surface a first distance, and an insulating foot extending from the bottom surface a second distance, wherein the second distance is greater than the first distance. The second surgical module comprises a second enclosure comprising a top surface, a first receiving pocket defined in the top surface, wherein the first receiving pocket comprises a first base that is positioned a third distance from the top surface, and wherein the first receiving pocket is configured to receive the grounding foot from the first surgical module, and a second receiving pocket defined in the top surface, wherein the second receiving pocket comprises a second base that is positioned a fourth distance from the top surface, wherein the fourth distance is greater than the third distance, and wherein the second receiving pocket is configured to receive the insulating foot from the first surgical module. Further, when the grounding foot is positioned in the first receiving pocket and the insulating foot is positioned in the second receiving pocket, the grounding foot contacts the first base of the first receiving pocket and the insulating foot does not contact the second base of the second receiving pocket.

In another general aspect, the present disclosure provides a surgical system that comprises a first surgical module and a second surgical module. The first surgical module comprises a first enclosure comprising a bottom surface, a grounding foot extending from the bottom surface a first distance, and an insulating foot extending from the bottom surface a second distance, wherein the second distance is greater than the first distance. The second surgical module comprises a second enclosure comprising a top surface, a first receiving pocket defined in the top surface, wherein the first receiving pocket comprises a first base that is positioned a third distance from the top surface, and wherein the first receiving pocket is configured to receive the grounding foot from the first surgical module, and a second receiving pocket defined in the top surface, wherein the second receiving pocket comprises a second base that is positioned a fourth distance from the top surface, wherein the fourth distance is greater than the third distance, and wherein the second receiving pocket is configured to receive the insulating foot from the first surgical module. Further, when the grounding foot is positioned in the first receiving pocket and the insulating foot is positioned in the second receiving pocket, the grounding foot contacts the first base of the first receiving pocket and the insulating foot does not contact the second base of the second receiving pocket.

In another general aspect, the present disclosure provides a surgical platform that comprises a first surgical module and a second surgical module. The first surgical module is configured to be assembled in a stack configuration with the second surgical module. The first surgical module comprises a first bridge connector portion comprising first electrical connection elements and a first enclosure. The second surgical module comprises a second bridge connector portion and a metal contact attached to the outer housing. The second bridge connector portion comprises second electrical elements and an outer housing extending at least partially around the second electrical elements. The metal contact is configured to engage the enclosure of the first surgical module during assembly before the second electrical connection elements of the second bridge connector portion engage the first electrical connection elements of the first bridge connector portion.

Figure 65:
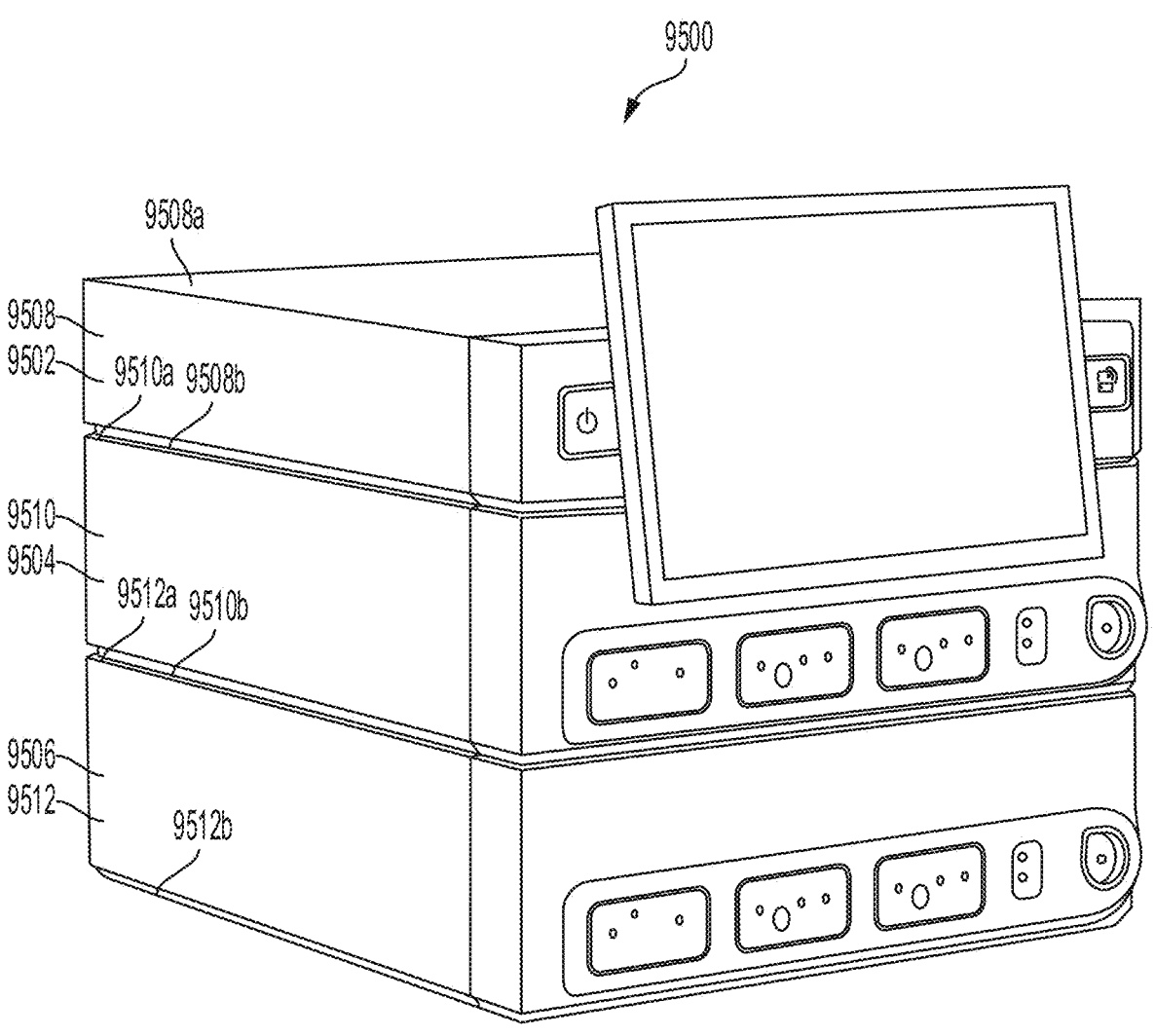
FIG. 65 is perspective view of a modular energy system, in accordance with at least one aspect of the present disclosure.

Referring to FIG. 65, three surgical modules, a first module 9502, a second module 9504, and a third module 9506, are assembled together in a stacked configuration by an end user to form a modular energy system 9500. Each module 9502, 9504, 9506, can be the same type of surgical module or different types of surgical modules. For example, each module 9502, 9504, 9506 can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGI-CAL HUBS and MODULAR ENERGY SYSTEM. As illustrated in FIG. 65, the first module 9502 is a header module, the second module 9504 is a generator module, and the third module 9506 is a generator module.

Each module 9502, 9504, 9506 can comprise an enclosure that can be made of a conductive material, such as metal. For example, the first module 9502 can comprise an enclosure 9508 comprising a top surface 9508a and a bottom surface 9508b. The second module 9504 can comprise an enclosure 9510 comprising a top surface 9510a and a bottom surface 9510b. The third module 9506 can comprise an enclosure 9512 comprising a top surface 9512a and a bottom surface 9512b. Each module 9502, 9504, 9506, can comprise secondary circuits that are referenced to module chassis ground via the respective enclosure 9508, 9510, 9512.

Each module 9502, 9504, 9506 can be configured to be assembled in a stacked configuration with an adjacent module to form the modular energy system 9500. For example, the bottom surface 9508b of the enclosure 9508 of the first module 9502 can be configured to engage the top surface 9510a of the enclosure 9510 of the second module 9504. The bottom surface 9510b of the enclosure 9510 of the second module 9504 can be configured to engage the top surface 9512a of the enclosure 9512 of the third module 9506. In various aspects, the modular energy system 9500 includes an additional surgical module or surgical modules or the modular energy system 9500 may not include one of the modules 9502, 9504, 9506.

In various aspects, to electrically ground a modular energy system, such as modular energy system 9500, multiple points of contact are established between adjacent modules to achieve a common ground. Thus, regardless of the stacked configuration of the modular energy system 9500, electrical grounding can be maintained throughout the entire modular energy system 9500. For example, an upper module stacked on top of a lower module can be grounded through the lower module in order to achieve the common ground or a lower module can be grounded through the upper module. For example, the first module 9502 can be grounded through the second module 9504 and the second module 9504 can be grounded through the third module 9506; thereby, a common ground is achieved in the modular energy system 9500. Thus, grounding of one of the modules 9502, 9504, 9506 can ground all of the modules 9502, 9504, 9506. Additionally, the multiple points of contact can facilitate efficient assembly of the stacked configuration of the modular energy system 9500 and the multiple points of contact can ensure that the modular energy system 9500 will maintain its configuration when experiencing external forces.

Figure 66A:
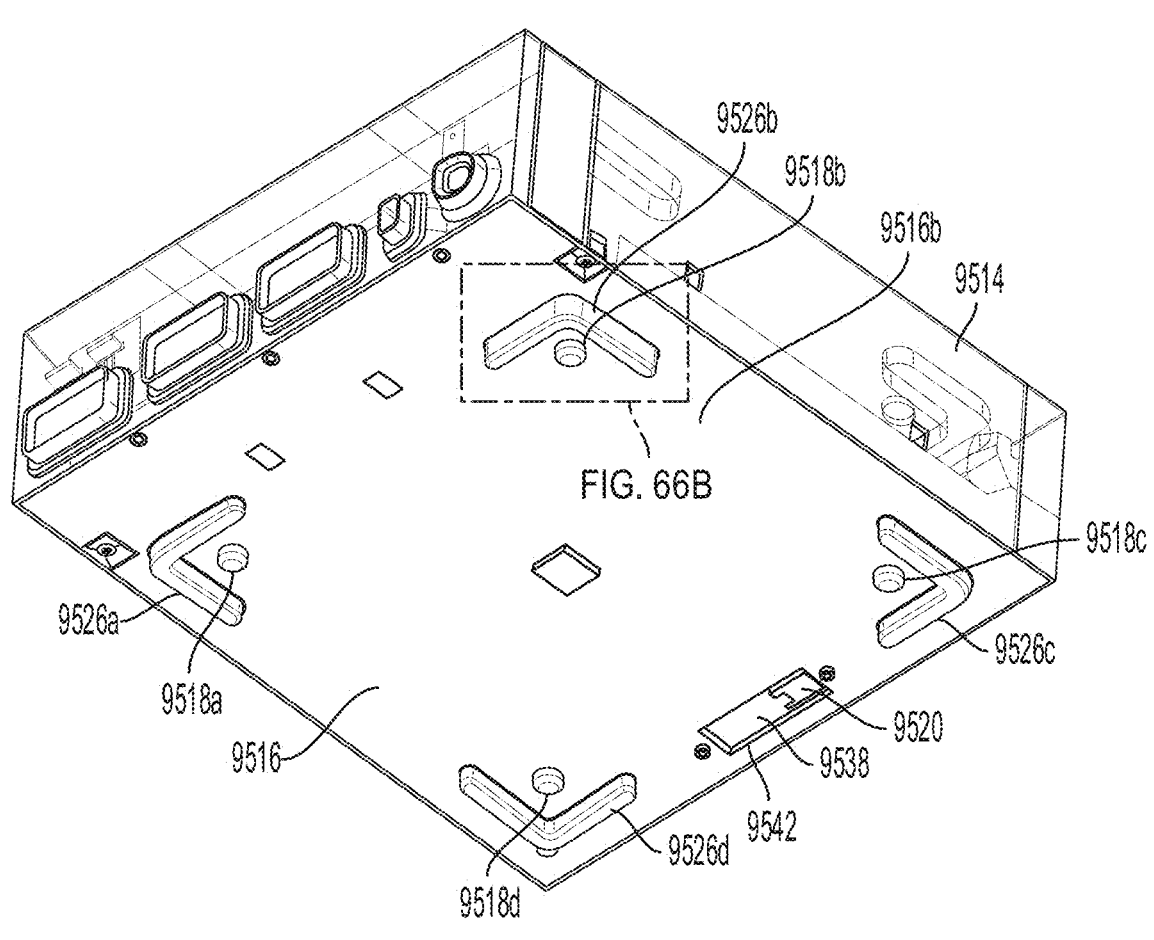
FIG. 66A is a bottom perspective view of a module of the modular energy system of FIG. 65.

Referring now to FIG. 66A, a bottom surface 9516b of an enclosure 9516 of a surgical module 9514 enclosure is shown. Module 9514 is representative of modules 9502, 9504, and 9506. The bottom surface 9516b of the enclosure 9516 can include one or more grounding features, such as, for example, two or more grounding features, three or more ground features, or four or more ground features. For example, as illustrated, the bottom surface 9516b can comprise four grounding features 9518a-d sized and spaced apart, such that the grounding features 9518a-d may engage grounding features of a separate module, thus providing direct contact between the modules at multiple points. The contact can ensure that a common ground is achieved between modules and that the module 9514 can maintain its position relative to a mating module when experiencing external forces.

The bottom surface 9516b of the enclosure 9516 comprises an opening 9542 that is shaped and configured to mount a bridge connector portion 9520 (e.g., a female bridge connector portion). The bridge connector portion 9520 includes a recess 9538 that is shaped and configured to receive a bridge connector portion (e.g., male bridge connector portion) from a separate module.

Figure 67:
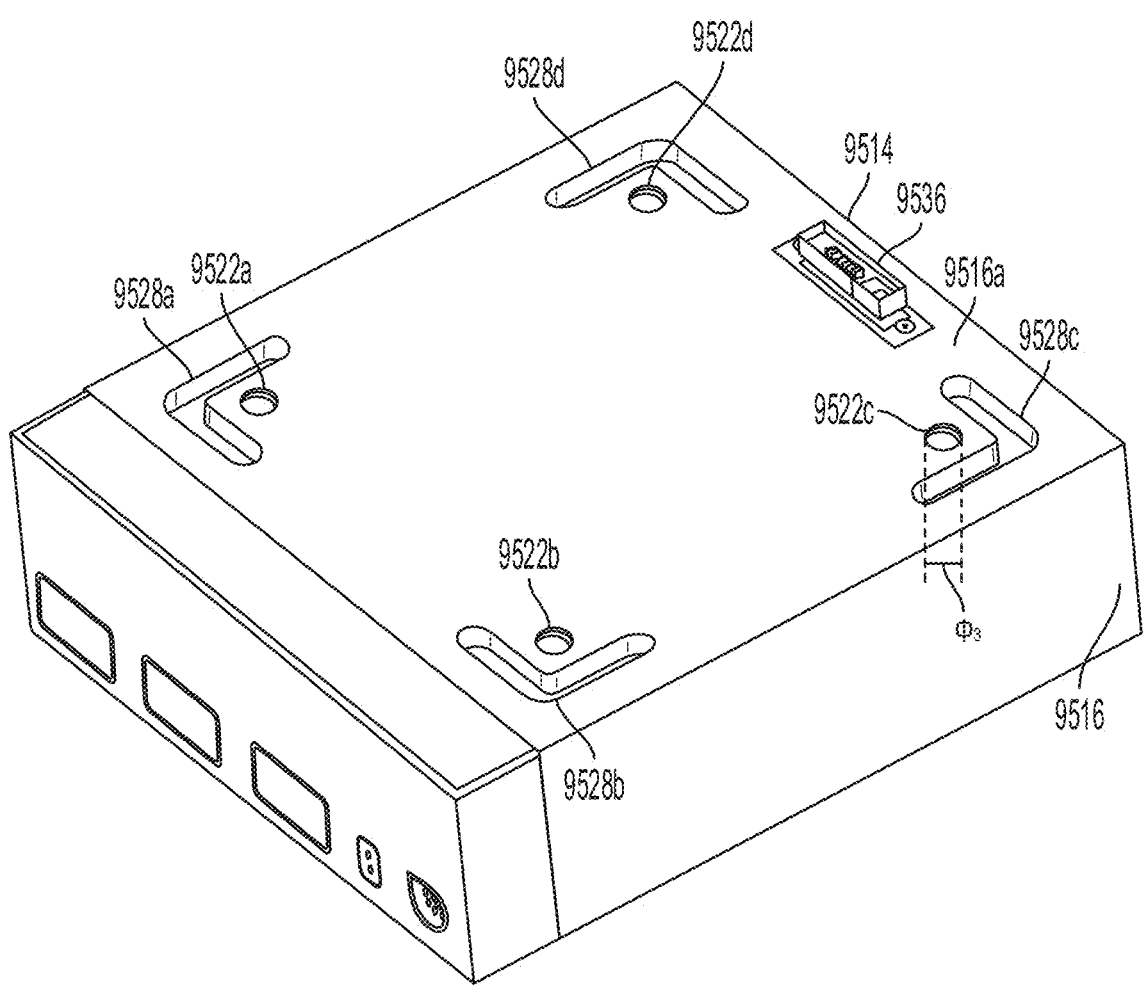
FIG. 67 is a top perspective view of a module of the modular energy system of FIG. 65.

Referring now to FIG. 67, a top surface 9516a of the enclosure 9516 of the module 9514 is shown. The top surface 9516a of the enclosure 9516 can include one or more grounding features, such as, for example, two or more grounding features, three or more grounding features, or four or more grounding features. For example, as illustrated, the top surface 9516a can comprise four grounding features 9522a-d. The grounding features 9522a-d on the top surface 9516a are sized and spaced apart such that the grounding features 9522a-d may engage grounding features of a separate module, thus providing direct contact between the modules at multiple points. The contact can ensure that a common ground is achieved between the modules and that the module 9514 can maintain its position relative to the mating module when experiencing external forces.

A bridge connector portion 9536 (e.g., a male bridge connector portion) is mounted to the top surface 9516a of the enclosure 9516 of the module 9514 and extends away from the module 9514. When an upper module is stacked on top of the module 9514, the bridge connector portion of the module 9514 is inserted into the recess of a female bridge connector portion of the upper surgical module, thereby establishing electrical and/or signal communication between the modules and/or alignment between the modules. In an alternative configuration where a male bridge connector portion is on the bottom surface of an upper module and the female connector portion is on the top surface of a lower module, when the upper module is stacked on top of the lower module, the male bridge connector portion of the upper module is inserted into the recess of the female bridge connector portion of the lower module, thereby establishing electrical and/or signal communication between the modules and/or alignment between the modules.

Figure 70:
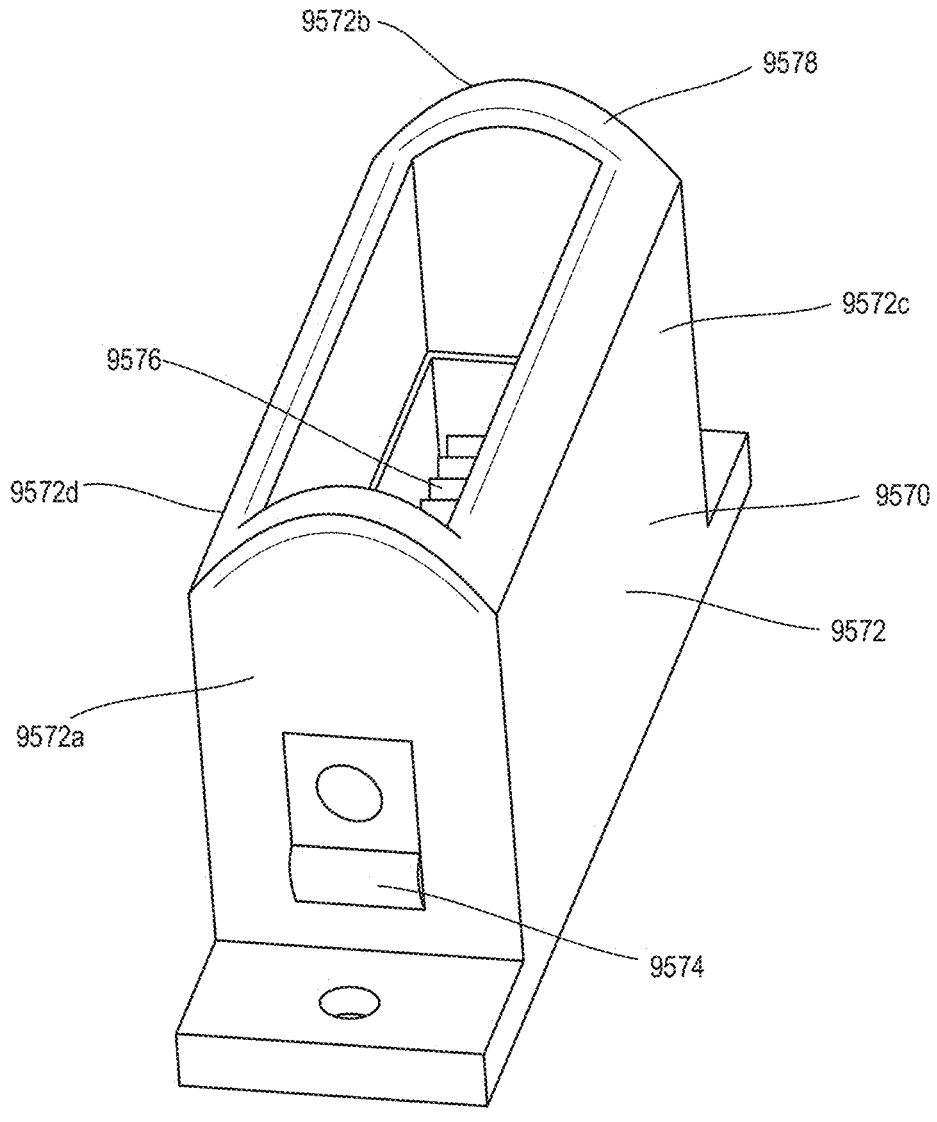
FIG. 70 illustrates a male bridge connector portion comprising a grounding feature of a modular surgical module, in accordance with at least one aspect of the present disclosure.

In various aspects, the bridge connector portion 9536 can comprise a grounding feature configured to achieve a common ground between modules. For example, referring to FIG. 70, a male bridge connector portion 9570, including a grounding feature 9574 attached to an outer housing 9572 of the male bridge connector portion 9570, is shown. The outer housing 9572 extends at least partially around the electrical connection elements 9576. The outer housing 9572 is rectangular and rounded along the length of the outer housing 9572. The outer housing 9572 includes rounded or curved-top faces 9578 that allow male and female bridge connector portions to align even when modules are at a difficult angle with another. In other words, the outer housing 9572 is shaped and/or sized to guide the electrical connection elements 9576 and grounding feature 9574 into a properly aligned engagement with a female bridge connector. The grounding feature 9574 is attached to a first side 9572a of the outer housing 9572 and is in electrical communication with an enclosure of a respective module and/or a ground of the respective module. In various aspects, another grounding feature (not shown) is attached to the second side 9572b of the outer housing 9572 and is in electrical communication with the enclosure of the respective module and/or the ground of the respective module. In various aspects, the first side 9572a and the second side 9572b are shorter than a third side 9572c and a fourth side 9572d of the outer housing 9572. The grounding feature 9574 can comprise a metal contact, such as, for example, a springing contact.

When an upper module is stacked on top of a lower module comprising the male bridge connector portion 9570 on a top surface of the lower module, the male bridge connector portion 9570 is inserted into the recess of a female bridge connector on the bottom surface of the upper surgical module. Upon insertion, the grounding feature 9574 can engage the enclosure of the upper surgical module. For example, the male bridge connector portion 9570 can be inserted into the recess 9538 of the module 9514 in FIG.

66A. Upon insertion, the grounding feature 9574 can directly contact the enclosure 9516 near the opening 9542 thereby achieving a common ground between a surgical module comprising the male bridge connector portion 9570 and the module 9514.

Further, the outer housing 9572 of the male bridge connector portion 9570 is shaped and/or sized to guide the grounding feature 9574 into direct contact with the enclosure of a separate module. In aspects where the grounding feature 9574 is a springing contact, the springing contact is transitioned into a biased configuration responsive to direct contact with the enclosure of the separate module. The springing contact can ensure that a proper common ground is achieved between modules.

Further, the grounding feature 9574 can be configured to engage the enclosure of a separate module during assembly before the electrical connection elements 9576 of the male bridge connector portion 9570 engage electrical connection elements of a bridge connector portion on the separate module. That is, the grounding feature 9574 can be positioned on the outer housing 9572 relative to the electrical connection elements 9576 such that the grounding feature 9574 will engage the enclosure of the separate module during assembly before the electrical connection elements 9576 of the male bridge connector portion 9570 engage the electrical elements of a bridge connector portion on the separate module. Therefore, a common ground can be achieved between modules prior to engagement of the bridge connector portions that can ensure user safety.

In addition to the grounding feature 9574 or alternatively to the grounding feature 9574, direct contact between the grounding features on a top surface of an enclosure of a lower module and the grounding features on the bottom surface of an enclosure of an upper module stacked on top of the lower module function to ground the upper module to the lower module, thereby providing multiple points of contact to maintain a path of least resistance (e.g., electrical resistance between modules). When the upper module is stacked on top of a lower module, the weight of the upper module maintains the grounding features on bottom surface of the upper module in electrical communication with the grounding features on the top surface of the lower module.

Furthermore, the grounding features 9518a-d and 9522a-d of the module 9514 can be arranged in a spread configuration to maintain a path of least resistance between surgical modules in the stacked configuration. For example, the grounding features 9518a-d can be spaced apart near the four corners of the bottom surface 9516b of the enclosure 9516 and the ground features 9522a-d can be spaced apart near the four corners of the top surface 9516a of the enclosure 9516. That is, the bottom surface 9516b can comprise one of grounding features 9518a-d at each corner, and the top surface 9516a can comprise one of grounding features 9522a-d at each corner. The positions of the grounding features 9518a-d on the bottom surface 9516b can mirror the positions of the grounding features 9522ad on the top surface 9516a, thereby providing stability to the stacked configuration.

The grounding features 9518a-d and 9522a-d can be molded into the enclosure 9516, or the grounding features 9518a-d and 9522a-d can be fastened to the enclosure. For example, the grounding features 9518a-d and 9522a-d can be at least one of a receiving pocket molded in the enclosure 9516, a grounding foot molded in the enclosure 9516, a conductive pin fastened to the enclosure 9516, or a conductive socket fastened to the enclosure 9516.

In various aspects, the grounding features 9518a-d extend away from the bottom surface 9516b of the enclosure 9516 and the module 9514 (e.g., form grounding feet) and are sized and spaced apart such that the grounding features 9518a-d may be received by receiving pockets of a separate module, thus providing direct contact between the modules in four distinct places. Further, in various aspects, the grounding features 9522a-d are configured as receiving pockets and are sized and spaced apart such that grounding feet of a separate surgical module can be seated into the grounding features 9522a-d, thus providing direct contact between the surgical modules in four distinct places. The direct contact can achieve a common ground, provide a path of least resistance, and maintain position of the module 9514 when experiencing external forces.

Figure 66B:
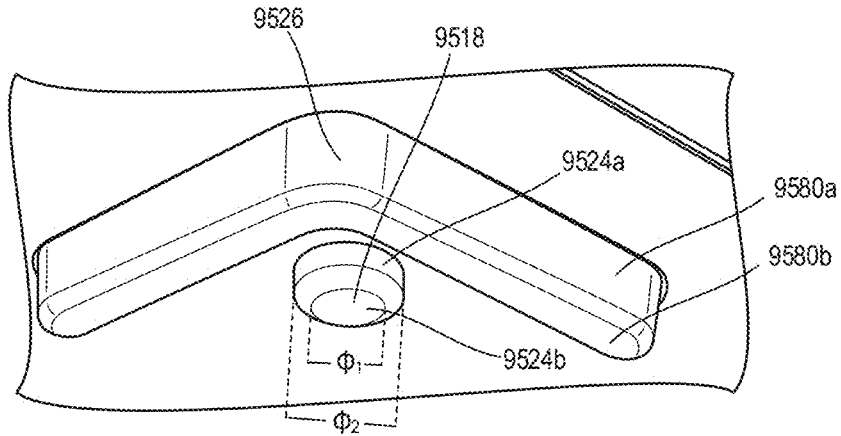
FIG. 66B is a close-up of the module of FIG. 66A.

The grounding features 9518a-d can have various shapes, such as, for example, circular, as illustrated in FIGS. 66A-B. A detailed view of a single grounding feature 9518 of grounding features 9518a-d can be seen in FIG. 66B. A base portion 9524a of the grounding feature 9518 can have a first diameter, $\phi_1$. The grounding feature 9518 can taper inwardly from the base portion 9524a to form a seating portion 9524b of the grounding feature 9518. The taper can facilitate alignment of the modules during assembly. The seating portion 9524b can have a second diameter, $\phi_2$, which is smaller than the first diameter, $\phi_1$, of the base portion 9524a. The seating portion 9524b can be configured to be seated in a receiving pocket of a top surface of an enclosure of a separate module.

Similarly, the grounding features 9522a-d can have various shapes, such as, for example, circular, as illustrated in FIG. 67. The grounding features 9522a-d can each comprise a third diameter, $\phi_3$, near the top surface 9516a, which can be sized to receive grounding feet on a bottom surface of an enclosure of a separate module and/or engage conductive posts on the bottom surface. For example, the third diameter, $\phi_3$, of the grounding features 9522a-d can be larger than the second diameter, $\phi_2$, of the seating portion 9524b of the grounding features 9518a-d. It is contemplated that the grounding features 9518a-d and 9522a-d can be of other shapes and sizes.

In aspects comprising grounding feet extending from the bottom surface of a module, the arrangement of the grounding features can leave the grounding features of the lowest/bottom module in a stacked arrangement of a modular energy system without corresponding receiving pockets in a separate module. One possible, albeit expensive, solution is to especially design a module to function as the lowest/bottom module in the stacked configuration of the modular energy system. However, an end user may mistakenly attempt to assemble this especially designed module in an intermediate position in the stacked configuration of the modular energy system, potentially leaving the grounding features of lowest/bottom module in the stacked configuration exposed. Moreover, when a series of modules are assembled together to form the stacked configuration of the modular energy system, it is envisioned that the stacked modular energy system is rested upon a flat surface, such as, for example, a cart, a table, or the like. Positioning the grounding features against such flat surfaces can be problematic. Further, it is desirable that any module from the stacked modular energy system be capable of being positioned in the lowest/bottom position in the stacked configuration without having to worry about achieving a specific arrangement of the modular energy system. Enabling agnostic positioning of the modules can facilitate ease of assembly of the modular energy system.

FIGS. 66A-B and 67 present a solution to the above-raised issues that account for when a surgical module is positioned on the lowest/bottom position (e.g., the third module 9506 in FIG. 65) in the stacked configuration of the modular energy system 9500 and rests on a flat surface. In various aspects, the bottom surface 9516b of the enclosure 9516 further includes an insulated foot or insulated feet. For example, referring again to FIG. 66A, the bottom surface 9516b includes four insulated feet 9526a-d extending from the bottom surface 9516b of the enclosure 9516. The insulated feet 9526a-d are configured to electrically isolate the enclosure 9516 from the flat surface and/or maintain position of the module 9514 relative to the flat surface when experiencing external forces. The grounding features 9518a-d extend from the bottom surface 9516b of the enclosure 9516 a first distance, $d_1$, and the insulated feet 9526a-d extend from the bottom surface 9516b of the enclosure 9516 a second distance, $d_2$, such that when the module 9514 is positioned on the lowest/bottom position in the stacked configuration of the modular energy system 9500, the grounding features 9518a-d do not rest on the flat surface. The insulated feet 9526a-d rest on the flat surface and can prevent the grounding features 9518a-d from engaging the flat surface.

The insulated feet 9526a-d can electrically isolate the enclosure 9516 from the flat surface. For example, the insulated feet 9526a-d can comprise an insulating material, such as rubber. It is contemplated that other insulating materials can be utilized to form the insulating feet 9526a-d. Additionally, the material of the insulated feet 9526a-d can be selected to create friction between the module 9514 and the flat surface in order to maintain the position of the module 9514 relative to the flat surface when experiencing external forces.

The insulated feet 9526a-d can be spaced apart in a spread configuration to provide stability to the module 9514 and/or surgical modules stacked on top of the module 9514. For example, the insulated feet 9526a-d can be spaced apart near the four corners of the bottom surface 9516b of the enclosure 9516. For example, one insulated foot of the insulated feet 9526a-d can be positioned in each corner of the bottom surface 9516b. The quantity of insulated feet 9526a-d can correspond to the quantity of grounding features 9518a-d.

The insulated feet 9526a-d can have various shapes, such as, for example, as illustrated in FIGS. 66A-B. The insulated foot 9526 can taper inwardly from a base portion 9580a to form a seating portion 9580b of the insulated foot 9526. The taper can facilitate alignment of the modules during assembly. The seating portion 9580b can be configured to be seated in a receiving pocket of a top surface of an enclosure of a separate module.

Each insulated foot 9526a-d can be configured in an "L" shape. For example, in FIG. 66B, the "L" shaped configuration of a single insulated foot 9526 of the insulated feet 9526a-d is shown. Referring to back FIG. 66A, the "L" shape configuration of the insulated feet 9526a-d can provide mechanical stability when the module 9514 is placed on top of the flat surface, ensuring that the module 9514 will maintain its position when experiencing external forces. It is contemplated that the insulated feet 9526a-d can be of other shapes and sizes.

In various aspects, the top surface 9516a of the enclosure 9516 further includes one or more receiving pockets sized and configured for receiving an insulated foot or insulated feet of a separate surgical module, such that the grounding features of the respective modules can directly contact to achieve a common ground. For example, referring again to FIG. 67, the top surface 9516a of the enclosure 9516 includes four insulated feet receiving pockets 9528a-d. The receiving pockets 9528a-d can be spaced apart in a spread configuration to align the module 9514 with the separate module. For example, the receiving pockets 9528a-d are spaced apart such that the insulated feet of a separate module will be positioned within the receiving pockets 9528a-d when the separate module is stacked on top of the module 9514. As illustrated in FIG. 67, the receiving pockets 9528a-d are spaced apart near the four corners of the top surface 9516a of the enclosure 9516. For example, one of the receiving pockets 9528a— d is positioned in each corner of the top surface 9516a of the enclosure 9516. The receiving pockets 9528a-d are sized and configured to receive insulated feet of a separate module.

The receiving pockets of the grounding features 9522a-d of the top surface 9516a of the module can each include a base that is positioned a third distance, $d_3$, from the top surface 9516a. In various aspects, the third distance, $d_3$, is less than or equal to the first distance, $d_1$, such that grounding feet of a separate module can contact the base of the receiving pockets of the grounding features 9522a-d. The receiving pockets 9528a-d each include a base that is positioned a fourth distance, $d_4$, from the top surface 9516a. In various aspects, the fourth distance, $d_4$, is greater than the second distance, $d_2$, such that the insulated feet of a separate module can be received by the receiving pockets 9528a-d.

Figure 68:
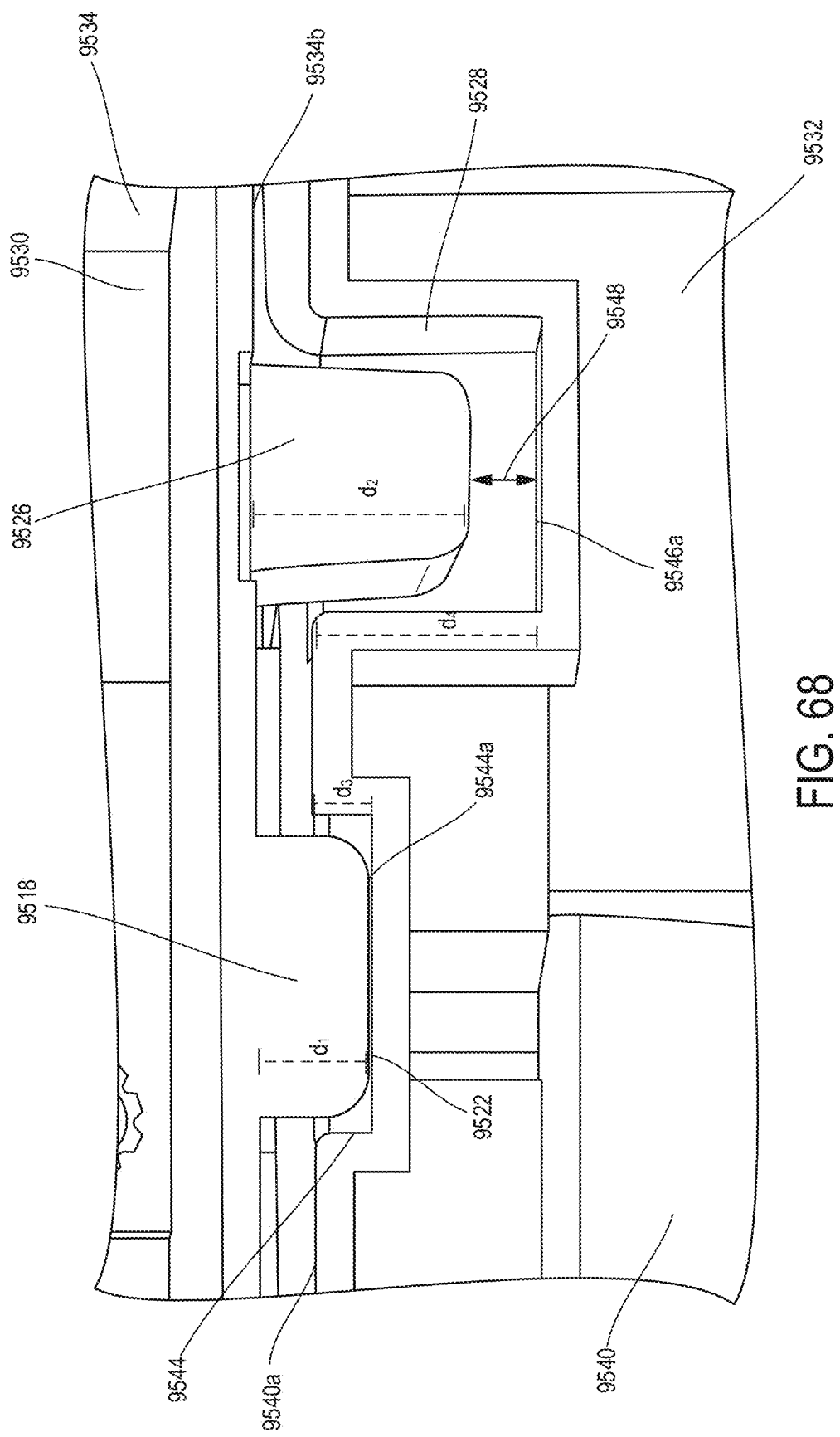
FIG. 68 is a cross-sectional view of an upper module seated onto a lower module of a modular energy system, in accordance with at least one aspect of the present disclosure.

FIG. 68 illustrates a cutaway view of a portion of an upper surgical module 9530 stacked on top of a lower surgical module 9532. The upper module 9530 and the lower module 9532 can be the same type of module or different types of modules. An insulated foot 9526 representative of insulated feet 9526a-d, a grounding feature 9518 representative of the grounding features 9518a-d, a grounding feature 9522 representative of grounding features 9522a-d, and an insulated foot receiving pocket 9528 representative of receiving pockets 9528a-d are shown in FIG. 68. The upper module 9530 includes the grounding feature 9518 and the insulated foot 9526 extending from the bottom surface 9534b of the enclosure 9534 of the upper module 9530. The grounding feature 9518 extends from the bottom surface 9534b of the enclosure 9534 of the upper module 9530 a first distance, $d_1$, while the insulated foot 9526 extends from the bottom surface 9534b of the enclosure 9534 of the upper module 9530 a second distance, dz. The second distance, $d_2$, is greater than the first distance, $d_1$. Therefore, if the upper module 9530 is set on a flat surface, the insulated foot 9526 may contact the flat surface prior to the grounding feature 9518 and can prevent the grounding feature 9518 from contacting the flat surface.

The lower module 9532 includes the grounding feature 9522 and the insulated foot receiving pocket 9528 on a top surface 9540a of an enclosure 9540 of the lower module 9532. The grounding feature 9522 comprises a grounding feature receiving pocket 9544 defined in the top surface 9540a. The receiving pocket 9544 is sized and configured to receive the grounding feature 9518 of the upper module 9530. The receiving pocket 9544 includes a base 9544a that is positioned a third distance, $d_3$, from the top surface 9540a. In various aspects, the third distance, $d_3$, is less than or equal to the first distance, $d_1$.

The receiving pocket 9528 is defined in the top surface 9540a of the enclosure 9540 of the lower module 9532. The receiving pocket 9528 is sized and configured to receive the insulated foot 9526 of the upper module 9530. The receiving pocket 9528 includes a base 9546a that is positioned a fourth distance, $d_4$, from the top surface 9540a. As illustrated, the fourth distance, $d_4$, is greater than the second distance, $d_2$.

Owing to the size and configuration of the grounding feature 9518, insulated foot 9526, the grounding feature 9522, and the receiving pocket 9528, when the upper module 9530 is stacked on top of the lower module 9532, the grounding feature 9518 is seated in the receiving pocket 9544 of the ground feature 9522 such that the grounding feature 9518 makes direct contact with the base 9544a of the receiving pocket 9544. While the grounding feature 9518 makes direct contact with the base 9544a, the insulated foot 9526 does not make contact with the base 9546a of the receiving pocket 9528 and a clearance 9548 is defined between the insulated foot 9526 and the base 9546a of the receiving pocket 9528. Thus, the grounding features 9518 and 9522 are in direct contact with each other and a common ground is achieved.

Figure 71:
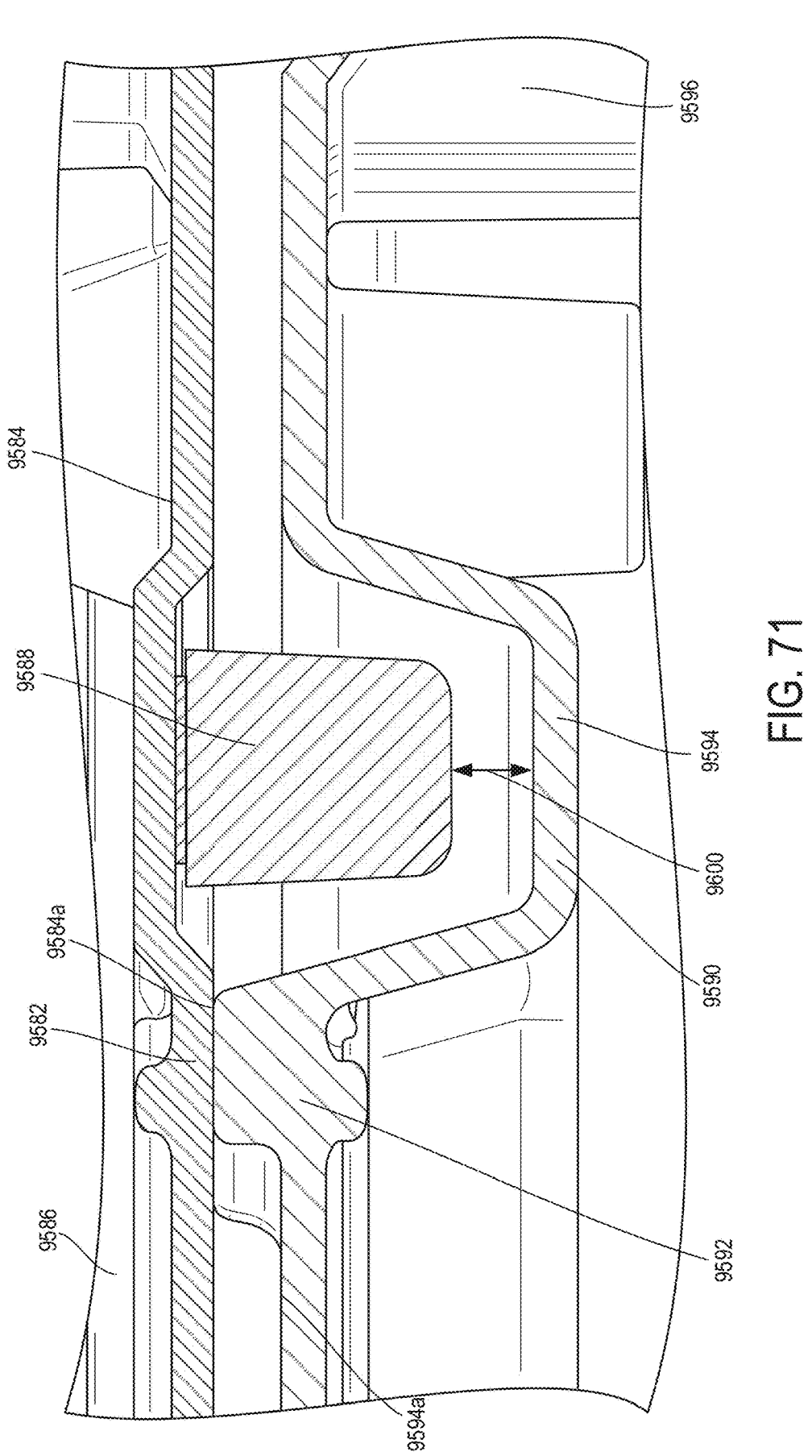
FIG. 71 is a cross-sectional view of an upper module seated onto a lower module of a modular energy system, in accordance with at least one aspect of the present disclosure.

In an alternative configuration, referring to FIG. 71, a grounding feature 9592 can extend away from a top surface 9594a of an enclosure 9594 of a module 9596 (e.g., form grounding feet). Further, in various aspects, a grounding feature 9582 of a bottom surface 9584a of an enclosure 9584 of a separate module 9586 can be configured as a receiving surface, which is sized such that grounding feet of a separate surgical module can be seated onto or otherwise in contact with the grounding features 9592, thus providing direct contact between the surgical modules. The grounding feature 9592 can be a substantially planar surface and may not protrude from the bottom surface 9584a of the enclosure 9584. The module 9596 can comprise a receiving pocket 9590 defined in the top surface 9594a that is sized and configured to receive the insulated foot 9588 of the module 9586. While the grounding feature 9582 makes direct contact with the grounding feature 9592, the insulated foot 9588 does not make contact with the receiving pocket 9590 and a clearance 9600 is defined between the insulated foot 9588 and the receiving pocket 9590.

Accordingly, when an upper module is stacked on top of a lower module to form a stack configuration, the grounding features of the upper module are in direct contact with the grounding features of the lower module and the insulated feet of the upper module are floating in the receiving pockets of the lower module, thereby defining a clearance therebetween. When the lower surgical module is removed from the stack configuration and the upper module is to be positioned on a flat surface, the insulated feet of the upper module make direct contact with the flat surface, while the grounding features of the upper module do not make contact with the flat surface, owing to the insulated feet extending a greater distance from the bottom surface of the enclosure of the upper module than the grounding features.

The above described configuration allows each module to have identical grounding features, insulated feet, and receiving pockets, regardless of the position of the module within the stacked arrangement of a modular energy system, thereby enabling efficient assembly of the modular energy system 9500.

Figures 69A, 69B:
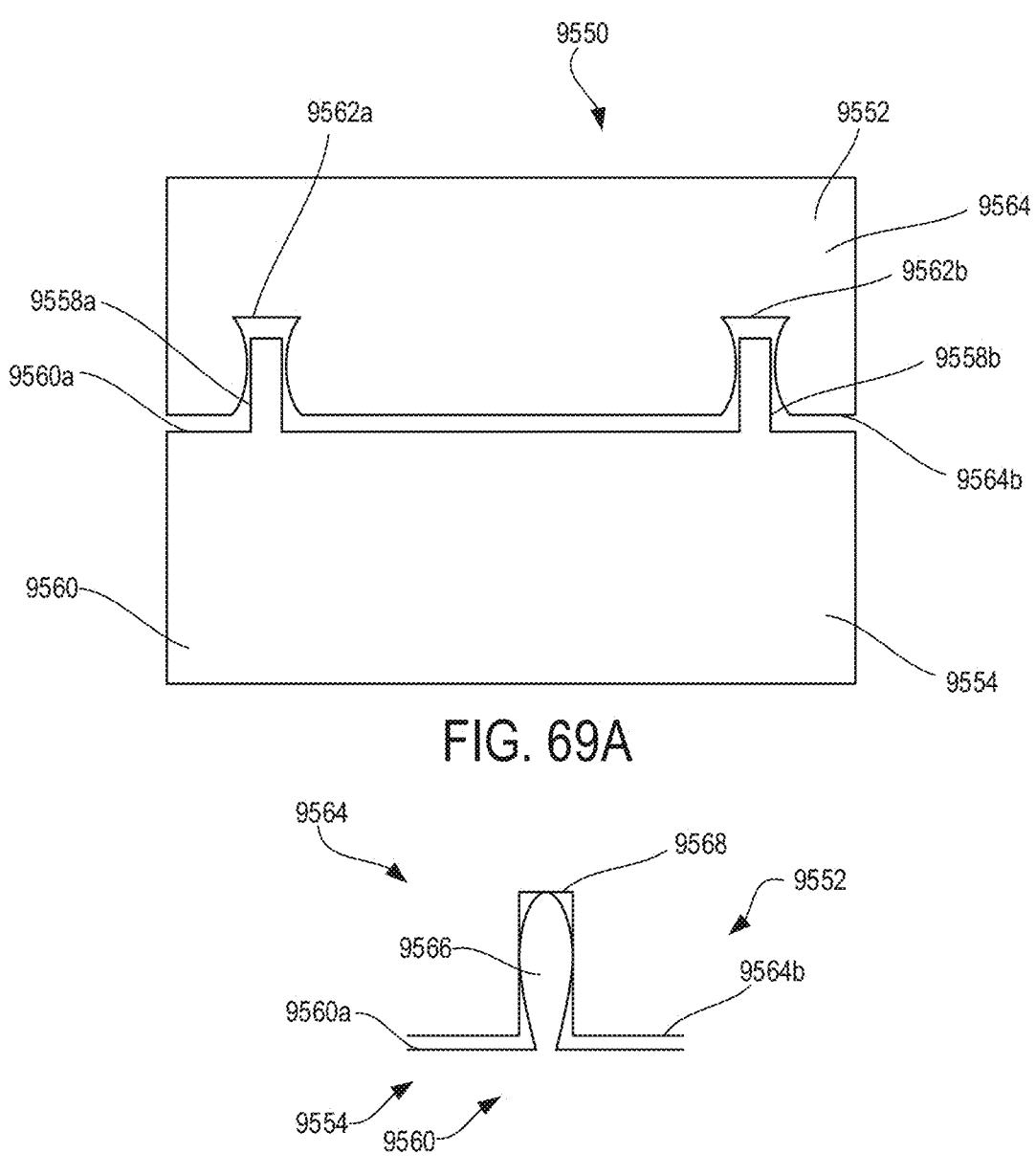
FIG. 69A illustrates an upper module and a lower module of a modular energy system in an assembled configuration, in accordance with at least one aspect of the present disclosure.
FIG. 69B illustrates a post/socket configuration for connecting an upper module and a lower module of a modular energy system, in accordance with at least one aspect of the present disclosure.

Referring to FIGS. 69A and 69B, an upper surgical module 9552 and a lower surgical module 9554 in a stack configuration of a portion of a modular energy system 9550 are shown. The upper module 9552 and the lower module 9554 can be the same type of module or different types of modules.

As illustrated in FIG. 69A, two grounding features 9558a-b of the lower module 9554 are shown. Each grounding feature 9558a-b can individually be configured as a conductive post or a conductive socket. As illustrated, the grounding features 9558*a-b* are configured as conductive posts extending from a top surface 9560*a* of an enclosure 9560 of the of the lower module 9554. In various aspects, conductive posts 9558*a-b* can be integrated into the enclosure 9560 of the lower module 9554 or the conductive posts 9558*a-b* can be fastened to the enclosure 9560 of the lower module 9554. For example, the conductive posts 9558*a-b* can be fastened to the enclosure 9560 of the lower module 9554 with nuts and/or with or without lock washers.

Two grounding features 9562*a-b* of the upper module 9552 are shown. Each grounding feature 9562*a-b* can be individually configured as a conductive post or a conductive socket. As illustrated, the grounding features 9562*a-b* are configured as conductive sockets defined in a bottom surface 9564*b* of an enclosure 9564 of the upper module 9552. When the upper and lower modules 9552, 9554 are in a stacked configuration, the conductive posts 9558*a-b* of the lower module 9554 can be retained in the corresponding conductive socket 9562*a-b* of the upper module 9552.

The post/socket configuration of the modules 9552, 9554 can improve alignment between the modules. For example, the grounding features 9558*a-b* can be sized and configured to engage the grounding features 9562*a-b* prior to engagement of a bottom bridge connector portion (not shown) of the upper module 9552 (e.g., bridge connector portion 9520 in FIG. 66A) and a top bridge connector portion (not shown) of the lower module 9554 (e.g., bridge connector portion 9536 in FIG. 67) such that proper alignment of the bridge connector portions is achieved during assembly of the modules 9552, 9554 into a stacked configuration. In various aspects, it may desirable to achieve a common ground between adjacent modules prior to engagement of the respective bridge connector portions of the adjacent modules to ensure user safety. Thus, the grounding features 9558*a-b* and 9562*a-b* can be configured to engage each other prior to the respective bridge connector portions.

In various aspects, as illustrated in FIG. 69A, the post/socket configuration can be implemented with rigid conductive posts 9558*a-b* on the lower module 9554 and springing conductive sockets 9562*a-b* on the upper module 9552 that are transitioned into a biased configuration upon receiving their corresponding posts 9588-*b*. Alternatively, as illustrated in FIG. 69B, the post/socket configuration can be implemented with a springing post 9566 on the lower module 9554 and a rigid socket 9568 on the upper module 9552. The springing sockets and/or springing posts can ensure that a proper common ground is achieved between the surgical modules 9552, 9554. A springing post can be a spring-loaded connector and a springing socket can be a spring-loaded socket connector.

Energy Module Bridge Connector

In various aspects, an end user is permitted to assemble any suitable number of modules into a variety of different stacked configurations that support electrical energy flow therebetween. Each of the different types of modules provides different functionality, thereby allowing individuals to customize the functions provided by each surgical platform by customizing the modules that are included in each surgical platform. The modular energy system is assembled or is modified by an end user either prior to or during a surgical procedure. Since the manufacturer is not involved with the final assembly of a modular energy system, suitable precautions are taken to ensure proper stacking of an assembled modular energy system and/or alignment of modules within the modular energy system.

As discussed above, the one or more modules can be connected together in a variety of different stacked configurations to form various modular energy systems. When positioned in the variety of different stacked configurations, the surgical modules are configured to communicate and transmit power therebetween. It is contemplated that external wiring connections can be utilized in order to electrically couple the modules when stacked together to facilitate the transmission of communication signals and power. However, it is desirable that the modules be connectable together without the need for external wiring to facilitate safe assembly and disassembly by an end user. To that end, the modules can include bridge connectors that are configured to transmit power and/or communication signals between the modules in the modular energy system when the modules are assembled or engaged together.

In one general aspect, the present disclosure provides a connector positioned on the top and a socket on the bottom of a stackable energy module, which can carry communication and power through multiple units (i.e., modules). The connector shape facilitates mechanical alignment, then grounding, then electrical contact of a series of power and communication lines when multiple energy modules are assembled together into a modular energy system.

In another general aspect, the present disclosure provides a bridge circuit that is segmented into identical boards residing within each module and is connected by connectors shaped to align and connect a variable number of stacked modules together (including a header module).

In another general aspect, the present disclosure provides a module connector configured to have a first or stowed configuration and second or extended configuration. The modular connectors for energy modules (and/or other modules of a modular energy system) can carry both communication and power between modules, where the connector is configured to be transitioned between the stowed configuration, which has a first low profile, and the extended configuration, which provides for both an electrical and mechanical connection between modules.

In yet another general aspect, the present disclosure provides a surgical platform comprising a first surgical module and a second surgical module. The first surgical module is configured to be assembled in a stack configuration with the second surgical module. The first surgical module includes a first bridge connector portion, which comprises a first outer housing and first electrical connection elements. The second surgical module comprises a second bridge connector portion, which comprises a second outer housing and second electrical connection elements. The second outer housing is shaped and configured to engage the first outer housing during the assembly before second electrical connection elements engage the first electrical connection elements.

In yet another general aspect, the present disclosure provides a surgical platform comprising a first surgical module and a second surgical module. The first surgical module comprises a first enclosure comprising a bottom surface, a first bridge connector, wherein the first bridge connector comprises a recess, a first printed circuit board (PCB), and a first wire assembly connected to the first PCB. The first wire assembly extends from the first PCB to the first bridge connector and the first wire assembly is operably coupled to the first bridge connector. The second surgical module comprises a second enclosure comprising a top surface, a second bridge connector, a second PCB, and a second wire assembly connected to the second PCB. The second bridge connector extends away from the top surface and the second bridge connector is configured to be positioned in the recess of the first bridge connector of the first surgical module. The second wire assembly extends from the second PCB to the second bridge connector and the second wire assembly is operably coupled to the second bridge connector. When the second bridge connector is positioned in the first bridge connector, the second wire assembly is electrically coupled with the first wire assembly.

Figure 72:
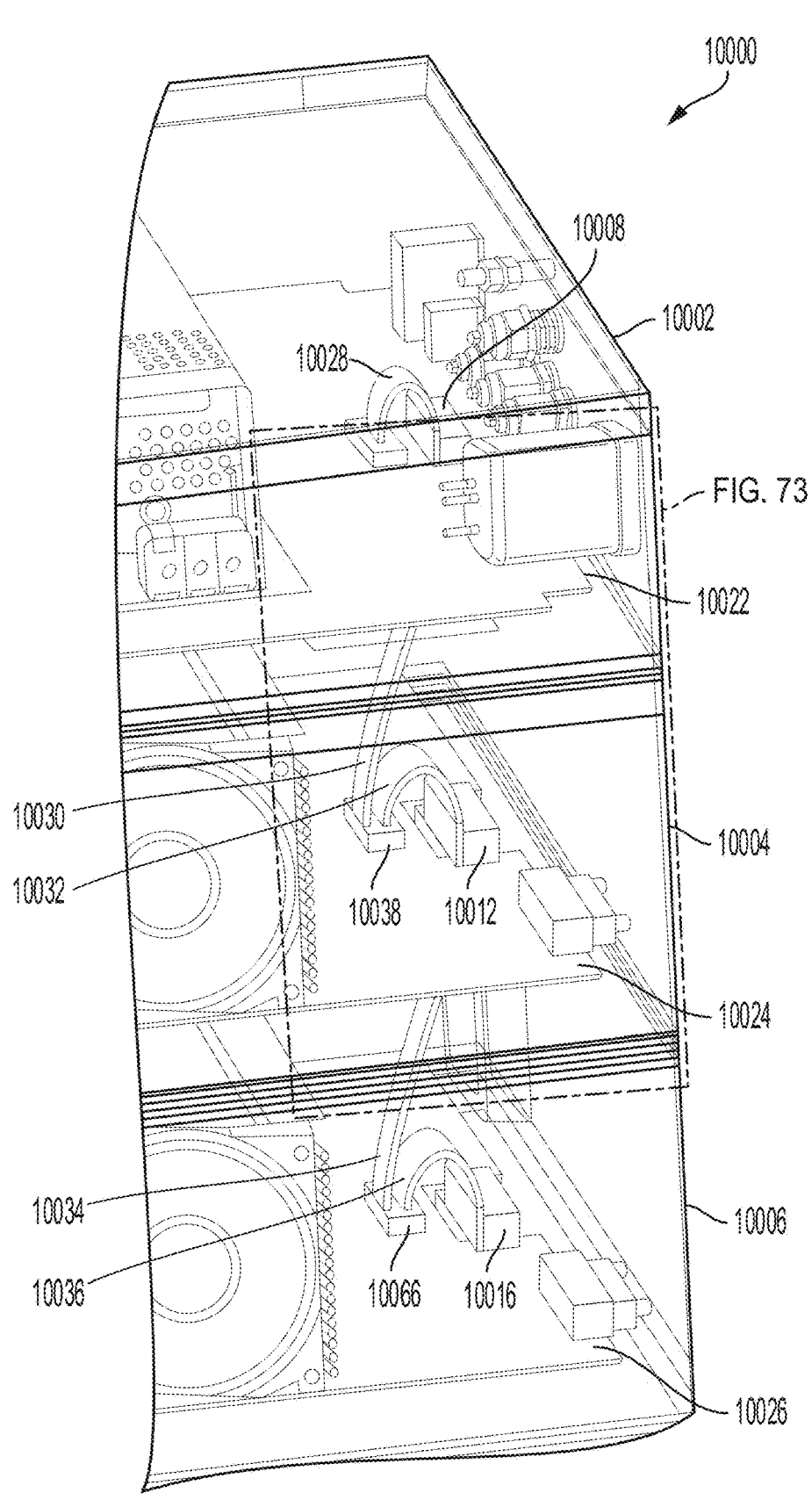
FIG. 72 illustrates a modular energy system, in accordance with at least one aspect of the present disclosure.
Figure 73:
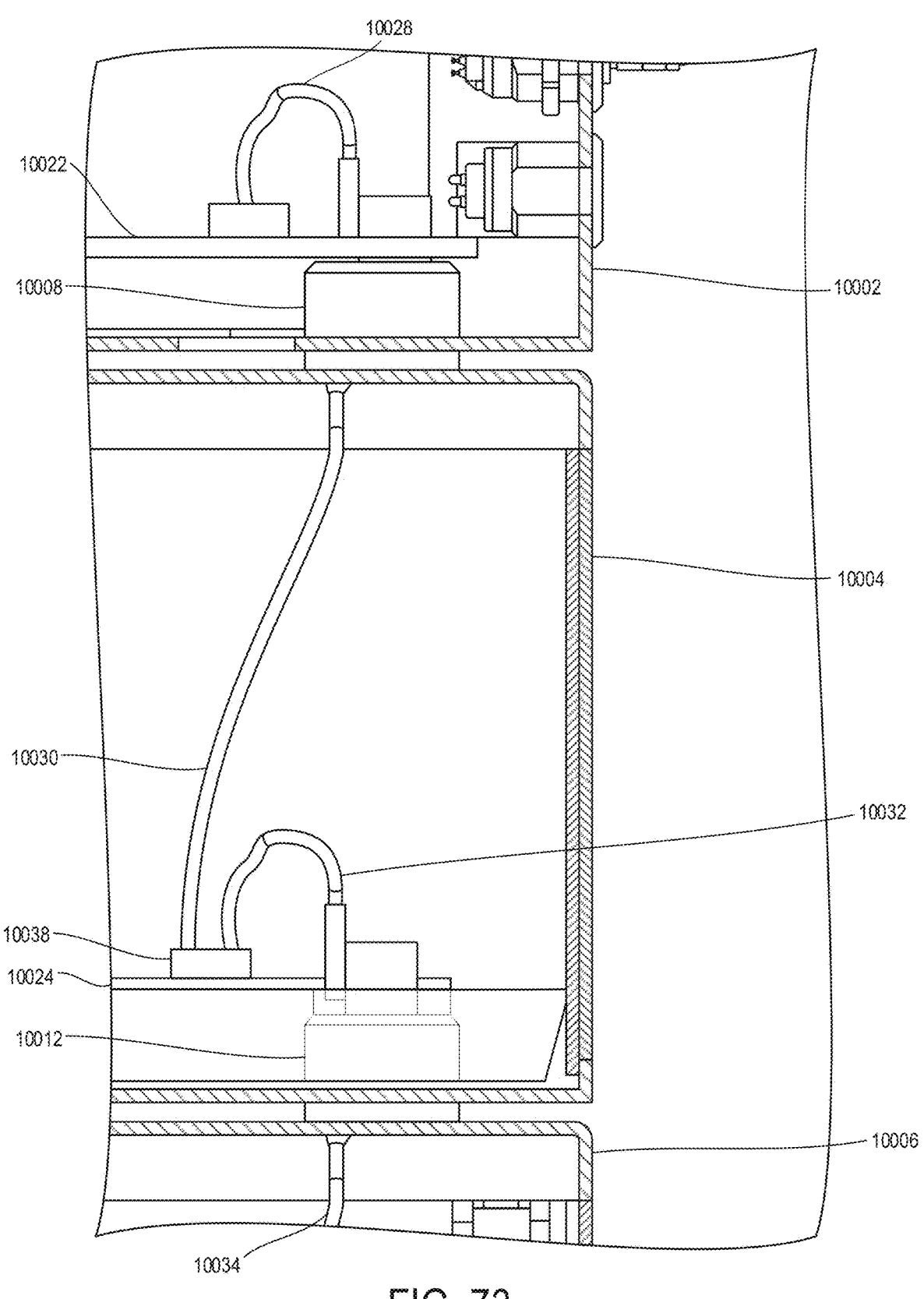
FIG. 73 illustrates various electrical connections in the modular energy system of FIG. 72.

Referring now to FIGS. 72 and 73, a configuration is shown in which three surgical modules, a first module 10002, a second module 10004, and a third module 10006, are assembled together in a stacked configuration by an end user utilizing an internal wiring arrangement to facilitate the transmission of communication signals and power between modules in a modular energy system 10000. Each module 10002, 10004, and 10006, can be the same type of surgical module or different types of surgical modules. For example, each module 10002, 10004, and 10006, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module 10002, 10004, and 10006, can include a bridge connector. For example, the first module 10002 can comprise a lower bridge connector 10008, the second module 10004 can comprise an upper bridge connector 10010 (FIG. 74) and a lower bridge connector 10012, and the third module 10006 can comprise an upper bridge connector (not shown) and a lower bridge connector 10016. Each bridge connector, 10008, 10010, 10012, and 10016, can include an outer housing extending at least partially around electrical connection elements of the respective bridge connector.

Figure 74:
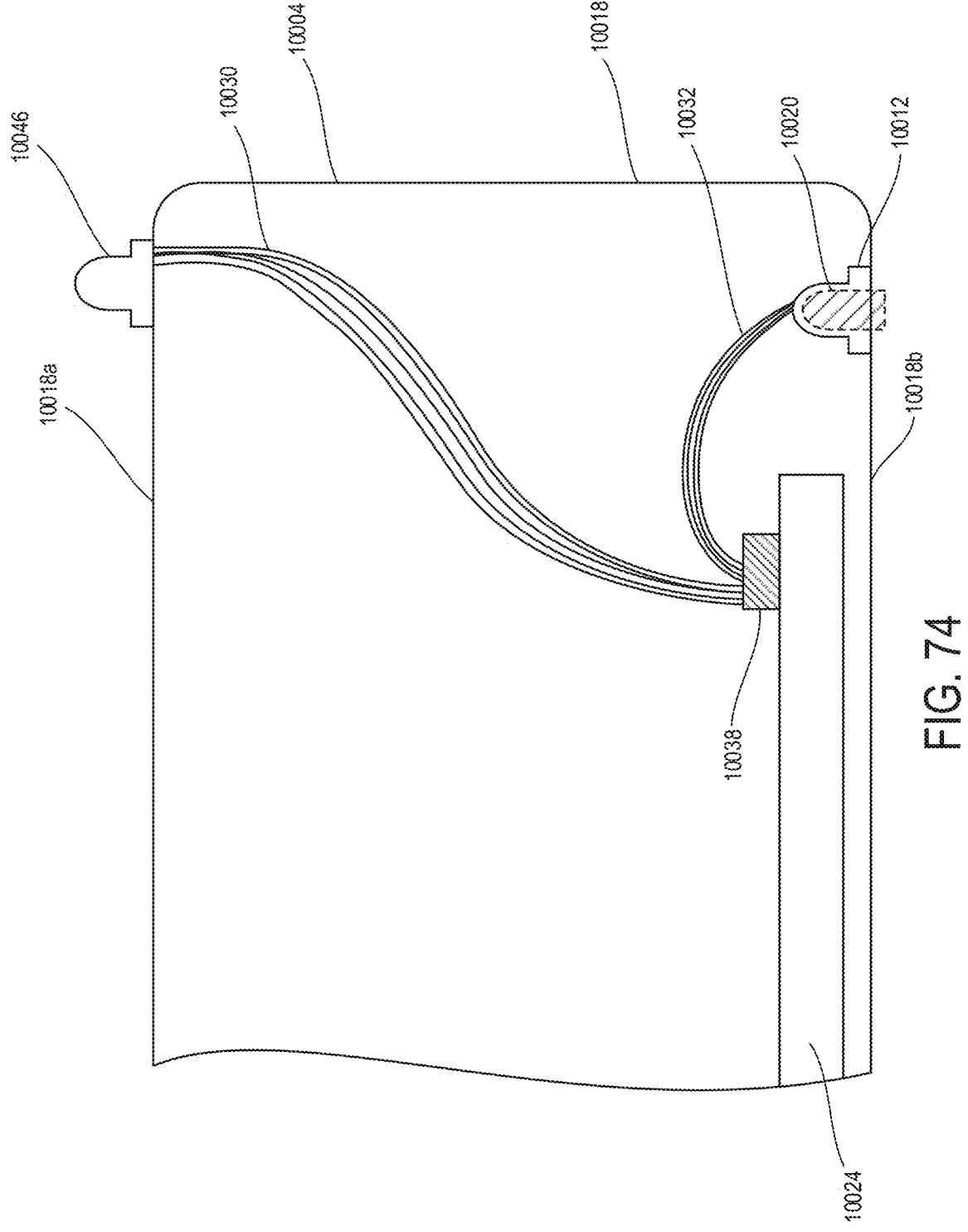
FIG. 74 illustrates a module of the modular energy system of FIG. 72.

Referring to FIG. 74, a detailed view of an embodiment of the second module 10004 is provided. It is understood the first module 10002 and the third module 10006 can be configured as the second module 10004 illustrated in FIG. 74. The upper bridge connector 10010 of the second module 10004 is mounted to a top surface 10018*a* of the enclosure 10018 and extends away from the second module 10004. The lower bridge connector 10012 of the second module 10004 is mounted to the bottom surface 10018*b* of the enclosure 10018 of the second module 10004. The lower bridge connector 10012 includes a recess 10020 that is shaped and configured to receive an upper bridge connector from a separate module. For example, when the second module 10004 is stacked on top of the third module 10006, the upper bridge connector of the third module 10006 is inserted into the recess 10020 of the lower bridge connector 10016 of the second module 10004, thus, aligning the second module 10004 with the third module 10006.

Referring to back to FIGS. 72 and 73, each module, 10002, 10004, and 10006, further includes a PCB. For example, the first module 10002 includes a first PCB 10022, the second module 10004 includes a second PCB 10024, and the third module 10006 includes a third PCB 10026.

Additionally, each module, 10002, 10004, and 10006, includes a flexible wire harness (e.g., flexible cable) electrically connected to the respective PCB, 10022, 10024, and 10026, by any suitable number of connections. For example, the first module 10002 includes a first flexible wire harness 10028 extending from the first PCB 10022 and operably coupled to the lower bridge connector 10008 of the first module 10002 to connect the first PCB 10022 with electrical connection elements of the lower bridge connector 10008. The first flexible wire harness 10028 is positioned within the first module 10002 and, thus, may facilitate quicker assembly of a modular energy system.

The second module 10004 includes a second flexible wire harness 10030 and a third flexible wire harness 10032 extending from the second PCB 10024. The second flexible wire harness 10030 is operably coupled to the upper bridge connector 10010 of the second module 10004 to connect the second PCB 10024 with electrical connection elements of the upper bridge connector 10010. The third flexible wire harness 10032 is operably coupled to the lower bridge connector 10012 of the second module 10004 to connect the second PCB 10024 with electrical connection elements of the lower bridge connector 10012. The second and third flexible wire harnesses 10030 and 10032 are positioned within the second module 10002 and, thus, may facilitate quick assembly of a modular energy system.

The third module 10006 includes a fourth flexible wire harness 10034 and a fifth flexible wire harness 10036 extending from the third PCB 10026. The fourth flexible wire harness 10034 is operably coupled to the upper bridge connector of the third module 10006 to connect the third PCB 10026 with electrical connection elements of the upper bridge connector of the third module 10006. The fifth flexible wire harness 10036 is operably coupled to the lower bridge connector 10016 of the third module 10006 to connect the third PCB 10026 with the electrical connection elements of the lower bridge connector 10016. The fourth and fifth flexible wire harnesses 10034 and 10036 are positioned within the third module 10002 and thus, may facilitate quick assembly of a modular energy system.

When an upper bridge connector of a lower module is positioned in a lower bridge connector of an upper module (e.g., the electrical connection elements of the bridge connectors are electrically coupled), the upper flexible wire harness connected to the upper bridge connector of the lower module is electrically coupled with the lower flexible wire harness connected to the lower bridge connector of the upper module. When coupled, power and communication signals are able to flow from the lower module to the upper module (and/or from the upper module to the lower module) by way of the internal flexible wire harnesses and the PCBs. For example, when the upper bridge connector 10014 of the third module 10006 is positioned in the lower bridge connector 10012 of the second module 10004, the fourth flexible wire harness 10034 is electrically coupled with the third flexible wire harness 10032. Thus, power and communications signals are able to flow from the third module 10006 to the second module 10004 by way of the third and fourth flexible wire harnesses, 10032 and 10034, and the respective PCBs, 10023 and 10026.

Referring back to FIGS. 72-74, in one instance, a board connector 10038 is mounted on the second PCB 10024 and a board connector 10066 is mounted on the third PCB 10026. The second flexible wire harness 10030 is configured to extend from the upper bridge connector 10010 and connect to the board connector 10038, while the third flexible wire harness 10032 is configured to extend from the lower bridge connector 10012 and connect to the board connector 10038. The fourth flexible wire harness 10034 is configured to extend from the upper bridge connector of the third module 10006 and connect to the board connector 10066, while the fifth flexible wire harness 10036 is configured to extend from the lower bridge connector 10016 and connect to the board connector 10066.

Similar to the scenario described above, when an upper module is connected with a lower module by way of respective bridge connectors, the upper and lower modules are able to communicate and transmit power therebetween by way of the PCBs, the board connectors, and the flexible wire harnesses. For example, referring to FIG. 73, power and communications signals are able to flow from the third module 10006 to the second module 10004 by way of the third and fourth flexible wire harnesses, 10032 and 10034, the board connectors, 10038 and 10066, and the respective PCBs, 10024 and 10026.

Figure 75:
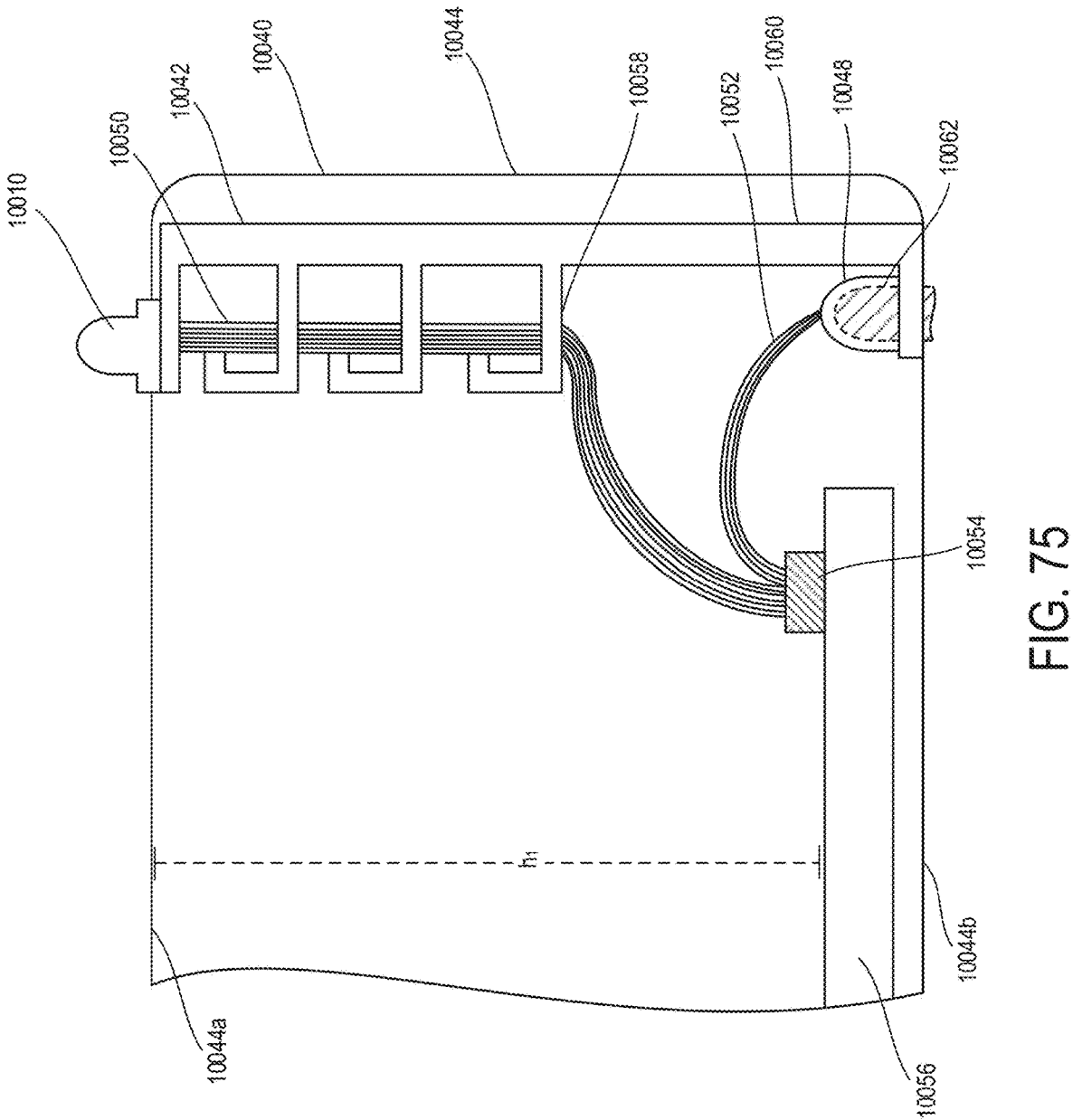
FIG. 75 illustrates a module of a modular energy system, which includes a rigid wire harness, in accordance with at least one aspect of the present disclosure.

Referring now to FIG. 75, a separate embodiment of a module 10040 is shown. The module 10040 illustrated in FIG. 75 is similar in many respects to the second module 10004 shown and described in FIGS. 72-74. However, instead of a flexible wire harness, a rigid wire harness 10042 is utilized. The rigid wire harness 10042 can be sized and configured to stand between a top surface 10044a of an enclosure 10044 of the module 10040 and a bottom surface 10044b of the enclosure 10044 of the module 10040. The rigid wire harness 10042 can extend the full, or at least substantially the full, height, $h_1$, of the module 10040. Further, the upper and lower bridge connectors, 10046 and 10048, are operably coupled (e.g., directly mated) to the rigid wire harness 10042 rather than to the enclosure 10044 of the module 10040. In at least one example, the upper and lower bridge connectors, 10046 and 10048, are integrated with the rigid wire harness 10042.

In the example of FIG. 75, upper wires 10050 extend from a board connector 10054 on the PCB 10056, along the rigid wire harness 10042, and connect to the upper bridge connector 10046. In addition, lower wires 10052 extend from the board connector 10054 and connect to the lower bridge connector 10048. The lower bridge connector 10048 includes a recess 10062 that is shaped and configured to receive an upper bridge connector from a separate module.

A series of holding members 10058 can extend from the rigid wire harness 10042, which are configured to wrap, or at least partially wrap, around the upper wires 10050 to support the upper wires 10050 within a predetermined distance from the rigid wire harness 10042. In the example of FIG. 75, the holding members 10058 extend from a backbone column 10060 that supports the upper and lower bridge connectors, 10046 and 10048.

The ability to mate the rigid wire harness 10042 with the upper bridge connector 10046 and lower bridge connector 10048 provides a distinct advantage when assembling the module 10040. As the rigid wire harness 10042 is one piece and extends the full, or at least substantially the full, height, $h_1$, of the module 10040, the rigid wire harness 10042 can be inserted into the module 10040 during assembly of the module 10040 and stand free. Once assembled into the module 10040, the upper and lower bridge connecters, 10046, 10048, can be mated directly with the rigid wire harness 10042, thereby eliminating the need to mount the upper and lower bridge connectors, 10046, 10048, to the top and bottom surfaces, 10044a, 10044b, of the enclosure 10044, respectively, thus, reducing assembly time. The rigid wire harness 10042 can limit force applied to an enclosure 10044 of the module 10040 during assembly of a modular energy system and can reliably establish and/or maintain connections between bridge connectors.

Figure 91:
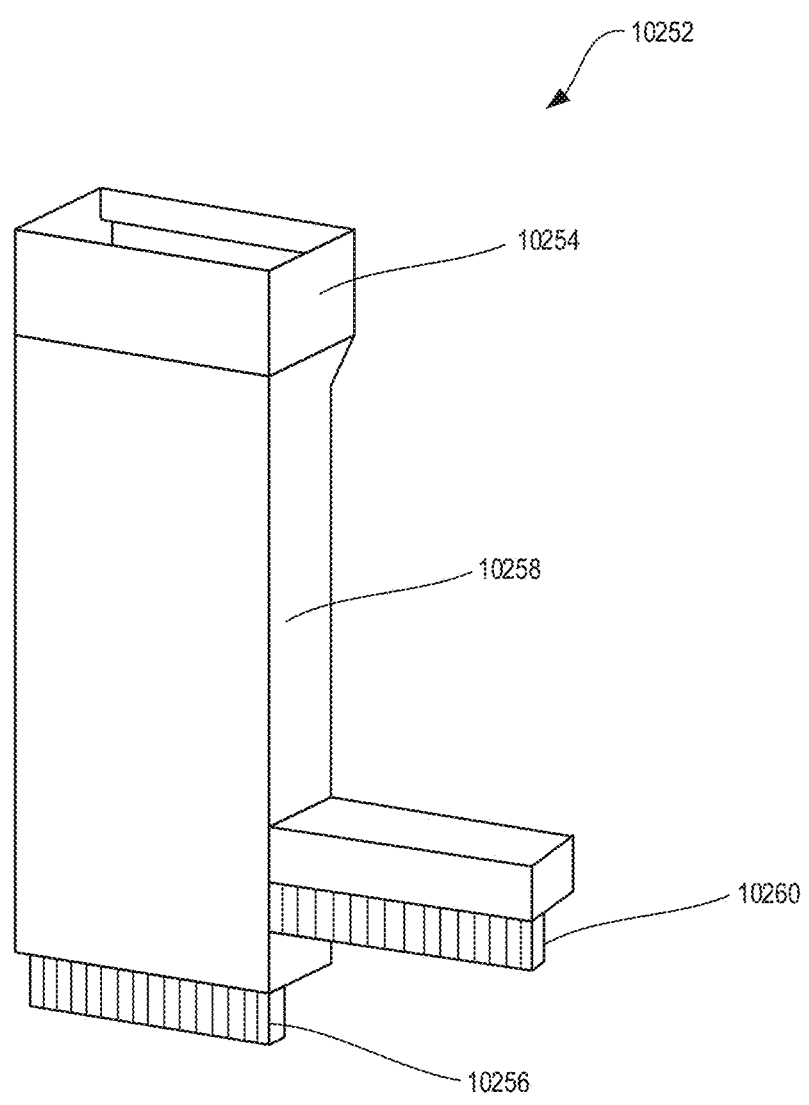
FIG. 91 illustrates a rigid connector, in accordance with at least one aspect of the present disclosure.

Referring to FIG. 91, in a separate embodiment, the flexible wire hardness or rigid wire harness can be replaced by a rigid connector 10252 as shown. The rigid connector 10252 can comprise an integrated upper bridge connector 10254, an integrated lower bridge connector 10256, a PCB extending between the bridge connectors, 10254 and 10256, and a PCB connector 10260. The PCB of the rigid connector 10252 can establish electrical and/or signal communication between the upper bridge connector 10254, the lower bridge connector 10256, and/or the PCB connector 10260. The PCB connector 10260 can be connected to a PCB of a module to establish electrical and/or signal communication between the rigid connector 10252 and the PCB of the module. Further, the rigid connector 10252 can comprise an outer housing 10258 that is over-molded around the PCB of the rigid connector 10252 and can be configured to mate to the enclosure of a module.

The rigid connector 10252 can be sized and configured to stand between a top surface of an enclosure of a module and a bottom surface of the enclosure of the module. The PCB connector 10252 can extend the full, or at least substantially the full, height of the module.

Figure 92:
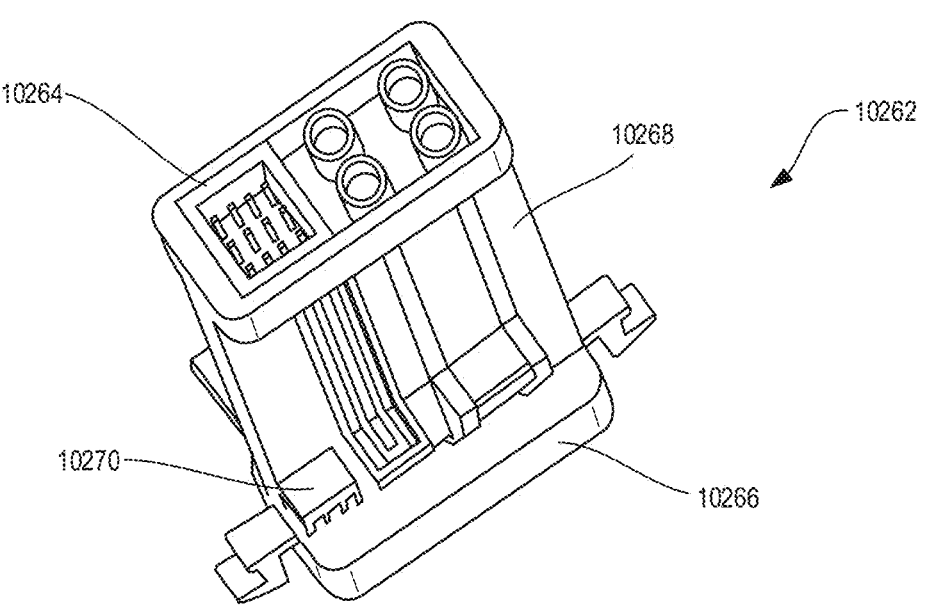
FIG. 92 illustrates a rigid connector, in accordance with at least one aspect of the present disclosure.
Figure 93:
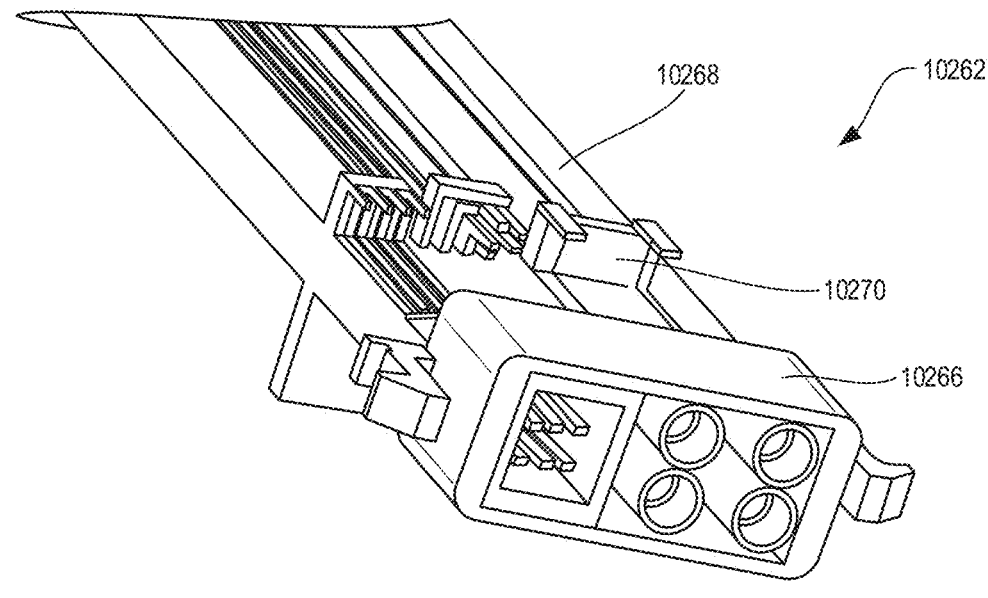
FIG. 93 illustrates a detailed view of the rigid connector of FIG. 92.

Referring to FIGS. 92-93, a separate embodiment of a rigid connector 10262 is provided. The rigid connector 10262 can comprise an integrated upper bridge connector 10264, an integrated lower bridge connector 10256, a PCB 10268 extending between the bridge connectors, 10264 and 10266, and a PCB connector 10270. The PCB 10268 can establish electrical and/or signal communication between the upper bridge connector 10264, the lower bridge connector 10266, and/or the PCB connector 10270. The PCB connector 10270 can be connected to a PCB of a module to establish electrical and/or signal communication between the rigid connector 10262 and the PCB of the module.

The rigid connector 10262 can be sized and configured to stand between a top surface of an enclosure of a module and a bottom surface of the enclosure of the module. The rigid connector 10262 can extend the full, or at least substantially the full, height of the module. The rigid connector 10252 in FIG. 91 and/or the rigid connector 10262 in FIGS. 92-93 can reduce assembly time.

In various aspects, as noted above, the modules of a modular energy system are connected via bridge connectors. Due to the weight of the modules, a user may find it difficult to align bridge connectors during stacking of the modules or assembly of the modular energy system. In certain instances, the user may damage the electrical connection elements of the bridge connectors during stacking. The bridge connectors, 10070 and 10074, illustrated in FIGS. 76-78 allow for modules to be stacked and connected together while being insensitive to the angle that male and female portions of the connectors initially mate. The bridge connector 10070 can be operably coupled to the modules as described herein. For example, the bridge connector 10070 can be the upper bridge connector on any one or more of the modules 10002, 10004, 10006, and 10040 in FIGS. 72-74, and the bridge connector 10074 can be the lower bridge connector on any one or more of the modules 10002, 10004, 10006, and 10040 in FIGS. 72-74.

Figure 76:
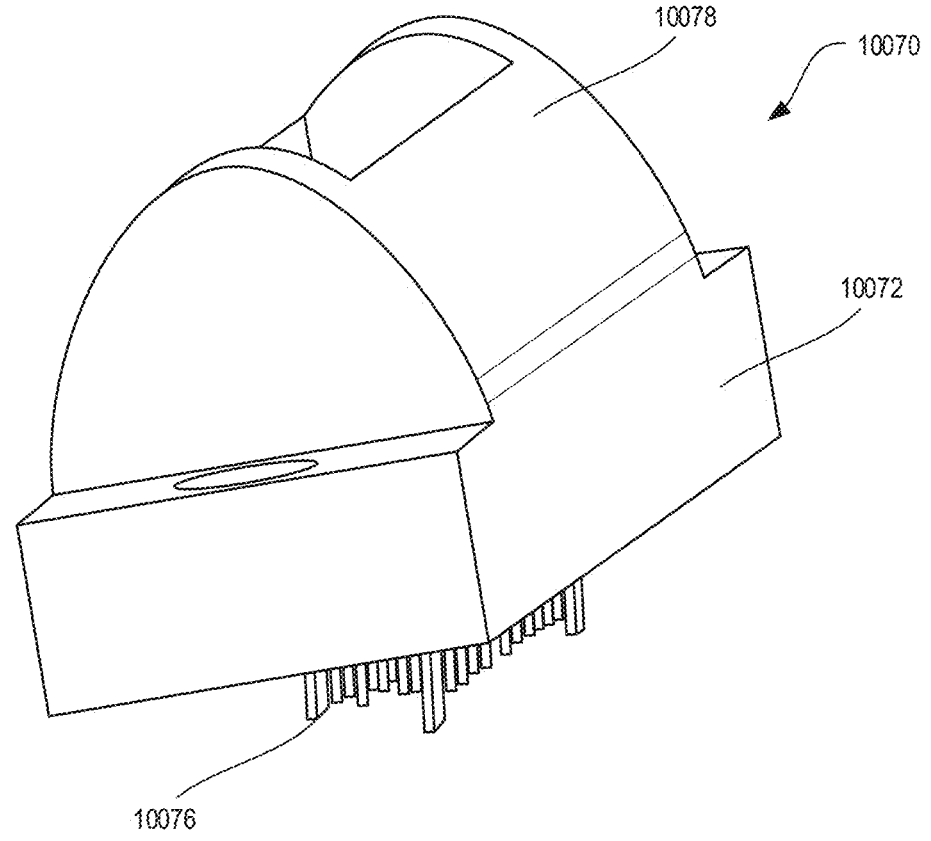
FIG. 76 is a perspective view of a male bridge connector of a modular energy system, in accordance with at least one aspect of the present disclosure.
Figure 77:
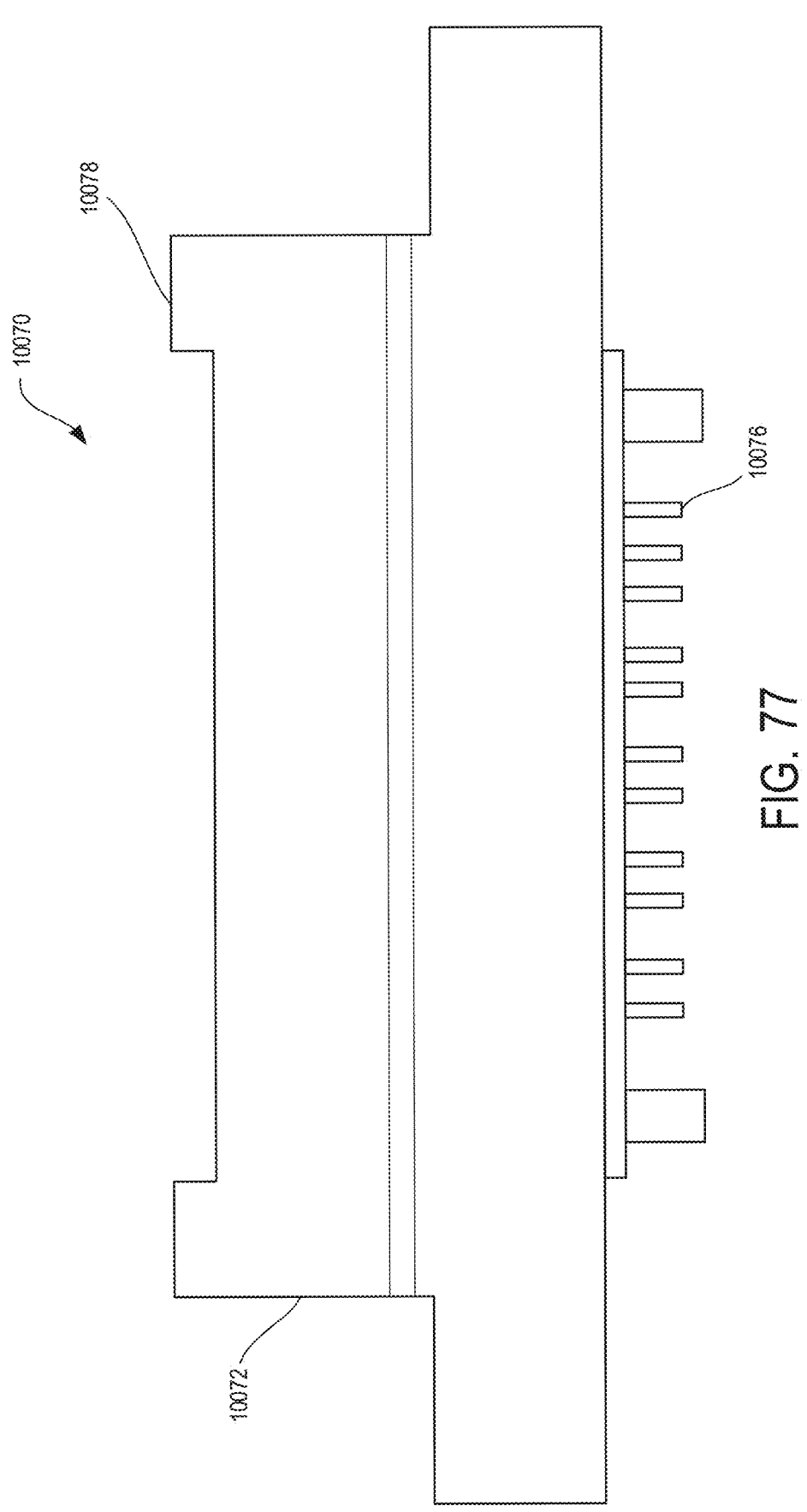
FIG. 77 is a cross-sectional view of the male bridge connector of FIG. 76.

As illustrated in FIGS. 76-77, the bridge connector 10070 includes an outer housing 10072 that extends at least partially around the electrical connection elements 10076 (e.g., pins). For example, the electrical connection elements 10076 can be recessed within the outer housing 10072. The outer housing 10072 is shaped and configured to engage an outer housing of a separate bridge connector during assembly of a stacked configuration of a modular energy system before the electrical connection elements 10076 engage the electrical connection elements of the separate bridge connector.

Figure 78:
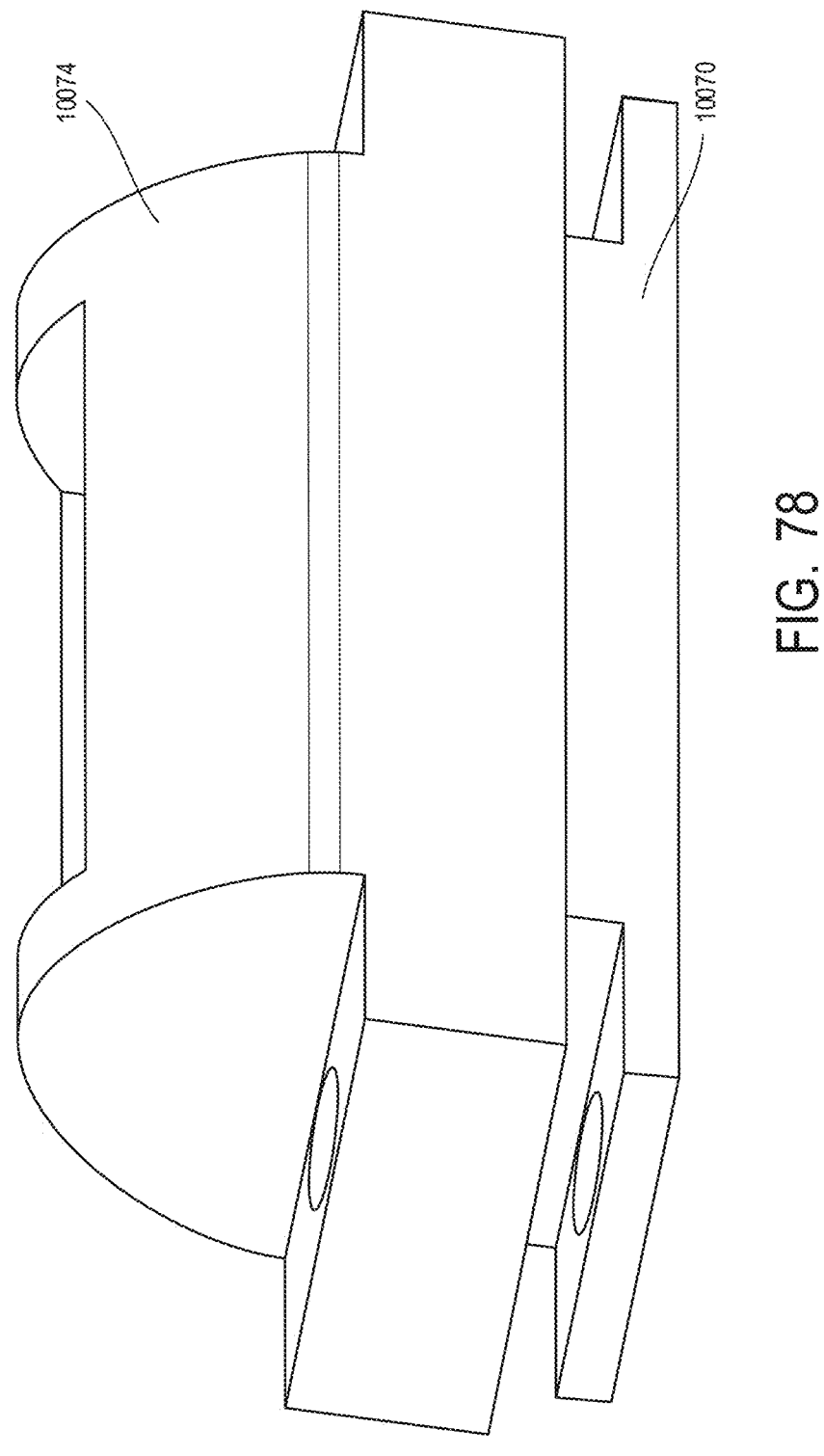
FIG. 78 is a perspective view of male and female bridge connectors of a modular energy system in an assembled configuration, in accordance with at least one aspect of the present disclosure.

As illustrated in FIGS. 76-77, the bridge connector 10070 is a male bridge connector. The bridge connector 10070 and a female bridge connector are shaped and configured to cooperate to properly align the electrical connection elements of the female bridge connector with the electrical connection elements 10076 during assembly of a stacked configuration of a modular energy system. For example, an assembled configuration of the bridge connector 10070 with a female bridge connector 10074 is illustrated in FIG. 78.

The outer housing 10072 is rectangular and rounded along the length of the outer housing 10072. In various aspects, the bridge connector 10070 protrudes from a top surface of a first module and a female bridge connector 10074 is recessed into a bottom surface of a separate module. The outer housing 10072 includes rounded or curved top faces 10078 that allow male and female bridge connectors to align even when modules are at a difficult angle with another. In other words, the outer housing 10072 is shaped and/or sized to guide the electrical connection elements 10076 of the bridge connector 10070 into a properly aligned engagement with the bridge connector 10074, thereby establishing electrical and/or signal communication between the modules and/or alignment between the modules. Further, an outer housing 10078 of the bridge connector 10074 can be shaped and/or sized to guide the electrical connection elements of the bridge connector 10074 into a properly aligned engagement with the bridge connector 10070, thereby establishing electrical and/or signal communication between the modules and/or alignment between the modules. The bridge connectors, 10070 and 10074, illustrated in FIGS. 76-78 can facilitate alignment of the respective electrical connection elements regardless of the angle that male and female portions of the connectors initially mate. Therefore, the modular energy system can be more rapidly assembled into a stacked configuration and the electrical connections therebetween can be more reliable.

As stated herein, the modules of a modular energy system can be connected via bridge connectors and, due to the weight of the modules, a user may find it difficult to keep the modules level during stacking. In certain instances, the user may pay more attention to the mechanical assembly of the modules (e.g., leveling) and less attention to the electrical connections between the modules. Thus, the electrical connection can be improper and/or damaged during stacking of the modules. Separating the mechanical assembly from the electrical assembly of the modules can facilitate faster assembly of the modular energy system and/or increase the reliability of electrical connections between modules in the modular energy system.

Figure 79:
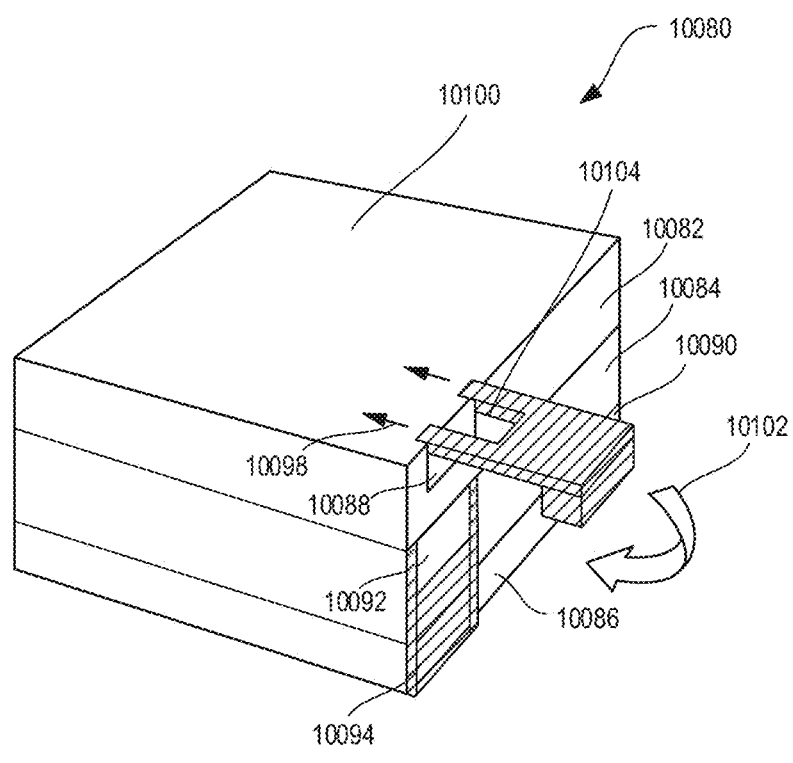
FIG. 79 illustrates a modular energy system, in accordance with at least one aspect of the present disclosure.
Figure 80:
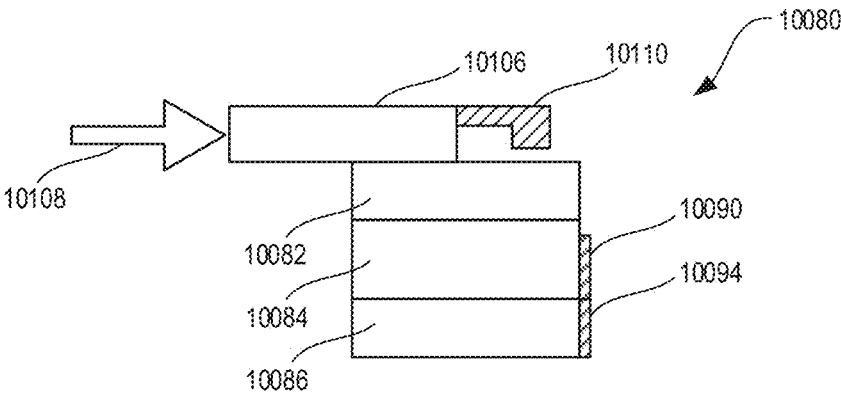
FIG. 80 illustrates various electrical connections in the modular energy system of FIG. 79.

Referring now to FIGS. 79 and 80, a configuration is shown in which three surgical modules, a first module 10082, a second module 10084, and a third module 10086, are assembled together in a stacked configuration by an end user utilizing a park and hide module connection to facilitate the transmission of communication signals and power between modules. Each module, 10082, 10084, and 10086, can be the same type of surgical module or different types of surgical modules. For example, each module 10082, 10084, 10086, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module, 10082, 10084, and 10086, can include a park and hide bridge connector. For example, the first module 10082 can comprise an upper bridge connector 10088 and a park and hide bridge connector 10090, the second module 10084 can comprise an upper bridge connector 10092 and a park and hide bridge connector 10094, and the third module 10086 can comprise an upper bridge connector. The bridge connectors, 10088, 10090, 10092, and 10094, are positioned on a surface of the respective module, 10082, 10084, 10086, which may not engage and/or face another module when assembled together in a stacked configuration. In other words, the bridge connectors, 10088, 10090, 10092, and 10094, can be accessible and be manipulated to establish or to de-establish electrical connections when the modules, 10082, 10084, and 10086, are in the stacked configuration.

The connectors, 10090 and 10094, can comprise three positions, a hide position, an extended position, and an engaged position. As illustrated in FIG. 79, the connector 10090 is in an extended position and can be moved into the hide position by translating the connector 10090 in the direction 10098. Thus, the connector 10090 can be hidden within the enclosure 10100 of the first module 10082 such that the connector 10090 can be protected from damage during and/or inhibited from interfering with stacking of the modular energy system 10080.

After stacking of the modular energy system 10080, the connector 10090 can be moved from the hide position, into the extended position as illustrated in FIG. 79, and thereafter into the engaged position by rotating the connector 10090 in the direction 10102. For example, the connector 10094 of the second module 10084 has been rotated into the engaged position and operably coupled to the upper bridge connector of the third module 10086, thereby establishing electrical and/or signal communication between the second module 10084 and the third module 10086. Separating the mechanical assembly from the electrical assembly of the modules utilizing a park and hide bridge connector can enable the user to more reliably establish the electrical connection and inhibit accidental damage of a connector.

Additionally, the connector 10090 can include an opening 10104 configured to enable access to the upper bridge connector 10088 while the connector 10090 is in the engaged position. Thus, referring to FIG. 80, an additional module 10106 can be added to the first three modules, 10082, 10084, and 10086, of the modular energy system 10080 by resting the additional module 10106 first on top of the first module 10082 and sliding the additional module 10106 across the top surface of first module 10092, in the direction indicated by the arrow 10108, until the additional module 10106 and the first module 10082 are assembled into the stacked configuration and/or aligned. Thereafter, a park and hide connector 10110 of the additional module 10106 can be rotated from the extended position as illustrated in FIG. 80 into the engaged position (not shown), thereby establishing electrical and/or signal communication between the first module 10082 and the additional module 10106.

Figures 81, 82, 90:
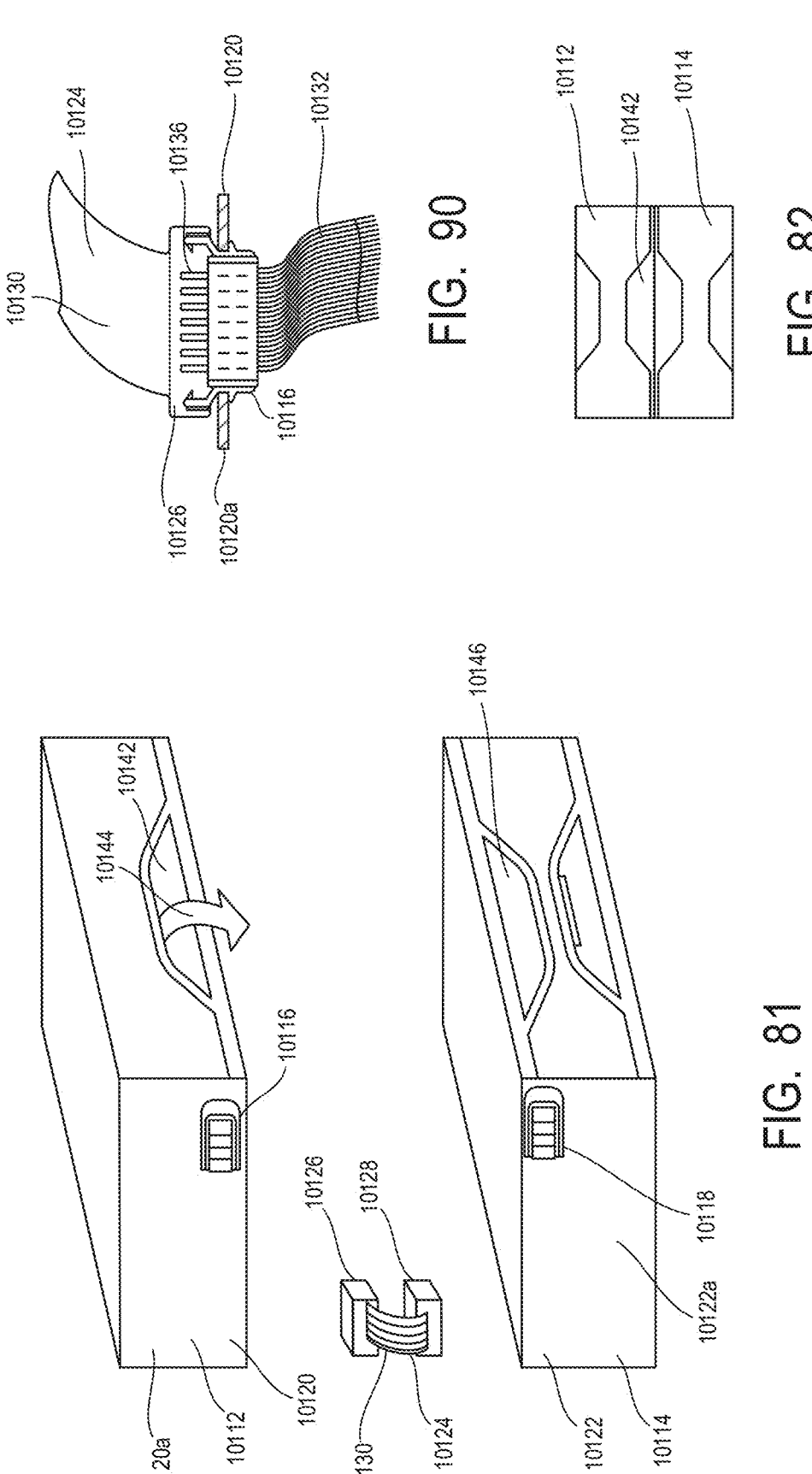
FIG. 81 illustrates a modular energy system, in accordance with at least one aspect of the present disclosure.
FIG. 82 illustrates a side view of the modular energy system of FIG. 81.
FIG. 90 illustrates various electrical connections in the modular energy system of FIG. 81.

Referring now to FIGS. 81 and 82, a configuration is shown in which two surgical modules, a first module 10112 and a second module 10114, are assembled together in a stacked configuration by an end user utilizing a jumper cable to facilitate the transmission of communication signals and power between modules. Each module, 10112 and 10114, can be the same type of surgical module or different types of surgical modules. For example, each module, 10112 and 10114, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module, 10112 and 10114, can include a bridge connector. For example, the first module 10112 can comprise a bridge connector 10116 and the second module 10114 can comprise a bridge connector 10118. The bridge connectors, 10016 and 10018, are positioned on a surface of the respective module 10112 and 10114, which may not engage and/or face another module when assembled together in a stacked configuration. For example, as illustrated in FIG. 81, the bridge connector 10116 is protruding from a back surface 10120*a* of the enclosure 10120 of the first module 10112 and the bridge connector 10118 is protruding from a back surface 10122*a* of an enclosure 10122 of the second module 10114. In other words, the bridge connectors, 10116 and 10118, can be accessible and manipulated to establish or to de-establish electrical connections between modules when in the stacked configuration.

The bridge connector 10116 and 10118 can be a male blade connector. A jumper cable 10124 can be operably coupled to the bridge connectors, 10116 and 10118, thereby establishing electrical and/or signal communication between the first module 10112 and the second module 10114. The jumper cable 10124 can comprise two ends, 10126 and 10128, and wires 10130 extending therebetween. In one aspect, each end, 10126 and 10128, is a female blade connector. The ends, 10126 and 10128, of the jumper cable 10124 can be configured to respectively engage the bridge connectors, 10016 and 10018, of the modules, 10112 and 10114, to electrically and/or communicatively couple the modules, 10112 and 10114.

Referring to FIG. 90, the jumper cable 10124 is connected to the bridge connector 10116 of the first module 10112. The bridge connector 10116 can comprise electrical elements 10136, which are electrically connected to wires 10132, and the wires 10132 can be electrically connected to a PCB (not shown) within the first module 10112 by any suitable number of connections.

Securing the modules together in the stacked configuration can prevent modules assembled in the stacked configuration from becoming misaligned while adding an additional module. Thus, various latches and latching mechanisms are provided to secure modules to one another.

For example, the first module 10112 can be stacked on top of the second module 10114 as illustrated in FIGS. 81 and 82. To secure the modules, 10112 and 10114, together, a flip-down latch 10142 of the first module 10112 can be rotated along direction 10144 from a first position as illustrated in FIG. 81 to a second position as illustrated in FIG. 82. The flip-down latch 10142 can engage a joining portion 10146 of the second module 10114, thereby establishing a mechanical connection between the modules, 10112 and 10114. The joining portion 10146 can be, for example, a recessed portion on the enclosure 10122*a* of the second module 10114. The joining portion 10146 can have features configured to engage and mate with the flip-down latch 10142. In various aspects, the modules, 10112 and 10114, can comprise two or more flip down latches.

Referring to FIG. 83, a configuration is shown in which three modules, a first module 10148, a second module 10150, and a third module 10152, are assembled together in a stacked configuration by an end user. Thereafter, a cord assembly 10154 of the second module 10150 can be configured to engage a joining portion 10156 of the third module 10152, thereby mechanically connecting the modules, 10150 and 10152, together as illustrated in FIG. 83. In some examples, the cord assembly 10154 can also establish electrical and/or signal communication between the second module 10150 and the third module 10152. Similarly, a lever assembly 10158 of the first module 10148 can be configured to engage a joining portion 10160 of the second module 10150, thereby mechanically connecting the modules, 10148 and 10150, together. The lever assembly 10158 can also establish electrical and/or signal communication between the first module 10148 and the second module 10150. Accordingly, a modular energy system can comprise various latches and latching mechanisms that are the same or that are different as illustrated in FIG. 83.

Referring to FIGS. 84A and 84B, a configuration is shown in which the modules of a modular energy system can comprise a flip-down latch. For example, two modules, a first module 10162 and a second module 10164, are assembled together in a stacked configuration by an end user. The first module 10162 is connected to the second module 10164 by a flip-down latch 10166. Thereafter, an additional module 10168 can be stacked on top of the first module 10162 and secured to the first module 10162 by a flip-down latch 10170.

Referring to FIGS. 85A, 85B, 86, and 87, a configuration is shown in which the modules of a modular energy system can comprise a rotatable latch assembly configured to secure the modules together in the stacked configuration. In one aspect, as illustrated in FIGS. 85A and 85B, three modules, a first module 10246, a second module 10248, and a third module 10250, are assembled together in a stacked configuration by an end user. The first module 10246 comprises rotatable latch assemblies 10238, the second module 10248 comprises rotatable latch assemblies 10240, and the third module 10250 comprises rotatable latch assemblies 10242. The first module 10246 is connected to the second module 10248 by the rotatable latch assemblies 10240. The second module 10248 is connected to the third module 10250 by the rotatable latch assemblies 10242.

Each rotatable latch assembly, 10238, 10240, and 10242, comprises a handle and a hook assembly. For example, referring to FIG. 85B, rotatable latch assembly 10238 comprises handle 10238*a* and hook assembly 10240*b*. The handle 10238*a* can be rotated from a disengaged position where the hook assembly 10238*b* is positioned within the enclosure 10244 of the first module 10246 to an engaged positioned where the hook assembly 10238*b* protrudes from a top surface 10244*a* of the enclosure 10244 and is configured to engage a joining portion of an enclosure of a separate module. Thus, an upper module and a lower module can be secured together in a stacked configured when the rotatable latch assemblies of the lower module are configured in the engaged position. The upper and lower modules can be disassembled from a stacked configuration when the rotatable latch assemblies of the lower module are configured in the disengaged position.

Figures 86, 87, 88, 89:
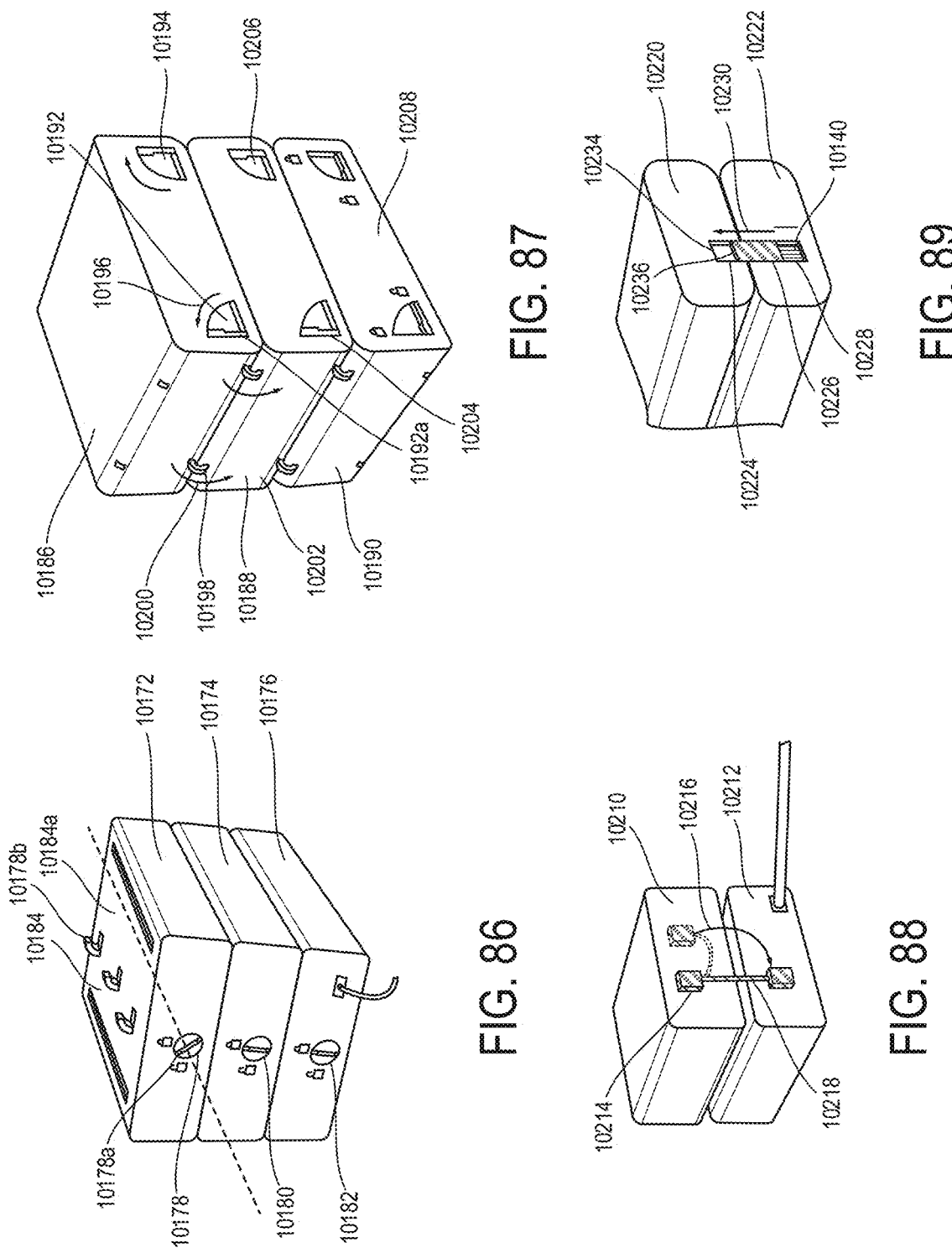
FIG. 86 illustrates a modular energy system comprising a latch assembly, in accordance with at least one aspect of the present disclosure.
FIG. 87 illustrates a modular energy system comprising a latch assembly, in accordance with at least one aspect of the present disclosure.
FIG. 88 illustrates a modular energy system comprising a cord assembly, in accordance with at least one aspect of the present disclosure.
FIG. 89 illustrates a modular energy system comprising a plug, in accordance with at least one aspect of the present disclosure.

In one aspect, as illustrated in FIG. 86, three modules, a first module 10172, a second module 10174, and a third module 10176, are assembled together in a stacked configuration by an end user. The first module comprises rotatable latch assembly 10178, the second module comprises rotatable latch assembly 10180, and the third module comprises rotatable latch assemblies 10182. The first module 10172 is connected to the second module 10174 by the rotatable latch assembly 10180. The second module 10174 is connected to the third module 10176 by the rotatable latch assembly 10182.

Each rotatable latch assembly, 10178, 10180, and 10182, comprises a handle and a hook assembly. For example, the rotatable latch assembly 10178 comprises a handle 10178*a* and a hook assembly 10178*b*. The handle 10178*a* can be rotated from a disengaged position where the hook assembly 10178*b* is positioned within the enclosure 10184 of the first module 10172 to an engaged positioned where the hook assembly 10178*b* protrudes from a top surface 10184*a* of the enclosure 10184 and is configured to engage a joining portion of an enclosure of a separate module. Thus, an upper module and a lower module can be secured together in a stacked configured when the rotatable latch assembly of the lower module is configured in the engaged position. The upper and lower modules can be disassembled from a stacked configuration when the rotatable latch assembly of the lower module is configured in the disengaged position.

Referring to FIG. 87, a configuration is shown in which three modules, a first module 10186, a second module 10188, and a third module 10190, are assembled together in a stacked configuration by an end user. The first module 10186 comprises a first latch assembly 10192 and a second latch assembly 10194. Upon moving the handle 10192*a* of the first latch assembly 10192 in the direction 10196, a hook assembly 10198 of the first latch assembly moves in the direction 10200 and engages the enclosure 10202 of the second module 10188, thereby mechanically securing the first module 10186 to the second module 10188. The second latch assembly 10194 operates in a similar manner to the first latch assembly 10192.

Similarly, the second module 10188 comprises a first latch assembly 10204 and a second latch assembly 10206. The latch assemblies, 10204 and 10206, can engage the enclosure 10208 of the third module 10190, thereby mechanically securing the second module 10188 to the third module 10190.

Referring to FIG. 88, a configuration is shown in which two modules, a first module 10210 and a second module 10212, are assembled together in a stacked configuration by an end user. The first module 10210 comprises a cord assembly 10214, which can be configured to engage with a corresponding connector or portion of another module (such as the second module 10212). Accordingly, the cord assembly 10214 can be transition between a first position 10216, in which the core assembly 10214 can be secured to the first module 10210 (and thus disengaged from the second module 10212), and a second position 10218. Upon configuring the cord assembly 10214 in the second position 10218, the first module 10210 can be mechanically secured to the second module 10212 by the cord assembly 10214. In one aspect, the cord assembly 10214 can also establish electrical and/or signal communication between the first module 10210 and the second module 10212. That is, the cord assembly 10214 can be attached to a PCB of the first module 10210 and connected to a bridge connector of the second module 10212. However, the cord assembly 10212 can be sized and configured to maintain the position of the first module 10210 with respect to the second module 10212.

Referring to FIG. 89, two modules, a first module 10220 and a second module 10222, are assembled together in a stacked configuration by an end user. The first module 10220 comprises a recess 10224 configured to receive a plug 10226 and the second module 10222 comprises a recess 10228 that is also configured to receive the plug 10226. The plug 10226 can be slidably disposed within or slidably connected to either the recess 10224 of the first module 10220 or the recess 10228 of the second module 10222. The plug 10226 can be moveable between a first position and a second position. In one aspect, in the first position, the plug 10226 can be solely within the recess 10228 of the second module 10222. The plug 10226 can be translated in the direction 10230 and into the recess 10226 in order to mechanically secure the first module 10220 and the second module 10222. In an alternative aspect, in the first position, the plug 10226 can be positioned within the recess 10224 of the first module 10220 and then translated to engage the corresponding recess 10228 of the second module 10222 to mechanically engage the first and second modules 10220, 10222 together.

In various aspects, the plug 10226 is electrically connected to a wire harness 10140 and comprises first electrical connection elements on an end 10236 of the plug 10226. The recess 10226 can comprise a bridge connector portion 10234 comprising second electrical connection elements. The plug 10226 can be translated in direction 10230 and can contact the second electrical connection elements, thereby establishing electrical and/or signal communication between the first module 10220 and the second module 10222.

In various aspects, the bridge connector can be electrically coupled to a flexible power supply (e.g., an H-bridge type power supply) that is configured to provide current and voltage feedback and control. The flexible power supply can be configured to a variety of different applications, including fixed pulsing power delivery, pulse-width modulation (PWM) pulsing power delivery, closed-loop control (i.e., based upon feedback provided to the power supply), delivery of AC and/or DC power, power mitigation (e.g., as is described in U.S. patent application Ser. No. 16/562,203, titled POWER AND COMMUNICATION MITIGATION ARRANGEMENT FOR MODULAR SURGICAL ENERGY SYSTEM, filed concurrently herewith, which is hereby incorporated by reference herein), and/or separate patient isolation of hardware. These and other functions can be enabled for any module coupled to the flexible power supply through the connections between the opposing bridge connectors as the modules are engaged together.

Passive Header Module Display

As discussed above under the heading MODULAR ENERGY SYSTEM, energy systems can be designed for modularity, which is to say that an energy system can be assembled from different numbers and types of modules according to users' needs for any given surgical procedure or task. In particular, a modular energy system 2000 (FIGS. 24-30) can include a header module 2002, which can in turn include a display screen 2006 for displaying/rendering a user interface (UI) 2050 (FIG. 30) that displays data associated with all of the modules 2001 (FIGS. 24-30) that are connected to the header module 2002. Accordingly, the header module 2002 provides a single, consolidated UI 2050 to display content for all of the modules 2001, which is beneficial for a number of reasons, some of which are described in U.S. patent application Ser. No. 16/562,123, titled METHOD FOR CONSTRUCTING AND USING A MODULAR SURGICAL ENERGY SYSTEM WITH MULTIPLE DEVICES, filed concurrently herewith, which is hereby incorporated by reference herein. However, an issue could potentially arise in such a system structure if the header module 2002 and the individual modules 2001 are both responsible for making calculations pertaining to data sensed with respect to the individual modules 2001. Namely, this introduces the possibility for errors if the system updates of the header module 2002 and the individual modules 2001 are mismatched. Stated differently, if the header module 2002 has downloaded the most recent system update, but the individual modules 2001 have not (or vice versa), then the mismatched system versions could create errors if both the header module 2002 and the individual modules 2001 are responsible for performing computations on sensed data. To address this potential issue, in one aspect, the individual modules 2001 can be configured to perform all computations on sensed data and the header module 2002 can be configured to passively display all of the data this is transmitted to it from the individual modules 2001. Utilizing a header module 2002 that simply passively renders or displays the received data, without performing independent computations with respect to the received data, addresses these potential issues with modules 2001 having mismatched system versions. However, such a system structure with a passive header module 2002 can potentially create a separate issue pertaining to the display of safety critical content (e.g., the power level at which the energy module 2004 (FIGS. 24-30)). Namely, if the header module 2002 is passively displaying content, then it would not know if the displayed safety critical content was correct. Accordingly, for the modules 2001 of that generate safety critical data that is then displayed via the header module 2002, the modular energy system 2000 must be configured to verify that the safety critical UI content is being displayed correctly because, although the modules 2001 may themselves know whether safety critical data/content is correct, this information may not be known by header module 2002. Therefore, a solution for the modular energy system 2000 is needed to verify (and correct, as needed) safety critical UI content generated from module data and displayed by the header module 2002 or UI module 3002 (FIG. 31) without prior, independent knowledge by the header module 2002 or UI module 3002 of whether the displayed content is correct.

In one general aspect, the modular energy system is configured to execute local verification loops between the modules to verify the proper display of safety critical UI content to achieve end-to-end monitoring and verification of safety critical UI content.

In another general aspect, a modular energy system includes a header module and one or more other modules, where each of the non-header modules generates data that is delivered to the header module, which in turn passively displays UI content based on the delivered data. Thus, the modules are can be referred to as "smart" and the header module can be referred to as "passive" use of a passive header module minimizes need and time to deliver software updates to the modular energy system because the header module need not be separately updated from the other modules in order for the modular energy system to function.

Figure 94:
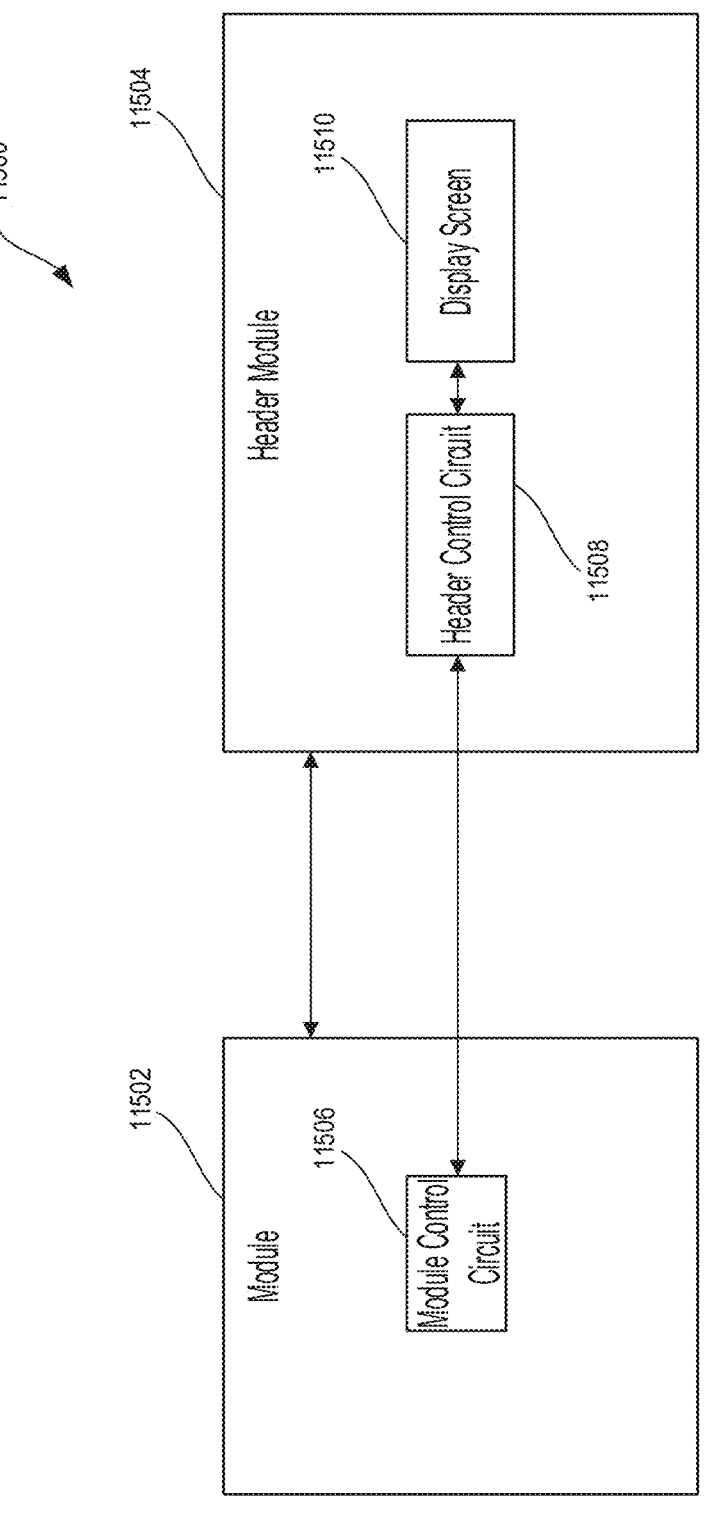
FIG. 94 is a block diagram of a modular energy system, in accordance with at least one aspect of the present disclosure.

FIG. 94 is a block diagram of a modular energy system 11500, in accordance with at least one aspect of the present disclosure. In one aspect, the modular energy system 11500 can include a header module 11504 that is connected to a module 11502, which can include a variety of different module types, such as the modules 2001 described above in connection with FIGS. 24-30. The module 11502 can include a control circuit 11506. The module control circuit 11506 can include a controller 3082 (FIG. 34), for example. The header module 11504 can include a control circuit 11508 and a display screen 11510 that is communicably coupled to the control circuit 11508. The header control circuit 11508 can include a UI processor 3040 (FIG. 33), for example. The display screen 11510 can be configured to display a UI 2050 for displaying operational information/parameters pertaining to the modular energy system 11500 and/or receiving input from the user, as described above. The header control circuit 11508 can be configured to control the display screen 11510 to cause the UI 2050 to display various UI elements or content (e.g., text, icons, or widgets) as dictated by the header control circuit 11508. When the module 11502 and the header module 11504 are connected, the module control circuit 11506 and the header control circuit 11508 can be communicably coupled such that they are able to send and receive data/signals therebetween. In one aspect, the header control circuit 11508 cause control the display screen 11510 to cause the UI 2050 to display UI content based on data received from the module 11502.

In various aspects, the modular energy system 11500 can be configured to execute a process to verify safety critical UI content generated from module data and displayed by the header module 11504 without prior, independent knowledge by the header module 11504 of whether the displayed content is correct. As one example, the module control circuit 11506 and/or header control circuit 11508 can be configured to execute a process 11600 illustrated in FIG. 95 for verifying displayed UI content, in accordance with at least one aspect of the present disclosure. The process 11600 can be embodied as, for example, instructions stored in one or more memories coupled to the module control circuit 11506 and/or header control circuit 11508 that, when executed by the module control circuit 11506 and/or header control circuit 11508, cause the module control circuit 11506 and/or header control circuit 11508 to perform the enumerated steps of the process 11600. In the following description of the process 11600, reference should also be made to FIG. 94.

Accordingly, the module control circuit 11506 executing, at least in part, the process 11600 can generate 11602 data pertaining to its own functions or other functions of the modular energy system 11500. Some of the generated 11602 data can include safety critical data. If, for example, the modular 11502 is an energy module 2204, the safety critical data could include the power level at which a particular energy modality driven by the energy module 2204 is set or the mode in which the energy modality is being driven (e.g., cut, coagulation, or spray). As one can imagine, the energy module power level or operational mode is safety critical because applying too much energy or the wrong type of energy to the patient can cause injuries (e.g., by cutting tissue when the surgeon had intended to coagulate the tissue). Other safety critical data can include whether the module 11502 has detected a loose electrical connection within, to, or from the module 11502; whether the power consumption of the module 11502 has exceeded a threshold (e.g., the power threshold rated for the module 11502 according to the modules, surgical instruments, and/or tools connected thereto); whether the current drawn by the module 11502 has exceeded a threshold; and/or detection of an improper operational parameter (e.g., whether the power level or mode is in appropriate for detected tissue parameters or whether an incorrect type of scope has been connected to the visualization module 2042 (FIG. 28) for the surgical procedure type). UI content to be rendered/displayed by the header module 11504 based on such safety critical data can be verified to ensure that it is being accurately reported to users via the UI 2050. The module control circuit 11506 can then transmit 11604 the generated data for receipt by the header module 11504 via, for example, the data bus/interface 3008 (FIGS. 33-35). Any data generated 11602 by the module 11502 that is determined to be safety critical can include a label, tag, or identifier indicating its status as safety critical data when transmitted 11604 to the header module 11504.

Accordingly, the module control circuit 11506 can verify 11606 that the transmitted data was fully and/or correctly received by the header module 11502. In one aspect, the module control circuit 11506 can verify 11606 the correct receipt of the data via a checksum to identify errors that may occur during transmission or storage of the data transmitted to the header module 11504. This step of confirming that the data was correctly received by the header module 11502 can ensure that, if there is determined to be an error in the displayed UI content later in the process 11600, the module control circuit 11506 and/or header control circuit 11508 can determine whether the source of the error was with the data transmission process or an error by the header module 11504 in displaying the UI content.

Accordingly, the header control circuit 11508 executing, at least in part, the process 11600 can render 11608, 11610 any non-safety critical content and any safety critical content on the display screen 11510 via the UI 2050. The content rendered via the UI 2050 can take the form of text, numerals, icons, widgets, and any other indicia or UI element. For example, if the transmitted data includes the energy mode power level and mode, then that data can be displayed in the form of text and numerical UI content, as is shown in FIG. 30, for example.

In one aspect, the header control circuit 11508 can further check 11612 the health of the display screen 11510. This may involve, for example, ensuring that all electrical connections to the display 11510 are properly made, that the display 11510 has a homogenous image display with smooth gradients, and/or that the display 11510 does not have improper response times. If there is an issue with the health of the display 11510, the header control circuit 11508 can generate an alert to the user, such as an audible alert (e.g., ringing sound), a tactile alert (e.g. vibration), or some other suitable alert provided via a touchscreen 3046 (FIG. 33), a LCD 3048 (FIG. 33), and/or an audio output 3052 (FIG. 33). This step of checking the health of the display screen 11510 can ensure that, if there is determined to be an error in the displayed UI content later in the process 11600, the module control circuit 11506 and/or header control circuit 11508 can determine whether the source of the error was with the display screen 11510 itself or an error by the header module 11504 in causing the display screen 11510 to display the UI content.

Accordingly, the header control circuit 11508 can transmit 11614 to the module 11502 any rendered UI content that was based on data that was indicated as safety critical by the module 11502. As with the initial transmission of the data, the safety critical UI content can be transmitted 11614 to the module 11502 via, for example, the data bus/interface 3008.

Accordingly, the module control circuit 11506 can determine 11616 whether the displayed safety critical UI content coincides with the transmitted safety critical data. If it is determined that the displayed safety critical UI content does not coincide with the transmitted safety critical data, then the module control circuit 11506 and/or header control circuit 11508 can take a variety of different actions, including providing a visual, audible, and/or haptic alert to the user (e.g., via the display screen 11510), deactivating the module 11502, and/or deactivating a surgical instrument or tool coupled to the module 11502. For example, if the module 11502 is an energy module 2004 and the module control circuit 11506 determines 11616 that the displayed energy module power level does not coincide with the actual energy module power level, then the module control circuit 11506 can cause the energy module 2004 to de-energize the surgical instrument connected to the energy module 2004 (i.e., stopping delivering power thereto) and the header control circuit 11508 can cause the display screen 11510 to display an alert.

In this way, the process 11600 by and between the module control circuit 11506 and/or header control circuit 11508 provides a verification loop that allows the header module 11504 to passively display safety critical data received from the module 11502 (obviating the need for the header module 11504 to always receive system updates in concert with the module 11502), while still ensuring that safety critical content is being properly and correctly displayed to users.

In one aspect, the display screen 11510 can be directly or physically coupled to the header module 11504. In another aspect, the display screen 11510 can be a remote UI, such as a nurse's screen in a control tower in the operating room or a video overlay on an endoscope monitor, for example.

In one aspect, the verification loop embodied by the process 11600 can be executed across a secondary bus/interface separate from the bus/interface 3008 described in connection with FIGS. 33-35, which may or may not be dedicated to the verification of the display of safety critical UI content. The secondary bus/interface could serve as a back up to the bus/interface 3008 in case of a failure of the bus/interface 3008 to ensure that the modular energy system 11500 is monitoring and verifying any displayed safety critical UI content even in the event that the primary bus/interface 3008 of the modular energy system 11500 has failed.

Figure 95:
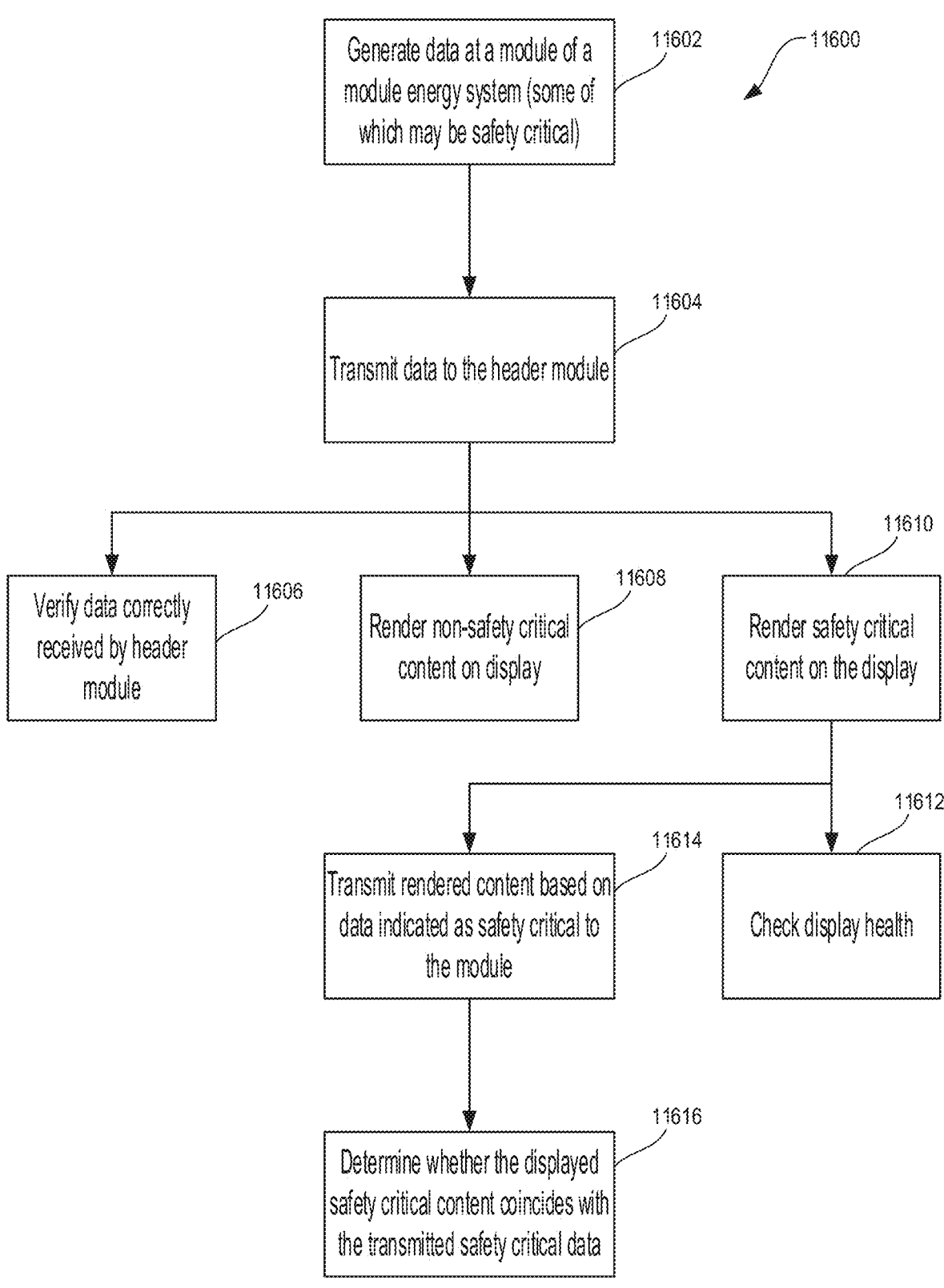
FIG. 95 is a logic flow diagram of a process for verifying displayed UI content, in accordance with at least one aspect of the present disclosure.

It should be further noted that although FIG. 94 illustrates a single module 11502 connected to the header module 11504 and the process 11600 described in connection with FIG. 95, the techniques described herein are equally applicable to modular energy systems 11500 including any number of modules connected to the header module 11504. In the event of there being more than one module being connected to the header module 11504, the described techniques can be executed by and between the header control circuit 11508 and any control circuits of the connected modules.

Energy Module Port Configurations

As discussed above under the heading MODULAR ENERGY SYSTEM, an energy module 2004 (FIGS. 24-30) can include a variety of different ports and associated circuitry that are configured to deliver various energy modalities, such as bipolar ports, monopolar ports, ultrasonic ports, and/or combination energy ports. Each type of energy port can have a different arrangement electrical contacts or pins, which can be referred to as a "pin out." In various aspects, the ports can have pin outs that allow them to engage with multiple types of electrical connectors having different plug or electrical connector arrangements. This can be beneficial because it allows ports to be able to flexible engage different types of electrical connectors, which in turn may have different numbers and/or arrangements of plugs or electrical connectors as dictated by the needs of the circuitry of the different surgical tools. However, ports that are able to engage multiple electrical connectors can create an issue because if a single port can engage with two different connector types, then the two different connectors could potentially be simultaneously engaged with the port unless the port's pin out is configured to prevent such a situation. Two electrical connectors for two different surgical instruments simultaneously being connected to and driven from a single port can be a dangerous situation because it can cause power fluctuations, arcing between the electrical connectors, and other issues.

In one general aspect, the monopolar port of an energy module can include a large diameter pin and a set of (e.g., three) small diameter pins that interfere so that a connector can only be engaged with one of the large diameter pin or the set of small diameter pins at a time.

Figures 96A, 96B:
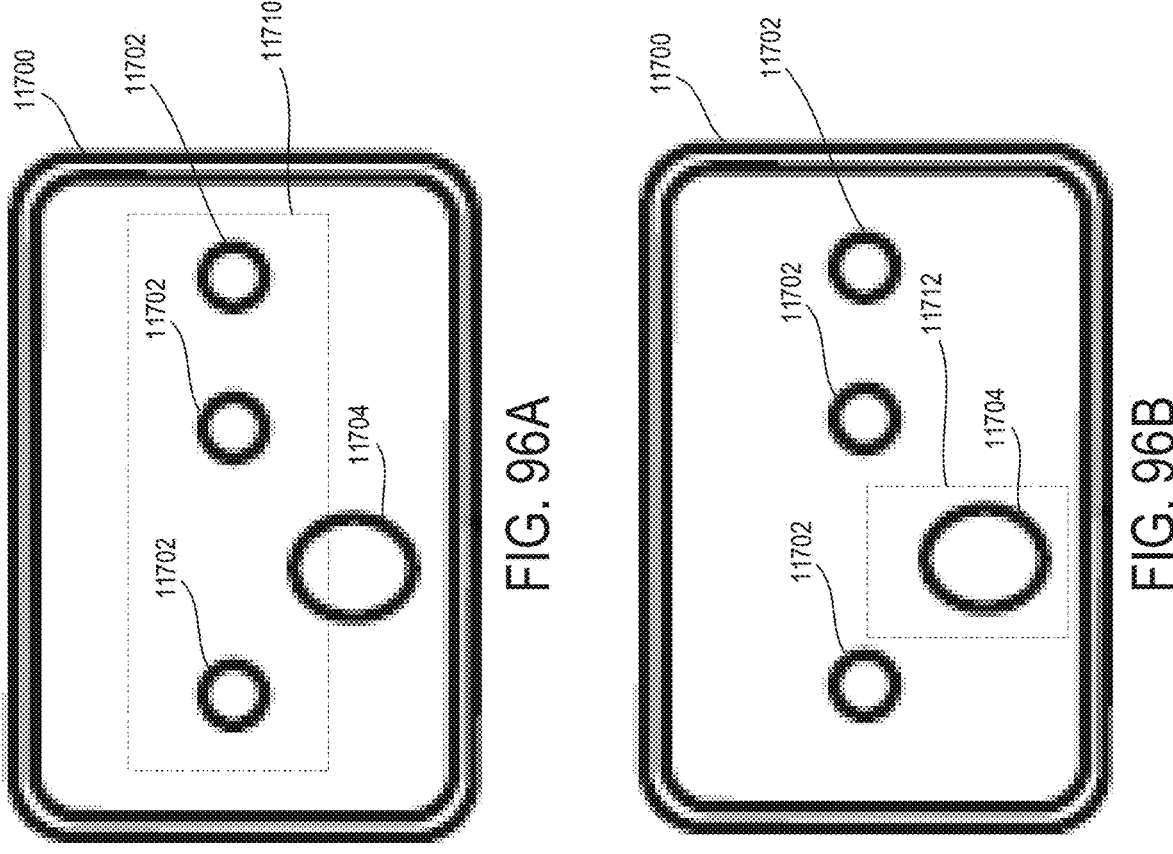
FIG. 96A is a monopolar port engaged with a first connector type, in accordance with at least one aspect of the present disclosure.
FIG. 96B is a monopolar port engaged with a second connector type, in accordance with at least one aspect of the present disclosure.

In one aspect, as shown in FIGS. 96A and 96B, the monopolar port 11700 can comprise different sets of electrical contacts that are configured to engage with different types of connectors. For example, the monopolar port 11700 can include a first set of one or more electrical contacts configured to engage a first connector type and a second set of one or more electrical contacts configured to engage a second connector type. The various electrical contacts can include receptacles or female contacts disposed on the surface of the monopolar port 11700 that are sized and shaped to receive a corresponding male contact of a particular connector type. The electrical contacts of the monopolar port 11700 can be circular or a variety of other shapes.

In the particular example shown in FIGS. 96A and 96B, the monopolar port 11700 can include a set of first electrical contacts 11702 that are configured to collectively engage with a first connector type 11710 and a second electrical contact 11704 that is configured to engage with a second connector 11712. The first electrical contacts 11702 can have a first diameter and the second electrical contacts 11704 can have a second diameter. In one aspect, the second diameter can be larger than the first diameter. Further, the first electrical contacts 11702 are positioned in a linear arrangement across the monopolar port 11700 and the second electrical contact 11704 is positioned offset from the longitudinal axis of the linearly arranged first electrical contacts 11702. The first electrical contacts 11702 and the second electrical contact 11704 are positioned relative to each other is selected such that a first connector 11710 engaged with the first electrical contacts 11702 obstructs the second electrical contact 11704, preventing or otherwise interfering with the ability of a second electrical connector 11712 to engage with the second electrical contact 11704, as is shown in FIG. 96A. Further, the first electrical contacts 11702 and the second electrical contact 11704 are positioned relative to each other is selected such that a second connector 11712 engaged with the second electrical contact 11704 obstructs the first electrical contacts 11702, preventing or otherwise interfering with the ability of a first electrical connector 11710 to engage with the first electrical contacts 11702, as is shown in FIG. 96B. In the particular example shown in FIGS. 96A and 96B, there are three first electrical contacts 11702 and the second electrical contact 11704 is arranged between a distal one of the first electrical contacts 11702 and a pair of the first electrical contacts 11702; however, different numbers and arrangements of the first and second electrical contacts 11702, 11704 are possible.

This interfering arrangement of the electrical contacts 11702, 11704 may advantageously improve the safety of a monopolar port 11700. Further, such an arrangement is additionally possible for other types of ports (i.e., ports configured to deliver different energy modalities). By preventing the user from inserting connectors for more than one monopolar electrosurgical surgical instrument, the risk of an electrical circuit overload of the monopolar energy port involving an electrical fire or unsafe power surge, for example, advantageously may be reduced or prevented.

Consolidated User Interface

One challenge with capital energy systems for surgical procedures is that they all include their own control interfaces. In addition to having to individually control each of the capital energy systems, users must also learn the individual nuances associated with controlling all of the various interfaces. This problem often cannot be avoided because surgical procedures regularly employ multiple different types of energy systems. Being forced to individually control every single energy system via a different control interface, each of which often has its own idiosyncrasies, slows down surgical procedures and introduces the possibility for errors if individuals are not fully accustomed to every single control interface with which they are forced to interact. As described above, the present disclosure describes a modular energy system configured to serve as a single, consolidated capital energy system for an OR. In conjunction with the modular energy system described hereinabove, it can further be beneficial to provide a single, consolidated UI for controlling all of the different modules that make up the modular energy system.

In various aspects, the present disclosure provides a visual interface for a modular energy system, which can include a header module that is removably connectable to a variety of different modules, such as an energy module, as is described above under the heading MODULAR ENERGY SYSTEM. The visual interface can be configured to change the appearance and size of module controls based on sensing connected module(s). Further, the visual interface can be configured to visually coordinate the activation status and ready status with the physical port of an energy module. The majority of the screen area of the visual interface can be dedicated to the main energy modules, with secondary modules placed in reduced menu states for occasional interaction. Further, the visual interface can provide alarms and notifications, which can overlap with the control interface(s) when alarms/notifications pop up.

In one aspect, the present disclosure also provides a modular energy system where user preferences can be stored and accessed through menus provided by the modular energy system visual interface in order to prepopulate device settings across multiple modules based on the procedure type selected by the user(s) (among other selection options).

Figure 97:
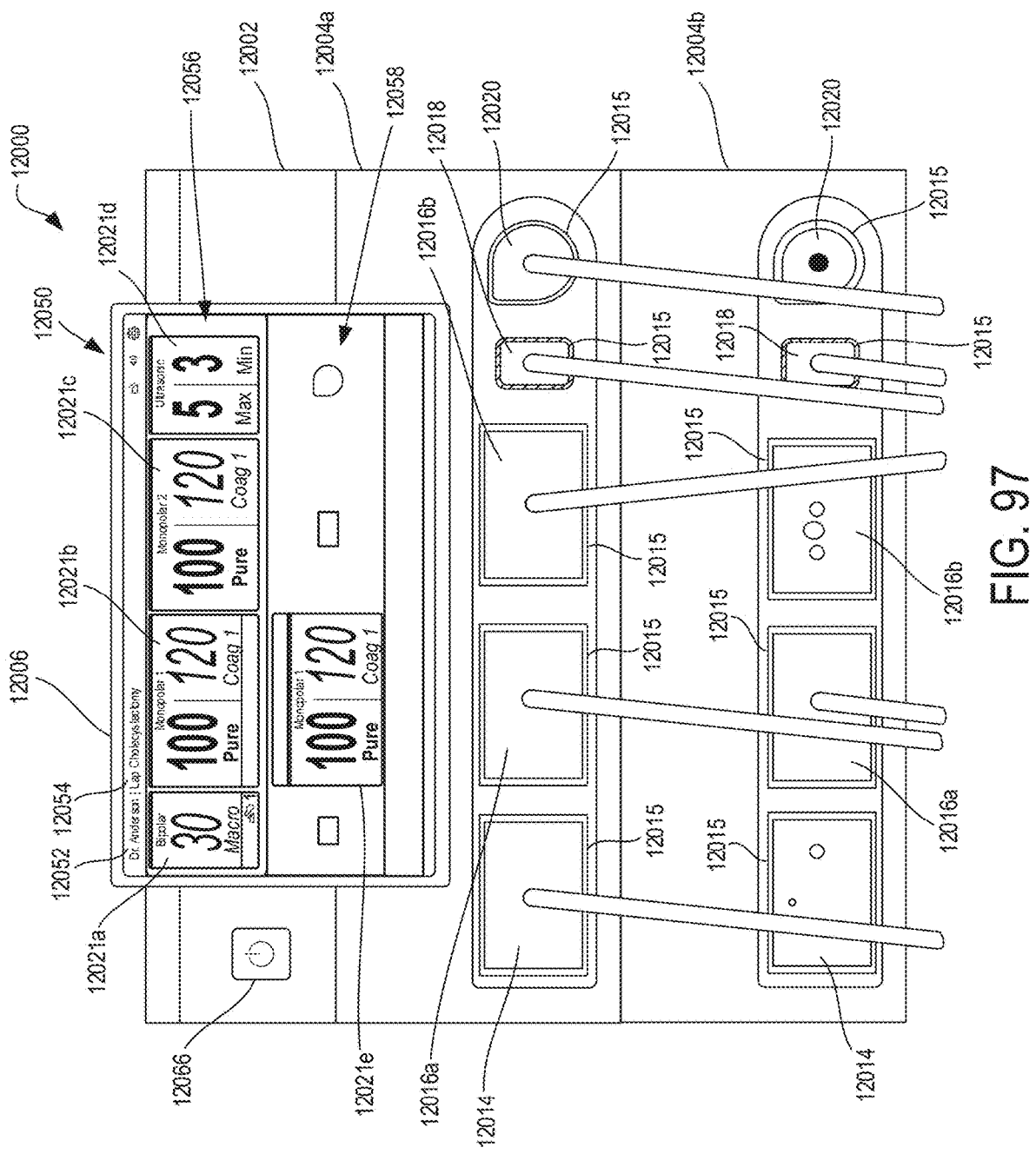
FIG. 97 is a front view of an illustrative modular energy system including a consolidated user interface (UI), in accordance with at least one aspect of the present disclosure.

FIG. 97 is a front view of an illustrative modular energy system 12000 including a consolidated UI, in accordance with at least one aspect of the present disclosure. The modular energy system 12000 can include multiple energy modules (shown in FIG. 97 with two energy modules 12004a, 12004b), a header module 12002, and a display screen 12006 supporting a UI 12050, as described above under the heading MODULAR ENERGY SYSTEM. The display screen 12006 can include a touchscreen for receiving user inputs and/or manipulating or controlling the UI 12050 displayed thereby. In some aspects, all of the modules that are connected to the header module 12002 can be controlled by a single UI (i.e., the UI 12050) that is disposed on or integral to the header module 12002. Consolidating all of the controls for the individual modules into a single, responsive UI that controls the module energy system 12000 as a whole provides a simpler way to control and monitor multiple pieces of surgical equipment at once. This approach drastically reduces footprint and complexity of surgical systems within an OR.

The modular energy system 12000 shown in FIG. 97 may be similar to other modular energy systems described herein such as modular energy system 2000. All of the modules that make up the modular energy system 12000 may be controlled by a single UI supported by or otherwise associated with the header module 12002. This may advantageously consolidate the control of all of the modules in the modular energy system 12000 into a single responsive UI, obviating the need to individually control each of the modules through their own UIs. As a result, the modular energy system 12000 beneficially may provide a simpler way to control and monitor multiples pieces of equipment simultaneously. In one aspect, the UI can be embodied as a graphical UI (GUI). The modular energy system 12000 comprises a display screen 12006 that may be similar to other display screens described herein, such as the display screen 2006 described in connection with FIG. 30. In one aspect, the display screen 12006 can be structurally incorporated into the header module 12002 (which may be similar to header modules described herein, such as the header module 2002 described in connection with FIGS. 24-29). In other aspects, the display screen 12006 can be removably connectable to the header module 12002 and/or communicably connectable to the header module 2002 (e.g., via wired or wireless connections). The UI provided by the header module 12002 may comprise UI elements or components for displaying information to users and/or receiving inputs from users. The UI elements can include interactive components and/or noninteractive components, such as widgets, icons, or menus. The UI elements provided by the UI 12050 can be utilized to control system wide settings (e.g., system volume); settings, modes, or functions for energy modules 12004a, 12004b connected to the header module 12002; assignment or functions of accessories that are connected to the header module 12002; and so on. Further, the UI 12050 can be configured to indicate a variety of different information to users, such as the surgeon profile that is signed into the module energy system 12000, the surgical procedure type being performed, and so on. For example, as shown in FIG. 38, the UI 12050 displayed on the display screen 12006 can display the surgical procedure type 12054, which in the illustrated example is a laparoscopic cholecystectomy, and the name 12052 (or another identifier, such as an identification number or a user name) of the clinician performing the given surgical procedure. In addition to the UI 12050, the header module 12002 can additionally include physical controls for controlling the functions of the modular energy system 12000, such as a power button 12066.

To illustrate the concepts of the modular energy system UI, the modular energy system 12000 is depicted as including a first energy module 12004a and second energy module 12004b (which can be similar to energy modules described herein, such as the energy modules 3004, 3012 described in connection with FIGS. 31-35) that are connected to the header module 12002 in a stacked configuration; however, the modular energy system 12000 is not limited to this or any other particular number, type, or arrangement of modules. As described above, the modular energy system 12000 can be arranged in a number of different configurations and include a variety of different modules. Further, the energy modules 12004a, 12004b can be configured to function as power and data interfaces between the header module 12002 and/or adjacent modules in the stacked configuration of the modular energy system 12002. Each of the energy modules 12004a, 12004b may include a port assembly 12012a, 12012b. The port assemblies 12012a, 12012b (which can be similar to the port assembly 2012 described in connection with FIG. 25A, for example) can include multiple different port types for delivering different energy modalities to corresponding surgical instruments that are connectable thereto, as described above. In one particular implementation, the port assemblies 12012a, 12012b may include a bipolar port 12014, a first monopolar port 12016a, a second monopolar port 12016b, a neutral electrode port 12018 (also referred to as a monopolar return pad port), and/or a combination energy port 12020; however, in other aspects, the port assemblies 12012a, 12012b can include other combinations of port types. Further, the modular energy system 12000 can include additional modules such as a technology module 2040 (FIG. 24) or a visualization module 2042 (FIG. 24), for example. These other modules can likewise serve as power and data interfaces between the header module 12002 and/or adjacent modules in the modular energy system 12002.

The UI 12050 displayed via the display screen 12006 may display a representation for each module connected to the modular energy system 12000. In one aspect, the UI 12050 can comprise UI components or elements that correspond to each of the modules connected to the header module 12002. As modules are connected and disconnected from the header module 12002, new UI elements for newly connected modules can be added to the UI 12050 and currently displayed UI elements fore disconnected modules can be removed from the UI 12050. Accordingly, the other UI elements displayed on the UI 12050 can be resized, repositioned, or otherwise reconfigured to accommodate the UI elements for newly connected modules or occupy the space on the UI 12050 vacated by the UI elements for disconnected modules. In other words, as modules are connected and disconnected from the modular energy system 12000, the illustrated graphical features on the UI 12050 can change. For example, the UI 12050 can alter to eliminate a display area for a module that is now disconnected from the modular energy system 12000. Conversely, as more modules are connected to the header module 12002, the display areas may scale or increase in number in corresponding relationship to the increase in connected modules. In general, the UI 12050 can provide a particular zone that is designated for each module connected to the header module 12002. Further, in one aspect, the arrangement or position of the modules' UI components within the UI 12050 can correspond to the physical arrangement of the modules within the stacked configuration of the modular energy system 12000 and/or the physical position of various components of the modules to which the UI components correspond, such that the UI 12050 visually coincides with the physical arrangement of the modular energy system 12000 so that the information and/or controls provide by the modules' UI elements can be easily located. Various techniques for detecting when modules are connected/disconnected from the modular energy system 12000 and modules' relative positions within the stack of the modular energy system 12000 are disclosed in U.S. patent application Ser. No. 16/562,142, titled METHOD FOR ENERGY DISTRIBUTION IN A SURGICAL MODULAR ENERGY SYSTEM, filed concurrently herewith, which is hereby incorporated by reference herein in its entirety.

As noted above, in one aspect, the UI 12050 can include a number of UI portions that correspond to the modules connected to the UI. For example, the UI 12050 illustrated in FIG. 97 includes a first UI portion 12056 that corresponds to the first module (which, in this particular example, is a first energy module 12004a) connected to the header module 12002 and a second UI portion 12058 that corresponds to the second module (which, in this particular example, is a second energy module 12004b) connected to the header module 12002. Further, in this particular example, the first UI portion 12056, which corresponds to the first energy module 12004a, can be located along an upper portion of the UI 12050 to coincide with the relative position of the first energy module 12004a within the modular energy system 12000. Similarly, the second UI portion 12058, which corresponds to the second energy module 12004*b*, can be located along a bottom portion of the UI 12050 to coincide with the relative position of the second energy module 12004*b* within the modular energy system 12000. Additionally, the various UI elements displayed in each UI portion can correspond to the type of module that the UI portion is dedicated to. For example, the first UI portion 12056, which corresponds to the first energy module 12004*a*, can include four UI elements 12021*a*-12021*d* that correspond to the bipolar port 12014, the first monopolar port 12016*a*, the second monopolar port 12016*b*, and the combination energy port 12020, respectively. In one aspect, the UI portion for a connected energy module can be configured to display the UI element 12021*a-d* corresponding to each of the ports 12014, 12016*a*, 12016*b*, 12020 of the first energy module 12014*a* only when a surgical instrument is connected thereto. In the example shown in FIG. 97, a surgical instrument is connected to each of the ports 12014, 12016*a*, 12016*b*, 12020; therefore, each of the corresponding UI elements 12021*a-d* are displayed on the UI portion 12056. Conversely, the second UI portion 12058 is only displaying a single UI element 12021*e* corresponding to the first monopolar port 12016*a* of the second energy module 12014*b* because the first monopolar port 12016*a* is the only port of the second energy module 12014*b* to which a surgical instrument is connected. When a surgical instrument is not connected to a particular port, the corresponding UI portion(s) 12056, 12058 can be configured to display, for example, static images, such as a shape corresponding to the shape of the unused port so that a user can easily ascertain which particular port type is unused. As with also be appreciated from the example shown in FIG. 97, the positions of the UI elements 12021*a-d* within the UI 12050 can further coincide with the relative physical position of the ports 12014, 12016*a*, 12016*b*, 12020.

The UI elements for energy modules can be configured to display information (e.g., operational parameters) related to the surgical instrument connected to the port 12014, 12016*a*, 12016*b*, 12020 associated with the particular UI element. For example, a first UI element 12021*a* indicates that the first energy module 12014*a* is set to energize the bipolar electrosurgical instrument connected thereto to deliver energy at 30 watts in a macro mode; a second UI element 12021*b* indicates that the first energy module 12014*a* is set to energize a first monopolar electrosurgical instrument connected thereto to deliver energy at 100 watts in a pure therapeutic cut mode and 120 watts in a first coagulation mode; a third UI element 12021*c* indicates that the first energy module 12014*a* is set to energize a second monopolar electrosurgical instrument connected thereto to deliver energy at 100 watts in the pure therapeutic cut mode and 120 watts in the first coagulation mode; a fourth UI element 12021*d* indicates that the first energy module 12014*a* is set to energize an ultrasonic surgical instrument connected thereto to deliver energy at a maximum power level five and a minimum power level three; and a fifth UI element 12021*e* indicates that the second energy module 12014*b* is set to energize a third electrosurgical monopolar instrument connected thereto to deliver energy at 100 watts in the pure therapeutic cut mode and 120 watts in the first coagulation mode. The power level of the ultrasonic instrument could be measured by the amperes of current delivered to the piezoelectric crystal contained within the instrument. Each of the various UI elements 12021*a-e* in the UI portions 12056, 12058 can display information associated with the respective energy module 12004*a-b* and/or surgical instrument connected thereto as long as that instrument is plugged into the modular energy system 12000. Further, the UI elements 12021*a-e* can also function as widgets that are manipulable or otherwise controllable by users to change the settings associated with the energy module 12004*a-b* and/or surgical instrument to which the UI element 12021*a-e* corresponds. For example, the UI elements 12021*a-e* can allow uses to change the amount of energy being delivered by the energy module 12004*a-b*, change the mode in which the surgical instrument is being operated.

Figure 36B:
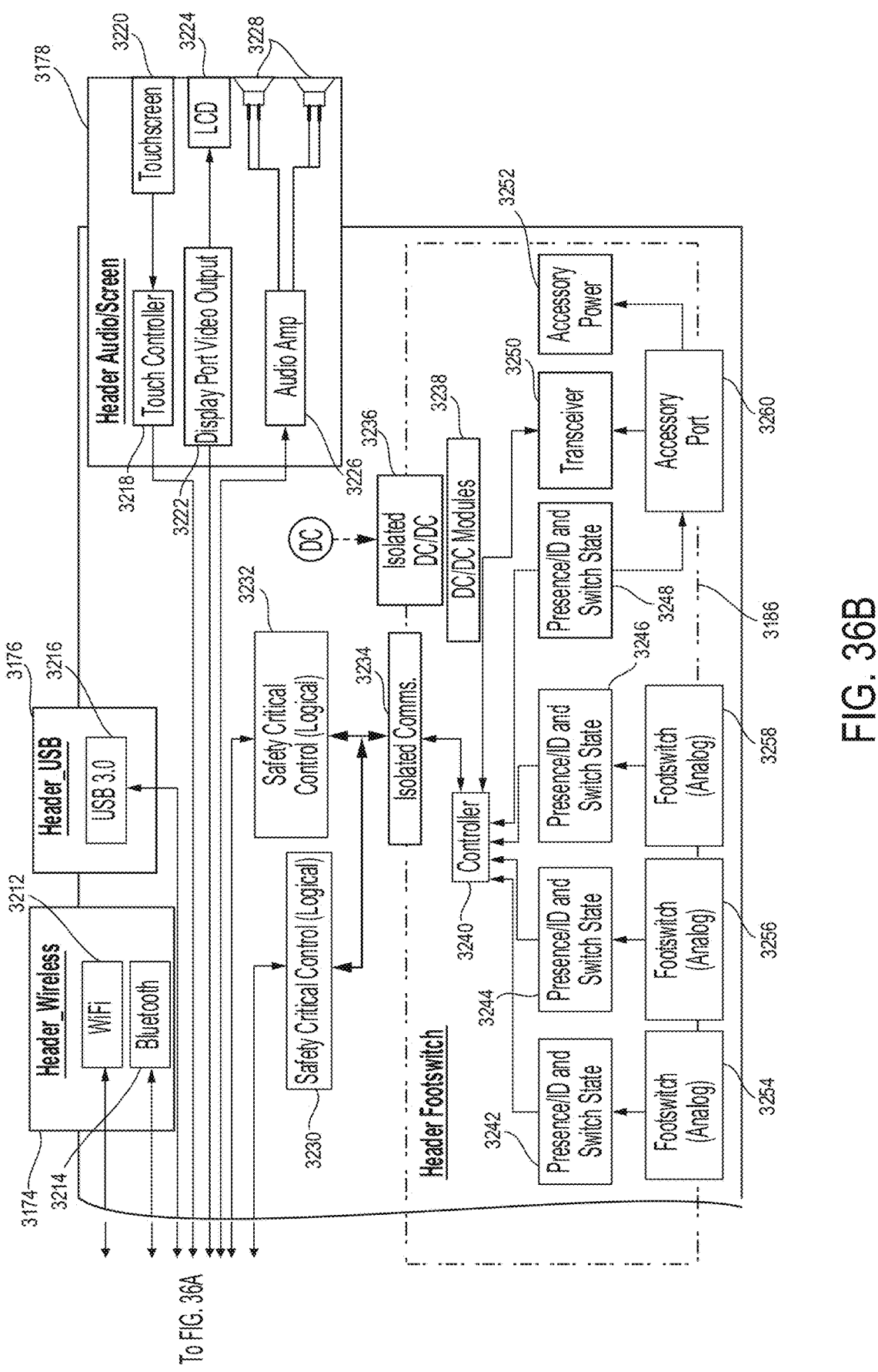
Figure 98:
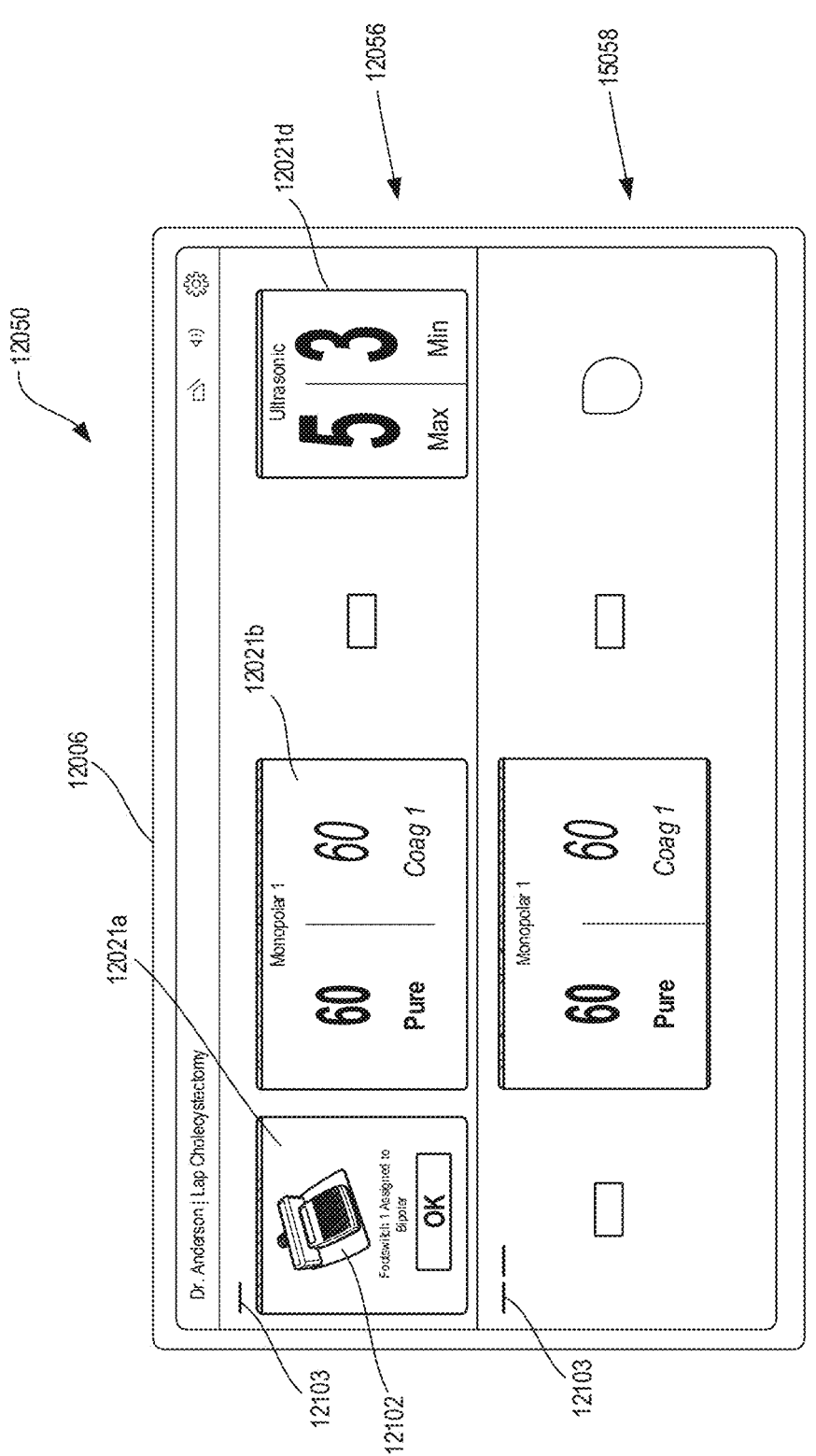
FIG. 98 is a view of a graphical UI of an illustrative modular energy system configuration, in accordance with at least one aspect of the present disclosure.

FIG. 98 is a view of a UI 12050 of an illustrative modular energy system configuration, in accordance with at least one aspect of the present disclosure. In one aspect, the UI 12050 comprises a footswitch assignment widget 12102. The UI 12050 can be configured to display the footswitch assignment widget 12102 when a user of the modular energy system 12000 has connected a surgical instrument or tool that requires connection to a footswitch, such as a single- or dual-pedal footswitch 2032, 2034 (FIG. 24). A control circuit of the modular energy system 12000, such as the control unit 3024 (FIG. 32) or the controller 3240 (FIG. 36B), can be configured to determine when a connected surgical instrument requires a footswitch and then control the UI 12050 to display a footswitch assignment widget 12102. In one aspect, the control circuit of the modular energy system 12000 can be configured to automatically assign a connected footswitch to a newly connected surgical instrument. As noted above, a footswitch or another accessory can be connected to the header module 12002 via an analog footswitch port 3254, 3256, 3258 (FIG. 36B). At this point, the footswitch assignment widget 12102 can be rendered on the UI 12050 to inform the user that a footswitch has been assigned to the connected surgical instrument, which, in the example shown in FIG. 98, is a bipolar surgical instrument. The footswitch assignment widget 12102 may be the same or similar to the control icon or widget displayed on the instrument settings panel of the surgical instrument that can be utilized to pair the surgical instrument with a system accessory, such as one of the footswitches 2032, 2034.

The UI 12050 can further comprise a location icon 12103*a-b* (or other UI element) indicating the position of the module within the stacked configuration of the modular energy system 12000 that the UI portions 12056, 12058 correspond to. As discussed above, the different UI portions 12056, 12058 of the UI 12050 can each correspond to a particular module connected to the header module 12002, in which each portion may display controls, data, user prompts, and other information corresponding to the particular module. In one aspect, the location icon 12103*a-b* can include a number of dashes or other indicia that indicates the particular module that the UI portion 12056, 12058 corresponds to. For example, one dash can correspond to the first or uppermost module within the stacked configuration of the modular energy system 12000, two dashes can correspond to the second energy module within the stacked configuration of the modular energy system 12000, and so on. Each dash of the location icon 12103 could also have a particular color or other indicia to differentiate the different location icons 12103 from each other. The color of the location icon 12103*a-b* can correspond to the UI portion or module with which it is associated. For example, the first UI portion 12056 and the corresponding first location icon 12103*a* could both include a first color (e.g., red), while the second UI portion 12056 and the corresponding second location icon 12103*b* could both include a second color (e.g., green).

In one aspect, the UI 12050 can be configured to coordinate the coloring of at least some of its UI components with the coloring of components of the modules connected to the header module 12002. For example, referring back to FIG. 97, each of the UI portions 12056, 12058 and/or associated UI elements 12021a-e can be configured to include or otherwise be coordinated with the colors emitted by light assemblies 12015 of the corresponding energy module 12004a-b. That is, the colors displayed by the UI 12050 can correspond to the port lighting of the energy modules 12004a-b. By coordinating the coloring between the physical components of the modules (e.g., the ports 12014, 12016a, 12016b, 12020 of the energy modules 12004a-b) and the UI components (e.g., the UI elements 12121a-e), the UI 12050 can allow users to quickly and easily ascertain which UI components are associated with which module components. The light assemblies 12015 may be similar to the light assemblies 2015 described above with respect to FIG. 30. Also, as described above, each of the light assemblies 12015 can be configured to change color when a plug of a surgical instrument or tool is fully inserted into a respective port of the port assembly, according to the mode or function of the surgical instrument, whether there is an error associated with the surgical instrument and/or the modules, and so on. Accordingly, the UI 12050 can be configured to change the coloring of the associated UI components to coincide therewith.

The UI portions 12056, 12058 and/or the UI elements 12021a-e rendered on the display screen 12006 can also change appearance and size based on sensing the connection of a module to the header module 12002. For example, the UI 12050 can change to display a first UI portion 12056 on the display screen 12006 that corresponds to the first energy module 12004a in response to the first energy module 12004a being connected to the header module 12002. Also, the lighting assemblies 12015 for each module and/or the UI portions 12056, 12058 can be used to visually coordinate the activation and ready status of the physical port that they are associated with. Further, the UI 12050 can further change to display a second UI portion 12058 of the display screen 12006 in response to the second energy module 12004b being connected to the header module 12002.

Figure 99:
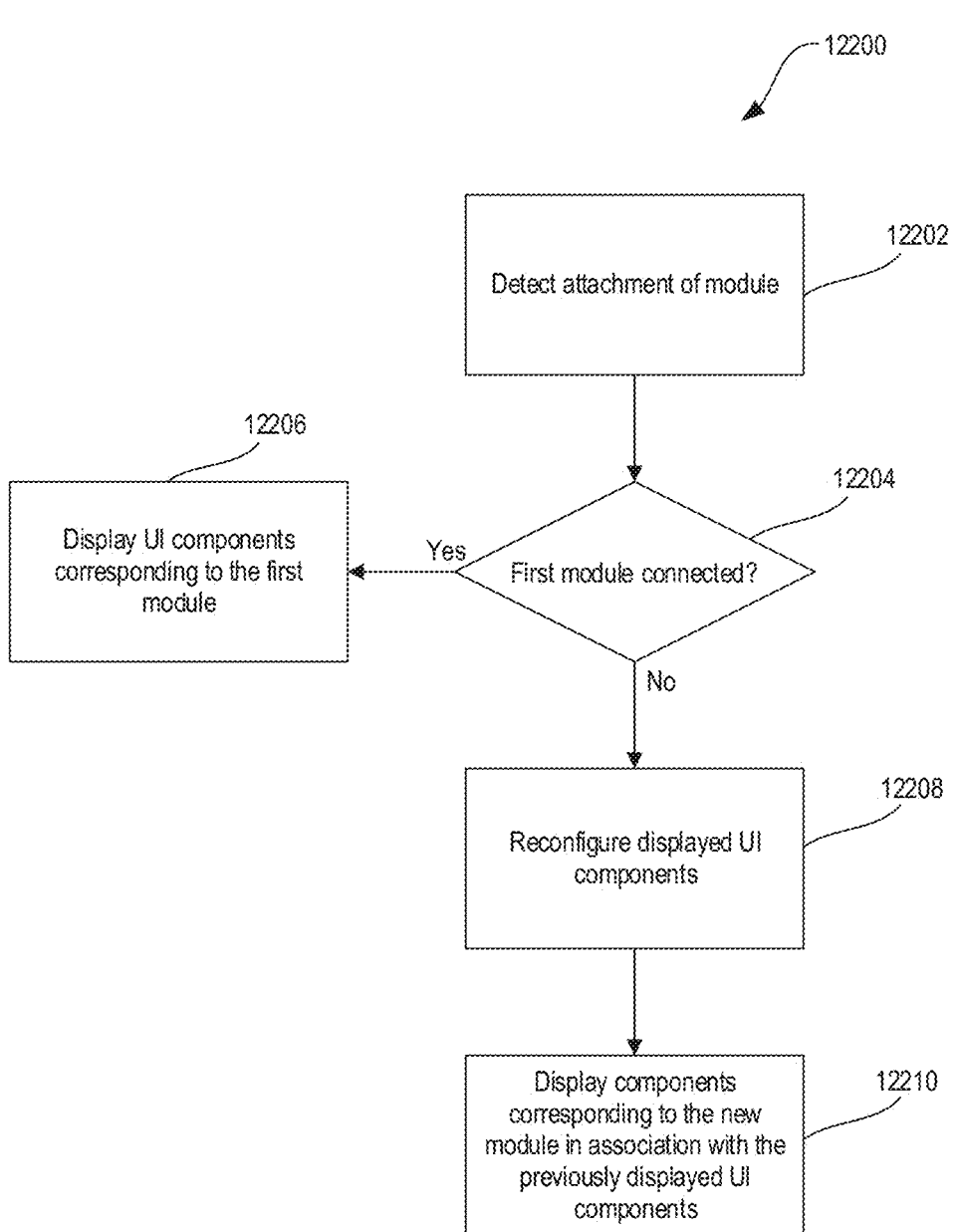
FIG. 99 is a logic flow diagram of a process for displaying UI components for connected modules, in accordance with at least one aspect of the present disclosure.

In one aspect, FIG. 99 is a logic flow diagram of a process 12200 for displaying UI components for connected modules, in accordance with at least one aspect of the present disclosure. The process 12200 can be embodied as, for example, instructions stored in a memory coupled to a control circuit (e.g., the control unit 3024 (FIG. 32) or the UI processor 3040 (FIG. 33)) that, when executed by the control circuit, cause the control circuit to perform the enumerated steps of the process 12200. In the following description of the process 12200, reference should also be made to FIGS. 97 and 98.

Accordingly, the control circuit detects 12202 attachment of a module, such as an energy module, to the header module 12002. The control circuit then determines 21204 whether the connected module is the first module that has been connected to the header module 12002, i.e., is the first module other than the header module 12002 in the modular energy system 12000 that is being assembled. If it is the first connected module, then the process 12200 proceeds along the YES branch and the control circuit, which is coupled to the display screen 12006, controls the display screen 12006 to display 12206 a UI component corresponding to the connected module type via the UI 12050. For example, the control circuit can cause the display screen 12006 to display the first UI portion 12056, including the associated UI elements 12021a-d, in response to the first energy module 12004a being connected to the header module 12002. If it is not the first connected module (i.e., there are already one or more modules connected to the header module 12002 in the modular energy system 12000), then the process 12200 proceeds along the NO branch and the control circuit controls the display screen 12006 to resize, reposition, or otherwise reconfigure 12208 the currently displayed UI components of the UI 12050 and display 12210 a UI component corresponding to the newly connected module type via the UI 12050. For example, the control circuit can cause the display screen 12006 to resize/reposition the first UI portion 12056 and its associated UI element(s) 12021a-d and correspondingly display the second UI portion 12058, including its associated UI element(s) 12021e, in response to the second energy module 12004b being added to the module stack of the modular energy system 12000. In this way, the UI 12050 can be configured to dynamically change according to the number and types of modules that are connected together to form the modular energy system 12000 and thereby provide a single, consolidated UI for collective controlling all of the connected modules.

Referring back to FIGS. 97 and 98, in one aspect, particular module types can be categorized within the UI 12050 as main or secondary modules. Secondary modules can be represented by smaller display areas on the display screen 12006. In particular, secondary modules can be placed in a reduced menu state so that they do not occupy an excessive amount of space on the display screen 12006 while remaining available for occasional user interaction. Further, the UI 12050 can comprise a particular area for displaying alarms and notifications as they are generated. For example, the alarms and notifications could be displayed along a top header portion of the display screen 12006.

In one aspect, the header module 12002 can further be configured to store user preferences, including prepopulated device settings across multiple modules in the modular energy system 12000. The UI 12050 can then be used to access these prepopulated device settings via UI menus. Additionally, the particular prepopulated settings can be determined by the modular energy system 12000 based on the surgical procedure selected by the user.

Modular Energy System Audio Techniques

Conventional surgical capital equipment can be designed to provide users with audiovisual feedback when surgical instruments driven thereby are activated or otherwise in use. For example, surgical capital equipment can be configured to output audible feedback when a surgical instrument is energized in order to ensure that the surgical staff is aware that the surgical instrument has been activated. In one implementation, this could take the form of an audio tone that is emitted by the capital equipment when an electrosurgical and/or ultrasonic surgical instrument connected thereto is energized. For conventional surgical capital equipment, when there are multiple different pieces of capital equipment within an OR that are actively in use, these activation tones can be distinguished from each other, even when the tones are very similar to each other, because of the fact that the capital equipment is located at different positions within the OR. Because the capital equipment generating the audio tones are located at different positions, this inherently creates different acoustic effects for each of the tones that allows the tones to be distinguished from each other. However, as is described above under the heading MODULAR ENERGY SYSTEM, the modular energy systems described herein are designed to replace the disparate pieces of surgical capital equipment and provide a single, consolidated system for driving all of the surgical instruments in use during a surgical procedure. This could create an issue with audio feedback because the different energy modules are located at a single location within the OR (namely, in the modular energy system stack), and thus, it could be challenging for users to differentiate between the same or similar tones being emitted from the modules because the tones are no longer originating from different locations within the OR. Therefore, there is a need for modular energy systems to implement various techniques to modulate audio feedback and/or generate unique audio feedback based upon the configuration of the modular energy system and other factors.

In one general aspect, a modular energy system can include at least two energy modules, which can each include multiple (e.g., four) ports. The modular energy system can be configured to construct unique audio signals for each port based on the number, type, and operational status of the connected modules. In one aspect, the signals can be constructed through modulation of at least two separate signals.

In one aspect, a modular energy system (e.g., the modular energy system(s) of FIGS. 24-37) can be configured to employ an audio control system that is configured to generate tones played by the modular energy system and confirm that the correct tone is being played for a given function being performed by the modular energy system. By ensuring that it is outputting the correct tone for each given function, the control system can prevent incorrect audio feedback from being provided to surgical staff members and other users during the course of a surgical procedure.

Figure 100:
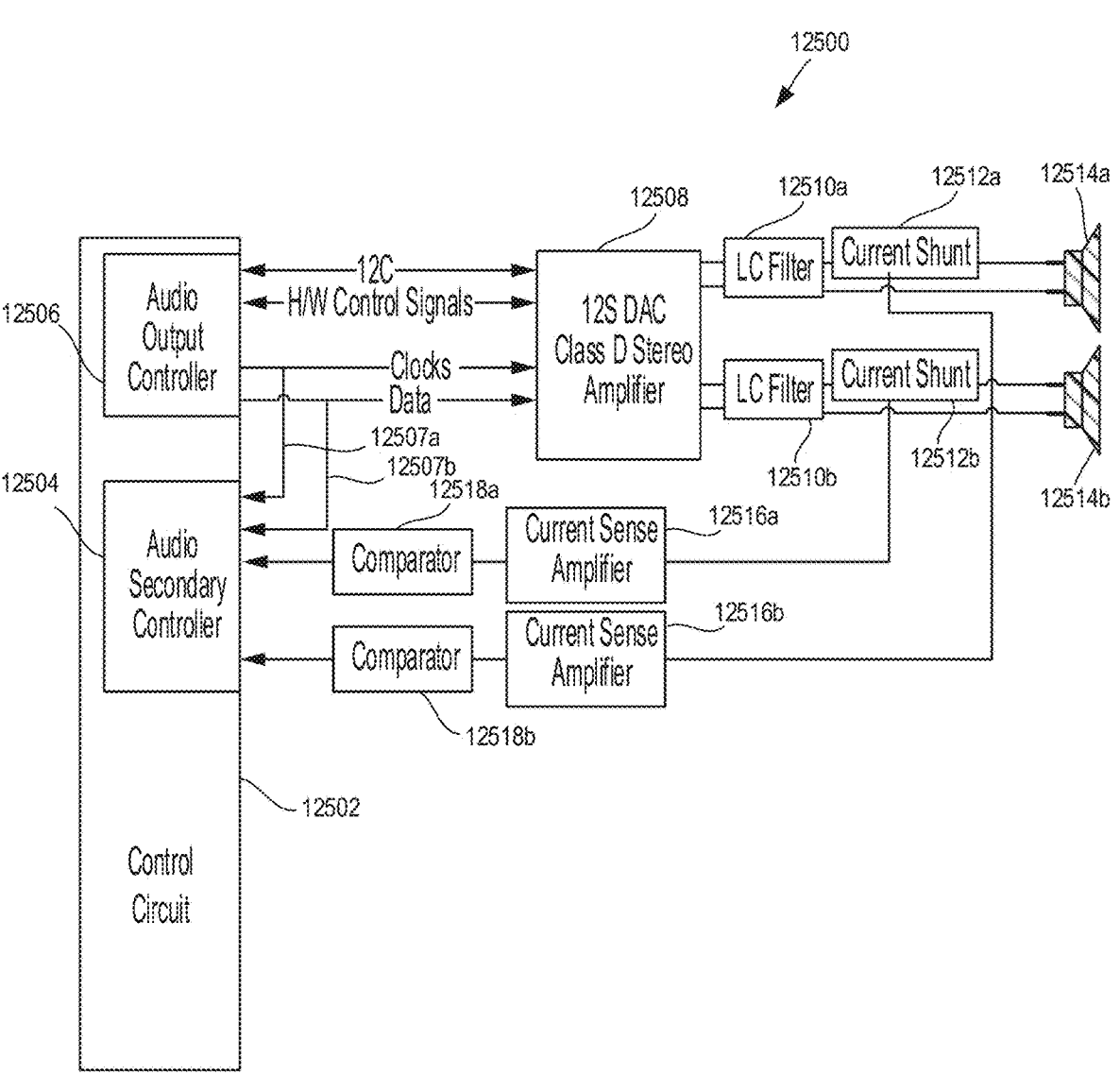
FIG. 100 is a block diagram of an audio control system for a modular energy system, in accordance with at least one aspect of the present disclosure.

For example, FIG. 100 is a block diagram of an audio control system 12500 for a modular energy system. The audio control system 12500 can include a control circuit 12502, which can in turn include an audio output controller 12506 and an audio secondary controller 12504. The audio output controller 12506 can be configured to generate audio signals, which can include digital audio signals, that are provided to an audio amplifier 12508 (e.g., a 12S digital-to-analog (DAC) class D stereo amplifier) for output by one or more audio output devices 12514*a-b* (e.g., speakers). The audio secondary controller 12504 is further coupled to the audio output controller 12506 via the circuit connections 12507*a-b*, such that the audio secondary controller 12504 receives the audio signals from the audio output controller 12506 prior to them being emitted by the audio output devices 12514*a-b*. In one aspect, the audio signal output by the audio output controller 12506 can include a segment that includes or represents an audio signal identifier (ID) that uniquely identifies the particular tone to which the audio signal corresponds. The audio signal output by the audio output controller 12506 can be generated from, for example, an audio file that includes the audio signal ID.

Accordingly, the audio secondary controller 12504 can receive, via the circuit connections 12507*a-b*, the signal, including the audio signal ID embedded therein, output by the audio output controller 12506. The audio signal ID, which can be embedded in extra bits of the digital audio signal output by the audio output controller 12506, can be used to confirm that the audio output controller 12506 is outputting an appropriate signal to the audio amplifier 12508 (i.e., that the audio output controller 12506 is attempting to play the proper tone). In one aspect, the audio secondary controller 12504 can be configured to compare the audio signal from the digital audio signal output by the audio output controller 12506 to an expected audio signal. In one further aspect, the audio secondary controller 12504 can be configured to compare the audio signal ID from the audio output controller 12506 to an expected audio signal ID to determine whether the correct signal is being output by the audio output controller 12506. In an alternative aspect, the audio secondary controller 12504 can be configured to compare the entirety of the output audio signal or the portion of the output audio signal utilized by the audio amplifier 12508 to create the audio tone to an expected audio signal to determine whether the correct signal is being output by the audio output controller 12506. The expected audio signal and/or audio signal ID against which the audio secondary controller 12506 compares the received actual output audio signal and/or signal ID can be determined by the audio secondary controller 12506 through independent knowledge of the modular energy system status or other processes.

The audio control system 12500 can further include one or more LC filters 12510*a-b* coupled to current shunts 12512*a-b* and the audio output devices 12514*a-b*. Further, the audio control system 12500 can include current sense amplifiers 12516*a-b* coupled to the current shunts 12512*a-b* and comparators 12518*a-b* coupled to the current sense amplifiers 12516*a*— b. The output of the comparators 12518*a-b* is coupled to the audio secondary controller 12504.

Accordingly, the audio secondary controller 12504 can receive, via the current shunts 12512*a-b* and associated components, a current measurement signal of the audio signal output by the audio amplifier 12508. In one aspect, the audio secondary controller 12504 can be configured to compare the current measurement signal to a threshold for determining if the audio amplifier output is within an expected intensity range. By determining whether the audio amplifier output is within the expected intensity range, the audio secondary controller 12504 can confirm that the audio amplifier 12508 is functioning at a sufficient level (i.e., is driving enough power to the audio output devices 12514*a-b*) and/or that the audio output devices 12514*a-b* are functioning and/or connected properly (i.e., the audio output devices 12514*a-b* are connected to the audio amplifier 12508 and based upon the lack of an open or short circuit).

In one aspect, the audio secondary controller 12504 can be configured to further or alternatively compare the direct output of the audio output controller 12506 and the output being fed to the audio output devices 21514*a-b* to confirm that the audio output devices 21514*a-b* are outputting the correct tone given the generated audio signal.

In yet another aspect, the audio secondary controller 12504 can be configured to identify the specific tone being output via the audio output devices 21514*a-b* according to the current measurement signal received from the current shunts 12512*a-b* and associated components. Accordingly, the audio secondary controller 12504 can be configured to determine whether the tone, which was determined via the current measurement signal, is appropriate for the given situation or modular energy system status. For example, the audio secondary controller 12504 can be configured to determine whether the correct activation tone is being played via the audio output devices 21514*a-b* when an instrument is activated/energized. Therefore, the audio secondary controller 12504 can ensure both that the tone is appropriate and that the audio amplifier 12508 is functioning properly.

Because a modular energy system (e.g., the modular energy system(s) of FIGS. 24-37) can include an energy module that can simultaneously energize multiple instruments and the activation or energization of each instrument can have a unique tone associated with it, the modular energy system can, in some situations, be outputting multiple overlapping tones. Further, the modular energy system could also output other tones associated with alerts or messages being provided to users that can overlap with other tones being output by the modular energy system. Because of the close proximity between the energy module(s) and the other audio-emitting modules of the modular energy system due to the nature of its stacked configuration, these overlapping tones could potentially interfere with each other or be difficult for users to audibly discern from each other. In one aspect, the modular energy system can be configured to generate unique audio outputs when multiple audio-emitting functions are being performed by the modular energy system. In other words, the modular energy system can be configured to generate a single unique audio output, rather than multiple overlapping audio outputs. Therefore, the modular energy system can ensure that all provided audible feedback is readily discernible by the users. In one further aspect, the unique audio output can be generated based upon the particular combination of tones that would otherwise have been output in an overlapping manner.

In one aspect, every audio file representing a tone output by the modular energy system can include an embedded ID that is unique to that audio file. The functions of the modular energy system that can be assigned audio files that are to be output when the functions are being formed can include, for example, energizing or activating a particular instrument type or providing a particular type of alert or message. Each different surgical instrument drivable by the modular energy system and alert/message that can be provided by the modular energy system could have a different tone associated with it in order to provide users confirmatory audible feedback as to each individual function type being performed by the modular energy system. In one aspect, each audio file can include a first series of bits (e.g., 16 bits) representing the digital audio signal for the tone and a second series of bits (e.g., 8 bits) representing the header or ID for the tone. Upon determining that a particular function is being performed by the modular energy system, the audio output controller 12506 can be configured to retrieve the appropriate audio file corresponding to the function and then pass a sequence of bits, including the digital audio signal and the associated ID to the amplifier 12508 (which ignores the ID bits when generating the output audio waveform). Accordingly, the audio secondary controller 12504 can be configured to read the output of the audio amplifier 12508 and ensure that the embedded ID corresponds to the appropriate audio file corresponding to a particular function being performed by the modular energy system, as is generally described above. The embedded audio file IDs can also be utilized in the process of generating unique tones from combinations of the individual audio files.

Figure 101:
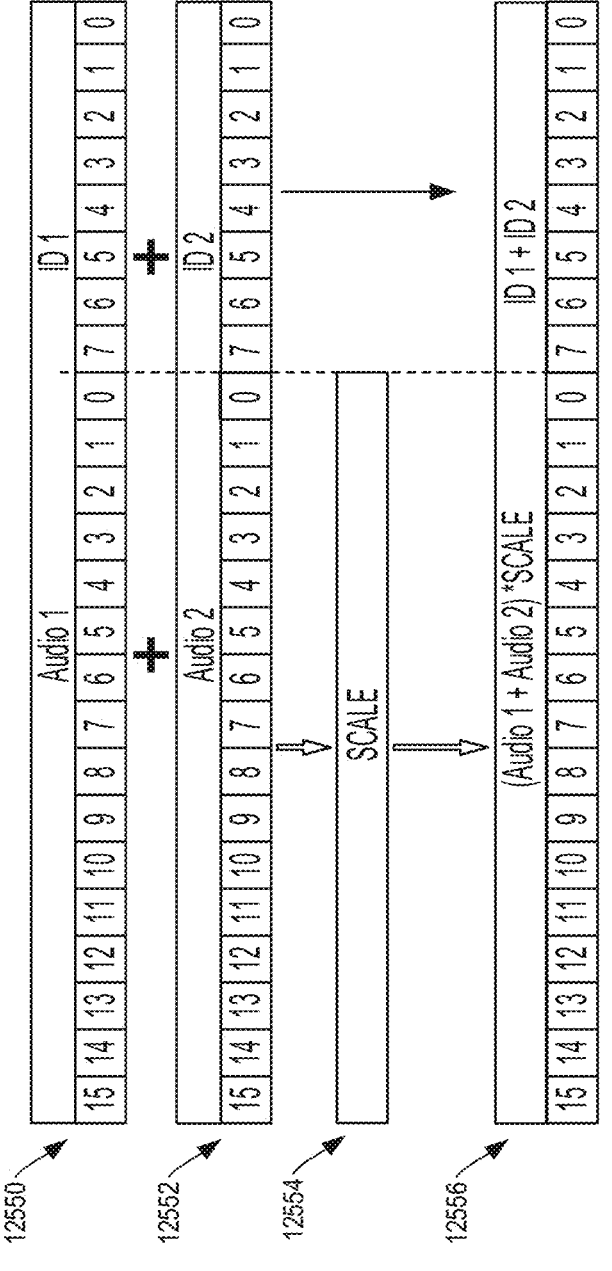
FIG. 101 is a diagram of a technique for generating unique audio outputs, in accordance with at least one aspect of the present disclosure.

In one aspect, the audio control system 12500 can be configured to generate unique tones that are based on particular combinations of individual tones for functions that are being simultaneously performed by the modular energy system. For example, FIG. 101 is a diagram of a technique for generating unique audio outputs. The technique embodied by FIG. 101 can be executed by the control circuit 12502 of the audio control system 12500 in FIG. 100, for example. In one aspect, the control circuit 12502 can be configured to generate a unique tone from a combination of individual tones that is output by the audio control system 12500 in lieu of the individual tones and provide a unique ID for confirming that the proper tone is being generated and output based upon the input individual tones.

In one aspect, the audio file IDs can be selected such that the sum of a given number of any of the IDs is not equal to any of the IDs. In other words, the IDs can be selected such that the sum of a given number of the IDs is a value that is unique from the selected IDs. One method for generating a list of such IDs is by considering each possible ID number from the lowest allowable ID to the highest allowable ID. In particular, each candidate ID can only added to a list of valid IDs if: (i) it is not equal to a sum of a combination of existing valid IDs and (ii) when summed with existing valid IDs (or a sum of a combination of existing IDs), the result is also not equal to other existing valid IDs or sums of combinations of IDs. This method guarantees that any number is either itself a unique individual ID or is a unique sum of a combination of IDs where the set of constituent individual IDs is exactly known. This method can be embodied as a set of steps, a closed-form or algorithmic mathematical expression, and so on. Ensuring that each combination of IDs is unique both from other combinations of the IDs and from the values of the IDs themselves allows the control circuit 12502 to differentiate between each particular combination of tones being generated by the audio control system 12500 and, thereby, verify that the correct tone is being played by the modular energy system for any combination of functions. For example, if two tones are being combined together, the IDs can include 1, 3, 7, 15, 25, 41, 61, 89, and so on. As can be seen in this example, the sum of any pair of the IDs is a unique value. Different IDs can be selected if three or more tones are being mixed or combined together, as the number of IDs being added together affects which particular values can be summed to produce unique values. TABLE 1, which is below, provides an approximation of the number of unique tone ID numbers that can be generated based upon the number of bits utilized for the audio file ID.

TABLE 1

| Number of ID Bits | Maximum Number of Unique Two-Tone Combinations | Maximum Number of Unique Three-Tone Combinations |
|---|---|---|
| 8 | 15 | 7 |
| 16 | 137 | 52 |
| 20 | 388 | 145 |
| 24 | 647 | 393 |

Accordingly, the control circuit 12502 can retrieve a first audio file, represented by the first diagram element 12550, and a second audio file, represented by the second diagram element 12552. Each of the audio files includes a portion corresponding to the digital audio signal (i.e., "Audio 1" and "Audio 2"). In this particular example, the digital audio signal is 16 bits, but this is simply an example, and the audio portion is not limited to any particular number of bits. In an alternative aspect, instead of the audio portion representing a digital audio signal that is then fed to the amplifier 12508 for output thereby, the audio portion can represent a unique value or ID that corresponds to a tone that is retrievable by the control circuit 12502 from a memory. Further, each of the audio files includes a portion corresponding to the ID (i.e., "ID 1" and "ID 2") associated with each of the tones. In this particular example, the header or ID is 8 bits, but this is, once again, simply an example, and the ID portion is not limited to any particular number of bits (and indeed, TABLE 1 above provides examples of the ID alternatively being 16, 20, or 24 bits).

Accordingly, the control circuit 12502 can sum the IDs (e.g., using binary addition) from the retrieved audio files to generate a combination ID (i.e., "ID 1+ID 2"). Further, the control circuit 12502 can sum the audio portions (e.g., using binary addition) from the retrieved audio files and then apply a scale factor, represented by the third diagram element 12554, to generate a unique output tone (i.e., "(Audio 1+Audio 2)*SCALE"). The concatenated combined audio and ID portions are represented by the fourth diagram element 12556.

Accordingly, the audio output controller 12506 can be configured to pass the sequence of bits concatenated combined audio and ID portions, which are represented by the fourth diagram element 12556 and generated using the technique described above, to the amplifier 12508 (which ignores the ID bits when generating the output audio waveform). Accordingly, the audio secondary controller 12504 can be configured to read the output of the audio output controller 12506 and ensure that the embedded ID corresponds to the combined IDs of the audio files from which the audio output was generated. Because the audio file IDs were preselected such that each combination of the IDs produces a corresponding ID that is unique to that particular combination, the audio secondary controller 12504 can thus compare the output generated by the audio output controller 12506 to the summed IDs from the appropriate audio files and ensure that the output of the audio output controller 12506 is correct for the particular combination of tones.

It should be noted that although the technique illustrated in FIG. 101 is shown and described in the context of combining two individual tones to output a unique tone and ID, the technique should not be construed to be limited to the combination of two tones. As described above, the technique is also equally applicable to the combination of three or more individual tones to generate a unique tone and ID. Further, the technique illustrated in FIG. 101 can be either pre-generated or performed during run-time.

In one aspect, a modular energy system (e.g., the modular energy system(s) of FIGS. 24-37) can be configured to generate audio outputs that are differentiable by electronic systems according to an identifier signal embedded within a non-audible range of the generated audio output. Therefore, the modular energy system can be configured to confirm that it is playing the correct tone for a given action it is performing by isolating and comparing the identifier signal embedded within the audio output to the correct identifier for the action. Alternatively, other systems within the vicinity of the modular energy system could be configured to determine what actions the modular energy system is performing based upon the identifier signal embedded within the audio outputs thereof. Further, the identifier signal can be embedded within a non-audible frequency range so that the audible character of the tone is not altered.

Figure 102:
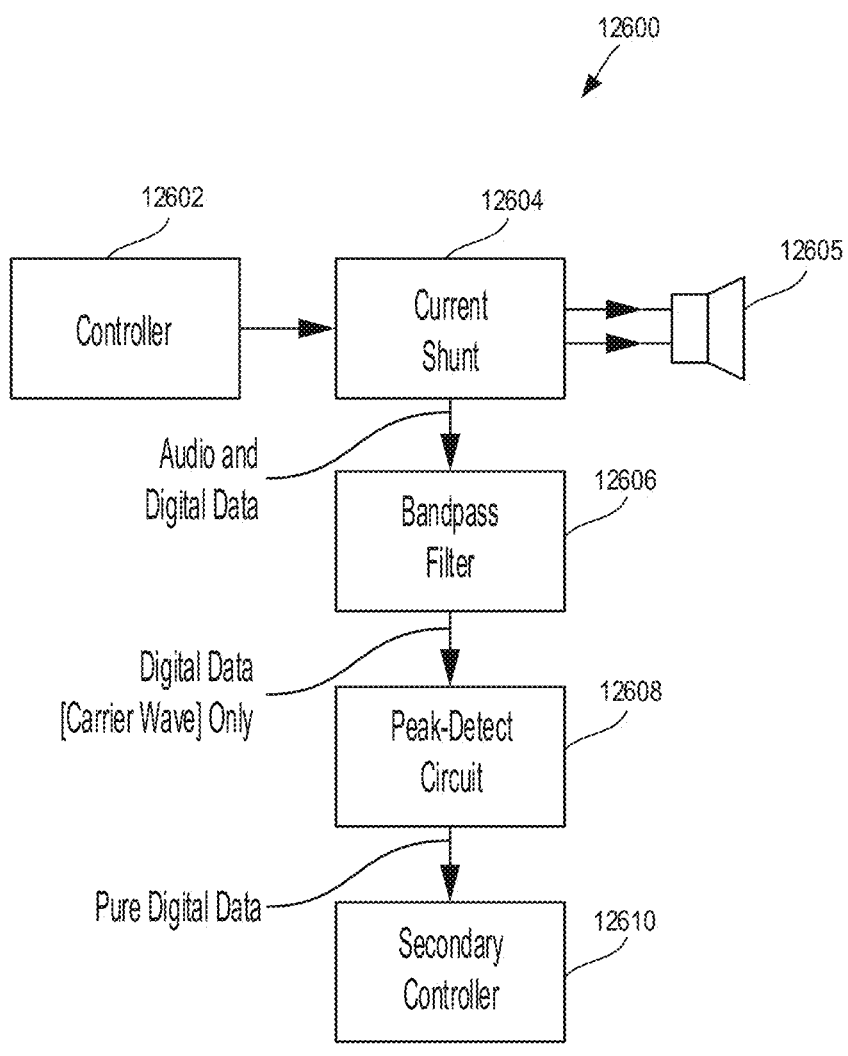
FIG. 102 is a block diagram of an audio control system for a modular energy system, in accordance with at least one aspect of the present disclosure.

For example, FIG. 102 is a block diagram of an audio control system 12600 for a modular energy system, in accordance with at least one aspect of the present disclosure. The audio control system 12600 includes a controller 12602 (e.g., a control circuit or a processor) coupled to an audio output device 12605. Further referring to FIG. 103, which is a graph of audio level (e.g., acoustic intensity level, which is measurable in dB), represented by the vertical axis 12652, versus frequency, which is represented by the horizontal axis 12654, for an audio signal, the controller 12602 can be configured to cause the audio output device 12605 to output an audible acoustic signal 12658, which is embodied as a tone or sound that is emitted based on the particular function or action that is being taken by the modular energy system (e.g., energizing a surgical instrument). This audible acoustic signal 12658 can vary depending upon the function of the modular energy system, the number and types of other tones being output by the modular energy system, and a variety of other factors, as described above. The audible acoustic signal 12658 can vary over a particular frequency range terminating at a frequency $f_c$, which is below the audible frequency threshold 12656 for human hearing. The controller 12602 can be further configured to embed an identifier acoustic signal 12660 within the audio output that is at a frequency or range of frequencies above an audible frequency threshold 12656 (e.g., 20 kHz). The identifier acoustic signal 12660 can be centered or based at a frequency $f_i$, which, as noted above, can be above the audible frequency threshold 12656 for human hearing.

Figures 103, 104:
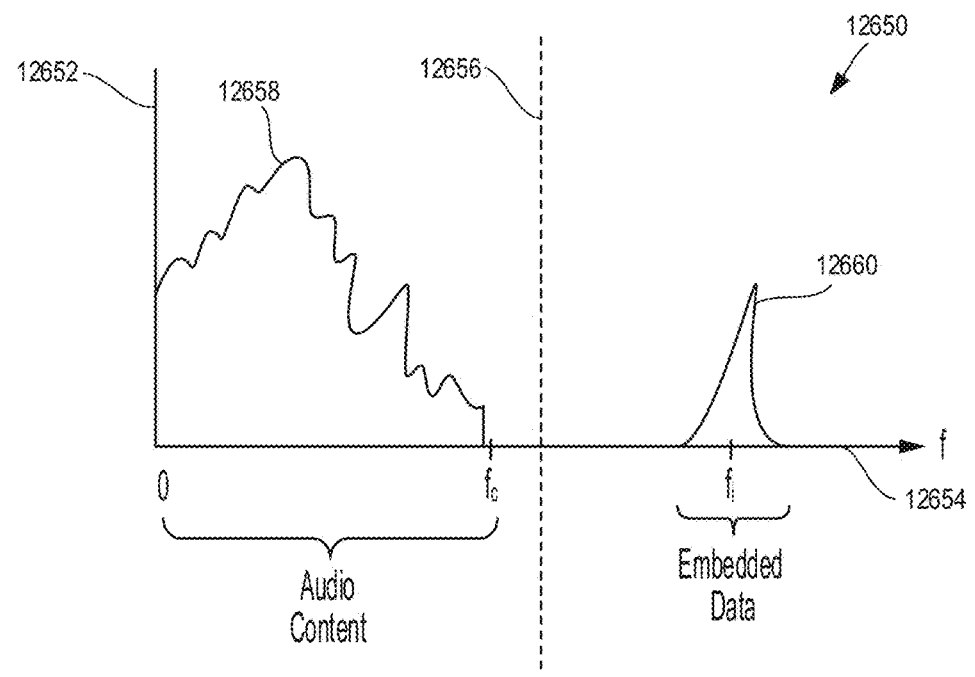
FIG. 103 is a graph of audio level versus frequency for an audio signal, in accordance with at least one aspect of the present disclosure.
FIG. 104 is a series of graphs representative of a process for modulating a carrier wave to carry digital data, in accordance with at least one aspect of the present disclosure.

In one aspect, the identifier acoustic signal 12660 can be embodied as a digital signal encoding data, such as an identifier code indicating the function being performed by the modular energy system. The identifier acoustic signal 12660 can be embodied as a digital signal utilizing a variety of different techniques. For example, FIG. 104 is a series of graphs 12700, 12702, 12704 representative of a process for modulating a carrier wave 12712 to carry digital data. In each of the graphs 12700, 12702, 12704, the vertical axis 12706 represents signal amplitude, and the horizontal axis 12708 represents time. It should be noted that the values of the vertical and horizontal axes 12706, 12708 represent relative values and are provided only for illustrative purposes. The first graph 12700 represents the digital signal 12710 that can be output by the controller 12602. In this example, the digital signal 12710 represents an 8-bit identifier having a value of "01010110." Accordingly, this value can represent an identifier code unique to the action or function being performed by the modular energy system. Each different action or function can be assigned different identifiers so that they are uniquely differentiable by the modular energy system or an external system. Further, the second graph 12702 represents a carrier signal 12712, which can be at the frequency $f_i$, described above. Accordingly, the carrier signal 12712 can be modulated to encode the identifier represented by the digital signal 12710 to generate the modulated signal 12714 shown in the third graph 12704. Therefore, the modulated signal 12714, which is at the frequency $f_i$, can encode the identifier. In one aspect, this signal modulation technique can be performed "on the fly" by the audio control system 12600. In another aspect, the modulated signal 12714 can be pre-embedded within a file for the audio tone (e.g., a .wav file) so that the modulated signal 12714 is output by the modular energy system any time that the audio tone file is played.

Referring back to FIG. 102, the audio control system 12600 can further include a bandpass filter 12606 coupled to a current shunt 12604 coupling the controller 12602 to the audio output device 12605. The bandpass filter 12606 can be configured to pass frequencies within a particular range of the frequency $f_i$ of the identifier acoustic signal 12660, i.e., a range of $f_i$–x to $f_i$+y, where x and y are selected based upon the desired tuning of the bandpass filter 12606. Accordingly, the bandpass filter 12606 can pass the modulated signal 12714 for further processing. The audio control system 12600 can further include a peak-detection circuit 12608 and a secondary controller 12610 that are configured to detect the peak amplitude of the modulated signal 12714 for each particular time interval and thereby decode the modulated signal 12714 to ascertain the encoded identifier. In one aspect, the secondary controller 12610 can further be configured to determine the function being performed by the modular energy system for which the acoustic signal is being output, compare the decoded identifier to the stored identifier assigned to the function, and then determine whether the decoded identifier corresponds to the stored identifier. If the values do not correspond, then that can indicate that the modular energy system and/or the audio control system 12600 is causing the incorrect tone to be output for the given modular energy system function. The secondary controller 12610 can thereafter output a user warning (e.g., via a UI 2050 (FIG. 30)), cause the controller 12602 to change the tone being output via the audio output device 12605, and/or take another corrective action. Conversely, if the values do correspond, then that can indicate that the modular energy system and/or the audio control system 12600 is causing the correct tone to be output for the given modular energy system function. Accordingly, corrective actions are unnecessary and the second controller 12610 does not take any corrective actions. This process can be beneficial because it embeds an identifier within the audio output generated by the modular energy system without altering the audible character of the outputs, and a large number of digital identifiers can be encoded within the audio output (e.g., $2^n$ identifiers, where n is the number of bits in the digital signal 12710).

Figure 105:
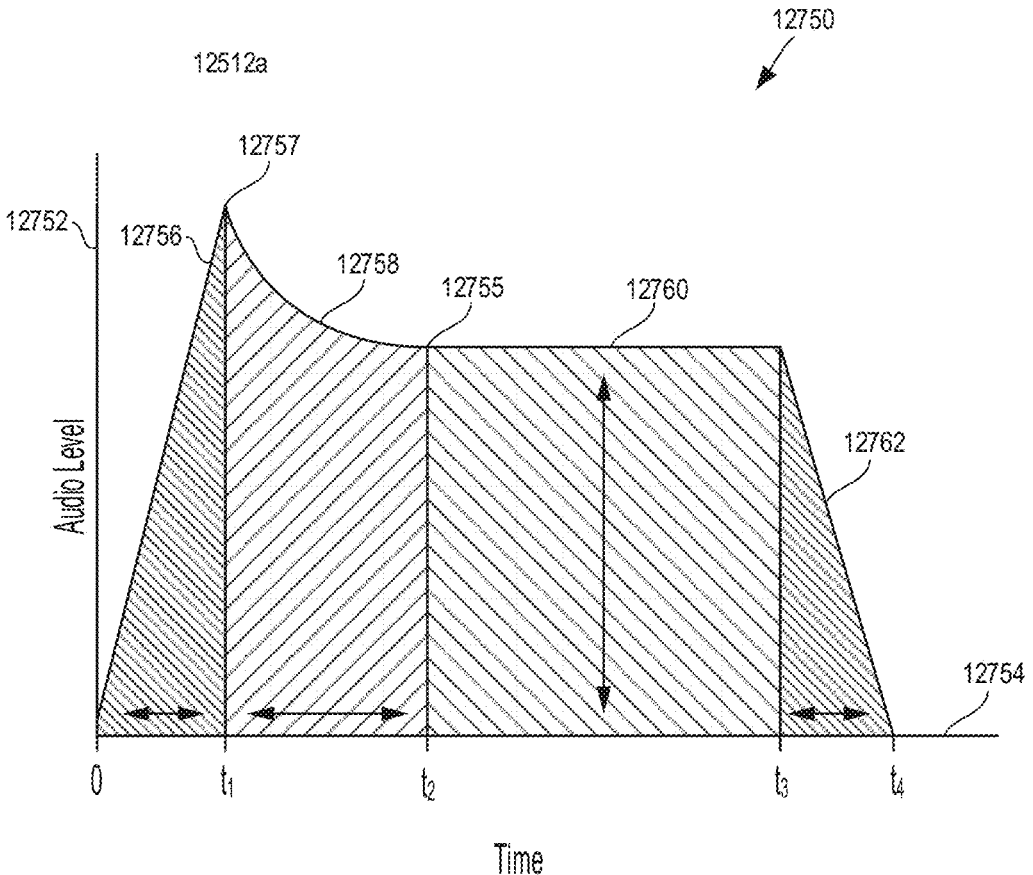
FIG. 105 is a graph of audio level versus time for an audio signal, in accordance with at least one aspect of the present disclosure.

In one aspect, a modular energy system (e.g., the modular energy system(s) of FIGS. 24-37) can be configured to modulate a generated tone to have distinct audio levels at different times of the tones. This can be utilized to, for example, cause the generated tones to have a higher audio level at the beginning of the tone in order to assist users in audibly distinguishing between multiple different tones that have been activated in a close proximity to each other or between tones that have been ongoing and newly activated tones. For example, FIG. 105 is a graph 12750 of audio level (e.g., acoustic intensity level, which is measurable in dB), represented by the vertical axis 12752, versus time, represented by the horizontal axis 12754, for an audio signal 12755. The audio signal 12755 can be generated by the audio control system 12500 illustrated in FIG. 100, the audio control system 12600 illustrated in FIG. 102, or any other such control systems.

In the illustrated implementation, the control system causes the audio level of the audio signal 12755 to increase sharply 12756 to a peak level 12757 during an initial time period from the point of initial activation of the audio signal 12755 to $t_1$. Thereafter, the control system causes the audio level to decay 12758 from time $t_1$ to time $t_2$ to a sustained level 12760, which is then maintained from time $t_2$ to time $t_3$. At time $t_3$, the control system then causes the audio level of the audio signal 12755 to decay 12762 to zero at time $t_4$ as the modular energy system completes the function associated with the audio signal 12755 or the audio signal 12755 is otherwise completed. For example, the control system can determine that a surgical instrument connected to the modular energy system has been activated, retrieve the appropriate audio file for the given surgical instrument type, and then cause the tone encoded by the audio file to be output at a higher audio level during an initial time period before decaying to a standard or sustained level for the tone. When the instrument is no longer activated, then the control system can halt playing the tone (i.e., the audio level for the phone will decay to zero, as shown in FIG. 105). By causing the audio signal 12755 to peak 12757 at a value higher than the sustained level 12760 during an initial time period, the control system can thus allow users to audibly distinguish between different tones being output by the modular energy system in a close proximity to each other because it creates an especially identifiable initial portion of the tone that coincides with the activation of the function with which the tone is associated. Therefore, users can distinguish between which tone corresponds to which function according to the sequence in which the initial portions of the tones are heard by the users. Further, users can distinguish between newly activated and ongoing tones according to the different audio levels of the initial portions of the newly activated tones and the ongoing tones.

Figure 106:
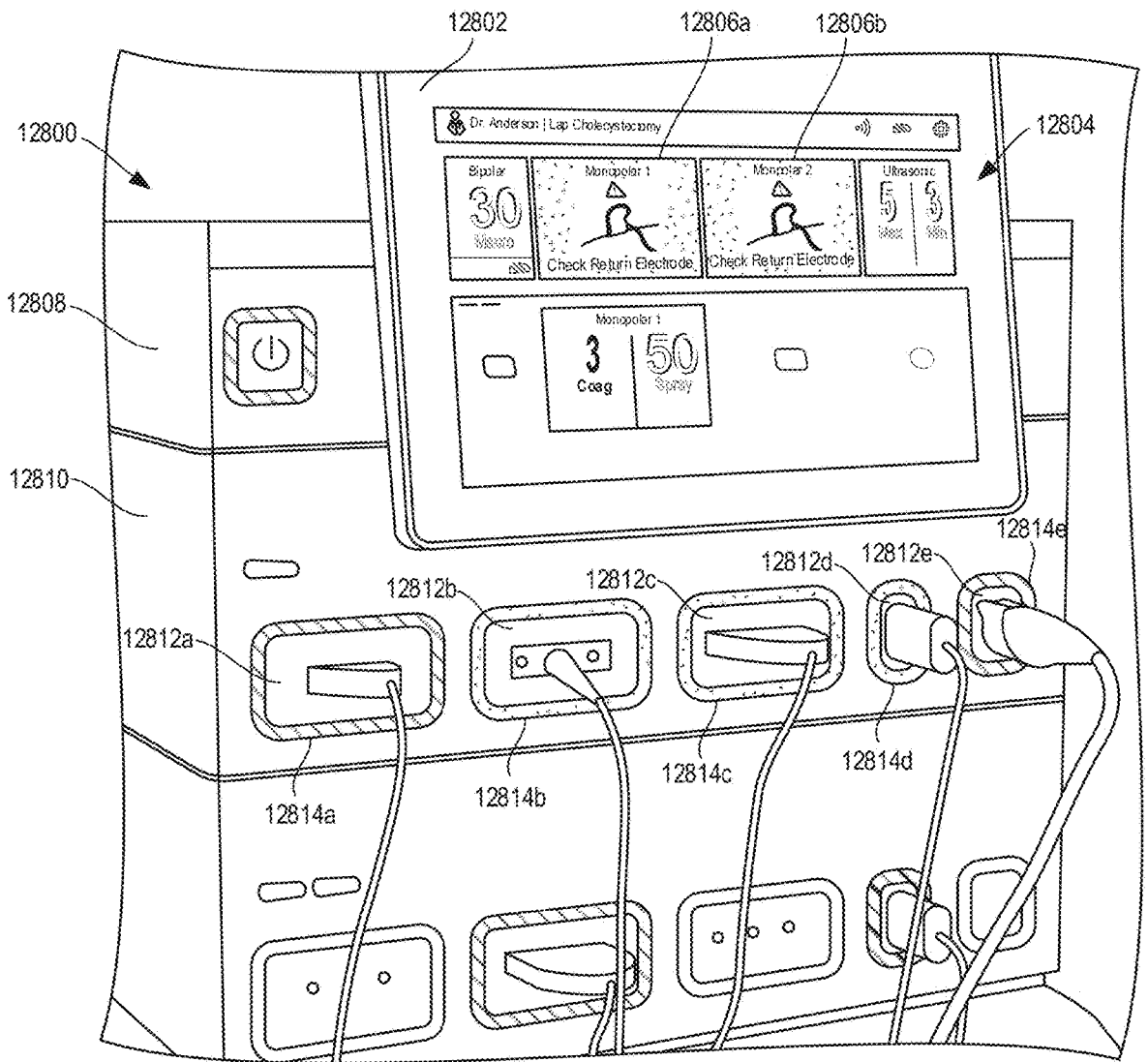
FIG. 106 is a perspective view of a modular energy system configured to provide audiovisual feedback to users, in accordance with at least one aspect of the present disclosure.

In one aspect, an example of which is shown in FIG. 106, a modular energy system 12800 can be configured to provide both audio and visual feedback in tandem with each other. As described above, a modular energy system 12800 can include a header module 12808 that can be connected to one or more energy modules 12810 or other module types. The header module 12808 and the energy modules 12810 can be configured to provide various types of visual feedback. For example, the header module 12808 can support or be associated with a display screen 12802, which can in turn display a UI 12804. The UI 12804 can in turn be configured to provide various information or alerts as feedback to users, such as "check return electrode" alerts 12806a, 12806b. Further, an energy module 12810 can include light piping elements 12814a-e disposed about its ports 12812a-e, which can be configured to light up in various colors, flash in particular patterns or sequences, or take other actions to convert information to users. In one aspect, the modular energy system 12800 can be configured to generate tones or audio signals in tandem with the visual feedback provided by the UI alerts, light piping elements 12814a-e, or other visual feedback provided by the modular energy system 12800. For example, the header module 12808 and/or energy module 12810 can be configured to determine when visual feedback is being provided and accordingly cause an appropriate tone to be generated by the modular energy system 12800. The generated tone can be generated or modulated by any of the techniques described hereinabove. For example, when a "check return electrode" alert 12806a, 12806b is being displayed on the UI 12804 and/or the light piping 12814b-d for the monopolar ports 12812b-c and the neutral electrode port 12812d is displaying an alert color indicating that there is an error with the return electrode, the modular energy system 12800 can be configured to correspondingly output a "check return electrode" tone. Further, the "check return electrode" tone can be unique and, thus, audibly distinguishable by users from other tones output by the modular energy system 12800 for other functions or alerts.

Footswitch Identification and Mapping

As surgical systems become more modular and capital equipment increases in capability and capacity, the number of permutations in which various pieces of surgical equipment can be connected and combined together is increasing. Additionally, more is required of surgical system accessories as the functionality of surgical systems increases. With conventional surgical equipment, users may have to continually disconnect and reconnect surgical system accessories between multiple different surgical systems (or components thereof) during the course of a surgical procedure. Therefore, there exists a need for surgical systems and accessories that are adaptable in their ability to connect to surgical systems (such as hubs and/or modular energy systems, as described above) and are configured to be electronically reassigned to various aspects of the surgical systems once physically connected thereto. Accordingly, in various non-limiting aspects of the present disclosure, a surgical system is provided that can adaptably connect to system accessories and reassign those system accessories once they are connected.

For example, in the non-limiting aspect of FIG. 25A, an energy module 2004 of a modular energy system includes a port assembly 2012 with a number of different ports configured to deliver different energy modalities to corresponding surgical instruments that are connectable thereto. A non-limiting example of an accessory that can be adaptably connected to such an energy module 2004 is a footswitch. Once connected, the footswitch could be electronically assigned and reassigned to any of the ports of the port assembly 2012 and used to activate various energy modalities of the energy module 2004. For example, a user may depress a pedal of a connected footswitch to activate a transducer, which causes a signal to be transmitted to the energy module 2004 to which the footswitch is connected, which in turn causes the generator to energize a surgical instrument connected to the port to which the footswitch is assigned. The footswitch could further include any number of pedals that can be configured to perform a particular function of the energy module. For example, in one non-limiting aspect, the footswitch could comprise a first pedal to activate and/or control an ultrasonic mode and a second pedal to activate and/or control an electrosurgical mode. As another example, the first pedal of the footswitch could be configured to activate and/or control a first monopolar mode and the second pedal could be configured to activate and/or control a second monopolar mode. These particular examples are provided for illustrative purposes only and other non-limiting aspects of the present disclosure include other pedals configured to perform other functions of an energy module of the surgical system. Accordingly, the footswitch pedals can be configured in various ways to accommodate a specific drive mode of the energy module or user preference.

In one aspect, the present disclosure provides a modular energy system that is configured to include multiple connected energy modules, which can each have at least one footswitch. The modular energy system can provide a footswitch interface configured to assign a compatible footswitch (or other control device) to a port on any of the connected modules, without physically changing the position of the footswitch connector.

Figure 107:
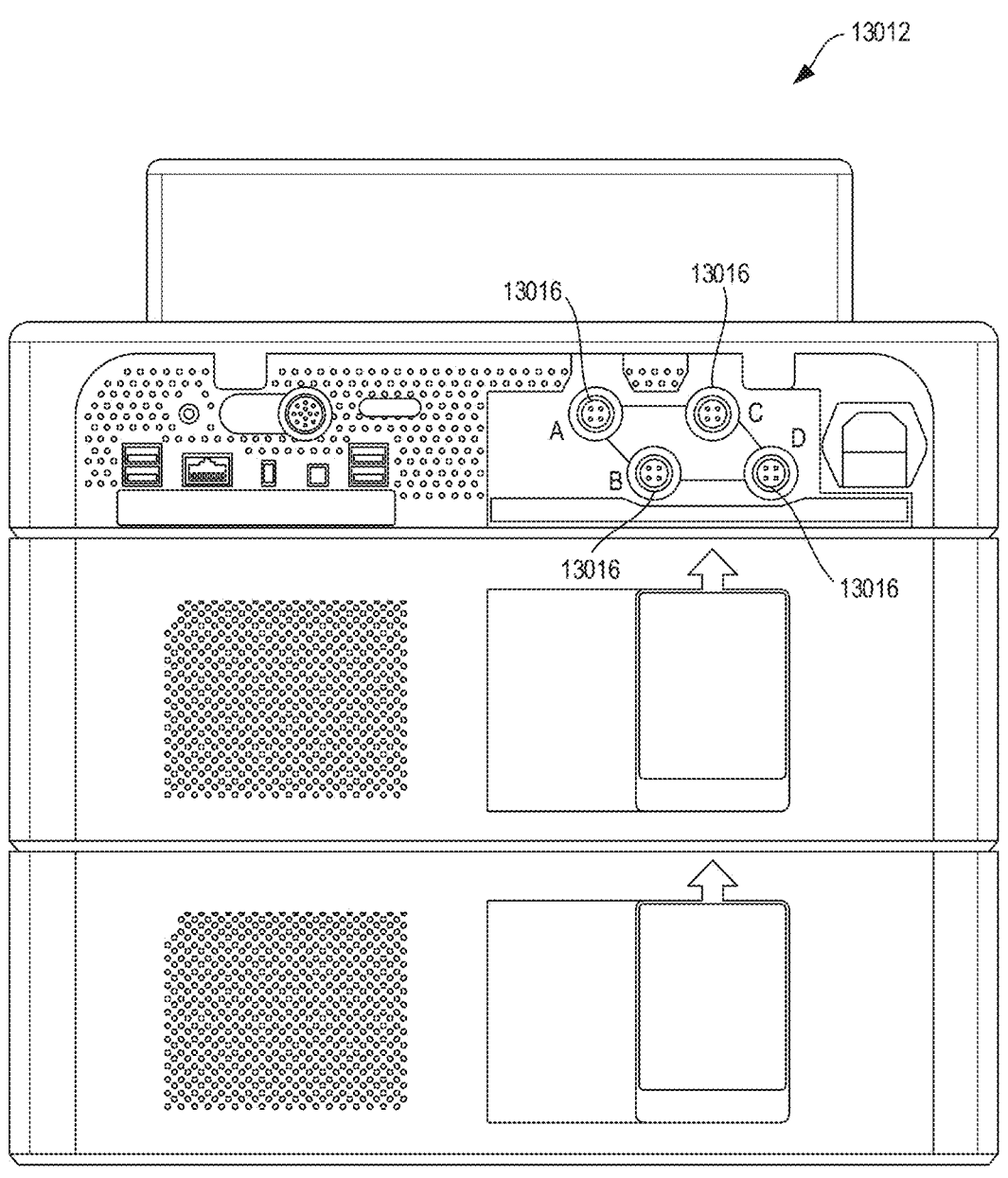
FIG. 107 is an energy module including a plurality of system accessory ports, in accordance with at least one aspect of the present disclosure.

Referring now to FIG. 107, a modular energy system 13012, including system accessory ports 13016 configured to accommodate the physical connection of a system accessory, is depicted in accordance with at least one aspect of the present disclosure. For example, a system accessory such as a footswitch can be connected to the modular energy system 13012 via the ports 13016. In one aspect, the ports 13016 of FIG. 107 are standardized and configured to accommodate any system accessory with a standardized connector. In other non-limiting aspects of the present disclosure, the ports are not standardized and each is specifically configured to accommodate a particular system accessory. The energy module of FIG. 107 includes four ports 13016. However, other aspects of the present disclosure include a varying numbers of ports 13016 configured to connect any number of footswitches. Likewise, although the ports 13016 of FIG. 107 are depicted on the back of a header module of the modular energy system 13012, other aspects of the present disclosure include ports located on the front, sides, and top of other modules of the energy module, among other locations. According to the aspect of FIG. 107, the ports 13016 can be labeled with indicia (e.g., "A," "B," "C," and "D") to better facilitate the physical tracking and mapping of the footswitches that are connected to the modular energy system 13012. For example, the user interface 13042 of FIG. 118 can include footswitch icons 13078 (FIG. 119) that include corresponding indicia (e.g., "A," "B," "C," and "D") that coincide with the ports 13016 of the modular energy system 13012, thereby indicating which footswitch icon 13078 corresponds to which connected footswitch. However, according to other non-limiting aspects of the present disclosure, alternate means of tracking and mapping each of the physical ports 13016 are used to track and map footswitches, including numbers, colors, textures, and other means of identification.

Figure 108:
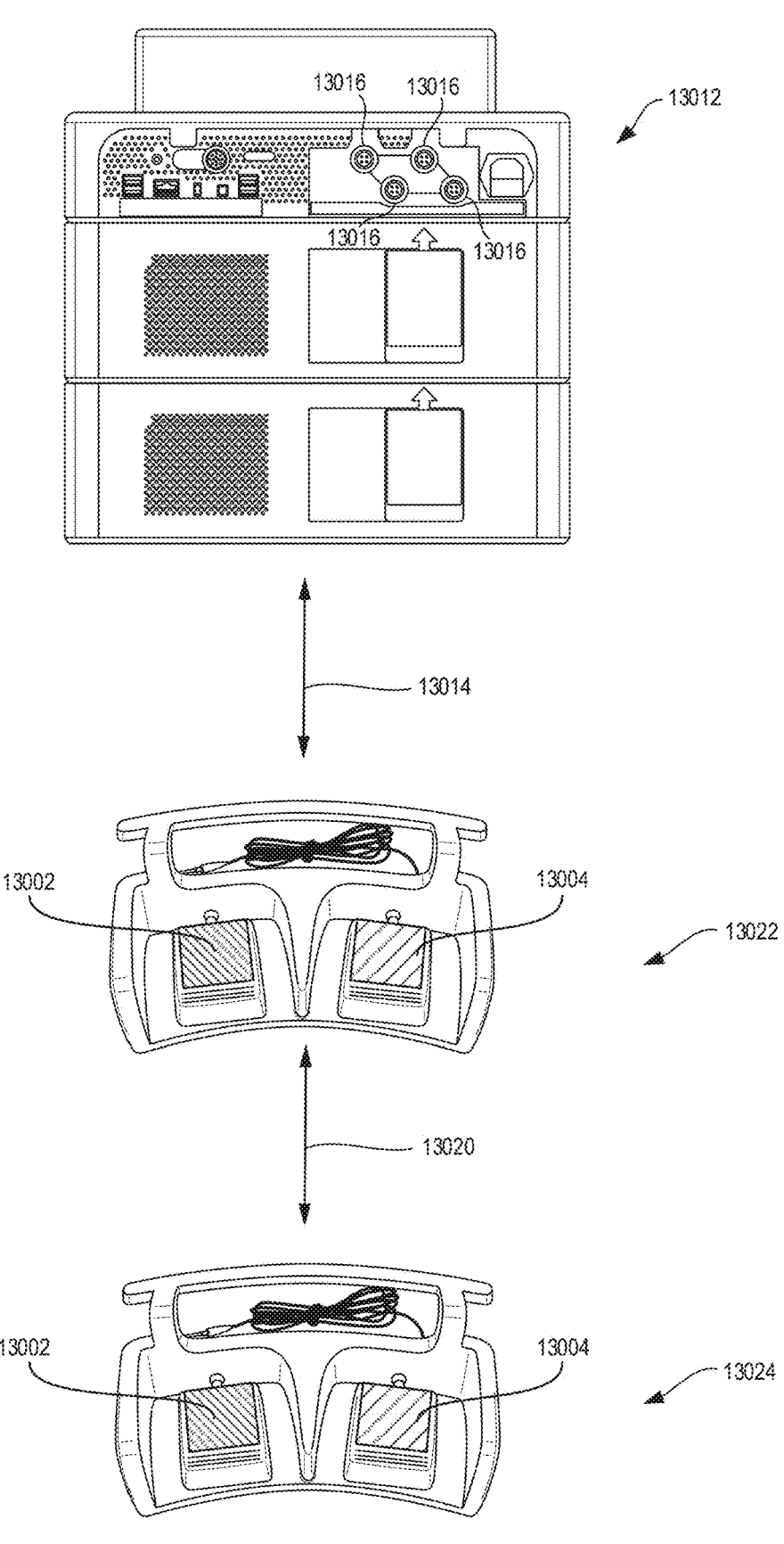
FIG. 108 is a diagram of footswitches physically connected to an energy module, in accordance with at least one aspect of the present disclosure.

Referring to FIG. 108, a diagram of a first footswitch 13022 and second footswitch 13024 physically connected to a modular energy system 13012 is depicted in accordance with at least one aspect of the present disclosure. According to the aspect of FIG. 108, the first footswitch 13022 and second footswitch 13024 can be physically connected via a first cable 13020, and one of the first footswitch 13022 or second footswitch 13024 can be physically connected to the modular energy system 13012 through one of the ports 13016 via a second cable 13014 such that both of the footswitches 13022, 13024 are physically connected to the modular energy system 13012 in a daisy-chained fashion. In other non-limiting aspects of the present disclosure, other footswitches and/or system accessories can be connected to the modular energy system 13012 through the first footswitch 13022 and/or second footswitch 13024. Accordingly, any number of footswitches and/or system accessories can be connected to the modular energy system 13012, regardless of how many ports 13016 the modular energy system 13012 includes.

Figure 109:
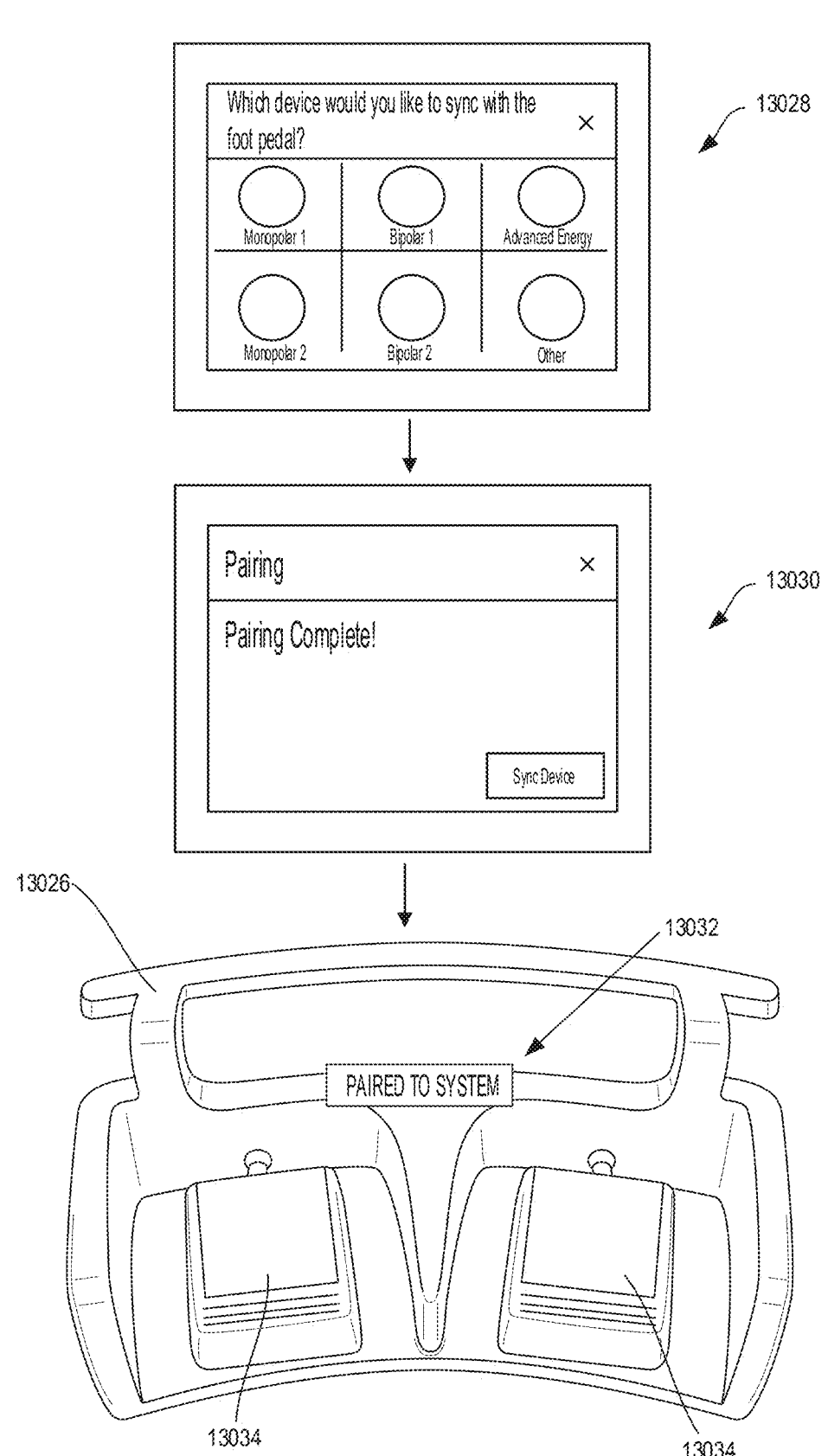
FIG. 109 is a diagram of a process of wirelessly connecting a footswitch to an energy module, in accordance with at least one aspect of the present disclosure.

Referring now to FIG. 109, a diagram of a process of wirelessly connecting a footswitch to an modular energy system is depicted in accordance with at least one aspect of the present disclosure. According to the non-limiting aspect of FIG. 109, a wirelessly enabled footswitch 13026 can include a wireless communication module and a wirelessly enabled modular energy system can includes wireless transceiver configured to receive and/or send a wireless signal. Thus, the wirelessly enabled footswitch 13026 can wirelessly communicate with and/or connect to a modular energy system via a variety of different wireless communication technologies, mediums (e.g., a wireless local access network (WLAN) or a cellular network), and/or communication protocols (e.g., Bluetooth or Wi-Fi). According to the aspect of FIG. 109, the wirelessly enabled footswitch 13026 can be connected to the modular energy system when a user initiates a pairing process via the user interface of the modular energy system. For example, the user interface can present the user with a pairing display 13028 that prompts the user to select a wirelessly enabled accessory, such as the footswitch 13026, that is recognized by the wirelessly enabled modular energy system. In FIG. 109, the user has selected the wirelessly enabled footswitch 13026 to pair with the wirelessly enabled modular energy system, and the user interface can present the user with a display 13030 confirming that the wireless connection was successful. Additionally, if the wirelessly enabled footswitch 13026 is configured with a reconfigurable display 13032, it can present the user with a confirmation that the wirelessly enabled footswitch 13026 has been successfully connected to the wirelessly enabled module energy system. The present disclosure further contemplates another aspect where the modular energy system 13012 and footswitches 13022, 13024 of FIG. 108 are wirelessly enabled in addition to being configured for physical connection. Accordingly, various system accessories and footswitches 13022, 13024 can be simultaneously connected to the modular energy system 13012, some via a physical connection and others via a wireless connection. As previously discussed, the modular energy system 13012 can automatically apply default settings to each of the first footswitch 13022 and second footswitch 13024 upon connection.

Referring now to FIGS. 110-114, various views of a modular energy system 13012 and user interface 13042 configured for use with a footswitch are shown in accordance with at least one aspect of the present disclosure. A footswitch and/or other system accessory can be connected to the modular energy system 13012 of FIGS. 110-114 using any of the aforementioned hardware and/or methods. Among other things, the modular energy system 13012 and user interface 13042 of FIGS. 110-114 can be used to assign and reassign connected footswitches and/or other system accessories to various ports of the energy modules 13041, 13043 without manipulating the physical connections and/or wireless connection settings between the system accessories and the modular energy system 13012. The modular energy system 13012 of FIGS. 110-114 includes a first energy module 13041 and a second energy module 13043. However, the present disclosure contemplates other aspects, including any number of energy modules. The energy modules 13041, 13043 include ports 13036, 13038*a*, 13038*b*, 13039, 13040 that are similar to those depicted in the port assembly of FIG. 25A. For example, the energy modules 13041, 13043 each include a bipolar port 13036, a first monopolar port 13038*a*, a second monopolar port 13038*b*, a neutral electrode port 13039, and a combination energy instrument port 13040. However, the principles discussed herein are not limited to the aforementioned ports and can be applied to any other port and/or combination of ports of the modular energy system 13012.

The modular energy system 13012 of FIGS. 110-114 further includes a user interface 13042, which displays an icon 13046, 13048*a*, 13048*b*, 13050 associated with some of the ports 13036, 13038*a*, 13038*b*, 13040 of each of the energy modules 13041, 13043. As used herein, an icon is a virtual representation of a component of the modular energy system 13012, system accessory, or instrument. For example, an icon can include an image, shape, color, and/or any combination thereof to help the user identify the component, system accessory, or instrument it represents. Specifically, for energy modules 13041, 13043 having the illustrated port arrangement, the user interface 13042 accordingly includes a bipolar port icon 13046, a first monopolar port icon 13048*a*, a second monopolar port icon 13048*b*, and a combination energy port icon 13050 for each of the energy modules 13041, 13043. The icons are arranged in a first row 13051 and a second row 13053, corresponding with the first energy module 13041 and the second energy module 13043, respectively. However, alternate arrangements of icons 13046, 13048*a*, 13048*b*, 13050 are further contemplated by the present disclosure. The user interface 13042 further displays whether a connected instrument is footswitch compatible via a global footswitch-enabled port icon 13045. Thus, the user can easily identify which of the ports 13036, 13038*a*, 13038*b*, 13040 are compatible with a footswitch and/or other system accessory by locating which of the various port icons 13046, 13048*a*, 13048*b*, 13050 are marked with or include a global footswitch-enabled port icon 13045.

Figure 110:
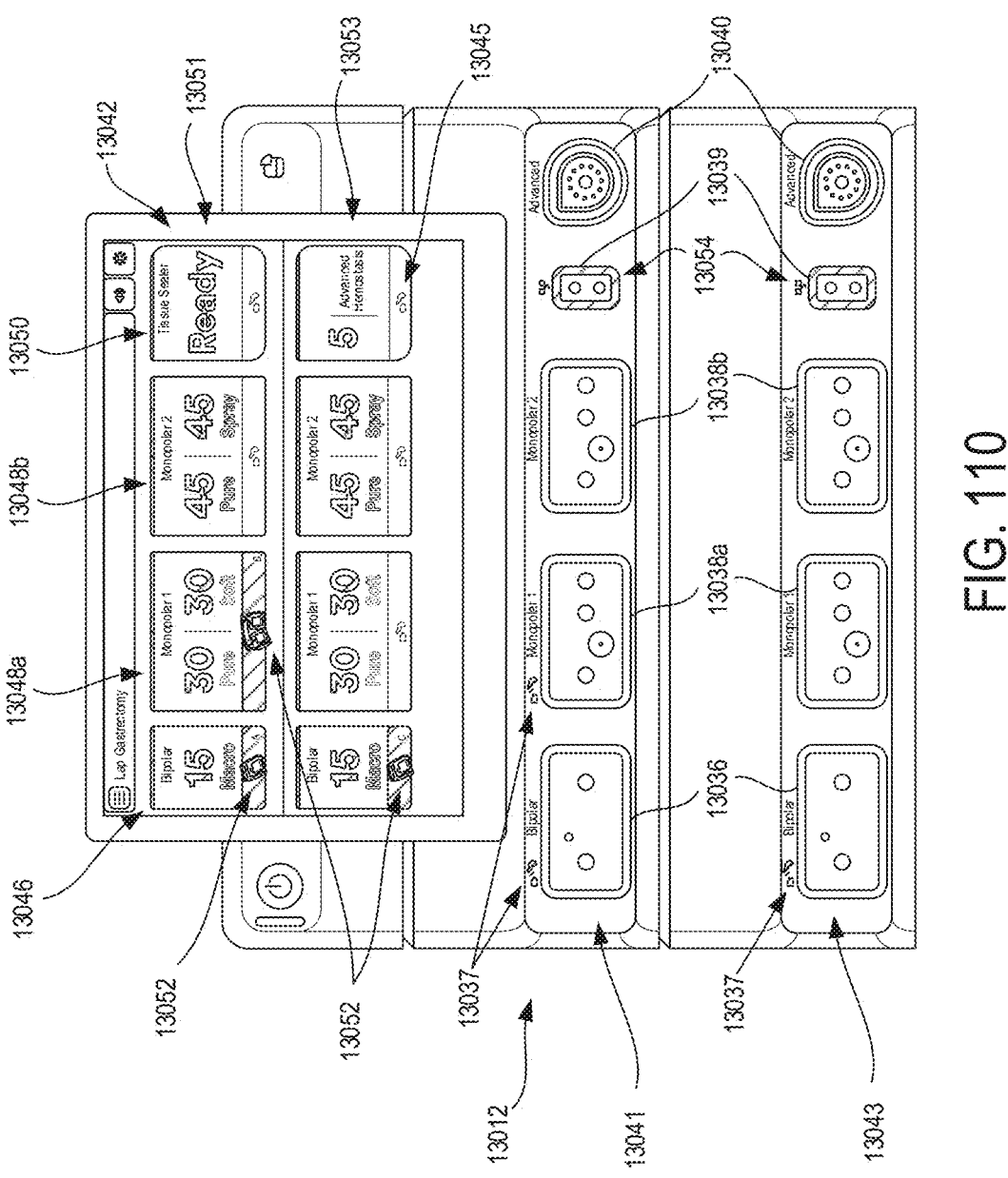
FIG. 110 is a front view of an energy module, in accordance with at least one aspect of the present disclosure.

The user interface 13042 of FIGS. 110-114 can be further configured to display a footswitch widget 13052 either on or in association with the various port icons 13046, 13048*a*,

13048*b*, 13050. The footswitch widget 13052 indicates that a footswitch has been assigned to the particular port 13036, 13038*a*, 13038*b*, 13040 corresponding to the port icon 13046, 13048*a*, 13048*b*, 13050 with which the footswitch widget 13052 is associated. Further, the footswitch widget 13052 can be manipulated by a user (through the display screen 2006, which can include a touchscreen) to electronically change which of the ports 13036, 13038*a*, 13038*b*, 13040 the particular footswitch is assigned to. As used herein, a widget is a software component that the user can interact with through direct manipulation, thereby directing a control circuit (e.g., the system control unit 3024 (FIG. 33) or the UI processor 3040 (FIG. 33)) configured to control the display screen 2006 (FIG. 30) and/or the user interface 13042 displayed thereon to execute a desired instruction. In FIG. 110, the user interface 13042 displays a footswitch widget 13052 on both bipolar port icons 13046 and the first monopolar port icon 13048*a* of the first row 13051. This indicates that footswitches have been assigned to the bipolar ports 13036 of the first and second energy modules 13041, 13043 and the first monopolar port icon 13048*a* of the first energy module 13041. The footswitch-assigned instrument port widget 13052 can be specifically tailored to correspond to the exact footswitch and/or other accessory that is assigned to the port. For example, the footswitch widget 13052 can include a visual display of a single-pedal footswitch or two-pedal footswitch, depending on what type of footswitch is assigned to that instrument.

In one aspect, the user interface 13042 can allow users to reassign any footswitches connected to the modular energy system 13012 by manipulating the widgets 13052 or other control elements displayed via the user interface 13042. For example, the user can drag and/or otherwise attach a footswitch-assigned port widget 13052 of FIG. 110 to any of the port icons 13046, 13048*a*, 13048*b*, 13050, including a footswitch-enabled port icon 13045, thereby instructing the control circuit to reassign that footswitch to a different port 13036, 13038*a*, 13038*b*, 13040. The control circuit can be coupled to the user interface 13042 and can be further configured to control the energy module(s) 13041, 13043 and/or surgical instrument(s) connected thereto based on the port icon 13046, 13048*a*, 13048*b*, 13050 on which the footswitch-assigned port widget 13052 is placed. This process will be described in further detail in the forthcoming discussion of FIGS. 46-50. After a footswitch has been reassigned to a new port, the user interface 13042 can be further configured to provide a confirmation that the reassignment was successful. Accordingly, the previously assigned port icons 13046, 13048*a*, 13048*b*, 13050 will no longer display a footswitch widget 13052 and will instead display a footswitch-enabled port icon 13045.

Still referring to FIG. 110, once a footswitch has been assigned to an instrument, the user interface will illuminate the port icon 13046, 13048*a*, 13048*b*, 13050 a "confirmation" color. The "confirmation" color is represented via crosshatching in FIG. 110. Likewise, the modular energy system 13012 can illuminate a light tube 13054 surrounding the port 13036, 13038*a*, 13038*b*, 13040 to which the assigned instrument is connected. In one aspect, the confirmation color displayed via the user interface 13042 for a particular port icon 13046, 13048*a*, 13048*b*, 13050 can coincide with the color that the light tube 13054 is illuminated for the corresponding port 13036, 13038*a*, 13038*b*, 13040. For example, the footswitch-assigned port widget 13052 and/or the port icons 13046, 13048*a* associated therewith can be illuminated a color (e.g., green), indicating that a footswitch has been assigned to the corresponding ports. In one aspect, the modular energy system 13012 can further or alternatively illuminate a footswitch assignment indicator 13037 associated with each of the bipolar ports 13036 of the first and second energy modules 13041, 13043, and a footswitch assignment indicator 13037 associated with the first monopolar port 13038*a* of the first energy module 13041 green, thereby confirming that a footswitch has been assigned to those ports. In another aspect, the light tubes 13054 surrounding the neutral electrode port 13039 of the first and second energy modules 13041, 13043 can also be illuminated a color (e.g., green), confirming that the neutral electrode return has been successfully connected to the modular energy system 13012. By having the colors directly associated with the energy ports (via the light tubes 13054) coincide with the colors indicated on the user interface 13042 for that port, the modular energy system 13012 can allow users to easily identify the instruments that have been assigned to the footswitch. The light tubes surrounding ports to which unassigned instruments are connected can remain unlit until the user reassigns the footswitch to those instruments. Therefore, the user has a clear visual indication as to exactly which instruments are assigned to a footswitch and which ports are actively in use at any point during the use of the modular energy system 13012.

Figure 111:
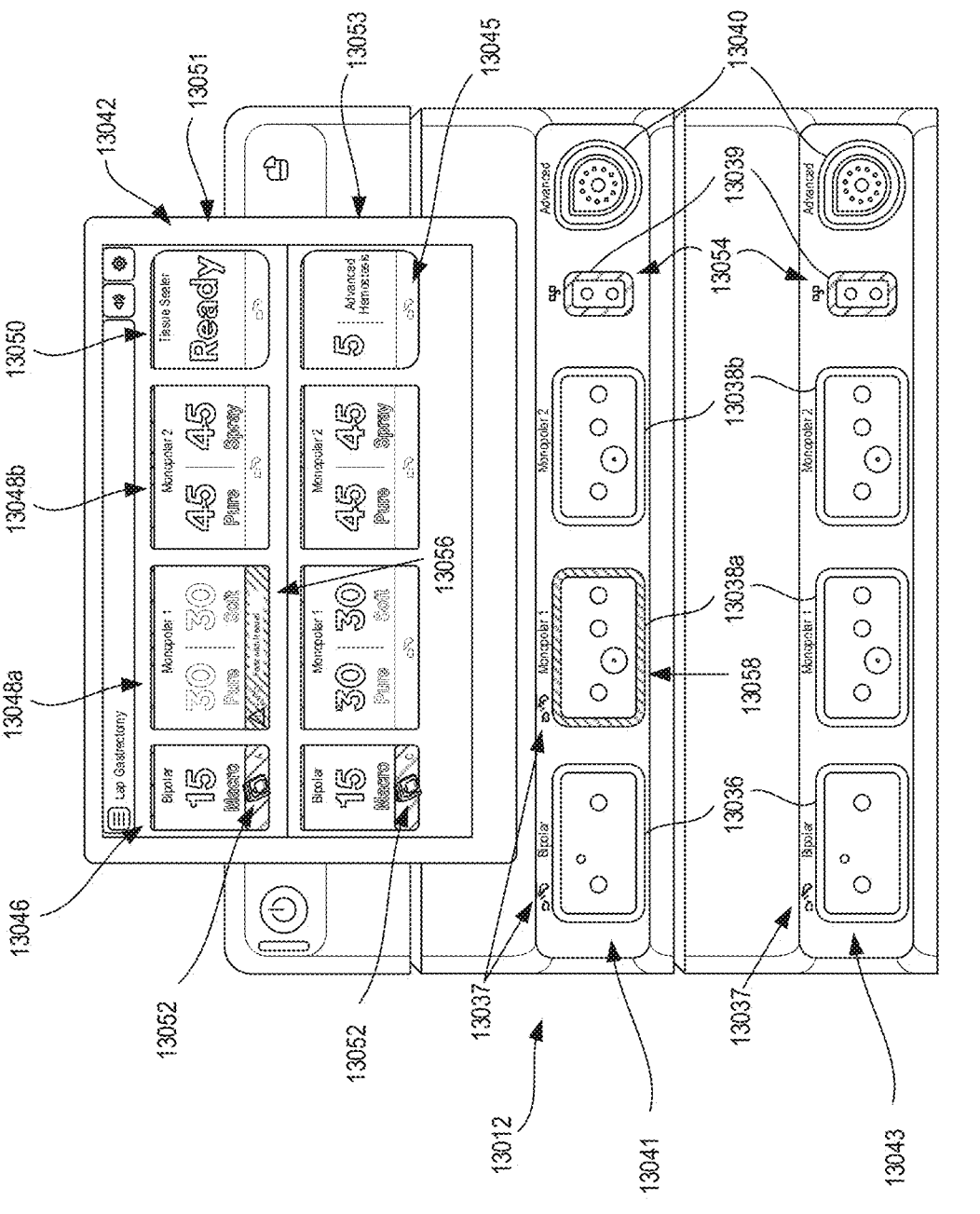
FIG. 111 is a front view of an energy module, in accordance with at least one aspect of the present disclosure.

Referring now to FIG. 111, a front view of the modular energy system 13012 of FIG. 110 is shown in accordance with another aspect of the present disclosure. Here, the user interface 13042 is communicating a "required assignment" notification 13056, indicating to the user that a footswitch has not been assigned to the first monopolar port 13038*a*. As used herein, a notification can include a text, colors, or an audible alert, among other things to communicate information to the user. In the aspect of FIG. 111, a non-hand-activated monopolar instrument was connected to the first energy module 13041, but no footswitch has been assigned to it yet. Accordingly, the "required assignment" notification 13056 displayed below the monopolar port icon 13048*a* is illuminated in a "required assignment" color. The "required assignment" can display various texts, images, or colors indicating what specifically is required. For example, the "required assignment" notification of FIG. 111 says "Footswitch Needed." The "required assignment" notification 13056 can include, for example, alternate crosshatching in a particular color (e.g., orange). Accordingly, the modular energy system 13012 can illuminate the footswitch assignment indicator 13037 associated with the bipolar port 13036 of the first and second energy modules 13041, 13043 a color (e.g., green), thereby confirming that a footswitch has been assigned to those ports. However, the footswitch assignment indicator 13037 associated with the first monopolar port 13038*a* of the first energy module 13041 can be illuminated in a color corresponding to the same color of the icon 13048*a*, indicating that a footswitch is not assigned to that port 13038*a*. Likewise, the modular energy system 13012 can illuminate a light tube 13058 surrounding the first monopolar instrument port 13038*a* of the first energy module 13041 corresponding to the same color of the icon 13048*a*. Light tubes 13054 surrounding the other ports can maintain their own individual colors, markings, and/or other indicia in accordance with their own individual statuses. Therefore, the user has a clear visual indication as to exactly which ports and/or instruments require attention and are implicated by the "required assignment" notification 13056 displayed by the user interface 13042.

Figure 112:
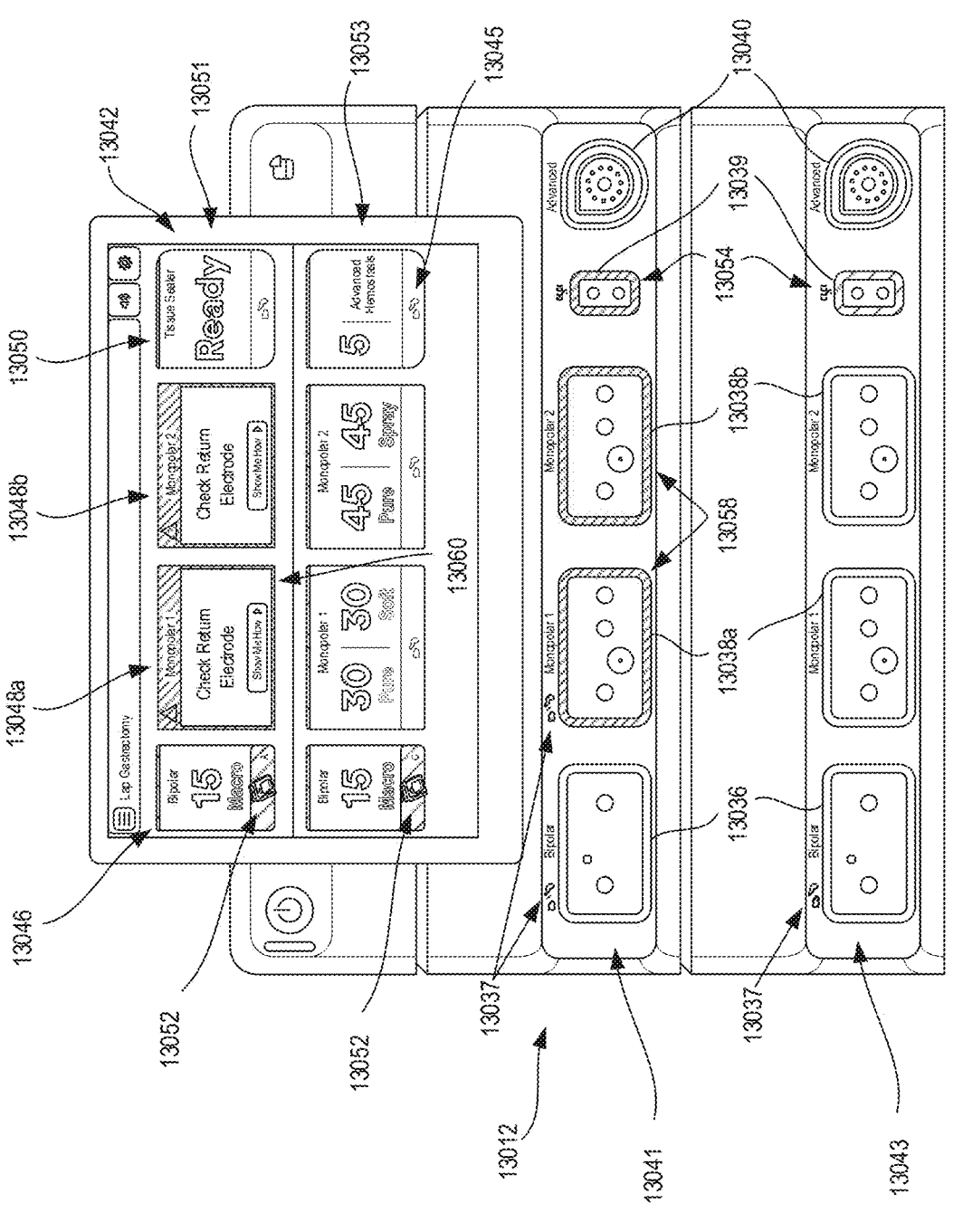
FIG. 112 is a front view of an energy module, in accordance with at least one aspect of the present disclosure.

Referring now to FIG. 112, a front view of the modular energy system 13012 of FIGS. 110 and 111 is shown in accordance with another aspect of the present disclosure.

Here, the user interface 13042 is communicating an "instrument error" notification 13060, indicating to the user that an instrument is improperly connected or requires attention. In FIG. 112, the "instrument error" message 13060 is communicating to the user that a neutral electrode return is not properly connected to the neutral electrode port 13039 of the first energy module 13041. Accordingly, the "instrument error" notification 13060 is displayed below the first and second monopolar port icons 13048*a*, 13048*b* and the monopolar port icons 13048*a*, 13048*b* are illuminated an "instrument error" color. The "instrument error" notification 13060 can include, for example, alternate crosshatching in a particular color (e.g., red). Accordingly, the modular energy system 13012 can illuminate the footswitch assignment indicator 13037 associated with each of the bipolar ports 13036 of the first and second energy modules 13041, 13043, and a footswitch assignment indicator 13037 associated with the first monopolar port 13038*a* of the first energy module 13041 a color (e.g., green), thereby confirming that a footswitch has been assigned to those ports. However, the modular energy system 13012 can illuminate a light tube 13058 surrounding the first and second monopolar instrument ports 13038*a*, 13038*b* of the first energy module 13041 corresponding to the port icons 13048*a*, 13048*b* the same color. Therefore, the user has a clear visual indication as to exactly which instruments require attention and are implicated by the "instrument error" notification 13060 displayed by the user interface 13042 and whether or not the instrument is assigned to a footswitch.

Figure 113:
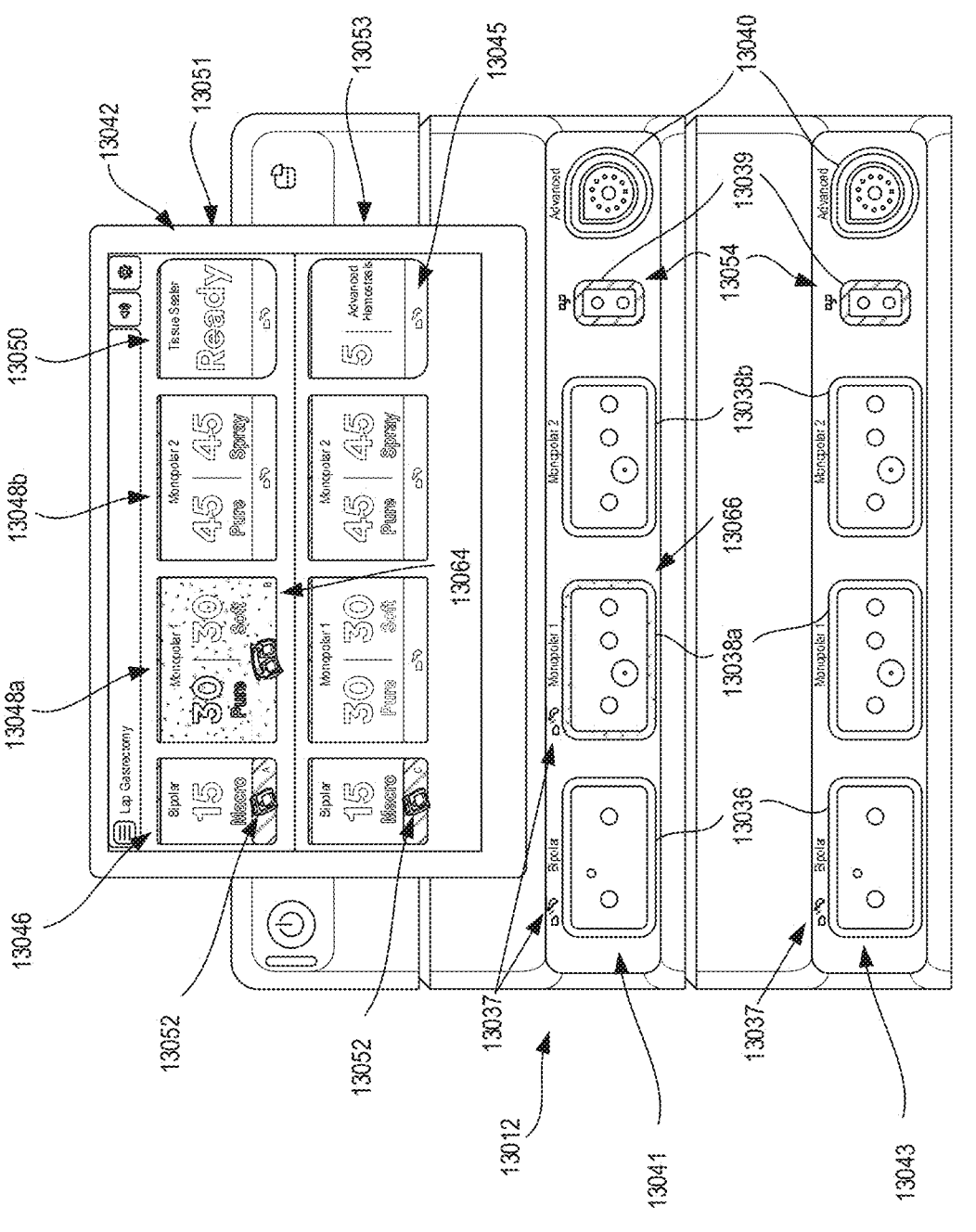
FIG. 113 is a front view of an energy module, in accordance with at least one aspect of the present disclosure.

Referring now to FIG. 113, a front view of the modular energy system 13012 of FIGS. 110-112 is shown in accordance with another aspect of the present disclosure. Here, the user interface 13042 is providing the user with an "activated port" notification 13064. The "activated port" notification can indicate which energy mode of energy module 13041, 13043 is activated, and specifically, which port 13036, 13038*a*, 13038*b*, 13040 of that energy module 13041, 13043 is activated for use. For example, in the aspect of FIG. 113, a "cut" mode of the first energy module 13041 is activated by the modular energy system 13012, thereby enabling an instrument connected to a first monopolar port 13038*a* to cut tissue. Accordingly, the "activated instrument" notification 13064 can be displayed within the monopolar port icon 13048*a* of the first row 13051 and the monopolar port icon 13048*a* can include a first indicia (e.g., a color). The "activated port" notification 13064 associated with the "cut" mode can include, for example, alternate crosshatching in a first color (e.g., yellow). Additionally and/or alternatively, the port icons 13046, 13048*b*, 13050 can be faded out, removed, or otherwise visually minimized by the user interface 13042. Likewise, the modular energy system 13012 can illuminate a light tube 13066 surrounding the activated port 13038*a*. Thus, the light tube 13066 and various elements of the user interface 13042 can communicate to the user which port 13036, 13038*a*, 13038*b*, 13040 of which energy module 13041, 13043 is activated.

Figure 114:
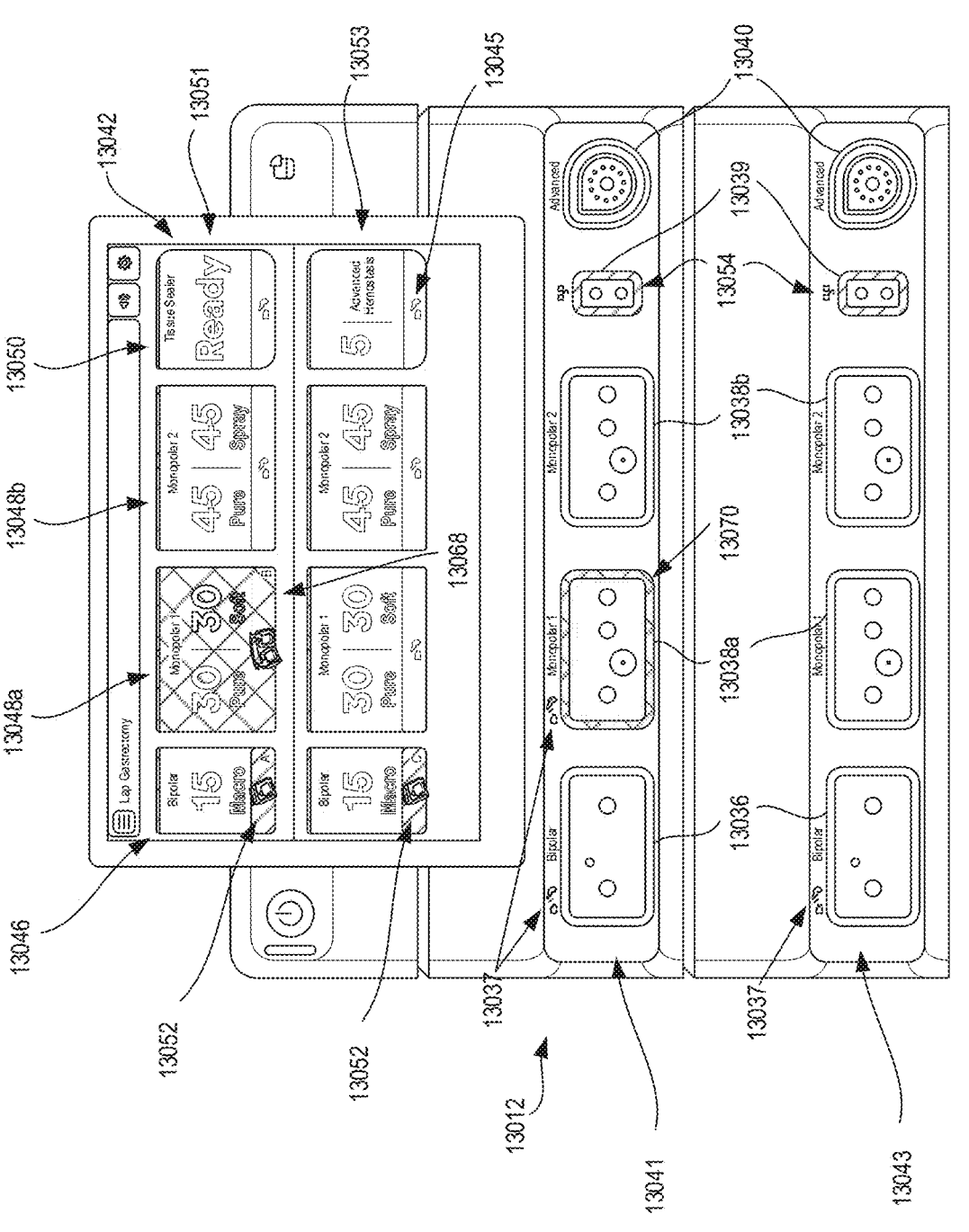
FIG. 114 is a front view of an energy module, in accordance with at least one aspect of the present disclosure.

FIG. 114 depicts a similar user interface 13042 to that of FIG. 113 in accordance with another aspect of the present disclosure. However, in the aspect of FIG. 114, a "coagulate" mode of the first energy module 13041 is activated by the modular energy system 13012, thereby enabling an instrument connected to a first monopolar port 13038*a* to coagulate tissue. Accordingly, the "activated instrument" notification 13068 can be displayed within the monopolar port icon 13048*a* of the first row 13051, and the monopolar port icon 13048*a* can include a second indicia. The second indicia can be different from the first indicia in order to visually distinguish the different modes in which a connected surgical instrument can operate. The "activated port" notification 13068 associated with a "coagulate" mode can include, for example, alternate crosshatching in a second color (e.g., blue). Additionally and/or alternatively, the port icons 13046, 13048*b*, 13050 can be faded out, removed, or otherwise visually minimized by the user interface 13042. Likewise, the modular energy system 13012 can illuminate a light tube 13070 surrounding the activated port 13038*a*.

Referring now to FIGS. 115-119, various displays of a user interface 13042 of an energy module are shown in accordance with at least one aspect of the present disclosure. In addition to the features depicted in FIGS. 115-119, the user interface is contemplated to further display an instrument settings panel that includes controls that are unique to each instrument. In some aspects, the user interface 13042 can include controls that allow the user to increase or decrease the intensity of an instrument's output 13071, adjust its functions 13073, and/or pair it with connected system accessories (e.g., a footswitch 13052). The user interface 13042 can further provide access to advanced instrument settings and access information about the instrument. For example, the instrument settings panel can be accessed by interacting with a settings icon 13075. These features, among others, are contemplated by the present disclosure, including various combinations thereof. Accordingly, the user interface 13042 can be extremely flexible and may be reconfigured to accommodate the specific needs of an electrosurgical procedure.

The user interface 13042 of FIGS. 115-119 is further configured to optimize the use of a connected footswitch. For example, if the user plugs in a non-hand-activated instrument, the user interface 13042 will display a warning if no footswitch is connected. Alternatively and/or additionally, the instrument settings are dimmed, as the instrument cannot be activated without a footswitch. Furthermore, the user interface 13042 is configured to notify the user when a footswitch has been assigned to an instrument, and allows the user to reassign, unassign, or otherwise change the settings associated with the connected footswitch in accordance with at least the aspects depicted in FIGS. 115-119. In other non-limiting aspects, the user interface 13042 is further configured to communicate with a control circuit and automatically assign footswitches to non-hand-activated instruments in accordance with default settings.

Figure 115:
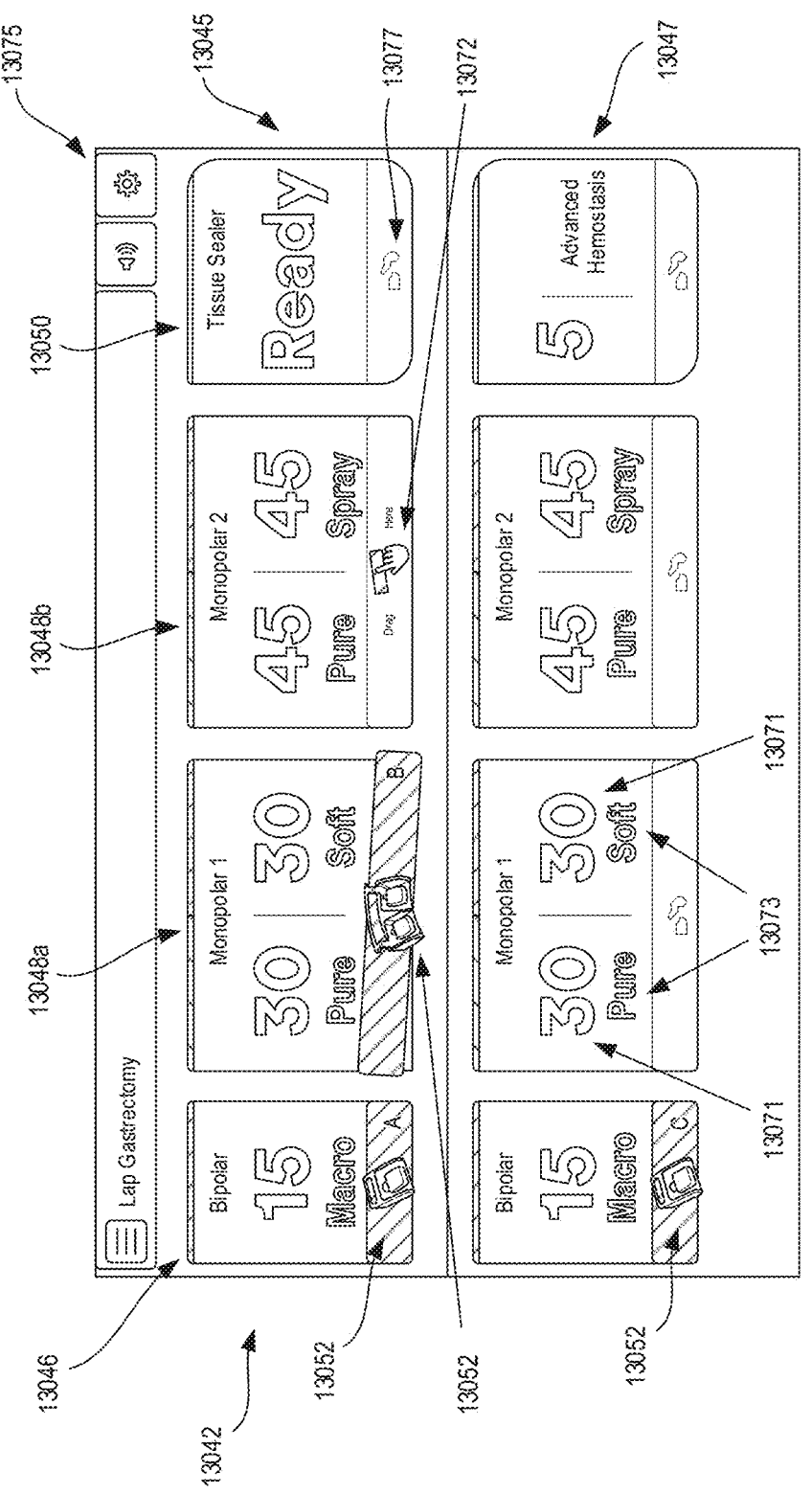
FIG. 115 is a display of a user interface, in accordance with at least one aspect of the present disclosure.

Referring now to FIG. 115, a display of the user interface 13042 of an energy module is shown in accordance with at least one aspect of the present disclosure. The user interface of FIG. 115 can display port icons 13046, 13048*a*, 13048*b*, 13050 associated with ports of a first energy module 13045 and second energy module 13047. Although the user interface of FIG. 115 is configured for use with two energy modules 13045, 13047, the present disclosure contemplates other aspects where the user interface is configured for use with any number of energy modules.

As depicted in FIG. 115, the port icons 13046, 13048*a*, 13048*b*, 13050 can include a global footswitch icon 13077, if the port is compatible for use with a footswitch or other system accessory. When a user wants to assign a footswitch to a specific port, they interact with the global footswitch icon 13077 of the desired port icon 13046, 13048*a*, 13048*b*, 13050. Accordingly, the user interface 13042 displays a footswitch assignment overlay that can allow the user to assign and reassign footswitches to the desired port icon 13046, 13048*a*, 13048*b*, 13050 using the footswitch widgets 13052. When the user interacts with the global footswitch icon 13077 of the desired port icon 13046, 13048*a*, 13048*b*,

13050, a "drag here" prompt 13072 will appear on that port icon 13046, 13048*a*, 13048*b*, 13050 and any footswitch widgets 13052 that can be reassigned to the selected port icon 13046, 13048*a*, 13048*b*, 13050 will be visually distinguished from footswitch widgets 13052 that cannot be reassigned to the selected port icon 13046, 13048*a*, 13048*b*, 13050. The user can move a compatible footswitch widget 13052 to the selected port icon 13046, 13048*a*, 13048*b*, 13050, thereby reassigning the footswitch to that port.

For example, in FIG. 115, the user has selected the global footswitch icon 13077 of the second monopolar port icon 13048*b* for the first energy module 13045, thereby initiating the process of assigning a footswitch to the second monopolar port of the first energy module 13045. In response, the second monopolar port icon 13048*b* displays a "drag here" prompt 13072. In response to being selected, the footswitch widget 13052 can be configured to visually confirm that it has been selected (e.g., by pivoting back and forth). In the illustrated example, the footswitch widget 13052 associated with the two-pedal footswitch assigned to the first monopolar port icon 13048*a* of the first energy module 13045 has begun to pivot back and forth, indicating that it can be reassigned to the second monopolar port icon 13048*b* of the first energy module 13045. Although the footswitch widget 13052 in FIG. 115 is pivoting back and forth, other methods of visually distinguishing compatible footswitch widgets 13052 are contemplated by the present disclosure (e.g., change color, become brighter, display text). Notably, the footswitch widgets 13052 associated with the single-pedal footswitches currently assigned to the bipolar instruments connected to the first and second energy modules 13045, 13047 are not pivoting, because they are not compatible for reassignment to the second monopolar port icon 13048*b*. However, other methods of visually distinguishing incompatible footswitch widgets 13052 are contemplated by the present disclosure (e.g., change color, become dimmer, display text). The user can drag the pivoting footswitch widget 13052 on the first monopolar port icon 13048*a* to the second monopolar port icon 13048*b*, thereby reassigning the footswitch from the first monopolar port icon 13048*a* to the second monopolar port icon 13048*b*. After the footswitch is reassigned, the user interface 13042 removes the footswitch assignment overlay. Although FIG. 115 depicts the assignment process for the second monopolar port icon 13048*b* of the first energy module 13045, selecting the global footswitch icon 13077 of any port icon 13046, 13048*a*, 13048*b*, 13050 will commence a similar process, wherein each footswitch widget 13052 associated with a connected footswitch that is compatible for assignment to the selected instrument will begin to pivot back and forth.

Figure 116:
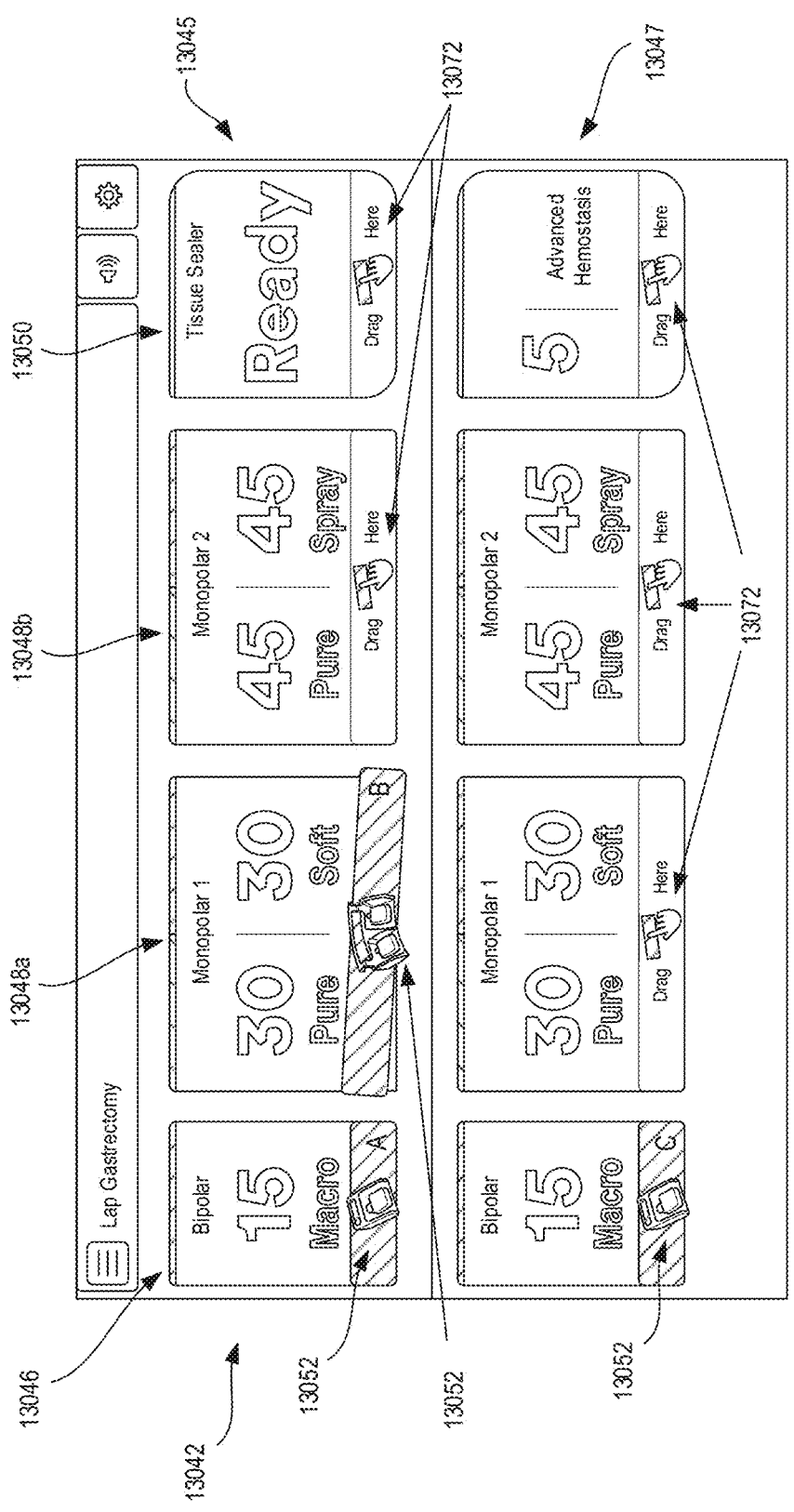
FIG. 116 is a display of a user interface, in accordance with at least one aspect of the present disclosure.

Referring now to FIG. 116, another display of the user interface 13042 of an energy module is shown in accordance with at least one aspect of the present disclosure. Contrary to the aspect of FIG. 115, the user has selected a footswitch widget 13052 that they want to reassign to a different port icon 13046, 13048*a*, 13048*b*, 13050. In response, the user interface 13042 can display a footswitch reassignment overlay distinguishing port icons 13046, 13048*a*, 13048*b*, 13050 that are compatible with the selected footswitch widget 13052. For example, in FIG. 116, the user has selected the footswitch widget 13052 currently assigned to the first monopolar port icon 13048*a* of the first energy module 13045. Accordingly, the second monopolar port icon 13048*b* and the combination energy port icon 13050 of the first energy module 13045 and the first monopolar port icon 13048*a*, the second monopolar port icon 13048*b*, and the combination energy port icon 13050 of the second energy module 13047 display a "drag here" prompt 13072 indicating that they are compatible with the selected footswitch for reassignment. The "drag here" prompts 13072 indicate to the user that the selected footswitch can be assigned to those ports. Although the compatible port icons 13048a, 13048b, 13050 of FIG. 116 display a "drag here" prompt, other methods of visually distinguishing compatible ports are contemplated by the present disclosure (e.g., change color, become brighter, display text). Additionally, the selected footswitch widget 13052 has begun to pivot back and forth, indicating which footswitch is selected and about to be reassigned. However, other methods of visually distinguishing the selected footswitch widget 13052 are contemplated by the present disclosure (e.g., change color, become brighter, display text). Because the selected footswitch widget 13052 is associated with a two-pedal footswitch, it is compatible with any of the connected instruments. However, if the user selected a footswitch widget 13052 associated with a single-pedal footswitch, the "drag here" prompt 13072 could appear on the bipolar port icons 13046 and combination energy port icons 13050.

Figure 117:
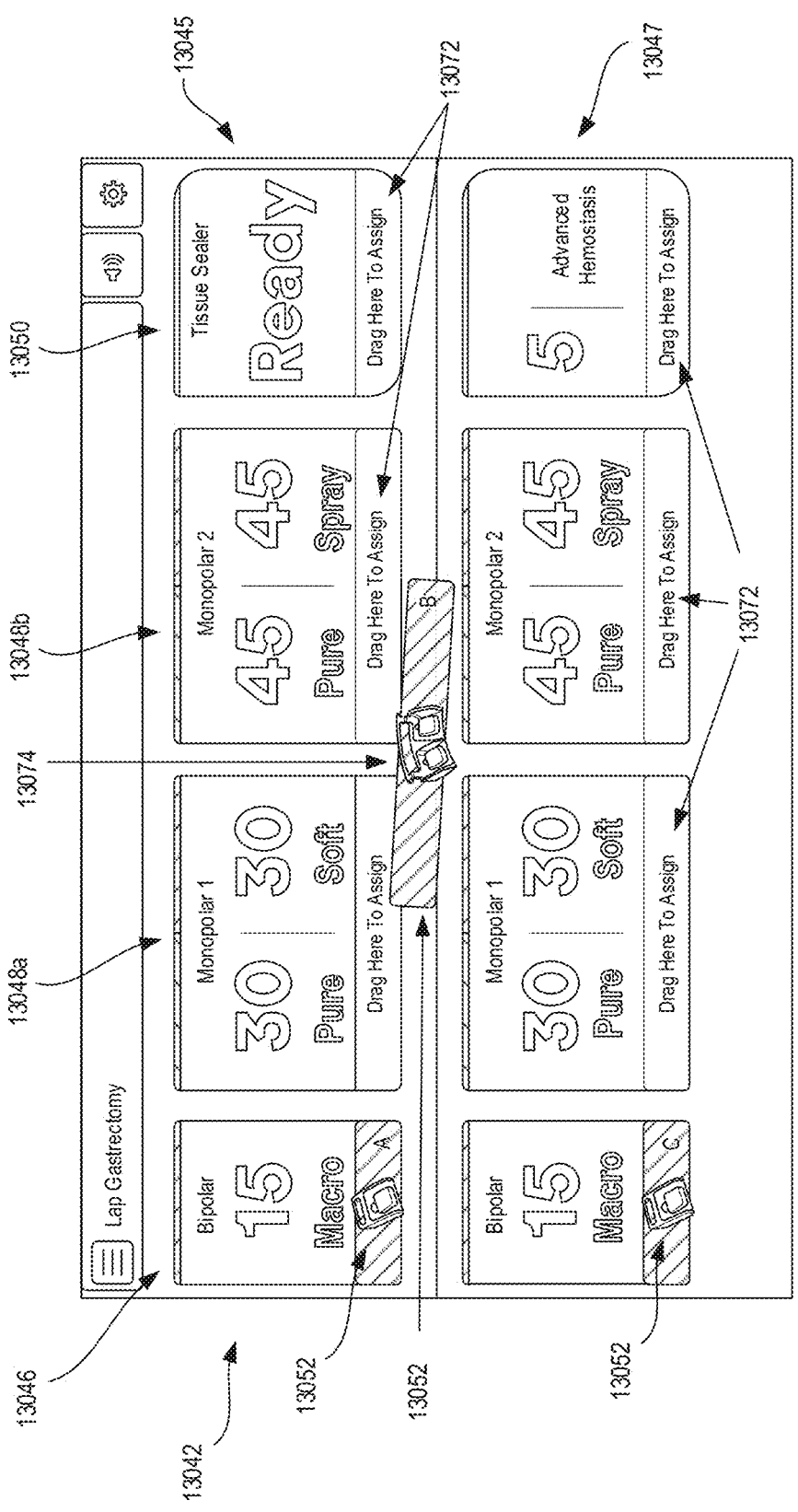
FIG. 117 is a display of a user interface, in accordance with at least one aspect of the present disclosure.

Referring now to FIG. 117, another display of the user interface 13042 of an energy module is shown in accordance with at least one aspect of the present disclosure. In FIG. 117, the user is in the process of reassigning a footswitch from the first monopolar port icon 13048a of the first energy module 13045 to the second monopolar port icon 13048b of the first energy module 13045, using the method depicted in FIG. 116. Specifically, the user has interacted with the footswitch widget 13052 previously assigned to the first monopolar port icon 13048a of the first energy module 13045, which initiated the footswitch reassignment overlay and resulted in the display of multiple "drag here" prompts 13072 on compatible port icons 13048a, 13048b, 13050. Notably, the bipolar port icons 13046 associated with the bipolar instruments connected to the top and bottom energy modules do not display a "drag here" prompt 13072, because single-pedal footswitches are currently assigned to them. Thus, they are unavailable for reassignment. The user is in the process of dragging the footswitch widget 13052 from the first monopolar port icon 13048a of the first energy module 13045 to the second monopolar port icon 13048b of the first energy module 13045. Although the user is dragging the footswitch widget 13052 in FIG. 117, alternate methods of moving the footswitch widget are contemplated by the present disclosure.

Figure 118:
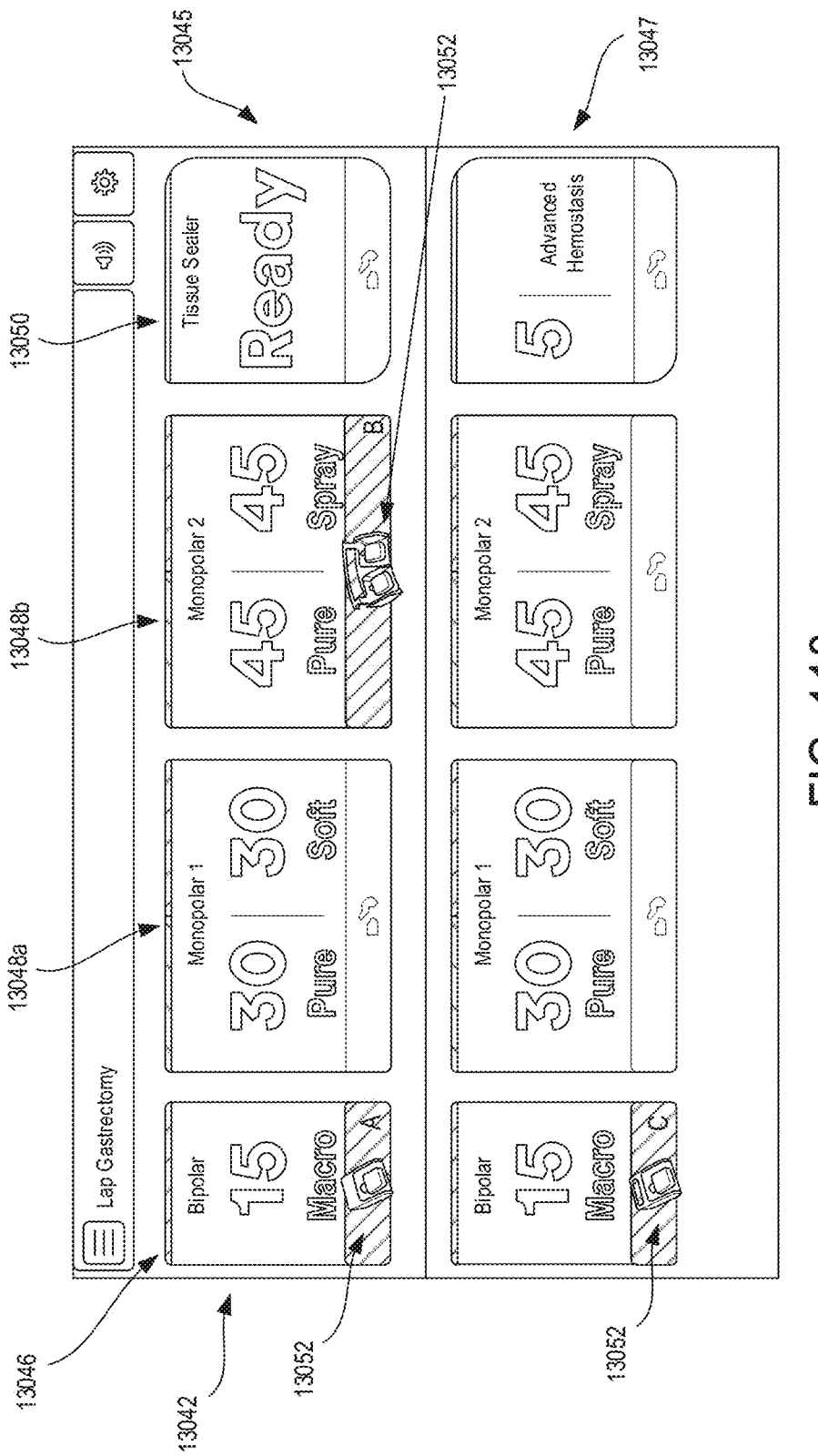
FIG. 118 is a display of a user interface, in accordance with at least one aspect of the present disclosure.

Referring now to FIG. 118, another display of the user interface 13042 of an energy module is shown in accordance with at least one aspect of the present disclosure. In FIG. 118, the user has completed the process of reassigning a footswitch from the first monopolar port icon 13048a of the first energy module 13045 to the second monopolar port icon 13048b of the first energy module 13045, as depicted in FIG. 117. Accordingly, the footswitch reassignment overlay is no longer displayed, the "drag here" prompts have disappeared, and the user interface has illuminated the second monopolar port icon 13048b the "confirmation" color. The "confirmation" color is represented via crosshatching in FIG. 118.

Figure 119:
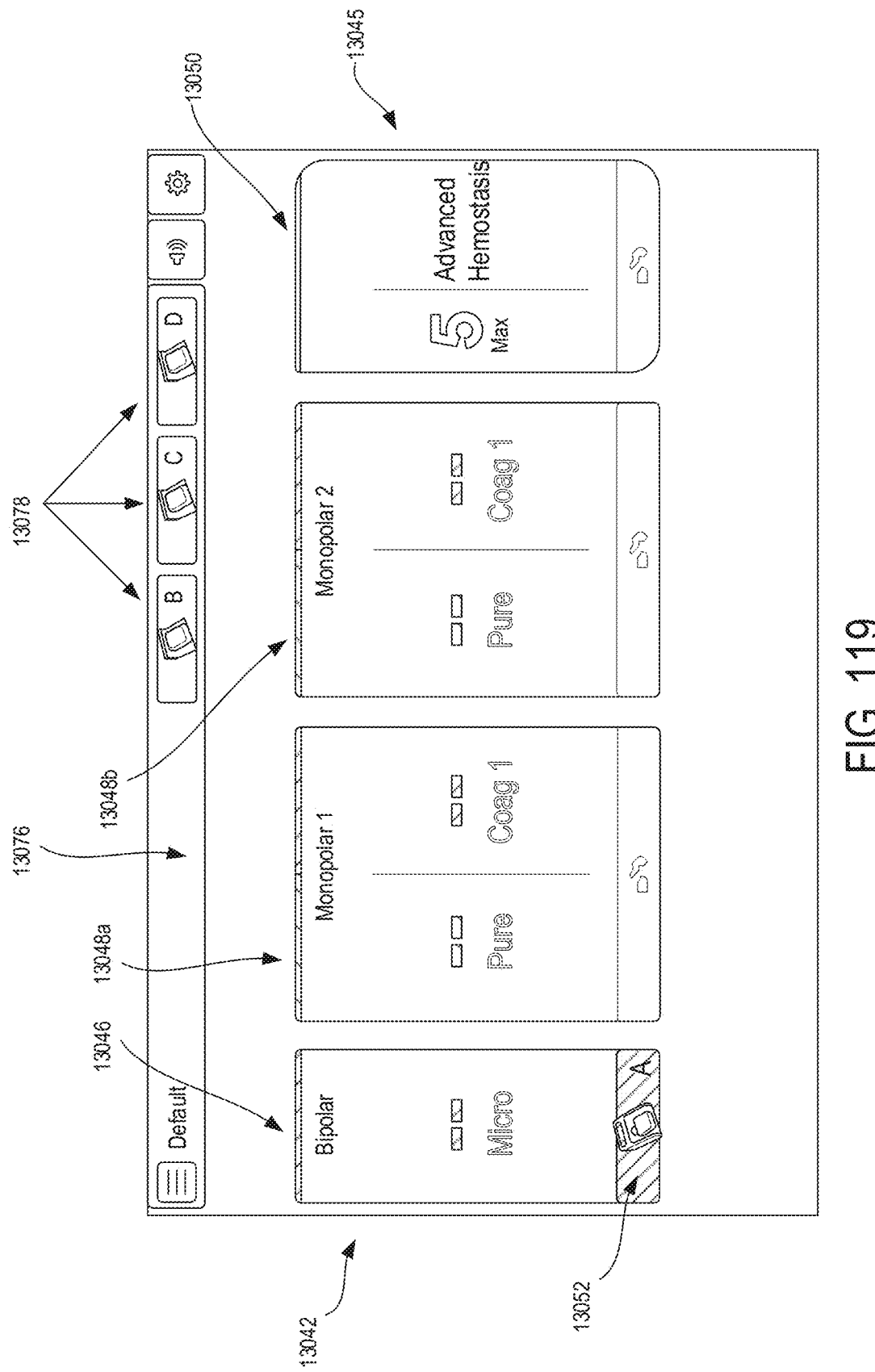
FIG. 119 is a display of a user interface, in accordance with at least one aspect of the present disclosure.

Referring now to FIG. 119, another display of the user interface 13042 of an energy module is shown in accordance with at least one aspect of the present disclosure. According to the aspect of FIG. 119, the user interface 13042 can have a designated area 13076 for unassigned footswitch icons 13078. Accordingly, if a footswitch is connected to the modular energy system, but has not been assigned to an instrument, an unassigned footswitch icon 13078 can appear on the user interface 13042 in the designated area 13076.

Although the aspect of FIG. 119 depicts the designated area 13076 at the top of the display, other locations are contemplated by the present disclosure. When a user wants to assign an unassigned footswitch to an instrument, he or she can follow a process similar to those depicted in FIGS. 115-118. Specifically, the user can interact with either the unassigned footswitch icon 13078 or the desired port icon 13046, 13048a, 13048b, 13050, thereby initiating the footswitch reassignment overlay, and move the footswitch icon 13078 to the desired port icon 13046, 13048a, 13048b, 13050. Upon proper assignment, the user interface will illuminate the port icon 13046, 13048a, 13048b, 13050 to which the footswitch has been assigned the "confirmation" color. Although the modular energy system of FIG. 109 has only a first energy module 13045, the present disclosure contemplates other aspects where user interface 13042 displays port icons 13046, 13048a, 13048b, 13050 associated with the ports of any number of energy modules.

Figure 120:
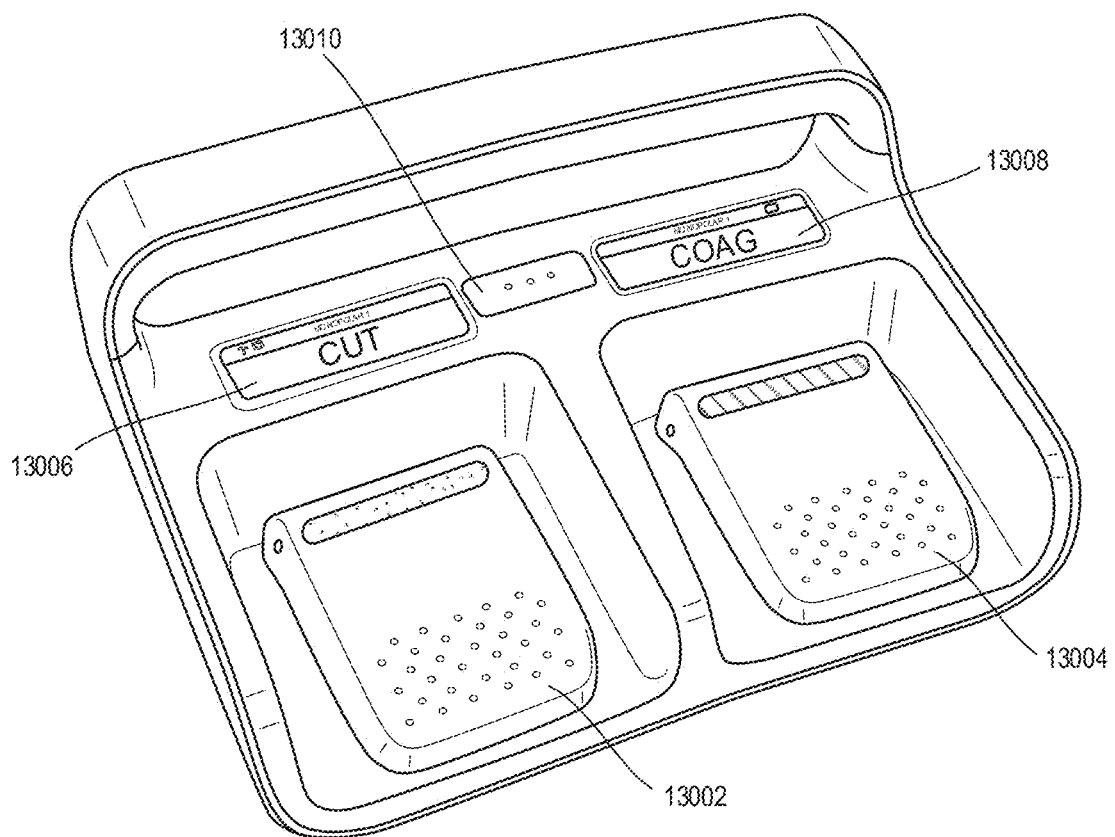
FIG. 120 is a perspective view of a footswitch, in accordance with at least one aspect of the present disclosure.

Referring to FIG. 120, a perspective view of a footswitch 13000 is shown in accordance with at least one aspect of the present disclosure. The footswitch 13000 is interchangeably compatible with different energy ports, energy modules, drive modes, and/or instruments. As previously discussed and depicted in FIGS. 115-119, the footswitch 13000 of FIG. 120 can be reassigned by the user interface of a modular energy system. For example, although the footswitch 13000 can be connected through a single port of the surgical system via a corresponding accessory port 13016, as depicted in FIGS. 107 and 108, it can be reassigned for use during a monopolar, bipolar, or combination energy mode of the modular energy system without altering the connection.

According to the aspect of FIG. 120, the footswitch 13000 includes a first foot pedal 13002 and second foot pedal 13004. The first foot pedal 13002 and second foot pedal 13004 can activate an instrument connected to a port of the modular energy system to perform a variety of functions. For example, in FIG. 120, the first foot pedal 13002 can be assigned to activate a cut energy mode of the energy module, and the second foot pedal 13004 can be assigned to activate a coagulation energy mode of the energy module. However, each of the first foot pedal 13002 and second foot pedal 13004 can be reassigned to activate a different function of the modular energy system via the user interface. Although the footswitch 13000 of FIG. 120 includes a first foot pedal 13002 and second foot pedal 13004, this particular example is merely for illustrative purposes and other non-limiting aspects of the present disclosure include a single foot pedal. For example, in one non-limiting aspect, a footswitch includes a single foot pedal assignable to bipolar or combination energy ports of the modular energy system. Still other non-limiting aspects of the present disclosure include more than two foot pedals. For example, in one non-limiting aspect, a footswitch includes three pedals assignable to activate a variety of energy modes of the modular energy system. Accordingly, the footswitch 13000 can be configured to include any number of foot pedals depending the intended application.

In further reference to FIG. 120, the footswitch 13000 includes a first reconfigurable display 13006 and second reconfigurable display 13008 positioned above each of the first foot pedal 13002 and second foot pedal 13004. The first reconfigurable display 13006 and second reconfigurable display 13008 can inform the user of the energy mode that each of the first foot pedal 13002 and second foot pedal 13004 are assigned to activate. Accordingly, the text, color, or other indicia displayed by the reconfigurable displays 13006, 13008 can correspond to the particular mode or function to which the respective foot pedal 13002, 13004 is assigned. The reconfigurable displays 13006, 13008 employ any number of display technologies, including, but not limited to: light-emitting diode displays (LED), liquid crystal displays (LCD), electroluminescent displays (ELD), electronic paper, and digital light processing displays (DLP), among others. In the particular aspect of FIG. 120, the first foot pedal 13002 is configured to activate a connected electrosurgical instrument to cut tissue. Accordingly, the first reconfigurable display 13006 can display the word "CUT." Likewise, the second foot pedal 13004 is configured to activate a connected electrosurgical instrument to coagulate tissue. Accordingly, the second reconfigurable display 13008 can display the word "COAG." However, when the user interface assigns each of the first foot pedal 13002 or second foot pedal 13004 to activate a different energy mode of the modular energy system, each of the first reconfigurable display 13006 and second reconfigurable display 13008 is reconfigured to display the new function. The reconfigurable displays 13006, 13008 can be automatically reconfigured by the modular energy system or manually changed by the user. Although the footswitch 13000 of FIG. 120 includes two reconfigurable displays, one for each of its two foot pedals, other non-limiting aspects of the present disclosure include fewer reconfigurable displays than foot pedals, wherein the reconfigurable displays can inform the user of an assigned function of any of the foot pedals on the footswitch. Still other non-limiting aspects of the present disclosure forego a reconfigurable display altogether, using the user interface and/or display of the modular energy system to display the function of each foot pedal. Other non-limiting aspects of the present disclosure omit reconfigurable displays in preference for audible or haptic feedback to inform the user of the configured function of each foot pedal. Still other aspects of the footswitch include a combination of configurable displays, audible, and haptic feedback to communicate with the user.

According to the aspect of FIG. 120, the footswitch 13000 includes an additional function button 13010 configured to interface with the modular energy system to perform a number of programmed functions related to the ports, modules, drive modes, and/or connected instruments. For example, the additional function button 13010 of FIG. 120 can reassign the footswitch 13000 a different port of the modular energy system. If the procedure requires the use of a different instrument, the user could push the additional function button 13010 to reassign the footswitch 13000 to activate a second port of the modular energy system, without having to alter the physical connection or traverse the OR to access the user interface. Similar to the first foot pedal 13002 and second foot pedal 13004, the user interface can be used to reassign the additional function button 13010 to perform any number of alternate functions. For example, the additional function button 13010 can be configured to reassign the footswitch 13000 to an alternate module or drive mode of the modular surgical system. Alternatively, the additional function button 13010 can be configured to reassign the first foot pedal 13002 or second foot pedal 13004 to activate an alternate energy mode of the modular energy system.

The user interface can automatically apply default settings upon connection of the footswitch 13000 to the modular energy system. The user can select the default settings via the user interface of the surgical system, which are subsequently stored in a data storage device in communication with the surgical system. Upon connection, the modular energy system can identify the footswitch (e.g., via resistor identification). Accordingly, the modular energy system can automatically assign an identified footswitch 13000 to a particular port of an energy module based on the default settings. The default settings can further take into account the particular configuration of the surgical system (e.g., the number and types of energy modules from which the modular surgical system is formed, the number and types of footswitches 13000 coupled to the modular energy system, the number and arrangement of foot pedals collectively available across the footswitch(es) 13000 coupled to the modular energy system). In certain aspects of the present disclosure, the automatic identification and assignment of the footswitch 13000 in accordance with default settings serves as a failsafe. For example, bipolar and monopolar lap instruments generally require a footswitch 13000 prior to operation. In one aspect, a default setting is established to prevent the energy module from functioning prior to the identification and assignment of the required footswitch 13000. Thus, the user will have to connect a footswitch 13000 prior to commencing surgery. However, once connected, the footswitch 13000 and foot pedals 13002, 13004, will be automatically assigned. Accordingly, the default settings can be modified by the user to conform to preference and/or surgical requirements.

As another example, if the modular energy system is configured for bipolar surgery, the default settings will automatically configure a first single foot pedal footswitch for bipolar activation upon connection, based on the default settings. If a second single foot pedal footswitch is subsequently connected, the modular energy system will recognize that the first footswitch is already assigned to a bipolar port and automatically assign the second footswitch for combination energy port upon connection, based on the default settings. Alternatively, if the modular energy system is configured for monopolar surgery, the default settings could automatically assign a first footswitch with two foot pedals to activate a first monopolar port upon connection, based on the default settings. If a second footswitch with two foot pedals is subsequently connected, the modular energy system could recognize that the first footswitch is already assigned to the first monopolar port and automatically assign the second footswitch to activate a second monopolar port upon connection, based on the default settings. If a third footswitch with two foot pedals is subsequently connected, the modular energy system could recognize that the first footswitch is already assigned to the first monopolar port and that the second footswitch is already assigned to second monopolar port and automatically assign the third footswitch to a combination energy port upon connection, based on the default settings. Accordingly, the reconfigurable displays of each footswitch can inform the user of each foot pedal function as the modular energy system automatically assigns the footswitches, allowing for convenient confirmation that the default settings have been appropriately applied. Although the default settings can automatically assign each footswitch 13000 upon connection, reassignment is possible via the user interface. Accordingly, if the user decides to change the settings, he or she may do so by using the user interfaces or, in some aspects, by toggling settings via the additional function button 13010.

Disclosed is a surgical platform modular energy system that includes an energy module comprising one or more generators. The energy module may include a real time clock a control circuit coupled to the real time clock. The control circuit is configured to detect the presence of a surgical instrument coupled to the energy module and monitor energization of the surgical instrument by the energy module and track usage of the surgical instrument in real time based on the real time clock and to deactivate the surgical after a predetermined period of usage based on the real time clock.

The energy module may include a two wire interface coupled to the control circuit. The two wire interface is configured as a power source and communication interface between the energy module and a monopolar neutral electrode.

The energy module may include a hand-switch detection circuit, a surgical instrument interface coupled to the hand-switch, and the control circuit coupled to the surgical instrument interface and the hand-switch detection circuit. The control circuit is configured to determine specific requirements of a surgical instrument coupled to the energy module via the surgical instrument interface.

The energy module may include a bidirectional current source coupled to the control circuit, the bidirectional current source comprising adjustable current and voltage setpoints, a first semiconductor switch to short the current source output to ground, controlled by the control circuit, a comparator coupled to the semiconductor switch to read a logic level of the current source output, an analog-to-digital (ADC) coupled to the bidirectional current source, the ADC configured to read an absolute value of an analog voltage output of the bidirectional current source output, a second semiconductor switch configured to short the bidirectional current source power supply to the output, controlled by the control circuit, a multiplexer (MUX) coupled to the bidirectional current source to switch between the current source output and differential data lines transceiver.

The energy module may include a port, a sensor coupled to the port and the control circuit, and an interface circuit coupled to the port, the sensor, and the control circuit. The sensor is configured to detect presence of a surgical instrument coupled to the port.

Flexible Neutral Electrode Circuit

Reusable monopolar neutral electrodes provide a semipermanent interface to an electrosurgical generator within a sterile field. This provides an opportunity to collect patient or instrument data from the sterile field and relay the information back to the electrosurgical generator. In also provides a means to incorporate unique user interface elements for controlling or getting status from the electrosurgical generator. These types of neutral electrode enhancements require electronic circuits to be incorporated into the electrode pad. The electronic circuits need to be powered and a communication interface to/from the generator must be provided.

Accordingly, in various aspects the present disclosure provides a neutral electrode circuit configuration that accommodates multiple types of neutral pad devices through the same port of an electrosurgical generator, such as, for example, the advanced energy receptacle 3100, RF monopolar receptacle 3136, NE receptacle 3292, or RF bipolar receptacle 3118 of the energy module 3270 shown in FIG. 37. In one aspect, the present disclosure provides a generator, including a control circuit and a two wire interface coupled to the control circuit. The two wire interface is configured as a power source and communication interface between the generator and a monopolar neutral electrode as described hereinbelow.

FIG. 121 illustrates a communication circuit 16500 including a configurable current source circuit 16512 circuit to implement multiple communication protocols, in accordance with at least one aspect of the present disclosure. The communication circuit 16500 is located in the energy module 3270 shown in FIG. 37 and provides a flexible two wire interface configured as a power source and communication interface between an electrosurgical generator portion of the energy module 3270, for example, and a monopolar neutral electrode in a surgical instrument 16520. The energy module 3270 includes a control circuit 16502 to implement a control protocol between the control circuit 16502 and a controller 16508 through an isolation circuit 16504 (e.g., isolation transformer, optical coupler, etc.). The control protocol includes 1-Wire, I²C, LIN, discrete GPIO, AAB, among others. The controller 16508 may include an I²C compatible digital potentiometer such as, for example, a 256-position dual channel I²C compatible digital resistor (e.g., AD5248) or a DAC. The controller 16508 also may include an I²C to GPIO 8-bit general-purpose I/O expander that provides remote I/O expansion for the control circuit 16502 via the I²C-bus interface (e.g., PCAL6408A). The controller 16508 also may include an integrated interface I/O expander 1-wire 8-channel addressable switch (e.g., DS2408).

The controller 16508 also may include a LIN to GPIO interface (UJA1023). The UJA1023 is a stand-alone Local Interconnect Network (LIN) I/O slave that contains a LIN 2.0 controller, an integrated LIN transceiver which is LIN 2.0/SAE J2602 compliant and LIN 1.3 compatible, a 30 kΩ termination resistor necessary for LIN-slaves, and eight I/O ports which are configurable via the LIN bus. An automatic bit rate synchronization circuit adapts to any (master) bit rate between 1 kbit/s and 20 kbit/s. For this, an oscillator is integrated. The LIN protocol will be handled autonomously and both Node Address (NAD) and LIN frame Identifier (ID) programming will be done by a master request and an optional slave response message in combination with a daisy chain or plug coding function. The eight bidirectional I/O pins are configurable via LIN bus messages.

The controller 16508 also may include a universal asynchronous receiver transmitter (UART) communication interface with CPLD (e.g., Altera MaxV). The UART converts parallel data (8 bit) to serial data. The UART transmits bytes of data sequentially one bit at a time from source and receive the byte of data at the destination by decoding sequential data with control bits. As the entire processes require no clock input from source hence it is termed as asynchronous communication.

The controller 16508 is coupled to a drive circuit 16510 to configure $V_{DD2}$, $V_{Thresh}$, $I_{Out}$, and $SW_{Filt}$, as further described hereinbelow. The drive circuit 16510 includes a configurable current source circuit 16512 to implement multiple communication protocols, in accordance with at least one aspect of the present disclosure. The configurable current source circuit 16512 may be used to implement a number of standard communication protocols including 1-Wire protocol, LIN protocol as well as custom protocols. As is known in the art, 1-Wire protocol is based on a serial communication protocol that uses a single data line plus ground reference between a master and a slave. The 1-Wire protocol slaves are available in various form factors. The minimum function of 1-Wire protocol slaves is a 64-bit ID number. The 1-Wire device is a communications bus system designed by Dallas Semiconductor Corp. that provides low-speed (16.3 kbps) data, signaling, and power over a single conductor. A LIN (Local Interconnect Network) is a serial network protocol used for communication between components in vehicles.

The configurable current source circuit 16512 is a current source with adjustable current and voltage set-points controlled by the control circuit 16502 (e.g., FPGA, microprocessor, microcontroller, discrete logic). An n-channel MOS- FET 16518, other suitable semiconductor switch, is employed for shorting the output of the configurable current source circuit 16512 to ground. This serves to signal a logic low to the circuit in the electrode. A comparator 16514 is provided for reading the logic state of the output. The output of the comparator 16514 is coupled to the control circuit 16502 through an isolation circuit 16506 (e.g., isolation transformer, optical coupler, etc.). A switch 16516 is provided to switch a filter network in and out of the drive circuit 16510.

Figure 122:
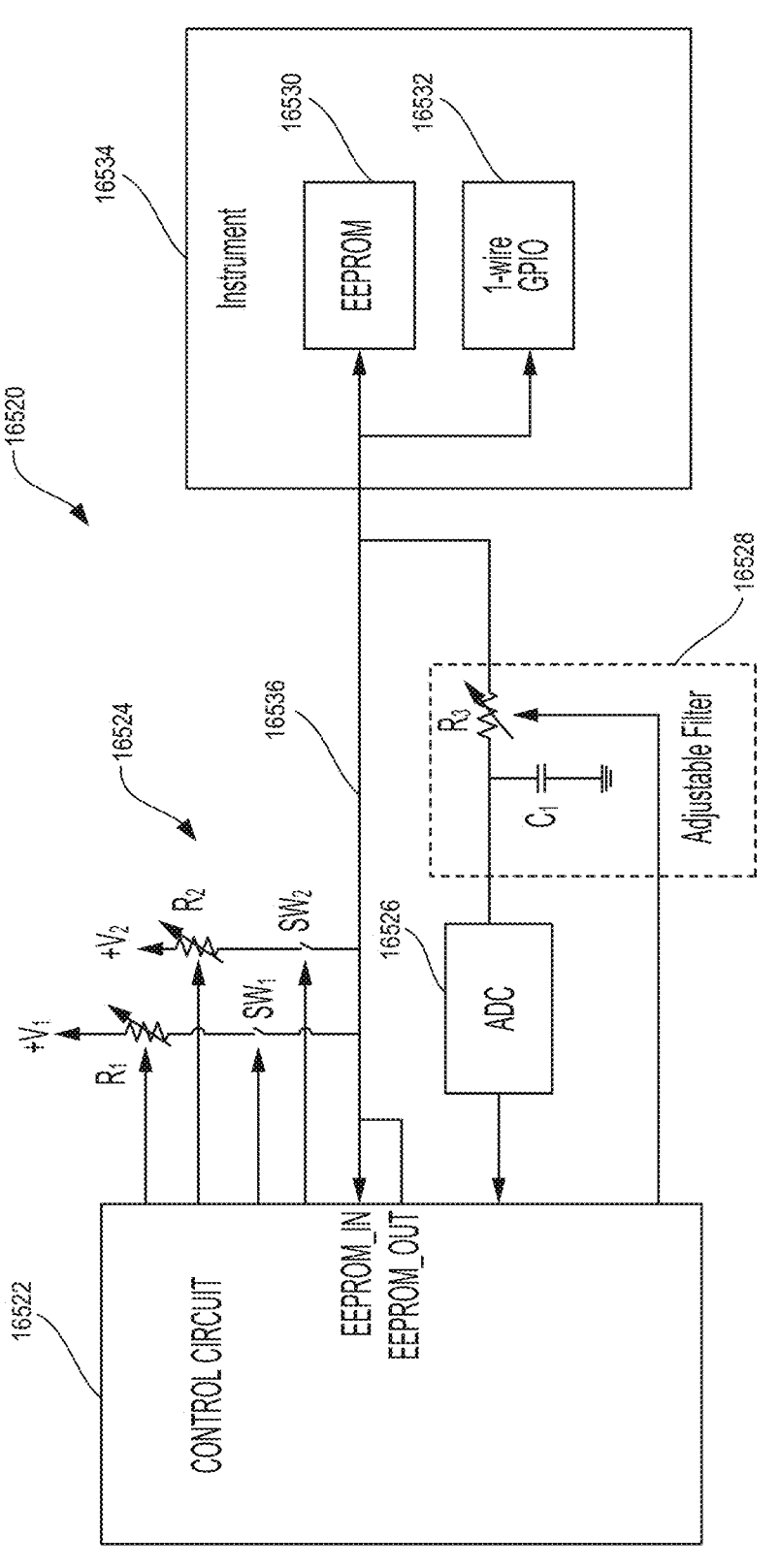
FIG. 122 is a schematic diagram of a communication circuit including an adjustable filter to implement multiple communication protocols, in accordance with at least one aspect of the present disclosure.

FIG. 122 is a schematic diagram of a communication circuit 16520 including an adjustable filter 16526 to implement multiple communication protocols, in accordance with at least one aspect of the present disclosure. The communication circuit 16520 includes a control circuit 16522, which may be implemented as an FPGA, microprocessor, microcontroller, or discrete logic, a dual I²C digital potentiometer circuit 16524 (e.g., AD5248) or a DAC, an ADC 16526, an adjustable filter 16528, and an EEPROM 16530 coupled to a 1-Wire general purpose input/output (GPIO) circuit 16532. In one aspect, the communication circuit 16520 provides first and second communication protocol arrangements for driving primary and secondary devices through a single port, or communication line 16536 of an electrosurgical generator, such as, for example, the advanced energy receptacle 3100, RF monopolar receptacle 3136, NE receptacle 3292, or RF bipolar receptacle 3118 of the energy module 3270 shown in FIG. 37. The communication circuit 16520 is configured for communicating with devices connected to the energy module 3270 using first and second communication protocols, where the first protocol is used to communicate to a primary device and the second protocol is used to communicate to at least one secondary device through the first device.

The control circuit 16522 controls the dual I²C digital potentiometer circuit 16524 by setting the value of R1 and R2 and the state of first and second semiconductor switches SW1 and SW2 to set the current into the adjustable filter 16528. In one aspect, the digital potentiometer circuit 16524 may be implemented with a DAC. The ADC 16526 converts the analog filter voltage and provides the corresponding digital value to the control circuit 16522. In one aspect, the ADC 16526 has a sampling rate of up to 10 MSPS. A suitable ADC may have a sampling rate of 1-100 MSPS, for example. In one aspect, the adjustable filter 16528 may have a bandwidth of ~500 kHz to 5 MHz. A suitable adjustable filter may have a bandwidth of 100 kHz to 500 MHz, for example.

The 1-Wire GPIO circuit 16532 provides a serial protocol using a single data line plus ground reference for communication. The 1-Wire GPIO circuit 16532 employs only two wires: a single data line plus a ground reference. A 1-Wire master circuit initiates and controls the communication with one or more 1-Wire slave devices on the 1-Wire bus. Each 1-Wire slave device has a unique, unalterable, factory-programmed, 64-bit identification number (ID), which serves as device address on the 1-Wire bus, which may be stored in the EEPROM 16530. The 8-bit family code, a subset of the 64-bit ID, identifies the device type and functionality.

In one configuration, the 1-Wire GPIO circuit 16532 is a voltage-based digital system that works with two contacts, data and ground, for half-duplex bidirectional communication. Compared to other serial communication systems such as I²C or SPI, the 1-Wire GPIO circuit 16532 device may be configured for use in a momentary contact environment. Either disconnecting from the 1-Wire protocol bus or a loss of contact puts the 1-Wire protocol slaves into a defined reset state. When the voltage returns, the slaves wake up and signal their presence.

First and Second Communication Protocol Arrangement for Driving Primary and Secondary Devices Through A Port In various aspects, the present disclosure provides a first and second communication protocol arrangement for driving primary and secondary devices through a single energy output port of an energy source such as, for example, the advanced energy receptacle 3100, RF monopolar receptacle 3136, NE receptacle 3292, or RF bipolar receptacle 3118 of the energy module 3270 shown in FIG. 37. In one aspect, the present disclosure provides a communication arrangement for devices connected to an energy source, where a first protocol is used to communicate to a primary device and a second protocol is used to communicate to at least one secondary device through the first device.

Figure 123:
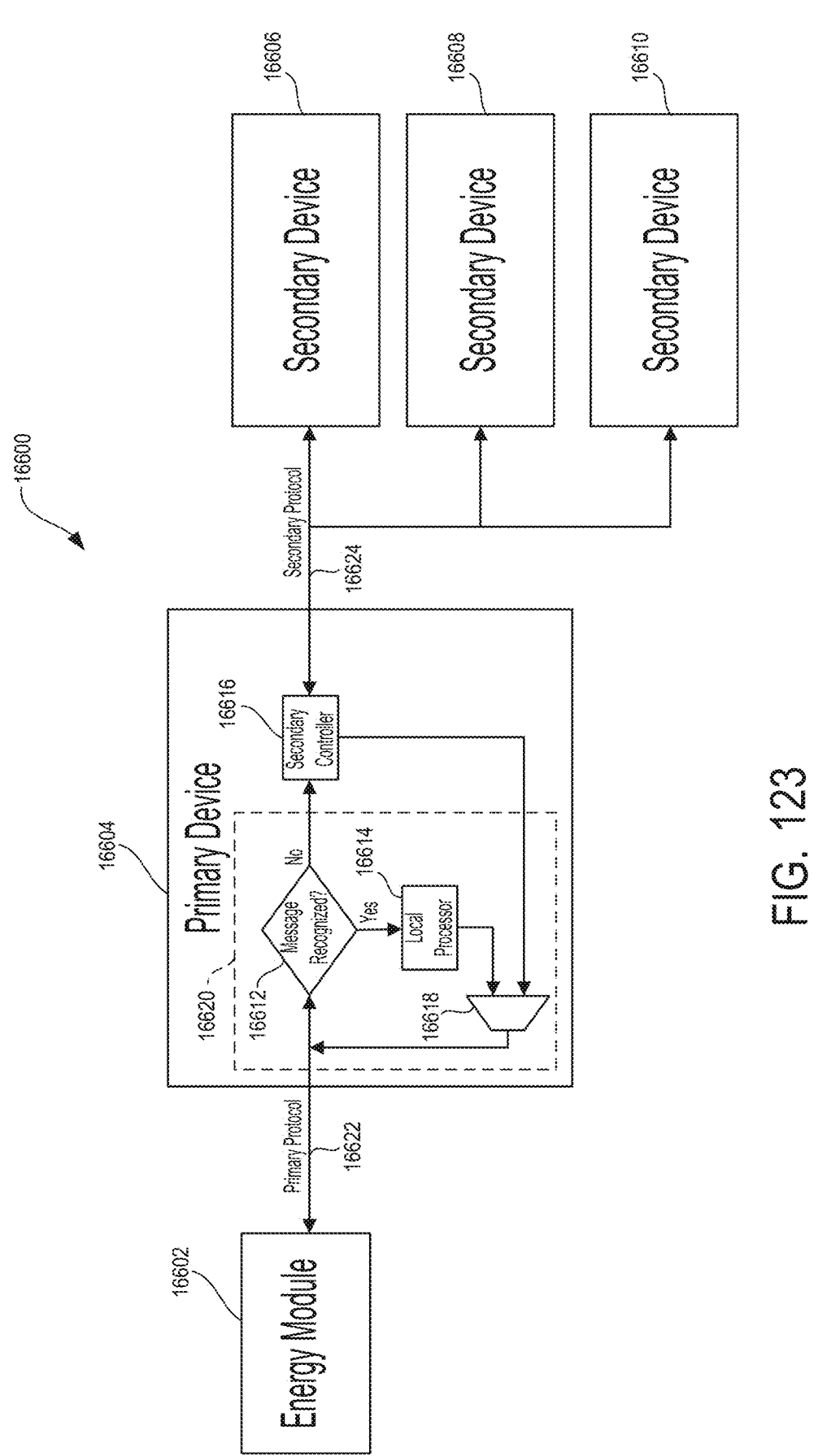
FIG. 123 is a diagram of a communication system employing a primary communication protocol to communicate with a primary device and a secondary communication protocol synchronized to the primary protocol for communicating with expansion secondary devices, in accordance with at least one aspect of the present disclosure.

FIG. 123 is a diagram 16600 of a communication system 16600 employing a primary communication protocol to communicate with a primary device 16604 and a secondary communication protocol synchronized to the primary protocol for communicating with expansion secondary devices 16606, 16608, 16610, in accordance with at least one aspect of the present disclosure. An energy module 16602, such as the energy module 3270 shown in FIG. 37, for example, is coupled to a primary device 16604 and communicates with the primary device 16604 with a first communication protocol. The primary device 16604 is coupled to one or more than one secondary device 16606, 16608, 16610 and communicates with the secondary device 16606, 16608, 16610 with a second communication protocol. Accordingly, the energy module 16602 can effectively communicate with the secondary devices 16606, 16608, 16610 without the secondary device 16606, 16608, 16610 being plugged directly into the energy module 16602. This provides flexibility for expanding the number of devices that the energy module 16602 can communicate with without increasing the number of communication ports on the energy module 16602. The primary device 16604 and secondary devices 16606, 16608, 16610 may be selected from a wide variety of electrosurgical/ultrasonic instruments, such as, for example, the surgical instruments 1104, 1106, 1108 shown in FIG. 22, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The primary device 16604 and secondary devices 16606, 16608, 16610 include circuitry and logic to enable communication with each other and the energy module 16602 using a plurality of protocols described herein, such as, for example, standard communication protocols including CAN, CAN-FD, LIN, 1-Wire, I²C, as well as custom protocols for communicating with and powering proprietary application specific integrated circuits (ASICs) located in the devices 16604, 16606, 16608, 16610.

The primary device 16604 includes a primary controller 16620, e.g., a first control circuit, comprising a communication logic circuit 16612 to determine whether to process 16614 a message locally or send it to a secondary controller 16616, e.g., a second control circuit. The communication logic circuit 16612 is coupled to a first communication line 16622 to send and receive messages to and from the energy module 16602. The communication logic circuit 16612 is coupled to the secondary controller 16616, which is configured to send and receive messages to and from the secondary devices 16606, 16608, 16610 over a second communication line 16624. The communication logic circuit 16612 also is coupled to a local processor 16614.

Accordingly, if a message from the energy module 16602 is recognized by the communication logic circuit 16612, the message is processed locally by the local processor 16614. If the message from the energy module 16602 is not recognized by the communication logic circuit 16612, the message from the generator is provided to the secondary controller 16616, which also receives messages from the secondary devices 16606, 16608, 16610 using the secondary protocol over the second communication line 16624.

The communication circuit 16520 of FIG. 122 may be configured for communicating with the primary device 16604 connected to the energy module 16602 (e.g., the energy module 3270) using the primary and secondary communication protocols via a multiplexer 16618. The first protocol, e.g., primary protocol, is used to communicate to the primary device 16604 and the second protocol, e.g., secondary protocol, is used to communicate to at least one of the secondary devices 16606, 16608, 16610 through the primary device 16604.

A description of one example of a communication arrangement comprising a primary protocol 16622 and a secondary protocol 16624 synchronized to the primary protocol 16622 is described hereinbelow with reference to FIGS. 131A-134. The primary protocol 16622 and the secondary protocol 16624 are used to drive the primary device 16604 and the secondary devices 16606, 16608, 16610 through a single port of the energy module 16602.

Flexible Hand-Switch Circuit

Electrosurgical generators can support a wide variety of surgical instruments. Electronic circuits within each surgical instrument can range from simple activation switches to more advanced circuits including sensors, microcontrollers, memory devices, etc. By optimizing the interface between the generators and the surgical instruments in terms of communication speed, number of wires, and available power enables simple, low cost surgical instruments to be employed within the same infrastructure required to support more sophisticated surgical instruments.

In one aspect, the present disclosure provides a hand-switch circuit that accommodates multiple types of communication protocols of a variety of different hand-switches that are compatible with the output port of an energy source. In another aspect, the present disclosure provides a generator, comprising a hand-switch detection circuit, a surgical instrument interface coupled to the hand-switch detection circuit, and a control circuit coupled to the surgical instrument interface and the hand-switch detection circuit. The control circuit is configured to determine specific requirements of a surgical instrument coupled to the generator via the surgical instrument interface. In another aspect, the hand-switch detection circuit provides multiple flexibility between communication protocols and flexibility for parasitic powering.

Accordingly, in various aspects the present disclosure provides a flexible hand-switch circuit configuration where the interface between the generator and the surgical instrument can be configured to meet the specific requirements of a given surgical instrument. In various aspects, the interface supports simple analog switch detection, standard communication protocols including controller area network (CAN), CAN with flexible data rates (CAN-FD), a LIN, I²C, as well as custom protocols for communicating with and powering proprietary application specific integrated circuits (ASICs).

The LIN broadcast serial network comprises 16 nodes including one master node and typically up to 15 slave nodes. All messages are initiated by the master with at most one slave replying to a given message identifier. The master node also can act as a slave by replying to its own messages. Because all communications are initiated by the master it is not necessary to implement a collision detection. The master and slaves are typically microcontrollers, but may be implemented in specialized hardware or ASICs in order to save cost, space, or power. The LIN bus is an inexpensive serial communications protocol, which effectively supports remote application within a local network. In one aspect, the LIN may be employed to complement an existing CAN network leading to hierarchical networks. Data is transferred across the bus in fixed form messages of selectable lengths. The master task transmits a header that consists of a break signal followed by synchronization and identifier fields. The slaves respond with a data frame that consists of between 2, 4, and 8 data bytes plus 3 bytes of control information.

Figure 124:
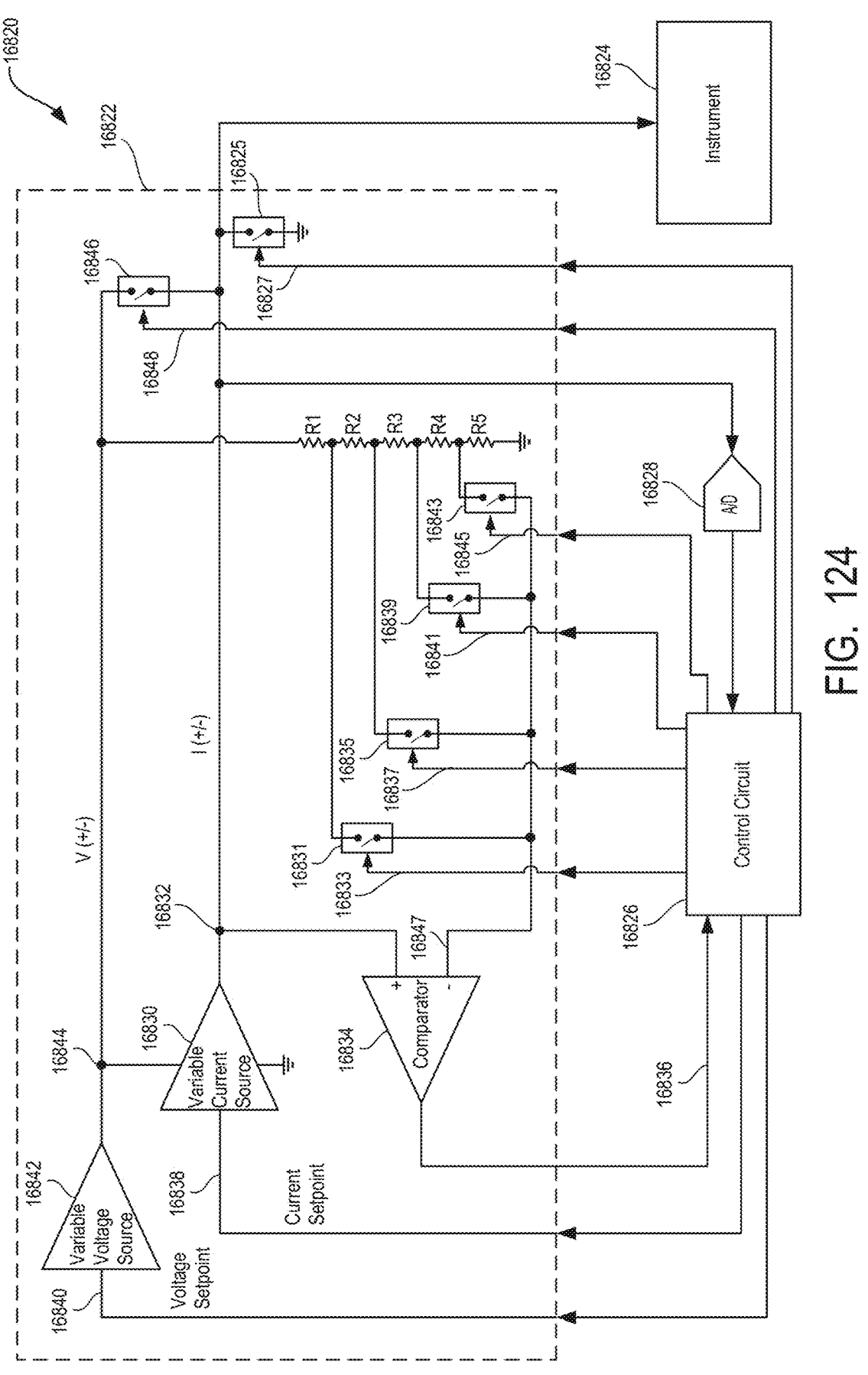
FIG. 124 is a schematic diagram of a flexible hand-switch circuit system, in accordance with at least one aspect of the present disclosure.

FIG. 124 is a schematic diagram of a flexible hand-switch circuit system 16820, in accordance with at least one aspect of the present disclosure. The flexible hand-switch circuit system 16820 comprises a flexible hand-switch circuit 16822 coupled to an instrument 16824, a control circuit 16826, and an analog-to-digital converter 16828 (ADC). The flexible hand-switch circuit 16822 provides flexibility between communicating with a surgical instrument 16824 via a plurality of protocols and providing parasitic power to circuits in the surgical instrument 16824 over a single wire. The flexible hand-switch circuit 16822 accommodates multiple types of communication protocols for a variety of different hand-switches that are compatible with the energy port of the energy module, such as for example, the energy module 3270 shown in FIG. 37. With reference now back to FIG. 124, the flexible hand-switch circuit 16822 receives control inputs from a control circuit 16826 and drives current and/or logic signals from a current source 16830 output 16832 into a comparator 16834, which provides an output 16836 to the control circuit 16826, as described hereinbelow. The output 16832 of the current source 16830 can source or sink current I (+/−) based on a current set-point 16838 and a voltage set-point 16840 applied to the current source 16830. In one aspect, the comparator 16834 may be selected from the AD790 family of integrated circuits available form Analog Devices. The comparator 16834 is a fast (45 ns) precise voltage comparator that may operate from either a single 5 V supply or a dual ±15 V supply. In the single-supply mode, the AD790's inputs may be referred to ground. In the dual-supply mode the comparator 16834 can handle large differential voltages across its input terminals to ease the interface to large amplitude and dynamic signals.

The flexible hand-switch circuit 16822 comprises a bidirectional variable current source 16830 with an adjustable current set-point 16838 and an adjustable voltage set-point 16840. The control circuit 16826 sets the current and voltage set-points 16838, 16840. An operational amplifier 16842 receives the voltage set-point 16840 and drives an output 16844. The output 16844 of the operational amplifier 16840 is coupled to a switch 16846 controlled by the control circuit 16826 through control output 16848 to connect or disconnect the output 16832 of the current source 16830 to the supply voltage rail. In one aspect, the operational amplifier 16842 may be selected from the OPAx132 series of FET-input operational amplifiers available form Texas Instruments. Such amplifiers provide high speed and excellent DC performance with a combination of high slew rate and wide bandwidth to provide fast settling time. Such amplifiers may be selected for general-purpose, data acquisition, and communications applications, especially where high source impedance is encountered.

The control circuit 16826 is coupled to a switch 16825 through control output 16827 to connect or disconnect the current source output 16832 to ground. When the control circuit 16826 sends a signal to the control output 16827, the switch 16825 shorts the current source output 16832 to ground. Shorting the current source output 16832 to ground provides a logic signal to a control circuit (e.g., FPGA, microprocessor, microcontroller, discrete logic, ASIC) located in the instrument 16824. The control circuit 16826 may comprise an FPGA, microprocessor, microcontroller, discrete logic, ASIC, among other circuits.

The comparator 16834 is coupled to the current source 16830 output 16832 and is configured to read a logic signal on the output 16832 of the current source 16830. The output 16836 of the comparator 16834 provides the logic signal to the control circuit 16826. An ADC 16828 is configured to read the absolute value of the analog voltage of the current source 16830 output 116832 and provides that to the control circuit 16826. The current source 16830 and the comparator 16834 bandwidth is wide enough to support a LIN and 1-Wire protocols with pulse widths down to approximately 0.5 us. Switches 16831, 16835, 16839, 16843 controlled by respective control lines 16833, 16837, 16839, 16845 by the control circuit 16826 and resistors R1-R5 set a desired voltage threshold 16847 at the input of the comparator 16834 to compare with the output 16832 of the current source 16830.

The control circuit 16826 (e.g., FPGA, microprocessor, microcontroller, discrete logic, ASIC) is coupled to switch 16846 through control line 16848 to short the current source 16830 power supply V (+/−) to the current source 16830 output 16832. When the control circuit 16826 sends a signal to the switch 16846 through the control line 16848, the switch 16846 shorts the current source 16830 output 16832 to the power supply V (+/−). This provides a technique for sourcing a large amount of current to a control circuit in the instrument 16824 while communications are inactive or interspersed within communication frames to support applications such as a high power LED or a haptic feedback motor.

In one aspect, the switches 16846, 16825, 16831, 16835, 16839, 16843 may be implemented as semiconductor switches. The semiconductor switches may comprise transistors and in various implementations may comprise n-channel and/or p-channel MOSFET transistors configured as analog or digital switches.

Flexible Generator-to-Instrument Communications

In various aspects, the present disclosure provides a modular energy system 2000 (FIGS. 24-30) comprising a variety of different modules 2001 that are connectable together in a stacked configuration. The modules 2001 of the modular energy system 2000 can include, for example, a header module 2002 (which can include a display screen 2006), an energy module 2004, a technology module 2040, and a visualization module 2042. Energy modules 3004 (FIG. 34), 3012 (FIG. 35), and 3270 (FIG. 37) illustrate the energy module 2004 with more particularity. Accordingly, for conciseness and clarity of disclosure, reference herein to the energy module 2004 should be understood to be a reference to any one of the energy modules 3004 (FIG. 34), 3012 (FIG. 35), and 3270 (FIG. 37). An example of a communication protocol is described in commonly owned U.S. Pat. No. 9,226,766, which is herein incorporated by reference in its entirety.

It will be appreciated that the energy module 2004 may include a variety of electrosurgical/ultrasonic generators that need to be able to electrically identify and communicate with a wide variety of electrosurgical/ultrasonic instruments, such as, for example, the surgical instruments 1104, 1106, 1108 shown in FIG. 22, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The energy modules 2004 and the electrosurgical/ultrasonic instruments 1104, 1106, 1108 may have vastly different communication needs in terms of such things as data bandwidth, latency, circuit cost, power requirements, cybersecurity robustness, and noise immunity. Accordingly, there is a need for the modular energy system 2000, and in particular the energy modules 2004 of the modular energy system 2000, to support multiple communication protocols. At the same time, ergonomic and cost concerns dictate that the total number of conductors in an electrosurgical/ultrasonic instrument cable be kept to a minimum.

Accordingly, in one aspect, the present disclosure provides a flexible technique for employing a minimum number of conductors to support several different electrical communication protocols separately or in combination. In one aspect, the resistance value of a presence resistor across two pins in the surgical instrument 1104, 1106, 1108 is initially measured by the energy module 2004 in order to establish which one or ones of the various supported protocols are to be enabled (simultaneously or time-serially) for the energy module 2004 to communicate with the particular surgical instrument 1104, 1106, 1108 type currently plugged in, and which conductors will be mapped to which electrical signals of the enabled protocol or protocols.

Figure 125:
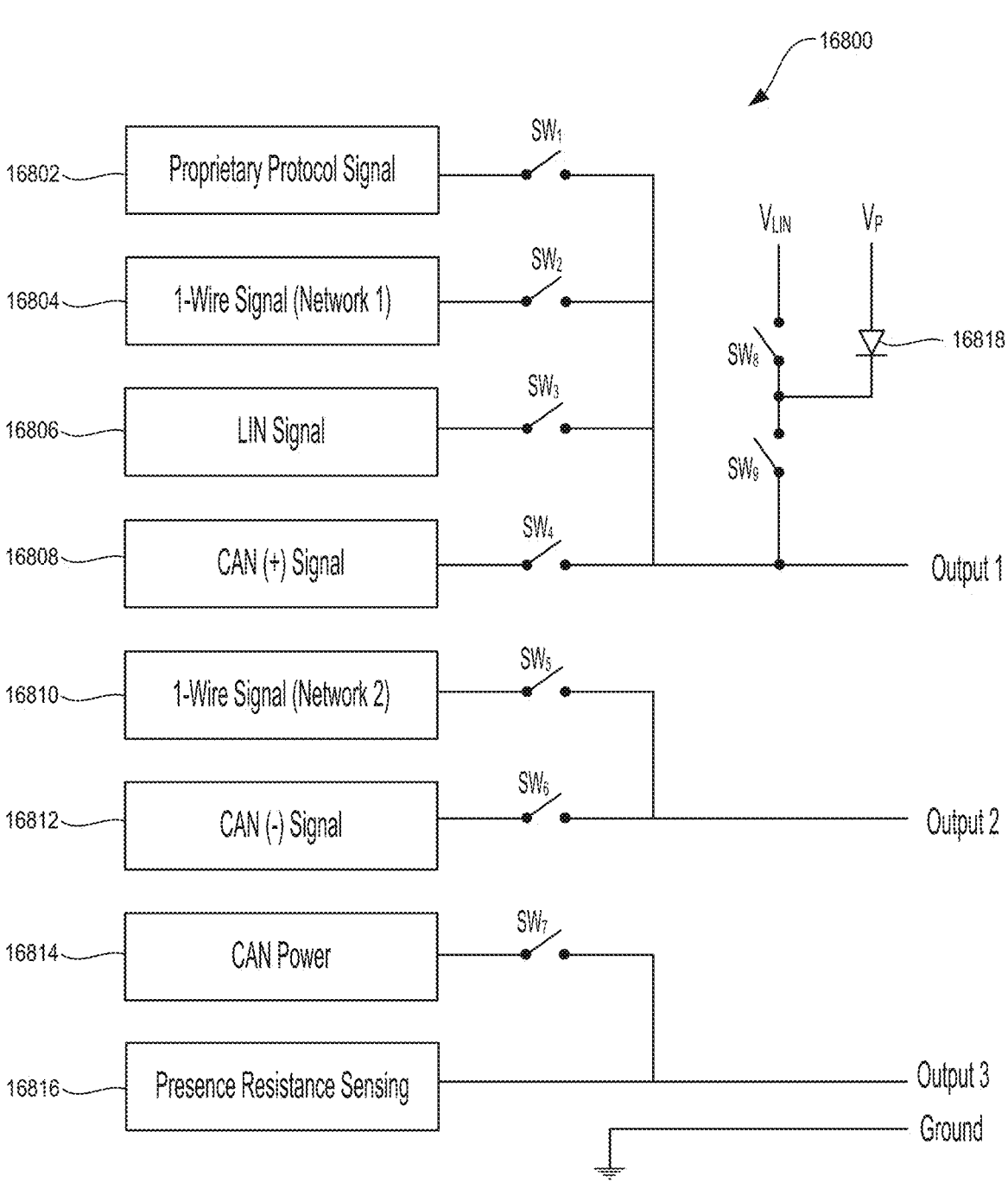
FIG. 125 is an interconnection diagram employing a minimum number of conductors to support several different electrical communication protocols separately or in combination, in accordance with at least one aspect of the present disclosure.

FIG. 125 is an interconnection diagram 16800 employing a minimum number of conductors to support several different electrical communication protocols separately or in combination, in accordance with at least one aspect of the present disclosure. In the interconnection diagram 16800, a plurality of protocol signal sources 16802-16814 are connected to three output conductors Output 1, Output 2, and Output 3 through a plurality of switches $SW_1$-$SW_7$ controlled by a control circuit in the energy module 2004. A presence resistance sensing circuit 16816 coupled to the Output 3 conductor directly. Thus, when the instrument is attached, the presence resistance sensing circuit 16816 sense that the instrument is connected to energy module 2004. A LIN voltage source $V_{LIN}$ is connected to the Output 1 conductor via a switch $SW_8$ and switch $SW_9$, which is optionally provided if all voltage sources have switches. A proprietary protocol voltage source $V_P$, which is less than $V_{LIN}$, is connected to the Output 1 conductor through switch $SW_9$. A diode 16818 may be substituted for an active switch on the lowest voltage source $V_P$.

As shown in FIG. 125, a proprietary protocol signal 16802 is multiplexed to the Output 1 conductor of the energy module receptacle through a switch $SW_1$. A 1-Wire protocol signal 16804 (Network 1) is multiplexed to the Output 1 conductor of the energy module receptacle through a switch $SW_2$ and a 1-Wire protocol signal 16810 (Network 2) is multiplexed to the Output 2 conductor of the energy module receptacle through a switch $SW_5$. The proprietary protocol signal 16802 voltage source $V_P$ is connected to the Output 1 conductor of the energy source 2004 receptacle through the diode 16818 and switch SW$_9$. A LIN protocol signal 16806 is multiplexed to the Output 1 conductor of the energy module receptacle through a switch SW$_3$. The LIN protocol signal 16806 voltage source V$_{LIN}$ is connected to the Output 1 conductor of the energy source 2004 receptacle through switch SW$_8$ and optionally SW$_9$.

The CAN protocol is a three-wire protocol that employs a differential pair, e.g., a CAN (+) signal 16808 and a CAN (−) signal 16812, with a separate power line, e.g., CAN Power 16814. As shown, the CAN (+) signal 16808 is multiplexed of the Output 1 conductor of the energy module receptacle by SW$_4$, the CAN (−) signal 16812 is multiplexed to the Output 2 conductor of the energy module receptacle by switch SW$_6$, and the CAN power 16814 is multiplexed to the Output 3 conductor of the energy module receptacle by switch SW$_7$.

The switches SW$_1$-SW$_7$ as well as SW$_8$-SW$_9$ are controlled through a control circuit of the energy module 2004 such as, for example, control circuit 3082 in energy modules 3004 (FIGS. 34, 35), control circuit 3082 of energy module 3270 (FIG. 37), based on the particular communication protocol to be employed. The proprietary protocol signal, 1-Wire signal, LIN signal and the CAN (+) can be applied to the Output 1 via a single wire.

In one aspect, as shown in FIG. 125, all voltage sources V$_{LIN}$, V$_P$ and current sources for the protocol signals 16802-16814 in the energy module 2004 generators are initially disconnected from the Output 1, Output 2, Output 3 conductors of the instrument receptacle (i.e., all switches shown in FIG. 125 are initially open when no instrument is attached) except for just those necessary to look for and measure the presence resistance value in the attached instrument (i.e., just the presence resistance sensing circuit 16816). Upon identification of a specific presence resistance value by the energy module 2004, an initial protocol (or set of simultaneous protocols) is electrically configured by the closing of specific switches SW$_1$-SW$_9$ in FIG. 125, under software control in the energy module 2004. The following Table 1 provides an example of a switch configuration for a specific example set of protocols matching those in FIG. 125, although this concept is not limited to just this specific set.

In the example illustrated in FIG. 125 and Table 1, the 1-Wire protocol signal 16810 on Network 2 can be enabled simultaneously with any of the other protocols except the CAN protocol signals 16808, 16812. Once communications with the instrument are established with the initial protocol, the energy module 2004 and instrument can potentially coordinate to mutually switch to other protocols as desired, time-serially, with the energy module 2004 reconfiguring the switches SW$_1$-SW$_9$ in synchronization with the instrument reconfiguring to accommodate the next protocol on its end.

Although labeled as "outputs" in FIG. 125 and Table 1 above, each of the three signal conductors Output 1, Output 2, Output 3 in this illustrated example can function bi-directionally, with input monitoring circuitry on the energy module 2004 side (not shown) that can either be selectively switched in, or continuously attached. Additionally, filtering circuitry (also not shown) can be provided on one or more of the three signal conductor lines Output 1, Output 2, Output 3, either switchable, or continuously attached.

V1 and V2 in this example are not separate communication protocols per se, but rather provide a means for transmitting power to the instrument, interspersed with data being transmitted over the same conductors via their respective communication protocols. Additional such multiplexed power sources can be added beyond the two shown in the example illustrated in FIG. 125 and Table 1. V3 provides power to the instrument in conjunction with the CAN protocol signal 16808, 16812 or optionally with the other protocols in the example, although requiring an additional wire in the instrument cable.

A variety of methods may be employed for V3 and the presence resistance sensing circuitry 16816 to co-exist on a single conductor as shown in the example illustrated in FIG. 125 and Table 1, including preserving the ability of the energy module 2004 to monitor instrument presence while V3 is being output.

Figure 126:
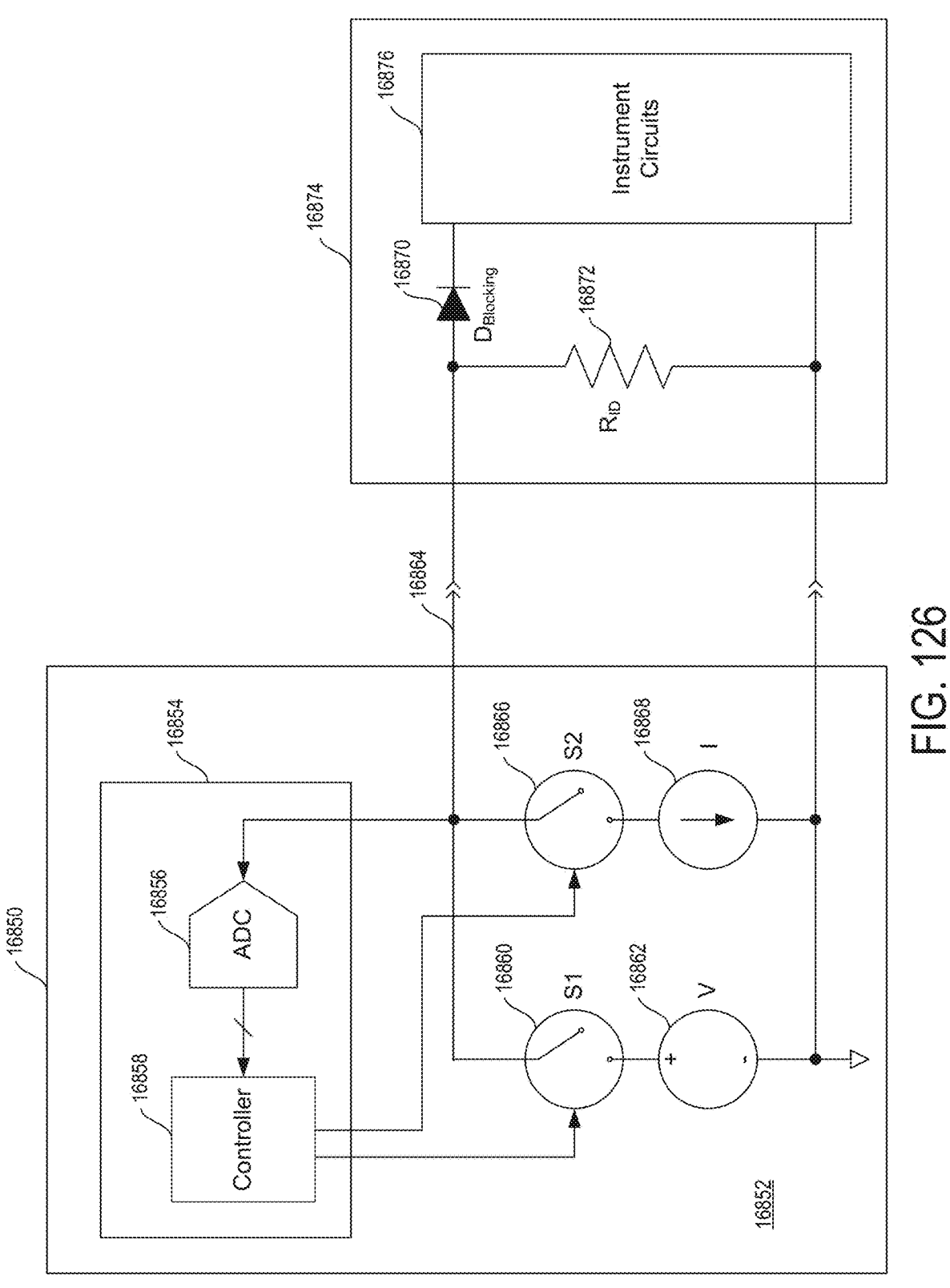
FIG. 126 is a schematic diagram of an energy module comprising a multiplexer circuit for multiplexing presence identification (ID) resistance $R_{ID}$ sensing and CAN (or other DC) power onto a single signal wire, in accordance with at least one aspect of the present disclosure.

FIG. 126 is a schematic diagram of an energy module 16850 comprising a multiplexer circuit 16852 for multiplexing presence identification (ID) resistance R$_{ID}$ 16872 sensing and CAN (or other DC) power onto a single signal wire 16864, in accordance with at least one aspect of the present disclosure. The multiplexer circuit 16852 comprises a monitoring and control circuit 16854 comprising an analog-to-

TABLE 1

| Protocol | SW1 | SW2 | SW3 | SW4 | SW5 | SW6 | SW7 | SW8 | SW9 | Out1 | Out2 | Out3 |
|---|---|---|---|---|---|---|---|---|---|---|---|---|
| None (initial) | O | O | O | O | O | O | O | O | O | NC | NC | PR |
| Proprietary | CL | O | O | O | DC | DC | DC | O | O | Prop+ | DC | DC |
| Proprietary Power | CL | O | O | O | DC | DC | DC | O | CL | V1 | DC | DC |
| 1-Wire (Net1) | O | CL | O | O | DC | DC | DC | O | O | 1W+ | DC | DC |
| LIN | O | O | CL | O | DC | DC | DC | O | O | LIN+ | DC | DC |
| LIN Power | O | O | CL | O | DC | DC | DC | CL | CL | V2 | DC | DC |
| CAN | O | O | O | CL | O | CL | CL | O | O | CAN+ | CAN− | V3 |
| 1-Wire (Net2) | DC | DC | DC | O | CL | O | DC | DC | DC | DC | 1W+ | DC |

Where:
O = Open;
CL = Closed;
DC = Don't care;
NC = No connection;
V1 = Proprietary protocol voltage source;
V2 = LIN protocol voltage source;
V3 = CAN power; and
PR = Presence resistance (to ground) in the instrument.

digital converter 16856 (ADC) coupled to a controller 16858. The multiplexer circuit 16852 further comprises a voltage (V) source 16862 coupled to the signal wire 16864 via a first switch 16860 controlled by the controller 16858. The multiplexer circuit 16852 further comprises a current source (I) source 16868 coupled to the signal wire 16864 via a second switch 16866 controlled by the controller 16858. The energy module 16850 is coupled to an instrument 16874 via the single signal wire 16864. The instrument 16874 comprises a presence resistor R$_{ID}$ 16872 and a blocking diode D$_{Blocking}$ 16870 coupled to the instruments circuits 16876.

The ADC 16856 and the controller 16858 manage the positive and negative voltages applied to the single signal wire 16864 by controlling the state of the first and second switches 16860, 16866. The voltage source 16862 provides power for the CAN or the instrument circuits 16876. The current source 16868 generates a negative current and produces a negative voltage on the single signal wire 16864. The ID resistor R$_{ID}$ 16872 is used by the controller 16858 to identify the instrument 16874. The instrument circuits 16876 include a CAN or other digital circuits including voltage regulation circuits.

In one aspect, the reverse (negative) current source 16868 in the energy module 16850 combined with the blocking diode 16870 in the instrument 16874 that employs the CAN protocol and/or other digital circuits 16876 enables the energy source 16850 to monitor the identification and connection of legacy instruments and new generation instruments configured with the legacy ID circuitry. The current source 16868 also enables the energy module 16850 to monitor the identification and connection of new generation instruments 16874 that have CAN and/or digital circuitry 16876 employing CAN and other communication protocols with the instrument 16874, and providing power to the digital circuits 16876 in the instrument 16874.

Accordingly, the energy module 16850 provides a CAN-FD (flexible data rate) interface with backwards comparability, CAN noise immunity and high data rate, communication with the instrument 16874 without needing a custom electronic circuit such as an ASIC in the instrument 16874 and provides a foundation for additional capabilities added to future instruments.

In one aspect, the controller 16858 identifies the instrument 16874. If the instrument 16874 is a legacy instrument or a new generation instrument (resistor only), the controller 16858 opens the first switch 16860 and closes the second switch 16866 to enable the reverse current source 16868 to generate a negative voltage on the single signal wire 16864. Using an operational amplifier absolute value circuit or other technique the negative voltage on the single signal wire 16864 is fed to the ADC 16856. The controller 16858 continues to monitor the connection of the instrument 16874 until the instrument 16874 is disconnected (unplugged, etc.). After identifying the instrument 16874, the controller 16858 maintains the current source 16868 to the instrument 16874. There will be a voltage across the ID resistor R$_{ID}$ 16872 as long as the instrument 16874 is connected to the energy module 16850. If the voltage on the signal wire 16864 becomes the open circuit voltage, the controller 16858 determines that the instrument 16874 is unplugged.

If the instrument 16874 is a new generation instrument with a CAN circuit or other digital circuits 16876, the reverse current source 16868 generates a negative voltage. Using an operational amplifier absolute value circuit or other technique, the voltage on the single signal wire 16864 is fed to the ADC 16856. The controller 16858 monitors for the instrument 16874 to be disconnected (unplugged, etc.). After identifying the instrument 16874, the controller 16858 switches to providing a positive voltage to the instrument 16874 by opening the second switch 16866 and closing the first switch 16860 to couple the voltage source 16862 to the single signal wire 16864. There will be a current through the ID resistor R$_{ID}$ 16872 as long as the instrument 16874 is connected to the energy module 16850. There will be additional current consumed by the instrument circuits 16876. If the current to the instrument 16874 becomes less than the ID resistor R$_{ID}$ 16872 current, the controller 16858 determines that the instrument 16874 is unplugged. The energy module 16850 communicates with the instrument 16874 over CAN or provides power to instrument circuits 16876 by applying a voltage in excess of 5V so that a voltage regulator in the instrument 16874 or the energy module 16850 can supply 5V to the instrument circuits 16876. A voltage drop in the instrument cable, e.g., the single signal wire 16864, and a voltage drop across the blocking diode D$_{Blocking}$ 16870 also needs to be overcome and to provide headroom for the voltage regulator.

Figure 127A:
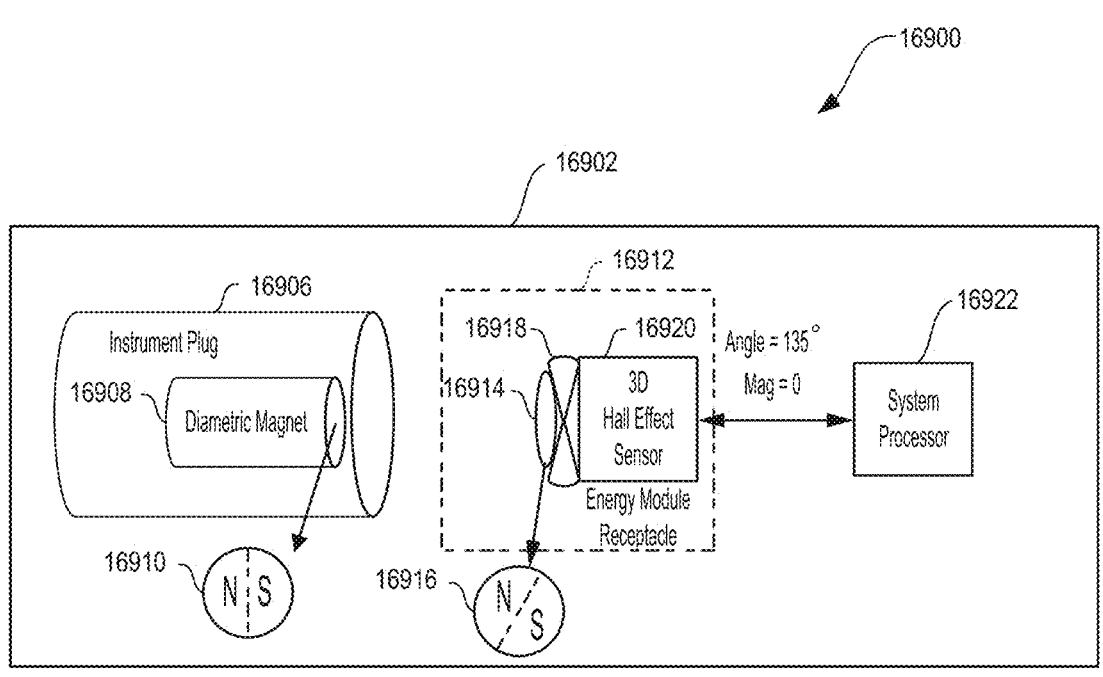
FIGS. 127A-127B illustrate a magnetic device presence identification system, in accordance with at least one aspect of the present disclosure, where
Figure 127B:
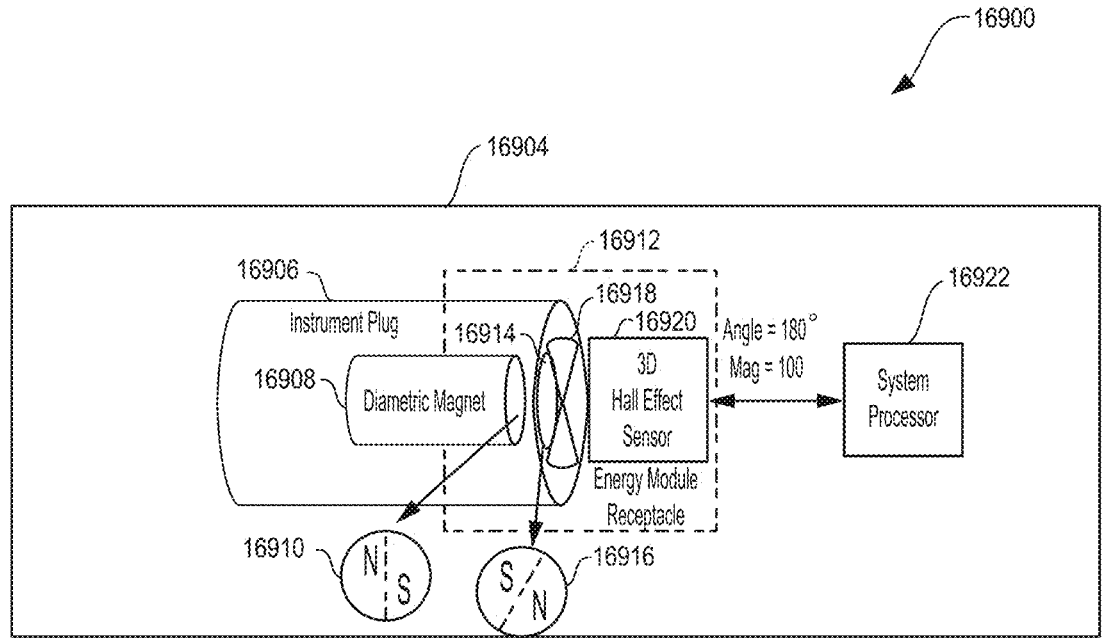

FIGS. 127A-127B illustrate a magnetic device presence identification system 16900, in accordance with at least one aspect of the present disclosure. FIG. 127A depicts the magnetic device presence identification system 16900 in an unplugged state 16902 and FIG. 127B depicts the magnetic device presence identification system 16900 in a plugged state 16904. As shown in FIG. 127A, the magnetic device presence identification system 16900 includes an instrument plug 16906 comprising a diametric magnet 16908 having an end face 16910 in a first north/south (N/S) magnetic field orientation. The instrument plug 16906 is configured to be inserted into an energy module receptacle 16912. The energy module receptacle 16912 includes a diametric magnet 16914 having an end face 16916 in a second north/south (N/S) magnetic field orientation. The diametric magnet 16914 is attached to a freely rotating element 16918.

A 3D magnetic Hall-effect sensor 16920 is configured to sense the magnitude and the orientation angle of the magnetic field acting on the diametric magnet 16914 attached to the freely rotating element 16918. This information is provided to the system processor 16922 or control circuit, for example, for processing whether a device such as a surgical instrument is presently connected to the energy module receptacle 16912 and the identity of the device, such as surgical instrument type, for example. For example, the magnitude of the magnetic field determines whether the instrument is plugged into the energy module receptacle 16912 and the angle of rotation of the end face 16916 of the diametric magnet 16914 relative to the end face 16910 of the diametric magnet 16908 on the instrument plug 16906 determines the instrument ID.

As illustrated in FIG. 127A, in the unplugged state 16902, if the magnitude of the magnetic field sensed by the Hall-effect sensor 16920 is below a first threshold, then the system processor 16922 determines that there is no instrument plugged into the energy module receptacle 16912. Also, without the influence of an external magnetic field generated by the diametric magnet 16908 on the instrument plug 16906, rotation angle of the diametric magnet 16914 attached to the freely rotating element 16918 is biased to a first predetermined angle. As shown in FIG. 127A, the magnitude is 0 and the angle of rotation is 135°. It will be appreciated, the first magnitude threshold and the first rotation angle may be selected within a range of values such as for example, a magnitude of 0-50% of maximum and a rotation angle of 11° to 169° or 191° to 349°.

As shown in FIG. 127B, the magnetic device presence identification system 16900 is in a plugged state 16904. Accordingly, the magnetic field from the end face 16910 of the diametric magnet 16908 on the instrument plug 16906 causes the Hall-effect sensor 16920 to sense 100% magnitude and causes the diametric magnet 16914 attached to the freely rotating element 16918 to rotate 180° relative to the end face 16910 of the diametric magnet 16908 on the instrument plug 16906. Accordingly, the system processor 16922 determines that an instrument is present at the energy module receptacle 16912 and based on the rotation angle of 180°, the system processor 16922 determines the instrument type, such as, for example, one of the surgical instruments 1104, 1106, 1108 shown in FIG. 22, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. It will be appreciated that the relative angle of rotation may be selected in the following ranges: between 350° and 10° and between 170° to 190° and excluding 11° to 169° and 191° to 349°.

Figure 128A:
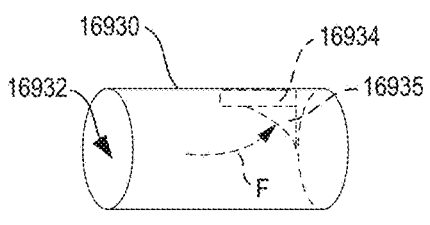
FIGS. 128A-128B illustrate a mechanical sensing port receptacle comprising a depressible switch, in accordance with at least one aspect of the present disclosure, where
Figure 128B:
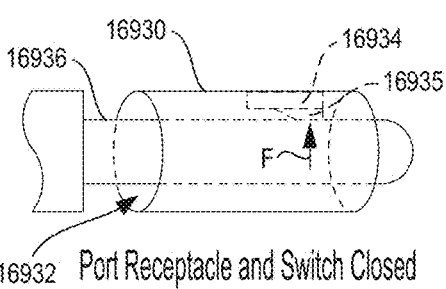

FIGS. 128A-128B illustrate a mechanical sensing port receptacle 16930 comprising a depressible switch 16934, in accordance with at least one aspect of the present disclosure. In one aspect, with reference to FIG. 25A for context, an energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012. Any one of the ports of the ports of the port assembly 2012 may include the mechanical sensing port receptacle 16930 configured to detect the presence of a surgical instrument plugged into the energy module 2004.

In one aspect, the mechanical sensing port receptacle 16930 defining an aperture 16932 to form a socket that includes a sliding contact configuration for receiving a plug 16936 of the surgical instrument. The depressible switch 16934 is disposed within the aperture 16932. The mechanical sensing port receptacle 16930 may further include one or more electrical contacts arranged to accommodate a variety of different instrument plug configurations and establish an electrical connection between the energy module 2004 (FIGS. 24-30) and the surgical instrument. Although the mechanical sensing port receptacle 16930 of FIG. 128A is depicted as having a cylindrical configuration, other configurations are contemplated by the present disclosure to accommodate instrument plugs of various shapes and sizes. According to the non-limiting aspect of FIG. 128A, the depressible switch 16934 is embedded in an inner region of the aperture 16932 defined by the mechanical sensing port receptacle 16930 such that the depressible switch 16934 is actuated when a force F is applied to an actuator 16935 portion of the depressible switch 16934. The depressible switch 19024 is also configured to transition from an open state (unactuated) where it is in an undepressed (see FIG. 128A), to a closed state (actuated) where it is depressed (see FIG. 128B) when a force F is applied by the sliding plug 16936. The mechanical sensing port receptacle 16930 is further configured to send a binary signal to a control circuit of the energy module 2004 to indicate whether the depressible switch 16934 is in an open state or a closed state.

According to the non-limiting aspect of FIG. 128A, the depressible switch 16934 is depicted in an undepressed unactuated condition because no prong of an instrument plug 16936 is inserted within the aperture 16932 of the mechanical sensing port receptacle 16930. Thus, the depressible switch 16934 of FIG. 128A is shown in an open state and a binary signal is provided to the control circuit indicating that no instrument plug 16936 is inserted or connected to the energy module 2004 (FIGS. 24-30). FIG. 128B depicts the instrument plug 16936 inserted into the aperture 16932 of the mechanical sensing port receptacle 16930. As depicted in FIG. 128B, the plug 16936 of the surgical instrument mechanically engages the actuator 16935 of the depressible switch 16934 and applies a force F to the actuator 16935 to depress the actuator 16935 to transition the depressible switch 16934 to the closed state. Accordingly, the mechanical sensing port receptacle 16930 provides a binary signal to a control circuit of the energy module 2004 to indicate that an instrument plug 16936 is connected to the energy module 2004.

Figure 129A:
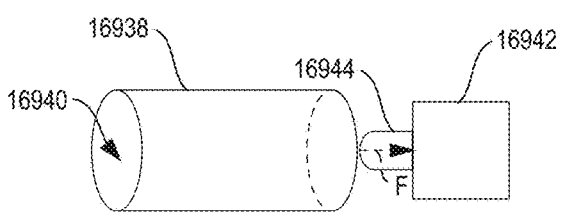
FIGS. 129A-129B illustrate a mechanical sensing port receptacle comprising a push button switch, in accordance with at least one aspect of the present disclosure, where
Figure 129B:
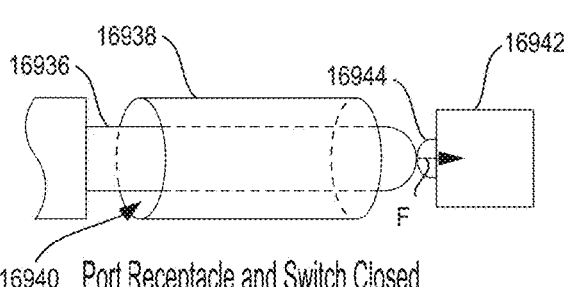

FIGS. 129A-129B illustrate a mechanical sensing port receptacle 16938 comprising a push button switch 16942, in accordance with another aspect of the present disclosure. The mechanical sensing port receptacle 16938 of FIG. 129A includes a push button configuration. Similar to the sliding contact configuration of FIGS. 128A-128B, any one of the ports of the port assembly 2012 shown in FIGS. 24-30 may include the mechanical sensing port receptacle 16938 of FIGS. 129A-129B configured to detect the presence of a surgical instrument plugged into the energy module 2004 (FIGS. 24-30).

In lieu of the depressible switch 16934, the push button switch configuration includes a push button switch 16942 comprising an actuator 16944. The mechanical sensing port receptacle 16938 defines an aperture 16932 to form a socket for receiving an instrument plug 16936. According to a non-limiting aspect of the mechanical sensing port receptacle 16938 depicted in FIGS. 129A-129B, the push button switch 16942 is located distal to the mechanical sensing port receptacle 16938 such that the actuator 16944 of the push button switch 16942 is proximate a distal end of the aperture 16940. The actuator 16944 of the push button switch 16942 is configured to actuate when the distal end of the instrument plug 16936 applies a force F to the actuator 16944 causing it to transition from an open state where it is in an undepressed (see FIG. 129A) to a closed state where it is depressed (see FIG. 129B). The mechanical sensing port receptacle 16938 is further configured to send a binary signal to a control circuit of the energy module 2004 (FIGS. 24-30) to indicate whether the push button switch 16942 is in an open state or a closed state.

According to the non-limiting aspect of FIG. 129A, the push button switch 16942 is depicted in an undepressed unactuated condition because the instrument plug 16936 is not yet inserted within the aperture 16940 of the mechanical sensing port receptacle 16938 and thus no force F is applied to the actuator 16944. Thus, the push button switch 16942 of FIG. 129A is in an open state and the mechanical sensing port receptacle 16938 provides a binary signal to a control circuit indicating that the instrument plug 16936 is not connected to the energy module 2004 (FIGS. 24-30). Alternatively, FIG. 129B depicts an instrument plug 16936 inserted into the aperture 16940 of the mechanical sensing port receptacle 16938. As depicted in FIG. 129B, the instrument plug 16936 mechanically engages and applies a force F to the actuator 16944 of the push button switch 16942 to depress and actuate the push button switch 16942, thus transitioning the push button switch 16942 to the closed state. Accordingly, the mechanical sensing port receptacle 16938 provides a binary signal to a control circuit of the energy module 2004 indicating that an instrument plug 16936 is connected to the energy module 2004.

Figure 130A:
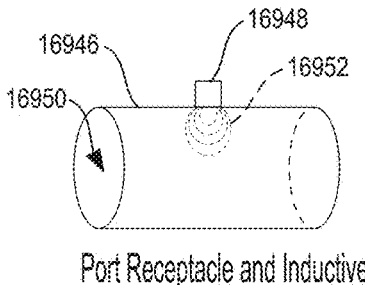
FIGS. 130A-130B illustrate an electrical sensing port receptacle comprising a non-contact proximity switch, in accordance with at least one aspect of the present disclosure, where
Figure 130B:
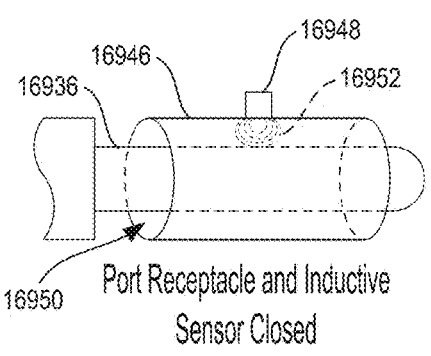

FIGS. 130A-130B illustrate an electrical sensing port receptacle 16946 comprising a non-contact proximity switch, in accordance with one aspect of the present disclosure. The electrical sensing port receptacle 16946 includes a non-contact proximity switch configuration comprising an inductive sensor 16948, for example, to provide a contact-less short-range sensing configuration for sensing conductive targets such as the instrument plug 16936. The electrical sensing port receptacle 16946 defines an aperture 16950 to form a socket for receiving the instrument plug 16936. The inductive sensor 16948 of FIGS. 130A-130B is configured to sense the proximity of a metal object, such as the instrument plug 16936. The inductive sensor 16948 includes an induction loop or detector coil, such as those found in typical inductance-to-digital converter, coil magnetometers, and/or the like. When power is applied to the detector coil, an electromagnetic field 16952 is generated. As the metal instrument plug 16936 approaches the proximity of the electromagnetic field 16952, the metal instrument plug 16936 interacts with the electromagnetic field 16952 and the inductive sensor 16948 transitions from an open state, wherein the instrument plug 16936 is not inserted into the aperture 16950 of the electrical sensing port receptacle 16946, to a closed state, wherein the instrument plug 16936 is inserted into the aperture 16950 of the electrical sensing port receptacle 16946. The electrical sensing port receptacle 16946 is further configured to provide a binary signal to a control circuit of the energy module 2004 (FIGS. 24-30) to indicate whether the inductive sensor 16948 is in an open state or a closed state.

According to the non-limiting aspect of FIG. 130A, the instrument plug 16936 is not inserted within the aperture 16950 of the electrical sensing port receptacle 16946 and accordingly, does not interact with the electromagnetic field 16952. Thus, the inductive sensor 16948 of FIG. 130A is in an open state and the electrical sensing port receptacle 16946 provides a binary signal to a control circuit of the energy module 2004 (FIGS. 24-30) to indicate that the instrument plug 16936 is not connected to the energy module 2004. Alternatively, as the instrument plug 16936 is inserted into the aperture 16950 of the electrical sensing port receptacle 16946 it will interact with the electromagnetic field 16952, thus transitioning the inductive sensor 16948 to the closed state. Accordingly, the electrical sensing port receptacle 16946 provides a binary signal to the control circuit of the energy module 2004 to indicate that the instrument plug 16936 is connected to the energy source 2004. In some non-limiting aspects, the binary signal might be subsequently processed via software to mitigate the effects of noise associated with activation. Still other non-limiting aspects are configured to filter out certain radio frequency (RF) signals of to mitigate the effect of electrical noise and unintended interference with the electromagnetic field 16952.

In one aspect, the inductive sensor 16948 may be an inductance-to-digital converter LDC1000 provided by Texas Instruments. The inductance-to-digital converter is a contact-less short-range sensor that enables sensing of conductive targets. Using a coil as a sensing element, the inductance-to-digital converter precise measurement of linear/angular position, displacement, motion, compression, vibration, metal composition, and many other applications.

Various combinations of aforementioned mechanical/electrical sensing port receptacles 16930, 16938, 16946 shown FIGS. 128A-130B can be used to detect and identify different types of instrument plugs. For example, two or more separate switches, including a depressible switch, a push button, and/or an inductive proximity switch, can be used to distinguish whether the instrument is a lap or hand tool is connected to the port. The mechanical/electrical sensing port receptacles 16930, 16938, 16946 then provide a signal to a control circuit of the energy module 2004 (FIGS. 24-30) indicating the specific type of instrument that is connected to the energy module 2004, and the control circuit reacts accordingly.

In various aspects, the instruments and devices disclosed herein comprise radio frequency identification (RFID) circuits. A user may initiate a detection sequence via a display of a user interface of an RFID enabled energy source or instrument by selecting a pairing mode option. Selecting the pairing mode option will transition a user interface to another display which prompts the user to pair a device. In one non-limiting aspect, an RFID circuit is affixed to an RFID enabled instrument, and an RFID scanner is affixed to an RFID enabled energy source. Having initiated the pairing mode, the user positions the RFID circuit affixed to the RFID enabled instrument in proximity to the RFID scanner of the RFID enabled energy source. Additionally or alternatively, an RFID circuit could be affixed to inventory management paperwork associated with the instrument. Accordingly, a user could initiate pairing mode and position the RFID circuit of the inventory management paperwork in proximity to the RFID scanner of the RFID enabled energy source, thereby pairing the RFID enabled instrument to the RFID enabled energy source. Upon scanning the instrument or paperwork to the reader of the electrosurgical generator, the user interface of the RFID enabled energy source will provide a visual confirmation that the RFID enabled instrument has been successfully detected by and paired to the RFID enabled energy source. Once the RFID enabled instrument is detected, the control circuit will subsequently identify the RFID enabled instrument and communicate any relevant messages to the user.

In some non-limiting aspects, the RFID circuits store data associated with each particular RFID enabled instrument. For example, the RFID chips might store data associated with the instrument's use, including a number of runs performed, the amount of time the device has been used, and/or the like. Accordingly, the RFID enabled energy source may be programmed to preclude the pairing of RFID enabled instruments that have exceeded a predetermined use threshold. Further non-limiting aspects include RFID circuits include data associated with the instrument's compatibility. Accordingly, RFID enabled energy source will preclude the pairing of RFID enabled instruments that cannot, or should not, be connected via the aforementioned port configurations. Still other non-limiting aspects of an RFID enabled energy source that includes an RFID chip within the energy source itself. For example, the RFID chip can be used to track an energy source throughout the hospital. Similarly, other non-limiting aspects include RFID circuits that are further configured to interact with an inventory management system. For example, the RFID circuits could be used to track the utilization of each RFID enabled instrument and energy source. In such non-limiting aspects, when the number of useable instruments falls below a minimum threshold determined by the hospital, the inventory management system is configured to order more instruments.

As previously described with reference to FIG. 123, the present disclosure provides a communication system 16600 employing a primary communication protocol 16622 to communicate with a primary device 16604 and a secondary communication protocol 16624 for communicating with expansion secondary devices 16606, 16608, 16610. With reference now to FIGS. 123 and 131A-134, the present disclosure now turns to a description of one example of a communication arrangement comprising the primary protocol 16622 and the secondary protocol 16624 synchronized to the primary protocol 16622 for communicating with and driving the primary device 16604 and the secondary devices 16606, 16608, 16610 through a single port of the energy module 16602, in accordance with at least one aspect of the present disclosure. FIGS. 131A-131D are signal timing diagrams for the primary and secondary protocols 16622, 16624 that illustrate the relationship of the secondary protocol 16624 to the primary protocol 16622, in accordance with at least one aspect of the present disclosure. The timing diagrams illustrated in FIGS. 131A-131D occur over a full duplex primary communications frame 16651 of the primary protocol 16622. Each of the timing diagrams illustrated in FIGS. 131A-131D shows a different secondary communication frame 16653, 16655, 16657, 16659 of the secondary protocol 16624. FIG. 132 illustrates a timing diagram for a reset command. FIG. 133 illustrates a timing diagram for a broadcast status request. FIG. 134 illustrates a timing diagram for an individual status request.

Figure 131A:
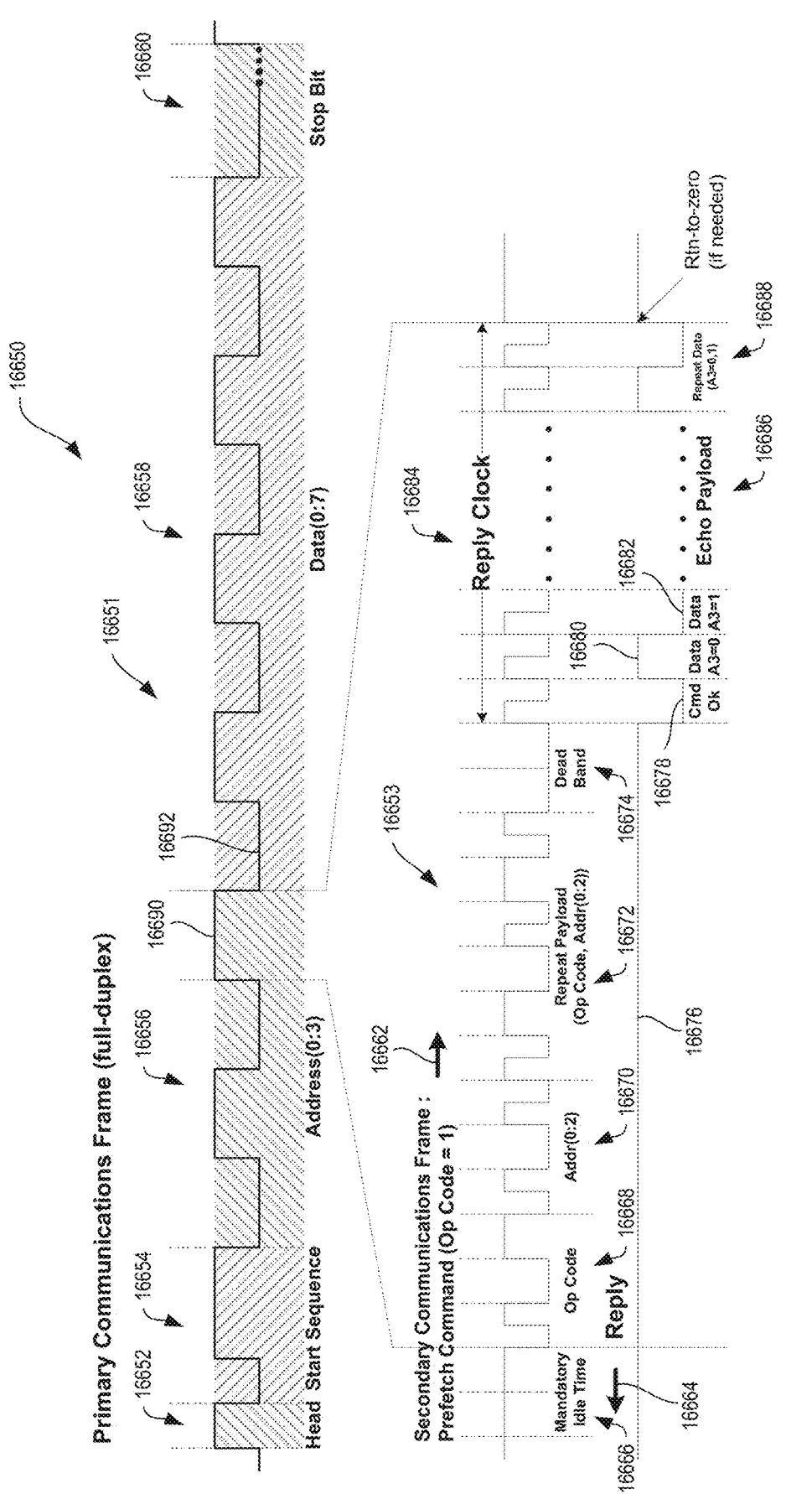
Figure 131B:
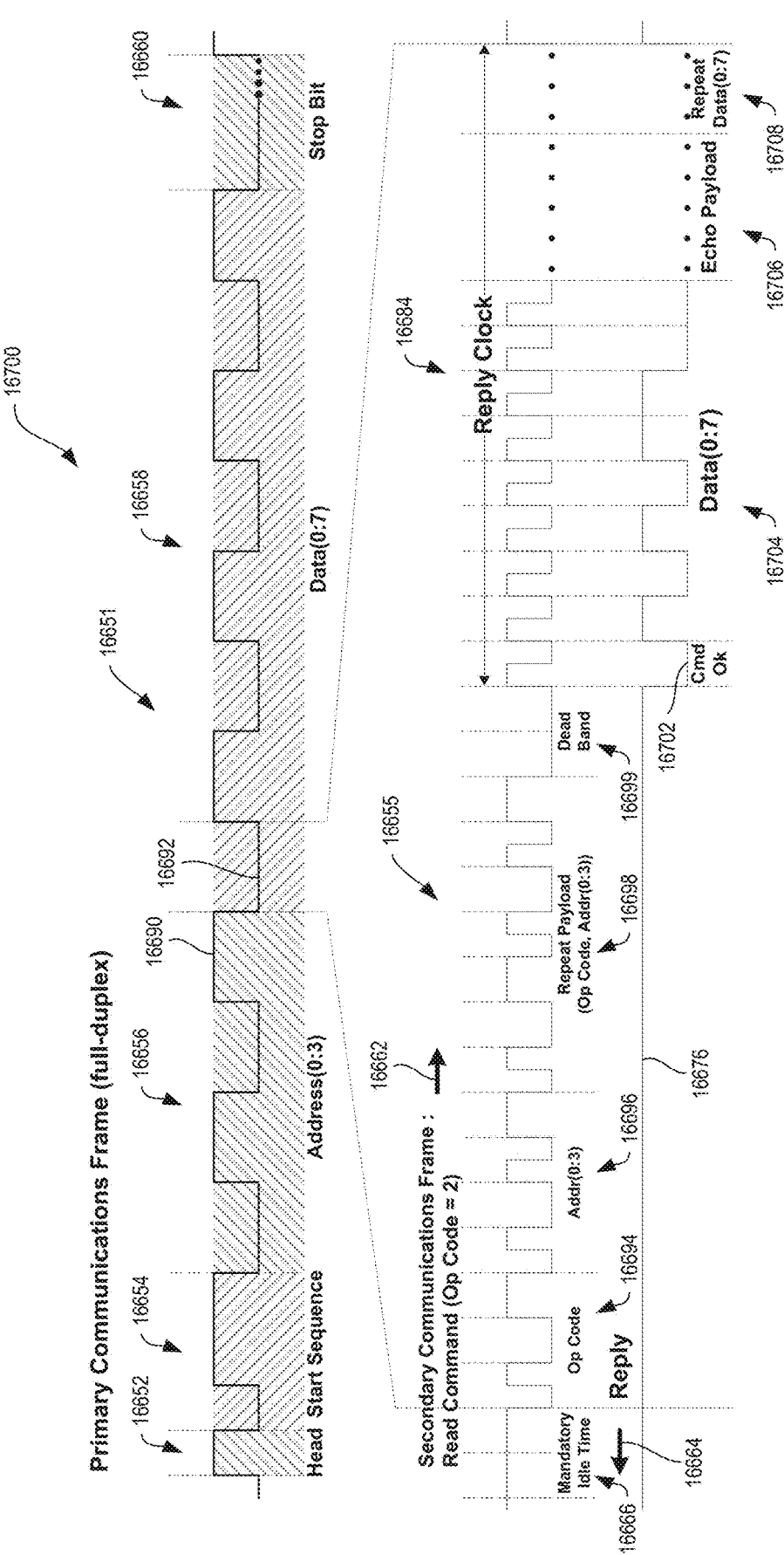
FIG. 131B illustrates a timing diagram of the primary communication frame and a secondary communications frame during a read command following the prefetch command illustrated in FIG. 131A, in accordance with at least one aspect of the present disclosure.
Figure 132:
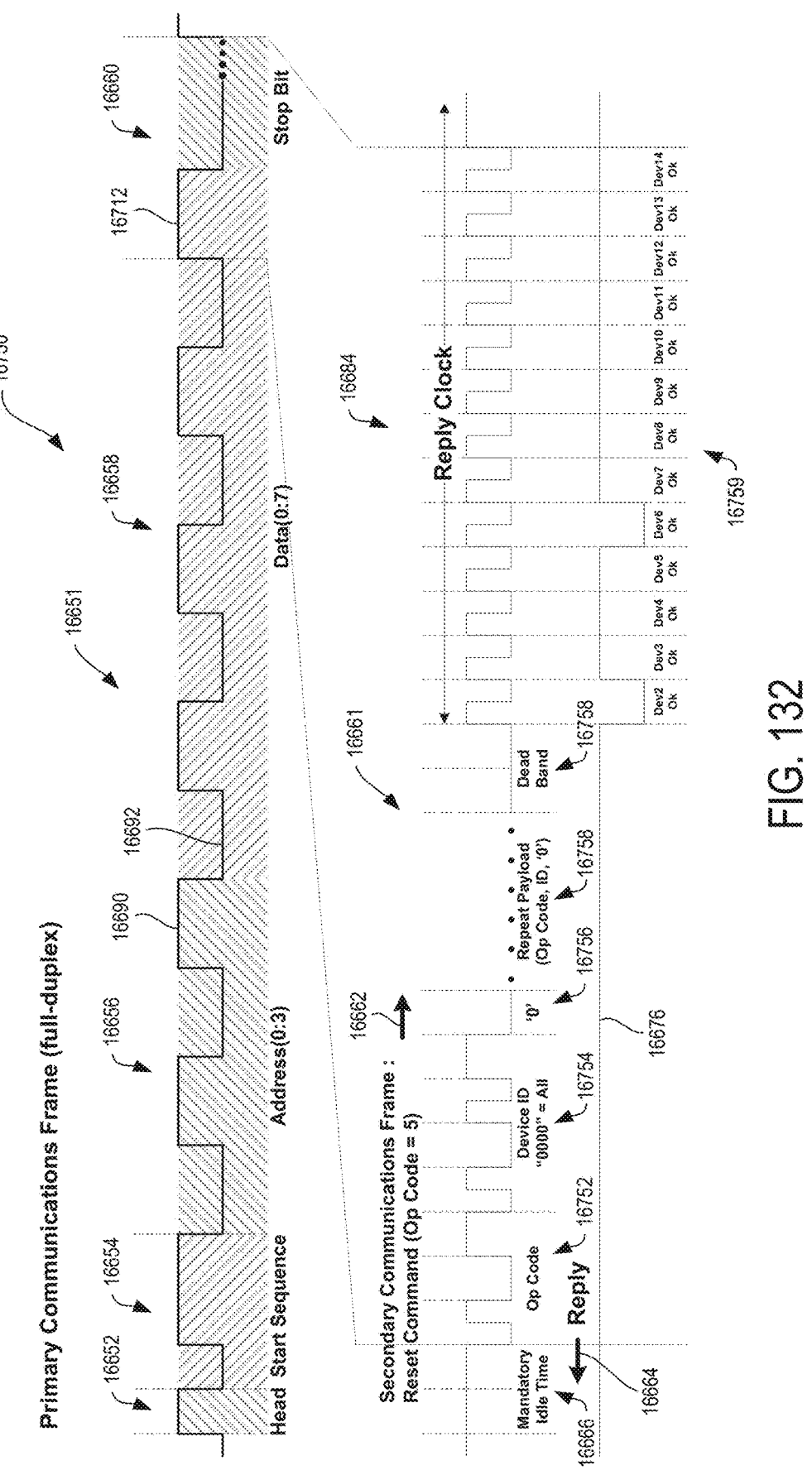

FIG. 131A illustrates a timing diagram 16650 of a primary communication frame 16651 and a secondary communications frame 16653 during a prefetch command, in accordance with at least one aspect of the present disclosure. During the prefetch command, the primary device 16604 is able to perform some set up tasks ahead of time to enable response processing in time during the read command, which is described with reference to FIG. 131B. With reference now to FIGS. 123 and 131A, the primary communication frame 16651 of the primary protocol 16622 is a bit-by-bit bidirectional read and write protocol. In the example illustrated in FIG. 131A, the primary communication frame 16651 includes a header 16652, a start sequence 16654, four address bits 16656 (Address (0:3) or simply A0:A3), eight data bits 16658 (Data (0:7) or simply D0:D7), and a stop bit 16660. The secondary communications frame 16653 is synchronized to and is a slave to the primary communications frame 16651. In this example, the secondary communications frame 16653 is synchronized to the fourth address bit 16690 (A3) of the primary communications frame 16651. During receipt of the fourth address bit 16690 (A3) from the energy module 16602, the primary device 16604 pre-fetches the least significant bit (LSB) from both possible addresses (A3=0, A3=1), where A3=0 addresses one set of data mapped in any one of the secondary devices 16606, 16608, 16610 and A3=1 addresses another set of data mapped in any one of the secondary devices 16606, 16608, 16610. The correct LSB is sent to the energy module 16602 during the first bit 16692 (Data (0)) period as shown in FIG. 131B.

The secondary communications frame 16653 occurs during the period of the fourth address bit 16690 and thus operates at a higher rate than the primary communication frame 16651. Within the period of the fourth address bit 16690 and at the start of the secondary communications frame 16653 is a mandatory idle time 16666. During receipt of the fourth address bit 16690 (A3) from the energy module

16602, the primary device 16604 sends 16662 to the secondary devices 16606, 16608, 16610 coupled to the primary device 16604 a pre-fetch command 16668 (Op code=1), followed by the first three address bits 16670 (Address (0:2)), repeats the payload 16672 (Op Code, Address (0:2), and establishes a dead band 16674 prior to replying all occurring while the reply line 16676 is held high.

A reply 16664 from a secondary device 16606, 16608, 16610 is initiated when the reply line 16676 goes low. During the reply 16664 period, the data from the addressed space in any one of the secondary devices 16606, 16608, 16610 is transferred back to the primary device 16604 under control of the reply clock 16684. During the first reply clock 16684 period, the reply line 16676 goes low 16678 (Cmd Ok). During the rising edge of the next reply clock 16684 pulse, the reply line 16676 is set high 16680 to transmit the data addressed by the LSB A3=0. The primary device 16604 samples the reply line 16676 during the falling edge of the reply clock 16684 pulse. During the rising edge of the next reply clock 16684 pulse, the reply line is set low 16682 to transmit the data addressed by the LSB A3=1. Subsequently, one of the secondary devices 16606, 16608, 16610 echoes the payload 16686 and repeats the data 16688 (A3=0, 1). The secondary communications frame 16653 ends prior to the end of the fourth LSB address bit 16690 (Address (3)) period. The reply line 16676 is set back to high and can return to zero if needed. Accordingly, as a result of the prefetch command, the primary device 16604 receives both possibilities for the first data bit 16692 (Data (0)) based on the LSB A3=0 and A3=1.

FIG. 131B illustrates a timing diagram 16700 of the primary communication frame 16651 and a secondary communications frame 16655 during a read command following the prefetch command illustrated in FIG. 131A, in accordance with at least one aspect of the present disclosure. With reference now to FIGS. 123 and 131B, the secondary communications frame 16655 occurs during the exchange of the data bit 16692 D0 to/from the energy module 16602 to fetch the rest of the data word 16704 Data (D0:D7) associated with the Address (A0:A3). In this example, the secondary communications frame 16655 is synchronized to the first data bit 16692 (D0) of the primary communications frame 16651. Within the period of the first data bit 16692 (D0) and at the start of the secondary communication frame 16655 is a mandatory idle time 16666.

After the mandatory idle time 16666, the primary device 16604 sends 16662 a read command 16694 (Op Code=2) to all of the secondary devices 16606, 16608, 16610 mapped by the address 16696 (A0:A3) and then repeats the payload 16698 (Op Code, Address (0:3) before a dead band 16699. A reply 16664 from a secondary device 16606, 16608, 16610 is initiated when the reply line 16676 goes low. During the first reply clock 16684 period, the reply line 16676 goes low 16702 (Cmd Ok). During the reply 16664 period, the rest of the data word 16704 (Data (0:7)) from the addressed space in any one of the secondary devices 16606, 16608, 16610 is transferred back to the primary device 16604 under control of the reply clock 16684. Subsequently, the secondary device 16606, 16608, 16610 echoes the payload 16706 and repeats the data 16708 (Data (0:7)). The secondary communications frame 16655 ends prior to the end of the first bit 16692 (Data (0)) period. The reply line 16676 is set back to high and can return to zero if needed.

Figure 131C:
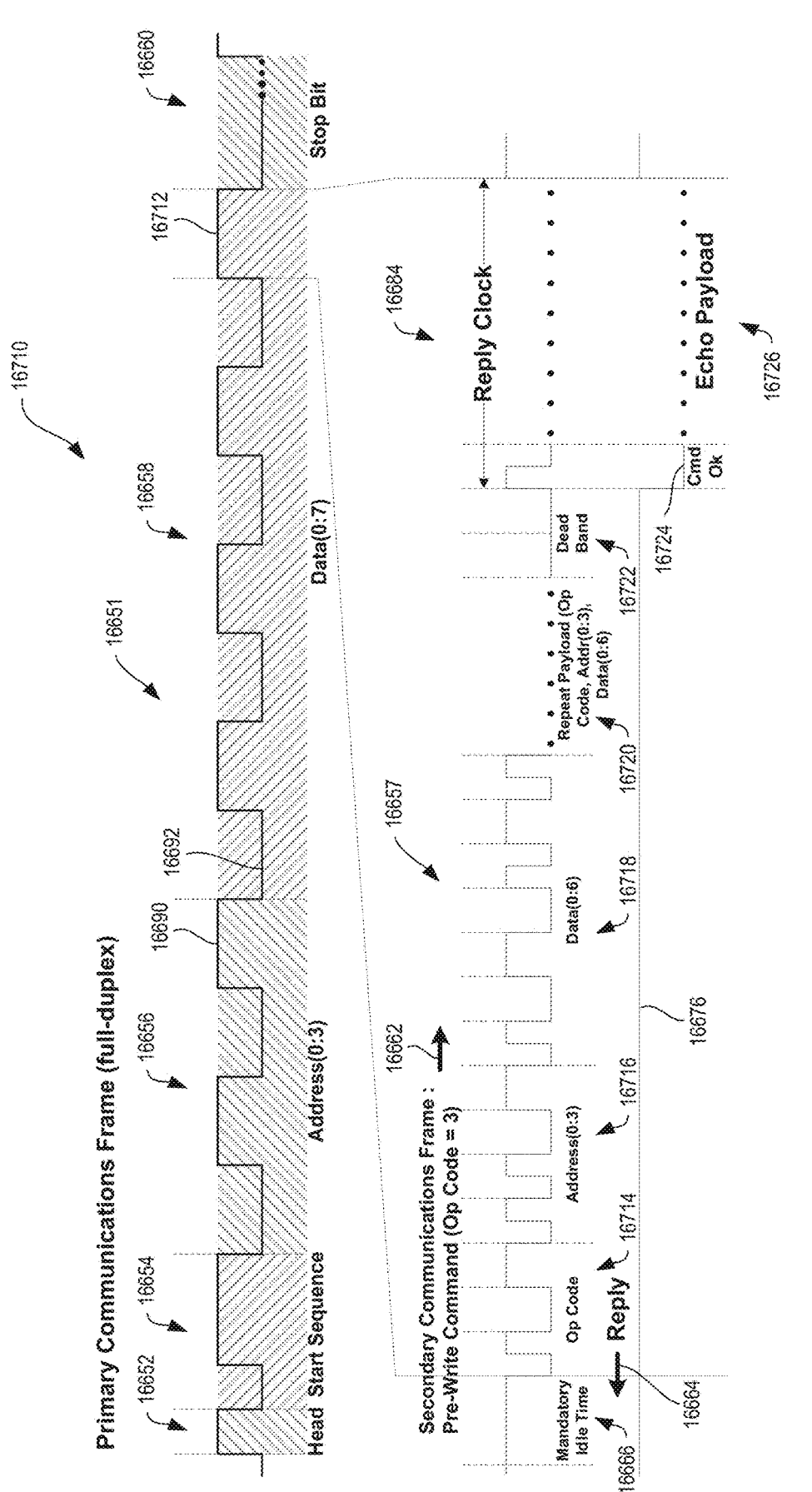
FIG. 131C illustrates a timing diagram of the primary communication frame and a secondary communications frame during a pre-write command following the read command illustrated in FIG. 131B, in accordance with at least one aspect of the present disclosure.

FIG. 131C illustrates a timing diagram 16710 of the primary communication frame 16651 and a secondary communications frame 16657 during a pre-write command following the read command illustrated in FIG. 131B, in accordance with at least one aspect of the present disclosure. With reference now to FIGS. 123 and 131C, the secondary communications frame 16657 writes the first seven data bits (D0:D6) received from the energy module 16602 during the eighth 16712 bit transfer time. This reduces the write time during the stop bit 16660, allowing enough time to Not-Acknowledge (Nack) the energy module 16602 in the case of a failed write. In this example, the secondary communications frame 16657 is synchronized to the eighth data bit 16712 (D7) of the primary communications frame 16651. Within the period of the eighth data bit 16712 (Data (7)) and at the start of the secondary communication frame 16657 is a mandatory idle time 16666.

After the mandatory idle time 16666, the primary device 16604 sends 16662 a pre-write command 16714 (Op Code=3) to all of the secondary devices 16606, 16608, 16610 mapped by the address 16716 (Address (0:3)) and then sends the first seven data bits 16718 (Data (0:6)) received from the energy module 16602 and repeats the payload 16720 (Op Code, Address (0:3), Data (0:6) before a dead band 16722. A reply 16664 from a secondary device 16606, 16608, 16610 is initiated when the reply line 16676 goes low 16724 (Cmd Ok). The secondary communications frame 16657 then echoes the payload 16726 prior to the end of the eighth bit 16712 (Data (7)) period.

Figure 131D:
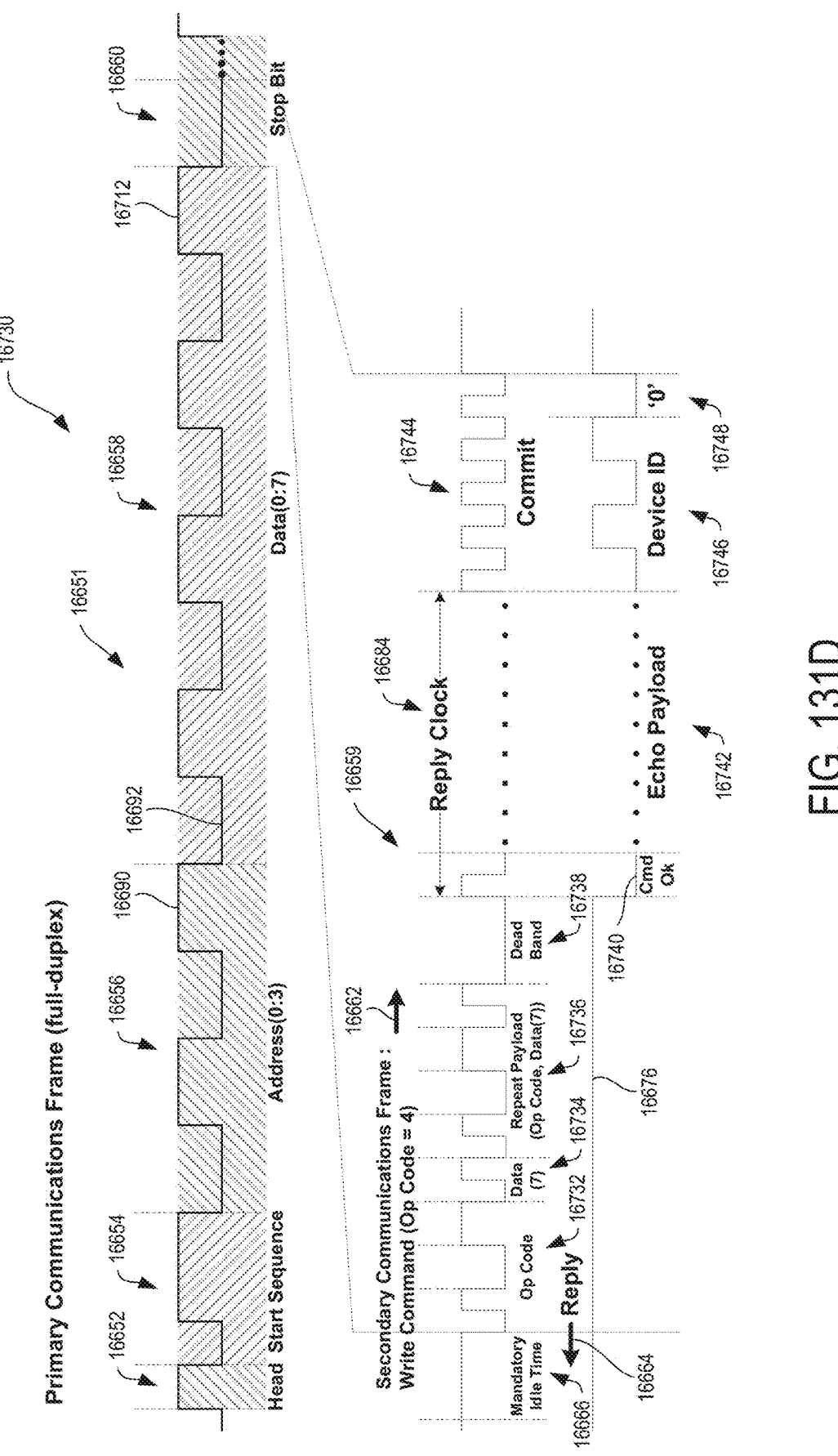
FIG. 131D illustrates a timing diagram of the primary communication frame and a secondary communications frame during a write command following the pre-write command illustrated in FIG. 131C, in accordance with at least one aspect of the present disclosure.

FIG. 131D illustrates a timing diagram 16730 of the primary communication frame 16651 and a secondary communications frame 16659 during a write command following the pre-write command illustrated in FIG. 131C, in accordance with at least one aspect of the present disclosure. With reference now to FIGS. 123 and 131D, the secondary communications frame 16659 transmits the last data bit 16734 (Data (7)) during the stop bit 16660 period. Once a full data word (Data (0:7)) is received by the primary device 16604 from the energy module 16602, the primary device 16604 sends 16662 a write command 16732 (Op Code=4) to transmit the last data bit 16734 (Data (7)) and repeats the payload 16736 (Op Code, Data (7)) until the dead band 16738. After the reply line 16676 goes low 16740 (Cmd Ok) and echoes the payload 16742, the primary device 16604 commits to write by outputting five extra clock cycles 16744, where the first four symbols are a repeat of the responding device ID 16746 followed by a '0' 16748.

FIG. 132 illustrates a timing diagram 16750 of the primary communication frame 16651 and a secondary communications frame 16661 during a reset command, in accordance with at least one aspect of the present disclosure. With reference now to FIGS. 123 and 132, the primary device 16604 sends 16662 a reset command 16752 (Op Code=5) to reset one or all attached secondary devices 16759 (Dev2-Dev14). In this example, the secondary communications frame 16661 is transmitted during the period of the last data bit 16712 (Data (7)) and the stop bit 16660. The device ID 16754 "0000" is used to reset all attached devices 16759 (Dev2-Dev14). The primary device 16604 then sends a '0' 16756 and repeats the payload command 16758 (Op Code, ID, '0') until the dead band 16758. Each attached device 16759 (Dev2-Dev14) responds by pulling the reply line 16676 down during its assigned time slot. The payload is padded by one bit to distinguish it from other op codes. The primary device 16604 sends 16662 the reset command three times and votes on the response.

FIG. 133 illustrates a timing diagram 16760 of the primary communication frame 16651 and a secondary communications frame 16663 during a broadcast status request command, in accordance with at least one aspect of the present disclosure. With reference now to FIGS. 123 and 50, the primary device 16604 sends 16662 a broadcast status request command 16764 (Op Code=6) to request the status of each attached secondary device 16759 (Dev2-Dev14). In this example, the secondary communications frame 16663 is transmitted during the period of the sixth data bit 16762 (Data (5)). After sending 16662 the broadcast status request command 16764 the primary device 16604 repeats the payload 16766 (Op Code) until the dead band 16768. Each attached device 16759 (Dev2-Dev14) responds by pulling the reply line 16676 down during its assigned time slot.

FIG. 134 illustrates a timing diagram 16770 of the primary communication frame 16651 and a secondary communications frame 16665 during an individual status request command, in accordance with at least one aspect of the present disclosure. With reference now to FIGS. 123 and 51, the primary device 16604 sends 16662 an individual status request command 16774 (Op Code=7) to request a status byte 16786 from a single device. In this example, the secondary communications frame 16665 is transmitted during the period of the seventh data bit 16772 (Data (6)) for an automatic request or the eight data bit 16712 (Data (7)). After sending 16662 the individual status request command 16774 the primary device 16604 sends 16662 the device ID "00" 16788 and repeats the payload 16778 (Op Code, ID, "00") until the dead band 16782. The payload is padded by two bits to distinguish it from other op codes. When the reply line 16676 goes low 16784 (Cmd Ok) the addressed device sends the requested byte 16786, echoes the payload 16788, and repeats the data 16790 (Data (0:7) of information.

Although the above primary communication frame 16651 and secondary communications frames 16653, 16655, 16657, 16659, 16661, 16663, 16665 are described by way of specific examples, those skilled in the art will appreciate that other implementations fall within the scope of the present disclosure. For example, the timing may vary, the bits on which the secondary communications frames 16653, 16655, 16657, 16659, 16661, 16663, 16665 are synchronized to the primary communications frame 16651 may vary, and the specific data, format of data, and size of data exchanged during the primary communication frame 16651 and secondary communications frames 16653, 16655, 16657, 16659, 16661, 16663, 16665 may vary without limiting the scope of the communication arrangement comprising a primary protocol 16622 and a secondary protocol 16624 synchronized to the primary protocol 16622 for driving primary devices 16604 and secondary devices 16606, 16608, 16610 through a single port of the energy module 16602 as described with reference to FIGS. 123 and 131A-134.

Smart Return Pad Sensing

Aspects of the present disclosure are presented for systems and methods for identifying characteristics of a return pad in a monopolar electrosurgical system using contact quality monitoring (CQM) and near field communication (NFC) signals. In a monopolar electrosurgical environment, typically a surgical instrument having a single electrode is applied to a surgical site of a patient. Electrosurgical energy may be applied to the patient to conduct ablation or other kinds of treatment, and it is critical that the energy not end at the patient, lest burns or worse may occur. A neutral electrode (NE) or non-active electrode, oftentimes manifested in the form of a grounding pad or return pad that touches the patient in a wide area, is used to draw the energy through the patient and complete the energy path to ground.

The connectivity of the return pad to the patient is therefore crucial. It is regularly a concern that sensing the performance and position of the return pad be monitored or determined in some way, as the patient is not awake during surgery and therefore cannot provide any signal that there is overheating or something else is wrong. It is also desired to know there is a problem with connectivity or other health and status of return pads before burns occur, which might be the first non-aided indication a surgeon may know that the connectivity of the return pad was faulty.

Contact Quality Monitoring generally is the process of monitoring the monopolar system to ensure it is working properly, such as by monitoring the contact quality of the return pad. Additional information may also be helpful in managing the monopolar system, such as ensuring that the proper return pad is used in the surgical operation. With existing circuitry already available for performing CQM, it may be desirable to augment the structure to allow for more information to be obtained from the monopolar system.

Disclosed herein are some example systems and methods for obtaining additional health and status information from the monopolar system using NFC signals and CQM signals. In some aspects, resistance or impedance materials are sensed that may help identify what kind of return pad is being used, including what is the structure of the pad. In some aspects, NFC signals are used to identify characteristics of the return pad. In some aspects, the NFC signal may be transmitted in a modulated wave arrangement to communicate to a generator that is configured to supply the electrosurgical energy in the monopolar system.

In some aspects, the grounding or return pad may include two separate materials that form an interconnecting or interwoven mesh and both act as non-active electrodes when both contact the patient. A non-zero impedance may separate conductive lines connecting the two separate materials that may be analyzed to obtain a defining signature about that is linked to structural characteristics about the return pad. For example, a resistive material may be secured along the edges of the two materials and positioned in between them. When a signal is transmitted to the return pad, the resistive material may react and an impedance value may be derived from it. A CQM controller may be configured to measure these impedance signals of one or more return pads and may transmit appropriate messages to the generator.

Referring to FIG. 135, shown is an example circuit diagram illustrating several features about a CQM controller, in accordance with at least one aspect of the present disclosure. On the left side in solid lines is shown a CQM controller 17105, while the right side in dashed lines represents other components in the monopolar surgical system that it interacts with. The right side includes a monopolar (MP) active electrode 17130, and two neutral electrode (NE) return pads 17135 and 17140, respectively. These two NE return pads may be viewed as separate pads from an electrical standpoint, but functionally they are combined to operate as one return pad where both touch the patient. Between the two NE pads 17135 and 17140 is a non-zero impedance, labeled $Z_{Split}$. A sub-therapeutic signal passed through the two return pads 17135 and 17140 may be used to obtain impedance measurements of $Z_{Split}$ that may be used to identify the type of pads and their structure, in accordance with at least one aspect of the present disclosure.

Shown also is a transformer 17125 that is configured to transfer the energy of the signals from the monopolar system over to the CQM controller 17105 and vice versa. The CQM controller 17105 may be configured to couple a CQM interrogation pulse to the NE return pads 17135 and 17140 via the transformer 17125. The CQM interrogation pulse may be a continuous signal or time domain multiplexed with other signals. In some aspects, this drive signal may be differential or single ended in other cases. In some aspects, the transformer 17125 may include a wide enough bandwidth to allow for multiple fundamental frequencies, including allowing for signals with different fundamental frequencies to be sent in a time domain multiplexed manner. For example, the transformer 17125 may have 1 Mhz bandwidth or below, in some aspects.

Current sense $I_{SENSE}$ 17115 and voltage sense $V_{SENSE}$ 17145 transmit the signal to the A/D converter 17110, which then allow for the signal to be digitally processed by the CQM controller. In some aspects, the voltage and current sense may be differential, while in other cases they may be single ended. In some aspects, a redundant current sense $I_{sense2}$ 17120 is included to ensure proper functioning to mitigate component failures of important circuitry. A redundant voltage sense may also be included, not shown. These may allow for the voltage and current measurements obtained from $Z_{Split}$ to be digitized via the A/D converter 17110. In this way, additional processing may be performed to obtain cleaner signals and help ensure that the return pad is appropriately in contact with the patient and functioning properly, generally. As some examples, digital filtering may then be performed, frequency-domain analysis can be performed, and the digitized signal may allow for signal demodulation and data recovery. Performing digital signal processing on the converted digitized signal may help prevent nuisance alarms, for example, as the noise in the signal may be filtered out in this way.

Referring to FIG. 136, shown is an example design layout of a return pad configured to facilitate its identification using a pre-configured non-zero impedance, in accordance with at least one aspect of the present disclosure. As shown, and unlike typical return pads, the return pad 17200 now includes two unique mesh portions 17205 and 17210, illustrated by orthogonal diagonal lines in FIG. 136. Each portion is itself a neutral or non-active electrode, and may be made of similar materials used to make traditional grounding pads, noting that they are two separate portions that do not directly contact one another. As shown, the two mesh portions 17205 and 17210 form a split-plate pad scheme, with interlocking or interweaving structures that stretch through most of the overall return pad 17200. This allows for both of the portions 17205 and 17210 to touch substantially the same areas of the patient. The two pieces 17205 and 17210 are connected to separate NE conductive return lines 17225 and 17230, respectively, both of which are connected to a single discrete resistor in the body of a connector 17220. A resistance material or medium 17215 is present between the two mesh portions 17205 and 17210 and is directly connected to both of them.

The conductive lines 17225 and 17230 may be separated by a non-zero impedance, which is measured by the energy generator 17235 that supplies energy through the monopolar surgical system. The non-zero impedance may include the discrete resistor in the body of the connector 17220, or the resistive material 17215. As shown, the conductive lines 17225 and 17230 are connected to the NEs 17205 and 17210, which are physically separated by the resistive material 17215, and therefore the conductive lines are also separated by the resistive material 17215. In some aspects, the material 17215 in between the NEs 17205 and 17210 may be a dielectric material that produces a complex impedance, supplying both a phase and an impedance. An impedance measurement may be obtained that may uniquely define what type of return pad is being used in the operation, for example, by installing a particular amount of resistive material 17215 or installing a different type of material 17215 that has a predetermined amount of impedance. Using the monitoring methodology described in FIG. 121 to obtain an impedance measurement, the CQM controller may thus be able to identify the type of pad and the structure of the pad. In some aspects, the resistive medium 17215 may provide a particular amount of impedance when measured, based on the way the return pad is constructed and what it is used for. Some return pads may need to provide a higher amount of impedance given their function, and this difference may be reflected in the impedance measurements determined at the resistive medium 17215.

Referring to FIG. 137, shown is a block diagram with structures similar to FIG. 135 that also include means for identifying the return pad using NFC signals, in accordance with at least one aspect of the present disclosure. Shown here is the energy generator 17250 that includes a CQM controller 17255 and a demodulation module 17265. The signals to and from the energy generator may pass through the transformer 17270, similar to the transformer in FIG. 135. This is communicatively coupled to the return pad 17260.

In the return pad 17260, electrode 1 17272 and electrode 2 17285 may be like the neutral electrodes 17205 and 17210 in FIG. 136, and NEs 17135 and 17140 in FIG. 135. The impedance $Z_{Split}$ 17280 represents the non-zero impedance separating the electrodes 17275 and 17285, like the non-zero impedance described in FIG. 136. Here, the return pad 17260 also includes an NFC tag 17300 that may be embedded into the return pad 17260 without any additional circuitry required. It may be attached to a voltage clamp 17295 and an existing bandpass filter 17290.

The NFC tag may provide a second way to identify the return pad, in accordance with at least one aspect of the present disclosure. The CQM controller 17255 may generate an NFC carrier wave at a frequency suitable for the NFC tag 17300. In some aspects, the NFC carrier wave may be time-domain multiplexed with the CQM interrogation pulse, so that the CQM controller may continue to perform its main function of contact quality monitoring. In some aspects, the NFC tag may require a non-standard frequency in order to access the information. The NFC tag 17300 may modulate the carrier wave to transmit identification data contained in the NFC tag. This may be transmitted back to the energy generator 17250. The signal may then be demodulated at the demodulation module 17265 and the data may be received. The band pass filter 17290 may be used to isolate the CQM interrogation pulse from the NFC carrier wave when both are transmitted in a modulated signal, described more in FIG. 138 as an example. During this process, the voltage clamp 17295 may protect the NFC tag from any excessive voltage during monopolar energy delivery. The position of the filter and the voltage clamp may be such that monopolar return current from the neutral electrodes 17275 and 17285 may be unimpeded when flowing back to the energy generator.

Referring to FIG. 138, shown is an example of how two signals may be combined to be processed by the CQM controller, in accordance with at least one aspect of the present disclosure. Shown here is an example carrier wave 17310 that may represent the NFC signal, while the message wave 17320 represents the CQM interrogation signal. These may be combined into an amplitude modulated wave 17330 that contains the proper impedance information transmitted as an NFC signal. As discussed above, this signal may then be filtered by the band pass filter 17290 to register with the NFC tag 17300, and upon return to the energy generator, the modulated signal may be demodulated at the demodulation module 17265 to obtain the identifying information supplied by the NFC tag. The interrogation pulse is still present in the modulated signal, and may be filtered out at a different stage to perform the normal contact quality monitoring. It may be seen now that designing return pads to produce a particular impedance measurement that can be uniquely specific to each type of pad, and then transmitted using NFC, can provide additional information about the return pad while still allowing for proper contact quality monitoring.

Referring to FIG. 139, chart 17400 provides an example designation of types of return pads that may be categorized based on different impedance measurements, in accordance with at least one aspect of the present disclosure. As shown, the impedance measurements for each type of pad do not overlap with each other, allowing for a unique identification. These impedance measurements may be specified and manufactured for each return pad such that the readings may be obtained properly by a CQM controller. The resistive material, or the non-zero impedance generally as discussed in FIG. 136, may be built or manufactured into each type of return pad to produce this amount of impedance in each system. For example, a thinner amount of resistive material may be used, and/or different materials that produce the range of impedance may be placed in particular devices as opposed to others. Thus, when employing the identification methods described in FIGS. 135 and 136, the impedance readings in the left column of chart 17400 will be obtained, which will correspond to the type of return pad as described in the middle column.

In some aspects, in addition or alternatively, the NFC tag embedded into the return pad and as described in FIG. 137 may similarly be used to provide the same kind of identifying information. The measure of impedance may not need to be provided, but instead other uniquely identifying information may be provided by the NFC tag to signal to the CQM controller what type of return pad is being monitored, according to the description in the middle column of chart 17400, for example. In some aspects, the NFC tag may also provide other characteristic information about the return pad, such as thickness of the pad, spec information, date of manufacture, and so forth.

Referring to FIG. 140, shown is an example time series of a message channel used for time-domain multiplexing the different types of signals between the energy generator and the return pad, in accordance with at least one aspect of the present disclosure. Here, the time-domain multiplexing schedule is divided into three sections that repeat. The CQM interrogation pulse 17450 may be transmitted first, then time may be given for an NFC frame 17460 to be received, and then some period of idle time 17470 may separate the next period. In some cases, the amount of time for each of these sections may not be the same, as there may be more idle time 17470, for example, or the length of time needed for the NFC frame 17460 may be longer than the CQM interrogation pulse 17450, or the pulse may need to be wider.

In some aspects, situational awareness may be employed to learn and adapt to the different impedance readings of various grounding pads. For example, the initial impedance measurements received by the CQM device may lead a hub having situational awareness to acknowledge and identify what type of grounding pad is present. Once this is determined, the hub may be configured to tabulate the performance and outcomes of the surgical procedure and tie it to the type of grounding pad that was used. Any inadvertent burns or other performance characteristics about the grounding pad may be correlated to the type of surgical procedure that occurred. A cloud system in communication with multiple hubs may store dozens or hundreds of these types of data points and develop patterns that can be used to gauge the performance of grounding pads in the context of the surgical procedures they are used in. By comparing the performance of the return pads in the same type of procedure to other types of return pads, it may be possible to determine how best to utilize the return pads or see where there are flaws or vulnerabilities, as some examples.

Furthermore, situational awareness may be applied to the type of monopolar devices used, or the amount of energy supplied in combination with the surgical procedure and the grounding pad used. Using similar methods for tabulating data, a cloud system may be able to find patterns in how grounding pads may interact with the overall surgical system they are used in, if any patterns arise. This can also include measurements over time and any spikes in energy, and in the context in which those spikes might arise.

If there are any faults or burns that occur that the grounding pad could not effectively handle, patterns may be devised to see if there are any unique precursors that might suggest these faults are about to occur. Warning signals could then be developed and applied to the system. Similarly, if the grounding pad consistently reacts poorly after some event, patterns around any uniquely identifying data may be developed and warning signals could be applied to the system.

Automatic Ultrasonic Energy Activation Circuit Design for Modular Surgical Systems Aspects of the present disclosure are presented for a circuit design that provides automatic ultrasonic energy activation for a modular surgical system. In some aspects, a control circuit in an ultrasonic surgical instrument may be connected to a modular energy system that allows therapeutic energy to pass from a generator to the ultrasonic surgical instrument after automatically activating the ultrasonic functionality based on some threshold criterion being satisfied. In some aspects, the ultrasonic instrument may include a capacitive touch sensor that sends a signal to automatically activate the therapeutic ultrasonic energy when the touch sensor contacts appropriate tissue.

In a surgical environment, many instruments may be used to safely and cleanly perform surgical procedures. Multiple attendants may be on hand to provide one or more surgeons with different instruments at different timely moments, where the timing may be crucial for providing optimal care. Multiple surgical modules providing power to different surgical instruments may also be present around the patient. The chances of making an error increases the more instruments, moving parts, and variables there are. To improve safety and surgical operations, it is desirable to automate as many functions as possible, provided of course the automation fits precisely within the proper context of the surgical procedure.

As such, it would be desirable to automatically activate ultrasonic therapeutic energy at the appropriate time, as well as automatically turn off the ultrasonic energy correctly. Thus, in some aspects, a sensor coupled to the end effector may provide accurate feedback for precisely when the ultrasonic energy should be applied or turned off. In some aspects, a capacitive touch sensor that is configured to measure a voltage drop across a portion of a capacitive touch screen due to a conductive contact, such as contact with the patient tissue or the user of the ultrasonic instrument. In this way, the timing of activating the ultrasonic instrument may correspond precisely to when it is needed.

FIG. 141 illustrates an example implementation of automatic activation of ultrasonic energy, in accordance with at least one aspect of the present disclosure. Here, an ultrasonic generator 17505 is electrically coupled to an instrument 17510 being held by a user. In this case, a capacitive touch surface 17520 is secured to the main body portion of the ultrasonic instrument, in range of the user being able to touch it with a finger while manipulating the instrument. In other cases, the capacitive touch sensor 17520 may be secured to the end effector 17515, which will be discussed more below. The capacitive touch sensor 17520 then responds by sending a signal to activate a visual indicator, such as LED 17525. This provides feedback that the capacitive sensor is activated. In some cases the capacitive touch sensor 17520 may be an electrode that responds to conductive activity, while in other cases the capacitive sensor may be a surface or a projective pad, similar to the content in capacitive touch screens.

Referring to FIG. 142, shown is a block diagram illustration of various components of an ultrasonic instrument 17602 with automatic activation capabilities using a capacitive touch sensor 17620, in accordance with at least one aspect of the present disclosure. The housing 17610 of the ultrasonic instrument 17602 may include a control circuit 17615, such as an ASIC or FPGA. The control circuit 17615 may be electrically coupled to an ultrasonic generator 17605 configured to activate an ultrasonic transducer 17604 to apply therapeutic ultrasonic energy to the tissue 17635 clamped between an ultrasonic blade 17630 and a clamp jaw 17625. The clamp jaw 17625 may include a conductive pad 17710 or a pad with an integrated electrode. A non-therapeutic electrical signal may be applied between the conductive pad 17710 or a pad with an integrated electrode and the electrically conductive ultrasonic blade 17630 to charge the tissue 17635 capacitance 17640 and detect the presence of tissue 17635 by a capacitive touch sensor 17620 included in the housing 17610. The capacitive touch sensor 17620 is coupled to the control circuit 17615. Power may be supplied to the capacitive touch sensor 17620 through the AVDD port, providing power to the analog capacitive touch sensor 17620. When a conductive medium such as tissue 17635 contacts both the conductive pad 17710 and the electrically conductive ultrasonic blade 17630, the capacitive touch sensor 17620 detects the presence of the tissue 17635 and provides a signal to the control circuit 17615 to indicate the presence of tissue 17635. The control circuit 17615 may then determine to activate the generator 17605 to supply electrical energy to an ultrasonic transducer 17604 to activate the ultrasonic blade 17630 of the end effector to apply therapeutic energy to the tissue 17635 clamped between the ultrasonic blade 17630 and the jaw 17625 of the end effector. The ultrasonic blade 17630 delivers the therapeutic ultrasonic energy after the capacitive touch sensor 17620 is appropriately triggered by the presence of tissue 17635. The jaw 17625 and the ultrasonic blade 17630 are shown clamped to tissue 17635 of a patient, and the diagram is completed showing capacitance 17640 of the body of the patient.

Referring to FIG. 143, shown is another variant of the instrument having automatic ultrasonic activation with the capacitive touch sensor positioned at the end effector, in accordance with at least one aspect of the present disclosure. Like in FIG. 142, the instrument 17610 is coupled to a generator 17605 and include the control circuit 17615. In this case, the capacitive touch sensor 17705 may be positioned at the end effector, secured to either the jaw 17625 or the ultrasonic blade 17630, for example. The sensor 17705 may be configured to come into contact with tissue 17635 of the patient when the jaw 17625 is opened and then clamped onto a portion of the tissue 17635. While the position of the sensor 17705 is underneath the ultrasonic blade 17630, in one aspect the sensor 17705 may be positioned on the inside of the jaw 17625 so as to be facing the patient tissue 17635 when the jaw 17625 is clamped down on the tissue 17635.

In some cases, the signal of the capacitive touch sensor may activate when a circuit including the capacitive touch sensor 17705 is completed once the tissue 17635 is clamped between the jaw 17625 and the ultrasonic blade 17630. A conductive pad 17710 or a pad with an integrated electrode may be configured to deliver non-therapeutic energy, which will pass through to the capacitive touch sensor once the tissue 17635 is clamped between the jaw 17625 and the ultrasonic blade 17630. That is, the tissue 17635 of the patient may be used to complete the current path. With the completion of the current path, then the non-therapeutic energy flowing between the conductive pad 17710, the tissue 17635, and the ultrasonic blade 17630 may be used to activate the capacitive touch sensor 17705, and thereby cause the sensor 17705 to send a signal as an input back to the control circuit 17615 to activate the therapeutic energy to the ultrasonic blade 17630. In this configuration, one conductor may be coupled to the ultrasonic blade 17630 and one conductor may be coupled to the conductive pad 17710 to deliver non-therapeutic energy.

In some aspects, the capacitive touch sensor 17705 at the end effector may receive power directly from the control circuit 17615, bypassing the ultrasonic blade 17630. In this case, the capacitive touch sensor 17705 may be activated and ready to respond to when it touches a capacitive source, such as the tissue 17635. Then, the capacitive sensor 17705 may deliver a trigger or activation signal as input to the control circuit 17615, which then may turn on the therapeutic energy to the ultrasonic blade 17630.

Referring to FIG. 144, in another variant, in some aspects, a pair of capacitive touch sensors 17805, 17705 may need to register some capacitive reading simultaneously in order for the therapeutic energy to automatically activate. Here, a second touch sensor 17805 secured to the clamp jaw 17625 is also included. While the position of the sensor 17805 shown is toward the top of the clamp jaw 17625, the sensor 17805 may be positioned on the bottom of the clamp jaw 17625 where it can contact the tissue 17635 at the same time as the sensor 17705 can also touch the tissue 17635 (see above where it is discussed that the positioning of sensor 17705 is on the inside portion of the jaws). In this case, non-therapeutic energy may be supplied to both of the sensor 17805, 17705, and both may be configured to provide inputs to the control circuit 17615 which they sense a reading. Only when both provide their signal inputs to the control circuit 17615 may the control circuit 17615 then provide therapeutic energy to the ultrasonic blade 17630.

While an ultrasonic blade is discussed in these examples, other types of elements at the end effector may be used to supply the therapeutic energy. These may include grippers, clamps, teeth, flat panels, and so on.

Referring to FIG. 145, is a logic diagram 17900 of a process depicting a control program or a logic configuration for automatically activating therapeutic ultrasonic energy by an instrument, in accordance with at least one aspect of the present disclosure. These steps may be consistent with the descriptions in FIGS. 141-144. A control circuit of the surgical instrument may deliver 17905 a non-therapeutic energy signal to a capacitive touch sensor. The signal may be used to power on the touch sensor. In some cases, the capacitive touch sensor may be positioned at an end effector of the surgical instrument, in position to sense when tissue of a patient is touching the end effector via the capacitive touch sensor. In some cases, the energy may be delivered directly to the capacitive touch sensor, while in other cases the energy may be delivered through completion of a circuit with a conductive portion of the end effector, such as the ultrasonic blade and through the blade and the capacitive touch sensor making contact with the patient tissue.

The capacitive touch sensor may determine 17910 it has received a capacitive reading, say by touching the tissue of the patient. There are a number of ways in which these readings may be achieved that are known to persons of skill in the art, such as through surface capacitive sensors or projective capacitive sensors, and aspects are not so limited. Once a reading is obtained, the capacitive touch sensor may transmit 17915 back to the control circuit an activation signal as an input. Then, in response to the input signal, the control circuit may automatically deliver 17920 therapeutic energy to the end effector, say at an ultrasonic blade or other element configured to utilize the therapeutic energy.

As mentioned previously, in some cases the control circuit may require more than one activation signal from more than one source, in order to confirm in an even more secure manner that the end effector is touching patient tissue at multiple places. Once one activation signal no longer is transmitting to the control circuit, then the control circuit may automatically stop delivering the therapeutic energy.

In some aspects, a power monitoring and sequencing circuit may be employed to monitor power rails that supplies the circuits associated with the energy module used to supply energy to the ultrasonic surgical instrument. Power monitoring and sequencing can be employed to avoid risk of incorrect shutdown of certain circuits due to a non-critical power supply fault. In one implementation, an integrated, four-channel voltage monitoring and sequencing device, such as the ADM1186-1 and ADM1186-2 by Analog Devices, may be employed to monitor multiple voltage supply rails. During a power-up sequence, a state machine in the integrated circuit enables each power supply in turn. The supply output voltage is monitored to determine whether it rises above a predefined upper voltage threshold within a predefined duration called the blanking time. If a supply rail rises above the upper voltage threshold, the next enable output in the sequence is turned on. In addition to the blanking time, the user can also define a sequence time delay before each enable output is turned on. The integrated circuits may be used individually or cascaded.

Coordinated Energy Outputs of Separate But Connected Modules

Aspects of the present disclosure are presented for providing coordinated energy outputs of separate but connected modules, in some cases using communication protocols such as the Data Distribution Service standard (DDS). For modular components, such as those used in the descriptions of FIGS. 1-11, it is useful to have the overall system monitor and coordinate energy use between each of the modules so that the system overall may not be overloaded. It is critical for the OR environment to be controlled, and having energy spikes or energy dips due to power loading issues may disrupt the expected outcomes of one or more surgical procedures. Rather than compute or synchronize every module in a preplanned procedure, in some aspects, communication occurs between multiple modules so as to coordinate how the modules operate in relation to one another. It may not be desirable to synchronize every module in a timed or orchestrated way, since unexpected results can occur during procedures and adjustments must be available.

Thus, in some aspects, there is provided a communication circuit between a header or main device, a first module, and a second module, each including connection to a segment of a common backplane, where the output from a first module can be adjusted by sensing a parameter from a second module. In some aspects, the signal can pass from the first module through the header to the second module, or in other cases directly from the first module to the second module. While the example aspects discuss just a first and a second module, it can be readily seen that these same principles and structures can be applied to multiple modules, such that the described architecture may be scalable to a large degree.

In some aspects, the communication protocol is supported by the DDS standard, and a second custom software layer to manage information transfer. In other cases, other known communication standards may be used. In some aspects, the first module delivers an energy output in the form of RF, ultrasonic, microwave, smoke evacuation or insufflation, power level or irrigation, and so on in the form of a concrete output that surgically modifies or is the result of a surgical modification, and the signal from a second generator is impedance, temperature, blanching appearance, or a particulate count from a smoke evacuator, and so in the form of a quantifiable statistic or measurement.

Referring to FIG. 146, shown is an example block diagram of multiple modules that may be connected together consistent with the descriptions of FIGS. 1-11 that include communications interfaces that allow for coordinated energy output between multiple modules, according to some aspects. A first main device or header 18000 provides the initial links to other modules, as well as connections to outside communications, such as through the Ethernet physical connection 18010. The header 18000 also includes a module processor 18005 with a firewall configuration and routing capabilities to other modules. The firewall prevents interference of the other modules from the external communications, which may come through the external communications interface 18015. It is more secure to have a physical connection such as the gigabit Ethernet connection 18010, but other means may also be possible, such as high speed wireless access connected to a fiber optic line.

On the other side of the firewall and through the routing in the module processor 18005, another separate communication link, e.g., through another Ethernet physical connection, attaches a primary communications interface 18025 to a functional module 18020. This may be a first module, configured to facilitate a first type of procedure and energy output, such as some surgical function such as RF energy, ultrasonic energy, and the like. Shown here are multiple functional modules 18020, labeled as module #1, #2, and N, where N is any other positive integer greater than 2. There is a module processor 18030 in each of the functional modules, as well as a data communication switch 18035, shown here as a gigabit Ethernet switch as just one example of the type of switches possible. As shown, each functional module 18020 is communicatively coupled to the subsequent functional module in serial via the primary communications interface 18025, while just the first functional module is communicatively coupled to the header 18000. In other cases, the modules may be communicatively coupled in other arrangements, such as in a daisy chain, a round robin or in a combination of parallel pipelines.

As shown, the power to the Ethernet/data communication switch infrastructure is segregated from the local modules power so as to allow the data communication interface to remain powered while any local power to any module is removed or modified. This is denoted by the $V_{SW}$ label in comparison to the $V_{local}$ labels associated with the module processors. In addition, the communications interfaces to the modules are segregated from the outside data communications interface so as to maintain a more secure local environment.

In some aspects, energy output coordination between a first and second module may be based on sensing a parameter with the second module and correspondingly adjusting power to the first module. The parameter may include some health and status parameter about how the second module is performing, such as impedance received at an end effector coupled to the second module, temperature readings, blanching appearance at a surgical site, particulate count from a smoke evacuator, amount of liquid evacuated, and so forth. In response, the first module may adjust energy output for various kinds of functionality, such as RF output, ultrasonic energy output, microwave energy, smoke evacuation or insufflation, power levels to irrigation, and so on.

There are several example use cases for this configuration of having one header 18000 with careful communication breaks while still connected to multiple modules. For example, the header 18000 may be able to have direct communication to a control tower, where the header 18000 can then provide relay communications to any of the functional modules. In addition, there can be direct connection of any two overall modular systems, with each system having its own header 18000 and their own sets of connected functional modules. This can increase the number of modules in the system overall. Furthermore, this configuration may provide connection to more than two pieces of equipment through use of the Ethernet switch. In this way, this proposed architecture may theoretically be able to connect an arbitrary number of surgical modules, so long as adequate power is budgeted for the $V_{SW}$ domain.

The speed of information transfer between two or more modules may be very important in making energy output adjustments, as the timeliness may affect the clinical effectiveness of not only the adjustments but of the overall procedure itself. As such, in some aspects, the communications may be governed by the DDS standard. This allows for information transfer to occur at a high-level of functionality as a framework standard, in comparison with the lower level transport standard, as an example. In some aspects, the following core framework functions may be applied to the architecture shown in FIG. 121 using DDS:

Data resource model—Data objects may be defined using a standard interface definition language (IDL) and corresponding code can be auto-generated.

ID and addressing—Keys may be used to identify unique instances of data objects, and partitions will likely be used to segregate traffic specific to associated modules and therefore reduce the amount of traffic they will need to process.

Data type system—DDS provides a rich type system that is leveraged via a simple declaration within an IDL file.

Data resource lifecycle—Data objects will likely need to have lifetimes associated with them. Associations, which are temporary by nature, are one example of data objects that will require a lifecycle.

State management—One way which this is useful is eliminating the need to synchronize power-up of the modules within the modular system.

Publish—subscribe—From the standpoint of minimizing regression test effort, it is beneficial to decouple publishing from subscribing.

Request-reply—This function will be beneficial with publication of visualizations to the user interface (UI). In that case, that history may not be stored, and instead the system may rely on request-reply since that information will be large in size and therefore impractical to store redundantly in the form of historical data.

Discovery—This eliminates the need for static configuration of topic publishers and subscribers, and therefore simplifies the configuration process during manufacture.

Exception handling—In addition to communication timeouts, other exception conditions exist including exceed max latency, etc. The more specific exceptions that are supported within the framework, the less application code that needs to be authored to serve the same purpose.

Data quality-of-service—This will also be used to detect lack of timely delivery of time-sensitive information (such as activation requests), expire stale data, etc.

Data security—Granular security on a topic-by-topic, or domain-by-domain basis obviates the need to implement this at the application level. This also includes scenarios such as authentication of entities prior to letting them participate in the exchange of data.

Governance—A file-based configuration mechanism simplifies development and deployment.

In some aspects, situational awareness may be utilized to improve the energy coordination of modules, based on the architecture shown in FIG. 146. For example, with appropriate sensors to or feedback to record power consumption and performance of each module, a cloud system in communication with the header 18000 may be configured to develop statistics of the energy performance of each module over a period of time. The coordination between the modules may also be recorded, and then the results based on those settings can be tabulated. If there are any suboptimal performance metrics, and with enough examples from using similar kinds of setups in different surgical procedures, the cloud system may be configured to develop patterns for how to better coordinate energy outputs between the multiple modules.

Aspects of the present disclosure also include methods for automatically activating a bipolar surgical system in one or more of the modular systems using the DDS standard. FIGS. 147A and 147B illustrate a logic diagram of an example process for how this may be implemented. A modular component of the system described in any of FIGS. 1-11 for example may be used in this process. Starting at block 18102, a bipolar instrument, such as an electrosurgical device with bipolar electrodes, may be plugged into the system via a bipolar port or other port recognized as using a bipolar feature. Several examples of this are described above. At block 18104, the modular system that is in communication with the plugged in bipolar instrument may determine with an auto-bipolar feature is enabled, consistent with aspects described herein. If it is not, then the process may proceed down the path to section 39-1 to FIG. 147B, ultimately to block 18148, where the system will be in standby until there is a manual activation button.

However, if the auto-bipolar feature is available and enabled, then at block 18106, the system may enable bipolar relays or other similar relays, such as AE bipolar relays. Once the relays are enabled, at block 18108, the system may determine if there is any activation button or signal being pressed or activated, indicating a manual activation still. If so, then at block 18110, the relays may be overridden and the system will not enable the bipolar relays automatically and instead wait for activation to occur.

However, if there is no manual activation still, then at block 18112, the bipolar relays will be enabled, and the system may engage in an automatic bipolar activation using relevant components of an energy generator, the box that which defines these components are delineated by the connections 39-2 and 39-5 and extending to FIG. 122B. Instructions to these components may be transmitted using the DDS communication standard, as an example, although other communication standards may be used in some aspects. At block 18114, the energy generator may create a bipolar monitoring signal by a direct digital synthesizer 18128. This signal may be magnified by an amplifier 18116 and then transmitted via a transformer 18118 to both voltage sense $V_{SENSE}$ 18120 and current sense $I_{SENSE}$ 18130. The signal may then be received by a controller 18122 on the isolated patient side, such as by an FPGA or other control circuit. This signal may also cross the isolation barrier at block 18124, back to a master controller 18126. The master controller may possess the instructions of whether to activate the bipolar instrument or not, and may also provide instructions to not enable the bipolar relays, going back to block 18110. If the master controller 18126 determines that the activation is not yet ready, then the process may repeat starting back at the direct digital synthesizer 18128.

Continuing down the path from the signal being transmitted via the transformer 18118 to $I_{SENSE}$ 18130, extending through path 39-3 and referring now to FIG. 147B, the signal may then pass through a blocking capacitor 18130, which may serve a variety of functions, such as helping to correct any charge imbalance in the signal, preventing prolonged DC current, or limiting the maximum net charge of the signal to prevent any damage after being transmitted by the transformer 18118. Furthermore, the energy generator components may provide leakage detection 18132 to ensure that the energy has not leaked that might cause a loss of the signal. After these checks of the signal are conducted, the feedback may go back to the controller 18122 shown in FIG. 147A via the path 39-4 and continue through the process as described above.

Once the aforementioned processing of the auto-bipolar signal has occurred through the energy generator, at block 18136, the auto bipolar signal is sent to the bipolar instrument. At block 18138, a determination is made at the end effector for an impedance measurement comparison. For example, an impedance measurement at the end effector is returned and the controller may determine if this impedance measurement is less than the impedance of when the end effector is open, or is not touching any tissue. This may effectively determine if the bipolar instrument is clamped appropriately onto the surgical area, and if so, it may be determined that the instrument can be activated automatically. This signal may repeat for continuous gauging until it is determined that the end effector is ultimately clamped onto tissue at a surgical site. Once it is, then at block 18140, the controller may drive the generator to increase voltage and current to reach a user-set power level. Finally, at block 18142, the controller may continuously monitor the impedance to maintain the user-defined power level and current until the impedance is greater than or equal to the impedance in the open position, signaling that the end effector is not touching tissue anymore, or in other cases may signal that the impedance of the tissue has changed sufficiently such that therapeutic energy should no longer be applied. The auto-activation signal may be continuously sent to continuously gauge the status of the end effector by following this process in a repeated fashion.

Referring to FIG. 148A, and as highlighted in block 18202, a variant for activating auto bipolar capabilities using a control circuit of an energy generator as described herein. The blocks 18204, 18206, 18208, 18220, and 18226 (see FIG. 148B) mirror their respective blocks as shown in FIG. 148A.

In this example, different hardware 18248 may be utilized to enable auto-bipolar functionality. Instructions to these components may be transmitted using the DDS communication standard, as an example, although other communication standards may be used in some aspects. The boundaries for this are defined by the paths 40-2 to 40-6, extending to FIG. 148B. For example, at block 18210, if there is an auto-bipolar port or similar port enabled, the system may load a query clock signal, such as a low voltage 40 kHz or less signal, to an impulse transformer at block 18212. Following path 40-3, and referring now to FIG. 148B, this is used for a relay stage at block 18228, which will be discussed more below.

Referring back to FIG. 148A, and at block 18208, if there is not any activation button or signal being pressed to indicate the activation of the bipolar functionality, then the process proceeds to block 18214, where the energy generator components to support the auto bipolar functionality is used to create an output drive signal. This may be controlled by a direct digital synthesizer 18218. The drive signal may be amplified by amplified 18216, which then proceeds along path 40-4 to FIG. 148B.

From block 18206 where it is determined that an auto-bipolar port is enabled, the lines both to block 18210 and 18214 are simultaneously possible because the auto-bipolar port may be enabled while there is no activation button or signal being pressed. This scenario suggests that the auto-bipolar activation feature is truly being relied on. With that in mind, referring now to FIG. 148B, at block 18228, with both the query clock signal from block 18210 and the drive signal from block 18214 (see FIG. 148B), the process continues to a relay stage, where three settings may be available. The first setting is to enable auto-bipolar detection using the drive signal that is synced with the clock signal. The second setting is to enable the direct digital synthesizer to generate an analog version of digital input of an interrogation signal, which may be achieved by transmitting a different drive signal. Any of these types of signals may be sent to a transformer 18230, and similarly to FIGS. 147A and 147B, the signal may proceed to the various components, e.g., $V_{SENSE}$ 18244, controller at the patient side 18246, $I_{SENSE}$ 18232, blocking capacitor 18234, leakage detection circuit 18248, and back up to the master controller 18222 after crossing the isolation barrier 18224 via path 40-5 as shown in FIG. 148A.

With the signal appropriately processed, at block 18236, the auto-bipolar signal may be sent to the bipolar instrument. As before in FIG. 147B, at block 18238, the system may determine whether to enable the bipolar instrument by comparing the current impedance to a threshold. If the clamped jaws are touching a material that may be conductive, the impedance will drop and it if the impedance sufficiently signals that the jaws have clamped onto tissue, the auto-bipolar signal may indicate that the bipolar energy can activate automatically. At block 18240, the system may signal to the generator to increase the voltage and current to reach the appropriate user-set power levels, and may continuously output the energy according to the user-defined power levels until the impedance measurement exceeds a threshold, at block 18242. This may indicate that the jaws are no longer completing a circuit through conductive tissue, indicating that the jaws may be in the open configuration.

Referring to FIG. 149, shown is an example diagram of just the circuit components in a system for conducting automatic activation of a bipolar instrument, according to some aspects. The diagram includes a header module 18300 and a generator module 18315 that is configured to send energy to a bipolar instrument, expressed as element 18375 having conductive lines flowing into and out of tissue resistance 18370 that represents the impedance of the patient.

The header module 18300 includes a header controller 18310 and a user interface (U/I) 18305. The header module may be controlled in part by a foot switch 18385, but in other cases the foot switch 18385 may be another kind of manual control known to persons in the industry who utilize bipolar surgical instrument systems.

The header controller 18310 is in communication with the generator controller 18320 via a communication standard, such as the Data Distribution Service (DDS). This may allow for efficient communication that can handle the proper speed in which automatic activation based on impedance sensing may demand. In other cases, other communication protocols may be used, although preferably standards that allow for sufficiently quick communication may be preferred.

The generator controller 18320 may be communicatively coupled to a direct digital synthesizer 18330, which feeds into a power amplifier 18330. The signal from the power amplifier is transmitted via transformer 18335, where a set of resistors is set up to provide proper measurements of the voltage and current to be measured from the end effector of the bipolar instrument. Thus, on the other side of the secondary coil of the transformer 18335, the monitoring setup includes a pair of voltage dividers 18340 and a shunt resistor 18345. The transformer 18335 provides energy to a bipolar port 18380 that connects to the instrument 18375. Energy flows through one line of the bipolar instrument and into the patient, experiencing some impedance 18370 and passes back through the second line of the bipolar instrument and back through the port 18380. The impedance load created by this loop may be measured using current sense amplifier 18350 and voltage sense amplifier 18355. A current signal isolation transformer 18390 may transfer the current signal to the current sense amplifier 18350. A voltage signal isolation transformer 19395 may transfer the voltage signal to the voltage sense amplifier 18355. The signals may be converted to digital values using the analog to digital converter 18360. This reading may be fed back to the generator controller 18320, and depending on the result, may instruct the buck regulator 18365 to deliver therapeutic energy to the transformer 18335 for transmission to the bipolar instrument 18375.

Referring to FIG. 150, shown is another variant of a logic diagram of a process depicting a control program or a logic configuration for conducting automatic bipolar activation in a bipolar instrument. The logic diagram may correspond to the circuit elements described in FIG. 149. To start, the bipolar instrument 18375 should be connected to the bipolar port 18380 of the generator module 18315, so that proper communication is complete between the header module 18300, the generator module 18315, and the bipolar instrument 18375. The bipolar instrument 18375 may be identified 18405 by the generator controller 18320. The generator controller 18320 may then inform 18410 the header controller that the bipolar instrument is connected to the bipolar port of the generator module. At this point, the generator controller 18320 may conduct 18415 a check of whether an autobipolar mode is enabled via the header module U/I. If it is not, then the header controller 18310 may inform the generator controller 18320 that autobipolar mode is disabled and therefore may command 18420 the generator controller 18320 to enter manual bipolar mode. This may lead to manual manipulation by activating 18470 the bipolar instrument using the foot switch 18385 or similar device.

On the other hand, if autobipolar mode is enabled, then the header controller 18310 may inform 18425 the generator controller 18320 via DDS protocol (or other communication standard) to start autonomous bipolar mode. From here, the generator controller 18320 will first direct a sub-therapeutic signal to the bipolar instrument 18375 in order to determine if the bipolar instrument 18375 should activate with therapeutic energy. To do this, the generator controller 18320 may load 18430 the direct digital synthesizer 18325 with an RF bipolar wave shape, and the output of the DDS 18325 is then fed to the power amplifier 18330. The wave shape may be formed based on a look up table, or by following a function based on an amount of energy as input. The generator controller 18320 may then drive the buck regulator 18365 with a square wave signal, in some cases at duty cycle, which will result in a small DC voltage feeding the transformer 18335. This will cause a sub therapeutic output from the transformer 18335 to be fed 18435 to the bipolar instrument 18375, which ultimately flows into the tissue of the patient as represented by the load resistor 18370. This small DC voltage is used to simply check whether the end effector of the bipolar instrument 18375 is properly connected to the tissue of the patient, so that the therapeutic energy may be automatically activated.

The energy flowing through the patient tissue 18370 and back into the return path of the bipolar instrument 18375 creates a current sense signal from the shunt resistor 18345 via the current signal isolation transformer 18390, which provides 18440 the signal to the current sense amplifier 18350. The current sense amplifier 18350 then feeds 18445 this signal ultimately to the analog to digital converter 18360—in some cases via a multiplexer, not shown—to create a digitized current signal. Similarly, a voltage sense signal is picked up from the voltage divider resistors 18340 via the voltage signal isolation transformer 18395 and is provided 18450 to the voltage sense amplifier 18355. The voltage sense amplifier 18355 feeds 18455 this signal ultimately to the analog to digital converter 18360 to create a digitized voltage signal.

The A/D converter 18360 may then transmit these digitized signals to the generator controller 18320. The generator controller 18320 may then calculate 18460 tissue impedance of the patient, represented by the load resistor 18370, using the sensed voltage and sensed current digitized signals. From here, the generator controller 18320 may perform a series of checks to determine if it is appropriate to automatically enable bipolar therapeutic energy activation. The controller 18320 may first check 18465 if autobipolar mode is (still) enabled. If it is not, then control may transfer to the foot switch 18385, and from there it is determined if bipolar energy activation is instructed 18470 by the foot switch 18385. However, if autobipolar mode is enabled, then the controller 18320 also checks 18475 if the calculated tissue impedance is within a predetermined treatable tissue impedance range suitable to activate therapeutic energy. If it is not, then the process repeats with the generator controller 18320 driving the buck regulator 18365 to send 18435 a small DC voltage to the transformer 18335 to inspect the bipolar end effector with sub-therapeutic energy. However, if the measured impedance is within range, then the generator controller 18320 may instead drive 18480 the buck regulator 18365 with a square wave at duty cycle, resulting in a higher DC voltage. This is fed to the transformer 18335, resulting in a therapeutic energy output that may be preset by inputs at the header U/I 18305. This therapeutic energy is transmitted to the bipolar instrument 18375 from the transformer 18335, which is then applied to the patient tissue as represented by the load resistor 18370.

If autobipolar mode is not enabled, then using the foot switch 18385 or something similar, an instruction may be given to request 18470 energy activation to the generator controller 18320, resulting in the generator controller 18320 driving 18480 the buck regulator 18365 with a higher DC voltage to provide therapeutic energy, in a manner described above.

After activating therapeutic energy, the current sense amplifier 18350 and the voltage sense amplifier 18355 are still available to continually monitor (18440 and 18450) the tissue impedance. They may accomplish this by relying on the therapeutic energy signal flowing through the patient tissue. This may be used to determine when to automatically turn off the therapeutic energy, such as when a later tissue impedance measurement no longer is within the predetermined treatable tissue impedance range.

In some cases, being outside the predetermined treatable tissue impedance range can signal either that the bipolar jaws of the bipolar instrument 18375 are no longer properly connected to the patient tissue, or that the patient tissue is sufficiently coagulated such that the tissue impedance is dramatically higher. At that point, it is no longer desirable to continue applying therapeutic energy, which would instead result in burns or other damage to the tissue and therefore the logic diagram shown herein may be suitable for automatically stopping the therapeutic energy.

In some aspects, situational awareness may be utilized to improve the automatic detection and activation of a bipolar instrument, according to any of the logic diagrams of FIGS. 147A and 147B, 148A and 148B, and 150. The system may record for how long automatic activation of the bipolar instrument occurs before being turned off, as well as if the surgeon or technician records any feedback indicating the automatic detection didn't work as intended. For example, if the impedance threshold needs adjusting, or if the jaws clamping down on tissue did not activate the energy automatically because the impedance threshold was not properly met, these kinds of instances may be recorded and analyzed. As another example, the impedance may change at the surgical site over time, so the threshold values may also need to be adjusted over the course of a procedure. By recording the impedance values and any instances of unintended activations or deactivations over time, a cloud system connected to the auto-bipolar system may utilize situational awareness to adjust thresholds as needed in future procedures. In addition, if the same type of procedure is conducted frequently, situational awareness may be used to anticipate at what point potential pitfalls may occur during a procedure, say after the bipolar instrument is turned on for too long or after an overall amount of time that the bipolar instrument is turned on.

Managing Simultaneous Monopolar Outputs Using Duty Cycle And Synchronization

Aspects of the present disclosure are presented for managing simultaneous outputs of surgical instruments. In some aspects, methods are presented for synchronizing the current frequencies. In some aspects, methods are presented for conducting duty cycling of energy outputs of two or more instruments. In some aspects, systems are presented for managing simultaneous monopolar outputs of two or more instruments, including providing a return pad that properly handles both monopolar outputs in some cases. Managing the outputs of multiple instruments may be important to safely performing procedures because of some unwanted side effects of using multiple instruments. For example, a beat frequency may be present between two monopolar instruments operating on the same patient simultaneously, when the frequencies of their currents are close to each other but not exactly the same. This may create an unwanted current envelope between the two instruments that could cause burns or other unintended side effects.

Referring to FIG. 151, shown are a set of graphs that present one problem with utilizing two monopolar surgical instruments on the same patient, in accordance with at least one aspect of the present disclosure. Graph 18502 shows an example current output frequency of a first electrosurgical unit ESU 1. Graph 18504 shows an example current output frequency of a second electrosurgical unit ESU 2. Qualitatively, one can see that the frequencies are similar, but they are not exactly the same. It may be common that surgical instruments may emit a current with roughly the same frequency, say to within +/−10 Hz, in order to provide the appropriate type of electrosurgical energy to the patient.

However, when two or more of these instruments are acting on the same patient simultaneously, a beat frequency can arise. Acting on the same patient, the effect of the current frequencies on the patient are added, resulting in constructive and destructive interference at different times. Because the frequencies are very similar but not identical, at some points the currents will combine constructively, while after one or more periods later, the currents will phase out to generate destructive interference. This oscillation between constructive and destructive interference causes a beat frequency. Graph 18506 shows an example of the combined result of the two currents of ESU 1 and ESU 2 having slightly different current frequencies as they act on the patient. The beat frequency envelope is shown. Having a beat frequency may result in unwanted pulses, that may be reflected in the impedance spectrum as seen by an electrosurgical unit. This is reflected in graph 18508. The beat frequency may create a degree of unwanted impedance pulses that may inhibit the effectiveness of one or both of the instruments at periodic times according to the beat frequency.

The impedance deviation at the beat frequency, as seen by ESU1 and ESU2 may reflect the degree of coupling between the two instruments. If the impedance deviation at the beat frequency is low, such as ±10 ohms, this may be considered low coupling between the two instruments. On the other hand, if the impedance deviation at the beat frequency is more drastic, such as ±50 ohms, this may be considered to be high coupling, as an example. Graph 18510 represents qualitatively the impedance graph resulting from a beat frequency with low coupling, as represented by the minimal impedance deviation at the beat frequency. Graph 18512 represents qualitatively the impedance graph resulting from a beat frequency with high coupling, as represented by the more drastic impedance deviation at the beat frequency. High coupling may be considered more undesirable, as the impedance deviation at the beat frequency causes more unintended interference with the surgical procedure. It is therefore desirable to develop methods for adjusting for unwanted effects of simultaneous activation of electrosurgical instruments on a patient.

Referring to FIG. 152, the example logic diagram of a process depicting a control program or a logic configuration as shown provides a high level algorithm that may be performed by a system including one or more generators and a control circuit in communication with two ESUs, in accordance with at least one aspect of the present disclosure. The example logic diagram may describe what measures can be taken when coupling between two instruments is identified. Two ESUs having slightly different frequencies may be powered 18520 on, and thus the energy outputs may produce two different frequencies. When turned on simultaneously, this creates a beat frequency as described above. A control circuit may measure 18522 the beat frequency by measuring the impedance as seen by one of the ESUs. The impedance may be reflective of the beat frequency, whether it is low or it is high. This is the measure of coupling between the two instruments.

The control circuit may determine 18524 if the coupling exceeds a predetermined threshold, signaling that the coupling is too high. If it is not too high, then the control circuit may allow 18526 operation to continue. In some aspects, the control circuit may allow 18528 operation to continue with encryption in place, such as including an encryption measure to require additional security measures to be overcome in order to provide any change in operation settings between the two instruments.

On the other hand, if the coupling is too high, then a number of measures may be taken, either singly or in combination. For example, an alert may be provided 18530 to a user of the instruments. The control circuit may send a message to a hub that is in communication with both of the ESUs, and any combination of flashing lights, audible sounds, and messages across a reading panel may occur that informs the operator(s) that there is coupling between the instruments that is too high. The control circuit may limit 18532 the available modes between one or both of the instruments that takes into account the high coupling. There still may be some operations that are still acceptable with this problem present, such as utilizing other instruments that are not as dangerous or that are not affected by the presence of impedance at the beat frequency. Another adjustment can include 18534 reducing the power output of one or both of the instruments. While the frequencies may remain the same, the effect of the coupling between instruments may be reduced with a lower power output. Lastly, if the coupling is too severe, the control circuit may simply prevent 18536 operation of one or both of the instruments.

Referring to FIG. 153, shown is a high level logic diagram of a process depicting a control program or a logic configuration for what a control circuit may analyze through when operations may call for simultaneous operation of two instruments, in accordance with at least one aspect of the present disclosure. The logic diagram in FIG. 123 includes the discussion of determining coupling as described in FIGS. 151 and 152. Initially, a control circuit or other processor determines 18540 whether simultaneous activation of two ESUs is desired. This may be based on an entry of what kind of surgical procedure is going to be conducted, where some procedures call for the use of simultaneous instruments. At other times, the constraints of a new kind of procedure may be entered that include the use of instruments simultaneously. If there is no simultaneous activity needed, then operation proceeds 18542 normally.

If on the other hand, simultaneous activation is called for, then there may be several possibilities of actions to take in order to account for any coupling between the two devices. For example, without even accounting for the presence of coupling or to what degree, a control circuit may allow 18544 only a certain set of output mode combinations. These may be specified only to those that would not be affected by coupling or would not cause any coupling. The control circuit may instead limit 18546 the output power of each ESU to a reduced amount, say to half of their normal limits. This may offset or mitigate any effects of coupling such that the impedance measured by either ESU has a low impact. In some aspects, the control circuit may adjust 18548 the current output for one or both of the ESUs based on the amount of coupling between the ESUs. Some additional example details for how this may be conducted is described more in FIG. 154.

Continuing on, in some aspects, if simultaneous activation is desired, the control circuit may limit 18550 total activation time based on the degree or amount of coupling present between the ESUs. Some additional example details are described for this in FIG. 155. In some aspects, the control circuit may adjust 18552 the output of one or both of the ESUs based on the activation time of one or both of the ESUs based on the amount of coupling between the ESUs. Some additional example details for how this may be manifested are described in FIG. 156.

Referring to FIG. 154, shown is a more detailed logic diagram of a process depicting a control program or a logic configuration for how a control circuit may adjust the output between two ESUs to account for simultaneous activation of the two ESUs, in accordance with at least one aspect of the present disclosure. This may be an extension of the control circuit adjusting 18548 the current output for one or both of the ESUs based on the amount of coupling between the ESUs as described with reference to FIG. 153. The control circuit may start out by detecting 18560 any coupling between the two ESUs. The ways to detect the coupling may be consistent with those described in FIGS. 151 and 152. The control circuit may determine 18564 if the detected coupling exceeds a predetermined threshold, signaling that the coupling is too high. If it is not, then it may not be necessary to make any changes, and so no change to the output is performed 18566. On the other hand, if the coupling is too high, then the control circuit may adjust 18568 the output of one or both of the ESUs. This adjustment may be in proportion to how far off the coupling is from an acceptable range. The changes in the output may be based on a function reflecting proportional amounts of change in the output relative to a ratio of how high the coupling is compared to an acceptable range. In other cases, the output may be changed based on a lookup table or series of charts that may divide the severity of the coupling into multiple tiers.

Referring to FIG. 155, shown is a more detailed logic diagram of a process depicting a control program or a logic configuration for how a control circuit may adjust the activation time of one or more ESUs to account for simultaneous activation of the two ESUs, in accordance with at least one aspect of the present disclosure. This may be an extension of the function of the control circuit limiting 18550 total activation time based on the degree or amount of coupling present between the ESUs as described with reference to FIG. 123. The control circuit may start out by detecting 18580 any coupling between the two ESUs. The ways to detect the coupling may be consistent with those described in FIGS. 151 and 152. The control circuit may determine 18584 if the detected coupling exceeds a predetermined threshold, signaling that the coupling is too high. If it is not, then it may not be necessary to make any changes, and so no time limit may need to be placed 18586 on the activation of the ESUs. On the other hand, if the coupling is too high, then the control circuit may limit 18588 the activation time of one or both of the ESUs. The control circuit may activate a timer that leads to deactivating one or both of the ESUs after it expires. The amount of the activation time may be proportional to the severity of the coupling, in accordance with at least one aspect of the present disclosure.

Referring to FIG. 156, shown is a more detailed logic diagram of a process depicting a control program or a logic configuration for how a control circuit may adjust the output of one or more ESUs based on current activation time to account for simultaneous activation of the two ESUs, in accordance with at least one aspect of the present disclosure. This may be an extension of the function of the control circuit adjusting 18552 the output of one or both of the ESUs based on the activation time of one or both of the ESUs based on the amount of coupling between the ESUs as described with reference to FIG. 153. As a precursor, the control circuit may start out by detecting any coupling between the two ESUs. The ways to detect the coupling may be consistent with those described in FIGS. 151 and 152. The control circuit may then detect 18600 the strength of the coupling, which may be tied to the magnitude of the impedance deviation at the beat frequency and methods may be consistent with those described in FIGS. 151 and 152. The control circuit may also monitor 18602 the total activation time. The control circuit may determine 18604 if the output has been on for too long, based on the total activation time reading 18602 and in relation to the strength of the coupling 18600. The amount of activation time permissible may depend on the strength of the coupling. A look up table may guide how long the activation time should go, based on different coupling measurements. In other cases, the control circuit may respond to a function that interrelates the strength of coupling with the activation time. If the output has not gone on too long, then it may not be necessary to make any changes yet, and so no changes may be yet needed 18606. On the other hand, if it has been too long, then the control circuit may direct 18608 an adjustment to one or more of the ESUs. The adjustment can include simply turning off one or both the ESUs, or may include throttling down the power to one or both. In other cases, the functionality of one or both of the ESUs may be limited.

In some aspects, methods are also presented for correcting the outputs between two ESUs by synchronizing the frequencies and/or phase differences to one another. In some cases, while making automatic adjustments in the presence of coupling, as described in FIGS. 151-156, the control circuit may also be configured to tune one of the instruments to the other instrument, in an effort to simply eliminate the coupling that is previously observed. Referring to FIG. 157, shown are some graphs that conceptually illustrate what synchronizing corrections should respond to. Graph 18620 shows a waveform of measured impedance between two ESUs, as observed by one of the ESUs. The x-axis may represent the difference between current frequencies of the two ESUs, while the y-axis may represent the impedance value. The offset of the y-axis may represent a phase difference between the two current waveforms.

Graphs 18622 and 18624 illustrate examples of frequency differences to be synchronized, in accordance with at least one aspect of the present disclosure. Graph 18622 shows a large difference between two frequency current outputs, where the period in the graph is small (i.e., the frequency is larger). In contrast, the graph 18624 shows a small difference between the two frequency current outputs, where the graph is more gradual and the period is much larger. These are consistent with a lower beat frequency and a higher beat frequency, respectively.

Graphs 18626 and 18628 show examples of differences in phase that may also need to be corrected. Here, both graphs are flat lines, eliminating the beat frequency component, or in other words illustrating that the frequencies are the same between the two outputs. All that remains is a non-zero constant impedance. However, even in the absence of a beat frequency component, a phase difference may exist between the two outputs. In graph 18628, the phase difference is higher, as reflected by a lower impedance value. In graph 18626, the phase difference is not as drastic, as reflected by a higher impedance value resulting from less coupling between the two ESU outputs. In general, aspects of the present disclosure include methods for measuring these differences between two ESUs and then making adjustments to synchronize the frequencies and phase of the two current outputs.

Referring to FIG. 158, shown are logic diagrams of a process depicting a control program or a logic configuration for reflecting how a control circuit may synchronize frequencies between two ESUs, in accordance with at least one aspect of the present disclosure. Here, only one ESU will be adjusted, as the first ESU 1 will remain a constant 18640. ESU 2 will be adjusted consistent with logic diagram lowchart 18642. Initially, ESU 2 will begin with transmitting 18644 output energy at a default frequency. This frequency may be whatever the preconfigured setting is for the instrument, and it may happen to be similar but not identical to the frequency of ESU 1. The impedance oscillation frequency may be measured 18646, which may represent the difference in frequency between ESU 1 and ESU 2. This may be consistent with the beat frequency and impedance described in FIGS. 151 and 152. The control circuit may determine 18650 if the frequency difference, or the oscillation frequency, is low enough. This may be based on a comparison to a predefined threshold. If the oscillation frequency is low enough, then the output may continue 18648 at the current frequency. The process may repeat 18646 continually. On the other hand, if the oscillation frequency is measured to be too high and in need of adjustment, the control circuit may send 18652 an instruction to adjust the frequency of ESU 2. The adjustment may be to change the frequency equal to the difference in the frequency between ESU 2 and ESU 1.

Referring to FIG. 159, shown are logic diagrams of a process depicting a control program or a logic configuration for reflecting how a control circuit may synchronize the phases between two ESUs, in accordance with at least one aspect of the present disclosure. Here, only one ESU will be adjusted, as the first ESU 1 will remain a constant 18660. ESU 2 will be adjusted consistent with the logic diagram 18662. Initially, ESU 2 may begin 18664 with transmitting output energy at a default frequency, or in some cases starting the frequency at the last setting from FIG. 158. Magnitude of impedance as observed by ESU 2 may be measured 18666, which may represent the phase difference between ESU 1 and ESU 2. The control circuit may determine 18670 if the impedance measured is high enough. This may be based on a comparison to a predefined threshold. If the impedance is high enough, then the output may continue 18668 at the current phase. The process may repeat 18666 continually. On the other hand, if the impedance is measured to be too low and in need of adjustment, the control circuit may send 18672 an instruction to adjust the phase of the output of ESU 2. The adjustment may be to shift the phase proportional to the impedance value as seen by ESU 2, rather than merely try to change the absolute setting of the phase of ESU 2.

Referring to FIGS. 160A-160D, shown are example configurations for how two instruments, ESU 1 and ESU 2, may be interrelated to participate in a simultaneous operation on a patient and be in position to be compared against one another for synchronization. For example, in diagram 18680 of FIG. 160A, an overall system may designate ESU 1 as a master instrument, and ESU 2 may be designated as the slave instrument. Therefore, ESU 2 will be designated to match up to ESU 1 during synchronization. As another example, in diagram 18682 of FIG. 160B, the system may have ESU 1 and ESU 2 in dual roles to allow for reciprocal synchronization between the two. That is, either can be set to default, while the other will be adjusted accordingly. In other cases, both devices may be adjusted incrementally in relation to the other.

Figure 160A:
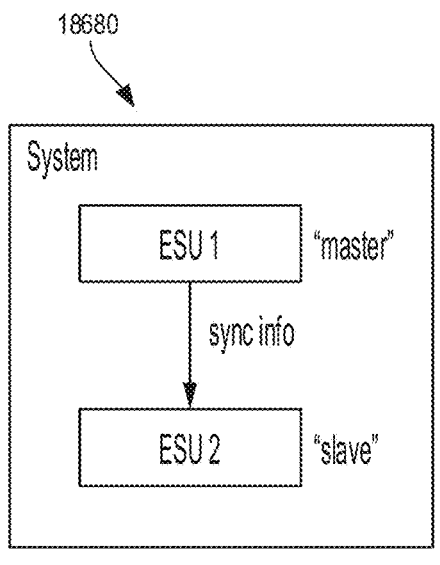
Figure 160B:
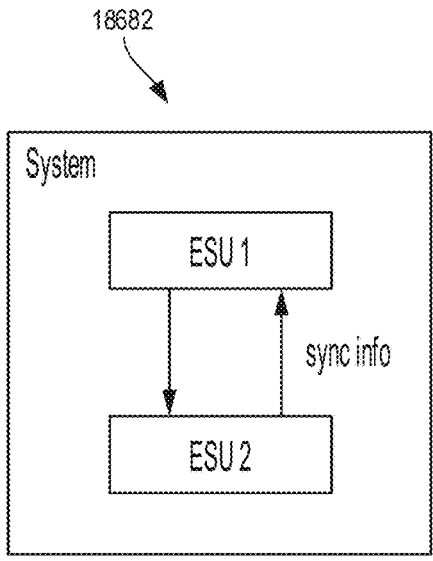
Figure 160C:
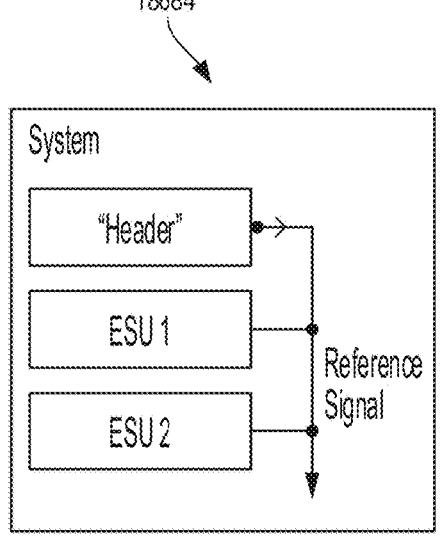

As another example, diagram 18684 of FIG. 160C shows how a header module may control both devices ESU 1 and ESU 2 through a common reference signal. In this case, the control circuit may reside in the header module. The reference signal may be sent from the header module to either ESU 1 or ESU 2 in whatever may be deemed an appropriate manner for adjustment. The header module may designate ESU 1 to remain constant, while ESU 2 is adjusted, for example, or vice versa. The header module may receive feedback through an output feedback port, or a return path of the reference signal, in order to determine what adjustments to make.

Figure 160D:
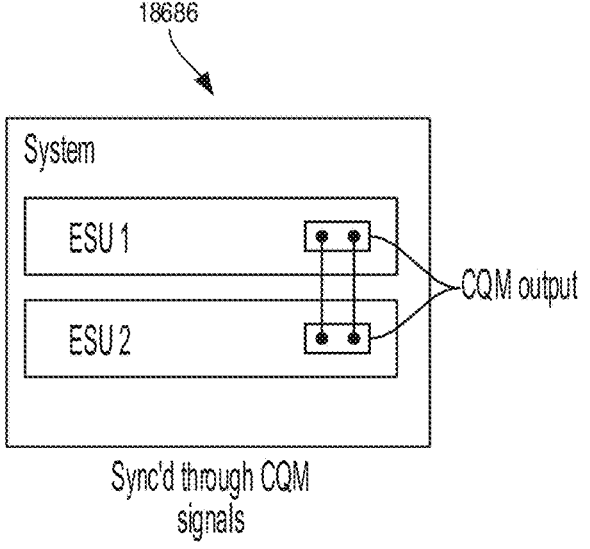

As another example, diagram 18686 of FIG. 160D shows how contact quality monitoring (CQM) may be used to synchronize between ESU 1 and ESU 2. The diagram shows signal lines between both ESU 1 and ESU 2, as well as leading to a CQM output. The CQM module may receive outputs from both ESU 1 and ESU 2 and from that may be able to determine what adjustments should be made. A signal line leading back to both ESU 1 and ESU 2 can be used to transmit instructions to both ESU 1 and ESU 2 for adjusting the output. In all of these examples of FIGS. 77A-77D, the kinds of adjustments and how they are determined may be consistent with any of FIGS. 151-159.

Referring to FIG. 161, in some aspects, an alternative adjustment for handing simultaneous outputs may include sending both signals through a duty cycle schedule. Rather than adjust the waveforms of the instruments, the outputs may be quickly alternated, such that each output appears to transmit nearly continuously but in reality transmits intermittently in alternating fashion. Graph 18700 shows simultaneous outputs 18702 and 18704 of two electrosurgical units, ESU 1 and ESU 2, respectively, over time. As previously discussed, simultaneous transmission of the outputs can create unintended side effects, which should be avoided or mitigated. As shown in graph 18706, the outputs of ESU 1 and ESU 2 may be quickly alternated, as shown in the waveforms 18708 and 18710. The alternating intervals may be short enough so as to not be perceived as switching by the tissue of the user. In order to counteract the drop in time applied, the output may be doubled within each interval. This may allow enough energy to be concentrated into short bursts during each interval to make the user perceive that the treatment is still effectively the same. In this way, there are no side effects from literal simultaneous action, while the effective treatment as experienced by the body of the patient may be essentially the same.

Referring to FIG. 162, shown is a variant of the duty cycle methodology that includes transmitting pulsed outputs in alternating fashion, in accordance with at least one aspect of the present disclosure. In some cases, the output of the ESUs may be suitable to be in the form of pulses, in which case scheduling their transmissions using duty cycling may be an appropriate remedy to addressing the simultaneous output problem. As shown in graph 18720, pulses 18722 from a first ESU are expressed in the graph of ESU output over time, and are alternated with pulses 18724 from a second ESU. As shown, only one ESU pulse is emitted at a time. Each ESU output may be equivalent to a single ESU pulse case, such that there is no simultaneous transmission. As shown, this may represent an example output of pulses for a "spray coagulation" operation, as one example.

Referring to FIG. 163, shown is a logic diagram of a process depicting a control program or a logic configuration that expresses the methodology for performing duty cycling as a way to address simultaneous operation of two or more instruments, in accordance with at least one aspect of the present disclosure. This may be consistent with the concepts described in FIGS. 161 and 162. A control circuit may be used to determine 18740 if simultaneous operation of a second ESU along with a first ESU is desired. This may be based on an inputted program that is used to govern a wider surgical operation. In other cases, a user may simply input a setting to signal that simultaneous operation is needed. If it is not needed, then operation may continue 18742 as normal. If it is needed, however, then the power output for both instruments may be doubled 18744 and then the outputs of both instruments may be duty cycled 18746 to 50% each. The intervals of each instrument may be specified by the control circuit, to determine how long each instrument should transmit its energy. This may be based on a user specification, while in other cases it may be based on situational awareness and past historical analysis. The cycle may repeat to determine 18740 if simultaneous operation of a second ESU along with a first ESU is desired until the user or the program specifies that simultaneous operation is no longer needed.

Referring to FIG. 164, shown is a more complex logic diagram of a process depicting a control program or a logic configuration for how a control circuit may conduct duty cycling to address simultaneous energy outputs of two or more electrosurgical units, in accordance with at least one aspect of the present disclosure. The control circuit may take into account multiple factors before determining an appropriate duty cycle schedule. The control circuit may measure 18760 an amount of coupling between two ESUs when they are transmitting simultaneously. The methods for measuring the coupling may be consistent with any of those described in FIGS. 161-162. In addition, the control circuit may obtain 18762 energy output settings of both ESU 1 and ESU 2. These may include the magnitude of the energy, and if that energy level should change over a period of time. These may be specified by a user or a program that defines the parameters for performing an operation on the patient. Furthermore, the control circuit may obtain 18764 parameters for total activation time of the two instruments. This may help define the boundaries of a duty cycle schedule. Last, the control circuit may also obtain 18766 settings for energy delivery, such as if the energy should be shaped in a series of pulses or if the energy should be transmitted in a steady manner.

The control circuit may combine 18768 all of these factors to determine a duty cycle limitation, constrained by a schedule defining how long and how frequently to alternate the outputs. The schedule may reflect what types of energy delivery is to be used, how long the schedule should occur, what is the energy output level (e.g., double what is the original power settings), and even if it is appropriate for duty cycling to be used. The limitations of the duty cycling may be based on how long alternating the outputs can be maintained while still achieving the desired performance. This may include how long the patient tissue can withstand a double output power of each instrument in short intervals. The limitations may also include conditional limits, such as whether a certain amount of impedance is ever reached at the target surgical sites, due to the increased power or prolonged level of using duty cycling.

The control circuit may continually monitor 18770 whether a duty cycle limitation is ever reached, or is approaching the limit. The operation may continue 18772 as is if no limits are reached. However, if the limit is reached or is approaching, the methodology may take some measures to account for this. The control circuit may stop activation 18774 of the duty cycled outputs. An alert may be provided 18776 in an audible or visible manner or in some combination. A warning may be provided 18778 to the user, but activation may continue. This may be appropriate when some form of soft limits are set, such as an intermittent time limit that serves as a signal to check on the conditions but does not require operation to cease, for example. The user then has a cue to perform an inspection before deciding to cease operation. The duty cycle limit may be adjusted 18780 in some cases. As an example, if the limit is reached and there is no discernible issue, the limit may be extended or expanded. The time limit that is reached may be extended, or an impedance limit that is reached can be increased. In other cases, the user may simply wait a period of time before proceeding, in order to wait for conditions to subside. The control circuit may adjust 18782 the energy output based on the limit being reached. The energy output may be reduced to avoid the limit again, for example.

Referring to FIG. 165, in some aspects, a system for handling simultaneous activation of instruments may include a return pad and system in the event the two instruments are part of a monopolar system. As shown in FIG. 165, in some aspects, the system 18800 may include a housing to support a first ESU 18802 (ESU 1) and a second ESU 18804 (ESU 2). These may be monopolar surgical units, including a first lead 18808 connected to the first ESU 18802, and a second lead 18806 connected to the second ESU 18804. In addition, a single return pad 18810 is configured to touch the patient, with a splitter line going back to both the first and second ESUs 18802 and 18804. The methods described above for mitigation and adjusting, and for performing either synchronization or duty cycling may applied to this configuration.

Referring to FIGS. 166A and 166B, in some aspects, the system may include a contact quality monitoring (CQM) configuration to not only perform CQM but to also be used in providing an interface between the two ESUs for use in coordinating simultaneous activation, consistent with the descriptions above involving CQM. Shown in FIG. 166A is a typical CQM setup, using two pads on one area 18820 connected to one ESU 18822. However, to handle simultaneous activation of two instruments, in some aspects, as shown in FIG. 166B, the system 18824 may house the two ESUs 18826 and 18828 which may be connected to two different pads 18830 and 18832, respectively. Each of the pads may have two conductive pads in place, so that the impedance between both pairs may be measured for performing CQM. Normal CQM may be performed within each pad 18830 and 18832, but an additional dimension of CQM between the two overall pads may also be facilitated that measures the degree of separation between the two overall pads. One or more larger pads may be placed underneath the patient and may be connected back to the ESUs 18826 and 18828, like what is shown in FIG. 165, to complete the circuit.

Referring to FIG. 167, shown is an example methodology for utilizing one or more return pads to handle simultaneous activation of monopolar electrosurgical instruments, in accordance with at least one aspect of the present disclosure. This logic diagram of a process depicting a control program or a logic configuration may be consistent with the descriptions in FIGS. 165 and 166A and 166B, as well as handling simultaneous activation of two electrosurgical units according to the descriptions in FIGS. 151-164. Initially, a control circuit connected to a return pad may determine 18684 whether simultaneous activation of two monopolar instruments is desired. If not, the operation of a single monopolar instrument and system may proceed 18842 as normal. If it is desired, however, then the control circuit may check 18844 whether a suitable return pad is connected to both ESUs. An example of this is shown in FIG. 165. The control circuit may need to determine 18850 if the return pad is of a type suitable for handling both monopolar instruments. This may be based on obtaining a device ID of the return pad, where only a certain set of IDs are certified to be acceptable return pads in this context, as one example. The control circuit also may determine 18852 if the pad is connected to both ESUs. The control circuit may obtain readings of the return pad from both ESU paths to check, for example.

If the setup is appropriate, then the control circuit may permit 18846 simultaneous activation of the monopolar instruments. In some aspects, the control circuit may still limit 18848 the simultaneous activation by placing restrictions on the instrument operations. This may be appropriate in cases where two monopolar instruments are not normally configured for simultaneous operation, so some of the functionality may need to be restricted. This may include limiting some functionality of one or both instruments, and/or limiting the maximum power output of one or both of the instruments. Other limitations consistent with adjusting to simultaneous operation, as described in FIGS. 161-164, may also be relevant here.

On the other hand, if the return pad is not functioning properly or is not suitable for simultaneous operation, then certain measures may be taken. The control circuit may prevent 18854 operation of either of the monopolar instruments from occurring. The setup of the return pad will then need to be reconfigured before operation can continue. In some cases, some functionality may be permissible 18856 while other restrictions are placed. Some simple actions may be permissible, but the use of the electrosurgical energy, particularly as a simultaneous operation with the other instrument, may not be permitted, for example. An alert also may be delivered 18858, signaling that the patient is at high risk for burns, for example.

Device Detection Upon Insertion to Port

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, the system described in U.S. Provisional Patent Application No. 62/826,588, titled MODULAR ENERGY SYSTEM INSTRUMENT COMMUNICATION TECHNIQUES, filed on Mar. 29, 2019, addresses the consumer need for the consolidation of capital equipment and other surgical technology, a decrease in equipment footprint within the OR, a streamlined equipment interface, and a more efficient surgical procedure by which the number of devices that surgical staff members need to interact with is reduced.

However, as electrosurgical and/or ultrasonic surgical systems become more modular and capital equipment becomes increasingly more streamlined, the number of ports by which various pieces of equipment can be connected is decreasing. Additionally, each port is required to accommodate a variety of different types of equipment. Thus, there exists an even greater need for surgical systems that automatically detect, identify, and manage auxiliary equipment upon connection to a hub. Accordingly, in various non-limiting aspects of the present disclosure, apparatuses are provided for detecting an instrument's presence on monopolar and bipolar energy ports of electrosurgical generators.

In various aspects, the present disclosure provides a modular energy system 2000 (FIGS. 24-30) comprising a variety of different modules 2001 that are connectable together in a stacked configuration. The modules 2001 of the modular energy system 2000 can include, for example, a header module 2002 (which can include a display screen 2006), an energy module 2004, a technology module 2040, and a visualization module 2042. Energy modules 3004 (FIG. 34), 3012 (FIG. 35), and 3270 (FIG. 37) illustrate the energy module 2004 with more particularity. Accordingly, for conciseness and clarity of disclosure, reference herein to the energy module 2004 should be understood to be a reference to any one of the energy modules 3004 (FIG. 34), 3012 (FIG. 35), and 3270 (FIG. 37). An example of a communication protocol is described in commonly owned U.S. Pat. No. 9,226,766, which is herein incorporated by reference in its entirety.

It will be appreciated that the energy module 2004 may include a variety of electrosurgical/ultrasonic generators that need to be able to electrically identify and communicate with a wide variety of electrosurgical/ultrasonic instruments, such as, for example, the surgical instruments 1104, 1106, 1108 shown in FIG. 22, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The energy modules 2004 and the electrosurgical/ultrasonic instruments 1104, 1106, 1108 may have vastly different communication needs in terms of such things as data bandwidth, latency, circuit cost, power requirements, cybersecurity robustness, and noise immunity. Accordingly, there is a need for the modular energy system 2000, and in particular the energy modules 2004 of the modular energy system 2000, to support multiple communication protocols. At the same time, ergonomic and cost concerns dictate that the total number of conductors in an electrosurgical/ultrasonic instrument cable be kept to a minimum.

In various general aspects, the present disclosure provides a modular energy system with multiple separate modules and a header that automatically detects the presence of a device inserted into a port. In one aspect, the energy module may store actual and/or default device settings are temporarily within the modular energy system so that they automatically follow the device to additional ports if it is unplugged and re-inserted to a different port. In one aspect, an alert message may be provided to notify a user that a device has been reinserted and the default settings for the device are different than the last used settings. This functionality may be enabled by providing communication protocols, data storage, instrument tracking, and device detection functionality in the modular energy system. In another aspect, the device user preferences may be uploaded into the modular energy system, and device settings may be populated based on user preference data automatically when the device is detected in a port. Accordingly, in one general aspect, the present disclosure provides an energy module comprising a control circuit, a port, a sensor coupled to the port and the control circuit, and an interface circuit coupled to the port, the sensor, and the control circuit, wherein the sensor is configured to detect presence of a surgical instrument coupled to the port. Various example implementations of such detection circuits and techniques are described hereinbelow.

Referring to FIG. 168, various ports of an energy module 19000 component of a modular energy system 2000 (FIGS. 24-30) where the energy module 19000 is configured to detect presence of a connector are illustrated in accordance with at least one non-limiting aspect of the present disclosure. In various aspects, the energy module 19000 comprises optical sensing ports 19001, mechanical ports 19002, and force sensing ports 19003. In some non-limiting aspects, the energy module 19000 may be configured for either monopolar, bipolar electrosurgery, ultrasonic surgery, or combinations thereof. The various presence detecting ports disclosed below may vary in configuration depending on whether the energy module 19000 is configured for monopolar or bipolar electrosurgery, and both configurations are contemplated by the present disclosure. For example, in one non-limiting aspect, the energy module 19000 includes ports that are universally configured for both monopolar and bipolar instruments. In other non-limiting aspects, the energy module 19000 includes ports that are exclusively configured for either monopolar or bipolar instruments. Still other non-limiting aspects include a combination of ports exclusively configured for monopolar instruments and ports exclusively configured for bipolar instruments. All of the ports depicted in FIG. 168 are configured to mechanically and/or electrically engage with an instrument plug to facilitate the electrical connection of an instrument to the energy module 19000, and include varying sensor configurations—which will be discussed in detail below—to detect the presence of the instrument plug, identify the specific type of instrument, and manage it accordingly.

In some non-limiting aspects of the present disclosure, data associated with a specific instrument might be stored on a data storage device in communication with the energy module 19000. For example, the data storage device in communication with the energy module 19000 can be volatile including various forms of random access memory (RAM), or non-volatile including a mechanical hard drive, a solid-state hard drive, a programmable read-only memory (PROM), an erasable programmable read-only memory (EPROM), or an electrically erasable programmable read-only memory (EEPROM). Additionally, the data storage device can be internal to the energy module 19000, or remotely located and in wireless communication with the energy module 19000, such as a cloud-based storage device. Accordingly, when an instrument is connected to a port 19001, 19002, 19003 of the energy module 19000, a control circuit of the energy module is configured to detect its presence. Upon detection, the control circuit is further configured to identify the specific instrument connected, and access the data storage device to assess whether any data associated with the specific instrument is available for review and management. For example, data associated with the instrument may include instrument specific settings, requirements, usage metrics, errors, and/or the like. If no data associated with the specific instrument is stored, the control circuit is further configured to create and store such data accordingly. Furthermore, the control circuit is configured to generate new data regarding the specific instrument's settings and real time usage to be stored on the data storage device and accessed in the future. The control circuit can be configured to generate such data automatically, or in response to a user's input. Accordingly, when a specific instrument is connected to a different port 19001, 19002, 19003 of the energy module 19000, the control circuit will identify it, access the data associated with the instrument, communicate to the user that it has been reconnected, and alert the user that different settings should be applied prior to use. In some aspects, the control circuit might be further configured to automatically adjust the settings in accordance with the data associated with the instrument. In still further aspects, the control circuit communicates an error message to the user if a required piece of equipment is not properly connected, or presents data associated with the historical use of the instrument to the user. In still another aspect, the data storage device is remotely located, enabling similar functionality to be applied to multiple energy modules 19000 with access to the data storage device. Thus, the same instruments to be used across an entire hospital or region, with the control circuits automatically accessing the specific settings, requirements, and usage metrics upon detection and identification of the instrument.

Referring now to FIG. 169, a perspective view of an optical sensing port 19001 is depicted in accordance with at least one non-limiting aspect of the present disclosure. Here, the energy module 19000 of FIG. 169 is an energy module 19004. The optical sensing port 19001 of FIG. 169 has a thru-beam configuration including at least one pair of break-beam sensors 19005. According to the thru-beam configuration of FIG. 169, the pair of break-beam sensors 19005 include an emitter 19006 and a receiver 19007. However, other non-limiting aspects of the thru-beam configuration 19004 may include alternate break-beam sensors 19005, such as photoelectric sensors, lasers, proximity sensors, and/or the like. The emitter 19006 is configured to transmit a beam of energy 19008, and the receiver 19007 is configured to receive the beam of energy 19008. Although the thru-beam configuration 19002 of FIG. 171 includes beam of energy 19008 of infrared wavelength (e.g. 700 nanometers to 1 millimeter), other non-limiting aspects may use a beam of energy 19008 of alternate wavelengths as preferred. For example, alternate wavelengths may include ultrasonic, microwave, both short and long-wave radio frequencies, and/or the like.

In further reference to the non-limiting aspect of FIG. 169, the optical sensing port 19001 further includes one or more electrical contacts 19009, which may be arranged to accommodate a variety of different instrument plug configurations and establish an electrical connection between a circuit card of the energy module 19004 and an instrument. When an instrument is plugged into the optical sensing port 19001, its presence is detected based on the resulting interference of the beam of energy 19008. For example, when an instrument is connected to the optical sensing port 19001, the instrument plug interferes with the beam of energy 19007, thereby preventing the receiver 19007 from receiving the beam of energy 19008. Thus, when a control circuit of the energy module 19000 (as depicted in FIG. 168) initiates the emission of a beam of energy 19008 from the emitter 19005 and does not subsequently receive the beam of energy 19008 via the receiver 19006, it detects the presence of the instrument plug and reacts accordingly.

Optical sensing ports 19001 may further include various means for port illumination and identification. For example, the optical sensing port 19001 of FIG. 169 includes one or more light emitting diodes (LEDs) 19010, and a light pipe 19011. Aside from illuminating the port, the LED 19010 and light pipe 19011 configuration may emit various colors that identify the port and provide a visual status of the connection. For example, in the non-limiting aspect of an energy module 19004 of FIG. 177, the LED's 19010 and light tubes 19011 can be illuminated a particular color to communicate which port is active when multiple instruments are plugged into the energy module 19004 at the same time. Additionally, the LED's 19010 and light tubes 19011 can be lit one or more colors to indicate to the user that an error exists in association with the instrument connected to each port 19001. For example, if a user forgot to connect a grounding pad, the LED's 19010 and light tube 19011 might illuminate red, indicating that a required instrument has not been connected to the electrosurgical Referring now to FIG. 170, the optical sensing port 19001 of FIG. 169 is depicted in top view. In FIG. 170, a monopolar instrument plug 19012 is connected to the optical sensing port 19001 of FIG. 170. However, in other non-limiting aspects, the optical sensing port 19001 is further configured to accommodate a bipolar instrument plug. The monopolar instrument plug 19012 is inserted into the exterior face 19013 of the energy module 19004, and prongs 19014 of the monopolar instrument plug 19012 traverse through the port interface and engage the electrical contacts 19009, thereby establishing an electrical connection between the instrument and a control circuit of the energy module 19004. When the monopolar instrument plug 19012 is properly connected to the energy module 19004, the prongs 19014 of the monopolar instrument plug 19012 traverse an interior plane 19015 of the energy module 19004 on which the pair of break-beam sensors 19005 is mounted and exist in a beam path between the emitter 19006 and the receiver 19007. In FIG. 170, the emitter 19006 has initiated the emission of a beam of energy 19008. However, because the prongs 19014 of the monopolar instrument plug 19012 exist in the beam path between the emitter 19006 and the receiver 19007, they create a mechanical interference of the beam of energy 19008. Thus, the receiver 19007 does not receive the beam of energy 19008, and the energy module 19004 detects the presence of the monopolar instrument plug 19012.

Alternate thru-beam configurations of an optical sensing port 19001 may include two or more pairs of break-beam sensors to detect and identify different types of instrument plugs. For example, FIG. 171 illustrates another non-limiting aspect of an optical sensing port 19001 with two pairs of break-beam sensors in front view. Here, the optical sensing port 19001 includes a first emitter 19016 and a first receiver 19017 configured in a first direction D1, and a second emitter 19018 and a second receiver 19019 configured in a second direction D2. Although first direction D1 and second direction D2 of FIG. 171 are depicted as substantially perpendicular to one another, the configuration is application specific. Accordingly, the present disclosure contemplates other non-limiting aspects of optical sensing ports 19001 that include two or more pairs of break-beam sensors in different configurations to accommodate for instrument plugs of varying designs.

In the non-limiting aspect of the optical sensing port 19001 of FIG. 171, the second emitter 19018 and second receiver 19019 are used by the control circuit of the energy module 19004 to supplement the first emitter 19016 and first receiver 19017 and to determine more information about the physical presence and particular configuration of an instrument plug connected to the optical sensing port 19001. For example, a hand or robotically controller instrument may have a different instrument plug configuration than a lap instrument, and the control circuit may use signals received from the second pair of break-beam sensors to identify that the instrument that has been connected to the energy module 19004 (as depicted in FIG. 171) is either one or the other. Thus, the second pair of break-beam sensors enhances the detection and identification of a specific type of instrument plug and/or instrument connected to the energy module 19004. Subsequent to the detection and identification, the control circuit is configured to react accordingly.

Referring now to FIG. 172, another optical sensing port 19001 is depicted in accordance with at least one non-limiting aspect of the present disclosure. The optical sensing port 19001 of FIG. 172 includes a reflective configuration instead of the thru-beam configurations depicted in FIGS. 169-171. The reflective configuration includes a photoelectric emitter 19020 and a phototransistor 19021. The optical sensing port 19001 of FIG. 172 further includes one or more electrical contacts 19009, which may be arranged to accommodate a variety of different instrument plug configurations and establish an electrical connection between a control circuit of the energy module and instrument.

Similar to the thru-beam configurations of FIGS. 169-171, the reflective configuration of FIG. 172 is used to detect the presence of an instrument plug in the optical sensing port 19001. The photoelectric emitter 19013 emits light in the form of photons and the phototransistor 19014 is activated when exposed to a beam of photons 19022. In the non-limiting aspect of a reflective configuration of FIG. 172, both the emitter 19020 and phototransistor 19021 are located on the same side of the optical sensing port 19001. A monopolar instrument plug 19012 is connected to the optical sensing port 19001. However, in other non-limiting aspects, the optical sensing port 19001 is further configured to accommodate a bipolar instrument plug. When the monopolar instrument plug 19012 is inserted into the optical sensing port 19001, prongs 19014 of the monopolar instrument plug 19012 traverse through the port interface and engage the electrical contacts 19009, thereby establishing an electrical connection between the instrument and a control circuit of the energy module 19004.

As is depicted in FIG. 172, when the monopolar instrument plug 19012 is properly connected to the optical sensing port 19001, the prongs 19014 of the monopolar instrument plug 19012 traverse an interior plane 19015 of the optical sensing port 19001 on which the photoelectric emitter 19020 and a phototransistor 19021 are mounted and exist in a beam path of the photoelectric emitter 19020. In FIG. 172, the photoelectric emitter 19020 has initiated the emission of a beam of photons 19022. When properly connected to the optical sensing port 19001, the prongs 19014 of the monopolar instrument plug 19012 exist in the beam path of the photoelectric emitter 19020, they reflect the beam of photons 19022 back towards the phototransistor 19021. When the beam of photons 19022 hit the phototransistor 19021, the phototransistor 19021 is activated and the optical sensing port 19001 detects the presence of the monopolar instrument plug 19012. Accordingly, when no monopolar instrument plug 19012 is connected, the prongs 19014 do not reflect the beam of photons 19022 emitted by photoelectric emitter 19020 and the optical sensing port 19001 recognizes that the no instrument is connected.

According to the non-limiting aspect of FIG. 172, both the emitter 19020 and phototransistor 19021 are located on the same side of the optical sensing port 19001. However, in other non-limiting aspects of the reflective configuration, a diffuse-reflective sensor phototransistor 19021 is located on the opposite side of the photoelectric emitter 19020 and is configured to sense a difference between an uninterrupted beam of photons 19022 and a beam of photons 19022 that has been diffused by the prongs 19014 of the monopolar instrument plug 19012. Furthermore, although the reflective configuration of FIG. 172 includes just one photoelectric emitter 19020 and one phototransistor 19021, alternate configurations and quantities are contemplated by the present disclosure to enhance the detection and identification of varying instruments. For example, multiple photoelectric emitters 19020 and one phototransistors 19021 can be used to accommodate for instrument plugs of varying configurations similar to the break-beam configuration of FIG. 171.

In some non-limiting aspects of the present disclosure, the aforementioned optical sensing ports 19001 of FIGS. 168-172 include printed circuit boards (PCBs) upon which the sensing components are mounted. In some non-limiting aspects, the sensors are configured to measure the aforementioned physical parameters (e.g., beam of energy, beam of photons) and output an analog signal, which may be sent to a control circuit implemented by a field programmable gate array (FPGA), discrete logic, microcontroller, microprocessor, or combinations thereof. In one aspect, the control circuit may be specifically configured to process the signal and compare it to a programmed threshold for subsequent handling by a control circuit of the energy module 19000. In other non-limiting aspects of the present disclosure, the sensors are configured to directly convert the measured parameter into a digital output (e.g., a binary signal) which is transmitted directly to the control circuit. Still other non-limiting aspects of the present disclosure include both sensors configured for analog output and signals configured for digital output. The selection of sensors is customizable and application specific.

Referring now to FIGS. 173A and 173B, a mechanical sensing port 19001 is depicted in accordance with at least one non-limiting aspect of the present disclosure. FIGS. 173A-173B illustrate a mechanical sensing port receptacle 16930 comprising a depressible switch 16934. In one aspect, with reference to FIG. 25A for context, an energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016*a*, a second monopolar port 2018*b*, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012. Any one of the ports of the ports of the port assembly 2012 may include the mechanical sensing port receptacle 16930 configured to detect the presence of a surgical instrument plugged into the energy module 2004.

In one aspect, the mechanical sensing port receptacle 16930 defining an aperture 16932 to form a socket that includes a sliding contact configuration for receiving a plug 16936 of the surgical instrument. The depressible switch 16934 is disposed within the aperture 16932. The mechanical sensing port receptacle 16930 may further include one or more electrical contacts arranged to accommodate a variety of different instrument plug configurations and establish an electrical connection between the energy module 2004 (FIGS. 24-30) and the surgical instrument. Although the mechanical sensing port receptacle 16930 of FIG. 173A is depicted as having a cylindrical configuration, other configurations are contemplated by the present disclosure to accommodate instrument plugs of various shapes and sizes. According to the non-limiting aspect of FIG. 173A, the depressible switch 16934 is embedded in an inner region of the aperture 16932 defined by the mechanical sensing port receptacle 16930 such that the depressible switch 16934 is actuated when a force F is applied to an actuator 16935 portion of the depressible switch 16934. The depressible switch 19024 is also configured to transition from an open state (unactuated) where it is in an undepressed (see FIG. 173A), to a closed state (actuated) where it is depressed (see FIG. 173B) when a force F is applied by the sliding plug 16936. The mechanical sensing port receptacle 16930 is further configured to send a binary signal to a control circuit of the energy module 2004 to indicate whether the depressible switch 16934 is in an open state or a closed state.

According to the non-limiting aspect of FIG. 173A, the depressible switch 16934 is depicted in an undepressed unactuated condition because no prong of an instrument plug 16936 is inserted within the aperture 16932 of the mechanical sensing port receptacle 16930. Thus, the depressible switch 16934 of FIG. 173A is shown in an open state and a binary signal is provided to the control circuit indicating that no instrument plug 16936 is inserted or connected to the energy module 2004 (FIGS. 24-30). FIG. 173B depicts the instrument plug 16936 inserted into the aperture 16932 of the mechanical sensing port receptacle 16930. As depicted in FIG. 173B, the plug 16936 of the surgical instrument mechanically engages the actuator 16935 of the depressible switch 16934 and applies a force F to the actuator 16935 to depress the actuator 16935 to transition the depressible switch 16934 to the closed state. Accordingly, the mechanical sensing port receptacle 16930 provides a binary signal to a control circuit of the energy module 2004 to indicate that an instrument plug 16936 is connected to the energy module 2004.

Referring now to FIGS. 174A and 174B, another mechanical sensing port 19001 is depicted in accordance with at least one non-limiting aspect of the present disclosure. FIGS. 174A-174B illustrate a mechanical sensing port receptacle 16938 comprising a push button switch 16942, in accordance with another aspect of the present disclosure. The mechanical sensing port receptacle 16938 of FIG. 174A includes a push button configuration. Similar to the sliding contact configuration of FIGS. 173A-173B, any one of the ports of the port assembly 2012 shown in FIGS. 24-30 may include the mechanical sensing port receptacle 16938 of FIGS. 174A-174B configured to detect the presence of a surgical instrument plugged into the energy module 2004 (FIGS. 24-30).

In lieu of the depressible switch 16934, the push button switch configuration includes a push button switch 16942 comprising an actuator 16944. The mechanical sensing port receptacle 16938 defines an aperture 16932 to form a socket for receiving an instrument plug 16936. According to a non-limiting aspect of the mechanical sensing port receptacle 16938 depicted in FIGS. 174A-174B, the push button switch 16942 is located distal to the mechanical sensing port receptacle 16938 such that the actuator 16944 of the push button switch 16942 is proximate a distal end of the aperture 16940. The actuator 16944 of the push button switch 16942 is configured to actuate when the distal end of the instrument plug 16936 applies a force F to the actuator 16944 causing it to transition from an open state where it is in an unde-pressed (see FIG. 174A) to a closed state where it is depressed (see FIG. 174B). The mechanical sensing port receptacle 16938 is further configured to send a binary signal to a control circuit of the energy module 2004 (FIGS. 24-30) to indicate whether the push button switch 16942 is in an open state or a closed state.

According to the non-limiting aspect of FIG. 174A, the push button switch 16942 is depicted in an undepressed unactuated condition because the instrument plug 16936 is not yet inserted within the aperture 16940 of the mechanical sensing port receptacle 16938 and thus no force F is applied to the actuator 16944. Thus, the push button switch 16942 of FIG. 174A is in an open state and the mechanical sensing port receptacle 16938 provides a binary signal to a control circuit indicating that the instrument plug 16936 is not connected to the energy module 2004 (FIGS. 24-30). Alter-natively, FIG. 174B depicts an instrument plug 16936 inserted into the aperture 16940 of the mechanical sensing port receptacle 16938. As depicted in FIG. 174B, the instru-ment plug 16936 mechanically engages and applies a force F to the actuator 16944 of the push button switch 16942 to depress and actuate the push button switch 16942, thus transitioning the push button switch 16942 to the closed state. Accordingly, the mechanical sensing port receptacle 16938 provides a binary signal to a control circuit of the energy module 2004 indicating that an instrument plug 16936 is connected to the energy module 2004.

Referring now to FIGS. 175A and 175B, another mechanical sensing port 19001 is depicted in accordance with at least one non-limiting aspect of the present disclo-sure. FIGS. 175A-175B illustrate an electrical sensing port receptacle 16946 comprising a non-contact proximity switch, in accordance with one aspect of the present disclo-sure. The electrical sensing port receptacle 16946 includes a non-contact proximity switch configuration comprising an inductive sensor 16948, for example, to provide a contact-less short-range sensing configuration for sensing conduc-tive targets such as the instrument plug 16936. The electrical sensing port receptacle 16946 defines an aperture 16950 to form a socket for receiving the instrument plug 16936. The inductive sensor 16948 of FIGS. 175A-175B is configured to sense the proximity of a metal object, such as the instrument plug 16936. The inductive sensor 16948 includes an induction loop or detector coil, such as those found in typical inductance-to-digital converter, coil magnetometers, and/or the like. When power is applied to the detector coil, an electromagnetic field 16952 is generated. As the metal instrument plug 16936 approaches the proximity of the electromagnetic field 16952, the metal instrument plug 16936 interacts with the electromagnetic field 16952 and the inductive sensor 16948 transitions from an open state, wherein the instrument plug 16936 is not inserted into the aperture 16950 of the electrical sensing port receptacle 16946, to a closed state, wherein the instrument plug 16936 is inserted into the aperture 16950 of the electrical sensing port receptacle 16946. The electrical sensing port receptacle 16946 is further configured to provide a binary signal to a control circuit of the energy module 2004 (FIGS. 24-30) to indicate whether the inductive sensor 16948 is in an open state or a closed state.

According to the non-limiting aspect of FIG. 175A, the instrument plug 16936 is not inserted within the aperture 16950 of the electrical sensing port receptacle 16946 and accordingly, does not interact with the electromagnetic field 16952. Thus, the inductive sensor 16948 of FIG. 175A is in an open state and the electrical sensing port receptacle 16946 provides a binary signal to a control circuit of the energy module 2004 (FIGS. 24-30) to indicate that the instrument plug 16936 is not connected to the energy module 2004. Alternatively, as the instrument plug 16936 is inserted into the aperture 16950 of the electrical sensing port receptacle 16946 it will interact with the electromagnetic field 16952, thus transitioning the inductive sensor 16948 to the closed state. Accordingly, the electrical sensing port receptacle 16946 provides a binary signal to the control circuit of the energy module 2004 to indicate that the instrument plug 16936 is connected to the energy source 2004. In some non-limiting aspects, the binary signal might be subsequently processed via software to mitigate the effects of noise associated with activation. Still other non-limiting aspects are configured to filter out certain radio frequency (RF) signals of to mitigate the effect of electrical noise and unintended interference with the electromagnetic field 16952.

In one aspect, the inductive sensor 16948 may be an inductance-to-digital converter LDC1000 provided by Texas Instruments. The inductance-to-digital converter is a con-tact-less short-range sensor that enables sensing of conduc-tive targets. Using a coil as a sensing element, the induc-tance-to-digital converter precise measurement of linear/angular position, displacement, motion, compression, vibration, metal composition, and many other applications.

Various combinations of aforementioned mechanical/electrical sensing port receptacles 16930, 16938, 16946 shown FIGS. 173A-175B can be used to detect and identify different types of instrument plugs. For example, two or more separate switches, including a depressible switch, a push button, and/or an inductive proximity switch, can be used to distinguish whether the instrument is a lap or hand tool is connected to the port. The mechanical/electrical sensing port receptacles 16930, 16938, 16946 then provide a signal to a control circuit of the energy module 2004 (FIGS. 24-30) indicating the specific type of instrument that is connected to the energy module 2004, and the control circuit reacts accordingly. It will be appreciated that the switches 16394, 16942 and the non-contact proximity switch described in connection with FIGS. 173A-175B may optionally be operated in a normally opened or normally closed configuration. Accordingly, although the present disclosure may describe the switches 16394, 16942 and the non-contact proximity switch as being open in their nominal state, the switches 16394, 16942 and the non-contact proximity switch may be configured as normally closed and the system could detect an open state, for example.

Referring now to FIG. 176, a force sensing port 19003 is depicted in accordance with at least one non-limiting aspect of the present disclosure. The force sensing port 19003 of FIG. 176 includes a force sensitive resistor 19030 embedded into an inner surface of the force sensing port 19003. In the non-limiting aspect of FIG. 176, the force sensitive resistor 19030 uses a resistive touch film 19031. However, other non-limiting aspects of a force sensing port 19003 according to the present disclosure include capacitive touch sensors, projected capacitive sensors, surface acoustic wave (SAW) sensors, infrared touch sensors, and/or the like. According to the force sensing port 19003 of FIG. 176, the resistive touch film 19031 includes one or more layers of film which, in an unbiased condition, are separated from an underlying electrical circuit 19032. However, the resistive touch film 19031 is moveably configured relative to the electrical circuit in response to an applied force such that the one or more layers come into contact with the underlying electrical circuit 19032, thereby altering an electrical parameter of the electrical circuit 19032. For example, the electrical parameter may be resistance, current, voltage, and/or the like. In some non-limiting aspects, the force sensitive resistor 19030 is further configured to generate a specific coordinate location of where on the resistive touch film 19031 the force was specifically applied, based at least in part on the altered electrical parameter. The force sensing port 19003 of FIG. 176 further includes one or more electrical contacts 19009, which may be arranged to accommodate a variety of different instrument plug configurations and establish an electrical connection between a control circuit of an energy module 19000 and an instrument. Although the force sensing port 19003 of FIG. 176 is rectangular, other configurations are contemplated by the present disclosure to accommodate instrument plugs of various shapes and sizes.

According to the non-limiting aspect of FIG. 176, the force sensing port 19003 is configured to detect an instrument plug when it comes into physical contact with the force sensitive resistor 19030. Specifically, when no instrument plug is connected to the force sensing port 19003, the resistive touch film 19031 is in an unbiased state and electrical parameters of the underlying electrical circuit 19032 remain unaltered. Thus, the force sensing port 19003 sends a signal to the control circuit indicating that no instrument plug is connected to the energy module 19000. Alternatively, when an instrument plug is connected to the force sensing port 19003, the instrument plug applies a force to the resistive touch film 19031 in a particular location towards the electrical circuit, thereby moving it towards the underlying electrical circuit 19032 and altering an electrical parameter. Accordingly, the force sensing port 19003 sends a signal to the control circuit indicating that an instrument plug is connected to the energy module 19000. In some non-limiting aspects, the signal includes the specific coordinate location of where on the resistive touch film 19031 the force was specifically applied.

Instruments that are connected to the energy module 19000 may vary in instrument plug size, shape, and overall configuration. For example, a hand instrument may have a different instrument plug configuration than a lap instrument. Accordingly, the force sensing port may be configured to enhance the detection and identification of a specific instrument connected to the energy module. For example, some non-limiting aspects of a force sensitive port include two or more surface regions with embedded force sensitive resistors of varying geometries, with each region configured to sense different forces applied by an instrument plug and send a discrete signal to the control circuit. Each signal is used to provide the control circuit with additional information about the geometry of the instrument plug, thereby enhancing the detection and identification of an instrument connected to the force sensing port of the energy module 19000. Still other non-limiting aspects of a force sensitive port include just one surface region with an embedded force sensitive resistor, and the force sensitive resistor is configured to generate two or more specific coordinate location which are sent as two or more discrete signals which are used to provide the control circuit with additional information about the geometry of the instrument plug, thereby enhancing the detection and identification of an instrument connected to the force sensing port of the energy module 19000.

Referring now to FIG. 177, the energy module 19000 is depicted in accordance with at least one aspect of the present disclosure. The energy module 19004 includes several force sensing ports of varying configurations and functions. Specifically, the energy module 19004 of FIG. 177 includes a force sensing port configured for bipolar instruments 19034, two force sensing ports configured for monopolar instruments 19035, a port configured for a neutral electrode return 19036, and an advanced energy combination port 19038. Each of the bipolar port 19034 and monopolar ports 19035 is configured as a force sensing port 19003 and includes a force sensitive resistor 19030 and a resistive touch film 19031. The neutral electrode return port 19036 further includes a contact configured to electrically engage and electrically erasable programmable read-only memory (EEPROM) that might be included in the connected instrument. If instrument specific EEPROM is detected, a control circuit 19033 of the energy module 19004 will read and write to the EEPROM as appropriate.

The energy module 19004 of FIG. 177 further includes an embedded LED 19010 and light pipe 19011 configuration to illuminate the port. The LEDs 19010 and light pipe 19011 may emit various colors that identify the port and provide a visual status of the connection. For example, in the non-limiting aspect of an energy module 19004 of FIG. 177, the LED's 19010 and light tubes 19011 can be illuminated a particular color to communicate which port is active when multiple instruments are plugged into the energy module 19004 at the same time. Additionally, the LED's 19010 and light tubes 19011 can be lit one or more colors to indicate to the user that an error exists in association with the instrument connected to each port 19001. For example, if a user forgot to connect a grounding pad, the LED's 19010 and light tube 19011 might illuminate red, indicating that a required instrument has not been connected to the energy module 19004. The energy module 19004 further includes a control circuit in the form of a daughter board 19033, which is in electrical communication with each of the force sensing ports 19003. Each of the force sensing ports 19003 further includes one or more electrical contacts 19009 configured to engage an instrument plug.

Referring now to FIG. 178, a logic diagram of a process depicting a control program or a logic configuration for detecting, identifying, and managing instruments connected to various ports of an energy module 19039 is depicted in accordance with at least one aspect of the present disclosure. First, the control circuit uses at least one of the ports of FIGS. 168-177 to detect that an instrument has been connected 19040. The control circuit then identifies the specific type of instrument that has been connected to the energy module based on signals received from the numerous port configurations 19041. For example, if a hand instrument or lap instrument are connected, the respective instrument connectors engage with the ports differently, thereby sending different signals to the control circuit. The control circuit then commands the energy module to display prompts on a user interface corresponding to the specific type of instrument that has been connected to the energy module 19042. Once the user follows all of the corresponding prompts, the control circuit commands the port to illuminate, thereby communicating that it is active, or inactive. If it is inactive, the lights are used to visually communicate any associated error to the user 19043. For example, the port might illuminate red if monopolar instrument is detected but no corresponding neutral electrode is detected. The control circuit then checks for the presence of any instrument specific EEPROM 19044. If instrument specific EEPROM is detected, the control circuit 19033 of the energy module 19004 will read and write to the EEPROM as appropriate. If no instrument specific EEPROM is detected, the control circuit commands energy module into a standard instrument mode 19045.

Referring now to FIGS. 179A-179E, a block diagram of a system for detecting instruments to a energy module 19000 using radio frequency identification (RFID) circuits is depicted in accordance with at least one aspect of the present disclosure. A user initiates the detection sequence via a display of a user interface 19050 of the RFID enabled energy module 19000 by selecting a pairing mode option 19051, as is depicted in FIG. 179A. Selecting the pairing mode option 19051 will transition the user interface 19050 to another display which prompts the user to pair a device, as is further depicted in FIG. 179B. According to the non-limiting aspect of FIG. 179C, an RFID circuit 19046 is affixed to an RFID enabled instrument 19047, and an RFID scanner 19048 is affixed to an RFID enabled energy module 19000. Having initiated the pairing mode, the user positions the RFID circuit 19046 affixed to the RFID enabled instrument 19047 in proximity to the RFID scanner 19048 of the RFID enabled energy module 19000, as is depicted in FIG. 179C. Additionally or alternatively, an RFID circuit 19046 could be affixed to inventory management paperwork 19049 associated with the instrument 19047, as is depicted in FIG. 179D. Accordingly, a user could initiate pairing mode and position the RFID circuit 19046 of the inventory management paperwork 19049 in proximity to the RFID scanner 19048 of the RFID enabled energy module, thereby pairing the RFID enabled instrument 19047 to the RFID enabled energy module 19000. Upon scanning the instrument 19047 or paperwork 19049 to the reader 19048 of the energy module 19004, the user interface 19050 of the RFID enabled energy module 19000 will provide a visual confirmation 19058 that the RFID enabled instrument 19047 has been successfully detected by and paired to the RFID enabled energy module 19000, as is depicted in FIG. 179E. Once the RFID enabled instrument 19047 is detected, the control circuit will subsequently identify the RFID enabled instrument 19047 and communicate any relevant messages to the user.

In some non-limiting aspects, the RFID circuits store data associated with each particular RFID enabled instrument. For example, the RFID circuits might store data associated with the instrument's use, including a number of runs performed, the amount of time the device has been used, and/or the like. Accordingly, the RFID enabled energy module might be programmed to preclude the pairing of RFID enabled instruments that have exceeded a predetermined use threshold. Further non-limiting aspects include RFID circuits include data associated with the instrument's compatibility. Accordingly, RFID enabled energy module will preclude the pairing of RFID enabled instruments that cannot, or should not, be connected via the aforementioned port configurations. Still other non-limiting aspects of an RFID enabled energy module that includes an RFID circuit within the energy module itself. For example, the RFID circuit can be used to track an energy module 19000 throughout the hospital. Similarly, other non-limiting aspects include RFID circuits that are further configured to interact with an inventory management system. For example, the RFID circuits could be used to track the utilization of each RFID enabled instrument and energy module. In such non-limiting aspects, when the number of useable instruments falls below a minimum threshold determined by the hospital, the inventory management system is configured to order more instruments.

Referring now to FIGS. 180A-180E, a block diagram of a system for detecting instruments to a energy module 19000 using a battery installation process is depicted in accordance with at least one aspect of the present disclosure. A wirelessly enabled instrument 19054 includes a wireless communication module 19052, as is depicted in FIG. 180C, and a wirelessly enabled energy module 19000 includes wireless receiver configured to receive a wireless signal. The wireless module 19052 can be configured to communicate via wireless local access network (WLAN), radio frequency (RF), Bluetooth, microwave, and/or cellular network; although other forms of wireless communication are contemplated by the present disclosure. The wirelessly enabled instrument 19054 of FIG. 180C is configured to accommodate a removable battery 19056, as is depicted in FIG. 180D. When the removable battery 19056 is installed, the wirelessly enabled instrument 19054 establishes an electrical communication with the wireless communication module 19052. For example, the instrument depicted in FIG. 180C includes a cavity in the back designed to accommodate the removable battery 19056. However, alternate configurations of the wirelessly enabled instrument 19054 and removable battery 19056 are also contemplated by the present disclosure.

As is depicted in FIG. 180A, a user initiates the detection sequence via a user interface 19050 of the wirelessly enabled energy module by selecting a pairing mode option 19051. The selection of the pairing mode option 19051 commences the process of pairing, as is further depicted in FIG. 180B. Having initiated the pairing mode, the user installs a removable battery 19056 into the cavity wirelessly enabled instrument 19054, as depicted in FIG. 180C. When the battery is installed, electrical communication is established and the wireless communication module 19052 is activated, as depicted in FIG. 180D. Once the wireless communication module 19052 is activated, it sends a wireless signal to the wireless receiver of the wirelessly enabled energy module, thereby pairing the wirelessly enabled instrument 19054. Accordingly, the user interface 19050 of the wirelessly enabled energy module will provide a visual confirmation 19058 that the wirelessly enabled instrument 19054 has been successfully detected by and paired to the wirelessly enabled energy module, as is depicted in FIG. 180E. Once the wirelessly enabled instrument 19054 is detected, the control circuit will subsequently identify the wirelessly enabled instrument 19054 and communicate any relevant messages to the user.

Referring now to FIG. 181, a circuit diagram of an electrical circuit configured to detect whether an instrument is connected to a energy module 19000 is depicted in accordance with at least one aspect of the present disclosure. According to the aspect of FIG. 181, the energy module 19000 includes a patient isolated side 19066 and a secondary side 19068. The energy module 19000 has a first port receptacle 19070 and a second port receptacle 19072, each of which are serve as the termination point of a respective half of a logic circuit. The first port receptacle 19070 and second port receptacle 19072 further constitute opposing ends of an open switch configured to receive a pin 19074 of an instrument. The circuit diagram of FIG. 181 includes a first logic gate 19078 and a second logic gate 19079. Although the logic gates 19078 depicted in the logic flow diagram of FIG. 181 are "AND gates," the present disclosure further contemplates aspects that include "OR gates," "NOT gates," "NAND gates," "NOR gates," "EOR gates," and/or the like. A first power supply 19076 is configured to provide each of the first logic gate 19078 and second logic gate 19079 with a first input that is "high" when the energy module 19000 is active. Although the first power supply 19076 depicted in FIG. 181 is 6V, the specific value can vary depending on the preferred application. A first half of the logic circuit connected to the first port receptacle 19070 includes a pull-down resistor 19080, and a power active ground 19082. A second half of the logic circuit connected to the second port receptacle 19072 includes a second power supply 19084, and a pull-up resistor 19086. Although the second power supply 19084 depicted in FIG. 181 is 12V, the specific value can vary depending on the preferred application. Both the pull up resistor 19086 and pull down resistor 19080 are each specifically configured to define a second input of each the logic gates 19078, 19079 in the absence of a driving signal. Accordingly, the specific values of the pull up resistor 19086 and pull down resistor 19080 can vary depending on the preferred application.

According to the non-limiting aspect of FIG. 181, when no instrument is connected to the energy module 19000, the switch remains open and the pull up resistor 19086 and pull down resistor 19080 both produce a second input that is "low" to each of the logic gates 19078, 19079, respectively. However, when an instrument is connected to the energy module 19000, the pin 19074 of the instrument establishes an electrical connectivity between the first port receptacle 19070 and second port receptacle 19072, thereby shorting the logic circuit and closing the switch. Once the switch is closed, the second power supply 19084 is able to provide a second input that is "high" to each of the logic gates 19078, 19079. When both the first and second input of each of the logic gates 19078, 19079 are "high," the requisite logic condition of each of the logic gates 19078, 19079 is satisfied and an output signal is sent by each of the logic gates 19078, 19079 in response. In the circuit of FIG. 181, the first logic gate 19078 sends an output signal indicating the presence of the pin 19074 to a control circuit such as a microprocessor 19090. The second logic gate 19078 sends an output signal indicating that a "cut" button of the instrument has been pressed to the microprocessor 19092. Each of the output signals are sent through an opto-isolator 19088, which is used to transfer the resulting electrical signal to the control circuit. Opto-isolators 19088 use light to transmit the signal, thus protecting the control circuit 19090 and other components of the energy module 19000 from high voltages that might adversely affect the system. However, other non-limiting aspects of the present disclosure exclude opto-isolators 19088. In response to receiving the either output signal from the opto-isolator 19088, the control circuit is configured to detect the presence of the instrument within the port, and may identify and manage it accordingly. Additionally, the circuit of FIG. 181 is further configured to detect the presence of an instrument when a "cut" button is pressed on the instrument. When a user presses a "cut" button on the instrument, a cutting voltage ($V_{CUT}$) is sent as a "high" input to the logic gate 19079 compared to the 6V provided by the first power source 19076, thereby satisfying the requisite logic condition of the logic gate 19078 and sending an output signal to the microprocessor 19092 indicating that an instrument is present.

Referring now to FIG. 182, a circuit diagram of an electrical circuit configured to detect whether an instrument is connected to a energy module 19000 is depicted in accordance with another aspect of the present disclosure. The circuit of FIG. 182 is similar to the circuit of FIG. 181, including first port receptacle 19070, a second port receptacle 19072, a first logic gate 19078, a second logic gate 19079, a first power supply 19076, a pull-down resistor 19080, a power active ground 19082, a second power supply 19084, and a pull-up resistor 19086. However, the circuit of FIG. 182 further includes a separate integrated circuit 19094 on the patient isolated side 19066 of the energy module 19000, configured to receive both output signals provided by the first logic gate 19078 and second logic gate 19079, respectively. For example, the integrated circuit 19094 can be a microprocessor, an FPGA, or an ASIC, and/or the like. The integrated circuit 19066 of the circuit of FIG. 182 is incorporated onto the patient isolated side 19066 of the energy module 19000. Accordingly, the integrated circuit can be independently receive and process signals from the first logic gate 19078 and second logic gate 19079, before they are sent for further processing by the microprocessor 19090. Therefore, the microprocessor 19090 receives a previously processed signal regarding the detection and identification of the instrument connected to the energy module 19000 and manage it accordingly.

Referring now to FIG. 183, a circuit diagram of an electrical circuit configured to detect whether an instrument is connected to a energy module 19000 is depicted in accordance with still another aspect of the present disclosure. The circuit of FIG. 183 differs from those of FIGS. 181-182 in that it includes only a first logic gate 19068, and a "cut" or "coagulate button" 19096. A first power supply 19076 is configured to provide the first logic gate 19078 with a first input that is "high" when the energy module 19000 is active. Although the first power supply 19076 depicted in FIG. 181 is 6V, the specific value can vary depending on the preferred application. Additionally, the circuit includes a second power supply 19084, and a pull-up resistor 19086. Although the second power supply 19084 depicted in FIG. 181 is 12V, the specific value can vary depending on the preferred application. The pull up resistor 19086 is specifically configured to define a second input of each the first logic gate 19078 in the absence of a driving signal. Accordingly, the specific value of the pull up resistor 19086 can vary depending on the preferred application.

According to the non-limiting aspect of FIG. 183, when the "cut" or "coagulate" button 19096 is not pressed, the switch remains open and the pull up resistor 19086 produces a second input that is "low" to the first logic gate 19078. However, when a user presses the "cut" or "coagulate" button 19096, the switch is closed. Once the switch is closed, the second power supply 19084 is able to provide a second input that is "high" to each of the logic gates 19078, 19079. When both the first and second input of each of the first logic gate 19078 is "high," the requisite logic condition of each of the first logic gate 19078 is satisfied and an output signal is sent by the first logic gate 19078 in response. In the circuit of FIG. 183, the first logic gate 19078 sends an output signal indicating that a "cut" button of the instrument has been pressed to the microprocessor 19092. The output signals are sent through an opto-isolator 19088, which is used to transfer the resulting electrical signal to the control circuit. Opto-isolators 19088 use light to transmit the signal, thus protecting the control circuit 19090 and other components of the energy module 19000 from high voltages that might adversely affect the system. However, other non-limiting aspects of the present disclosure exclude opto-isolators 19088. In response to receiving the either output signal from the opto-isolator 19088, the control circuit is configured to detect the presence of the instrument within the port, and may identify and manage it accordingly. Additionally, the circuit of FIG. 181 is further configured to detect the presence of an instrument when a "cut" button is pressed on the instrument. When a user presses a "cut" button on the instrument, a cutting voltage ($V_{CUT}$) is sent as a "high" input to the logic gate 19079 compared to the 6V provided by the first power source 19076, thereby satisfying the requisite logic condition of the logic gate 19078 and sending an output signal to the microprocessor 19092 indicating that an instrument is present.

Referring now to FIG. 184, a block diagram of a system for detecting instruments to an energy module 19004 using a wireless capital equipment key is depicted in accordance with at least one aspect of the present disclosure. According to the non-limiting aspect of FIG. 184, a wirelessly enabled instrument 19054 includes a wireless communication module 19052, and a wirelessly enabled energy module 19004 includes wireless key port 19098 into which the user may connect a wireless key 19100 configured to receive a wireless signal. The wireless key 19100 further includes with a port on its end configured to accommodate another electrosurgical instrument 19101. Thus, use of the wireless key 19100 enables the user to connect a first electrosurgical instrument wirelessly and a second electrosurgical instrument through a single port of the energy module. For example, the second electrosurgical instrument 19101 of FIG. 184 is a wired advanced energy instrument connected through the wireless key 19100. The wireless module 19052 can be configured to communicate with the wireless key 19100 via wireless local access network (WLAN), radio frequency (RF), Bluetooth, microwave, and/or cellular network; although other forms of wireless communication are contemplated by the present disclosure. The wireless key 19100 might further include an external facing port to facilitate the connection of a wired instrument. Alternatively, the wirelessly enabled energy module 19004 may include a universal serial bus (USB) port 19102 and the wireless key 19100 might include a USB dongle 19104. Thus, the user can wirelessly connect a first electrosurgical instrument through the USB port, and a second electrosurgical instrument through an instrument port of the energy module 19004.

According to the block diagram of FIG. 184, a user initiates the detection sequence by connecting the wireless key 19100 to the wireless key port 19098. Once the wireless communication module 19052 is activated, it sends a wireless signal to the wireless key 19100 connected to the wireless key port 19098 of the wirelessly enabled energy module, thereby detecting the wirelessly enabled instrument 19054. Once the wirelessly enabled instrument 19054 is detected, the control circuit will subsequently identify the wirelessly enabled instrument 19054 and communicate any relevant messages to the user.

Referring now to FIG. 185, a block diagram of a system for detecting instruments to an energy module 19004 using a wireless mesh network is depicted in accordance with at least one aspect of the present disclosure. According to the non-limiting aspect of FIG. 185, a wirelessly enabled energy module 19004 is configured to establish a wireless mesh network via a wireless router 19106. When activated, the wirelessly enabled energy module 19004 broadcasts a mesh network to ancillary wireless routers 19106 and wireless repeaters 19108, each configured to distribute the network within a wide range, thereby creating nodes. For example, wireless routers 19106 and wireless repeaters 19108 might be independently distributed throughout the OR as stand-alone devices. Alternatively, various other pieces of capital equipment might include integrated wireless routers 19106 and wireless repeaters 19108, and be configured to receive and redistribute the wireless signal received from the wirelessly enabled energy module 19004. For example, in one non-limiting aspect, the wireless routers 19106 and repeaters 19108 are integrated into the nodal instruments 19110. Thus, the system is advantageous over traditional networks, because each of the ancillary wireless routers 19106 and repeaters 19108 propagates the original signal from the central wireless router 19106 of the wirelessly enabled energy module 19004, thereby enhancing the strength received by each ancillary device and nodal instrument 19110. The resulting mesh network may be scaled while maintaining signal strength and the ability to send and receive data, due to its decentralized nature which improves the user's ability to streamline the OR.

According to the non-limiting aspect of FIG. 185, a user initiates the detection sequence by activating the wirelessly enabled energy module 19004 and thus, the wireless router 19106. Once the wireless router 19106 of the wirelessly enabled energy module 19004 is activated, it sends a wireless signal to the ancillary wireless routers 19106 and repeaters 19108, which in turn retransmit the signal to the other wireless routers 19106 and repeaters 19108, thereby creating a mesh network of surrounding nodes. When a nodal instrument 19110 receives the wireless signal from the mesh network, it communicates a confirmation signal including data associated with the nodal instrument 19110 to the wirelessly enabled energy module 19004. Non-limiting examples of data associated with the nodal instrument 19110 include information identifying the specific type of nodal instrument 19110, information identifying any specific connection requirements associated with the nodal instrument 19110, and any additional connections that are required prior to using the nodal instrument 19110. Upon receiving the confirmation signal, the wirelessly enabled energy module 19004 detects the nodal instrument 19054. Upon detection, the control circuit will subsequently identify the nodal instrument 19110 and communicate any relevant messages to the user.

Instrument Tracking Arrangement Based On Real
Time Clock Information

Before explaining various aspects of surgical devices and
generators in detail, it should be noted that the illustrative
examples are not limited in application or use to the details
of construction and arrangement of parts illustrated in the
accompanying drawings and description. The illustrative
examples may be implemented or incorporated in other
aspects, variations and modifications, and may be practiced
or carried out in various ways. Further, unless otherwise
indicated, the terms and expressions employed herein have
been chosen for the purpose of describing the illustrative
examples for the convenience of the reader and are not for
the purpose of limitation thereof. Also, it will be appreciated
that one or more of the following-described aspects, expres-
sions of aspects, and/or examples, can be combined with any
one or more of the other following-described aspects,
expressions of aspects and/or examples.

The present disclosure relates to various surgical systems,
including modular electrosurgical and/or ultrasonic surgical
systems. Operating rooms (ORs) are in need of streamlined
capital solutions because ORs are a tangled web of cords,
devices, and people due to the number of different devices
that are needed to complete each surgical procedure. This is
a reality of every OR in every market throughout the globe.
Capital equipment is a major offender in creating clutter
within ORs because most capital equipment performs one
task or job, and each type of capital equipment requires
unique techniques or methods to use and has a unique user
interface. Accordingly, the system described in U.S. Provi-
sional Patent Application No. 62/826,588, titled MODU-
LAR ENERGY SYSTEM INSTRUMENT COMMUNICA-
TION TECHNIQUES, filed on Mar. 29, 2019, addresses the
consumer need for the consolidation of capital equipment
and other surgical technology, a decrease in equipment
footprint within the OR, a streamlined equipment interface,
and a more efficient surgical procedure by which the number
of devices that surgical staff members need to interact with
is reduced.

However, as electrosurgical and/or ultrasonic surgical
systems become more modular and capital equipment
becomes increasingly more streamlined, the number of ports
by which various pieces of equipment can be connected is
decreasing. Additionally, each port is required to accommo-
date a variety of different types of equipment. Thus, there
exists an even greater need for surgical systems that auto-
matically detect, identify, and manage auxiliary equipment
upon connection to a hub. Accordingly, in various non-
limiting aspects of the present disclosure, apparatuses are
provided for detecting an instrument's presence on monopo-
lar and bipolar energy ports of electrosurgical generators.

In order to prevent single use devices from being used
outside their safe operating window, electrosurgical/ultra-
sonic surgical devices can include a mechanism for shutting
off the functionality of the electrosurgical/ultrasonic surgical
device after a predetermined number of hours. Conventional
electrosurgical/ultrasonic generators do not include a real
time clock and the clock for measuring the predetermined
number of hours is based on the generator on/run time and
is not based on actual elapsed time. In order to mitigate this
condition, electrosurgical/ultrasonic surgical devices used
with conventional electrosurgical/ultrasonic generators are
limited to one generator. This may not be favorable in
situations where surgery may occur from both sides of the
surgical table and may require changing electrosurgical/
ultrasonic generators during long surgical procedures.

Accordingly, in one aspect the present disclosure provides
data storage and device tracking arrangement that tracks a
device based on real clock timing and energy module
attachment history. In one general aspect, the present dis-
closure provides an energy module comprising a real time
clock and a control circuit coupled to the real time clock.
The control circuit is configured to detect the presence of a
surgical instrument coupled to the energy module, monitor
energization of the surgical instrument by the energy mod-
ule, track usage of the surgical instrument in real time based
on the real time clock, deactivate the surgical instrument
after a predetermined period of usage based on the real time
clock.

In various aspects, the present disclosure provides a
modular energy system 2000 (FIGS. 24-30) comprising a
variety of different modules 2001 that are connectable
together in a stacked configuration. The modules 2001 of the
modular energy system 2000 can include, for example, a
header module 2002 (which can include a display screen
2006), an energy module 2004, a technology module 2040,
and a visualization module 2042. Energy modules 3004
(FIG. 34), 3012 (FIG. 35), and 3270 (FIG. 37) illustrate the
energy module 2004 with more particularity. Accordingly,
for conciseness and clarity of disclosure, reference herein to
the energy module 2004 should be understood to be a
reference to any one of the energy modules 3004, 3012,
3270. An example of a communication protocol is described
in commonly owned U.S. Pat. No. 9,226,766, which is
herein incorporated by reference in its entirety.

It will be appreciated that the energy module 2004 may
include a variety of electrosurgical/ultrasonic generators that
need to be able to electrically identify and communicate
with a wide variety of electrosurgical/ultrasonic instruments,
such as, for example, the surgical instruments 1104, 1106,
1108 shown in FIG. 22, where the surgical instrument 1104
is an ultrasonic surgical instrument, the surgical instrument
1106 is an RF electrosurgical instrument, and the multifunc-
tion surgical instrument 1108 is a combination ultrasonic/RF
electrosurgical instrument. The energy modules 2004 and
the electrosurgical/ultrasonic instruments 1104, 1106, 1108
may have vastly different communication needs in terms of
such things as data bandwidth, latency, circuit cost, power
requirements, cybersecurity robustness, and noise immunity.
Accordingly, there is a need for the modular energy system
2000, and in particular the energy modules 2004 of the
modular energy system 2000, to support multiple commu-
nication protocols. At the same time, ergonomic and cost
concerns dictate that the total number of conductors in an
electrosurgical/ultrasonic instrument cable be kept to a mini-
mum. Each of the energy modules 3004 (FIG. 34), 3012
(FIG. 35), and 3270 (FIG. 37) include a real time clock 3109
coupled to a control circuit 3082 for tracking usage of the
surgical instruments 1104, 1106, 1108 shown in FIG. 22
coupled to the energy modules 3004, 3012, 3270.

In various general aspects, as described with reference to
FIGS. 168-185 and incorporated herein, the present disclo-
sure provides a modular energy system with multiple sepa-
rate modules and a header that automatically detects the
presence of a device inserted into a port. In one general
aspect, the present disclosure provides an energy module
comprising a control circuit, a port, a sensor coupled to the
port and the control circuit, and an interface circuit coupled
to the port, the sensor, and the control circuit, wherein the
sensor is configured to detect presence of a surgical instru-
ment coupled to the port. The control circuit is configured to
detect the presence of a surgical instrument coupled to the
energy module, monitor energization of the surgical instrument by the energy module, track usage of the surgical instrument in real time based on the real time clock, deactivate the surgical instrument after a predetermined period of usage based on the real time clock. Various example implementations of such detection circuits and techniques are described hereinbelow.

With reference now to FIG. 186, a real time instrument tracking system 19500 is depicted, in accordance with at least one aspect of the present disclosure. For example, the energy module 3270 (shown in more detail in FIG. 37), and equally applicable to the energy module 3004 (shown in more detail in FIG. 34) and energy module 3012 (shown in more detail in FIG. 35), once the control circuit 3082 detects the presence of a surgical instrument 1106, for example, or any one of the electrosurgical/ultrasonic instruments 1104, 1108, the control circuit 3082 reads the time for the real time clock 3109 and stores it in a memory, such as an EEPROM 19504, located in the surgical instrument 1106. In various aspects the present disclosure can provide tracking functionality for any of the components or modules of the modular energy system 3000 described herein. In one aspect, the modular energy system 3000 components described herein may comprise a real time clock such as, for example, the real time clock 3109 located in any one of the energy modules 3004, 3012, 3270 as well as the header/user interface module 3002. It will be appreciated, however, that the real time clock 3109 may be located in other modules of the modular energy system 3000 such as, for example, the user interface module 3030 (FIG. 33), communication module 3032 (FIG. 33), header module 3150 (FIG. 35) to provided flexibility into allowing multiple energy modules 3004, 3012, 3270 to be operational while still ensuring that the surgical instrument 1106 coupled to one of the energy modules 3004, 3012, 3270 is functioning within a safe operating window. With the real time clock 3109 provided in each of the energy modules 3004, 3012, 3270, the surgical instrument 1106 EEPROM 19504 map can be leveraged to maintain its own real time usage (RTU) regardless of which energy module 3004, 3012, 3270 it is connected to. In addition to the EEPROM 19504, the surgical instrument 1106 may include a control circuit 19502 such as a microprocessor-controlled, logic, or FPGA electronic device that interfaces objects in the physical world to a distributed control system, for example. The surgical instrument 1106 can store its original use time in real time in the EEPROM 19504, or other memory device as described herein, and the energy module 3004, 3012, 3270 can be used to implement a new technique of shutting off the functionality of the surgical instrument 1106 based on RTU of the surgical instrument 1106.

Electrosurgical/ultrasonic instruments 1104, 1106, 1108 coupled to any of the energy modules 3004, 3012, 3270 of the modular energy system 3000 can be tracked with the real time clock 3109. The real time clock 3109 may be located in any one of or all of the energy modules 3004, 3012, 3270 or may be located in the header/user interface module 3002. In order to prevent electrosurgical/ultrasonic instruments 1104, 1106, 1108 intended for single use from being used outside of their safe operating window, the electrosurgical/ultrasonic instruments 1104, 1106, 1108 can be shut off after operating for a predetermined length of time based on their RTU as determined by the real time clock 3109. With the real time clock 3109 located in the energy modules 3004, 3012, 3270 instead of the electrosurgical/ultrasonic instruments 1104, 1106, 1108, controlling the length of time that an electrosurgical/ultrasonic instruments 1104, 1106, 1108 can be operated is based on the actual elapsed time. In this configuration, the electrosurgical/ultrasonic instruments 1104, 1106, 1108 are not limited to a single energy module 3004, 3012, 3270, which is desirable during surgical procedures that may occur from both sides of a surgical table and sometimes require a change of energy modules 3004, 3012, 3270 during lengthy surgical procedures.

In various aspects, the real time clock 3109 of the energy module 3004, 3012, 3072, or header/user interface module 3002, provides a method of tracking real time usage of the electrosurgical/ultrasonic instruments 1104, 1106, 1108 via various parameters. One parameter is the initial plug in of the electrosurgical/ultrasonic instruments 1104, 1106, 1108 into the first energy module 3004, 3012, 3072 measured in real time by the real time clock 3109. The real time of the initial plug in is stored by the control circuit 3082 into the EEPROM 19504 of the electrosurgical/ultrasonic instrument 1104, 1106, 1108. Another parameter is the total elapsed time since the initial plug in to provide better ability to detect actual elapsed time versus run time of the energy module 3004, 3012, 3072. Another parameter is elapsed time between connections of the electrosurgical/ultrasonic instruments 1104, 1106, 1108 into the energy module 3004, 3012, 3072, where a lengthy period between connections may indicate swapping patients and procedures. Another parameter is the elapsed time between energy module 3004, 3012, 3072 power cycles, where sometimes users power off, unplug, and reposition the energy module 3004, 3012, 3072. The real time clock 3109 allows the energy module 3004, 3012, 3072 to detect the period between power cycles in order to ensure it is still the same patient. Another parameter is the total run time of the electrosurgical/ultrasonic instrument 1104, 1106, 1108 and the number of energy modules 3004, 3012, 3072 used based on an energy module 3004, 3012, 3072 identifier, such as, for example, the serial number.

In one aspect, time related parameters can be stored in the EEPROM 19504 map located in the electrosurgical/ultrasonic instrument 1104, 1106, 1108 and checked by the energy modules 3004, 3012, 3072 each time the electrosurgical/ultrasonic instrument 1104, 1106, 1108 is plugged into the energy module 3004, 3012, 3072. This functionality enables the energy modules 3004, 3012, 3072 to determine the usage history of the electrosurgical/ultrasonic instrument 1104, 1106, 1108 and evaluate whether the single use of the electrosurgical/ultrasonic instrument 1104, 1106, 1108 has expired.

FIG. 187 is a logic diagram of a process 19510 depicting a control program or a logic configuration for tracking surgical instruments in real time, in accordance with at least one aspect of the present disclosure. With reference to the real time instrument tracking system 19500 of FIG. 186 in conjunction with FIG. 187, for example, a control circuit 3082 of an energy module 3004 of a modular energy system 3000 detects 19512 the presence of a surgical instrument 1106, or any one of the electrosurgical/ultrasonic instruments 1104, 1108, plugged into the energy module 3004, using any of the presence detection techniques described in connection with FIGS. 168-185. Returning now to FIG. 187, the control circuit 3082 reads 19514 the real time from the real time clock 3109 of the energy module 3004 or the header/user interface module 3002. If the control circuit 3082 determines 19516 that this is the first time the surgical instrument 1106 was plugged into the energy module 3004, the control circuit 3082 stores 19518 the real time in a memory of the surgical instrument 1106, such as the EEPROM 19504, for example. If the control circuit 3082 determines that this is not an initial connection, the control circuit 3082 reads 19522 the real time from the EEPROM 19504 of the surgical instrument 1106 and determines 19524 the total elapsed time. The control circuit 3082 compares 19526 the total elapsed time to the real time limit for the surgical instrument 1106 and determines whether the total elapsed time exceeds the real time limit for the surgical instrument 1106. If the real time limit has not been exceeded, the control circuit 19530 activates the energy module 3004 to energize the surgical instrument 1106. The energy module 3004 may be configured to deliver therapeutic or sub-therapeutic energy to the surgical instrument 1106. The control circuit 3082 then continues to read 19522 the real time from the EEPROM 19504 of the surgical instrument 1106 until the surgical instrument 1106 is disconnected from the energy module 3004 or the determined total elapsed time exceeds the real time limit for the surgical instrument 1106. When the determined total elapsed time is equal to or exceeds the real time limit for the surgical instrument 1106, the control circuit 3082 deactivates 19528 the surgical instrument 1106.

Determining 19524 the total elapsed time includes determining the total elapsed time since the initial plug in of the instrument 1106 into the energy module 3004 to provide better ability to detect actual elapsed time versus run time of the energy module 3004. Determining 19524 the total elapsed time includes determining elapsed time between connections of the surgical instrument 1106 to the energy module 3004, where a lengthy period between connections may indicate swapping patients and procedures. Determining 19524 the total elapsed time includes determining elapsed time between energy module 3004 power cycles, where sometimes users power off, unplug, and reposition the energy module 3004.

Regional Location Tracking of Components of A Modular Energy System

In one aspect, a surgical platform is provided. The surgical platform may comprise one or more components, and a regional location tracking module. The regional location tracking module may be configured to connect with an external device, receive geographic location data of the external device from the external device, and implement geographic location specific functionality based on the geographic location data received from the external device.

In another aspect, a method for determining a location of one or more components of a surgical platform is provided. The method may comprises responsive to detecting that an application executing on a user device is logged in, collecting, by the application, geographic location data of the user device from the user device. The method may further comprise receiving, by the application, a request for an activation code, wherein the activation code identifies the geographic location data.

In another aspect, a method for upgrading software logic for one or more components of a surgical platform via an application on a user device is provided. The method may comprise collecting geographic location data from the user device and providing an activation code, where the activation code identifies the geographic location data of the user device. The method may further comprise determining whether the geographic location data of the user device matches geographic location data pre-stored in the one or more components, and declining the upgrading of the software logic responsive to determining that the geographic location data of the user device does not match the geographic location data pre-stored in the one or more components.

Generally, conventional surgical devices or components (e.g., generators) do not have an ability to identify their location. However, a need or preference for features of the surgical devices/components may vary depending on region/country. For example, some features that are more preferred or necessary in one region (e.g., Japan) may be less preferred or unnecessary in other regions (e.g., United States). In some cases, surgical device/component providers may want to limit the use of the surgical devices/components (or some features of the devices/components) in certain regions due to various factors, including government regulations, regional marketing strategies, and so on. Without the geographic location information with respect to the surgical devices or components, it would be difficult for the surgical device/component providers to provide regionally specific (hardware/software) features for the surgical devices/components or limit the use of the surgical devices/components (or some features of the devices/components) in a specific region.

Although a GPS receiver can be separately purchased and installed in the existing conventional surgical devices/components to track the geographical location of the surgical devices/locations, it would require additional costs and efforts for the purchase and installation of the GPS receiver, and the installation process may be cumbersome or difficult. For example, there may be no proper space inside the existing conventional surgical devices/components for the installation of the GPS receiver. Although the GPS receiver can be installed outside of the surgical device/components (e.g., outer wall of the surgical devices/components), it would be difficult to manage the GPS receiver, and there is a risk of losing the GPS receiver.

Aspects of the present disclosure may address the above-identified deficiencies of the conventional surgical devices/components. For example, in various aspects, a surgical platform including an energy module, header module, expanded energy module, technology module, visualization module, various modules and other components that are combinable to customize surgical platforms, surgical system including communicably connectable surgical platforms, and/or header modules including a user interface, discussed with reference to FIGS. 24-30, in accordance with various aspects of the present disclosure, may be configured with geographic location tracking functionality, such as, for example, regional location tracking functionality. Regional location tracking functionality may be implemented in the component or system of the surgical platform via an application or other software module that can interface with an application or web interface located on a separate device. For example, an application or web interface could be used via a device of a user such as a sales representative. This would allow for identification of a regional location of surgical platform system or component based on the GPS location of the device. For example, the user device can establish a connection with the component or system of the surgical platform and transmit the GPS or other location information (e.g., cellular tower triangulation, etc.) to the component or system of the surgical platform. In this way the component or system of the surgical platform knows what its geographic location is and can implement geographic location specific functionality.

In some aspects, an installer may log into an application or web interface via a user device. The application/web interface may collect location data from the user device. The installer may request an activation code. The activation code may be provided to the installer via the user device. The activation code may identify regional location of the system or component of the surgical platform for storage. The installer then may input the activation code into the system or component of the surgical platform user interface. The regional location may be stored on the system or component of the surgical platform.

In some aspects, location may be determined by Bluetooth/WiFi communication between a bring your own device (BYOD) and the component or system of the surgical platform. The component or system of the surgical platform may check the GPS location on the BYOD to confirm location. In some aspects, location may be determined by connecting the component or system of the surgical platform to the user device/application and could periodically check its location. In some aspects, location may be determined by embedding a Global System for Mobile Communications (GSM) receiver in a header module to periodically check position. In some aspects, location may be determined by regional specific products that are programmed with a country/region code that would set the country/region of the component or system of the surgical platform when they are plugged in.

A few implementation features may include, for example, requiring re-registration for every software upgrade or after a certain period of time and/or requiring re-registration to occur during biomed output verification, among other implementation features. In some aspect, the user may begin a software upgrade process via the application/web interface on the user device. The application/web interface may collect location data from the user device and provides a code. The user may input a software activation code. The component or system of the surgical platform may determine whether the location of the user device matches the pre-stored location data of the component or system of the surgical platform. If there is no match, the software upgrade may be declined. If there is a match, the software upgrade may be provided to the component or system of the surgical platform matching the regional specific configuration. The component or system of the surgical platform is then ready for use.

Aspects of the regional location tracking of the various components or systems of the surgical platform according to the present disclosure may be advantageous because it may provide the ability to identify the regional location of the component or system of the surgical platform, allowing for regionally specific software features for the component or system of the surgical platform such as the generator or other component or system of the surgical platform. It may also allow the components or systems of the surgical platform to employ regionally specific instrument functionality preferences that can change as a function of region. Aspects of the present disclosure may also provide a cost-effective way of limiting the use of the surgical systems/components (or some features of the systems/components) in some regions, while allowing the use of the surgical systems/components and features thereof in other regions. Additional features and advantages of the disclosed method, system, and apparatus are described below.

FIG. 188 depicts a high-level schematic diagram of a system 20000 in accordance with at least one aspect of the present disclosure. The system 20000 may include a surgical platform 20010. The surgical platform 20010 may include one or more components 20020A-F. In various aspects, the one or more components 20020A-F may include an energy module (e.g., a generator), a header module, an expanded energy module, a technology module, a visualization mod-ule, a combinable module, or any combination thereof. In some aspects, the energy module (e.g., a generator) may produce a WiFi signal that is capable of supplying power to the system. In various aspects, the surgical platform 20010 may also include a regional location tracking module 20030, a storage unit/device 20040, and a surgical system 20050.

In some aspects, the regional location tracking module 20030 and/or the storage unit/device 20040 may be part of the one or more components 20020A-F and/or the surgical system 20050. In other aspects, the regional location tracking module 20030 and/or the storage unit/device 20040 may be separate from the one or more components 20020A-F and/or the surgical system 20050. Similarly, in some aspects, the one or more components 20020A-F may be part of the surgical system 20050. In other aspects, the one or more components 20020A-F may be separate from the surgical system 20050. In some aspects, the surgical system 20050 may be similar to the systems described in FIGS. 1, 2, 9, and 22-30. For example, the surgical system 20050 may include communicably connectable surgical platforms and/or header modules including a user interface.

The system 20000 may also include an application 20060 and an external device 20070. In some aspects, the application 20060 may be any software application or web interface. The application 20060 may be used via a device of a user, such as a sales representative. In various aspects, the external device may be a BYOD, including, but not limited to, a mobile device, computer, laptop, personal computer, tablet computer, or any other type of BYODs. The application 20060 may be running/executing on the external device 20070 (and/or on an application server). In some aspects, the application 20060 and the external device 20070 may be in communication with the surgical platform 20010 (e.g., the regional location tracking module 20030 or other components), for example, over a wired channel or a wireless channel.

In various aspects, the surgical platform 20010 (e.g., components 20020A-F, regional location tracking module 20030, etc.) may connect with the external device 20070, and receive geographic location data of the external device 200070 from the external device 20070. The surgical platform 20010 (e.g., components 20020A-F, regional location tracking module 20030, etc.) may implement geographic location specific functionality based on the geographic location data received from the external device 20070. The implementation of the geographic location specific functionality may include providing or limiting some functionalities of the surgical devices/components, including, but not limited to, language options (e.g., automatic language selection for Korean in Korea), specific automatic sequential operations of the surgical devices/components, specific default settings of surgical devices/components, different maximum/minimum values of outputs/inputs allowed in the surgical devices/components (e.g., minimum/maximum power values), and/or a specific version of the software of the surgical devices/components.

For example, in a country where a lung surgery is more frequent than other countries, a specific automatic sequential operation option for the treatment of the lung tissue (e.g., automatic control algorithm that would optimally ramp down the motor in response to an unexpectedly high force to close to avoid tearing the tissue) may be provided. In a country where a stomach surgery is more frequent, a specific automatic sequential operation option for the treatment of the stomach tissue (e.g., automatic control algorithm that would optimally ramp up the motor in response to an unexpectedly high force to close to ensure that the end effector is clamped properly on the tissue) may be provided. Also, the maximum/minimum values of outputs/inputs of the surgical devices/components (e.g., minimum/maximum power values), and/or availability of certain versions of the software of the surgical devices/components may vary depending on the region/country.

In various aspects, the surgical platform 20010 (e.g., components 20020A-F, regional location tracking module 20030, etc.) may determine a geographic location of the one or more components 20020A-F based on the geographic location data received from the external device 20070. For example, the surgical platform 20010 may assume or consider that the geographic location in the geographic location data received from the external device 20070 refers to the geographic location of the one or more components 20020A-F.

In various aspects, the surgical platform 20010 (e.g., components 20020A-F, regional location tracking module 20030, etc.) may determine a geographic location of the one or more components 20020A-F by Bluetooth or WiFi communication between the external device 20070 and the surgical platform 20010. When the regional location tracking module 20030/one or more components 20020A-F are connected to the external device 20070 via Bluetooth or WiFi channel, the regional location tracking module 20030/one or more components 20020A-F may receive or collect the location information from a Bluetooth/WiFi device/application. For example, when the external device establishes a connection with the component or system of the surgical platform, it may transmit the GPS or other location information (e.g., cellular tower triangulation, etc.) to the component or system of the surgical platform. In various aspects, some of the steps performed by the surgical platform may be performed by the application 20060 on behalf of the surgical platform.

In various aspects, the surgical platform 20010 (e.g., components 20020A-F, regional location tracking module 20030, etc.) may check a GPS location on the external device 20070 to confirm the geographic location data received from the external device 20070. In some aspects, a geographic location of the one or more components 20020A-F may be determined by connecting the one or more components 20020A-F to the external device 20070. For example, the geographic location of the one or more components 20020A-F may be determined by physically connecting the one or more components 20020A-F to the external device 20070 over a wired channel. In other examples, the geographic location of the one or more components 20020A-F may be determined by connecting the one or more components 20020A-F to the external device 20070 over a wireless channel. Examples of the wireless channel/connection may include RFID (read only or read/write), Bluetooth, Zigbee, WiFi, IR, or any other suitable wireless protocols.

In some aspects, the surgical platform 20010 (e.g., components 20020A-F, regional location tracking module 20030, etc.) may periodically (e.g., every hour, every day, every month, every three months, every year, etc.) check the geographic location data. For example, the regional location tracking module 20030 or the component 20020A-F may periodically receive the geographic location data from the external device 20070 periodically (e.g., every hour, every day, every month, every three months, every year, etc.) and check the received geographic location data whenever the geographic location data is received from the external device 20070.

In some aspects, the surgical platform 20010 may further include a GSM receiver. The GSM receiver may be embedded in the one or more components 20020A-F (e.g., header module). In some aspects, the regional location tracking module 20030 or the component 20020A-F may determine the geographic location of the one or more components 20020A-F using the GSM receiver. The regional location tracking module 20030 or the component 20020A-F may use the GSM receiver to periodically check the geographic location of the one or more components 20020A-F.

In various aspects, the geographic location of the one or more components 20020A-F may be determined by using a regional specific product that is programmed with a region code. For example, the region code may set the geographic location of the one or more components when the regional specific product is plugged into the one or more components 20020A-F.

The surgical platform 20010 may further include a processor. The processor may be any single-core or multicore processor, such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The surgical platform 20010 may also include a system memory. The system memory includes volatile memory and non-volatile memory. The basic input/output system (BIOS), containing the basic routines to transfer information between elements within a computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The surgical platform 20010 may also include removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the surgical platform may include software that acts as an intermediary between users and the basic computer resources described in a suitable operating environment. Such software includes an operating system. The operating system, which can be stored on the disk storage, acts to control and allocate resources of the computer system in the surgical platform. System applications take advantage of the management of resources by the operating system through program modules and program data stored either in the system memory or on the disk storage. It is to be appreciated that various components described herein can be implemented with various operating systems or combinations of operating systems.

FIG. 189 is a logic diagram of a process 20100 depicting a control program or a logic configuration for determining a geographical location of one or more components of a surgical platform, in accordance with at least one aspect of the present disclosure. Although the example process 20100 is described with reference to the logic diagram illustrated in FIG. 189, it will be appreciated that many other methods of performing the acts associated with the method may be used. For example, the order of some of the blocks may be changed, certain blocks may be combined with other blocks, and some of the blocks described are optional.

In the illustrated example, an application or logic 20060 executing on a user device may detect 20110 that it is logged in. For example, a user may log into the application 20060 via a user device (e.g., external device 20070), and the application or logic 20060 may detect 20110 this log-in activity. Then, the application may collect 20120 geographic location data of the user device from the user device. For example, responsive to detecting 20110 that the application or logic 20060 is logged-in by a user device (e.g., external device 20070), the application or logic 20060 may collect 20120 geographic location data of the user device from the user device.

In various aspects, the application or logic 20060 may receive 20130 a request for an activation code, where the activation code may identify the geographic location data of the user device. For example, the user may send a request for an activation code to the application or logic 20060, and the application or logic 20060 may receive 20130 the request for the activation code that may include or identify the geographic location data of the user device. Then, the application may provide 20140 the activation code via the user device. For example, the application or logic 20060 may provide 20140 the activation code to the user via the external device 20070. The activation code may include information about the geographic location of the external device 20070. In some aspects, the activation code itself may not give any information about the geographic location to a person reading the code, and it may need a machine translation/table that translates the meaning (e.g., geographic location) of the code (e.g., 35379=US; 27123=KR). In other aspects, the activation code itself may provide the geographic location information (e.g., US, KR, JP), and no machine translation/table may be needed to understand the activation code.

In some aspects, the application may connect 20150 with one or more components of a surgical platform. For example, the application or logic may be connected with the surgical platform 20010 (e.g., components 20020A-F; regional location tracking module 20030; or any system UI provided by the surgical platform 20010) through a wired or wireless channel. Then, the activation code may be inputted into the surgical platform 20010 (e.g., components 20020A-F; regional location tracking module 20030; or any system UI provided by the surgical platform 20010) via the application or logic. In some aspects, the user may directly input the provided activation code into the surgical platform 20010. In some aspects, the activation code may be automatically inputted into the surgical platform 20010 via the application or logic once it is generated by the application or logic.

In some aspects, the geographic location data may be stored 20160 on the one or more components of the surgical platform. The geographic location data may be stored on the one or more components of the surgical platform via the application or logic, components 20020A-F, regional location tracking module 20030, or any system UI provided by the surgical platform 20010. In some aspects, the geographic location data may be stored on the storage unit/device 20040.

In some aspects, the application or logic 20060 or any module/application in the system 20000 (e.g., regional location tracking module 20030) may verify the user device to determine whether the user device is an authorized device. For example, it may be determined that the user device is an authorized device responsive to determining that the user device includes an authorization code. It may be determined that the user device is not authorized responsive to determining that the user device does not include the authorization code. In some aspects, the authorization code may include any code issued by the surgical platform/component provider or any information of the surgical platform/component, including a unique device identifier or a serial number.

If it is determined that the user device is not authorized, the application or logic 20060 or any module/application in the system 20000 may prevent the user device from accessing the application and/or the surgical platform. For example, when a user attempts to login to the application or logic or to install the application or logic using an unauthorized device, such login or installation attempts may be denied. In other examples, when a user attempts to access the surgical platform using an unauthorized device, such access attempts may be denied. In this way, aspects of the present disclosure may prevent an unauthorized user (e.g., hacker) or device's attempts to access the application and/or the surgical platform and, ultimately, prevent attempts to arbitrarily set the geographic location of the surgical platform or components thereof.

FIG. 190 is a logic diagram of a process 20200 depicting a control program or a logic configuration for upgrading software logic for one or more components of a surgical platform based on a geographical location of the one or more components, in accordance with at least one aspect of the present disclosure. Although the example process 20200 is described with reference to the logic diagram illustrated in FIG. 190, it will be appreciated that many other methods of performing the acts associated with the method may be used. For example, the order of some of the blocks may be changed, certain blocks may be combined with other blocks, and some of the blocks described are optional.

In the illustrated example, an application may collect 20210 geographic location data from a user device. For example, in some aspects, a user may begin upgrade process via the application or logic 20060 on a user device (e.g., external device 20070), and once the upgrade process is started, the application or logic 20060 may collect 20210 geographic location data from the user device. In various aspects, the application may provide 20220 an activation code, where the activation code may identify the geographic location data of the user device. In some aspects, the activation code may be inputted 20230 into one or more components of a surgical platform. For example, the activation code may be inputted into the surgical platform 20010 (e.g., components 20020A-F; regional location tracking module 20030; or any system UI provided by the surgical platform 20010) via the application or logic 20060. In some aspects, the user may directly input the provided activation code into the surgical platform 20010. In some aspects, the activation code may be automatically inputted into the surgical platform 20010 once it is generated by the application or logic.

In some aspects, a surgical platform may determine 20240 whether the geographic location data of the user device matches geographic location data pre-stored in the one or more components. For example, the surgical platform 20010 (e.g., components, regional location tracking module, or any other element in the surgical platform) may determine whether the provided geographic location data of the user device matches geographic location data pre-stored in the surgical platform 20010 (e.g., components 20020A-F). If it is determined that the geographic location data of the user device matches the geographic location data pre-stored in the one or more components, the upgrading of software logic of the one or more components may be enabled 20250. Then, the software logic may be upgraded 20260. For example, if it is determined that the provided geographic location data of the user device matches the geographic location data pre-stored in the surgical platform 20010, the upgrading of software logic (e.g., from software version 1.0 to software version 2.0) of the surgical platform 20010 may be enabled. Then, the software logic may be upgraded 20260.

If it is determined that the geographic location data of the user device does not match the geographic location data pre-stored in the one or more components, the upgrading of software logic of the one or more components may be declined 20270. For example, if it is determined that the geographic location data of the user device does not match the geographic location data pre-stored in the surgical platform 20010, the upgrading of software logic of the surgical platform 20010 may be disenabled and/or declined. In some aspects, the steps described in blocks 20240-20270 may be performed by the application or logic 20060 or any other applications on behalf of the surgical platform 20010.

In some aspects, the surgical platform or the application may require this re-registration (e.g., verification of the location of the surgical platform/components) for every pre-identified event (e.g., software upgrade), after a certain period of time, or periodically (e.g., every month, every three months, every year, etc.). In some aspects, the surgical platform or the application may require the re-registration to occur during biomed output verification.

In this way, aspects of the present disclosure provide connectivity for components or systems of a surgical platform described with reference to FIGS. 24-30 that enables the surgical platform to confirm its location for regional tracking purposes. Regional tracking via BYOD enables regional specific instruments and software associated with the surgical platform to be automatically managed, and regional tracking would allow specific instrument and system functions to exist only in certain regions and would address unique region-specific user needs.

EXAMPLES

Various aspects of the subject matter described herein are set out in the following numbered examples:

Example 1—A method for constructing a surgical energy module system, wherein the method comprises providing a header module comprising a first array of connectors; providing a surgical energy module comprising a second array of connectors; and stacking the header module and the surgical energy module to electrically couple the first array of connectors and the second array of connectors to each other, wherein the stacking step electrically couples the first array of connectors and the second array of connectors.

Example 2—The method of Example 1, wherein stacking the header module and the surgical energy module comprises stacking the header module on top of the surgical energy module.

Example 3—The method of Examples 1 or 2, wherein the first array of connectors are positioned on a bottom of the header module and the second array of connectors are positioned on a top of the surgical energy module.

Example 4—The method of Example 3, wherein the surgical energy module comprises a first surgical energy module, and wherein the method further comprises providing a second surgical energy module comprising a third array of connectors; and stacking the second surgical energy module with the stacked first surgical energy module and header module to electrically couple the third array of connectors with the first array of connectors and the second array of connectors.

Example 5—The method of Examples 1, 2, 3, or 4, wherein the header module and the surgical energy module are configured to communicate data and power through the first array of connectors and the second array of connectors.

Example 6—The method of Examples 1, 2, 3, 4, or 5, further comprising providing a visualization module and stacking the visualization module with the header module and the surgical energy module.

Example 7—A method for constructing a modular surgical instrument control center, wherein the method comprises providing a header module comprising a first power backplane segment; providing a surgical module comprising a second power backplane segment; assembling the header module and the surgical module to electrically couple the first power backplane segment and the second power backplane segment to each other to form a power backplane; and applying power to the surgical module through the power backplane.

Example 8—The method of Example 7, wherein assembling the header module and the surgical module comprises assembling the header module on top of the surgical module.

Example 9—The method of Examples 7 or 8, wherein the first power backplane segment is positioned on a bottom of the header module and the second power backplane segment is positioned on a top of the surgical module.

Example 10—The method of Example 9, wherein the surgical module comprises a first surgical module, and wherein the method further comprises providing a second surgical module comprising a third power backplane segment; assembling the second surgical module with the assembled first surgical module and header module to electrically couple the third power backplane segment with the power backplane; and applying power to the second surgical module through the power backplane.

Example 11—The method of Examples 7, 8, 9, or 10, further comprising providing a visualization module and assembling the visualization module with the header module and the surgical module.

Example 12—A method for assembling a modular surgical control stack, wherein the method comprises providing a surgical energy module comprising a first data backplane segment; providing a surgical header module comprising a second data backplane segment; positioning the surgical header module on top of the surgical energy module such that the positioning of the surgical header module on top of the surgical energy module electrically and physically couples the first data backplane segment and the second data backplane segment to form a data backplane; and sending a data signal to the surgical energy module through the data backplane.

Example 13—The method of Example 12, wherein the first data backplane segment is positioned on a bottom of the surgical header module and the second data backplane segment is positioned on a top of the surgical energy module.

Example 14—The method of Example 13, wherein the surgical module comprises a first surgical energy module, and wherein the method further comprises providing a second surgical energy module comprising a third data backplane segment; positioning the second surgical energy module to electrically couple the third data backplane segment with the data backplane; and sending a second data signal to the second surgical energy module through the data backplane.

Example 15—The method of Examples 12, 13, or 14, further comprising providing a visualization module and assembling the visualization module with the header module and the surgical energy module.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A modular surgical system for use in a surgical procedure comprising:
a control module having a pulse generator configured to generate a clock pulse signal;
a first surgical module arrangeable in a stack configuration with the control module, wherein the first surgical module comprises:
a first timing circuit, wherein the clock pulse signal causes the first timing circuit to initiate a first timer; and
a first delay circuit, wherein the clock pulse signal causes the first delay circuit to transmit a first delayed sequence signal to the first timing circuit to finalize the first timer and set a first elapsed time, wherein the first timing circuit and the first delay circuit are electrically couplable with the pulse generator when the first surgical module is arranged in the stack configuration with the control module; and
a second surgical module arrangeable with the control module and the first surgical module in the stack configuration, wherein the second surgical module comprises:
a second timing circuit, wherein the clock pulse signal causes the second timing circuit to initiate a second timer; and
a second delay circuit, wherein the first delayed sequence signal causes the second delay circuit to transmit a second delayed sequence signal to the second timing circuit to finalize the second timer and set a second elapsed time, wherein the second timing circuit is electrically couplable with the pulse generator and the second delay circuit is electrically couplable with the first delay circuit when the second surgical module is arranged in the stack configuration with the control module and the first surgical module.

2. The modular surgical system of claim 1, wherein the first elapsed time is indicative of a physical position of the first surgical module in the stack configuration.

3. The modular surgical system of claim 2, wherein the second elapsed time is indicative of a physical position of the second surgical module in the stack configuration different from the physical position of the first surgical module.

4. The modular surgical system of claim 1, further comprising a display, wherein the display is configured to visually represent a physical position of the first surgical module relative to the control module based on the first elapsed time and visually represent a physical position of the second surgical module relative to the control module based on the second elapsed time.

5. The modular surgical system of claim 1, wherein the first delay circuit comprises a first resistor-capacitor (RC) delay circuit and a first flip-flop.

6. The modular surgical system of claim 5, wherein the first RC delay circuit is configured to receive the clock pulse signal, wherein the first RC delay circuit is configured to produce the first delayed sequence signal at a predetermined time after receiving the clock pulse signal, and wherein the first RC delay circuit is configured to transmit the first delayed sequence signal to a first clock input of the first flip-flop.

7. The modular surgical system of claim 6, further comprising a first means for providing a fast-rising edge at the first clock input of the first flip-flop based on the first delayed sequence signal.

8. The modular surgical system of claim 7, wherein the first means for providing is selected from the group consisting of: a comparator and a Schmitt-Trigger style buffer.

9. The modular surgical system of claim 7, wherein the first timing circuit comprises:
a first input pin electrically connected with the clock pulse generator when the first surgical module is arranged in the stack configuration with the control module, wherein the first input pin is configured to receive the clock pulse signal; and
a second input pin electrically connected with the first flip flop, wherein the first flip flop is configured to transmit a first output signal to the second input pin of the first timing circuit based on receiving the first delayed sequence signal from the first RC delay circuit.

10. The modular surgical system of claim 9, wherein the second delay circuit comprises a second RC delay circuit and a second flip-flop.

11. The modular surgical system of claim 10, wherein the first flip flop is configured to transmit the first output signal to the second RC delay circuit, wherein the second RC delay circuit is configured to produce the second delayed sequence signal at a predetermined time after receiving the first output signal, and wherein the second RC delay circuit is configured to transmit the second delayed sequence signal to a second clock input of the second flip-flop.

12. The modular surgical system of claim 10, wherein the second timing circuit comprises:

a third input pin electrically connected with the clock pulse generator when the second surgical module is arranged in the stack configuration with the control module and the first surgical module, wherein the third input pin is configured to receive the clock pulse signal; and a fourth input pin electrically connected with the second flip flop, wherein the second flip flop is configured to transmit a second output signal to the fourth input pin of the second timing circuit based on receiving the second delayed sequence signal from the second RC delay circuit.

13. The modular surgical system of claim 1, further comprising a third surgical module arrangeable with the control module, the first surgical module, and the second module in the stack configuration, wherein the third surgical module comprises:

a third timing circuit, wherein the clock pulse signal causes the third timing circuit to initiate a third timer; and a third delay circuit, wherein the second delayed sequence signal causes the third delay circuit to transmit a third delayed sequence signal to the third timing circuit to finalize the third timer and set a third elapsed time, wherein the third timing circuit is electrically couplable with the pulse generator and the third delay circuit is electrically couplable with the second delay circuit when the third surgical module is arranged in the stack configuration with the control module, the first surgical module, and the second module.

14. The modular surgical system of claim 1, wherein the first timing circuit comprises a microprocessor.

15. The modular surgical system of claim 1, wherein the first timing circuit comprises a field programmable gate array (FPGA).

* * * * *